(12) United States Patent
Sather et al.

(10) Patent No.: US 11,623,961 B2
(45) Date of Patent: Apr. 11, 2023

(54) ANTIBODIES AND CHIMERIC ANTIGEN RECEPTORS SPECIFIC FOR B-CELL MATURATION ANTIGEN

(71) Applicant: Juno Therapeutics, Inc., Seattle, WA (US)

(72) Inventors: Blythe D. Sather, Seattle, WA (US); Steven M. Shamah, Seattle, WA (US); Yan Chen, Seattle, WA (US); Rebecca Wu, Seattle, WA (US); Collin Hauskins, Seattle, WA (US); Csaba Pazmany, Seattle, WA (US); Jui Dutta-Simmons, Seattle, WA (US); Kimberly Harrington, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 51 days.

(21) Appl. No.: 16/760,411

(22) PCT Filed: Nov. 1, 2018

(86) PCT No.: PCT/US2018/058767
§ 371 (c)(1),
(2) Date: Apr. 29, 2020

(87) PCT Pub. No.: WO2019/089969
PCT Pub. Date: May 9, 2019

(65) Prior Publication Data
US 2020/0392236 A1 Dec. 17, 2020

Related U.S. Application Data

(60) Provisional application No. 62/596,772, filed on Dec. 8, 2017, provisional application No. 62/580,431, filed on Nov. 1, 2017.

(51) Int. Cl.
| | | |
|---|---|---|
| C07K 16/28 | (2006.01) | |
| A61P 35/00 | (2006.01) | |
| C12N 15/867 | (2006.01) | |
| C07K 14/535 | (2006.01) | |
| C07K 14/705 | (2006.01) | |

(52) U.S. Cl.
CPC .......... *C07K 16/2875* (2013.01); *A61P 35/00* (2018.01); *C07K 14/535* (2013.01); *C07K 14/70517* (2013.01); *C07K 14/70521* (2013.01); *C12N 15/867* (2013.01); *C07K 2317/52* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,208,020 A | 5/1993 | Chari et al. |
| 5,219,740 A | 6/1993 | Miller et al. |
| 5,283,173 A | 2/1994 | Fields et al. |
| 5,416,064 A | 5/1995 | Chari et al. |
| 5,424,297 A | 6/1995 | Rubio et al. |
| 5,468,614 A | 11/1995 | Fields et al. |
| 5,504,090 A | 4/1996 | Neely et al. |
| 5,545,627 A | 8/1996 | Jacobson et al. |
| 5,565,566 A | 10/1996 | Olsson |
| 5,635,483 A | 6/1997 | Pettit et al. |
| 5,635,517 A | 6/1997 | Muller et al. |
| 5,670,501 A | 9/1997 | Peck et al. |
| 5,712,291 A | 1/1998 | D'Amato |

(Continued)

FOREIGN PATENT DOCUMENTS

| | | |
|---|---|---|
| CN | 103 492 406 | 1/2014 |
| CN | 108 239 144 | 7/2018 |

(Continued)

OTHER PUBLICATIONS

US 8,252,592 B2, 08/2012, Sadelain (withdrawn)
Jena et al. (Blood Aug. 19, 2010 116(7): 1035-1044) (Year: 2010).*
U.S. Appl. No. 16/844,759, filed Apr. 9, 2020, by Brentjens et al. (Copy not provided). (Copy not submitted herewith pursuant to the waiver of 37 C.F.R. § 1.98(a)(2)(iii) issued by the Office on Sep. 21, 2004).
Adams et al., "Development of KITE-585 A fully human BCMA CAR T-cell therapy for the treatment of multiple myeloma," AACR Annual Meeting 2017. Abstract 4979. Presented on Apr. 4, 2017.

(Continued)

*Primary Examiner* — Peter J Reddig
(74) *Attorney, Agent, or Firm* — Morrison & Foerster LLP

(57) ABSTRACT

Provided herein are BCMA-binding molecules, including anti-BCMA antibodies and antigen-binding fragments thereof such as heavy chain variable (VH) regions and single-chain antibody fragments, and chimeric receptors comprising the anti-BCMA binding molecules such as chimeric antigen receptors (CARs). In some embodiments, the anti-BCMA antibodies or antigen-binding fragments thereof specifically bind to BCMA-1. Among the anti-BCMA antibodies are human antibodies, including those that compete for binding to BCMA with reference antibodies, such as a non-human reference antibody. Also provided are genetically engineered cells expressing the CARs or BCMA-binding molecules and uses thereof such as in adoptive cell therapy.

35 Claims, No Drawings
Specification includes a Sequence Listing.

(56) References Cited

U.S. PATENT DOCUMENTS

| | | |
|---|---|---|
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,786,360 A | 7/1998 | Neely |
| 5,798,368 A | 8/1998 | Muller et al. |
| 5,877,296 A | 3/1999 | Hamann et al. |
| 5,981,524 A | 11/1999 | Peck et al. |
| 6,040,177 A | 3/2000 | Riddell et al. |
| 6,060,273 A | 5/2000 | Dirks et al. |
| 6,066,642 A | 5/2000 | Jacobson et al. |
| 6,111,090 A | 8/2000 | Gorman et al. |
| 6,117,998 A | 9/2000 | Neely |
| 6,207,453 B1 | 3/2001 | Maass et al. |
| 6,232,297 B1 | 5/2001 | Linden et al. |
| 6,281,230 B1 | 8/2001 | Muller et al. |
| 6,313,131 B1 | 11/2001 | Lawyer |
| 6,316,471 B1 | 11/2001 | Muller et al. |
| 6,322,771 B1 | 11/2001 | Linden et al. |
| 6,326,390 B1 | 12/2001 | Leung et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,410,319 B1 | 6/2002 | Raubitschek et al. |
| 6,451,995 B1 | 9/2002 | Cheung et al. |
| 6,458,810 B1 | 10/2002 | Muller et al. |
| 6,476,052 B1 | 11/2002 | Muller et al. |
| 6,602,684 B1 | 8/2003 | Umana et al. |
| 6,630,579 B2 | 10/2003 | Chari et al. |
| 7,025,962 B1 | 4/2006 | Gorman et al. |
| 7,070,995 B2 | 7/2006 | Jensen |
| 7,083,785 B2 | 8/2006 | Browning et al. |
| 7,091,353 B2 | 8/2006 | Robarge et al. |
| 7,132,255 B2 | 11/2006 | Blumberg |
| 7,141,575 B2 | 11/2006 | Gillespie et al. |
| 7,244,759 B2 | 7/2007 | Muller et al. |
| 7,265,209 B2 | 9/2007 | Jensen |
| 7,320,991 B2 | 1/2008 | Figg et al. |
| 7,354,762 B2 | 4/2008 | Jensen |
| 7,405,219 B2 | 7/2008 | Gillespie et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,498,298 B2 | 3/2009 | Doronina et al. |
| 7,521,541 B2 | 4/2009 | Eigenbrot et al. |
| 7,605,236 B2 | 10/2009 | Ruben et al. |
| 7,618,632 B2 | 11/2009 | Collins et al. |
| 7,855,275 B2 | 12/2010 | Eigenbrot et al. |
| 7,943,743 B2 | 5/2011 | Korman et al. |
| 8,008,449 B2 | 8/2011 | Korman et al. |
| 8,008,450 B2 | 8/2011 | Williams et al. |
| 8,080,554 B2 | 12/2011 | Sitkovsky et al. |
| 8,124,084 B2 | 2/2012 | Lefrancois et al. |
| 8,153,765 B2 | 4/2012 | Park et al. |
| 8,324,353 B2 | 12/2012 | Jensen |
| 8,339,645 B2 | 12/2012 | Jun |
| 8,354,509 B2 | 1/2013 | Carven et al. |
| 8,388,967 B2 | 3/2013 | Smith et al. |
| 8,389,282 B2 | 3/2013 | Sadelain et al. |
| 8,497,118 B2 | 7/2013 | Jensen |
| 8,586,023 B2 | 11/2013 | Shiku et al. |
| 8,591,886 B2 | 11/2013 | Ponath et al. |
| 8,603,477 B2 | 12/2013 | Afar et al. |
| 8,609,089 B2 | 12/2013 | Langermann et al. |
| 8,716,301 B2 | 5/2014 | Sitkovsky et al. |
| 8,716,315 B2 | 5/2014 | Figg et al. |
| 8,802,374 B2 | 8/2014 | Jensen |
| 8,883,500 B2 | 11/2014 | Sitkovsky et al. |
| 8,987,279 B2 | 3/2015 | Bamford et al. |
| 9,765,342 B2 | 9/2017 | Kochenderfer |
| 10,174,095 B2 | 1/2019 | Brogdon et al. |
| 10,562,972 B2 | 2/2020 | Brentjens et al. |
| 10,821,135 B2 | 11/2020 | Brentjens et al. |
| 10,918,665 B2 | 2/2021 | Brentjens et al. |
| 10,947,314 B2 | 3/2021 | Brentjens et al. |
| 11,000,549 B2 | 5/2021 | Brentjens et al. |
| 11,066,475 B2 | 7/2021 | Sather et al. |
| 2002/0131960 A1 | 9/2002 | Sadelain et al. |
| 2002/0164328 A1 | 11/2002 | Shinkawa et al. |
| 2003/0045552 A1 | 3/2003 | Robarge et al. |
| 2003/0115614 A1 | 6/2003 | Kanda et al. |
| 2003/0157108 A1 | 8/2003 | Presta |
| 2003/0170238 A1 | 9/2003 | Gruenberg et al. |
| 2004/0047858 A1 | 3/2004 | Blumberg et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0123546 A1 | 6/2005 | Umana et al. |
| 2006/0270045 A1 | 11/2006 | Cregg et al. |
| 2009/0082299 A1 | 3/2009 | Felber et al. |
| 2009/0169562 A1 | 7/2009 | Throsby et al. |
| 2010/0028330 A1 | 2/2010 | Collins et al. |
| 2010/0247521 A1 | 9/2010 | Jones et al. |
| 2010/0260748 A1 | 10/2010 | Elkins et al. |
| 2011/0003380 A1 | 1/2011 | Miltenyi et al. |
| 2011/0081311 A1 | 4/2011 | Pavlakis et al. |
| 2011/0117093 A1 | 5/2011 | Ruben et al. |
| 2012/0082661 A1 | 4/2012 | Kalled et al. |
| 2012/0114649 A1 | 5/2012 | Langermann et al. |
| 2012/0141413 A1 | 6/2012 | Pavlakis et al. |
| 2012/0177598 A1 | 7/2012 | Lefrancois et al. |
| 2012/0189622 A1 | 7/2012 | Tesar et al. |
| 2013/0149337 A1 | 6/2013 | Cooper et al. |
| 2013/0156774 A1 | 6/2013 | Kuchroo et al. |
| 2013/0287748 A1 | 10/2013 | June et al. |
| 2013/0336964 A1 | 12/2013 | Rovati et al. |
| 2014/0056922 A1 | 2/2014 | Sitkovsky et al. |
| 2014/0161828 A1 | 6/2014 | Armitage et al. |
| 2014/0193433 A1 | 7/2014 | Borges et al. |
| 2014/0271618 A1 | 9/2014 | Markel et al. |
| 2014/0377240 A1 | 12/2014 | Sitkovsky et al. |
| 2015/0218274 A1 | 8/2015 | Sabatos-Peyton et al. |
| 2015/0259420 A1 | 9/2015 | Triebel et al. |
| 2015/0283178 A1 | 10/2015 | June et al. |
| 2016/0313300 A1 | 10/2016 | Trotter et al. |
| 2018/0118842 A1 | 5/2018 | Brentjens et al. |
| 2018/0360880 A1 | 12/2018 | Brentjens et al. |
| 2019/0161553 A1 | 5/2019 | Sather et al. |
| 2020/0078404 A1 | 3/2020 | Ports et al. |
| 2020/0123266 A1 | 4/2020 | Brentjens et al. |
| 2020/0276239 A1 | 9/2020 | Brentjens et al. |
| 2020/0289565 A1 | 9/2020 | Green et al. |
| 2021/0324100 A1 | 10/2021 | Sather et al. |
| 2021/0346432 A1 | 11/2021 | Brentjens et al. |
| 2021/0393689 A1 | 12/2021 | Blythe et al. |

FOREIGN PATENT DOCUMENTS

| | | |
|---|---|---|
| EP | 0425235 | 5/1991 |
| EP | 0452342 | 10/1991 |
| EP | 1866339 | 12/2007 |
| EP | 1947183 | 7/2008 |
| EP | 2537416 | 12/2012 |
| JP | 2011-178691 | 9/2011 |
| RU | 2009138932 | 10/2013 |
| WO | WO 1992/008796 | 5/1992 |
| WO | WO 1994/011026 | 5/1994 |
| WO | WO 1994/028143 | 12/1994 |
| WO | WO 1997/030087 | 8/1997 |
| WO | WO 1998/003502 | 1/1998 |
| WO | WO 1998/054170 | 12/1998 |
| WO | WO 1998/058964 | 12/1998 |
| WO | WO 1999/20758 | 4/1999 |
| WO | WO 1999/22764 | 5/1999 |
| WO | WO 1999/40196 | 8/1999 |
| WO | WO 1999/052552 | 10/1999 |
| WO | WO 2000/014257 | 3/2000 |

(56) References Cited

FOREIGN PATENT DOCUMENTS

| | | |
|---|---|---|
| WO | WO 2000/061739 | 10/2000 |
| WO | WO 2001/03720 | 1/2001 |
| WO | WO 2001/029246 | 4/2001 |
| WO | WO 2002/031140 | 4/2002 |
| WO | WO 2002/055083 | 7/2002 |
| WO | WO 2002/059106 | 8/2002 |
| WO | WO 2002/068414 | 9/2002 |
| WO | WO 2003/011878 | 2/2003 |
| WO | WO 2003/084570 | 10/2003 |
| WO | WO 2003/085107 | 10/2003 |
| WO | WO 2003/085119 | 10/2003 |
| WO | WO 2004/056312 | 7/2004 |
| WO | WO 2005/007190 | 1/2005 |
| WO | WO 2005/035586 | 4/2005 |
| WO | WO 2005/035778 | 4/2005 |
| WO | WO 2005/053742 | 6/2005 |
| WO | WO 2005/055808 | 6/2005 |
| WO | WO 2005/115451 | 12/2005 |
| WO | WO 2006/083289 | 8/2006 |
| WO | WO 2006/099875 | 9/2006 |
| WO | WO 2006/121168 | 11/2006 |
| WO | WO 2007/005874 | 1/2007 |
| WO | WO 2007/133822 | 11/2007 |
| WO | WO 2008/116149 | 9/2008 |
| WO | WO 2008/147482 | 12/2008 |
| WO | WO 2009/072003 | 6/2009 |
| WO | WO 2009/080829 | 7/2009 |
| WO | WO 2009/101611 | 8/2009 |
| WO | WO 2009/114335 | 9/2009 |
| WO | WO 2010/003118 | 1/2010 |
| WO | WO 2010/019570 | 2/2010 |
| WO | WO 2010/027827 | 3/2010 |
| WO | WO 2010/033140 | 3/2010 |
| WO | WO 2010/054007 | 5/2010 |
| WO | WO 2010/077634 | 7/2010 |
| WO | WO 2010/104949 | 9/2010 |
| WO | WO 2010/125571 | 11/2010 |
| WO | WO 2011/028683 | 3/2011 |
| WO | WO 2011/051726 | 5/2011 |
| WO | WO 2011/066342 | 6/2011 |
| WO | WO 2011/085103 | 7/2011 |
| WO | WO 2011/090754 | 7/2011 |
| WO | WO 2012/066058 | 5/2012 |
| WO | WO 2012/079000 | 6/2012 |
| WO | WO 2012/092612 | 7/2012 |
| WO | WO 2012/129514 | 9/2012 |
| WO | WO 2012/143498 | 10/2012 |
| WO | WO 2012/163805 | 12/2012 |
| WO | WO 2013/006490 | 1/2013 |
| WO | WO 2013/039954 | 3/2013 |
| WO | WO 2013/054331 | 4/2013 |
| WO | WO 2013/071154 | 5/2013 |
| WO | WO 2013/072406 | 5/2013 |
| WO | WO 2013/072415 | 5/2013 |
| WO | WO 2013/082366 | 6/2013 |
| WO | WO 2013/123061 | 8/2013 |
| WO | WO 2013/126726 | 8/2013 |
| WO | WO 2013/154760 | 10/2013 |
| WO | WO 2013/166321 | 11/2013 |
| WO | WO 2014/022332 | 2/2014 |
| WO | WO 2014/031687 | 2/2014 |
| WO | WO 2014/055668 | 4/2014 |
| WO | WO 2014/059251 | 4/2014 |
| WO | WO 2014/087010 | 6/2014 |
| WO | WO 2014/089335 | 6/2014 |
| WO | WO 2014/134165 | 9/2014 |
| WO | WO 2014/191128 | 12/2014 |
| WO | WO 2014/210064 | 12/2014 |
| WO | WO 2015/079417 | 6/2015 |
| WO | WO 2015/142675 | 9/2015 |
| WO | WO 2015/157391 | 10/2015 |
| WO | WO 2015/158671 | 10/2015 |
| WO | WO 2016/014530 | 1/2016 |
| WO | WO 2016/014565 | 1/2016 |
| WO | WO 2016/090312 | 6/2016 |
| WO | WO 2016/090320 | 6/2016 |
| WO | WO 2016/090327 | 6/2016 |
| WO | WO 2016/094304 | 6/2016 |
| WO | WO 2016/210262 | 12/2016 |
| WO | WO 2017/031104 | 2/2017 |
| WO | WO 2017/040930 | 3/2017 |
| WO | WO 2017/058754 | 4/2017 |
| WO | WO 2017/087547 | 5/2017 |
| WO | WO 2017/172981 | 10/2017 |
| WO | WO 2017/181119 | 10/2017 |
| WO | WO 2017/222593 | 12/2017 |
| WO | WO 2018/075820 | 4/2018 |
| WO | WO 2018/197675 | 11/2018 |
| WO | WO 2018/201056 | 11/2018 |
| WO | WO 2018/204427 | 11/2018 |
| WO | WO 2019/090003 | 5/2019 |
| WO | WO 2019/090364 | 5/2019 |
| WO | WO 2020/092854 | 5/2020 |
| WO | WO 2021/113776 | 6/2021 |

OTHER PUBLICATIONS

Adams et al., "Selectivity and specificity of engineered T cells expressing KITE-585 a chimeric anitgen receptor targeting B-cell maturation antigen BCMA," AACR Annual Meeting 2017. Abstract 2135. Presented on Apr. 3, 2017.

Al-Hujaily et al., "Development of novel immunotherapies for multiple myeloma," Int J Mol Sci 2016;17:1506.

Ali et al., "Remissions of Multiple Myeloma during a First-in-Humans Clinical Trial of T Cell Expressing an Anti-B-Cell Maturation Antigen Chimeric Antigen Receptor," Blood (2015) 126(23):LBA-1.

Ali et al., "T cells expressing an anti-B-cell maturation antigen chimeric antigen receptor cause remissions of multiple myeloma," Blood (2016) 128(13):1688-1700.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Barderas et al., "Affinity maturation of antibodies assisted by in silico modeling," Proc. Natl. Acad. Sci. U.S.A. (2008) 105(26):9029-34.

Beavis et al., "Blockade of A2A receptors potently suppresses the metastasis of CD73+ tumors," PNAS (2013) 110(36): 14711-14716.

Berdeja et al., "First-in-human multicenter study of bb2121 anti-BCMA CAR T cell therapy for relapsed/refractory multiple myeloma: updated results," ASCO 2017. Abstract 3010. Presented Jun. 5, 2017.

Berger et al., "Phase I safety and pharmacokinetic study of CT-011, a humanized antibody interacting with PD-1, in patients with advanced hematologic malignancies," Clin Cancer Res (2008) 14(10):3044-3051.

Bertilaccio et al., "Low-Dose Lenalidomide Improves CAR-Based Immunotherapy in CLL by Reverting T-Cell Defects In Vivo," Blood (2013) 122:4171.

Blank et al., "Contribution of the PD-L1/PD-1 pathway to T-cell exhaustion: an update on implications for chronic infections and tumor evasion," Cancer Immunol Immunother (2007) 56(5):739-745.

Boris-Lawrie et al., "Recent advances in retrovirus vector technology," Cur. Opin. Genet. Develop. (1993) 3:102-109.

Brahmer et al., "Safety and Activity of Anti-PD-L1 Antibody in Patients with Advanced Cancer," N Engl J Med (2012) 366:2455-2465.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brown et al., "Tolerance of single, but not multiple, amino acid replacements in antibody VH CDR2: a means of minimizing B cells wastage from somatic hypermutation?" J. Immunol. (1996) 156(9):3285-3291.

(56) References Cited

OTHER PUBLICATIONS

Brummelkamp et al., "A system for stable expression of short interfering RNAs in mammalian cells," Science (2002) 296(5567):550-553.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Caron et al., "Engineered Humanized Dimeric Forms of IgG are More Effective Antibodies," J Exp. Med 176: 1191-1195 (1992).

Carpenter et al., "B-cell maturation antigen is a promising target for adoptive T-cell therapy of multiple myeloma," Clin Cancer Res (2013) 19(8):2048-2060.

Carroll et al., "Targeting the molecular basis for tumour hypoxia," Expert Rev Mol Med (2005) 7(6):1-16.

Casset et al. "A peptide mimetic of an anti-CD4 monoclonal antibody by rational design." BBRC, 307: 198-205 (2003).

Cavalieri et al., "Human T lymphocytes transduced by lentiviral vectors in the absence of TCR activation maintain an intact immune competence," Blood (2003) 102(2): 497-505.

Chari et al., "Immunoconjugates containing novel maytansinoids: promising anticancer drugs," Cancer Res. (1992) 52:127-131.

Chekmasova et al., "A Novel and Highly Potent CAR T Cell Drug Product for Treatment of BCMA-Expressing Hematological Malignances," ASH 2015 Abstract.

Chen et al. J. Mol. Bio. (1999) 293, 865-881.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Chowdhury et al, "Engineering hot spots for affinity enhancement of antibodies," Methods Mol. Biol. (2008) 207:179-196.

Chu et al., "CS1-specific chimeric antigen receptor (CAR)-engineered natural killer cells enhance in vitro and in vivo antitumor activity against human multiple myeloma," Leukemia (2014) 28(4):917-927.

Clackson et al., "Making antibody fragments using phage display libraries," Nature (1991) 352:624-628.

Clinical Trial Identifier NCT02215967, "Study of T Cells Targeting B-Cell Maturation Antigen for Previously Treated Multiple Myeloma," Retrieved on https://clinicaltrials.gov/ct2/show/NCT02215967. Retrieved on Feb. 8, 2019.

Clinical Trial Identifier NCT02546167, "CART-BCMA Cells for Multiple Myeloma," Retrieved on https://clinicaltrials.gov/ct2/show/NCT02546167. Retrieved on Oct. 22, 2018.

Clinical Trial Identifier NCT02658929, "Study of bb2121 in Multiple Myeloma," Retrieved on https://clinicaltrials.gov/ct2/show/NCT02658929. Retrieved on Oct. 22, 2018.

Clinical Trial Identifier NCT03070327, "BCMA Targeted CAR T Cells With or Without Lenalidomide for the Treatment of Multiple Myeloma," Retrieved on https://clinicaltrials.gov/ct2/show/NCT03070327. Retrieved on Feb. 8, 2019.

Clinical Trial Identifier NCT03502577, "BCMA-Specific CAR T-Cells Combined With a Gamma Secretase Inhibitor (JSMD194) to Treat Relapsed or Persistent Multiple Myeloma," Retrieved on https://clinicaltrials.gov/ct2/show/NCT03502577. Retrieved on Apr. 16, 2019.

Cohen et al., "B-cell Maturation Antigen (BMCA)-specific chimeric antigen receptor T cells (CART-BCMA) for multiple myeloma (MM): initial safety and efficacy from a phase I study," Blood (2016) 128:1147.

Cohen et al., "CAR-T Cell Therapy for Myeloma: State of the Art and Perspective on a Possible Cure," Lymphoma and Myeloma 2018. Presentation. Presented on Oct. 18, 2018.

Collins et al., "Chemical approaches to targeted protein degradation through modulation of the ubiquitin-proteasome pathway," Biochem J (2017) 474(7):1127-1147.

Cooper et al., "T-cell clones can be rendered specific for CD19: toward the selective augmentation of the graft-versus-B-lineage leukemia effect," Blood. (2003) 101:1637-1644.

Coquery et al., "Regulatory roles of the tumor necrosis factor receptor BCMA," Crit Rev Immunol (2012) 32(4):287-305.

Creative Biomart, Anti-Human TNFRSFI 7 scFv Stable Cell Line-CHO. (Aug. 30, 2013) [according to the properties of the posted document] (Retrieved from the Internet Mar. 23, 2016: <http://www.creativebiomart.net/pdf/CSC-P0544,TNFRSF17.pdt>); p. 1.

Cronstein et al., "Adenosine modulates the generation of superoxide anion by stimulated human neutrophils via interaction with a specific cell surface receptor," Ann NY Acad Sci (1985) 451:291-301.

Cronstein et al., "Engagement of adenosine receptors inhibits hydrogen peroxide (H2O2-) release by activated human neutrophils," Clin Immunol Immunopathol (1987) 42(1):76-85.

Darce, J.R. et al., "Regulated expression of BAFF-binding receptors during human B cell differentiation," J Immunol 2007; 179:7276-7286.

Davila et al., "CD19 CAR-targeted T cells induce long-term remission and B Cell Aplasia in an immunocompetent mouse model of B cell acute lymphoblastic leukemia," PLoS ONE (2013) 8(4): e61338.

De Felipe et al., "Skipping the co-expression problem: the new 2A "CHYSEL" technology," Genetics Vaccines and Therapy (2004) 2:13.

De Felipe et al., "Targeting of proteins derived from self-processing polyproteins containing multiple signal sequences," Traffic (2004) 5(8):616-626.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).

Deniger et al., "A pilor trial of the combination of vemurafenib with adoptive cell therapy in patients with metastatic melanoma," Clin Can Res (2017) 23(2):351-362.

Dondelinger et a., "Understanding the Significance and Implications of Antibody Numbering and Antigen-Binding Surface/Residue Definition," Fronts. Immunol. 9 (2018):1-15.

Dubowchik et al., "Doxorubicin immunoconjugates containing bivalent, lysosomally-cleavable dipeptide linkages," Bioorg. & Med. Chem. Letters (2002) 12:1529-1532.

Endo et al., "High-throughput, genome-scale protein production method based on the wheat germ cell-free expression system," Biotechnol. Adv. (2003) 21: 695-713.

Fecteau et al., "Lenalidomide inhibits the proliferation of CLL cells via a cereblon/p21WAF1/Cip1-dependent mechanism independent of functional p53," Blood (2014) 124:1637-1644.

Fedorov et al., "PD-1- and CTLA-4-based inhibitory chimeric antigen receptors (iCARs) divert off-target immunotherapy responses," Sci. Transl. Medicine (2013) 5(215).

Finger et al., "The human PD-1 gene: complete cDNA, genomic organization, and developmentally regulated expression in B cell progenitors," Gene (1997) 197(1-2):177-187.

Flatman et al., "Process analytics for purification of monoclonal antibodies," J. Chromatogr. (2007) B 848:79-87.

Fraiette et al., "Immunobiology ibrutinib enhances chimeric antigen receptor T-cell engraftment and efficacy in leukemia," Blood (2016) 127:1117-1127.

Frigyesi et al., "Robust isolation of malignant plasma cells in multiple myeloma," Blood (2014) 123(9): 1336-40.

Frigyesi et al., "Robust isolation of malignant plasma cells in multiple myeloma," Blood (2014) 123(9): Supplement.

Garfall et al., "Immunotherapy with chimeric antigen receptors for multiple myeloma," Discov Med (2014) 17(91):37-46.

Gerngross et al, "Advances in the production of human therapeutic proteins in yeasts and filamentous fungi," Nat. Biotech. (2004) 22:1409-1414.

(56) References Cited

OTHER PUBLICATIONS

Gershoni et al., "Epitope mapping—The first step in developing epitope-based vaccines," Biod, Adis International Ltd, 21 (3 ): 145-156 (2007).
Gildener-Leapman et al., "Promising systemic immunotherapies in head and neck squamous cell carcinoma," Oral Oncol (2013) 49(12):1089-1096.
Godin et al., "Microfluidics and photonics for Bio-System-on-a-Chip: a review of advancements in technology towards a microfluidic flow cytometry chip," J Biophoton. (2008) 1(5):355-376.
Hausler et al., "Anti-CD39 and anti-CD73 antibodies A1 and 7G2 improve targeted therapy in ovarian cancer by blocking adenosine-dependent immune evasion," Am J transl Res (2014) 6(2):129-139.
Hebeisen et al., "SHP-1 phosphatase activity counteracts increased T cell receptor affinity," J Clin Invest. (2013) 123(3):1044-1056.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hershfield, "PEG-ADA: an alternative to haploidentical bone marrow transplantation and an adjunct to gene therapy for adenosine deaminase deficiency," Hum Mutat (1995) 5(2):107-112.
Hill et al., "Gamma secretase inhibition increase recognition of multiple myeloma by BCMA-specific chimeric antigen receptor modified T cells," J Immunotherapy of Cancer (2017) 5(S2):010.
Hinman et al., "Preparation and characterization of monoclonal antibody conjugates of the calicheamicins: a novel and potent family of antitumor antibiotics," Cancer Res. (1993) 53:3336-3342.
Honegger A and Plückthun A, "Yet another numbering scheme for immunoglobulin variable domains: an automatic modeling and analysis tool," J Mol Biol, (2001) 8;309(3):657-70.
Hoogenboom et al., "Overview of antibody phage-display technology and its applications," Methods in Molecular Biology (2002) 178:1-37.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin. Cancer Res. (2013) 19:3153.
Hudecek et al., "The nonsignaling extracellular spacer domain of chimeric antigen receptors is decisive for in vivo antitumor activity," Cancer Immunol Res (2015) 3(2):125-135.
Irving et al., "Interplay between T cell receptor binding kinetics and the level of cognate peptide presented by major hisptocompatibility complexes governs CD8+ T cell responsiveness," JBC (2012) vol. 287 No. 27, 23068-23078.
Ito et al., "Identification of a primary target of thalidomide teratogenicity," Science (2010) 327:1345-1350.
Jeffrey et al., "Dipeptide-based highly potent doxorubicin antibody conjugates," Bioorganic & Med. Chem. Letters (2006) 16:358-362.
Jin et al., "CD73 on tumor cells impairs antitumor T-cell responses: a novel mechanism of tumor-induced immune suppression," Cancer Res (2010) 70(6):2245-2255.
Johnston, et al., "Biolistic transformation: microbes to mice," Nature (1990) 346: 776-777.
Kanda, Y. et al., "Comparison of cell lines for stable production of fucose-negative antibodies with enhanced ADCC," Biotechnol. Bioeng. (2006) 94(4):680-688.
Khalil et al., "The future of cancer treatment: immunomodulation, CARs and combination immunotherapy," Nature Reviews Clinical Oncology (2016) 13(5):273-290.
Kindt et al., Kuby Immunology 6th ed., W.H. Freeman and Co. (2007) p. 91.
King et al., "Monoclonal antibody conjugates of doxorubicin prepared with branched peptide linkers: inhibition of aggregation by methoxytriethyleneglycol chains," J. Med. Chem. (2002) 45:4336-4343.
Klebanoff et al., "Sorting through subsets: which T-cell populations mediate highly effective adoptive immunotherapy?," J Immunother. (2012) 35(9): 651-660.
Kochenderfer et al., "Adoptive transfer of syngeneic T cells transduced with a chimeric antigen receptor that recognizes murine CD19 can eradicate lymphoma and normal B cells", Blood (2010) 116(19):3875-3886.
Koste et al., "T-cell receptor transfer into human T cells with ecotropic retroviral vectors," Gene Therapy (2014) 21: 533-538.
Koyko et al., "Immunology," translation from English, edited by N.B. Serebryanaya, Mosow, "Akademiya," 2008, p. 37.
Kratz et al., "Prodrugs of anthracyclines in cancer chemotherapy," Current Med. Chem. (2006) 13:477-523.
Kuramitsu et al., "Lenalidomide enhances the function of chimeric antigen receptor T cells against the epidermal growth factor receptor variant III by enhancing immune synapses," Cancer Gene Therapy (2015) 22(10):487-495.
Lamminmaki et al. "Crystal Structure of a Recombinant Anti-estradiol Fab Fragment in Complex with 17β-Estradiol" JBC 276:36687-36694 (2001).
Lefranc et al., "IMGT unique numbering for immunoglobulin and T cell receptor variable domains and Ig superfamily V-like domains," Dev Comp Immunol (2003) 27(1):55-77.
Leone et al., "A2aR antagonists: Next generation checkpoint blockade for cancer immunotherapy," Comput Struct Biotechnol J. (2015) 13:265-272.
Li et al., "Optimization of humanized IgGs in glycoengineered Pichia pastoris," Nat. Biotech. (2006) 24:210-215.
Lim et al., "Anti-CD20 monoclonal antibodies: historical and future perspectives," Haematologica (2010) 95(1):135-143.
Lipson et al., "Durable cancer regression off-treatment and effective reinduction therapy with an anti-PD-1 antibody," Clin Cancer Res (2013) 19(2):462-468.
Liu et al., "Affinity-Tuned ErbB2 or EGFR Chimeric Antigen Receptor T Cells Exhibit an Increased Therapeutic Index against Tumors in Mice," Cancer Res (2015) 75(17) 3596-3607.
Liu et al., "Inclusion of Strep-tag II in design of antigen receptors for T-cell immunotherapy," Nat Biotechnol (2016) 34(4):430-434.
Lode et al., "Targeted therapy with a novel enediyene antibiotic calicheamicin theta(I) 1 effectively suppresses growth and dissemination of liver metastases in a syngeneic model of murine neuroblastoma," Cancer Res. (1998) 58:2925-2928.
Lopez-Girona et al., "Cereblon is a direct protein target for immunomodulatory and antiproliferative activities of lenalidomide and pomalidomide," Leukemia (2012) 26:2326-2335.
Lupton S. D. et al., "Dominant positive and negative selection using a hygromycin phosphotransferase-thymidine kinase fusion gene," Mol. and Cell Biol. (1991) 11:6.
MacCallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," Proc Natl Acad Sci U S A. Dec. 1989;86(23):9268-72.
Maynard et al., "Protection against anthrax toxin by recombinant antibody fragments correlates with antigen affinity," Nature Biotech. (2002) 20(6):597-601.
Meibohm (Keuester), Pharmacokinetics and Pharmacodynamics of Biotech Drugs, Wiley-VHC (2006) Chapter 3:45-91.
Menzies et al., "New combinations and immunotherapies for melanoma: latest evidence and clinical utility," Ther Adv Med Oncol (2013) 5(5):278-285.
Miller et al., "Improved retroviral vectors for gene transfer and expression," BioTechniques (1989) 7:980-990.
Miller et al., "Retrovirus packaging cells," Human Gene Therapy (1990) 1:5-14.
Millrine et al., "A brighter side to thalidomide: It's potential use in immunological Disorders," Trends in Mol Medicine (2017) 23(4):348-364.
Miyagishi et al., "U6 promoter-driven siRNAs with four uridine 3' overhangs efficiently suppress targeted gene expression in mammalian cells" Nat Biotechnol (2002) 20(5):497-500.
Monney et al., "Th1-specific cell surface protein Tim-3 regulates macrophage activation and severity of an autoimmune disease," Nature (2002) 415(6871):536-541.

(56) References Cited

OTHER PUBLICATIONS

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.

Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad. Sci. USA (2000) 97:829-834.

Nasonov et al., "Belimumab: progress v lechenii sistemnoj krasnoj volchanki", Nauch-praktich revmatol, 2012, 54(5), pp. 13-19.

Ngiow et al., "Anti-TIM3 Antibody Promotes T Cell IFN-γ-Mediated Antitumor Immunity and Suppresses Established Tumors," Cancer Res (2011) 71(10):3540-3551.

Novak et al., "Expression of BCMA, TACI, and BAFF-R in multiple myeloma: a mechanism for growth and survival," Blood (2004)103(2):689-694.

Ohta et al., "A2A adenosine receptor protects tumors from antitumor T cells," PNAS U.S.A. (2006) 103(35):13132-13137.

Okazaki et al., "Fucose depletion from human IgG1 oligosaccharide enhances binding enthalpy and association rate between IgG1 and FcgammaRIIIa," J. Mol. Biol. (2004) 336:1239-1249.

Oshima et al., "Immunomodulatory Drugs (IMiDs)," Nihon Rinsho (2014) 72(6):1130-1135.

Otahal et al., "Lenalidomide enhances antitumor functions of chimeric antigen receptor modified T cells," Oncoimmunology (2015) 5(4):e1115940.

Ott et al., "CTLA-4 and PD-1/PD-L1 Blockade: New Immunotherapeutic Modalities with Durable Clinical Benefit in Melanoma Patients," Clin Cancer Res (2013) 19(19):5300.

Ozhegov et al. "Dictionary of a Russian Language: 80,000 words and phraseological expressions," 4th ed. Supplemented, Mosow, "OOO 'A Temp'" 2006, p. 375.

Padlan et al. "Structure of an antibody-antigen complex: crystal structure of the HyHEL-10 Fab-lysozyme complex" PNAS 86:5938-5942 (1989).

Pardoll, "The blockade of immune checkpoints in cancer immunotherapy," Nature (2012) 12:252-264.

Park et al., "Treating cancer with genetically engineered T cells," Trends Biotechnol. (2011) 29(11): 550-557.

Pinna et al., "Novel investigational adenosine A2A receptor antagonists for Parkinson's disease," Expert Opin Investig Drugs (2009) 18:1619-1631.

Portolano et al., "Lack of promiscuity in autoantigen-specific H and L chain combinations as revealed by human H and L chain "roulette"," J. Immunol. (1993) 150:880-887.

Radvanyi et al., "Antagonist antibodies to PD-1 and B7-H1 (PD-L1) in the treatment of advanced human cancer—letter," Clin Cancer Res (2013) 19(19):5541.

Ramadoss et al., "An Anti-B Cell Maturation Antigen Bispecific Antibody for Multiple Myeloma," J. Am. Chem. Soc., 137:5288-5291 (2015).

Richardson et al., "Lenalidomide in multiple myeloma," Expert review of anticancer therapy (2006) 6(8):1165-1173.

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

Ripka et al., "Two Chinese hamster ovary glycosylation mutants affected in the conversion of GDP-mannose to GDP-fucose," Arch. Biochem. Biophys. (1986) 249:533-545.

Robert et al., "What is the role of cytotoxic T lymphocyte-associated antigen 4 blockade in patients with metastatic melanoma?," Oncologist (2009) 14(8):848-861.

Roberts et al., "Inhibition by adenosine of reactive oxygen metabolite production by human polymorphonuclear leucocytes," Biochem J (1985) 227(2):669-674.

Rosenberg, et al., "Cell transfer immunotherapy for metastatic solid cancer—what clinicians need to know," Nat Rev Clin Oncol. (2011) 8(10):577-85).

Rudikoff et al., "Single amino acid substitution altering antigen-binding specificity," ONAS (1982) 79(6):1979-1983.

Ryan et al., "Antibody targeting of B-cell maturation antigen on malignant plasma cells," Molecular Cancer Therapeutics, American Association for Cancer Research (2007) 6(11) : 3009-3018.

Sadelain et al., "The basic principles of chimeric antigen receptor design," Cancer Discov. (2013) 3(4): 388-398.

Sanchez et al. "Serum B-cell maturation antigen is elevated in multiple myeloma and correlates with disease status and survival," Br J Haematol (2012) 158(6):727-38.

Scarpa et al., "Characterization of recombinant helper retroviruses from Moloney-based vectors in ecotropic and amphotropic packaging cell lines," Virology (1991) 180:849-852.

Scatchard, "The attractions of proteins for small molecules and ions," Annals of the New York Academy of Sciences (1949) 51(4):660-672.

Schrier et al., "The effects of adenosine agonists on human neutrophil function," J Immunol (1986) 137(10):3284-3289.

Sharma et al., "Efficient sleeping beauty DNA transposition from DNA minicircles," Molec Ther Nucl Acids (2013) 2, e74.

Shinohara et al., "Structure and chromosomal localization of the human PD-1 gene (PDCD1)," Genomics (1994) 23:704-706.

Sitaraman et al., "High-throughput protein expression using cell-free system," Methods Mol. Biol. (2009) 498: 229-44.

Sitkovsky et al., "Hostile, hypoxia-A2-adenosinergic tumor biology as the next barrier to overcome for tumor immunologists," Cancer Immunol Re (2014) 2(7):598-605.

Spirin, et al., "High-throughput cell-free systems for synthesis of functionally active proteins," Trends Biotechnol. (2004) 22: 538-45.

Szoka et al., "Comparative properties and methods of preparation of lipid vesicles (liposomes)," Ann. Rev. Biophys. Bioeng. (1980) 9: 467.

Tai et al., "Antibody-Based Therapies in Multiple Myeloma," Bone Marrow Research (2011) Article ID: 924058.

Tai et al., "Novel anti-B-cell maturation antigen antibody-drug conjugate (GSK2857916) selectively induces killing of multiple myeloma," Blood (2014) 123(20):3128-3138.

Tai et al., "Targeting B-cell maturation antigen in multiple myeloma," Immunotherapy (2015) 7(11):1187-1199.

Terakura et al., "Generation of CD19-chimeric antigen receptor modified CD8+T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31 (10): 928-933.

Timmerman et al., "Functional reconstruction and synthetic mimicry of a conformational epitope using CLIPS technology," J Mol Recognit (2007) 20(5):283-299.

Topalian et al., "Safety, Activity, and Immune Correlates of Anti-PD-1 Antibody in Cancer," N Engl J Med (2012) 366:2443-2454.

Torgov et al., "Generation of an intensely potent anthracycline by a monoclonal antibody-beta-galactosidase conjugate," Bioconj. Chem. (2005) 16:717-721.

Tsukahara et al., "CD19 target-engineered T-cells accumulate at tumor lesions in human B-cell lymphoma xenograft mouse models," Biochem Biophys Res Commun (2013) 438(1): 84-9.

Turtle et al., "Engineered T cells for anti-cancer therapy," Curr. Opin. Immunol. (2012) 24(5): 633-39.

Vajdos et al. "Comprehensive functional maps of the antigen-binding site of an anti-ErbB2 antibody obtained with shotgun scanning mutagenesis." J. Mol. Biol. 320, 415-428 (2002).

Van Tendeloo et al., "High-level transgene expression in primary human T Tymphocytes and adult bone marrow CD34+ cells via electroporation-mediated gene delivery," Gene Therapy (2000) 7(16): 1431-1437).

Verhoeyen et al., "Lentiviral vector gene transfer into human T cells," Methods Mol Biol. (2009) 506: 97-114.

Vitetta et al., "Redesigning nature's poisons to create anti-tumor reagents," Science (1987) 238:1098.

(56) References Cited

OTHER PUBLICATIONS

Wada et al., "Sequencing CTLA-4 blockade with cell-based immunotherapy for prostate cancer," J Transl Med (2013) 11:89.
Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Weber, "Review: anti-CTLA-4 antibody ipilimumab: case studies of clinical response and immune-related adverse events," Oncologist (2007) 12(7):864-872.
White et al. "Antibody-Targeted Immunotherapy for Treatment of Malignancy" Ann. Rev. Med. 52:125-145 (2001).
Wigler et al., "Transfer of purified herpes virus thymidine kinase gene to cultured mouse cells," Cell (1997) 11: 223-232.
Wilson, "Tech.Sight. Analyzing biomolecular interactions," Science (2002) 295(5562):2103-2105.
Winkler et al., "Changing the antigen binding specificity by single point mutations of an anti-p24 (HIV-1) antibody," J. Immunol. (2000) 165(8):4505-14.
Wolff et al., "Monoclonal Antibody Homodimers: Enhanced Antitumor Activity in Nude Mice," Can Res (1993) 53:2560-2565.
Wu et al. "Humanization of a murine monoclonal antibody by simultaneous optimization of framework and CDR residues." J. Mol. Biol. 294, 151-162 (1999).
Wu et al., "Adoptive T-cell therapy using autologous tumor-infiltrating lymphocytes for metastatic melanoma: current status and future outlook," Cancer (2012) 18(2): 160-75.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng. (2004) 87: 614.
Zhang et al., "CD73: a novel target for cancer immunotherapy," Cancer Res (2010) 70(16):6407-6411.
Zheng et al., "A novel anti-CEACAM5 monoclonal antibody, CC4, suppresses colorectal tumor growth and enhances NK cells-mediated tumor immunity," PLoS One (2011) 6(6):e21146.
Zheng et al., "Enhancing adoptive cell therapy of cancer through targete delivery of small-molecule immunomodulators to internalizing or noninternalizing receptors," ACS NANO (2017) 11(3):3089-3100.
Coico (Koyko) et al., "Immunology," translation from English, edited by N.B. Serebryanaya, Mosow, "Akademiya," 2008, p. 37.
Gacerez et al., "How Chimeric Antigen Receptor Design Affects Adoptive T Cell Therapy," J Cell Physiol. (2016) 231(12): 2590-2598.
Harrington et al., "Development of JCARH125: Optimization of a Fully Human Anti-Bcma CAR for Use in the Treatment of Multiple Myeloma," Blood (2017) 130:1813.
Kapustin et al., "Cryptic splice sites and split genes," Nucleic Acids Res. (2011) 39(14):5837-5844.
Ormhoj et al., "CARs in the lead against Multiple Myeloma," Curr Hematol Malig Rep. (2017) 12(2): 119-125.
Parkman R., "Clonal analysis of murine graft-vs-host disease. I. Phenotypic and functional analysis of T lymphocyte clones," J. Immunol. (1986) 136(10):3543-3548.
U.S. Appl. No. 17/173,716, filed Feb. 11, 2021, by Brentjens et al. (Copy not provided). (Copy not submitted herewith pursuant to the waiver of 37 C.F. R. § 1.98(a)(2)(iii) issued by the Office on Sep. 21, 2004).
U.S. Appl. No. 17/781,693, filed Dec. 4, 2020, by Hauskins et al. (Copy not provided). (Copy not submitted herewith pursuant to the waiver of 37 C.F. R. § 1.98(a)(2)(iii) issued by the Office on Sep. 21, 2004).
Works et al., ASH Poster_FINAL (Dec. 6, 2017).
Works et al., "Lenalidomide Enhances Anti-BCMA Chimeric Antigen Receptor T Cell Function Against Multiple Myeloma," Blood (2017) 130:1794 abstract.

* cited by examiner

ANTIBODIES AND CHIMERIC ANTIGEN RECEPTORS SPECIFIC FOR B-CELL MATURATION ANTIGEN

CROSS-REFERENCE TO RELATED APPLICATIONS

This application is a national stage application under 35 U.S.C. § 371 of International Application No. PCT/US2018/058767, filed internationally on Nov. 1, 2018, which claims priority from U.S. provisional application No. 62/580,431, filed Nov. 1, 2017, entitled "ANTIBODIES AND CHIMERIC ANTIGEN RECEPTORS SPECIFIC FOR B-CELL MATURATION ANTIGEN," and U.S. provisional application No. 62/596,772, filed Dec. 8, 2017, entitled "ANTIBODIES AND CHIMERIC ANTIGEN RECEPTORS SPECIFIC FOR B-CELL MATURATION ANTIGEN," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042004300SeqList.txt, created Apr. 28, 2020, which is 381,551 bytes in size. The information in the electronic format of the Sequence Listing is incorporated by reference in its entirety.

FIELD

The present disclosure relates in some aspects to BCMA-binding molecules, in particular, to anti-BCMA antibodies, including antibody fragments. The present disclosure further relates to recombinant receptors containing such antibodies, including chimeric antigen receptors (CARs), which contain such antibodies. The disclosure further relates to genetically engineered cells expressing such receptors and antibodies, and use thereof in adoptive cell therapy.

BACKGROUND

B-cell maturation antigen (BCMA) is a transmembrane type III protein expressed on mature B lymphocytes. Upon binding of BCMA to its ligands, B cell activator of the TNF family (BAFF) and a proliferation inducing ligand (APRIL), a pro-survival cell signal is delivered to the B cell which has been found to be required for plasma cell survival. The expression of BCMA has been linked to several diseases including cancer, autoimmune disorders and infectious diseases. Due to the role of BCMA in various diseases and conditions, including cancer, BCMA is a therapeutic target. Various BCMA-binding molecules, including anti-BCMA antibodies and chimeric antigen receptors containing anti-BCMA antibody portions and cells expressing such chimeric antigen receptors, are available. Improved BCMA-binding molecules and engineered BCMA-targeting cells are needed. For example, there is a need for molecules and cells with reduced immunogenicity and fully human antibodies, including antibody fragments that specifically bind to BCMA, and chimeric receptors expressing such human antibodies for use in adoptive cell therapy. Provided herein are embodiments that meet such needs.

SUMMARY

Provided herein are BCMA-binding molecules, including polypeptides, such as anti-BCMA antibodies, including antigen-binding antibody fragments such as single domain antibodies (e.g. $V_H$ region alone), single-chain antibody fragments including scFv fragments, and polypeptides containing such antibodies, including fusion proteins, receptors, e.g., recombinant receptors, including chimeric receptors such as chimeric antigen receptors (CARs) containing the antibody as an antigen-recognition component. In particular embodiments, the antibodies are human antibodies, such as human single-chain antibody fragments including scFv s.

Provided herein are antibodies or antigen-binding fragments thereof, including those that specifically bind to BCMA, such as human BCMA. In some embodiments, the antibodies contain particular complementarity determining regions (CDRs), including heavy chain CDRs (i.e., CDR-H1, CDR-H2, and/or CDR-H3) and light chain CDRs (i.e., CDR-L1, CDR-L2, and/or CDR-L3), such as any described herein. In some embodiments, the antibody or antigen-binding fragment thereof includes a heavy chain variable ($V_H$) region. In some embodiments, the antibody or antigen-binding fragment thereof includes a $V_H$ region and a light chain variable ($V_L$) region.

In some embodiments, provided herein are antibodies or antigen-binding fragments thereof, wherein the antibody or antigen-binding fragment comprises a $V_H$ region comprising a heavy chain complementarity determining region 3 (CDR-H3) comprising the amino acid sequence selected from any one of SEQ ID NOs:7-11, 149-157, 279-287 and 376-378 or a CDR-H3 contained within the $V_H$ region amino acid sequence selected from any one of SEQ ID NOs:110-115, 247-256, 518-531 and 533.

In some aspects, provided herein are antibodies or antigen-binding fragments thereof, wherein the antibody or antigen-binding fragment comprises a $V_H$ region comprising at least 90% sequence identity to the $V_H$ region amino acid sequence selected from any one of SEQ ID NOs:110-115, 247-256, 518-531 and 533, such as at least 90%, 91%, 92%, 93%, 94%, 95%, 96%, 97%, 98%, or 99% sequence identity thereto.

In some of any such embodiments, the $V_H$ region comprises a CDR-H3 comprising the amino acid sequence $X_1X_2X_3X_4X_5X_6X_7X_8X_9X_{10}X_{11}X_{12}X_{13}X_{14}$ (SEQ ID NO:355), wherein $X_1$ is A, D, E, G, L, V or W; $X_2$ is A, D, G, L, P, Q or S; $X_3$ is A, D, G, L or Y; $X_4$ is D, G, P, R, S, V, Y or null; $X_5$ is D, I, P, S, T, Y or null; $X_6$ is A, G, I, S, T, V, Y or null; $X_7$ is A, D, E, F, L, P, S, Y or null; $X_8$ is P, Q, T, Y or null; $X_9$ is D, G, R, Y or null; $X_{10}$ is A, F, Y or null; $X_{11}$ is D, F or null; $X_{12}$ is F or null; $X_{13}$ is D, T or Y; and $X_{14}$ is I, L, N, V or Y.

In some of any such embodiments, the $V_H$ region includes a CDR-H3 comprising the amino acid sequence selected from any one of SEQ ID NOs:7-11, 149-157, 279-287 and 376-378 or a CDR-H3 contained within the $V_H$ region amino acid sequence selected from any one of SEQ ID NOs:110-115, 247-256, 518-531 and 533.

In some of any such embodiments, the $V_H$ region comprises a heavy chain complementarity determining region 1 (CDR-H1) comprising the amino acid sequence $X_1X_2X_3MX_4$ (SEQ ID NO:353) $X_1$ is D or S; $X_2$ is Y or S; $X_3$ is A, G, W, or Y; and $X_4$ is H, Q, or S; and/or a heavy chain complementarity determining region 2 (CDR-H2) comprising the amino acid sequence of $X_1IX_2X_3X_4X_5X_6X_7X_8X_9X_{10}X_{11}YX_{12}X_{13}X_{14}X_{15}X_{16}X_{17}$ (SEQ ID NO:354), wherein $X_1$ is F, G, H, V, W or Y; $X_2$ is N, R, S or V; $X_3$ is P, Q, S, V, W or Y; $X_4$ is K or null; $X_5$ is A or null; $X_6$ is D, G, N, S, or Y; $X_7$ is G or S; $X_8$ is G or S; $X_9$ is E, G, N, T or S; $X_{10}$ is I, K, or T; $X_{11}$ is E, G, N or Y; $X_{12}$ is A or V; $X_{13}$ is A, D or Q; $X_{14}$ is K or S; $X_{15}$ is F or V; $X_{16}$ is K or Q; and $X_{17}$ is E or G.

In some of any such embodiments, the $V_H$ region comprises a CDR-H1 comprising the amino acid sequence selected from any one of SEQ ID NOs:1-3 and 140-144; and/or a CDR-H2 comprising the amino acid sequence selected from any one of SEQ ID NOs:4-6, 145-148 and 372-374.

In some of any such embodiments, the $V_H$ region comprises a CDR-H1 contained within the $V_H$ region amino acid sequence selected from any one of SEQ ID NOs:110-115, 247-256, 518-531 and 533; and/or a CDR-H2 contained within the $V_H$ region amino acid sequence selected from any one of SEQ ID NOs:110-115, 247-256, 518-531 and 533.

In some embodiments, provided herein are antibodies or antigen-binding fragments thereof that include a CDR-H1 comprising the amino acid sequence selected from any one of SEQ ID NOs:1-3 and 140-144 or a CDR-H1 contained within the $V_H$ region amino acid sequence selected from any one of SEQ ID NOs:110-115, 247-256, 518-531 and 533; a CDR-H2 comprising the amino acid sequence selected from any one of SEQ ID NOs:4-6, 145-148 and 372-374 or a CDR-H2 contained within the $V_H$ region amino acid sequence selected from any one of SEQ ID NOs:110-115, 247-256, 518-531 and 533; and/or a CDR-H3 comprising the amino acid sequence selected from any one of SEQ ID NOs:7-11, 149-157, 279-287 and 376-378 or a CDR-H3 contained within the $V_H$ region amino acid sequence selected from any one of SEQ ID NOs:110-115, 247-256, 518-531 and 533.

In some of any such embodiments, the antibody or antigen-binding fragment thereof includes a $V_H$ region comprising a CDR-H1, CDR-H2, and CDR-H3 selected from a CDR-H1, CDR-H2, and CDR-H3 comprising the amino acid sequence of SEQ ID NOs:1, 4, and 7, respectively; a CDR-H1, CDR-H2, and CDR-H3 comprising the amino acid sequence of SEQ ID NOs:2, 5, and 8, respectively; a CDR-H1, CDR-H2, and CDR-H3 comprising the amino acid sequence of SEQ ID NOs:2, 5, and 9, respectively; a CDR-H1, CDR-H2, and CDR-H3 comprising the amino acid sequence of SEQ ID NOs:2, 5, and 10, respectively; a CDR-H1, CDR-H2, and CDR-H3 comprising the amino acid sequence of SEQ ID NOs:3, 6, and 11, respectively; a CDR-H1, CDR-H2, and CDR-H3 comprising the amino acid sequence of SEQ ID NOs:140, 145, and 149, respectively; a CDR-H1, CDR-H2, and CDR-H3 comprising the amino acid sequence of SEQ ID NOs:141, 145, and 149, respectively; a CDR-H1, CDR-H2, and CDR-H3 comprising the amino acid sequence of SEQ ID NOs:141, 145, and 150, respectively; a CDR-H1, CDR-H2, and CDR-H3 comprising the amino acid sequence of SEQ ID NOs:142, 146, and 151, respectively; a CDR-H1, CDR-H2, and CDR-H3 comprising the amino acid sequence of SEQ ID NOs:2, 5, and 152, respectively; a CDR-H1, CDR-H2, and CDR-H3 comprising the amino acid sequence of SEQ ID NOs:143, 147, and 153, respectively; a CDR-H1, CDR-H2, and CDR-H3 comprising the amino acid sequence of SEQ ID NOs:144, 148, and 154, respectively; a CDR-H1, CDR-H2, and CDR-H3 comprising the amino acid sequence of SEQ ID NOs:3, 6, and 155, respectively; a CDR-H1, CDR-H2, and CDR-H3 comprising the amino acid sequence of SEQ ID NOs:2, 5, and 156, respectively; a CDR-H1, CDR-H2, and CDR-H3 comprising the amino acid sequence of SEQ ID NOs:2, 5, and 157, respectively; a CDR-H1, CDR-H2, and CDR-H3 comprising the amino acid sequence of SEQ ID NOs:2, 6, and 376, respectively; a CDR-H1, CDR-H2, and CDR-H3 comprising the amino acid sequence of SEQ ID NOs:3, 372, and 376, respectively; a CDR-H1, CDR-H2, and CDR-H3 comprising the amino acid sequence of SEQ ID NOs:3, 6, and 376, respectively; a CDR-H1, CDR-H2, and CDR-H3 comprising the amino acid sequence of SEQ ID NOs:3, 6, and 377, respectively; a CDR-H1, CDR-H2, and CDR-H3 comprising the amino acid sequence of SEQ ID NOs:2, 373, and 152, respectively; a CDR-H1, CDR-H2, and CDR-H3 comprising the amino acid sequence of SEQ ID NOs:2, 5, and 378, respectively; or a CDR-H1, CDR-H2, and CDR-H3 comprising the amino acid sequence of SEQ ID NOs:2, 374, and 9, respectively.

In some embodiments, provided herein are antibodies or antigen-binding fragments thereof comprising a $V_H$ region comprising a CDR-H1, a CDR-H2, and a CDR-H3, respectively, comprising the amino acid sequence of a CDR-H1, a CDR-H2, and a CDR-H3 contained within the $V_H$ region amino acid sequence selected from any one of SEQ ID NOs:110-115, 247-256, 518-531 and 533.

In some of any such embodiments, the $V_H$ region comprises a framework region 1 (FR1), a FR2, a FR3, and/or a FR4 comprising at least 90% sequence identity, respectively, to a FR1, FR2, FR3, and/or FR4 contained within the $V_H$ region amino acid sequence selected from any one of SEQ ID NOs:110-115, 247-256, 518-531 and 533. In some embodiments, the $V_H$ region contains a framework region 1 (FR1), a FR2, a FR3, and/or a FR4 sequence comprising at least 90%, 91%, 92%, 93%, 94%, 95%, 96%, 97%, 98%, or 99% sequence identity, respectively, to a FR1, FR2, FR3, and/or FR4 contained within the $V_H$ region amino acid sequence selected from any one of SEQ ID NOs:110-115, 247-256, 518-531 and 533. In some embodiments, the $V_H$ region comprises a FR1, a FR2, a FR3, and/or a FR4, selected from: a FR1 comprising the amino acid sequence selected from any one of SEQ ID NOs:59-63, 195-203 and 434-439; a FR2 comprising the amino acid sequence selected from any one of SEQ ID NOs:64-66 and 204-209; a FR3 comprising the amino acid sequence selected from any one of SEQ ID NOs:67-69, 210-216, 441 and 443; and/or a FR4 comprising the amino acid sequence selected from any one of SEQ ID NOs:70-71, 217-220, 444 and 445.

In some of any such embodiments, the $V_H$ region comprises the amino acid sequence selected from any one of SEQ ID NOs:110-115, 247-256, 518-531 and 533.

In some of any such embodiments, the antibody or antigen-binding fragment does not comprise a light chain variable ($V_L$) region, does not comprise a light chain complementarity determining region (CDR-L1), CDR-L2, and/or CDR-L3, and/or is a single-domain antibody (sdAb) comprising only the $V_H$ region. In some embodiments, the antibody or antigen-binding fragment is an sdAb comprising only the $V_H$ region.

In some embodiments of any of the antibodies or fragments containing any of the above $V_H$ region sequences, the antibody or fragment further contains a $V_L$ region. In some such embodiments, the $V_L$ region comprises at least 90% sequence identity to the $V_L$ region amino acid sequence selected from any one of SEQ ID NOs:116-127, 257-267, 534-550 and 552-557, such as at least 90%, 91%, 92%, 93%, 94%, 95%, 96%, 97%, 98%, 99% sequence identity to the $V_L$ region amino acid sequence selected from any one of SEQ ID NOs:116-127, 257-267, 534-550 and 552-557.

In some of any such embodiments, the $V_L$ region comprises a light chain complementarity determining region 3 (CDR-L3) comprising the amino acid sequence $X_1X_2X_3X_4X_5X_6X_7X_8X_9X_{10}X_{11}X_{12}$, (SEQ ID NO:358), wherein $X_1$ is A, C, G, H, I, Q or S; $X_2$ is A, Q, S or V; $X_3$ is S, W or Y; $X_4$ is D, F, G, H or Y; $X_5$ is D, G, M, R, S or T; $X_6$ is A, G, H, L, R, S, T or Y; $X_7$ is L, P, R, S or null; $X_8$ is D, G, N, R, S, T or null; $X_9$ is A, G, H, L, P or null; $X_{10}$ is F, S or null; $X_{11}$ is L, P, W or Y; and $X_{12}$ is S, T or V.

In some of any such embodiments, the $V_L$ region comprises a CDR-L3 comprising the amino acid sequence selected from any one of SEQ ID NOs:47-58, 184-194, 415-427 and 429-433, or a CDR-L3 contained within the $V_L$ region amino acid sequence selected from any one of SEQ ID NOs:116-127, 257-267, 534-550 and 552-557.

In some of any such embodiments, the $V_L$ region comprises a light chain complementarity determining region 1 (CDR-L1) comprising the amino acid sequence of $X_1X_2X_3X_4X_5X_6X_7X_8X_9X_{10}X_{11}X_{12}X_{13}X_{14}$ $X_{15}$ $X_{16}$ $X_{17}$ (SEQ ID NO:356), wherein $X_1$ is G, K, R, S or T; $X_2$ is A, G or S; $X_3$ is G, N, S or T; $X_4$ is G, K, N, Q, R or S; $X_5$ is S or null; $X_6$ is D, N, V or null; $X_7$ is L, V or null; $X_8$ is H, S, Y or null; $X_9$ is S, T or null; $X_{10}$ is S or null; $X_{11}$ is D, G, I, N, S or null; $X_{12}$ is D, E, G, K, I, N or null; $X_{13}$ is F, G, K, N, R, S, Y or null; $X_{14}$ is D, K, N, T or null; $X_{15}$ is A, D, G, L, N, S, T or Y; $X_{16}$ is L or V; $X_{17}$ is A, H, N, Q or S; and/or a light chain complementarity determining region 2 (CDR-L2) comprising the amino acid sequence of $X_1X_2X_3X_4X_5X_6X_7$ (SEQ ID NO:357), wherein $X_1$ is A, D, E, N, S, V or W; $X_2$ is A, D, N, S or V; $X_3$ is A, D, H, I, N or S; $X_4$ is D, K, N, Q, R or T; $X_5$ is L, R or V; $X_6$ is A, E, P or Q; and $X_7$ is A, D, S or T.

In some of any such embodiments, the $V_L$ region comprises a CDR-L1 comprising the amino acid sequence selected from any one of SEQ ID NOs:26-36, 174-178, 380-392 and 394-398; and/or a CDR-L2 comprising the amino acid sequence selected from any one of SEQ ID NOs:37-46, 179-183, 399-409 and 411-414.

In some of any such embodiments, the $V_L$ region comprises a CDR-L1 contained within the $V_L$ region amino acid sequence selected from any one of SEQ ID NOs:116-127, 257-267, 534-550 and 552-557; and/or a CDR-L2 contained within the $V_L$ region amino acid sequence selected from any one of SEQ ID NOs:116-127, 257-267, 534-550 and 552-557.

In some of any such embodiments, the $V_L$ region comprises a CDR-L1 comprising the amino acid sequence selected from any one of SEQ ID NOs:26-36, 174-178, 380-392 and 394-398; a CDR-L2 comprising the amino acid sequence selected from any one of SEQ ID NOs:37-46, 179-183, 399-409 and 411-414; and a CDR-L3 comprising the amino acid sequence selected from any one of SEQ ID NOs:47-58, 184-194, 415-427 and 429-433.

In some of any such embodiments, the antibody or antigen-binding fragment thereof includes a $V_L$ region comprising a CDR-L1, CDR-L2, and CDR-L3 selected from: a CDR-L1, CDR-L2, and CDR-L3 comprising the amino acid sequence of SEQ ID NOs:26, 37, and 47, respectively; a CDR-L1, CDR-L2, and CDR-L3 comprising the amino acid sequence of SEQ ID NOs:27, 38, and 48, respectively; a CDR-L1, CDR-L2, and CDR-L3 comprising the amino acid sequence of SEQ ID NOs:28, 39, and 49, respectively; a CDR-L1, CDR-L2, and CDR-L3 comprising the amino acid sequence of SEQ ID NOs:29, 40, and 50, respectively; a CDR-L1, CDR-L2, and CDR-L3 comprising the amino acid sequence of SEQ ID NOs:30, 39, and 51, respectively; a CDR-L1, CDR-L2, and CDR-L3 comprising the amino acid sequence of SEQ ID NOs:31, 41, and 52, respectively; a CDR-L1, CDR-L2, and CDR-L3 comprising the amino acid sequence of SEQ ID NOs:32, 42, and 53, respectively; a CDR-L1, CDR-L2, and CDR-L3 comprising the amino acid sequence of SEQ ID NOs:30, 39, and 54, respectively; a CDR-L1, CDR-L2, and CDR-L3 comprising the amino acid sequence of SEQ ID NOs:33, 43, and 55, respectively; a CDR-L1, CDR-L2, and CDR-L3 comprising the amino acid sequence of SEQ ID NOs:34, 44, and 56, respectively; a CDR-L1, CDR-L2, and CDR-L3 comprising the amino acid sequence of SEQ ID NOs:35, 45, and 57, respectively; a CDR-L1, CDR-L2, and CDR-L3 comprising the amino acid sequence of SEQ ID NOs:36, 46, and 58, respectively; a CDR-L1, CDR-L2, and CDR-L3 comprising the amino acid sequence of SEQ ID NOs:174, 179, and 184, respectively; a CDR-L1, CDR-L2, and CDR-L3 comprising the amino acid sequence of SEQ ID NOs:174, 179, and 185, respectively; a CDR-L1, CDR-L2, and CDR-L3 comprising the amino acid sequence of SEQ ID NOs:174, 179, and 186, respectively; a CDR-L1, CDR-L2, and CDR-L3 comprising the amino acid sequence of SEQ ID NOs:174, 179, and 187, respectively; a CDR-L1, CDR-L2, and CDR-L3 comprising the amino acid sequence of SEQ ID NOs:175, 180, and 188, respectively; a CDR-L1, CDR-L2, and CDR-L3 comprising the amino acid sequence of SEQ ID NOs:174, 179, and 189, respectively; a CDR-L1, CDR-L2, and CDR-L3 comprising the amino acid sequence of SEQ ID NOs:176, 181, and 190, respectively; a CDR-L1, CDR-L2, and CDR-L3 comprising the amino acid sequence of SEQ ID NOs:177, 182, and 191, respectively; a CDR-L1, CDR-L2, and CDR-L3 comprising the amino acid sequence of SEQ ID NOs:174, 179, and 192, respectively; a CDR-L1, CDR-L2, and CDR-L3 comprising the amino acid sequence of SEQ ID NOs:178, 183, and 193, respectively; a CDR-L1, CDR-L2, and CDR-L3 comprising the amino acid sequence of SEQ ID NOs:178, 183, and 194, respectively; a CDR-L1, CDR-L2, and CDR-L3 comprising the amino acid sequence of SEQ ID NOs:30, 399, and 415, respectively; a CDR-L1, CDR-L2, and CDR-L3 comprising the amino acid sequence of SEQ ID NOs:380, 400, and 416, respectively; a CDR-L1, CDR-L2, and CDR-L3 comprising the amino acid sequence of SEQ ID NOs:33, 43, and 421, respectively; a CDR-L1, CDR-L2, and CDR-L3 comprising the amino acid sequence of SEQ ID NOs:381, 401, and 417, respectively; a CDR-L1, CDR-L2, and CDR-L3 comprising the amino acid sequence of SEQ ID NOs:382, 402, and 418, respectively; a CDR-L1, CDR-L2, and CDR-L3 comprising the amino acid sequence of SEQ ID NOs:383, 403, and 419, respectively; a CDR-L1, CDR-L2, and CDR-L3 comprising the amino acid sequence of SEQ ID NOs:384, 39, and 54, respectively; a CDR-L1, CDR-L2, and CDR-L3 comprising the amino acid sequence of SEQ ID NOs:385, 180, and 58, respectively; a CDR-L1, CDR-L2, and CDR-L3 comprising the amino acid sequence of SEQ ID NOs:175, 180, and 188, respectively; a CDR-L1, CDR-L2, and CDR-L3 comprising the amino acid sequence of SEQ ID NOs:386, 404, and 420, respectively; a CDR-L1, CDR-L2, and CDR-L3 comprising the amino acid sequence of SEQ ID NOs:387, 405, and 422, respectively; a CDR-L1, CDR-L2, and CDR-L3 comprising the amino acid sequence of SEQ ID NOs:388, 406, and 423, respectively; a CDR-L1, CDR-L2, and CDR-L3 comprising the amino acid sequence of SEQ ID NOs:388, 407, and 424, respectively; a CDR-L1, CDR-L2, and CDR-L3 comprising the amino acid sequence of SEQ ID NOs:389, 408, and 425, respectively; a CDR-L1, CDR-L2, and CDR-L3 comprising the amino acid sequence of SEQ ID NOs:390, 183, and 193, respectively; a CDR-L1, CDR-L2, and CDR-L3 comprising the amino acid sequence of SEQ ID NOs:391, 409, and 426, respectively; a CDR-L1, CDR-L2, and CDR-L3 comprising the amino acid sequence of SEQ ID NOs:392, 40, and 427, respectively; a CDR-L1, CDR-L2, and CDR-L3 comprising the amino acid sequence of SEQ ID NOs:394, 39, and 429, respectively; a CDR-L1, CDR-L2, and CDR-L3 comprising the amino acid sequence of SEQ ID NOs:395, 411, and 430, respectively; a CDR-L1, CDR-L2, and CDR-L3 comprising the amino acid sequence of SEQ ID NOs:396, 412, and 431, respectively; a CDR-L1, CDR-L2, and CDR-L3 comprising the amino acid sequence of SEQ ID NOs:396, 412, and 58, respectively; a CDR-L1, CDR-L2, and CDR-L3 comprising the amino acid sequence of SEQ ID NOs:397, 413, and 432, respectively; or a CDR-L1, CDR-L2, and CDR-L3 comprising the amino acid sequence of SEQ ID NOs:398, 414, and 433, respectively.

In some of any such embodiments, the $V_L$ region comprises the CDR-L1, CDR-L2, and CDR-L3, respectively, contained within the $V_L$ region amino acid sequence selected from any one of SEQ ID NOs:116-127, 257-267, 534-550 and 552-557.

In some of any such embodiments, the $V_L$ region comprises a framework region 1 (FR1), a FR2, a FR3, and/or a FR4 comprising at least 90% sequence identity, respectively, to a FR1, FR2, FR3, and/or FR4 of the amino acid sequence contained within the $V_L$ region amino acid sequence selected from any one of SEQ ID NOs:116-127, 257-267, 534-550 and 552-557. In some embodiments, the $V_L$ region comprises a framework region 1 (FR1), a FR2, a FR3, and/or a FR4 sequence having at least 90%, 91%, 92%, 93%, 94%, 95%, 96%, 97%, 98%, 99% sequence identity, respectively, to a FR1, FR2, FR3, and/or FR4 of the amino acid sequence contained within the $V_L$ region amino acid sequence selected from any one of SEQ ID NOs:116-127, 257-267, 534-550 and 552-557. In some embodiments, the $V_H$ region comprises a FR1, a FR2, a FR3, and/or a FR4, selected from a FR1 comprising the amino acid sequence selected from any one of SEQ ID NOs:72-82, 221-227, 446-459 and 461-466; a FR2 comprising the amino acid sequence selected from any one of SEQ ID NOs:83-92, 228-232, 467-477 and 479-482; a FR3 comprising the amino acid sequence selected from any one of SEQ ID NOs:93-101, 233-242, 483-495 and 497-501; and/or a FR4 comprising the amino acid sequence selected from any one of SEQ ID NOs:102-109, 243-246, 502-506 and 508.

In some of any such embodiments, the $V_L$ region comprises the amino acid sequence selected from any one of SEQ ID NOs:116-127, 257-267, 534-550 and 552-557.

Provided herein are antibodies or antigen-binding fragments thereof comprising a CDR-H1, a CDR-H2, and a CDR-H3, respectively, comprising the amino acid sequences of CDR-H1, CDR-H2, and CDR-H3 sequences contained within the $V_H$ region amino acid sequence selected from any one of SEQ ID NOs:110-115, 247-256, 518-531 and 533; and/or a CDR-L1, aCDR-L2, and aCDR-L3, respectively, comprising the amino acid sequences of CDR-L1, CDR-L2, and CDR-L3 sequences contained within the $V_L$ region amino acid sequence selected from any one of SEQ ID NOs:116-127, 257-267, 534-550 and 552-557.

Provided herein are antibodies or antigen-binding fragments thereof, wherein said antibody or antigen-binding fragment comprises a heavy chain variable ($V_H$) region having at least 90%, 91%, 92%, 93%, 94%, 95%, 96%, 97%, 98% or 99% sequence identity to the $V_H$ region amino acid sequence selected from any one of SEQ ID NOs:110-115, 247-256, 518-531 and 533; and a light chain variable ($V_L$) region having at least 90%, 91%, 92%, 93%, 94%, 95%, 96%, 97%, 98%, or 99% sequence identity to the $V_L$ region amino acid sequence selected from any one of SEQ ID NOs:116-127, 257-267, 534-550 and 552-557.

In some of any embodiments, said antibody or antigen-binding fragment comprises a $V_H$ region having at least 90%, 91%, 92%, 93%, 94%, 95%, 96%, 97%, 98% or 99% sequence identity to the $V_H$ region amino acid sequence selected from any one of SEQ ID NOs:110, 256 and 519; and a $V_L$ region having at least 90%, 91%, 92%, 93%, 94%, 95%, 96%, 97%, 98%, or 99% sequence identity to the $V_L$ region amino acid sequence selected from any one of SEQ ID NOs:47, 51, 194 and 416. In some of any embodiments, said antibody or antigen-binding fragment comprises a $V_H$ region having at least 90%, 91%, 92%, 93%, 94%, 95%, 96%, 97%, 98% or 99% sequence identity to the $V_H$ region amino acid sequence of SEQ ID NO:115; and a $V_L$ region having at least 90%, 91%, 92%, 93%, 94%, 95%, 96%, 97%, 98%, or 99% sequence identity to the $V_L$ region amino acid sequence of SEQ ID NO:536.

Provided herein are antibodies or antigen-binding fragments thereof, comprising: a heavy chain variable ($V_H$) region comprising a heavy chain complementarity determining region 1 (CDR-H1), CDR-H2, and CDR-H3, wherein: the CDR-H1 comprises the amino acid sequence selected from any one of SEQ ID NOs:1-3 and 140-144; the CDR-H2 comprises the amino acid sequence selected from any one of SEQ ID NOs:4-6, 145-148 and 372-374; and the CDR-H3 comprises the amino acid sequence selected from any one of SEQ ID NOs:7-11, 149-157, 279-287 and 376-378; and a light chain variable ($V_L$) region comprising a heavy complementarity determining region 1 (CDR-L1), CDR-L2, and CDR-L3, wherein: the CDR-L1 comprises the amino acid sequence selected from any one of SEQ ID NOs: 26-36, 174-178, 380-392 and 394-398; the CDR-L2 comprises the amino acid sequence selected from any one of SEQ ID NOs: 37-46, 179-183, 399-409 and 411-414; and the CDR-L3 comprises the amino acid sequence selected from any one of SEQ ID NOs:47-58, 184-194, 415-427 and 429-433.

In some of any embodiments, the CDR-H1 comprises the amino acid sequence selected from any one of SEQ ID NOs:1 and 2; the CDR-H2 comprises the amino acid sequence selected from any one of SEQ ID NOs:4 and 5; and the CDR-H3 comprises the amino acid sequence selected from any one of SEQ ID NOs: 7 and 157; and the CDR-L1 comprises the amino acid sequence selected from any one of SEQ ID NOs: 26, 30, 178 and 380; the CDR-L2 comprises the amino acid sequence selected from any one of SEQ ID NOs: 37, 39, 183 or 400; and the CDR-L3 comprises the amino acid sequence selected from any one of SEQ ID NOs: 47, 51, 194 and 416. In some of any embodiments, the CDR-H1 comprises the amino acid sequence of SEQ ID NO:2; the CDR-H2 comprises the amino acid sequence of SEQ ID NO:5; and the CDR-H3 comprises the amino acid sequence of SEQ ID NO:10; and the CDR-L1 comprises the amino acid sequence of SEQ ID NO:33; the CDR-L2 comprises the amino acid sequence of SEQ ID NO:43; and the CDR-L3 comprises the amino acid sequence of SEQ ID NO:421.

Provided herein are antibodies or antigen-binding fragments thereof, comprising a heavy chain variable ($V_H$) region and a light chain variable ($V_L$) region, wherein: the $V_H$ region comprises a CDR-H1, CDR-H2, and CDR-H3 comprising the amino acid sequence of SEQ ID NOS:1, 4, and 7, respectively, and the $V_L$ region comprises a CDR-L1, CDR-L2, and CDR-L3 comprising the amino acid sequence of SEQ ID NOS:26, 37, and 47, respectively; the $V_H$ region comprises a CDR-H1, CDR-H2, and CDR-H3 comprising the amino acid sequence of SEQ ID NOS:2, 5, and 8, respectively, and the $V_L$ region comprises a CDR-L1, CDR-L2, and CDR-L3 comprising the amino acid sequence of SEQ ID NOS:27, 38, and 48, respectively; the $V_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:28, 39, and 49, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:29, 40, and 50, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:30, 39, and 51, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:31, 41, and 52, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:32, 42, and 53, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:30, 39, and 54, respectively; the V$_H$ region comprises a CDR-H1, CDR-H2, and CDR-H3 comprising the amino acid sequence of SEQ ID NOS:2, 5, and 9, respectively, and the V$_L$ region comprises a CDR-L1, CDR-L2, and CDR-L3 comprising the amino acid sequence of SEQ ID NOS:33, 43, and 55, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:34, 44, and 56, respectively; the V$_H$ region comprises a CDR-H1, CDR-H2, and CDR-H3 comprising the amino acid sequence of SEQ ID NOS:3, 6, and 11, respectively, and the V$_L$ region comprises a CDR-L1, CDR-L2, and CDR-L3 comprising the amino acid sequence of SEQ ID NOS:35, 45, and 57, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:36, 46, and 58, respectively; the V$_H$ region comprises a CDR-H1, CDR-H2, and CDR-H3 comprising the amino acid sequence of SEQ ID NOS:140, 145, and 149, respectively, and the V$_L$ region comprises a CDR-L1, CDR-L2, and CDR-L3 comprising the amino acid sequence of SEQ ID NOS:174, 179, and 184, respectively; the V$_H$ region comprises a CDR-H1, CDR-H2, and CDR-H3 comprising the amino acid sequence of SEQ ID NOS:141, 145, and 149, respectively, and the V$_L$ region comprises a CDR-L1, CDR-L2, and CDR-L3 comprising the amino acid sequence of SEQ ID NOS:174, 179, and 185, respectively; the V$_H$ region comprises a CDR-H1, CDR-H2, and CDR-H3 comprising the amino acid sequence of SEQ ID NOS:141, 145, and 150, respectively, and the V$_L$ region comprises a CDR-L1, CDR-L2, and CDR-L3 comprising the amino acid sequence of SEQ ID NOS:174, 179, and 186, respectively; the V$_H$ region comprises a CDR-H1, CDR-H2, and CDR-H3 comprising the amino acid sequence of SEQ ID NOS:142, 146, and 151, respectively, and the V$_L$ region comprises a CDR-L1, CDR-L2, and CDR-L3 comprising the amino acid sequence of SEQ ID NOS:174, 179, and 187, respectively; the V$_H$ region comprises a CDR-H1, CDR-H2, and CDR-H3 comprising the amino acid sequence of SEQ ID NOS:2, 5, and 152, respectively, and the V$_L$ region comprises a CDR-L1, CDR-L2, and CDR-L3 comprising the amino acid sequence of SEQ ID NOS:175, 180, and 188, respectively; the V$_H$ region comprises a CDR-H1, CDR-H2, and CDR-H3 comprising the amino acid sequence of SEQ ID NOS:143, 147, and 153, respectively, and the V$_L$ region comprises a CDR-L1, CDR-L2, and CDR-L3 comprising the amino acid sequence of SEQ ID NOS:174, 179, and 189, respectively; the V$_H$ region comprises a CDR-H1, CDR-H2, and CDR-H3 comprising the amino acid sequence of SEQ ID NOS:144, 148, and 154, respectively, and the V$_L$ region comprises a CDR-L1, CDR-L2, and CDR-L3 comprising the amino acid sequence of SEQ ID NOS:176, 181, and 190, respectively; the V$_H$ region comprises a CDR-H1, CDR-H2, and CDR-H3 comprising the amino acid sequence of SEQ ID NOS:3, 6, and 155, respectively, and the V$_L$ region comprises a CDR-L1, CDR-L2, and CDR-L3 comprising the amino acid sequence of SEQ ID NOS:177, 182, and 191, respectively; the V$_H$ region comprises a CDR-H1, CDR-H2, and CDR-H3 comprising the amino acid sequence of SEQ ID NOS:2, 5, and 156, respectively, and the V$_L$ region comprises a CDR-L1, CDR-L2, and CDR-L3 comprising the amino acid sequence of SEQ ID NOS:174, 179, and 192, respectively; the V$_H$ region comprises a CDR-H1, CDR-H2, and CDR-H3 comprising the amino acid sequence of SEQ ID NOS:2, 5, and 157, respectively, and the V$_L$ region comprises a CDR-L1, CDR-L2, and CDR-L3 comprising the amino acid sequence of SEQ ID NOS:178, 183, and 193, respectively; the V$_H$ region comprises a CDR-H1, CDR-H2, and CDR-H3 comprising the amino acid sequence of SEQ ID NOS:2, 5, and 157, respectively, and the V$_L$ region comprises a CDR-L1, CDR-L2, and CDR-L3 comprising the amino acid sequence of SEQ ID NOS:178, 183, and 194, respectively; the V$_H$ region comprises a CDR-H1, CDR-H2, and CDR-H3 comprising the amino acid sequence of SEQ ID NOS:2, 6, and 376, respectively, and the V$_L$ region comprises a CDR-L1, CDR-L2, and CDR-L3 comprising the amino acid sequence of SEQ ID NOS:30, 399, and 415, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:380, 400, and 416, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:33, 43, and 421, respectively; the V$_H$ region comprises a CDR-H1, CDR-H2, and CDR-H3 comprising the amino acid sequence of SEQ ID NOS:3, 6, and 155, respectively, and the V$_L$ region comprises a CDR-L1, CDR-L2, and CDR-L3 comprising the amino acid sequence of SEQ ID NOS:177, 182, and 191, respectively; the V$_H$ region comprises a CDR-H1, CDR-H2, and CDR-H3 comprising the amino acid sequence of SEQ ID NOS:3, 372, and 376, respectively, and the V$_L$ region comprises a CDR-L1, CDR-L2, and CDR-L3 comprising the amino acid sequence of SEQ ID NOS:381, 401, and 417, respectively; the V$_H$ region comprises a CDR-H1, CDR-H2, and CDR-H3 comprising the amino acid sequence of SEQ ID NOS:3, 6, and 376, respectively, and the V$_L$ region comprises a CDR-L1, CDR-L2, and CDR-L3 comprising the amino acid sequence of SEQ ID NOS:382, 402, and 418, respectively; the V$_H$ region comprises a CDR-H1, CDR-H2, and CDR-H3 comprising the amino acid sequence of SEQ ID NOS:3, 6, and 377, respectively, and the V$_L$ region comprises a CDR-L1, CDR-L2, and CDR-L3 comprising the amino acid sequence of SEQ ID NOS:383, 403, and 419, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:384, 39, and 54, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:385, 180, and 58, respectively; the V$_H$ region comprises a CDR-H1, CDR-H2, and CDR-H3 comprising the amino acid sequence of SEQ ID NOS:2, 373, and 152, respectively, and the V$_L$ region comprises a CDR-L1, CDR-L2, and CDR-L3 comprising the amino acid sequence of SEQ ID NOS:175, 180, and 188, respectively; the V$_H$ region comprises a CDR-H1, CDR-H2, and CDR-H3 comprising the amino acid sequence of SEQ ID NOS:3, 6, and 11, respectively, and the V$_L$ region comprises a CDR-L1, CDR-L2, and CDR-L3 comprising the amino acid sequence of SEQ ID NOS:386, 404, and 420, respectively; the V$_H$ region comprises a CDR-H1, CDR-H2, and CDR-H3 comprising the amino acid sequence of SEQ ID NOS:2, 5, and 378, respectively, and the V$_L$ region comprises a CDR-L1, CDR-L2, and CDR-L3 comprising the amino acid sequence of SEQ ID NOS:33, 43, and 421, respectively; the V$_H$ region comprises a CDR-H1, CDR-H2, and CDR-H3 comprising the amino acid sequence of SEQ ID NOS:2, 5, and 9, respectively, and the V$_L$ region comprises a CDR-L1, CDR-L2, and CDR-L3 comprising the amino acid sequence of SEQ ID NOS:387, 405, and 422, respectively; the V$_H$ region comprises a CDR-H1, CDR-H2, and CDR-H3 comprising the amino acid sequence of SEQ ID NOS:2, 5, and 9, respectively, and the V$_L$ region comprises a CDR-L1, CDR-L2, and CDR-L3 comprising the amino acid sequence of SEQ ID NOS:388, 406, and 423, respectively; the V$_H$ region comprises a CDR-H1, CDR-H2, and CDR-H3 comprising the amino acid sequence of SEQ ID NOS:2, 5, and 9, respectively, and the V$_L$ region comprises a CDR-L1, CDR-L2, and CDR-L3 comprising the amino acid sequence of SEQ ID NOS:388, 407, and 424, respectively; the V$_H$ region comprises a CDR-H1, CDR-H2, and CDR-H3 comprising the amino acid sequence of SEQ ID NOS:3, 6, and 376, respectively, and the V$_L$ region comprises a CDR-L1, CDR-L2, and CDR-L3 comprising the amino acid sequence of SEQ ID NOS:389, 408, and 425, respectively; the V$_H$ region comprises a CDR-H1, CDR-H2, and CDR-H3 comprising the amino acid sequence of SEQ ID NOS:2, 5, and 157, respectively, and the V$_L$ region comprises a CDR-L1, CDR-L2, and CDR-L3 comprising the amino acid sequence of SEQ ID NOS:390, 183, and 193, respectively; the V$_H$ region comprises a CDR-H1, CDR-H2, and CDR-H3 comprising the amino acid sequence of SEQ ID NOS:2, 374, and 9, respectively, and the V$_L$ region comprises a CDR-L1, CDR-L2, and CDR-L3 comprising the amino acid sequence of SEQ ID NOS:391, 409, and 426, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:392, 40, and 427, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:394, 39, and 429, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:395, 411, and 430, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:28, 39, and 49, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:396, 412, and 431, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:396, 412, and 58, respectively; the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:397, 413, and 432, respectively; or the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:398, 414, and 433, respectively.

In some of any embodiments, the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:26, 37, and 47, respectively; the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:30, 39, and 51, respectively; the V$_H$ region comprises a CDR-H1, CDR-H2, and CDR-H3 comprising the amino acid sequence of SEQ ID NOS:2, 5, and 157, respectively, and the V$_L$ region comprises a CDR-L1, CDR-L2, and CDR-L3 comprising the amino acid sequence of SEQ ID NOS:178, 183, and 194, respectively; or the V$_H$ region comprises a CDR-H1, CDR-H2, and CDR-H3 comprising the amino acid sequence of SEQ ID NOS:1, 4, and 7, respectively, and the V$_L$ region comprises a CDR-L1, CDR-L2, and CDR-L3 comprising the amino acid sequence of SEQ ID NOS:380, 400, and 416, respectively. In some of any embodiments, the V$_H$ region comprises a CDR-H1, CDR-H2, and CDR-H3 comprising the amino acid sequence of SEQ ID NOS:2, 5, and 10, respectively, and the V$_L$ region comprises a CDR-L1, CDR-L2, and CDR-L3 comprising the amino acid sequence of SEQ ID NOS:33, 43, and 421, respectively.

Provided herein are antibodies or antigen-binding fragments thereof, comprising: a heavy chain complementarity determining region 1 (CDR-H1), CDR-H2, and CDR-H3, respectively, comprising the amino acid sequences of CDR-H1, CDR-H2, and CDR-H3 contained within the V$_H$ region amino acid sequence selected from any one of SEQ ID NOs:110-115, 247-256, 518-531 and 533; and/or a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence selected from any one of SEQ ID NOs:116-127, 257-267, 534-550 and 552-557.

In some of any embodiments, the CDR-H1, CDR-H2, and CDR-H3, respectively, comprise the amino acid sequences of CDR-H1, CDR-H2, and CDR-H3 contained within the $V_H$ region amino acid sequence selected from any one of SEQ ID NOs: 110, 256 and 519; and a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence selected from any one of SEQ ID NOs: 116, 120, 267 and 535.

In some of any embodiments, the CDR-H1, CDR-H2, and CDR-H3, respectively, comprise the amino acid sequences of CDR-H1, CDR-H2, and CDR-H3 contained within the $V_H$ region amino acid sequence of SEQ ID NO:115; and a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence of SEQ ID NO:536.

Provided herein are antibodies or antigen-binding fragments thereof, comprising a heavy chain variable ($V_H$) region and a light chain variable ($V_L$) region, wherein: the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:116; the $V_H$ region is or comprises a CDR-H1, CDR-H2 and CDR-H3 contained within the $V_H$ region amino acid sequence of SEQ ID NO:111, and the $V_L$ region is or comprises a CDR-L1, CDR-L2 and CDR-L3 contained within the $V_L$ region amino acid sequence of SEQ ID NO:117; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:118; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:119; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:120; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:121; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:122; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:123; the $V_H$ region is or comprises a CDR-H1, CDR-H2 and CDR-H3 contained within the $V_H$ region amino acid sequence of SEQ ID NO:112, and the $V_L$ region is or comprises a CDR-L1, CDR-L2 and CDR-L3 contained within the $V_L$ region amino acid sequence of SEQ ID NO:124; the $V_H$ region is or comprises a CDR-H1, CDR-H2 and CDR-H3 contained within the $V_H$ region amino acid sequence of SEQ ID NO:113, and the $V_L$ region is or comprises a CDR-L1, CDR-L2 and CDR-L3 contained within the $V_L$ region amino acid sequence of SEQ ID NO:125; the $V_H$ region is or comprises a CDR-H1, CDR-H2 and CDR-H3 contained within the $V_H$ region amino acid sequence of SEQ ID NO:114, and the $V_L$ region is or comprises a CDR-L1, CDR-L2 and CDR-L3 contained within the $V_L$ region amino acid sequence of SEQ ID NO:126; the $V_H$ region is or comprises a CDR-H1, CDR-H2 and CDR-H3 contained within the $V_H$ region amino acid sequence of SEQ ID NO:115, and the $V_L$ region is or comprises a CDR-L1, CDR-L2 and CDR-L3 contained within the $V_L$ region amino acid sequence of SEQ ID NO:127; the $V_H$ region is or comprises a CDR-H1, CDR-H2 and CDR-H3 contained within the $V_H$ region amino acid sequence of SEQ ID NO:247, and the $V_L$ region is or comprises a CDR-L1, CDR-L2 and CDR-L3 contained within the $V_L$ region amino acid sequence of SEQ ID NO:257; the $V_H$ region is or comprises a CDR-H1, CDR-H2 and CDR-H3 contained within the $V_H$ region amino acid sequence of SEQ ID NO:248, and the $V_L$ region is or comprises a CDR-L1, CDR-L2 and CDR-L3 contained within the $V_L$ region amino acid sequence of SEQ ID NO:258; the $V_H$ region is or comprises a CDR-H1, CDR-H2 and CDR-H3 contained within the $V_H$ region amino acid sequence of SEQ ID NO:249, and the $V_L$ region is or comprises a CDR-L1, CDR-L2 and CDR-L3 contained within the $V_L$ region amino acid sequence of SEQ ID NO:259; the $V_H$ region is or comprises a CDR-H1, CDR-H2 and CDR-H3 contained within the $V_H$ region amino acid sequence of SEQ ID NO:250, and the $V_L$ region is or comprises a CDR-L1, CDR-L2 and CDR-L3 contained within the $V_L$ region amino acid sequence of SEQ ID NO:260; the $V_H$ region is or comprises a CDR-H1, CDR-H2 and CDR-H3 contained within the $V_H$ region amino acid sequence of SEQ ID NO:251, and the $V_L$ region is or comprises a CDR-L1, CDR-L2 and CDR-L3 contained within the $V_L$ region amino acid sequence of SEQ ID NO:261; the $V_H$ region is or comprises a CDR-H1, CDR-H2 and CDR-H3 contained within the $V_H$ region amino acid sequence of SEQ ID NO:252, and the $V_L$ region is or comprises a CDR-L1, CDR-L2 and CDR-L3 contained within the $V_L$ region amino acid sequence of SEQ ID NO:262; the $V_H$ region is or comprises a CDR-H1, CDR-H2 and CDR-H3 contained within the $V_H$ region amino acid sequence of SEQ ID NO:253, and the $V_L$ region is or comprises a CDR-L1, CDR-L2 and CDR-L3 contained within the $V_L$ region amino acid sequence of SEQ ID NO:263; the $V_H$ region is or comprises a CDR-H1, CDR-H2 and CDR-H3 contained within the $V_H$ region amino acid sequence of SEQ ID NO:254, and the $V_L$ region is or comprises a CDR-L1, CDR-L2 and CDR-L3 contained within the $V_L$ region amino acid sequence of SEQ ID NO:264; the $V_H$ region is or comprises a CDR-H1, CDR-H2 and CDR-H3 contained within the $V_H$ region amino acid sequence of SEQ ID NO:255, and the $V_L$ region is or comprises a CDR-L1, CDR-L2 and CDR-L3 contained within the $V_L$ region amino acid sequence of SEQ ID NO:265; the $V_H$ region is or comprises a CDR-H1, CDR-H2 and CDR-H3 contained within the $V_H$ region amino acid sequence of SEQ ID NO:256, and the $V_L$ region is or comprises a CDR-L1, CDR-L2 and CDR-L3 contained within the $V_L$ region amino acid sequence of SEQ ID NO:266; the $V_H$ region is or comprises a CDR-H1, CDR-H2 and CDR-H3 contained within the $V_H$ region amino acid sequence of SEQ ID NO:256, and the $V_L$ region is or comprises a CDR-L1, CDR-L2 and CDR-L3 contained within the $V_L$ region amino acid sequence of SEQ ID NO:267; the $V_H$ region is or comprises a CDR-H1, CDR-H2 and CDR-H3 contained within the $V_H$ region amino acid sequence of SEQ ID NO:518, and the $V_L$ region is or comprises a CDR-L1, CDR-L2 and CDR-L3 contained within the $V_L$ region amino acid sequence of SEQ ID NO:534; the $V_H$ region is or comprises a CDR-H1, CDR-H2 and CDR-H3 contained within the $V_H$ region amino acid sequence of SEQ ID NO:519, and the $V_L$ region is or comprises a CDR-L1, CDR-L2 and CDR-L3 contained within the $V_L$ region amino acid sequence of SEQ ID NO:535; the $V_H$ region is or comprises a CDR-H1, CDR-H2 and CDR-H3 contained within the $V_H$ region amino acid sequence of SEQ ID NO:115, and the $V_L$ region is or comprises a CDR-L1, CDR-L2 and CDR-L3 contained within the $V_L$ region amino acid sequence of SEQ ID NO:536; the $V_H$ region is or comprises a CDR-H1, CDR-H2 and CDR-H3 contained within the $V_H$ region amino acid sequence of SEQ ID NO:520, and the $V_L$ region is or comprises a CDR-L1, CDR-L2 and CDR-L3 contained within the $V_L$ region amino acid sequence of SEQ ID NO:264; the $V_H$ region is or comprises a CDR-H1, CDR-H2 and CDR-H3 contained within the $V_H$ region amino acid sequence of SEQ ID NO:521, and the $V_L$ region is or comprises a CDR-L1, CDR-L2 and CDR-L3 contained within the $V_L$ region amino acid sequence of SEQ ID NO:537; the $V_H$ region is or comprises a CDR-H1, CDR-H2 and CDR-H3 contained within the $V_H$ region amino acid sequence of SEQ ID NO:522, and the $V_L$ region is or comprises a CDR-L1, CDR-L2 and CDR-L3 contained within the $V_L$ region amino acid sequence of SEQ ID NO:538; the $V_H$ region is or comprises a CDR-H1, CDR-H2 and CDR-H3 contained within the $V_H$ region amino acid sequence of SEQ ID NO:523, and the $V_L$ region is or comprises a CDR-L1, CDR-L2 and CDR-L3 contained within the $V_L$ region amino acid sequence of SEQ ID NO:539; the $V_H$ region is or comprises a CDR-H1, CDR-H2 and CDR-H3 contained within the $V_H$ region amino acid sequence of SEQ ID NO:519, and the $V_L$ region is or comprises a CDR-L1, CDR-L2 and CDR-L3 contained within the $V_L$ region amino acid sequence of SEQ ID NO:540; the $V_H$ region is or comprises a CDR-H1, CDR-H2 and CDR-H3 contained within the $V_H$ region amino acid sequence of SEQ ID NO:524, and the $V_L$ region is or comprises a CDR-L1, CDR-L2 and CDR-L3 contained within the $V_L$ region amino acid sequence of SEQ ID NO:541; the $V_H$ region is or comprises a CDR-H1, CDR-H2 and CDR-H3 contained within the $V_H$ region amino acid sequence of SEQ ID NO:525, and the $V_L$ region is or comprises a CDR-L1, CDR-L2 and CDR-L3 contained within the $V_L$ region amino acid sequence of SEQ ID NO:261; the $V_H$ region is or comprises a CDR-H1, CDR-H2 and CDR-H3 contained within the $V_H$ region amino acid sequence of SEQ ID NO:526, and the $V_L$ region is or comprises a CDR-L1, CDR-L2 and CDR-L3 contained within the $V_L$ region amino acid sequence of SEQ ID NO:542; the $V_H$ region is or comprises a CDR-H1, CDR-H2 and CDR-H3 contained within the $V_H$ region amino acid sequence of SEQ ID NO:527, and the $V_L$ region is or comprises a CDR-L1, CDR-L2 and CDR-L3 contained within the $V_L$ region amino acid sequence of SEQ ID NO:543; the $V_H$ region is or comprises a CDR-H1, CDR-H2 and CDR-H3 contained within the $V_H$ region amino acid sequence of SEQ ID NO:528, and the $V_L$ region is or comprises a CDR-L1, CDR-L2 and CDR-L3 contained within the $V_L$ region amino acid sequence of SEQ ID NO:544; the $V_H$ region is or comprises a CDR-H1, CDR-H2 and CDR-H3 contained within the $V_H$ region amino acid sequence of SEQ ID NO:529, and the $V_L$ region is or comprises a CDR-L1, CDR-L2 and CDR-L3 contained within the $V_L$ region amino acid sequence of SEQ ID NO:545; the $V_H$ region is or comprises a CDR-H1, CDR-H2 and CDR-H3 contained within the $V_H$ region amino acid sequence of SEQ ID NO:528, and the $V_L$ region is or comprises a CDR-L1, CDR-L2 and CDR-L3 contained within the $V_L$ region amino acid sequence of SEQ ID NO:546; the $V_H$ region is or comprises a CDR-H1, CDR-H2 and CDR-H3 contained within the $V_H$ region amino acid sequence of SEQ ID NO:522, and the $V_L$ region is or comprises a CDR-L1, CDR-L2 and CDR-L3 contained within the $V_L$ region amino acid sequence of SEQ ID NO:547; the $V_H$ region is or comprises a CDR-H1, CDR-H2 and CDR-H3 contained within the $V_H$ region amino acid sequence of SEQ ID NO:256, and the $V_L$ region is or comprises a CDR-L1, CDR-L2 and CDR-L3 contained within the $V_L$ region amino acid sequence of SEQ ID NO:548; the $V_H$ region is or comprises a CDR-H1, CDR-H2 and CDR-H3 contained within the $V_H$ region amino acid sequence of SEQ ID NO:530, and the $V_L$ region is or comprises a CDR-L1, CDR-L2 and CDR-L3 contained within the $V_L$ region amino acid sequence of SEQ ID NO:549; the $V_H$ region is or comprises a CDR-H1, CDR-H2 and CDR-H3 contained within the $V_H$ region amino acid sequence of SEQ ID NO:531, and the $V_L$ region is or comprises a CDR-L1, CDR-L2 and CDR-L3 contained within the $V_L$ region amino acid sequence of SEQ ID NO:550; the $V_H$ region is or comprises a CDR-H1, CDR-H2 and CDR-H3 contained within the $V_H$ region amino acid sequence of SEQ ID NO:519, and the $V_L$ region is or comprises a CDR-L1, CDR-L2 and CDR-L3 contained within the $V_L$ region amino acid sequence of SEQ ID NO:552; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:553; the $V_H$ region is or comprises a CDR-H1, CDR-H2 and CDR-H3 contained within the $V_H$ region amino acid sequence of SEQ ID NO:110, and the $V_L$ region is or comprises a CDR-L1, CDR-L2 and CDR-L3 contained within the $V_L$ region amino acid sequence of SEQ ID NO:118; the $V_H$ region is or comprises a CDR-H1, CDR-H2 and CDR-H3 contained within the $V_H$ region amino acid sequence of SEQ ID NO:533, and the $V_L$ region is or comprises a CDR-L1, CDR-L2 and CDR-L3 contained within the $V_L$ region amino acid sequence of SEQ ID NO:554; the $V_H$ region is or comprises a CDR-H1, CDR-H2 and CDR-H3 contained within the $V_H$ region amino acid sequence of SEQ ID NO:115, and the $V_L$ region is or comprises a CDR-L1, CDR-L2 and CDR-L3 contained within the $V_L$ region amino acid sequence of SEQ ID NO:555; the $V_H$ region is or comprises a CDR-H1, CDR-H2 and CDR-H3 contained within the $V_H$ region amino acid sequence of SEQ ID NO:524, and the $V_L$ region is or comprises a CDR-L1, CDR-L2 and CDR-L3 contained within the $V_L$ region amino acid sequence of SEQ ID NO:556; or the $V_H$ region is or comprises a CDR-H1, CDR-H2 and CDR-H3 contained within the $V_H$ region amino acid sequence of SEQ ID NO:519, and the V$_L$ region is or comprises a CDR-L1, CDR-L2 and CDR-L3 contained within the V$_L$ region amino acid sequence of SEQ ID NO:557, respectively.

In some of any embodiments, the V$_H$ region is or comprises a CDR-H1, CDR-H2 and CDR-H3 contained within the V$_H$ region amino acid sequence of SEQ ID NO:110, and the V$_L$ region is or comprises a CDR-L1, CDR-L2 and CDR-L3 contained within the V$_L$ region amino acid sequence of SEQ ID NO:116; the V$_H$ region is or comprises a CDR-H1, CDR-H2 and CDR-H3 contained within the V$_H$ region amino acid sequence of SEQ ID NO:110, and the V$_L$ region is or comprises a CDR-L1, CDR-L2 and CDR-L3 contained within the V$_L$ region amino acid sequence of SEQ ID NO:120; the V$_H$ region is or comprises a CDR-H1, CDR-H2 and CDR-H3 contained within the V$_H$ region amino acid sequence of SEQ ID NO:256, and the V$_L$ region is or comprises a CDR-L1, CDR-L2 and CDR-L3 contained within the V$_L$ region amino acid sequence of SEQ ID NO:267; or the V$_H$ region is or comprises a CDR-H1, CDR-H2 and CDR-H3 contained within the V$_H$ region amino acid sequence of SEQ ID NO:519, and the V$_L$ region is or comprises a CDR-L1, CDR-L2 and CDR-L3 contained within the V$_L$ region amino acid sequence of SEQ ID NO:535. In some of any embodiments, the V$_H$ region is or comprises a CDR-H1, CDR-H2 and CDR-H3 contained within the V$_H$ region amino acid sequence of SEQ ID NO:115, and the V$_L$ region is or comprises a CDR-L1, CDR-L2 and CDR-L3 contained within the V$_L$ region amino acid sequence of SEQ ID NO:536, respectively.

Provided herein are antibodies or antigen-binding fragments thereof comprising a V$_H$ region and a V$_H$ region and a V$_L$ regions comprising the amino acid sequence having at least 90% identity to SEQ ID NOs:110 and 116, respectively; a V$_H$ region and a V$_L$ regions comprising the amino acid sequence having at least 90% identity to SEQ ID NOs:111 and 117, respectively; a V$_H$ region and a V$_L$ regions comprising the amino acid sequence having at least 90% identity to SEQ ID NOs:110 and 118, respectively; a V$_H$ region and a V$_L$ regions comprising the amino acid sequence having at least 90% identity to SEQ ID NOs:110 and 119, respectively; a V$_H$ region and a V$_L$ regions comprising the amino acid sequence having at least 90% identity to SEQ ID NOs:110 and 120, respectively; a V$_H$ region and a V$_L$ regions comprising the amino acid sequence having at least 90% identity to SEQ ID NOs:110 and 121, respectively; a V$_H$ region and a V$_L$ regions comprising the amino acid sequence having at least 90% identity to SEQ ID NOs:110 and 122, respectively; a V$_H$ region and a V$_L$ regions comprising the amino acid sequence having at least 90% identity to SEQ ID NOs:110 and 123, respectively; a V$_H$ region and a V$_L$ regions comprising the amino acid sequence having at least 90% identity to SEQ ID NOs:112 and 124, respectively; a V$_H$ region and a V$_L$ regions comprising the amino acid sequence having at least 90% identity to SEQ ID NOs:113 and 125, respectively; a V$_H$ region and a V$_L$ regions comprising the amino acid sequence having at least 90% identity to SEQ ID NOs:114 and 126, respectively; a V$_H$ region and a V$_L$ regions comprising the amino acid sequence having at least 90% identity to SEQ ID NOs:115 and 127, respectively; a V$_H$ region and a V$_L$ regions comprising the amino acid sequence having at least 90% identity to SEQ ID NOs:247 and 257, respectively; a V$_H$ region and a V$_L$ regions comprising the amino acid sequence having at least 90% identity to SEQ ID NOs:248 and 258, respectively; a V$_H$ region and a V$_L$ regions comprising the amino acid sequence having at least 90% identity to SEQ ID NOs:249 and 259, respectively; a V$_H$ region and a V$_L$ regions comprising the amino acid sequence having at least 90% identity to SEQ ID NOs:250 and 260, respectively; a V$_H$ region and a V$_L$ regions comprising the amino acid sequence having at least 90% identity to SEQ ID NOs:251 and 261, respectively; a V$_H$ region and a V$_L$ regions comprising the amino acid sequence having at least 90% identity to SEQ ID NOs:252 and 262, respectively; a V$_H$ region and a V$_L$ regions comprising the amino acid sequence having at least 90% identity to SEQ ID NOs:253 and 263, respectively; a V$_H$ region and a V$_L$ regions comprising the amino acid sequence having at least 90% identity to SEQ ID NOs:254 and 264, respectively; a V$_H$ region and a V$_L$ regions comprising the amino acid sequence having at least 90% identity to SEQ ID NOs:255 and 265, respectively; a V$_H$ region and a V$_L$ regions comprising the amino acid sequence having at least 90% identity to SEQ ID NOs:256 and 266, respectively; a V$_H$ region and a V$_L$ regions comprising the amino acid sequence having at least 90% identity to SEQ ID NOs:256 and 267, respectively; a V$_H$ region and a V$_L$ regions comprising the amino acid sequence having at least 90% identity to SEQ ID NOs:518 and 534, respectively; a V$_H$ region and a V$_L$ regions comprising the amino acid sequence having at least 90% identity to SEQ ID NOs:519 and 535, respectively; a V$_H$ region and a V$_L$ regions comprising the amino acid sequence having at least 90% identity to SEQ ID NOs:115 and 536, respectively; a V$_H$ region and a V$_L$ regions comprising the amino acid sequence having at least 90% identity to SEQ ID NOs:520 and 264, respectively; a V$_H$ region and a V$_L$ regions comprising the amino acid sequence having at least 90% identity to SEQ ID NOs:521 and 537, respectively; a V$_H$ region and a V$_L$ regions comprising the amino acid sequence having at least 90% identity to SEQ ID NOs:522 and 538, respectively; a V$_H$ region and a V$_L$ regions comprising the amino acid sequence having at least 90% identity to SEQ ID NOs:523 and 539, respectively; a V$_H$ region and a V$_L$ regions comprising the amino acid sequence having at least 90% identity to SEQ ID NOs:519 and 540, respectively; a V$_H$ region and a V$_L$ regions comprising the amino acid sequence having at least 90% identity to SEQ ID NOs:524 and 541, respectively; a V$_H$ region and a V$_L$ regions comprising the amino acid sequence having at least 90% identity to SEQ ID NOs:525 and 261, respectively; a V$_H$ region and a V$_L$ regions comprising the amino acid sequence having at least 90% identity to SEQ ID NOs:526 and 542, respectively; a V$_H$ region and a V$_L$ regions comprising the amino acid sequence having at least 90% identity to SEQ ID NOs:527 and 543, respectively; a V$_H$ region and a V$_L$ regions comprising the amino acid sequence having at least 90% identity to SEQ ID NOs:528 and 544, respectively; a V$_H$ region and a V$_L$ regions comprising the amino acid sequence having at least 90% identity to SEQ ID NOs:529 and 545, respectively; a V$_H$ region and a V$_L$ regions comprising the amino acid sequence having at least 90% identity to SEQ ID NOs:528 and 546, respectively; a V$_H$ region and a V$_L$ regions comprising the amino acid sequence having at least 90% identity to SEQ ID NOs:522 and 547, respectively; a V$_H$ region and a V$_L$ regions comprising the amino acid sequence having at least 90% identity to SEQ ID NOs:256 and 548, respectively; a V$_H$ region and a V$_L$ regions comprising the amino acid sequence having at least 90% identity to SEQ ID NOs:530 and 549, respectively; a V$_H$ region and a V$_L$ regions comprising the amino acid sequence having at least 90% identity to SEQ ID NOs:531 and 550, respectively; a V$_H$ region and a V$_L$ regions comprising the amino acid sequence having at least 90% identity to SEQ ID NOs:519 and 552, respectively; a V$_H$ region and a $V_L$ regions comprising the amino acid sequence having at least 90% identity to SEQ ID NOs:110 and 553, respectively; a $V_H$ region and a $V_L$ regions comprising the amino acid sequence having at least 90% identity to SEQ ID NOs:110 and 118, respectively; a $V_H$ region and a $V_L$ regions comprising the amino acid sequence having at least 90% identity to SEQ ID NOs:533 and 554, respectively; a $V_H$ region and a $V_L$ regions comprising the amino acid sequence having at least 90% identity to SEQ ID NOs:115 and 555, respectively; a $V_H$ region and a $V_L$ regions comprising the amino acid sequence having at least 90% identity to SEQ ID NOs:524 and 556, respectively; or a $V_H$ region and a $V_L$ regions comprising the amino acid sequence having at least 90% identity to SEQ ID NOs:519 and 557, respectively.

In some of any embodiments, the antibody or antigen-binding fragment comprises a $V_H$ region and a $V_L$ regions comprising the amino acid sequence having at least 90% identity to SEQ ID NOs:110 and 116, respectively; a $V_H$ region and a $V_L$ regions comprising the amino acid sequence having at least 90% identity to SEQ ID NOs:110 and 120, respectively; a $V_H$ region and a $V_L$ regions comprising the amino acid sequence having at least 90% identity to SEQ ID NOS:256 and 267, respectively; or a $V_H$ region and a $V_L$ regions comprising the amino acid sequence having at least 90% identity to SEQ ID NOS:519 and 535, respectively. In some of any embodiments, the antibody or antigen-binding fragment comprises a $V_H$ region and a $V_L$ regions comprising the amino acid sequence having at least 90% identity to SEQ ID NOs:115 and 536, respectively.

In some embodiments, antibodies or antigen-binding fragments thereof comprise a $V_H$ region sequence that is at least at or about 91%, 92%, 93%, 94%, 95%, 96%, 97%, 98%, or 99% identical to such a SEQ ID NO and/or a $V_L$ region sequence that is at least at or about 91%, 92%, 93%, 94%, 95%, 96%, 97%, 98%, or 99% identical to such a SEQ ID NO.

In some embodiments, the $V_H$ and $V_L$ regions comprise the amino acid sequences of SEQ ID NOs:110 and 116, respectively; the $V_H$ and $V_L$ regions comprise the amino acid sequences of SEQ ID NOs:111 and 117, respectively; the $V_H$ and $V_L$ regions comprise the amino acid sequences of SEQ ID NOs:110 and 118, respectively; the $V_H$ and $V_L$ regions comprise the amino acid sequences of SEQ ID NOs:110 and 119, respectively; the $V_H$ and $V_L$ regions comprise the amino acid sequences of SEQ ID NOs:110 and 120, respectively; the $V_H$ and $V_L$ regions comprise the amino acid sequences of SEQ ID NOs:110 and 121, respectively; the $V_H$ and $V_L$ regions comprise the amino acid sequences of SEQ ID NOs:110 and 122, respectively; the $V_H$ and $V_L$ regions comprise the amino acid sequences of SEQ ID NOs:110 and 123, respectively; the $V_H$ and $V_L$ regions comprise the amino acid sequences of SEQ ID NOs:112 and 124, respectively; the $V_H$ and $V_L$ regions comprise the amino acid sequences of SEQ ID NOs:113 and 125, respectively; the $V_H$ and $V_L$ regions comprise the amino acid sequences of SEQ ID NOs:114 and 126, respectively; the $V_H$ and $V_L$ regions comprise the amino acid sequences of SEQ ID NOs:115 and 127, respectively; the $V_H$ and $V_L$ regions comprise the amino acid sequences of SEQ ID NOs:247 and 257, respectively; the $V_H$ and $V_L$ regions comprise the amino acid sequences of SEQ ID NOs:248 and 258, respectively; the $V_H$ and $V_L$ regions comprise the amino acid sequences of SEQ ID NOs:249 and 259, respectively; the $V_H$ and $V_L$ regions comprise the amino acid sequences of SEQ ID NOs:250 and 260, respectively; the $V_H$ and $V_L$ regions comprise the amino acid sequences of SEQ ID NOs:251 and 261, respectively; the $V_H$ and $V_L$ regions comprise the amino acid sequences of SEQ ID NOs:252 and 262, respectively; the $V_H$ and $V_L$ regions comprise the amino acid sequences of SEQ ID NOs:253 and 263, respectively; the $V_H$ and $V_L$ regions comprise the amino acid sequences of SEQ ID NOs:254 and 264, respectively; the $V_H$ and $V_L$ regions comprise the amino acid sequences of SEQ ID NOs:255 and 265, respectively; the $V_H$ and $V_L$ regions comprise the amino acid sequences of SEQ ID NOs:256 and 266, respectively; the $V_H$ and $V_L$ regions comprise the amino acid sequences of SEQ ID NOs:256 and 267, respectively; the $V_H$ and $V_L$ regions comprise the amino acid sequences of SEQ ID NOs:518 and 534, respectively; the $V_H$ and $V_L$ regions comprise the amino acid sequences of SEQ ID NOs:519 and 535, respectively; the $V_H$ and $V_L$ regions comprise the amino acid sequences of SEQ ID NOs:115 and 536, respectively; the $V_H$ and $V_L$ regions comprise the amino acid sequences of SEQ ID NOs:520 and 264, respectively; the $V_H$ and $V_L$ regions comprise the amino acid sequences of SEQ ID NOs:521 and 537, respectively; the $V_H$ and $V_L$ regions comprise the amino acid sequences of SEQ ID NOs:522 and 538, respectively; the $V_H$ and $V_L$ regions comprise the amino acid sequences of SEQ ID NOs:523 and 539, respectively; the $V_H$ and $V_L$ regions comprise the amino acid sequences of SEQ ID NOs:519 and 540, respectively; the $V_H$ and $V_L$ regions comprise the amino acid sequences of SEQ ID NOs:524 and 541, respectively; the $V_H$ and $V_L$ regions comprise the amino acid sequences of SEQ ID NOs:525 and 261, respectively; the $V_H$ and $V_L$ regions comprise the amino acid sequences of SEQ ID NOs:526 and 542, respectively; the $V_H$ and $V_L$ regions comprise the amino acid sequences of SEQ ID NOs:527 and 543, respectively; the $V_H$ and $V_L$ regions comprise the amino acid sequences of SEQ ID NOs:528 and 544, respectively; the $V_H$ and $V_L$ regions comprise the amino acid sequences of SEQ ID NOs:529 and 545, respectively; the $V_H$ and $V_L$ regions comprise the amino acid sequences of SEQ ID NOs:528 and 546, respectively; the $V_H$ and $V_L$ regions comprise the amino acid sequences of SEQ ID NOs:522 and 547, respectively; the $V_H$ and $V_L$ regions comprise the amino acid sequences of SEQ ID NOs:256 and 548, respectively; the $V_H$ and $V_L$ regions comprise the amino acid sequences of SEQ ID NOs:530 and 549, respectively; the $V_H$ and $V_L$ regions comprise the amino acid sequences of SEQ ID NOs:531 and 550, respectively; the $V_H$ and $V_L$ regions comprise the amino acid sequences of SEQ ID NOs:519 and 552, respectively; the $V_H$ and $V_L$ regions comprise the amino acid sequences of SEQ ID NOs:110 and 553, respectively; the $V_H$ and $V_L$ regions comprise the amino acid sequences of SEQ ID NOs:110 and 118, respectively; the $V_H$ and $V_L$ regions comprise the amino acid sequences of SEQ ID NOs:533 and 554, respectively; the $V_H$ and $V_L$ regions comprise the amino acid sequences of SEQ ID NOs:115 and 555, respectively; the $V_H$ and $V_L$ regions comprise the amino acid sequences of SEQ ID NOs:524 and 556, respectively; or the $V_H$ and $V_L$ regions comprise the amino acid sequences of SEQ ID NOs:519 and 557, respectively.

In some of any embodiments, the $V_H$ and $V_L$ regions of the antibody or antigen-binding fragment thereof comprise the amino acid sequences of SEQ ID NOs:110 and 116, respectively; the $V_H$ and $V_L$ regions of the antibody or antigen-binding fragment thereof comprise the amino acid sequences of SEQ ID NOs:110 and 120, respectively; the $V_H$ and $V_L$ regions of the antibody or antigen-binding fragment thereof comprise the amino acid sequences of SEQ ID NOS:256 and 267, respectively; or the $V_H$ and $V_L$ regions of the antibody or antigen-binding fragment thereof comprise the amino acid sequences of SEQ ID NOS:519 and 535, respectively. In some of any embodiments, the $V_H$ and $V_L$ regions of the antibody or antigen-binding fragment thereof comprise the amino acid sequences of SEQ ID NOs:115 and 536, respectively.

In some of any such embodiments, the antibody or antigen-binding fragment thereof specifically binds to a BCMA protein. In some embodiments, the BCMA protein is a human BCMA protein, a mouse BCMA protein, or a non-human primate BCMA protein. In some embodiments, the BCMA protein is a human BCMA protein. In some embodiments, the antibody or antigen-binding fragment further specifically binds to a mouse BCMA or a non-human primate BCMA. In some embodiments, the human BCMA protein comprises an amino acid sequence of SEQ ID NO:367 or 368.

In some of any such embodiments, the antibody or antigen-binding fragment thereof has a binding affinity for a BCMA protein with an $EC_{50}$ that is from or from about 0.1 nM to 400 nM, from or from about 0.5 nM to 200 nM, from or from about 1 nM to 100 nM, or from or from about 2 nM to 50 nM; or the antibody or antigen-binding fragment has a binding affinity for a BCMA protein with an $EC_{50}$ that is less than or less than about 400 nM, less than or less than about 300 nM, less than or less than about 200 nM, less than or less than about 100 nM, less than or less than about 50 nM, less than or less than about 25 nM or less than or less than about 5 nM.

In some of any such embodiments, the binding affinity of said antibody or antigen-binding fragment to a human BCMA protein is at least as high or substantially as high as the binding affinity of an antibody comprising the amino acid sequence of SEQ ID NOS:328, 329, 585 and/or 586 to the human BCMA. In some of any such embodiments, said antibody or antigen-binding fragment competes for binding to a human BCMA protein with an antibody comprising the amino acid sequence of SEQ ID NOs:328, 329, 585 and/or 586. In some of any such embodiments, said antibody or antigen-binding fragment specifically binds to the same or an overlapping epitope of a human BCMA protein as an antibody comprising the amino acid sequence of SEQ ID NOs:328, 329, 585 and/or 586.

In some of any such embodiments, said antibody or antigen-binding fragment does not compete for binding to a human BCMA protein with an antibody comprising the amino acid sequence of SEQ ID NOs:328, 329, 585 and/or 586. In some of any such embodiments, said antibody or antigen-binding fragment specifically binds to a different epitope of a human BCMA protein as an antibody comprising the amino acid sequence of SEQ ID NOs:328, 329, 585 and/or 586. In some of any such embodiments, said antibody or antigen-binding fragment inhibits the binding of an antibody comprising the amino acid sequence of SEQ ID NO:328, 329, 585 and/or 586 to a human BCMA protein by greater than or greater than about 80% or greater than or greater than about 90%. In some of any such embodiments, said human BCMA protein comprises an amino acid sequence of SEQ ID NO:367 or 368.

In some of any such embodiments, the antibody does not comprise CDR-H1, CDR-H2, CDR-H3, CDR-L1, CDR-L2 and/or CDR-L3 sequences having at least 90%, 91%, 92%, 93%, 94%, 95%, 96%, 97%, 98% or 99% identity to the CDR-H1, CDR-H2, CDR-H3 and/or CDR-L1, CDR-L2, CDR-L3 sequences contained within an antibody comprising the amino acid sequence of SEQ ID NOs:328, 329, 585 and/or 586. In some of any such embodiments, the antibody does not comprise the CDR-H1, CDR-H2, CDR-H3 and/or CDR-L1, CDR-L2, CDR-L3 sequences contained within an antibody comprising the amino acid sequence of SEQ ID NO:328 and/or an antibody comprising the amino acid sequence of SEQ ID NO:329, and/or an antibody comprising the amino acid sequence of SEQ ID NO:585, and/or an antibody comprising the amino acid sequence of SEQ ID NO:586. In some of any such embodiments, the antibody or antigen-binding fragment is human.

Provided herein are human antibodies or antigen-binding fragments thereof that specifically binds to the same or an overlapping epitope of a BCMA protein, which optionally is human BCMA, as the epitope specifically bound by a reference antibody, wherein the reference antibody is the antibody or antigen-binding fragment thereof or an antibody comprising the amino acid sequence of SEQ ID NOs:328, 329, 585 and/or 586, said human antibody or antigen-binding fragment comprising heavy and light chain CDRs that are distinct from the heavy and light chain CDRs contained within the antibody comprising the amino acid sequence of SEQ ID NOs:328, 329, 585 and/or 586.

Provided herein are human antibodies or antigen-binding fragments thereof that specifically binds to BCMA and competes for binding to BCMA with a reference antibody, which BCMA is optionally human BCMA, wherein the reference antibody is the antibody or antigen-binding fragment or an antibody comprising the amino acid sequence of SEQ ID NOs:328, 329, 585 and/or 586, said human antibody or antigen-binding fragment comprising heavy and light chain CDRs that are distinct from the heavy and light chain CDRs contained within the antibody comprising the amino acid sequence of SEQ ID NOs:328, 329, 585 and/or 586.

In some of any such embodiments, the human antibody or antigen-binding fragment thereof comprises a $V_H$ region, said $V_H$ region comprising a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or the antibody or antigen-binding fragment comprises a $V_L$ region, said $V_L$ region comprising a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

In some of any such embodiments, the human antibody or antigen-binding fragment thereof contains a CDR-H1 and/or CDR-H2 comprising a sequence 100% identical or with no more than one amino acid difference as compared to an amino acid sequence of a CDR-H1 and/or CDR-H2, respectively, within a sequence encoded by a germline nucleotide human heavy chain V segment; and/or contains a CDR-L1 and/or CDR-L2 comprising a sequence 100% identical or with no more than one amino acid difference as compared to an amino acid sequence of a CDR-L1 and/or CDR-L2, respectively, within a sequence encoded by a germline nucleotide human kappa or lambda v segment.

In some of any such embodiments, the antibody or antigen-binding fragment is recombinant. In some of any such embodiments, the antibody or antigen-binding fragment is monoclonal. In some of any such embodiments, the antibody or antigen-binding fragment is an antigen-binding fragment. In some of any such embodiments, the antibody or antigen-binding fragment is a single chain fragment.

In some of any such embodiments, the antibody is a fragment comprising $V_H$ and $V_L$ regions joined by a flexible linker. In some of any such embodiments, the fragment comprises an scFv. In some embodiments, the scFv comprises a linker comprising the amino acid sequence GGGGSGGGGSGGGGS (SEQ ID NO:361). In some embodiments, the scFv comprises the amino acid sequence selected from any one of SEQ ID NOs:128-139, 268-278, 558-576 and 578-583, or an amino acid sequence having at least 90%, 91%, 92%, 93%, 94%, 95%, 96%, 97%, 98%, or 99% sequence identity to the amino acid sequence selected from any one of SEQ ID NOs:128-139, 268-278, 558-576 and 578-583.

In some of any embodiments, the scFv comprises the amino acid sequence selected from any one of SEQ ID NOs: 128, 132, 278 and 502, or an amino acid sequence having at least 90%, 91%, 92%, 93%, 94%, 95%, 96%, 97%, 98%, or 99% sequence identity to the amino acid sequence selected from any one of SEQ ID NOs: 128, 132, 278 and 502. In some of any embodiments, the scFv comprises the amino acid sequence of SEQ ID NO:560, or an amino acid sequence having at least 90%, 91%, 92%, 93%, 94%, 95%, 96%, 97%, 98%, or 99% sequence identity to the amino acid sequence of SEQ ID NO:560.

In some embodiments, the receptor includes an antigen-binding domain that binds to the same or substantially the same epitope on BCMA, or competes for binding to BCMA with, any of the antibodies and fragments, or antibodies having the provided combinations of VH/VL or CDR sequences, described herein including in any of the foregoing embodiments. In some embodiments, the binding domain recognizes an epitope comprising a portion of one or more amino acid sequences within a BCMA polypeptide. In some aspects, such one or more amino acid sequences are or comprise: MLMAG (SEQ ID NO:616), YFDSL (SEQ ID NO:618), and QLRCSSNTPPL (SEQ ID NO:619). In some aspects, such one or more amino acid sequences are or comprise: MLMAG (SEQ ID NO:616), YFDSLL (SEQ ID NO:620), and QLRCSSNTPPL (SEQ ID NO:619). In some aspects, such one or more amino acid sequences are or comprise: MLMAG (SEQ ID NO:616), QNEYFDSLL (SEQ ID NO:617), and QLRCSSNTPPL (SEQ ID NO:619). In some aspects, such one or more amino acid sequences are or comprise: QNEYF (SEQ ID NO:613), CIPCQL (SEQ ID NO:614), and CQRYC (SEQ ID NO:615). In some aspects, such one or more amino acid sequences are or comprise: CSQNEYF (set forth in SEQ ID NO:611) and LLHACIPCQLR (set forth in SEQ ID NO:612).

Also provided herein is a single chain cell-surface protein comprising any of the single chain antibody fragments provided herein. In some embodiments, the single chain cell surface protein contains any of the provided single domain antibodies.

Provided is a single chain cell-surface protein comprising the scFv amino acid sequence selected from any one of SEQ ID NOs:128-139, 268-278, 558-576 and 578-583 or comprising the $V_H$ region amino acid sequence selected from any one of SEQ ID NOs:110-115, 247-256, 518-531 and 533. Also provided herein are single chain cell surface proteins comprising the scFv amino acid sequence selected from any one of SEQ ID NOs:128-139, 268-278, 558-576 and 578-583. In some of any such embodiments, the scFv comprises the amino acid sequence selected from any one of SEQ ID NOs:128, 132, 278 and 502. In some of any such embodiments, the scFv comprises the amino acid sequence of SEQ ID NO:560.

In some of any such embodiments, the antibody or antigen-binding fragment further comprises at least a portion of an immunoglobulin constant region. In some embodiments, the portion of an immunoglobulin constant region comprises at least a portion of the hinge region. In some embodiments, the portion of an immunoglobulin constant region comprises an Fc region. In some embodiments, the Fc region is an Fc region of a human IgG.

Also provided is a conjugate comprising any of the provided antibodies or antigen-binding fragments and a heterologous molecule or moiety. Also provided is a conjugate containing any of the provided single chain cell-surface proteins.

Also provided is a chimeric antigen receptor (CAR) including an extracellular portion containing any of the provided antibodies or antigen-binding fragments and an intracellular signaling domain. In some embodiments, the antibody or antigen-binding fragment comprises a $V_H$ only domain (e.g., an sdAb) or an scFv and the intracellular signaling domain comprises an ITAM. In some embodiments, the intracellular signaling domain comprises a signaling domain of a zeta chain of a CD3-zeta (CD3ζ) chain, optionally a human CD3 or a signaling portion thereof.

In some of any such embodiments, the CAR further comprises a transmembrane domain linking the extracellular domain and the intracellular signaling domain. In some embodiments, the transmembrane domain comprises a transmembrane portion of a costimulatory molecule, such as a T cell costimulatory molecule, e.g., CD28 and/or 4-1BB, optionally a human CD28. In some embodiments, the T cell costimulatory molecule is CD28 or 4-1BB. In some embodiments, the intracellular signaling domain also includes an intracellular domain of a T cell costimulatory molecule. In some aspects, the T cell costimulatory molecule is CD28 or 4-1BB. In some embodiments, the costimulatory signaling domain comprises an intracellular signaling domain of a 4-1BB, optionally a human 4-1BB.

In some embodiments of any of the provided CARs, the CAR contains an antibody or antigen-binding fragment thereof as provided herein, a transmembrane domain that is a portion of CD28 or variant thereof, and an intracellular signaling domain containing a signaling portion of CD28 or functional variant thereof and a signaling portion of CD3 zeta or functional variant thereof. In some of any such embodiments, the CAR further includes a spacer containing an Ig hinge, e.g., an IgG4 hinge, such as a hinge-only spacer. In some of any such embodiments, the CAR further includes a truncated EGFR sequence. In some of any such embodiments, the CAR further includes an Ig kappa signal sequence and/or a CD33 signal sequence.

In some embodiments of any of the provided CARs, the CAR contains an antibody or antigen-binding fragment thereof as provided herein, a transmembrane domain that is a portion of CD28 or variant thereof, and an intracellular signaling domain containing a signaling portion of a 4-1BB or functional variant thereof and a signaling portion of CD3 zeta or functional variant thereof. In some such embodiments, the CAR further includes a spacer containing an Ig hinge, e.g., an IgG4 hinge, such as a hinge-only spacer. In some of any such embodiments, the CAR further includes a truncated EGFR sequence. In some of any such embodiments, the CAR further includes an Ig kappa signal sequence and/or a CD33 signal sequence.

Further provided herein are nucleic acids encoding any of the provided antibodies or antigen-binding fragments thereof, any of the provided single chain cell-surface proteins, any of the provided conjugates, or any of the provided CARs. In some embodiments, the nucleic acid further encodes a GM-CSF signal sequence, a CD8 signal sequence, an Ig kappa signal sequence or a CD33 signal sequence.

Also provided are vectors comprising a nucleic acid provided herein. In some embodiments, the vector is an expression vector. In some of any such embodiments, the vector is a viral vector. In some of any such embodiments, the vector is a retroviral vector. In some of any such embodiments, the viral vector is a lentiviral vector. In some of any such embodiments, the lentiviral vector is derived from HIV-1.

Provided herein are cells that contain any of the provided antibodies or antigen-binding fragments thereof, any of the provided single chain cell-surface proteins, any of the provided conjugates, or any of the provided CARs. In some embodiments, the cell is an engineered cell expressing a receptor (e.g., a chimeric antigen receptor) comprising any of the provided antibodies or antigen-binding fragments thereof, any of the provided single chain cell-surface proteins, any of the provided conjugates, or any of the provided CARs. In some embodiments, the cell or engineered cell is a T cell. Also provided are engineered cells comprising a vector provided herein.

Provided are compositions or pharmaceutical compositions comprising any of the provided antibodies or antigen-binding fragments thereof, any of the provided single chain cell-surface proteins, any of the provided conjugates, any of the provided CARs or any of the provided cells. In some embodiments, the composition or pharmaceutical composition contains a pharmaceutically acceptable excipient.

Provided herein are also methods of treatment that include administering any one or more of the provided compositions or pharmaceutical compositions to a subject having a disease or disorder associated with BCMA. Provided are methods of treatment that include administering any of the provided antibodies or antigen-binding fragments, any of the provided single chain cell-surface proteins, any of the provided conjugates, any of the provided CARs or any of the provided cells (e.g., engineered T cell) to a subject having a disease or disorder associated with BCMA.

Provided herein are any of the provided compositions or pharmaceutical compositions for use in treating a disease or disorder associated with BCMA. Provided is use of any of the provided compositions or pharmaceutical compositions for the manufacture of a medicament for treating a disease or disorder associated with BCMA. Also provided herein are use of any of the compositions or pharmaceutical compositions described herein for the treatment of a disease or disorder associated with BCMA. In some embodiments, a composition or pharmaceutical composition provided herein comprises any of the provided antibodies or antigen-binding fragments, any of the provided single chain cell-surface proteins, any of the provided conjugates, any of the provided CARs or any of the provided cells (e.g., engineered T cell).

In some of any such embodiments, the disease or disorder associated with BCMA is associated with BCMA expression. In some of any such embodiments, the disease or disorder associated with BCMA is a B cell-related disorder. In some of any such embodiments, the disease or disorder associated with BCMA is an autoimmune disease or disorder. In some embodiments, the autoimmune disease or disorder is systemic lupus erythematosus (SLE), lupus nephritis, inflammatory bowel disease, rheumatoid arthritis (e.g., juvenile rheumatoid arthritis), ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some of any such embodiments, the disease or disorder associated with BCMA is a cancer. In some embodiments, the cancer is a BCMA-expressing cancer. In some embodiments, the cancer is a B cell malignancy. In any of such embodiments, the cancer is a lymphoma, a leukemia, or a plasma cell malignancy. In some embodiments, the lymphoma is Burkitt lymphoma (e.g., endemic Burkitt's lymphoma or sporadic Burkitt's lymphoma), non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). In some embodiments, the leukemia is chronic lymphocytic leukemia (CLL), plasma cell leukemia or acute lymphocytic leukemia (ALL). In some embodiments, the plasma cell malignancy is multiple myeloma (e.g., non-secretory multiple myeloma, smoldering multiple myeloma) or plasmacytoma. In some of the embodiments herein, the disease or disorder associated with BCMA is one or more of glioblastoma, lymphomatoid granulomatosis, post-transplant lymphoproliferative disorder, an immunoregulatory disorder, heavy-chain disease, primary or immunocyte-associated amyloidosis, and monoclonal gammopathy of undetermined significance.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

Provided are BCMA-binding molecules, including antibodies (including antigen-binding antibody fragments, such as heavy chain variable ($V_H$) regions and single chain fragments, including scFvs) and recombinant receptors, including chimeric receptors and single chain cell surface proteins containing such antibodies and antigen-binding fragments, nucleic acids encoding such antibodies and antigen-binding fragments and receptors, and cells, such as recombinant or engineered cells for expressing and production of these antibodies and antigen-binding fragments or receptors. Also provided are methods of making and using the antibodies and antigen-binding fragments as well as cells (e.g., engineered cells) expressing or containing the antibodies and antigen-binding fragments or receptors. Also provided are compositions, including pharmaceutical compositions, containing such antibodies, antigen-binding fragments, receptors or cells. In some aspects, the provided compositions, antibodies, antigen-binding fragments, receptors or cells can be used in connection with a therapy or a method of treatment.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

I. BCMA-Binding Molecules

Provided in some aspects are BCMA-binding molecules, such as BCMA-binding polypeptides. Such binding molecules include antibodies (including antigen-binding fragments) that specifically bind to BCMA proteins, such as a human BCMA protein. Also among the binding molecules are polypeptides containing such antibodies, including single chain cell surface proteins, e.g., recombinant receptors such as chimeric antigen receptors (CARs), containing such antibodies.

A. BCMA Antibodies

Provided are anti-BCMA antibodies, including functional antigen-binding fragments. In some embodiments, the antibodies or antigen-binding fragments include those that are single domain antibodies, containing a heavy chain variable ($V_H$) region that, without pairing with a light chain antigen-binding site (e.g., light chain variable ($V_L$) region) and/or without any additional antibody domain or binding site, are capable of specifically binding to BCMA. Also among the antibodies or antigen-binding fragments are multi-domain antibodies, such as those containing $V_H$ and $V_L$ domains, comprised of the $V_H$ domain or antigen-binding site thereof of the single-domain antibody. In some embodiments, the antibodies or antigen-binding fragments include a heavy chain variable region and a light chain variable region, such as scFvs. The antibodies include antibodies that specifically bind to BCMA, e.g., human BCMA. Among the provided anti-BCMA antibodies are human antibodies. The antibodies include isolated antibodies. Also provided are BCMA-binding molecules containing such antibodies, e.g., single-chain proteins, fusion proteins, and/or recombinant receptors such as chimeric receptors, including antigen receptors. The BCMA-binding molecules include isolated molecules.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89-L97 | L89--L97 | L89--L96 |
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes (see e.g. Table 2, Table 3 and Table 4), although it is understood that a provided antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method, or other known schemes. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antibody is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

Single-domain antibodies (sdAbs) are antibody fragments comprising all or a portion of the heavy chain variable region or all or a portion of the light chain variable region of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-BCMA antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. The term includes antigen-binding fragments of human antibodies.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and BCMA-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

a. Exemplary Antibodies

In some embodiments, the antibody, e.g., the anti-BCMA antibody or antigen-binding fragment thereof, contains a heavy and/or light chain variable ($V_H$ and/or $V_L$) region sequence as described, or a sufficient antigen-binding portion thereof. In some embodiments, the anti-BCMA antibody or antigen-binding fragment thereof, contains a $V_H$ region sequence or sufficient antigen-binding portion thereof that contains a CDR-H1, CDR-H2 and/or CDR-H3 as described. In some embodiments, the anti-BCMA antibody or antigen-binding fragment thereof, contains a $V_L$ region sequence or sufficient antigen-binding portion that contains a CDR-L1, CDR-L2 and/or CDR-L3 as described. In some embodiments, the anti-BCMA antibody or antigen-binding fragment thereof, contains a $V_H$ region sequence that contains a CDR-H1, CDR-H2 and/or CDR-H3 as described and contains a $V_L$ region sequence that contains a CDR-L1, CDR-L2 and/or CDR-L3 as described. Also among the provided antibodies are those having sequences at least at or about 90%, about 91%, about 92%, about 93%, about 94%, about 95%, about 96%, about 97%, about 98%, or about 99% identical to such a sequence.

In some embodiments, the antibody, e.g., antigen-binding fragment thereof, has a heavy chain variable ($V_H$) region having the amino acid sequence selected from any one of SEQ ID NOs:110-115, 247-256, 518-531 and 533, or an amino acid sequence that has at least 90%, 91%, 92%, 93%, 94%, 95%, 96%, 97%, 98%, or 99% sequence identity to the $V_H$ region amino acid selected from any one of SEQ ID NOs:110-115, 247-256, 518-531 and 533, or contains a CDR-H1, +CDR-H2, and/or CDR-H3 present in such a $V_H$ sequence.

In some embodiments, the $V_H$ region of the anti-BCMA antibody is one that includes a heavy chain complementarity determining region 3 (CDR-H3) comprising the amino acid sequence $X_1X_2X_3X_4X_5X_6X_7X_8X_9X_{10}X_{11}X_{12}X_{13}X_{14}$ (SEQ ID NO:355), wherein $X_1$ is A, D, E, G, L, V or W; $X_2$ is A, D, G, L, P, Q or S; $X_3$ is A, D, G, L or Y; $X_4$ is D, G, P, R, S, V, Y or null; $X_5$ is D, I, P, S, T, Y or null; $X_6$ is A, G, I, S, T, V, Y or null; $X_7$ is A, D, E, F, L, P, S, Y or null; $X_8$ is P, Q, T, Y or null; $X_9$ is D, G, R, Y or null; $X_{10}$ is A, F, Y or null; $X_{11}$ is D, F or null; $X_{12}$ is F or null; $X_{13}$ is D, T or Y; and $X_{14}$ is I, L, N, V or Y. In some such embodiments, in said CDR-H3, $X_1$ is V; $X_2$ is D; $X_3$ is G; $X_4$ is D; $X_5$ is Y; $X_6$ is V; $X_7$ is D; $X_8$ is null; $X_9$ is null; $X_{10}$ is null; $X_{11}$ is null; $X_{12}$ is null; $X_{13}$ is D; and $X_{14}$ is Y.

In some embodiments, the provided antibody or antigen-binding fragment thereof comprises a CDR-H3 comprising the amino acid sequence selected from any one of SEQ ID NOs:7-11, 149-157, 279-287 and 376-378 according to Kabat numbering. In some embodiments, the $V_H$ region of a provided antibody or antigen-binding fragment thereof contains a CDR-H3 having the amino acid sequence comprising the amino acid sequence selected from any one of SEQ ID NOs:7-11, 149-157, 279-287 and 376-378 according to Chothia numbering or AbM numbering. In some embodiments, the provided antibody or antigen-binding fragment thereof contains a CDR-H3 having the amino acid sequence of SEQ ID NO:9 according to Kabat numbering, Chothia numbering or AbM numbering. In any of such examples, the provided antibody or antigen-binding fragment thereof can contain a $V_H$ region sequence selected from any one of SEQ ID NOs:110-115, 247-256, 518-531 and 533 in which the corresponding CDR-H3 sequence contained therein (e.g. corresponding to amino acid residues H95 to H102 by Kabat numbering) is replaced by the CDR-H3 sequence selected from any one of SEQ ID NOs: 7-11, 149-157, 279-287 and 376-378 according to Kabat numbering or any one of SEQ ID NOs:7-11, 149-157, 279-287 and 376-378 according to Chothia numbering or AbM numbering.

In some embodiments, the provided antibody or antigen-binding fragment thereof comprises a CDR-H3 comprising the amino acid sequence selected from any one of SEQ ID NOs:7-10, 149, 153-157 and 376, according to Kabat numbering, Chothia numbering or AbM numbering. In some embodiments, the provided antibody or antigen-binding fragment thereof comprises a CDR-H3 comprising the amino acid sequence selected from any one of SEQ ID NOs: 7, 9, 10 and 157, according to Kabat numbering, Chothia numbering or AbM numbering. In some embodiments, the provided antibody or antigen-binding fragment thereof comprises a CDR-H3 comprising the amino acid sequence selected from any one of SEQ ID NOs: 10 and 157, according to Kabat numbering, Chothia numbering or AbM numbering.

In some embodiments, the $V_H$ region of a provided antibody or antigen-binding fragment thereof comprises a CDR-H3 contained within the $V_H$ region amino acid sequence selected from any one of SEQ ID NOs:110-115, 247-256, 518-531 and 533. In some embodiments, the $V_H$ region of a provided antibody or antigen-binding fragment thereof comprises a CDR-H3 contained within the $V_H$ region amino acid sequence of SEQ ID NO:112. In some embodiments, the $V_H$ region of a provided antibody or antigen-binding fragment thereof comprises a CDR-H3 contained within the $V_H$ region amino acid sequence selected from any one of SEQ ID NOs:110-113, 115, 248, 252-256 and 518-522. In some embodiments, the $V_H$ region of a provided antibody or antigen-binding fragment thereof comprises a CDR-H3 contained within the $V_H$ region amino acid sequence selected from any one of SEQ ID NOs:110, 112, 115, 256 and 519. In some embodiments, the $V_H$ region of a provided antibody or antigen-binding fragment thereof comprises a CDR-H3 contained within the $V_H$ region amino acid sequence selected from any one of SEQ ID NOs:115 and 256.

In some embodiments, the $V_H$ region of the antibody or antigen-binding fragment thereof is one that includes a heavy chain complementarity determining region 1 (CDR-H1) comprising the amino acid sequence of $X_1X_2X_3MX_4$ (SEQ ID NO:353) $X_1$ is D or S; $X_2$ is Y or S; $X_3$ is A, G, W, or Y; and $X_4$ is H, Q, or S. In some embodiments, in said CDR-H1, $X_1$ is D; $X_2$ is Y; $X_3$ is Y; and $X_4$ is S.

In some embodiments, the $V_H$ region of a provided antibody or antigen-binding fragment thereof contains a CDR-H1 having the amino acid sequence comprising the amino acid sequence selected from any one of SEQ ID NOs:1-3 and 140-144 according to Kabat numbering. In some embodiments, the $V_H$ region of a provided antibody or antigen-binding fragment thereof contains a CDR-H1 having the amino acid sequence comprising the amino acid sequence selected from any one of SEQ ID NOs:12-15 and 158-160 according to Chothia numbering. In some embodiments, the $V_H$ region of a provided antibody or antigen-binding fragment thereof contains a CDR-H1 having the amino acid sequence comprising the amino acid sequence selected from any one of SEQ ID NOs:19-22, 165-169 and 509 according to AbM numbering. In some embodiments, the $V_H$ region of a provided antibody or antigen-binding fragment thereof contains a CDR-H1 having the amino acid sequence of SEQ ID NO:2, 13 or 20. In any of such examples, the provided antibody or antigen-binding fragment thereof can contain a $V_H$ region sequence selected from any one of SEQ ID NOs:110-115, 247-256, 518-531 and 533 in which the corresponding CDR-H1 sequence contained therein (e.g. corresponding to amino acid residues H31 to H35 by Kabat numbering) is replaced by the CDR-H1 sequence selected from any one of SEQ ID NOs:1-3 and 140-144 according to Kabat numbering, any one of SEQ ID NOs:12-15 and 158-160 according to Chothia numbering, or any one of SEQ ID NOs:19-22, 165-169 and 509 according to AbM numbering.

In some embodiments, the $V_H$ region of a provided antibody or antigen-binding fragment thereof contains a CDR-H1 having the amino acid sequence comprising the amino acid sequence selected from any one of SEQ ID NOs:1-3, 141, 143 and 144 according to Kabat numbering, any one of SEQ ID NOs:12-15, 158 and 160 according to Chothia numbering, or any one of SEQ ID NOs:19-22, 166, 168 or 169 according to AbM numbering. In some embodiments, the $V_H$ region of a provided antibody or antigen-binding fragment thereof contains a CDR-H1 having the amino acid sequence comprising the amino acid sequence selected from any one of SEQ ID NOs: 1 and 2 according to Kabat numbering, any one of SEQ ID NOs: 12 and 13 according to Chothia numbering, or any one of SEQ ID NOs: 19 and 20 according to AbM numbering. In some embodiments, the $V_H$ region of a provided antibody or antigen-binding fragment thereof contains a CDR-H1 having the amino acid sequence comprising the amino acid sequence of SEQ ID NO:2 according to Kabat numbering, SEQ ID NO:13 according to Chothia numbering, or SEQ ID NO:20 according to AbM numbering.

In some embodiments, the $V_H$ region of a provided antibody or antigen-binding fragment thereof contains a CDR-H1 contained within the $V_H$ region amino acid sequence selected from any one of SEQ ID NOs:110-115, 247-256, 518-531 and 533. In some embodiments, the $V_H$ region of a provided antibody or antigen-binding fragment thereof contains a CDR-H1 contained within the $V_H$ region amino acid sequence of SEQ ID NO:112. In some embodiments, the $V_H$ region of a provided antibody or antigen-binding fragment thereof comprises a CDR-H1 contained within the $V_H$ region amino acid sequence selected from any one of SEQ ID NOs:110-113, 115, 248, 252-256 and 518-522. In some embodiments, the $V_H$ region of a provided antibody or antigen-binding fragment thereof comprises a CDR-H1 contained within the $V_H$ region amino acid sequence selected from any one of SEQ ID NOs:110, 112, 115, 256 and 519. In some embodiments, the $V_H$ region of a provided antibody or antigen-binding fragment thereof comprises a CDR-H1 contained within the $V_H$ region amino acid sequence selected from any one of SEQ ID NOs:115 and 256.

In some embodiments, the $V_H$ region of a provided antibody or antigen-binding fragment thereof is one that includes a heavy chain complementarity determining region 2 (CDR-H2) comprising the amino acid sequence of $X_1IX_2X_3X_4X_5X_6X_7X_8X_9X_{10}X_{11}YX_{12}X_{13}X_{14}X_{15}X_{16}X_{17}$ (SEQ ID NO:354), wherein $X_1$ is F, G, H, V, W or Y; $X_2$ is N, R, S or V; $X_3$ is P, Q, S, V, W or Y; $X_4$ is K or null; $X_5$ is A or null; $X_6$ is D, G, N, S, or Y; $X_7$ is G or S; $X_8$ is G or S; $X_9$ is E, G, N, T or S; $X_{10}$ is I, K, or T; $X_{11}$ is E, G, N or Y; $X_{12}$ is A or V; $X_{13}$ is A, D or Q; $X_{14}$ is K or S; $X_{15}$ is F or V; $X_{16}$ is K or Q; and $X_{17}$ is E or G. In some embodiments in said CDR-H2, $X_1$ is Y; $X_2$ is 5, $X_3$ is 5; $X_4$ is null; $X_5$ is null; $X_6$ is 5; $X_7$ is G; $X_8$ is 5; $X_9$ is T; $X_{10}$ is I; $X_{11}$ is Y; $X_{12}$ is A; $X_{13}$ is D; $X_{14}$ is 5; $X_{15}$ is V; $X_{16}$ is K; and $X_{17}$ is G.

In some embodiments, the $V_H$ region of a provided antibody or antigen-binding fragment thereof contains a CDR-H2 comprising the amino acid sequence selected from any one of SEQ ID NOs:4-6, 145-148 and 372-374 according to Kabat numbering. In some embodiments, the $V_H$ region of a provided antibody or antigen-binding fragment thereof contains a CDR-H2 comprising the amino acid sequence selected from any one of SEQ ID NOs:16-18, 161-164 and 514-516 according to Chothia numbering. In some embodiments, the $V_H$ region of a provided antibody or antigen-binding fragment thereof contains a CDR-H2 comprising the amino acid sequence selected from any one of SEQ ID NOs:23-25, 170-173 and 510-512 according to AbM numbering. In some embodiments, the $V_H$ region of a provided antibody or antigen-binding fragment thereof contains a CDR-H2 having the amino acid sequence of SEQ ID NO:5 according to Kabat numbering. In some embodiments, the $V_H$ region of a provided antibody or antigen-binding fragment thereof contains a CDR-H2 having the amino acid sequence of SEQ ID NO:17 according to Chothia numbering. In some embodiments, the $V_H$ region of a provided antibody or antigen-binding fragment thereof contains a CDR-H2 having the amino acid sequence of SEQ ID NO:24 according to AbM numbering. In any of such examples, the provided antibody or antigen-binding fragment thereof can contain a $V_H$ region sequence selected from any one of SEQ ID NOs:110-115, 247-256, 518-531 and 533 in which the corresponding CDR-H2 sequence contained therein (e.g. corresponding to amino acid residues H50 to H65 by Kabat numbering) is replaced by the CDR-H2 sequence selected from any one of SEQ ID NOs:4-6, 145-148 and 372-374, any one of SEQ ID NOs:16-18, 161-164 and 514-516 according to Chothia numbering, or any one of SEQ ID NOs:23-25, 170-173 and 510-512 according to AbM numbering.

In some embodiments, the $V_H$ region of a provided antibody or antigen-binding fragment thereof contains a CDR-H2 having the amino acid sequence comprising the amino acid sequence selected from any one of SEQ ID NOs:4-6, 145, 147, 148 and 372 according to Kabat numbering, any one of SEQ ID NOs:16-18, 161, 163, 164 and 514 according to Chothia numbering, or any one of SEQ ID NOs:23-25, 170, 172, 173 and 510 according to AbM numbering. In some embodiments, the $V_H$ region of a provided antibody or antigen-binding fragment thereof contains a CDR-H2 having the amino acid sequence comprising the amino acid sequence selected from any one of SEQ ID NOs: 4 and 5 according to Kabat numbering, any one of SEQ ID NOs: 16 and 17 according to Chothia numbering, or any one of SEQ ID NOs: 23 and 24 according to AbM numbering. In some embodiments, the $V_H$ region of a provided antibody or antigen-binding fragment thereof contains a CDR-H2 having the amino acid sequence comprising the amino acid sequence of SEQ ID NO:5 according to Kabat numbering, SEQ ID NO:17 according to Chothia numbering, or SEQ ID NO:24 according to AbM numbering.

In some embodiments, the $V_H$ region of a provided antibody or antigen-binding fragment thereof contains a CDR-H2 contained within the $V_H$ region amino acid sequence selected from any one of SEQ ID NOs:110-115, 247-256, 518-531 and 533. In some embodiments, the $V_H$ region of a provided antibody or antigen-binding fragment thereof contains a CDR-H2 contained within the $V_H$ region amino acid sequence of SEQ ID NO:112. In some embodiments, the $V_H$ region of a provided antibody or antigen-binding fragment thereof comprises a CDR-H2 contained within the $V_H$ region amino acid sequence selected from any one of SEQ ID NOs:110-113, 115, 248, 252-256 and 518-522. In some embodiments, the $V_H$ region of a provided antibody or antigen-binding fragment thereof comprises a CDR-H2 contained within the $V_H$ region amino acid sequence selected from any one of SEQ ID NOs:110, 112, 115, 256 and 519. In some embodiments, the $V_H$ region of a provided antibody or antigen-binding fragment thereof comprises a CDR-H2 contained within the $V_H$ region amino acid sequence selected from any one of SEQ ID NOs:115 and 256.

In some embodiments, the provided antibody or antigen-binding fragment thereof contains a CDR-H1 that is or comprises the amino acid sequence selected from any one of SEQ ID NOs:1-3 and 140-144 according to Kabat numbering; a CDR-H2 that is or comprises the amino acid sequence selected from any one of SEQ ID NOs:4-6, 145-148 and 372-374 according to Kabat numbering; and a CDR-H3 that is or comprises the amino acid sequence selected from any one of SEQ ID NOs:7-11, 149-157, 279-287 and 376-378 according to Kabat numbering. In some embodiments, the provided antibody or antigen-binding fragment thereof contains a CDR-H1 that is or comprises the amino acid sequence selected from any one of SEQ ID NOs:12-15 and 158-160 according to Chothia numbering; a CDR-H2 that is or comprises the amino acid sequence selected from any one of SEQ ID NOs:16-18, 161-164 and 514-516 according to Chothia numbering; and a CDR-H3 that is or comprises the amino acid sequence selected from any one of SEQ ID NOs:7-11, 149-157, 279-287 and 376-378 according to Chothia numbering. In some embodiments, the provided antibody or antigen-binding fragment thereof contains a CDR-H1 that is or comprises the amino acid sequence selected from any one of SEQ ID NO:19-22, 165-169 and 509 according to AbM numbering; a CDR-H2 that is or comprises the amino acid sequence selected from any one of SEQ ID NOs:23-25, 170-173 and 510-512 according to AbM numbering; and a CDR-H3 that is or comprises the amino acid sequence selected from any one of SEQ ID NOs:7-11, 149-157, 279-287 and 376-378 according to AbM numbering.

In some embodiments, the $V_H$ region of a provided antibody or antigen-binding fragment thereof comprises a CDR-H1, CDR-H2, and/or CDR-H3 according to Kabat numbering as shown in Table 2 and Table 4. In some embodiments, the $V_H$ region of a provided antibody or antigen-binding fragment thereof comprises a CDR-H1, CDR-H2, and/or CDR-H3 according to Chothia numbering as shown in Table 4. In some embodiments, the $V_H$ region of a provided antibody or antigen-binding fragment thereof comprises a CDR-H1, CDR-H2, and/or CDR-H3 according to AbM numbering as shown in Table 4.

In some embodiments, the provided antibody or antigen-binding fragment thereof comprises an $V_H$ region comprising a CDR-H1, CDR-H2, and CDR-H3 selected from the group consisting of: a CDR-H1, CDR-H2, and CDR-H3 comprising the amino acid sequence of SEQ ID NOs:1, 4, and 7, respectively; a CDR-H1, CDR-H2, and CDR-H3 comprising the amino acid sequence of SEQ ID NOs:2, 5, and 8, respectively; a CDR-H1, CDR-H2, and CDR-H3 comprising the amino acid sequence of SEQ ID NOs:2, 5, and 9, respectively; a CDR-H1, CDR-H2, and CDR-H3 comprising the amino acid sequence of SEQ ID NOs:2, 5, and 10, respectively; a CDR-H1, CDR-H2, and CDR-H3 comprising the amino acid sequence of SEQ ID NOs:3, 6, and 11, respectively; a CDR-H1, CDR-H2, and CDR-H3 comprising the amino acid sequence of SEQ ID NOs:140, 145, and 149, respectively; a CDR-H1, CDR-H2, and CDR-H3 comprising the amino acid sequence of SEQ ID NOs: 141, 145, and 149, respectively; a CDR-H1, CDR-H2, and CDR-H3 comprising the amino acid sequence of SEQ ID NOs:141, 145, and 150, respectively; a CDR-H1, CDR-H2, and CDR-H3 comprising the amino acid sequence of SEQ ID NOs:142, 146, and 151, respectively; a CDR-H1, CDR-H2, and CDR-H3 comprising the amino acid sequence of SEQ ID NOs:2, 5, and 152, respectively; a CDR-H1, CDR-H2, and CDR-H3 comprising the amino acid sequence of SEQ ID NOs:143, 147, and 153, respectively; a CDR-H1, CDR-H2, and CDR-H3 comprising the amino acid sequence of SEQ ID NOs:144, 148, and 154, respectively; a CDR-H1, CDR-H2, and CDR-H3 comprising the amino acid sequence of SEQ ID NOs:3, 6, and 155, respectively; a CDR-H1, CDR-H2, and CDR-H3 comprising the amino acid sequence of SEQ ID NOs:2, 5, and 156, respectively; a CDR-H1, CDR-H2, and CDR-H3 comprising the amino acid sequence of SEQ ID NOs:2, 5, and 157, respectively; a CDR-H1, CDR-H2, and CDR-H3 comprising the amino acid sequence of SEQ ID NOs:2, 6, and 376, respectively; a CDR-H1, CDR-H2, and CDR-H3 comprising the amino acid sequence of SEQ ID NOs:3, 372, and 376, respectively; a CDR-H1, CDR-H2, and CDR-H3 comprising the amino acid sequence of SEQ ID NOs:3, 6, and 376, respectively; a CDR-H1, CDR-H2, and CDR-H3 comprising the amino acid sequence of SEQ ID NOs:3, 6, and 377, respectively; a CDR-H1, CDR-H2, and CDR-H3 comprising the amino acid sequence of SEQ ID NOs:2, 373, and 152, respectively; a CDR-H1, CDR-H2, and CDR-H3 comprising the amino acid sequence of SEQ ID NOs:2, 5, and 378, respectively; a CDR-H1, CDR-H2, and CDR-H3 comprising the amino acid sequence of SEQ ID NOs:2, 374, and 9, respectively, according to Kabat numbering. In some embodiments, the provided antibody or antigen-binding fragment thereof comprises an $V_H$ region comprising a CDR-H1, CDR-H2, and CDR-H3 comprising the amino acid sequence of SEQ ID NOs:2, 5, and 9, respectively, according to Kabat numbering. In some embodiments, the provided antibody or antigen-binding fragment thereof comprises an $V_H$ region comprising a CDR-H1, CDR-H2, and CDR-H3 comprising the amino acid sequence of SEQ ID NOs:13, 17, and 9, respectively, according to Chothia numbering. In some embodiments, the provided antibody or antigen-binding fragment thereof comprises an $V_H$ region comprising a CDR-H1, CDR-H2, and CDR-H3 comprising the amino acid sequence of SEQ ID NOs:20, 24, and 9, respectively, according to AbM numbering.

For example, the antibody or antigen-binding fragment thereof provided herein comprises an $V_H$ region comprising a CDR-H1, CDR-H2, and CDR-H3 comprising the amino acid sequence selected from among: SEQ ID NOs:1, 4, and 7; SEQ ID NOs:2, 5, and 8; SEQ ID NOs:2, 5, and 9; SEQ ID NOs:2, 5, and 10; SEQ ID NOs:3, 6, and 11; SEQ ID NOs:140, 145, and 149; SEQ ID NOs:141, 145, and 149; SEQ ID NOs:141, 145, and 150; SEQ ID NOs:142, 146, and 151; SEQ ID NOs:2, 5, and 152; SEQ ID NOs:143, 147, and 153; SEQ ID NOs:144, 148, and 154; SEQ ID NOs:3, 6, and 155; SEQ ID NOs:2, 5, and 156; SEQ ID NOs:2, 5, and 157; SEQ ID NOs:2, 6, and 376; SEQ ID NOs:3, 372, and 376; SEQ ID NOs:3, 6, and 376; SEQ ID NOs:3, 6, and 377; SEQ ID NOs:2, 373, and 152; SEQ ID NOs:2, 5, and 378; SEQ ID NOs:2, 374, and 9, respectively, according to Kabat numbering.

In some embodiments, the antibody or antigen-binding fragment thereof provided herein comprises an $V_H$ region comprising a CDR-H1, CDR-H2, and CDR-H3 comprising the amino acid sequence selected from among: SEQ ID NOs:1, 4, and 7; SEQ ID NOs:2, 5, and 8; SEQ ID NOs:2, 5, and 9; SEQ ID NOs:2, 5, and 10; SEQ ID NOs:141, 145, and 149; SEQ ID NOs:143, 147, and 153; SEQ ID NOs:144, 148, and 154; SEQ ID NOs:3, 6, and 155; SEQ ID NOs:2, 5, and 156; SEQ ID NOs:2, 5, and 157; SEQ ID NOs:2, 6, and 376; SEQ ID NOs:3, 372, and 376; SEQ ID NOs:3, 6, and 376, respectively, according to Kabat numbering. In some embodiments, the antibody or antigen-binding fragment thereof provided herein comprises an $V_H$ region comprising a CDR-H1, CDR-H2, and CDR-H3 comprising the amino acid sequence selected from among: SEQ ID NOs:1, 4, and 7; SEQ ID NOs:2, 5, and 9; SEQ ID NOs:2, 5, and 10; and SEQ ID NOs:2, 5, and 157, respectively, according to Kabat numbering. In some embodiments, the antibody or antigen-binding fragment thereof provided herein comprises an $V_H$ region comprising a CDR-H1, CDR-H2, and CDR-H3 comprising the amino acid sequence selected from among: SEQ ID NOs:2, 5, and 10; and SEQ ID NOs:2, 5, and 157, respectively, according to Kabat numbering.

In some embodiments, the provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence selected from any one of SEQ ID NOs:110-115, 247-256, 518-531 and 533. In some embodiments, the provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence of SEQ ID NO:112. In some embodiments, the $V_H$ region of a provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence selected from any one of SEQ ID NOs:110-113, 115, 248, 252-256 and 518-522. In some embodiments, the $V_H$ region of a provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence selected from any one of SEQ ID NOs:110, 112, 115, 256 and 519. In some embodiments, the $V_H$ region of a provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence selected from any one of SEQ ID NOs:115 and 256.

In some embodiments of the antibody or antigen-binding fragment thereof provided herein, the $V_H$ region comprises any of the CDR-H1, CDR-H2 and CDR-H3 as described and comprises a framework region 1 (FR1), a FR2, a FR3 and/or a FR4 having at least 90%, 91%, 92%, 93%, 94%, 95%, 96%, 97%, 98%, or 99% sequence identity, respectively, to a FR1, a FR2, a FR3 and/or a FR4 contained within the $V_H$ region amino acid sequence selected from any one of SEQ ID NOs:110-115, 247-256, 518-531 and 533. For example, the anti-BCMA antibody or antigen-binding fragment thereof can comprise a CDR-H1, CDR-H2 and CDR-H3, respectively, contained within the $V_H$ region amino acid sequence selected from any one of SEQ ID NOs:110-115, 247-256, 518-531 and 533, and a framework region (e.g., a FR1, a FR2, a FR3 and/or a FR4) that contains at least 90%, 91%, 92%, 93%, 94%, 95%, 96%, 97%, 98%, 99% sequence identity to a framework region (e.g., a FR1, a FR2, a FR3 and/or a FR4) contained within the $V_H$ region amino acid sequence selected from any one of SEQ ID NOs:110-115, 247-256, 518-531 and 533. In some embodiments, the $V_H$ region comprises a FR1, a FR2, a FR3 and/or a FR4 selected from a FR1 comprising the amino acid sequence selected from any one of SEQ ID NOs:59-63, 195-203 and 434-439; a FR2 comprising the amino acid sequence selected from any one of SEQ ID NOs:64-66 and 204-209; a FR3 comprising the amino acid sequence selected from any one of SEQ ID NOs:67-69, 210-216, 441 and 443; and/or a FR4 comprising the amino acid sequence selected from any one of SEQ ID NOs:70-71, 217-220, 444 and 445. In some embodiments, the $V_H$ region comprises a FR1 comprising the amino acid sequence of SEQ ID NO:61, a FR2 comprising the amino acid sequence of SEQ ID NO:65, a FR3 comprising the amino acid sequence of SEQ ID NO:69, and/or a FR4 comprising the amino acid of SEQ ID NO:70.

In some embodiments, the provided antibody or antigen-binding fragment thereof comprises a $V_H$ region comprising the amino acid sequence selected from any one of SEQ ID NOs:110-115, 247-256, 518-531 and 533. In some embodiments, provided antibody or antigen-binding fragment thereof comprises a $V_H$ region comprising the amino acid sequence selected from any one of SEQ ID NOs: 110-113, 115, 248, 252-256 and 518-522. In some embodiments, provided antibody or antigen-binding fragment thereof comprises a $V_H$ region comprising the amino acid sequence selected from any one of SEQ ID NOs: 110, 112, 115, 256 and 519. In some embodiments, provided antibody or antigen-binding fragment thereof comprises a $V_H$ region comprising the amino acid sequence selected from any one of SEQ ID NOs:115 and 256.

Also provided are antibodies and antigen-binding fragments thereof having sequences at least at or about at least 90%, 91%, 92%, 93%, 94%, 95%, 96%, 97%, 98%, or 99% identical to such sequences. For example, provided herein is an antibody or antigen-binding fragment comprising a $V_H$ region comprising an amino acid sequence having at least 90%, 91%, 92%, 93%, 94%, 95%, 96%, 97%, 98%, or 99% sequence identity to a $V_H$ region amino acid sequence selected from any one of SEQ ID NOs:110-115, 247-256, 518-531 and 533.

In some embodiments, the antibody is a single domain antibody (sdAb) comprising only a $V_H$ region sequence or a sufficient antigen-binding portion thereof, such as any of the above described $V_H$ sequences (e.g., a CDR-H1, a CDR-H2, a CDR-H3 and/or a CDR-H4).

In some embodiments, an antibody provided herein (e.g., an anti-BCMA antibody) or antigen-binding fragment thereof comprising a $V_H$ region further comprises a light chain or a sufficient antigen binding portion thereof. For example, in some embodiments, the antibody or antigen-binding fragment thereof contains a $V_H$ region and a $V_L$ region, or a sufficient antigen-binding portion of a $V_H$ and $V_L$ region. In such embodiments, a $V_H$ region sequence can be any of the above described $V_H$ sequence. In some such embodiments, the antibody is an antigen-binding fragment, such as a Fab or an scFv. In some such embodiments, the antibody is a full-length antibody that also contains a constant region.

In some embodiments, the antibody, e.g., antigen-binding fragment thereof, has a light chain variable ($V_L$) region having the amino acid sequence selected from any one of SEQ ID NOs:116-127, 257-267, 534-550 and 552-557, or an amino acid sequence that has at least 90%, 91%, 92%, 93%, 94%, 95%, 96%, 97%, 98%, or 99% sequence identity to a $V_L$ region amino acid sequence selected from any one of SEQ ID NOs:116-127, 257-267, 534-550 and 552-557.

In some embodiments, the $V_L$ region of the antibody described herein (e.g., an anti-BCMA antibody) or antigen-binding fragment thereof is one that includes a light chain complementarity determining region 3 (CDR-L3) comprising the amino acid sequence $X_1X_2X_3X_4X_5X_6X_7X_8X_9X_{10}X_{11}X_{12}$, (SEQ ID NO:358), wherein $X_1$ is A, C, G, H, I, Q or S; $X_2$ is A, Q, S or V; $X_3$ is 5, W or Y; $X_4$ is D, F, G, H or Y; $X_5$ is D, G, M, R, S or T; $X_6$ is A, G, H, L, R, S, T or Y; $X_7$ is L, P, R, S or null; $X_8$ is D, G, N, R, S, T or null; $X_9$ is A, G, H, L, P or null; $X_{10}$ is F, S or null; $X_{11}$ is L, P, W or Y; and $X_{12}$ is S, T or V. In some embodiments, in said CDR-L3, $X_1$ is H; $X_2$ is V; $X_3$ is W; $X_4$ is D; $X_5$ is R; $X_6$ is 5; $X_7$ is R; $X_8$ is D; $X_9$ is H; $X_{10}$ is null; $X_{11}$ is Y; and $X_{12}$ is V.

In some embodiments, the provided antibody or antigen-binding fragment thereof contains a CDR-L3 comprising the amino acid sequence selected from any one of SEQ ID NOs:47-58, 184-194, 415-427 and 429-433 according to Kabat numbering, Chothia numbering or AbM numbering. In some embodiments, the provided antibody or antigen-binding fragment thereof contains a CDR-L3 having the amino acid sequence of SEQ ID NO:55 according to Kabat numbering, Chothia numbering or AbM numbering. In any of such examples, the provided antibody or antigen-binding fragment thereof can contain a $V_L$ region sequence selected from any one of SEQ ID NOs:116-127, 257-267, 534-550 and 552-557 in which the corresponding CDR-L3 sequence contained therein (e.g. corresponding to amino acid residues L89 to L97 by Kabat numbering) is replaced by the CDR-L3 sequence selected from any one of SEQ ID NOs:47-58, 184-194, 415-427 and 429-433 according to Kabat numbering, Chothia numbering or AbM numbering.

In some embodiments, the provided antibody or antigen-binding fragment thereof comprises a CDR-L3 comprising the amino acid sequence selected from any one of SEQ ID NOs:47-49, 51, 52, 55, 56, 185, 189-194, 415-418 and 421, according to Kabat numbering, Chothia numbering or AbM numbering. In some embodiments, the provided antibody or antigen-binding fragment thereof comprises a CDR-L3 comprising the amino acid sequence selected from any one of SEQ ID NOs: 47, 51, 55, 194, 416 and 421, according to Kabat numbering, Chothia numbering or AbM numbering. In some embodiments, the provided antibody or antigen-binding fragment thereof comprises a CDR-L3 comprising the amino acid sequence selected from any one of SEQ ID NOs: 194 and 421, according to Kabat numbering, Chothia numbering or AbM numbering.

In some embodiments, the $V_L$ region of a provided antibody or antigen-binding fragment thereof comprises a CDR-L3 contained within the $V_L$ region amino acid sequence selected from any one of SEQ ID NOs:116-127, 257-267, 534-550 and 552-557. In some embodiments, the $V_L$ region of a provided antibody or antigen-binding fragment thereof comprises a CDR-L3 contained within the $V_L$ region amino acid sequence of SEQ ID NO:124. In some embodiments, the $V_L$ region of a provided antibody or antigen-binding fragment thereof comprises a CDR-L3 contained within the $V_L$ region amino acid sequence selected from any one of SEQ ID NOs:116-118, 120, 121, 124, 125, 258, 262-267 and 534-538. In some embodiments, the $V_L$ region of a provided antibody or antigen-binding fragment thereof comprises a CDR-L3 contained within the $V_L$ region amino acid sequence selected from any one of SEQ ID NOs:116, 120, 124, 267, 535 and 536. In some embodiments, the $V_L$ region of a provided antibody or antigen-binding fragment thereof comprises a CDR-L3 contained within the $V_L$ region amino acid sequence selected from any one of SEQ ID NOs:267 and 536.

In some embodiments, the $V_L$ region of the antibody described herein (e.g., an anti-BCMA antibody) or antigen-binding fragment thereof is one that includes a light chain complementarity determining region 1 (CDR-L1) that contains the amino acid sequence: $X_1X_2X_3X_4X_5X_6X_7X_8X_9X_{10}X_{11}X_{12}X_{13}X_{14}X_{15}X_{16}X_{17}$ (SEQ ID NO:356), wherein $X_1$ is G, K, R, S or T; $X_2$ is A, G or S; $X_3$ is G, N, S or T; $X_4$ is G, K, N, Q, R or S; $X_5$ is S or null; $X_6$ is D, N, V or null; $X_7$ is L, V or null; $X_8$ is H, S, Y or null; X$_9$ is S, T or null; X$_{10}$ is S or null; X$_{11}$ is D, G, I, N, S or null; X$_{12}$ is D, E, G, K, I, N or null; X$_{13}$ is F, G, K, N, R, S, Y or null; X$_{14}$ is D, K, N, T or null; X$_{15}$ is A, D, G, L, N, S, T or Y; X$_{16}$ is L or V; X$_{17}$ is A, H, N, Q or S. In some embodiments, X$_1$ is G; X$_2$ is A; X$_3$ is N; X$_4$ is N; X$_5$ is null; X$_6$ is null; X$_7$ is null; X$_8$ is null; X$_9$ is null; X$_{10}$ is null; X$_{11}$ is I; X$_{12}$ is G; X$_{13}$ is 5; X$_{14}$ is K; X$_{15}$ is 5; X$_{16}$ is V; X$_{17}$ is H.

In some embodiments, the provided antibody or antigen-binding fragment thereof contains a CDR-L1 comprising the amino acid sequence selected from any one of SEQ ID NOs:26-36, 174-178, 380-392 and 394-398 according to Kabat numbering, Chothia numbering or AbM numbering. In some embodiments, the provided antibody or antigen-binding fragment thereof contains a CDR-L1 having the amino acid sequence of SEQ ID NO:33 according to Kabat numbering, Chothia numbering or AbM numbering. In any of such examples, the provided antibody or antigen-binding fragment thereof can contain a V$_L$ region sequence selected from any one of SEQ ID NOs:116-127, 257-267, 534-550 and 552-557 in which the corresponding CDR-L1 sequence contained therein (e.g. corresponding to amino acid residues L24 to L34 by Kabat numbering) is replaced by the CDR-L1 sequence selected from any one of SEQ ID NOs:26-36, 174-178, 380-392 and 394-398 according to Kabat numbering, Chothia numbering or AbM numbering.

In some embodiments, the V$_L$ region of a provided antibody or antigen-binding fragment thereof contains a CDR-L1 having the amino acid sequence comprising the amino acid sequence selected from any one of SEQ ID NOs:26-28, 30, 31, 33, 34, 174, 176-178 and 380-382, according to Kabat numbering, Chothia numbering or AbM numbering. In some embodiments, the V$_L$ region of a provided antibody or antigen-binding fragment thereof contains a CDR-L1 having the amino acid sequence comprising the amino acid sequence selected from any one of SEQ ID NOs:26, 30, 33, 178 and 380, according to Kabat numbering, Chothia numbering or AbM numbering. In some embodiments, the V$_L$ region of a provided antibody or antigen-binding fragment thereof contains a CDR-L1 having the amino acid sequence comprising the amino acid sequence selected from any one of SEQ ID NOs:33 and 178, according to Kabat numbering, Chothia numbering or AbM numbering.

In some embodiments, the V$_L$ region of a provided antibody or antigen-binding fragment thereof comprises a CDR-L1 contained within the V$_L$ region amino acid sequence selected from any one of SEQ ID NOs:116-127, 257-267, 534-550 and 552-557. In some embodiments, the V$_L$ region of a provided antibody or antigen-binding fragment thereof comprises a CDR-L1 contained within the V$_L$ region amino acid sequence of SEQ ID NO:124. In some embodiments, the V$_L$ region of a provided antibody or antigen-binding fragment thereof comprises a CDR-L1 contained within the V$_L$ region amino acid sequence selected from any one of SEQ ID NOs:116-118, 120, 121, 124, 125, 258, 262-267 and 534-538, according to Kabat numbering, Chothia numbering or AbM numbering. In some embodiments, the V$_L$ region of a provided antibody or antigen-binding fragment thereof comprises a CDR-L1 contained within the V$_L$ region amino acid sequence selected from any one of SEQ ID NOs:116, 120, 124, 267, 535 and 536, according to Kabat numbering, Chothia numbering or AbM numbering. In some embodiments, the V$_L$ region of a provided antibody or antigen-binding fragment thereof comprises a CDR-L1 contained within the V$_L$ region amino acid sequence selected from any one of SEQ ID NOs:267 and 536, according to Kabat numbering, Chothia numbering or AbM numbering.

In some embodiments, the V$_L$ region of the antibody provided herein (e.g., an anti-BCMA antibody) or antigen-binding fragment thereof is one that includes a light chain complementarity determining region 2 (CDR-L2) that contains the amino acid sequence of X$_1$X$_2$X$_3$X$_4$X$_5$X$_6$X$_7$ (SEQ ID NO:357), wherein X$_1$ is A, D, E, N, S, V or W; X$_2$ is A, D, N, S or V; X$_3$ is A, D, H, I, N or S; X$_4$ is D, K, N, Q, R or T; X$_5$ is L, R or V; X$_6$ is A, E, P or Q; and X$_7$ is A, D, S or T. In some embodiments, X$_1$ is D; X$_2$ is D; X$_3$ is D; X$_4$ is D; X$_5$ is R; X$_6$ is P; and X$_7$ is S.

In some embodiments, the provided antibody or antigen-binding fragment thereof contains a CDR-L2 comprising the amino acid sequence selected from any one of SEQ ID NOs:37-46, 179-183, 399-409 and 411-414 according to Kabat numbering, Chothia numbering or AbM numbering. In some embodiments, the provided antibody or antigen-binding fragment thereof contains a CDR-L2 having the amino acid sequence of SEQ ID NO:43 according to Kabat numbering, Chothia numbering or AbM numbering. In any of such examples, the provided antibody or antigen-binding fragment thereof can contain a V$_L$ region sequence selected from any one of SEQ ID NOs:116-127, 257-267, 534-550 and 552-557 in which the corresponding CDR-L2 sequence contained therein (e.g. corresponding to amino acid residues L50 to L56 by Kabat numbering) is replaced by the CDR-L2 sequence selected from any one of SEQ ID NOs:37-46, 179-183, 399-409 and 411-414 according to Kabat numbering, Chothia numbering or AbM numbering.

In some embodiments, the V$_L$ region of a provided antibody or antigen-binding fragment thereof comprises a CDR-L2 contained within the V$_L$ region amino acid sequence selected from any one of SEQ ID NOs:37-39, 41, 43, 44, 179, 181-183 and 399-401, according to Kabat numbering, Chothia numbering or AbM numbering. In some embodiments, the V$_L$ region of a provided antibody or antigen-binding fragment thereof comprises a CDR-L2 contained within the V$_L$ region amino acid sequence selected from any one of SEQ ID NOs:37, 39, 43, 183 and 400, according to Kabat numbering, Chothia numbering or AbM numbering. In some embodiments, the V$_L$ region of a provided antibody or antigen-binding fragment thereof comprises a CDR-L2 contained within the V$_L$ region amino acid sequence selected from any one of SEQ ID NOs:43 and 183, according to Kabat numbering, Chothia numbering or AbM numbering.

In some embodiments, the V$_L$ region of a provided antibody or antigen-binding fragment thereof comprises a CDR-L2 contained within the V$_L$ region amino acid sequence selected from any one of SEQ ID NOs:116-127, 257-267, 534-550 and 552-557. In some embodiments, the V$_L$ region of a provided antibody or antigen-binding fragment thereof comprises a CDR-L2 contained within the V$_L$ region amino acid sequence of SEQ ID NO:124. In some embodiments, the V$_L$ region of a provided antibody or antigen-binding fragment thereof comprises a CDR-L2 contained within the V$_L$ region amino acid sequence selected from any one of SEQ ID NOs:116-118, 120, 121, 124, 125, 258, 262-267 and 534-538. In some embodiments, the V$_L$ region of a provided antibody or antigen-binding fragment thereof comprises a CDR-L2 contained within the V$_L$ region amino acid sequence selected from any one of SEQ ID NOs:116, 120, 124, 267, 535 and 536. In some embodiments, the V$_L$ region of a provided antibody or antigen-binding fragment thereof comprises a CDR-L2 contained within the V$_L$ region amino acid sequence selected from any one of SEQ ID NOs:267 and 536.

In some embodiments, the provided antibody or antigen-binding fragment thereof contains a CDR-L1 that is or comprises the amino acid sequence selected from any one of SEQ ID NOs:26-36, 174-178, 380-392 and 394-398 according to Kabat numbering, Chothia numbering or AbM numbering; a CDR-L2 that is or comprises the amino acid sequence selected from any one of SEQ ID NOs:37-46, 179-183, 399-409 and 411-414 according to Kabat numbering, Chothia numbering or AbM numbering; and a CDR-L3 that is or comprises the amino acid sequence selected from any one of SEQ ID NOs:47-58, 184-194, 415-427 and 429-433 according to Kabat numbering, Chothia numbering or AbM numbering.

In some embodiments, the $V_L$ region of a provided antibody or antigen-binding fragment thereof comprises a CDR-L1, CDR-L2, and/or CDR-L3 according to Kabat numbering as shown in Table 2 and Table 4. In some embodiments, the $V_L$ region of a provided antibody or antigen-binding fragment thereof comprises a CDR-L1, CDR-L2, and/or CDR-L3 according to Chothia numbering as shown in Table 4. In some embodiments, the $V_L$ region of a provided antibody or antigen-binding fragment thereof comprises a CDR-L1, CDR-L2, and/or CDR-L3 according to AbM numbering as shown in Table 4.

In some embodiments of the antibody or antigen-binding fragment thereof provided herein, the $V_L$ region comprises a CDR-L1, a CDR-L2, and a CDR-L3 selected from among: a CDR-L1, CDR-L2, and CDR-L3 comprising the amino acid sequence of SEQ ID NOs:26, 37, and 47, respectively; a CDR-L1, CDR-L2, and CDR-L3 comprising the amino acid sequence of SEQ ID NOs:27, 38, and 48, respectively; a CDR-L1, CDR-L2, and CDR-L3 comprising the amino acid sequence of SEQ ID NOs:28, 39, and 49, respectively; a CDR-L1, CDR-L2, and CDR-L3 comprising the amino acid sequence of SEQ ID NOs:29, 40, and 50, respectively; a CDR-L1, CDR-L2, and CDR-L3 comprising the amino acid sequence of SEQ ID NOs:30, 39, and 51, respectively; a CDR-L1, CDR-L2, and CDR-L3 comprising the amino acid sequence of SEQ ID NOs:31, 41, and 52, respectively; a CDR-L1, CDR-L2, and CDR-L3 comprising the amino acid sequence of SEQ ID NOs:32, 42, and 53, respectively; a CDR-L1, CDR-L2, and CDR-L3 comprising the amino acid sequence of SEQ ID NOs:30, 39, and 54, respectively; a CDR-L1, CDR-L2, and CDR-L3 comprising the amino acid sequence of SEQ ID NOs:33, 43, and 55, respectively; a CDR-L1, CDR-L2, and CDR-L3 comprising the amino acid sequence of SEQ ID NOs:34, 44, and 56, respectively; a CDR-L1, CDR-L2, and CDR-L3 comprising the amino acid sequence of SEQ ID NOs:35, 45, and 57, respectively; a CDR-L1, CDR-L2, and CDR-L3 comprising the amino acid sequence of SEQ ID NOs:36, 46, and 58, respectively; a CDR-L1, CDR-L2, and CDR-L3 comprising the amino acid sequence of SEQ ID NOs:174, 179, and 184, respectively; a CDR-L1, CDR-L2, and CDR-L3 comprising the amino acid sequence of SEQ ID NOs:174, 179, and 185, respectively; a CDR-L1, CDR-L2, and CDR-L3 comprising the amino acid sequence of SEQ ID NOs:174, 179, and 186, respectively; a CDR-L1, CDR-L2, and CDR-L3 comprising the amino acid sequence of SEQ ID NOs:174, 179, and 187, respectively; a CDR-L1, CDR-L2, and CDR-L3 comprising the amino acid sequence of SEQ ID NOs:175, 180, and 188, respectively; a CDR-L1, CDR-L2, and CDR-L3 comprising the amino acid sequence of SEQ ID NOs:174, 179, and 189, respectively; a CDR-L1, CDR-L2, and CDR-L3 comprising the amino acid sequence of SEQ ID NOs:176, 181, and 190, respectively; a CDR-L1, CDR-L2, and CDR-L3 comprising the amino acid sequence of SEQ ID NOs:177, 182, and 191, respectively; a CDR-L1, CDR-L2, and CDR-L3 comprising the amino acid sequence of SEQ ID NOs:174, 179, and 192, respectively; a CDR-L1, CDR-L2, and CDR-L3 comprising the amino acid sequence of SEQ ID NOs:178, 183, and 193, respectively; a CDR-L1, CDR-L2, and CDR-L3 comprising the amino acid sequence of SEQ ID NOs:178, 183, and 194, respectively; a CDR-L1, CDR-L2, and CDR-L3 comprising the amino acid sequence of SEQ ID NOs:30, 399, and 415, respectively; a CDR-L1, CDR-L2, and CDR-L3 comprising the amino acid sequence of SEQ ID NOs:380, 400, and 416, respectively; a CDR-L1, CDR-L2, and CDR-L3 comprising the amino acid sequence of SEQ ID NOs:33, 43, and 421, respectively; a CDR-L1, CDR-L2, and CDR-L3 comprising the amino acid sequence of SEQ ID NOs:381, 401, and 417, respectively; a CDR-L1, CDR-L2, and CDR-L3 comprising the amino acid sequence of SEQ ID NOs:382, 402, and 418, respectively; a CDR-L1, CDR-L2, and CDR-L3 comprising the amino acid sequence of SEQ ID NOs:383, 403, and 419, respectively; a CDR-L1, CDR-L2, and CDR-L3 comprising the amino acid sequence of SEQ ID NOs:384, 39, and 54, respectively; a CDR-L1, CDR-L2, and CDR-L3 comprising the amino acid sequence of SEQ ID NOs:385, 180, and 58, respectively; a CDR-L1, CDR-L2, and CDR-L3 comprising the amino acid sequence of SEQ ID NOs:175, 180, and 188, respectively; a CDR-L1, CDR-L2, and CDR-L3 comprising the amino acid sequence of SEQ ID NOs:386, 404, and 420, respectively; a CDR-L1, CDR-L2, and CDR-L3 comprising the amino acid sequence of SEQ ID NOs:387, 405, and 422, respectively; a CDR-L1, CDR-L2, and CDR-L3 comprising the amino acid sequence of SEQ ID NOs:388, 406, and 423, respectively; a CDR-L1, CDR-L2, and CDR-L3 comprising the amino acid sequence of SEQ ID NOs:388, 407, and 424, respectively; a CDR-L1, CDR-L2, and CDR-L3 comprising the amino acid sequence of SEQ ID NOs:389, 408, and 425, respectively; a CDR-L1, CDR-L2, and CDR-L3 comprising the amino acid sequence of SEQ ID NOs:390, 183, and 193, respectively; a CDR-L1, CDR-L2, and CDR-L3 comprising the amino acid sequence of SEQ ID NOs:391, 409, and 426, respectively; a CDR-L1, CDR-L2, and CDR-L3 comprising the amino acid sequence of SEQ ID NOs:392, 40, and 427, respectively; a CDR-L1, CDR-L2, and CDR-L3 comprising the amino acid sequence of SEQ ID NOs:394, 39, and 429, respectively; a CDR-L1, CDR-L2, and CDR-L3 comprising the amino acid sequence of SEQ ID NOs:395, 411, and 430, respectively; a CDR-L1, CDR-L2, and CDR-L3 comprising the amino acid sequence of SEQ ID NOs:396, 412, and 431, respectively; a CDR-L1, CDR-L2, and CDR-L3 comprising the amino acid sequence of SEQ ID NOs:396, 412, and 58, respectively; a CDR-L1, CDR-L2, and CDR-L3 comprising the amino acid sequence of SEQ ID NOs:397, 413, and 432, respectively; a CDR-L1, CDR-L2, and CDR-L3 comprising the amino acid sequence of SEQ ID NOs:398, 414, and 433, respectively. In some embodiments of the antibody or antigen-binding fragment thereof provided herein, the $V_L$ region comprises a CDR-L1, CDR-L2, and CDR-L3 comprising the amino acid sequence of SEQ ID NOs:33, 43, and 55.

For example, the antibody or antigen-binding fragment thereof provided herein comprises an $V_L$ region comprising a CDR-L1, CDR-L2, and CDR-L3 comprising the amino acid sequence selected from among: SEQ ID NOs:26, 37, and 47; SEQ ID NOs:27, 38, and 48; SEQ ID NOs:28, 39, and 49; SEQ ID NOs:29, 40, and 50; SEQ ID NOs:30, 39, and 51; SEQ ID NOs:31, 41, and 52; SEQ ID NOs:32, 42, and 53; SEQ ID NOs:30, 39, and 54; SEQ ID NOs:33, 43, and 55; SEQ ID NOs:34, 44, and 56; SEQ ID NOs:35, 45, and 57; SEQ ID NOs:36, 46, and 58; SEQ ID NOs:174, 179, and 184; SEQ ID NOs:174, 179, and 185; SEQ ID NOs:174, 179, and 186; SEQ ID NOs:174, 179, and 187; SEQ ID NOs:175, 180, and 188; SEQ ID NOs:174, 179, and 189;

SEQ ID NOs:176, 181, and 190; SEQ ID NOs:177, 182, and 191; SEQ ID NOs:174, 179, and 192; SEQ ID NOs:178, 183, and 193; SEQ ID NOs:178, 183, and 194; SEQ ID NOs:30, 399, and 415; SEQ ID NOs:380, 400, and 416; SEQ ID NOs:33, 43, and 421; SEQ ID NOs:381, 401, and 417; SEQ ID NOs:382, 402, and 418; SEQ ID NOs:383, 403, and 419; SEQ ID NOs:384, 39, and 54; SEQ ID NOs:385, 180, and 58; SEQ ID NOs:175, 180, and 188; SEQ ID NOs:386, 404, and 420; SEQ ID NOs:387, 405, and 422; SEQ ID NOs:388, 406, and 423; SEQ ID NOs:388, 407, and 424; SEQ ID NOs:389, 408, and 425; SEQ ID NOs:390, 183, and 193; SEQ ID NOs:391, 409, and 426; SEQ ID NOs:392, 40, and 427; SEQ ID NOs:394, 39, and 429; SEQ ID NOs:395, 411, and 430; SEQ ID NOs:396, 412, and 431; SEQ ID NOs:396, 412, and 58; SEQ ID NOs:397, 413, and 432; SEQ ID NOs:398, 414, and 433, respectively.

In some embodiments, the antibody or antigen-binding fragment thereof provided herein comprises an $V_L$ region comprising a CDR-L1, CDR-L2, and CDR-L3 comprising the amino acid sequence selected from among: SEQ ID NOs:26, 37, and 47; SEQ ID NOs:27, 38, and 48; SEQ ID NOs:28, 39, and 49; SEQ ID NOs:30, 39, and 51; SEQ ID NOs:31, 41, and 52; SEQ ID NOs:33, 43, and 55; SEQ ID NOs:34, 44, and 56; SEQ ID NOs:174, 179, and 185; SEQ ID NOs:174, 179, and 189; SEQ ID NOs:176, 181, and 190; SEQ ID NOs:177, 182, and 191; SEQ ID NOs:174, 179, and 192; SEQ ID NOs:178, 183, and 193; SEQ ID NOs:178, 183, and 194; SEQ ID NOs:30, 399, and 415; SEQ ID NOs:380, 400, and 416; SEQ ID NOs:33, 43, and 421; SEQ ID NOs:381, 401, and 417; and SEQ ID NOs:382, 402, and 418, respectively, according to Kabat numbering, Chothia numbering or AbM numbering.

In some embodiments, the antibody or antigen-binding fragment thereof provided herein comprises an $V_L$ region comprising a CDR-L1, CDR-L2, and CDR-L3 comprising the amino acid sequence selected from among: SEQ ID NOs:26, 37, and 47; SEQ ID NOs:30, 39, and 51; SEQ ID NOs:33, 43, and 55; SEQ ID NOs:178, 183, and 194; SEQ ID NOs:380, 400, and 416; and SEQ ID NOs:33, 43, and 421, respectively, according to Kabat numbering, Chothia numbering or AbM numbering. In some embodiments, the antibody or antigen-binding fragment thereof provided herein comprises an $V_L$ region comprising a CDR-L1, CDR-L2, and CDR-L3 comprising the amino acid sequence selected from among: SEQ ID NOs:178, 183, and 194; and SEQ ID NOs:33, 43, and 421, respectively, according to Kabat numbering, Chothia numbering or AbM numbering.

In some embodiments, the provided antibody or antigen-binding fragment thereof contains a CDR-L1, CDR-L2, and CDR-L3, respectively, contained within the $V_L$ region amino acid sequence selected from any one of SEQ ID NOs:116-127, 257-267, 534-550 and 552-557. In some embodiments, the provided antibody contains a CDR-L1, CDR-L2, and CDR-L3, respectively, contained within the $V_L$ region amino acid sequence selected of SEQ ID NO:124. In some embodiments, the $V_L$ region of a provided antibody or antigen-binding fragment thereof comprises a CDR-L1, CDR-L2, and CDR-L3, respectively, contained within the $V_L$ region amino acid sequence selected from any one of SEQ ID NOs:116-118, 120, 121, 124, 125, 258, 262-267 and 534-538. In some embodiments, the $V_L$ region of a provided antibody or antigen-binding fragment thereof comprises a CDR-L1, CDR-L2, and CDR-L3, respectively, contained within the $V_L$ region amino acid sequence selected from any one of SEQ ID NOs:116, 120, 124, 267, 535 and 536. In some embodiments, the $V_L$ region of a provided antibody or antigen-binding fragment thereof comprises a CDR-L1, CDR-L2, and CDR-L3, respectively, contained within the $V_L$ region amino acid sequence selected from any one of SEQ ID NOs:267 and 536.

In some embodiments of the antibody or antigen-binding fragment thereof provided herein, the $V_L$ region comprises any of the CDR-L1, CDR-L2 and CDR-L3 as described and comprises a framework region 1 (FR1), a FR2, a FR3 and/or a FR4 having at least 90%, 91%, 92%, 93%, 94%, 95%, 96%, 97%, 98%, or 99% sequence identity, respectively, to a FR1, a FR2, a FR3 and/or a FR4 contained within the $V_L$ region amino acid sequence selected from any one of SEQ ID NOs:116-127, 257-267, 534-550 and 552-557. For example, the anti-BCMA antibody or antigen-binding fragment thereof can comprise a CDR-L1, CDR-L2 and CDR-L3, respectively, contained within the $V_L$ region amino acid sequence selected from any one of SEQ ID NOs:116-127, 257-267, 534-550 and 552-557, and a framework region (e.g., a FR1, a FR2, a FR3 and/or a FR4) that contains at least 90%, 91%, 92%, 93%, 94%, 95%, 96%, 97%, 98%, 99% sequence identity to a framework region (e.g., a FR1, a FR2, a FR3 and/or a FR4) contained within the $V_L$ region amino acid sequence selected from any one of SEQ ID NOs:116-127, 257-267, 534-550 and 552-557. In some embodiments, the $V_L$ region comprises a FR1, a FR2, a FR3 and/or a FR4 selected from a FR1 comprising the amino acid sequence selected from any one of SEQ ID NOs:72-82, 221-227, 446-459 and 461-466; a FR2 comprising the amino acid sequence selected from any one of SEQ ID NOs:83-92, 228-232, 467-477 and 479-482; a FR3 comprising the amino acid sequence selected from any one of SEQ ID NOs:93-101, 233-242, 483-495 and 497-501; and/or a FR4 comprising the amino acid sequence selected from any one of SEQ ID NOs:102-109, 243-246, 502-506 and 508. In some embodiments, the $V_L$ region comprises a FR1 comprising the amino acid sequence of SEQ ID NO:79, a FR2 comprising the amino acid sequence of SEQ ID NO:89, a FR3 comprising the amino acid sequence of SEQ ID NO:98, and/or a FR4 comprising the amino acid sequence of SEQ ID NO:108.

In some embodiments, the provided antibody or antigen-binding fragment thereof comprises a $V_L$ region comprising an amino acid sequence selected from any one of SEQ ID NOs:116-127, 257-267, 534-550 and 552-557. In some embodiments, the provided antibody or antigen-binding fragment thereof contains a $V_L$ region comprises the amino acid sequence of SEQ ID NO:124. In some embodiments, the provided antibody or antigen-binding fragment thereof comprises a $V_L$ region comprising an amino acid sequence selected from any one of SEQ ID NOs:116-118, 120, 121, 124, 125, 258, 262-267 and 534-538. In some embodiments, the provided antibody or antigen-binding fragment thereof comprises a $V_L$ region comprising an amino acid sequence selected from any one of SEQ ID NOs:116, 120, 124, 267, 535 and 536. In some embodiments, the provided antibody or antigen-binding fragment thereof comprises a $V_L$ region comprising an amino acid sequence selected from any one of SEQ ID NOs:267 and 536.

Also provided are antibodies having sequences at least at or about at least 90%, 91%, 92%, 93%, 94%, 95%, 96%, 97%, 98%, or 99% identical to such sequences.

In some embodiments, the $V_H$ region of the antibody or fragment comprises the amino acid sequence selected from any one of SEQ ID NOs:110-115, 247-256, 518-531 and 533 and the $V_L$ region of the antibody or fragment comprises the amino acid sequence selected from any one of SEQ ID NOs:116-127, 257-267, 534-550 and 552-557. In some embodiments, the $V_H$ region of the antibody or fragment comprises the amino acid sequence selected from any one of SEQ ID NOs: 110-113, 115, 248, 252-256 and 518-522 and the $V_L$ region of the antibody or fragment comprises the amino acid sequence selected from any one of SEQ ID NOs: 116-118, 120, 121, 124, 125, 258, 262-267 and 534-538. In some embodiments, the $V_H$ region of the antibody or fragment comprises the amino acid sequence selected from any one of SEQ ID NOs: 110, 112, 115, 256 and 519 and the $V_L$ region of the antibody or fragment comprises the amino acid sequence selected from any one of SEQ ID NOs: 116, 120, 124, 267, 535 and 536. In some embodiments, the $V_H$ region of the antibody or fragment comprises the amino acid sequence selected from any one of SEQ ID NOs: 115 and 256 and the $V_L$ region of the antibody or fragment comprises the amino acid sequence selected from any one of SEQ ID NOs: 267 and 536.

Also provided are antibodies and antigen-binding fragments thereof having sequences at least at or about at least 90%, 91%, 92%, 93%, 94%, 95%, 96%, 97%, 98%, or 99% identical to such sequences. For example, provided herein is an antibody or antigen-binding fragment containing a $V_L$ region comprising an amino acid sequence having at least 90%, 91%, 92%, 93%, 94%, 95%, 96%, 97%, 98%, or 99% sequence identity to a $V_L$ region amino acid sequence selected from any one of SEQ ID NOs:116-127, 257-267, 534-550 and 552-557 and/or comprising an amino acid sequence having at least 90%, 91%, 92%, 93%, 94%, 95%, 96%, 97%, 98%, or 99% sequence identity to a $V_H$ region amino acid sequence selected from any one of SEQ ID NOs:110-115, 247-256, 518-531 and 533. In some embodiments, the antibody or antigen-binding fragment contains a $V_L$ region comprising the amino acid sequence selected from any one of SEQ ID NOs:116-127, 257-267, 534-550 and 552-557 and a $V_H$ region the amino acid sequence selected from any one of SEQ ID NOs:110-115, 247-256, 518-531 and 533.

In some embodiments, the $V_H$ region of the antibody or antigen-binding fragment thereof comprises a CDR-H1, a CDR-H2, a CDR-H3, respectively, comprising the amino acid sequences of CDR-H1, CDR-H2, and CDR-H3 contained within the $V_H$ region amino acid sequence selected from any one of SEQ ID NOs:110-115, 247-256, 518-531 and 533; and the $V_L$ region of the antibody or antigen-binding fragment thereof comprises a CDR-L1, a CDR-L2, a CDR-L3, respectively, comprising the amino acid sequences of CDR-L1, CDR-L2, and CDR-L3, respectively contained within the $V_L$ region amino acid sequence selected from any one of SEQ ID NOs:116-127, 257-267, 534-550 and 552-557.

In some embodiments, the $V_H$ region of the antibody or fragment comprises a CDR-H1, a CDR-H2, a CDR-H3, respectively, comprising the amino acid sequences of CDR-H1, CDR-H2, and CDR-H3 contained within the $V_H$ region amino acid sequence selected from any one of SEQ ID NOs:110-115, 247-256, 518-531 and 533 and the $V_L$ region of the antibody or fragment comprises a CDR-L1, a CDR-L2, a CDR-L3, respectively, comprising the amino acid sequences of CDR-L1, CDR-L2, and CDR-L3, respectively contained within the $V_L$ region amino acid sequence selected from any one of SEQ ID NOs:116-127, 257-267, 534-550 and 552-557. In some embodiments, the $V_H$ region of the antibody or fragment comprises a CDR-H1, a CDR-H2, a CDR-H3, respectively, comprising the amino acid sequences of CDR-H1, CDR-H2, and CDR-H3 contained within the $V_H$ region amino acid sequence selected from any one of SEQ ID NOs:110-113, 115, 248, 252-256 and 518-522 and the $V_L$ region of the antibody or fragment comprises a CDR-L1, a CDR-L2, a CDR-L3, respectively, comprising the amino acid sequences of CDR-L1, CDR-L2, and CDR-L3, respectively contained within the $V_L$ region amino acid sequence selected from any one of SEQ ID NOs:116-118, 120, 121, 124, 125, 258, 262-267 and 534-538. In some embodiments, the $V_H$ region of the antibody or fragment comprises a CDR-H1, a CDR-H2, a CDR-H3, respectively, comprising the amino acid sequences of CDR-H1, CDR-H2, and CDR-H3 contained within the $V_H$ region amino acid sequence selected from any one of SEQ ID NOs:110, 112, 115, 256 and 519 and the $V_L$ region of the antibody or fragment comprises a CDR-L1, a CDR-L2, a CDR-L3, respectively, comprising the amino acid sequences of CDR-L1, CDR-L2, and CDR-L3, respectively contained within the $V_L$ region amino acid sequence selected from any one of SEQ ID NOs: 116, 120, 124, 267, 535 and 536. In some embodiments, the $V_H$ region of the antibody or fragment comprises a CDR-H1, a CDR-H2, a CDR-H3, respectively, comprising the amino acid sequences of CDR-H1, CDR-H2, and CDR-H3 contained within the $V_H$ region amino acid sequence selected from any one of SEQ ID NOs: 115 and 256 and the $V_L$ region of the antibody or fragment comprises a CDR-L1, a CDR-L2, a CDR-L3, respectively, comprising the amino acid sequences of CDR-L1, CDR-L2, and CDR-L3, respectively contained within the $V_L$ region amino acid sequence selected from any one of SEQ ID NOs:267 and 536.

In some embodiments, the antibody or antigen-binding fragment comprises a $V_H$ having at least 90% sequence identity to the $V_H$ sequence selected from any of SEQ ID NOs:110-115, 247-256, 518-531 and 533; and a $V_L$ having at least 90% sequence identity to the $V_L$ sequence selected from any of SEQ ID NOs:116-127, 257-267, 534-550 and 552-557.

In some embodiments, the antibody or antigen-binding fragment comprises a $V_H$ having at least 90% sequence identity to the $V_H$ sequence selected from any of SEQ ID NOs:110, 256 and 519; and a $V_L$ having at least 90% sequence identity to the $V_L$ sequence selected from any of SEQ ID NOs:47, 51, 194 and 416. In some embodiments, said antibody or antigen-binding fragment comprises a $V_H$ having at least 90% sequence identity to the $V_H$ sequence of SEQ ID NO:115; and a $V_L$ having at least 90% sequence identity to the $V_L$ sequence of SEQ ID NO:536.

In some embodiments, the antibody or antigen-binding fragment thereof comprises a $V_H$ comprising a CDR-H1, CDR-H2, and CDR-H3, wherein: the CDR-H1 comprises the sequence selected from any of SEQ ID NOs:1-3 and 140-144; the CDR-H2 comprises the sequence selected from any of SEQ ID NOs:4-6, 145-148 and 372-374; and the CDR-H3 comprises the sequence selected from any of SEQ ID NOs:7-11, 149-157, 279-287 and 376-378; and a $V_L$ comprising a CDR-L1, CDR-L2, and CDR-L3, wherein: the CDR-L1 comprises the sequence selected from any of SEQ ID NOs:26-36, 174-178, 380-392 and 394-398; the CDR-L2 comprises the sequence selected from any of SEQ ID NOs:37-46, 179-183, 399-409 and 411-414; and the CDR-L3 comprises the sequence selected from any of SEQ ID NOs:47-58, 184-194, 415-427 and 429-433.

In some embodiments, the CDR-H1 comprises the sequence selected from any of SEQ ID NOs:1 and 2; the CDR-H2 comprises the sequence selected from any of SEQ ID NOs:4 and 5; and the CDR-H3 comprises the sequence selected from any of SEQ ID NOs:7 and 157; and the CDR-L1 comprises the sequence selected from any of SEQ ID NOs:26, 30, 178 and 380; the CDR-L2 comprises the sequence selected from any of SEQ ID NOs:37, 39, 183 or 400; and the CDR-L3 comprises the sequence selected from any of SEQ ID NOs:47, 51, 194 and 416. In some embodiments, the CDR-H1 comprises the sequence of SEQ ID NO:2; the CDR-H2 comprises the sequence of SEQ ID NO:5; and the CDR-H3 comprises the sequence of SEQ ID NO:10; and the CDR-L1 comprises the sequence of SEQ ID NO:33; the CDR-L2 comprises the sequence of SEQ ID NO:43; and the CDR-L3 comprises the sequence of SEQ ID NO:421.

In some embodiments, the antibody or antigen-binding fragment thereof comprises a $V_H$ and a $V_L$, wherein: the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:26, 37, and 47, respectively; the $V_H$ comprises a CDR-H1, CDR-H2, and CDR-H3 comprising SEQ ID NOS: 2, 5, and 8, respectively, and the $V_L$ comprises a CDR-L1, CDR-L2, and CDR-L3 comprising SEQ ID NOS:27, 38, and 48, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:28, 39, and 49, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:29, 40, and 50, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS: 30, 39, and 51, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:31, 41, and 52, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:32, 42, and 53, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:30, 39, and 54, respectively; the $V_H$ comprises a CDR-H1, CDR-H2, and CDR-H3 comprising SEQ ID NOS:2, 5, and 9, respectively, and the $V_L$ comprises a CDR-L1, CDR-L2, and CDR-L3 comprising SEQ ID NOS: 33, 43, and 55, respectively; the $V_H$ comprises a CDR-H1, CDR-H2, and CDR-H3 comprising SEQ ID NOS:2, 5, and 10, respectively, and the $V_L$ comprises a CDR-L1, CDR-L2, and CDR-L3 comprising SEQ ID NOS:34, 44, and 56, respectively; the $V_H$ comprises a CDR-H1, CDR-H2, and CDR-H3 comprising SEQ ID NOS:3, 6, and 11, respectively, and the $V_L$ comprises a CDR-L1, CDR-L2, and CDR-L3 comprising SEQ ID NOS:35, 45, and 57, respectively; the $V_H$ comprises a CDR-H1, CDR-H2, and CDR-H3 comprising SEQ ID NOS:2, 5, and 10, respectively, and the $V_L$ comprises a CDR-L1, CDR-L2, and CDR-L3 comprising SEQ ID NOS:36, 46, and 58, respectively; the $V_H$ comprises a CDR-H1, CDR-H2, and CDR-H3 comprising SEQ ID NOS:140, 145, and 149, respectively, and the $V_L$ comprises a CDR-L1, CDR-L2, and CDR-L3 comprising SEQ ID NOS:174, 179, and 184, respectively; the $V_H$ comprises a CDR-H1, CDR-H2, and CDR-H3 comprising SEQ ID NOS: 141, 145, and 149, respectively, and the $V_L$ comprises a CDR-L1, CDR-L2, and CDR-L3 comprising SEQ ID NOS: 174, 179, and 185, respectively; the $V_H$ comprises a CDR-H1, CDR-H2, and CDR-H3 comprising SEQ ID NOS:141, 145, and 150, respectively, and the $V_L$ comprises a CDR-L1, CDR-L2, and CDR-L3 comprising SEQ ID NOS:174, 179, and 186, respectively; the $V_H$ comprises a CDR-H1, CDR-H2, and CDR-H3 comprising SEQ ID NOS:142, 146, and 151, respectively, and the $V_L$ comprises a CDR-L1, CDR-L2, and CDR-L3 comprising SEQ ID NOS:174, 179, and 187, respectively; the $V_H$ comprises a CDR-H1, CDR-H2, and CDR-H3 comprising SEQ ID NOS:2, 5, and 152, respectively, and the $V_L$ comprises a CDR-L1, CDR-L2, and CDR-L3 comprising SEQ ID NOS:175, 180, and 188, respectively; the $V_H$ comprises a CDR-H1, CDR-H2, and CDR-H3 comprising SEQ ID NOS:143, 147, and 153, respectively, and the $V_L$ comprises a CDR-L1, CDR-L2, and CDR-L3 comprising SEQ ID NOS:174, 179, and 189, respectively; the $V_H$ comprises a CDR-H1, CDR-H2, and CDR-H3 comprising SEQ ID NOS:144, 148, and 154, respectively, and the $V_L$ comprises a CDR-L1, CDR-L2, and CDR-L3 comprising SEQ ID NOS:176, 181, and 190, respectively; the $V_H$ comprises a CDR-H1, CDR-H2, and CDR-H3 comprising SEQ ID NOS:3, 6, and 155, respectively, and the $V_L$ comprises a CDR-L1, CDR-L2, and CDR-L3 comprising SEQ ID NOS:177, 182, and 191, respectively; the $V_H$ comprises a CDR-H1, CDR-H2, and CDR-H3 comprising SEQ ID NOS:2, 5, and 156, respectively, and the $V_L$ comprises a CDR-L1, CDR-L2, and CDR-L3 comprising SEQ ID NOS:174, 179, and 192, respectively; the $V_H$ comprises a CDR-H1, CDR-H2, and CDR-H3 comprising SEQ ID NOS:2, 5, and 157, respectively, and the $V_L$ comprises a CDR-L1, CDR-L2, and CDR-L3 comprising SEQ ID NOS:178, 183, and 193, respectively; the $V_H$ comprises a CDR-H1, CDR-H2, and CDR-H3 comprising SEQ ID NOS:2, 5, and 157, respectively, and the $V_L$ comprises a CDR-L1, CDR-L2, and CDR-L3 comprising SEQ ID NOS:178, 183, and 194, respectively; the $V_H$ comprises a CDR-H1, CDR-H2, and CDR-H3 comprising SEQ ID NOS:2, 6, and 376, respectively, and the $V_L$ comprises a CDR-L1, CDR-L2, and CDR-L3 comprising SEQ ID NOS:30, 399, and 415, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:380, 400, and 416, respectively; the $V_H$ comprises a CDR-H1, CDR-H2, and CDR-H3 comprising SEQ ID NOS:2, 5, and 10, respectively, and the $V_L$ comprises a CDR-L1, CDR-L2, and CDR-L3 comprising SEQ ID NOS:33, 43, and 421, respectively; the $V_H$ comprises a CDR-H1, CDR-H2, and CDR-H3 comprising SEQ ID NOS: 3, 6, and 155, respectively, and the $V_L$ comprises a CDR-L1, CDR-L2, and CDR-L3 comprising SEQ ID NOS:177, 182, and 191, respectively; the $V_H$ comprises a CDR-H1, CDR-H2, and CDR-H3 comprising SEQ ID NOS:3, 372, and 376, respectively, and the $V_L$ comprises a CDR-L1, CDR-L2, and CDR-L3 comprising SEQ ID NOS:381, 401, and 417, respectively; the $V_H$ comprises a CDR-H1, CDR-H2, and CDR-H3 comprising SEQ ID NOS:3, 6, and 376, respectively, and the $V_L$ comprises a CDR-L1, CDR-L2, and CDR-L3 comprising SEQ ID NOS:382, 402, and 418, respectively; the $V_H$ comprises a CDR-H1, CDR-H2, and CDR-H3 comprising SEQ ID NOS:3, 6, and 377, respectively, and the $V_L$ comprises a CDR-L1, CDR-L2, and CDR-L3 comprising SEQ ID NOS:383, 403, and 419, respectively; the $V_H$ comprises a CDR-H1, CDR-H2, and CDR-H3 comprising SEQ ID NOS:1, 4, and 7, respectively, and the $V_L$ comprises a CDR-L1, CDR-L2, and CDR-L3 comprising SEQ ID NOS:384, 39, and 54, respectively; the $V_H$ comprises a CDR-H1, CDR-H2, and CDR-H3 comprising SEQ ID NOS:2, 5, and 10, respectively, and the $V_L$ comprises a CDR-L1, CDR-L2, and CDR-L3 comprising SEQ ID NOS:385, 180, and 58, respectively; the $V_H$ comprises a CDR-H1, CDR-H2, and CDR-H3 comprising SEQ ID NOS:2, 373, and 152, respectively, and the V$_L$ comprises a CDR-L1, CDR-L2, and CDR-L3 comprising SEQ ID NOS:175, 180, and 188, respectively; the V$_H$ comprises a CDR-H1, CDR-H2, and CDR-H3 comprising SEQ ID NOS: 3, 6, and 11, respectively, and the V$_L$ comprises a CDR-L1, CDR-L2, and CDR-L3 comprising SEQ ID NOS:386, 404, and 420, respectively; the V$_H$ comprises a CDR-H1, CDR-H2, and CDR-H3 comprising SEQ ID NOS:2, 5, and 378, respectively, and the V$_L$ comprises a CDR-L1, CDR-L2, and CDR-L3 comprising SEQ ID NOS:33, 43, and 421, respectively; the V$_H$ comprises a CDR-H1, CDR-H2, and CDR-H3 comprising SEQ ID NOS:2, 5, and 9, respectively, and the V$_L$ comprises a CDR-L1, CDR-L2, and CDR-L3 comprising SEQ ID NOS:387, 405, and 422, respectively; the V$_H$ comprises a CDR-H1, CDR-H2, and CDR-H3 comprising SEQ ID NOS:2, 5, and 9, respectively, and the V$_L$ comprises a CDR-L1, CDR-L2, and CDR-L3 comprising SEQ ID NOS:388, 406, and 423, respectively; the V$_H$ comprises a CDR-H1, CDR-H2, and CDR-H3 comprising SEQ ID NOS: 2, 5, and 9, respectively, and the V$_L$ comprises a CDR-L1, CDR-L2, and CDR-L3 comprising SEQ ID NOS:388, 407, and 424, respectively; the V$_H$ comprises a CDR-H1, CDR-H2, and CDR-H3 comprising SEQ ID NOS:3, 6, and 376, respectively, and the V$_L$ comprises a CDR-L1, CDR-L2, and CDR-L3 comprising SEQ ID NOS:389, 408, and 425, respectively; the V$_H$ comprises a CDR-H1, CDR-H2, and CDR-H3 comprising SEQ ID NOS:2, 5, and 157, respectively, and the V$_L$ comprises a CDR-L1, CDR-L2, and CDR-L3 comprising SEQ ID NOS:390, 183, and 193, respectively; the V$_H$ comprises a CDR-H1, CDR-H2, and CDR-H3 comprising SEQ ID NOS:2, 374, and 9, respectively, and the V$_L$ comprises a CDR-L1, CDR-L2, and CDR-L3 comprising SEQ ID NOS:391, 409, and 426, respectively; the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:392, 40, and 427, respectively; the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:394, 39, and 429, respectively; the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS: 395, 411, and 430, respectively; the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:28, 39, and 49, respectively; the V$_H$ comprises a CDR-H1, CDR-H2, and CDR-H3 comprising SEQ ID NOS:2, 5, and 10, respectively, and the V$_L$ comprises a CDR-L1, CDR-L2, and CDR-L3 comprising SEQ ID NOS:396, 412, and 431, respectively; the V$_H$ comprises a CDR-H1, CDR-H2, and CDR-H3 comprising SEQ ID NOS:2, 5, and 10, respectively, and the V$_L$ comprises a CDR-L1, CDR-L2, and CDR-L3 comprising SEQ ID NOS:396, 412, and 58, respectively; the V$_H$ comprises a CDR-H1, CDR-H2, and CDR-H3 comprising SEQ ID NOS:2, 5, and 10, respectively, and the V$_L$ comprises a CDR-L1, CDR-L2, and CDR-L3 comprising SEQ ID NOS:397, 413, and 432, respectively; or the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:398, 414, and 433, respectively.

In some embodiments, the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:26, 37, and 47, respectively; the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:30, 39, and 51, respectively; the V$_H$ comprises a CDR-H1, CDR-H2, and CDR-H3 comprising SEQ ID NOS:2, 5, and 157, respectively, and the V$_L$ comprises a CDR-L1, CDR-L2, and CDR-L3 comprising SEQ ID NOS:178, 183, and 194, respectively; or the V$_H$ comprises a CDR-H1, CDR-H2, and CDR-H3 comprising SEQ ID NOS:1, 4, and 7, respectively, and the V$_L$ comprises a CDR-L1, CDR-L2, and CDR-L3 comprising SEQ ID NOS:380, 400, and 416, respectively. In some embodiments, the V$_H$ comprises a CDR-H1, CDR-H2, and CDR-H3 comprising SEQ ID NOS:2, 5, and 10, respectively, and the V$_L$ comprises a CDR-L1, CDR-L2, and CDR-L3 comprising SEQ ID NOS:33, 43, and 421, respectively.

In some embodiments, the antibody or antigen-binding fragment thereof comprises a CDR-H1, CDR-H2, and CDR-H3, respectively, comprising the sequences of CDR-H1, CDR-H2, and CDR-H3 within the V$_H$ sequence selected from any of SEQ ID NOs:110-115, 247-256, 518-531 and 533; and/or a CDR-L1, CDR-L2, and CDR-L3, respectively, comprising the sequences of CDR-L1, CDR-L2, and CDR-L3 within the V$_L$ sequence selected from any of SEQ ID NOs:116-127, 257-267, 534-550 and 552-557.

In some embodiments, the CDR-H1, CDR-H2, and CDR-H3, respectively, comprise the sequences of CDR-H1, CDR-H2, and CDR-H3 within the V$_H$ sequence selected from any of SEQ ID NOs:110, 256 and 519; and a CDR-L1, CDR-L2, and CDR-L3, respectively, comprising the sequences of CDR-L1, CDR-L2, and CDR-L3 within the V$_L$ sequence selected from any of SEQ ID NOs:116, 120, 267 and 535.

In some embodiments, the CDR-H1, CDR-H2, and CDR-H3, respectively, comprise the sequences of CDR-H1, CDR-H2, and CDR-H3 within SEQ ID NO:115; and a CDR-L1, CDR-L2, and CDR-L3, respectively, comprising the sequences of CDR-L1, CDR-L2, and CDR-L3 within SEQ ID NO:536.

In some embodiments, the antibody or antigen-binding fragment thereof comprises a V$_H$ and a V$_L$, wherein: the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:116; the V$_H$ is or comprises a CDR-H1, CDR-H2 and CDR-H3 within SEQ ID NO:111, and the V$_L$ is or comprises a CDR-L1, CDR-L2 and CDR-L3 within SEQ ID NO:117; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:118; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:119; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:120; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:121; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:122; the V$_H$ is or comprises a CDR-H1, CDR-H2 and CDR-H3 within SEQ ID NO:110, and the V$_L$ is or comprises a CDR-L1, CDR-L2 and CDR-L3 within SEQ ID NO:123; the V$_H$ is or comprises a CDR-H1, CDR-H2 and CDR-H3 within SEQ ID NO:112, and the V$_L$ is or comprises a CDR-L1, CDR-L2 and CDR-L3 within SEQ ID NO:124; the $V_H$ is or comprises a CDR-H1, CDR-H2 and CDR-H3 within SEQ ID NO:113, and the $V_L$ is or comprises a CDR-L1, CDR-L2 and CDR-L3 within SEQ ID NO:125; the $V_H$ is or comprises a CDR-H1, CDR-H2 and CDR-H3 within SEQ ID NO:114, and the $V_L$ is or comprises a CDR-L1, CDR-L2 and CDR-L3 within SEQ ID NO:126; the $V_H$ is or comprises a CDR-H1, CDR-H2 and CDR-H3 within SEQ ID NO:115, and the $V_L$ is or comprises a CDR-L1, CDR-L2 and CDR-L3 within SEQ ID NO:127; the $V_H$ is or comprises a CDR-H1, CDR-H2 and CDR-H3 within SEQ ID NO:247, and the $V_L$ is or comprises a CDR-L1, CDR-L2 and CDR-L3 within SEQ ID NO:257; the $V_H$ is or comprises a CDR-H1, CDR-H2 and CDR-H3 within SEQ ID NO:248, and the $V_L$ is or comprises a CDR-L1, CDR-L2 and CDR-L3 within SEQ ID NO:258; the $V_H$ is or comprises a CDR-H1, CDR-H2 and CDR-H3 within SEQ ID NO:249, and the $V_L$ is or comprises a CDR-L1, CDR-L2 and CDR-L3 within SEQ ID NO:259; the $V_H$ is or comprises a CDR-H1, CDR-H2 and CDR-H3 within SEQ ID NO:250, and the $V_L$ is or comprises a CDR-L1, CDR-L2 and CDR-L3 within SEQ ID NO:260; the $V_H$ is or comprises a CDR-H1, CDR-H2 and CDR-H3 within SEQ ID NO:251, and the $V_L$ is or comprises a CDR-L1, CDR-L2 and CDR-L3 within SEQ ID NO:261; the $V_H$ is or comprises a CDR-H1, CDR-H2 and CDR-H3 within SEQ ID NO:252, and the $V_L$ is or comprises a CDR-L1, CDR-L2 and CDR-L3 within SEQ ID NO:262; the $V_H$ is or comprises a CDR-H1, CDR-H2 and CDR-H3 within SEQ ID NO:253, and the $V_L$ is or comprises a CDR-L1, CDR-L2 and CDR-L3 within SEQ ID NO:263; the $V_H$ is or comprises a CDR-H1, CDR-H2 and CDR-H3 within SEQ ID NO:254, and the $V_L$ is or comprises a CDR-L1, CDR-L2 and CDR-L3 within SEQ ID NO:264; the $V_H$ is or comprises a CDR-H1, CDR-H2 and CDR-H3 within SEQ ID NO:255, and the $V_L$ is or comprises a CDR-L1, CDR-L2 and CDR-L3 within SEQ ID NO:265; the $V_H$ is or comprises a CDR-H1, CDR-H2 and CDR-H3 within SEQ ID NO:256, and the $V_L$ is or comprises a CDR-L1, CDR-L2 and CDR-L3 within SEQ ID NO:266; the $V_H$ is or comprises a CDR-H1, CDR-H2 and CDR-H3 within SEQ ID NO:256, and the $V_L$ is or comprises a CDR-L1, CDR-L2 and CDR-L3 within SEQ ID NO:267; the $V_H$ is or comprises a CDR-H1, CDR-H2 and CDR-H3 within SEQ ID NO:518, and the $V_L$ is or comprises a CDR-L1, CDR-L2 and CDR-L3 within SEQ ID NO:534; the $V_H$ is or comprises a CDR-H1, CDR-H2 and CDR-H3 within SEQ ID NO:519, and the $V_L$ is or comprises a CDR-L1, CDR-L2 and CDR-L3 within SEQ ID NO:535; the $V_H$ is or comprises a CDR-H1, CDR-H2 and CDR-H3 within SEQ ID NO:115, and the $V_L$ is or comprises a CDR-L1, CDR-L2 and CDR-L3 within SEQ ID NO:536; the $V_H$ is or comprises a CDR-H1, CDR-H2 and CDR-H3 within SEQ ID NO:520, and the $V_L$ is or comprises a CDR-L1, CDR-L2 and CDR-L3 within SEQ ID NO:264; the $V_H$ is or comprises a CDR-H1, CDR-H2 and CDR-H3 within SEQ ID NO:521, and the $V_L$ is or comprises a CDR-L1, CDR-L2 and CDR-L3 within SEQ ID NO:537; the $V_H$ is or comprises a CDR-H1, CDR-H2 and CDR-H3 within SEQ ID NO:522, and the $V_L$ is or comprises a CDR-L1, CDR-L2 and CDR-L3 within SEQ ID NO:538; the $V_H$ is or comprises a CDR-H1, CDR-H2 and CDR-H3 within SEQ ID NO:523, and the $V_L$ is or comprises a CDR-L1, CDR-L2 and CDR-L3 within SEQ ID NO:539; the $V_H$ is or comprises a CDR-H1, CDR-H2 and CDR-H3 within SEQ ID NO:519, and the $V_L$ is or comprises a CDR-L1, CDR-L2 and CDR-L3 within SEQ ID NO:540; the $V_H$ is or comprises a CDR-H1, CDR-H2 and CDR-H3 within SEQ ID NO:524, and the $V_L$ is or comprises a CDR-L1, CDR-L2 and CDR-L3 within SEQ ID NO:541; the $V_H$ is or comprises a CDR-H1, CDR-H2 and CDR-H3 within SEQ ID NO:525, and the $V_L$ is or comprises a CDR-L1, CDR-L2 and CDR-L3 within SEQ ID NO:261; the $V_H$ is or comprises a CDR-H1, CDR-H2 and CDR-H3 within SEQ ID NO:526, and the $V_L$ is or comprises a CDR-L1, CDR-L2 and CDR-L3 within SEQ ID NO:542; the $V_H$ is or comprises a CDR-H1, CDR-H2 and CDR-H3 within SEQ ID NO:527, and the $V_L$ is or comprises a CDR-L1, CDR-L2 and CDR-L3 within SEQ ID NO:543; the $V_H$ is or comprises a CDR-H1, CDR-H2 and CDR-H3 within SEQ ID NO:528, and the $V_L$ is or comprises a CDR-L1, CDR-L2 and CDR-L3 within SEQ ID NO:544; the $V_H$ is or comprises a CDR-H1, CDR-H2 and CDR-H3 within SEQ ID NO:529, and the $V_L$ is or comprises a CDR-L1, CDR-L2 and CDR-L3 within SEQ ID NO:545; the $V_H$ is or comprises a CDR-H1, CDR-H2 and CDR-H3 within SEQ ID NO:528, and the $V_L$ is or comprises a CDR-L1, CDR-L2 and CDR-L3 within SEQ ID NO:546; the $V_H$ is or comprises a CDR-H1, CDR-H2 and CDR-H3 within SEQ ID NO:522, and the $V_L$ is or comprises a CDR-L1, CDR-L2 and CDR-L3 within SEQ ID NO:547; the $V_H$ is or comprises a CDR-H1, CDR-H2 and CDR-H3 within SEQ ID NO:256, and the $V_L$ is or comprises a CDR-L1, CDR-L2 and CDR-L3 within SEQ ID NO:548; the $V_H$ is or comprises a CDR-H1, CDR-H2 and CDR-H3 within SEQ ID NO:530, and the $V_L$ is or comprises a CDR-L1, CDR-L2 and CDR-L3 within SEQ ID NO:549; the $V_H$ is or comprises a CDR-H1, CDR-H2 and CDR-H3 within SEQ ID NO:531, and the $V_L$ is or comprises a CDR-L1, CDR-L2 and CDR-L3 within SEQ ID NO:550; the $V_H$ is or comprises a CDR-H1, CDR-H2 and CDR-H3 within SEQ ID NO:519, and the $V_L$ is or comprises a CDR-L1, CDR-L2 and CDR-L3 within SEQ ID NO:552; the $V_H$ is or comprises a CDR-H1, CDR-H2 and CDR-H3 within SEQ ID NO:110, and the $V_L$ is or comprises a CDR-L1, CDR-L2 and CDR-L3 within SEQ ID NO:553; the $V_H$ is or comprises a CDR-H1, CDR-H2 and CDR-H3 within SEQ ID NO:110, and the $V_L$ is or comprises a CDR-L1, CDR-L2 and CDR-L3 within SEQ ID NO:118; the $V_H$ is or comprises a CDR-H1, CDR-H2 and CDR-H3 within SEQ ID NO:533, and the $V_L$ is or comprises a CDR-L1, CDR-L2 and CDR-L3 within SEQ ID NO:554; the $V_H$ is or comprises a CDR-H1, CDR-H2 and CDR-H3 within SEQ ID NO:115, and the $V_L$ is or comprises a CDR-L1, CDR-L2 and CDR-L3 within SEQ ID NO:555; the $V_H$ is or comprises a CDR-H1, CDR-H2 and CDR-H3 within SEQ ID NO:524, and the $V_L$ is or comprises a CDR-L1, CDR-L2 and CDR-L3 within SEQ ID NO:556; or the $V_H$ is or comprises a CDR-H1, CDR-H2 and CDR-H3 within SEQ ID NO:519, and the $V_L$ is or comprises a CDR-L1, CDR-L2 and CDR-L3 within SEQ ID NO:557, respectively.

In some embodiments, the $V_H$ is or comprises a CDR-H1, CDR-H2 and CDR-H3 within SEQ ID NO:110, and the $V_L$ is or comprises a CDR-L1, CDR-L2 and CDR-L3 within SEQ ID NO:116; the $V_H$ is or comprises a CDR-H1, CDR-H2 and CDR-H3 within SEQ ID NO:110, and the $V_L$ is or comprises a CDR-L1, CDR-L2 and CDR-L3 within SEQ ID NO:120; the $V_H$ is or comprises a CDR-H1, CDR-H2 and CDR-H3 within SEQ ID NO:256, and the $V_L$ is or comprises a CDR-L1, CDR-L2 and CDR-L3 within SEQ ID NO:267; or the $V_H$ is or comprises a CDR-H1, CDR-H2 and CDR-H3 within SEQ ID NO:519, and the $V_L$ is or comprises a CDR-L1, CDR-L2 and CDR-L3 within SEQ ID NO:535. In some embodiments, the $V_H$ is or comprises a CDR-H1, CDR-H2 and CDR-H3 within SEQ ID NO:115, and the $V_L$ is or comprises a CDR-L1, CDR-L2 and CDR-L3 within SEQ ID NO:536, respectively.

In some embodiments, the $V_H$ and $V_L$ regions of the antibody or antigen-binding fragment thereof comprise the amino acid sequences of SEQ ID NOs:110 and 116, respectively; the $V_H$ and $V_L$ regions of the antibody or antigen-binding fragment thereof comprise the amino acid sequences of SEQ ID NOs:111 and 117, respectively; the $V_H$ and $V_L$ regions of the antibody or antigen-binding fragment thereof comprise the amino acid sequences of SEQ ID NOs:110 and 118, respectively; the $V_H$ and $V_L$ regions of the antibody or antigen-binding fragment thereof comprise the amino acid sequences of SEQ ID NOs:110 and 119, respectively; the $V_H$ and $V_L$ regions of the antibody or antigen-binding fragment thereof comprise the amino acid sequences of SEQ ID NOs:110 and 120, respectively; the $V_H$ and $V_L$ regions of the antibody or antigen-binding fragment thereof comprise the amino acid sequences of SEQ ID NOs:110 and 121, respectively; the $V_H$ and $V_L$ regions of the antibody or antigen-binding fragment thereof comprise the amino acid sequences of SEQ ID NOs:110 and 122, respectively; the $V_H$ and $V_L$ regions of the antibody or antigen-binding fragment thereof comprise the amino acid sequences of SEQ ID NOs:110 and 123, respectively; the $V_H$ and $V_L$ regions of the antibody or antigen-binding fragment thereof comprise the amino acid sequences of SEQ ID NOs:112 and 124, respectively; the $V_H$ and $V_L$ regions of the antibody or antigen-binding fragment thereof comprise the amino acid sequences of SEQ ID NOs:113 and 125, respectively; the $V_H$ and $V_L$ regions of the antibody or antigen-binding fragment thereof comprise the amino acid sequences of SEQ ID NOs:114 and 126, respectively; the $V_H$ and $V_L$ regions of the antibody or antigen-binding fragment thereof comprise the amino acid sequences of SEQ ID NOs:115 and 127, respectively; the $V_H$ and $V_L$ regions of the antibody or antigen-binding fragment thereof comprise the amino acid sequences of SEQ ID NOs:247 and 257, respectively; the $V_H$ and $V_L$ regions of the antibody or antigen-binding fragment thereof comprise the amino acid sequences of SEQ ID NOs:248 and 258, respectively; the $V_H$ and $V_L$ regions of the antibody or antigen-binding fragment thereof comprise the amino acid sequences of SEQ ID NOs:249 and 259, respectively; the $V_H$ and $V_L$ regions of the antibody or antigen-binding fragment thereof comprise the amino acid sequences of SEQ ID NOs:250 and 260, respectively; the $V_H$ and $V_L$ regions of the antibody or antigen-binding fragment thereof comprise the amino acid sequences of SEQ ID NOs:251 and 261, respectively; the $V_H$ and $V_L$ regions of the antibody or antigen-binding fragment thereof comprise the amino acid sequences of SEQ ID NOs:252 and 262, respectively; the $V_H$ and $V_L$ regions of the antibody or antigen-binding fragment thereof comprise the amino acid sequences of SEQ ID NOs:253 and 263, respectively; the $V_H$ and $V_L$ regions of the antibody or antigen-binding fragment thereof comprise the amino acid sequences of SEQ ID NOs:254 and 264, respectively; the $V_H$ and $V_L$ regions of the antibody or antigen-binding fragment thereof comprise the amino acid sequences of SEQ ID NOs:255 and 265, respectively; the $V_H$ and $V_L$ regions of the antibody or antigen-binding fragment thereof comprise the amino acid sequences of SEQ ID NOs:256 and 266, respectively; the $V_H$ and $V_L$ regions of the antibody or antigen-binding fragment thereof comprise the amino acid sequences of SEQ ID NOs:256 and 267, respectively; the $V_H$ and $V_L$ regions of the antibody or antigen-binding fragment thereof comprise the amino acid sequences of SEQ ID NOs:518 and 534, respectively; the $V_H$ and $V_L$ regions of the antibody or antigen-binding fragment thereof comprise the amino acid sequences of SEQ ID NOs:519 and 535, respectively; the $V_H$ and $V_L$ regions of the antibody or antigen-binding fragment thereof comprise the amino acid sequences of SEQ ID NOs:115 and 536, respectively; the $V_H$ and $V_L$ regions of the antibody or antigen-binding fragment thereof comprise the amino acid sequences of SEQ ID NOs:520 and 264, respectively; the $V_H$ and $V_L$ regions of the antibody or antigen-binding fragment thereof comprise the amino acid sequences of SEQ ID NOs:521 and 537, respectively; the $V_H$ and $V_L$ regions of the antibody or antigen-binding fragment thereof comprise the amino acid sequences of SEQ ID NOs:522 and 538, respectively; the $V_H$ and $V_L$ regions of the antibody or antigen-binding fragment thereof comprise the amino acid sequences of SEQ ID NOs:523 and 539, respectively; the $V_H$ and $V_L$ regions of the antibody or antigen-binding fragment thereof comprise the amino acid sequences of SEQ ID NOs:519 and 540, respectively; the $V_H$ and $V_L$ regions of the antibody or antigen-binding fragment thereof comprise the amino acid sequences of SEQ ID NOs:524 and 541, respectively; the $V_H$ and $V_L$ regions of the antibody or antigen-binding fragment thereof comprise the amino acid sequences of SEQ ID NOs:525 and 261, respectively; the $V_H$ and $V_L$ regions of the antibody or antigen-binding fragment thereof comprise the amino acid sequences of SEQ ID NOs:526 and 542, respectively; the $V_H$ and $V_L$ regions of the antibody or antigen-binding fragment thereof comprise the amino acid sequences of SEQ ID NOs:527 and 543, respectively; the $V_H$ and $V_L$ regions of the antibody or antigen-binding fragment thereof comprise the amino acid sequences of SEQ ID NOs:528 and 544, respectively; the $V_H$ and $V_L$ regions of the antibody or antigen-binding fragment thereof comprise the amino acid sequences of SEQ ID NOs:529 and 545, respectively; the $V_H$ and $V_L$ regions of the antibody or antigen-binding fragment thereof comprise the amino acid sequences of SEQ ID NOs:528 and 546, respectively; the $V_H$ and $V_L$ regions of the antibody or antigen-binding fragment thereof comprise the amino acid sequences of SEQ ID NOs:522 and 547, respectively; the $V_H$ and $V_L$ regions of the antibody or antigen-binding fragment thereof comprise the amino acid sequences of SEQ ID NOs:256 and 548, respectively; the $V_H$ and $V_L$ regions of the antibody or antigen-binding fragment thereof comprise the amino acid sequences of SEQ ID NOs:530 and 549, respectively; the $V_H$ and $V_L$ regions of the antibody or antigen-binding fragment thereof comprise the amino acid sequences of SEQ ID NOs:531 and 550, respectively; the $V_H$ and $V_L$ regions of the antibody or antigen-binding fragment thereof comprise the amino acid sequences of SEQ ID NOs:519 and 552, respectively; the $V_H$ and $V_L$ regions of the antibody or antigen-binding fragment thereof comprise the amino acid sequences of SEQ ID NOs:110 and 553, respectively; the $V_H$ and $V_L$ regions of the antibody or antigen-binding fragment thereof comprise the amino acid sequences of SEQ ID NOs:110 and 118, respectively; the $V_H$ and $V_L$ regions of the antibody or antigen-binding fragment thereof comprise the amino acid sequences of SEQ ID NOs:533 and 554, respectively; the $V_H$ and $V_L$ regions of the antibody or antigen-binding fragment thereof comprise the amino acid sequences of SEQ ID NOs:115 and 555, respectively; the $V_H$ and $V_L$ regions of the antibody or antigen-binding fragment thereof comprise the amino acid sequences of SEQ ID NOs:524 and 556, respectively; the $V_H$ and $V_L$ regions of the antibody or antigen-binding fragment thereof comprise the amino acid sequences of SEQ ID NOs:519 and 557, respectively, or any antibody or antigen-binding fragment thereof that has at least 90% sequence identity to any of the above $V_H$ and $V_L$, such as at least 90%, 91%, 92%, 93%, 94%, 95%, 96%, 97%, 98%, or 99% sequence identity thereto. In some embodiments, the antibody or antigen-binding fragment comprises a $V_H$ and a $V_L$ regions comprising the sequence having at least 90% identity to SEQ ID NOs:110 and 116, respectively; a $V_H$ and a $V_L$ regions comprising the sequence having at least 90% identity to SEQ ID NOs:110 and 120, respectively; a $V_H$ and a $V_L$ regions comprising the sequence having at least 90% identity to SEQ ID NOS:256 and 267, respectively; or a $V_H$ and a $V_L$ regions comprising the sequence having at least 90% identity to SEQ ID NOS:519 and 535, respectively. In some embodiments, the antibody or antigen-binding fragment comprises a $V_H$ and a $V_L$ regions comprising the sequence having at least 90% identity to SEQ ID NOs:115 and 536, respectively.

For example, the $V_H$ and $V_L$ regions of the antibody or antigen-binding fragment thereof provided therein comprise the amino acid sequences selected from: SEQ ID NOs:110 and 116; SEQ ID NOs:111 and 117; SEQ ID NOs:110 and 118; SEQ ID NOs:110 and 119; SEQ ID NOs:110 and 120; SEQ ID NOs:110 and 121; SEQ ID NOs:110 and 122; SEQ ID NOs:110 and 123; SEQ ID NOs:112 and 124; SEQ ID NOs:113 and 125; SEQ ID NOs:114 and 126; SEQ ID NOs:115 and 127; SEQ ID NOs:247 and 257; SEQ ID NOs:248 and 258; SEQ ID NOs:249 and 259; SEQ ID NOs:250 and 260; SEQ ID NOs:251 and 261; SEQ ID NOs:252 and 262; SEQ ID NOs:253 and 263; SEQ ID NOs:254 and 264; SEQ ID NOs:255 and 265; SEQ ID NOs:256 and 266; SEQ ID NOs:256 and 267; SEQ ID NOs:518 and 534; SEQ ID NOs:519 and 535; SEQ ID NOs:115 and 536; SEQ ID NOs:520 and 264; SEQ ID NOs:521 and 537; SEQ ID NOs:522 and 538; SEQ ID NOs:523 and 539; SEQ ID NOs:519 and 540; SEQ ID NOs:524 and 541; SEQ ID NOs:525 and 261; SEQ ID NOs:526 and 542; SEQ ID NOs:527 and 543; SEQ ID NOs:528 and 544; SEQ ID NOs:529 and 545; SEQ ID NOs:528 and 546; SEQ ID NOs:522 and 547; SEQ ID NOs:256 and 548; SEQ ID NOs:530 and 549; SEQ ID NOs:531 and 550; SEQ ID NOs:519 and 552; SEQ ID NOs:110 and 553; SEQ ID NOs:110 and 118; SEQ ID NOs:533 and 554; SEQ ID NOs:115 and 555; SEQ ID NOs:524 and 556; SEQ ID NOs:519 and 557, respectively.

In some embodiments, the $V_H$ and $V_L$ regions of the antibody or antigen-binding fragment thereof provided therein comprise the amino acid sequences selected from: SEQ ID NOs:110 and 116; SEQ ID NOs:111 and 117; SEQ ID NOs:110 and 118; SEQ ID NOs:110 and 120; SEQ ID NOs:110 and 121; SEQ ID NOs:112 and 124; SEQ ID NOs:113 and 125; SEQ ID NOs:248 and 258; SEQ ID NOs:252 and 262; SEQ ID NOs:253 and 263; SEQ ID NOs:254 and 264; SEQ ID NOs:255 and 265; SEQ ID NOs:256 and 266; SEQ ID NOs:256 and 267; SEQ ID NOs:518 and 534; SEQ ID NOs:519 and 535; SEQ ID NOs:115 and 536; SEQ ID NOs:520 and 264; SEQ ID NOs:521 and 537; and SEQ ID NOs:522 and 538, respectively. In some embodiments, the $V_H$ and $V_L$ regions of the antibody or antigen-binding fragment thereof provided therein comprise the amino acid sequences selected from: SEQ ID NOs:110 and 116; SEQ ID NOs:110 and 120; SEQ ID NOs:112 and 124; SEQ ID NOs:256 and 267; SEQ ID NOs:519 and 535; and SEQ ID NOs:115 and 536, respectively. In some embodiments, the $V_H$ and $V_L$ regions of the antibody or antigen-binding fragment thereof provided therein comprise the amino acid sequences selected from: SEQ ID NOs:256 and 267; and SEQ ID NOs:115 and 536, respectively.

In some embodiments, the $V_H$ and $V_L$ regions of the antibody or antigen-binding fragment thereof comprise the sequences of SEQ ID NOs:110 and 116, respectively; the $V_H$ and $V_L$ regions of the antibody or antigen-binding fragment thereof comprise the sequences of SEQ ID NOs:110 and 120, respectively; the $V_H$ and $V_L$ regions of the antibody or antigen-binding fragment thereof comprise the sequences of SEQ ID NOS:256 and 267, respectively; or the $V_H$ and $V_L$ regions of the antibody or antigen-binding fragment thereof comprise the sequences of SEQ ID NOS:519 and 535, respectively. In some embodiments, the $V_H$ and $V_L$ regions of the antibody or antigen-binding fragment thereof comprise the sequences of SEQ ID NOs:115 and 536, respectively.

In some embodiments, the antibody or antigen binding fragment comprises one or more heavy chain variable ($V_H$) region and one or more light chain variable ($V_L$) region, in any order or orientation. In some embodiments, the antibody or antigen-binding fragment comprises a $V_H$ region and a $V_L$ region, and the $V_H$ region is amino-terminal to the $V_L$ region. In some embodiments, the antibody or antigen-binding fragment comprises a $V_H$ region and a $V_L$ region, and the $V_H$ region is carboxy-terminal to the $V_L$ region. In some embodiments, the $V_H$ region(s) and the $V_L$ region(s) are linked directly or indirectly, optionally via a linker.

In some embodiments, the antibody or antigen-binding fragment, e.g., scFv, may include a $V_H$ region or portion thereof, followed by the linker, followed by a $V_L$ region or portion thereof. In some embodiments, the antibody or antigen-binding fragment, e.g., the scFv, may include the $V_L$ region or portion thereof, followed by the linker, followed by the $V_H$ region or portion thereof.

In some embodiments, the antibody or antigen-binding fragment thereof is a single-chain antibody fragment, such as a single chain variable fragment (scFv) or a diabody or a single domain antibody (sdAb). In some embodiments, the antibody or antigen-binding fragment is a single domain antibody comprising only the $V_H$ region. In some embodiments, the antibody or antigen binding fragment is an scFv comprising a heavy chain variable ($V_H$) region and a light chain variable ($V_L$) region. In some embodiments, the single-chain antibody fragment (e.g. scFv) includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

Accordingly, the provided anti-BCMA antibodies include single-chain antibody fragments, such as scFvs and diabodies, particularly human single-chain antibody fragments, typically comprising linker(s) joining two antibody domains or regions, such $V_H$ and $V_L$ regions. The linker typically is a peptide linker, e.g., a flexible and/or soluble peptide linker, such as one rich in glycine and serine.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:359) or GGGS (3GS; SEQ ID NO:360), such as between 2, 3, 4, and 5 repeats of such a sequence. Exemplary linkers include those having or consisting of an sequence set forth in SEQ ID NO:361 (GGGGSGGGGSGGGGS). Exemplary linkers further include those having or consisting of the sequence set forth in SEQ ID NO:362 (GSTSGSGKPGSGEGSTKG).

Accordingly, in some embodiments, the provided embodiments include single-chain antibody fragments, e.g., scFvs, comprising one or more of the aforementioned linkers, such as glycine/serine rich linkers, including linkers having repeats of GGGS or GGGGS, such as the linker set forth in SEQ ID NO:361. In some embodiments, the linker has an amino acid sequence containing the sequence set forth in SEQ ID NO:361.

In some aspects, an scFv provided herein comprises the amino acid sequence selected from any one of SEQ ID NOs:128-139, 268-278, 558-576 and 578-583, or has an amino acid sequence having at least at or about 90%, 91%, 92%, 93%, 94%, 95%, 96%, 97%, 98%, or 99% sequence identity to the amino acid sequence selected from any one of SEQ ID NOs:128-139, 268-278, 558-576 and 578-583.

For example, the scFv provided herein comprises the amino acid sequence selected from any of SEQ ID NOS: 128, 129, 130, 131, 132, 133, 134, 135, 136, 137, 138, 139, 268, 269, 270, 271, 272, 273, 274, 275, 276, 277, 278, 558, 559, 560, 561, 562, 563, 564, 565, 566, 567, 568, 569, 570, 571, 572, 573, 574, 575, 576, 578, 579, 580, 581, 582 and 583, or has an amino acid sequence having at least at or about 90%, 91%, 92%, 93%, 94%, 95%, 96%, 97%, 98%, or 99% sequence identity to the amino acid sequence selected from any one of SEQ ID NOS: 128, 129, 130, 131, 132, 133, 134, 135, 136, 137, 138, 139, 268, 269, 270, 271, 272, 273, 274, 275, 276, 277, 278, 558, 559, 560, 561, 562, 563, 564, 565, 566, 567, 568, 569, 570, 571, 572, 573, 574, 575, 576, 578, 579, 580, 581, 582 and 583.

In some embodiments, the scFv provided herein comprises the amino acid sequence selected from any of SEQ ID NOS: 128, 129, 130, 132, 133, 136, 137, 269, 273, 274, 275, 276, 277, 278, 558, 559, 560, 561, 562 and 563, or has an amino acid sequence having at least at or about 90%, 91%, 92%, 93%, 94%, 95%, 96%, 97%, 98%, or 99% sequence identity to the amino acid sequence selected from any one of SEQ ID NOS: 128, 129, 130, 132, 133, 136, 137, 269, 273, 274, 275, 276, 277, 278, 558, 559, 560, 561, 562 and 563. In some embodiments, the scFv provided herein comprises the amino acid sequence selected from any of SEQ ID NOS: 128, 132, 136, 278, 559 and 560, or has an amino acid sequence having at least at or about 90%, 91%, 92%, 93%, 94%, 95%, 96%, 97%, 98%, or 99% sequence identity to the amino acid sequence selected from any one of SEQ ID NOS: 128, 132, 136, 278, 559 and 560. In some embodiments, the scFv provided herein comprises the amino acid sequence selected from any of SEQ ID NOS: 278 and 560 or has an amino acid sequence having at least at or about 90%, 91%, 92%, 93%, 94%, 95%, 96%, 97%, 98%, or 99% sequence identity to the amino acid sequence selected from any one of SEQ ID NOS: 278 and 560. In some embodiments, the scFv comprises the sequence selected from any of SEQ ID NOs:128, 132, 278 and 502, or an sequence having at least 90% sequence identity to the sequence selected from any of SEQ ID NOs:128, 132, 278 and 502. In some embodiments, the scFv comprises the sequence of SEQ ID NO:560, or an sequence having at least 90% sequence identity to the sequence of SEQ ID NO:560.

Table 2 provides the SEQ ID NOS: of exemplary antibodies or antigen-binding fragments and regions or domains thereof that are provided herein. In some embodiments, the BCMA-binding antibody or fragment thereof comprises a $V_H$ region that comprises the CDR-H1, CDR-H2, and CDR-H3 sequence and a $V_L$ region that comprises the CDR-L1, CDR-L2 and CDR-L3 sequence set forth in the SEQ ID NOS: listed in each row of Table 2 below (by Kabat numbering). In some embodiments, the BCMA-binding antibody or fragment thereof comprises a $V_H$ region sequence and a $V_L$ region sequence set forth in the SEQ ID NOS: listed in each row of Table 2 below, or an antibody comprising a $V_H$ and $V_L$ region amino acid sequence that has at least 90%, 91%, 92%, 93%, 94%, 95%, 96%, 97%, 98%, or 99% sequence identity to the $V_H$ region sequence and the $V_L$ region sequence set forth in the SEQ ID NOS: listed in each row of Table 2 below. In some embodiments, the BCMA-binding antibody or fragment thereof comprises a $V_H$ region sequence and a $V_L$ region sequence set forth in the SEQ ID NOS: listed in each row of Table 2 below. In some embodiments, the BCMA-binding antibody or fragment thereof comprises an scFv sequence set forth in the SEQ ID NOS: listed in each row of Table 2 below, or an antibody comprising an scFv amino acid sequence that has at least 90%, 91%, 92%, 93%, 94%, 95%, 96%, 97%, 98%, or 99% sequence identity to the scFv sequence set forth in the SEQ ID NOS: listed in each row of Table 2 below.

TABLE 2

Sequence identifier (SEQ ID NO) for Exemplary Antibodies and Domains

| Antigen-binding domain | CDR-H1 | CDR-H2 | CDR-H3 | CDR-L1 | CDR-L2 | CDR-L3 | $V_H$ | $V_L$ | scFv |
|---|---|---|---|---|---|---|---|---|---|
| BCMA-1 | 1 | 4 | 7 | 26 | 37 | 47 | 110 | 116 | 128 |
| BCMA-2 | 2 | 5 | 8 | 27 | 38 | 48 | 111 | 117 | 129 |
| BCMA-3 | 1 | 4 | 7 | 28 | 39 | 49 | 110 | 118 | 130 |
| BCMA-4 | 1 | 4 | 7 | 29 | 40 | 50 | 110 | 119 | 131 |
| BCMA-5 | 1 | 4 | 7 | 30 | 39 | 51 | 110 | 120 | 132 |
| BCMA-6 | 1 | 4 | 7 | 31 | 41 | 52 | 110 | 121 | 133 |
| BCMA-7 | 1 | 4 | 7 | 32 | 42 | 53 | 110 | 122 | 134 |
| BCMA-8 | 1 | 4 | 7 | 30 | 39 | 54 | 110 | 123 | 135 |
| BCMA-9 | 2 | 5 | 9 | 33 | 43 | 55 | 112 | 124 | 136 |
| BCMA-10 | 2 | 5 | 10 | 34 | 44 | 56 | 113 | 125 | 137 |
| BCMA-11 | 3 | 6 | 11 | 35 | 45 | 57 | 114 | 126 | 138 |
| BCMA-12 | 2 | 5 | 10 | 36 | 46 | 58 | 115 | 127 | 139 |

TABLE 2-continued

Sequence identifier (SEQ ID NO) for Exemplary Antibodies and Domains

| Antigen-binding domain | CDR-H1 | CDR-H2 | CDR-H3 | CDR-L1 | CDR-L2 | CDR-L3 | $V_H$ | $V_L$ | scFv |
|---|---|---|---|---|---|---|---|---|---|
| BCMA-13 | 140 | 145 | 149 | 174 | 179 | 184 | 247 | 257 | 268 |
| BCMA-14 | 141 | 145 | 149 | 174 | 179 | 185 | 248 | 258 | 269 |
| BCMA-15 | 141 | 145 | 150 | 174 | 179 | 186 | 249 | 259 | 270 |
| BCMA-16 | 142 | 146 | 151 | 174 | 179 | 187 | 250 | 260 | 271 |
| BCMA-17 | 2 | 5 | 152 | 175 | 180 | 188 | 251 | 261 | 272 |
| BCMA-18 | 143 | 147 | 153 | 174 | 179 | 189 | 252 | 262 | 273 |
| BCMA-19 | 144 | 148 | 154 | 176 | 181 | 190 | 253 | 263 | 274 |
| BCMA-20 | 3 | 6 | 155 | 177 | 182 | 191 | 254 | 264 | 275 |
| BCMA-21 | 2 | 5 | 156 | 174 | 179 | 192 | 255 | 265 | 276 |
| BCMA-22 | 2 | 5 | 157 | 178 | 183 | 193 | 256 | 266 | 277 |
| BCMA-23 | 2 | 5 | 157 | 178 | 183 | 194 | 256 | 267 | 278 |
| BCMA-24 | 2 | 6 | 376 | 30 | 399 | 415 | 518 | 534 | 558 |
| BCMA-25 | 1 | 4 | 7 | 380 | 400 | 416 | 519 | 535 | 559 |
| BCMA-26 | 2 | 5 | 10 | 33 | 43 | 421 | 115 | 536 | 560 |
| BCMA-27 | 3 | 6 | 155 | 177 | 182 | 191 | 520 | 264 | 561 |
| BCMA-28 | 3 | 372 | 376 | 381 | 401 | 417 | 521 | 537 | 562 |
| BCMA-29 | 3 | 6 | 376 | 382 | 402 | 418 | 522 | 538 | 563 |
| BCMA-30 | 3 | 6 | 377 | 383 | 403 | 419 | 523 | 539 | 564 |
| BCMA-31 | 1 | 4 | 7 | 384 | 39 | 54 | 519 | 540 | 565 |
| BCMA-32 | 2 | 5 | 10 | 385 | 180 | 58 | 524 | 541 | 566 |
| BCMA-33 | 2 | 373 | 152 | 175 | 180 | 188 | 525 | 261 | 567 |
| BCMA-34 | 3 | 6 | 11 | 386 | 404 | 420 | 526 | 542 | 568 |
| BCMA-35 | 2 | 5 | 378 | 33 | 43 | 421 | 527 | 543 | 569 |
| BCMA-36 | 2 | 5 | 9 | 387 | 405 | 422 | 528 | 544 | 570 |
| BCMA-37 | 2 | 5 | 9 | 388 | 406 | 423 | 529 | 545 | 571 |
| BCMA-38 | 2 | 5 | 9 | 388 | 407 | 424 | 528 | 546 | 572 |
| BCMA-39 | 3 | 6 | 376 | 389 | 408 | 425 | 522 | 547 | 573 |
| BCMA-40 | 2 | 5 | 157 | 390 | 183 | 193 | 256 | 548 | 574 |
| BCMA-41 | 2 | 374 | 9 | 391 | 409 | 426 | 530 | 549 | 575 |
| BCMA-42 | 1 | 4 | 7 | 392 | 40 | 427 | 531 | 550 | 576 |
| BCMA-44 | 1 | 4 | 7 | 394 | 39 | 429 | 519 | 552 | 578 |
| BCMA-45 | 1 | 4 | 7 | 395 | 411 | 430 | 110 | 553 | 579 |
| BCMA-46 | 1 | 4 | 7 | 28 | 39 | 49 | 110 | 118 | 130 |
| BCMA-47 | 2 | 5 | 10 | 396 | 412 | 431 | 533 | 554 | 580 |
| BCMA-48 | 2 | 5 | 10 | 396 | 412 | 58 | 115 | 555 | 581 |
| BCMA-49 | 2 | 5 | 10 | 397 | 413 | 432 | 524 | 556 | 582 |
| BCMA-51 | 1 | 4 | 7 | 398 | 414 | 433 | 519 | 557 | 583 |
| BCMA-52 | 496 | 507 | 513 | 517 | 532 | 551 | 577 | 587 | 442 |
| BCMA-55 | 588 | 589 | 590 | 591 | 592 | 593 | 594 | 595 | 478 |
| BCMA-C1, VH-VL | 288 | 290 | 292 | 302 | 304 | 306 | 324 | 326 | 585 |
| BCMA-C1, VL-VH | 288 | 290 | 292 | 302 | 304 | 306 | 324 | 326 | 328 |
| BCMA-C2, VH-VL | 289 | 291 | 293 | 303 | 305 | 307 | 325 | 327 | 329 |
| BCMA-C2, VL-VH | 289 | 291 | 293 | 303 | 305 | 307 | 325 | 327 | 586 |

Among the provided antibodies, e.g. antigen-binding fragments, are human antibodies. In some embodiments of a provided human anti-BCMA antibody, e.g., antigen-binding fragments, the human antibody contains a $V_H$ region that comprises a portion having at least 95%, 96%, 97%, 98%, 99%, or 100% sequence identity to an amino acid sequence encoded by a germline nucleotide human heavy chain V segment, a portion having at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or contains a $V_L$ region that comprises a portion having at least 95%, 96%, 97%, 98%, 99%, or 100% sequence identity to an amino acid sequence encoded by a germline nucleotide human kappa or lambda chain V segment, and/or a portion having at least 95%, 96%, 97%, 98%, 99%, or 100% sequence identity to an amino acid sequence encoded by a germline nucleotide human kappa or lambda chain J segment. In some embodiments, the portion of the $V_H$ region corresponds to the CDR-H1, CDR-H2 and/or CDR-H3. In some embodiments, the portion of the $V_H$ region corresponds to the framework region 1 (FR1), FR2, FR2 and/or FR4. In some embodiments, the portion of the $V_L$ region corresponds to the CDR-L1, CDR-L2 and/or CDR-L3. In some embodiments, the portion of the $V_L$ region corresponds to the FR1, FR2, FR2 and/or FR4.

In some embodiments, the human antibody or antigen-binding fragment thereof, contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody or antigen-binding fragment thereof, contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody or antigen-binding fragment thereof, contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody or antigen-binding fragment thereof, contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody or antigen-binding fragment thereof, contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody or antigen-binding fragment thereof, contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody or antigen-binding fragment thereof, contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V segment and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V segment and/or J segment. For example, in some such embodiments, the framework region sequence contained within the $V_H$ region and/or $V_L$ region differs by no more than 10 amino acids, such as no more than 9, 8, 7, 6, 5, 4, 3, 2 or 1 amino acid, compared to the framework region sequence encoded by a human germline antibody segment.

The antibody or antigen-binding fragment thereof, may contain at least a portion of an immunoglobulin constant region, such as one or more constant region domain. In some embodiments, the constant regions include a light chain constant region and/or a heavy chain constant region 1 (CH1). In some embodiments, the antibody includes a CH2 and/or CH3 domain, such as an Fc region. In some embodiments, the Fc region is an Fc region of a human IgG, such as an IgG1 or IgG4.

Also provided are nucleic acids, e.g., polynucleotides, encoding the antibodies and/or portions, e.g., chains, thereof. Among the provided nucleic acids are those encoding the anti-BCMA antibodies (e.g., antigen-binding fragment) described herein. Also provided are nucleic acids, e.g., polynucleotides, encoding one or more antibodies and/or portions thereof, e.g., those encoding one or more of the anti-BCMA antibodies (e.g., antigen-binding fragment) described herein and/or other antibodies and/or portions thereof, e.g., antibodies and/or portions thereof that binds other target antigens. The nucleic acids may include those encompassing natural and/or non-naturally occurring nucleotides and bases, e.g., including those with backbone modifications. The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

Also provided are vectors containing the nucleic acids, e.g., polynucleotides, and host cells containing the vectors, e.g., for producing the antibodies or antigen-binding fragments thereof. Also provided are methods for producing the antibodies or antigen-binding fragments thereof. The nucleic acid may encode an amino acid sequence comprising the $V_L$ region and/or an amino acid sequence comprising the $V_H$ region of the antibody (e.g., the light and/or heavy chains of the antibody). The nucleic acid may encode one or more amino acid sequence comprising the $V_L$ region and/or an amino acid sequence comprising the $V_H$ region of the antibody (e.g., the light and/or heavy chains of the antibody). In some embodiments, the nucleic acid, e.g., polynucleotide encodes one or more $V_H$ region and/or one or more $V_L$ region of the antibody, in any order or orientation. In some embodiments, the nucleic acid, e.g., polynucleotide encodes a $V_H$ region and a $V_L$ region, and the coding sequence for the $V_H$ region is upstream of the coding sequence for the $V_L$ region. In some embodiments, the nucleic acid, e.g., polynucleotide encodes a $V_H$ region and a $V_L$ region, and the coding sequence for the $V_L$ region is upstream of the coding sequence for the $V_H$ region.

In a further embodiment, one or more vectors (e.g., expression vectors) comprising such nucleic acids are provided. In a further embodiment, a host cell comprising such nucleic acids is provided. In one such embodiment, a host cell comprises (e.g., has been transformed with) a vector comprising a nucleic acid that encodes an amino acid sequence comprising the $V_H$ region of the antibody. In another such embodiment, a host cell comprises (e.g., has been transformed with) (1) a vector comprising a nucleic acid that encodes an amino acid sequence comprising the $V_L$ region of the antibody and an amino acid sequence comprising the $V_H$ region of the antibody, or (2) a first vector comprising a nucleic acid that encodes an amino acid sequence comprising the $V_L$ region of the antibody and a second vector comprising a nucleic acid that encodes an amino acid sequence comprising the $V_H$ region of the antibody. In some embodiments, a host cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such host cells are provided. In some embodiments, a composition containing one or more such host cells are provided. In some embodiments, the one or more host cells can express different antibodies, or the same antibody. In some embodiments, each of the host cells can express more than one antibody.

Also provided are methods of making the anti-BCMA antibodies (including antigen-binding fragments). For recombinant production of the anti-BCMA antibody, a nucleic acid sequence or a polynucleotide encoding an antibody, e.g., as described above, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the anti-BCMA antibody is provided, wherein the method comprises culturing a host cell comprising a nucleic acid sequence encoding the antibody, as provided above, under conditions suitable for expression of the antibody, and optionally recovering the antibody from the host cell (or host cell culture medium).

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides include, but are not limited to, COS cells, including COS 7 cells; 293 cells, including 293-6E cells; CHO cells, including CHO—S, DG44. Lec13 CHO cells, and FUT8 CHO cells; PER.C6® cells; and NSO cells. In some embodiments, the antibody heavy chains and/or light chains (e.g., $V_H$ region and/or $V_L$ region) may be expressed in yeast. See, e.g., U.S. Publication No. US 2006/0270045 A1. In some embodiments, a particular eukaryotic host cell is selected based on its ability to make desired post-translational modifications to the heavy chains and/or light chains (e.g., $V_H$ region and/or $V_L$ region). For example, in some embodiments, CHO cells produce polypeptides that have a higher level of sialylation than the same polypeptide produced in 293 cells.

In some embodiments, the antibody or antigen-binding fragment provided herein is produced in a cell-free system. Exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

The provided embodiments further include vectors and host cells and other expression systems for expressing and producing the antibodies and other antigen-binding proteins, including eukaryotic and prokaryotic host cells, including bacteria, filamentous fungi, and yeast, as well as mammalian cells such as human cells, as well as cell-free expression systems.

b. Exemplary Features

In some aspects, the provided antibodies or antigen-binding fragments thereof have one or more specified functional features, such as binding properties, including binding to particular epitopes.

In some embodiments, the antibodies or antigen-binding fragments thereof specifically bind to BCMA protein. In some embodiments provided herein, BCMA protein refers to human BCMA, a mouse BCMA protein, or a non-human primate (e.g., cynomolgus monkey) BCMA protein. In some embodiments of any of the embodiments herein, BCMA protein refers to human BCMA protein. The observation that an antibody or other binding molecule binds to BCMA protein or specifically binds to BCMA protein does not necessarily mean that it binds to a BCMA protein of every species. For example, in some embodiments, features of binding to BCMA protein, such as the ability to specifically bind thereto and/or to bind with a particular affinity to a particular degree, in some embodiments, refers to the ability with respect to a human BCMA protein and the antibody may not have this feature with respect to a BCMA protein of another species, such as mouse.

In some embodiments, the antibody or antigen-binding fragment binds to a mammalian BCMA protein, including to naturally occurring variants of BCMA, such as certain splice variants or allelic variants.

In some embodiments, the antibodies specifically bind to human BCMA protein, such as to an epitope or region of human BCMA protein, such as the human BCMA protein comprising the amino acid sequence of SEQ ID NO:367 (GenBank No. BAB60895.1), or SEQ ID NO:368 (NCBI No. NP_001183.2) or an allelic variant or splice variant thereof. In one embodiment, the human BCMA protein is encoded by a transcript variant or is an isoform that has the sequence of amino acids forth in SEQ ID NO:369. In some embodiments, the antibodies bind to cynomolgus monkey BCMA protein, such as the cynomolgus monkey BCMA protein set forth in SEQ ID NO:371 (GenBank No. EHH60172.1). In some embodiments, the antibodies bind to human BCMA but do not bind to or bind in a lower level or degree or affinity to cynomolgus monkey BCMA protein, such as the cynomolgus monkey BCMA protein set forth in SEQ ID NO:371 (GenBank No. EHH60172.1). In some embodiments, the antibodies do not bind to or bind in a lower level or degree or affinity to mouse BCMA protein, such as the mouse BCMA protein set forth in SEQ ID NO:370 (NCBI No. NP_035738.1). In some embodiments, the antibodies bind to mouse BCMA protein, such as the mouse BCMA protein set forth in SEQ ID NO:370 (NCBI No. NP_035738.1). In some embodiments, the antibodies bind to mouse BCMA protein, with lower affinity than its binding to a human BCM protein and/or a cynomolgus monkey BCMA protein. In some embodiments, the antibodies bind to mouse BCMA protein and/or a cynomolgus monkey BCMA protein with lower affinity than its binding to a human BCM protein. In some embodiments, the antibodies bind to mouse BCMA protein and/or a cynomolgus monkey BCMA protein with similar binding affinity compared to its binding to a human BCMA protein.

In one embodiment, the extent of binding of an anti-BCMA antibody to an unrelated, non-BCMA protein, such as a non-human BCMA protein or other non-BCMA protein, is less than at or about 10% of the binding of the antibody to human BCMA protein as measured, e.g., by a radioimmunoassay (RIA). In some embodiments, among provided antibodies are antibodies in which binding to mouse BCMA protein is less than or at or about 10% of the binding of the antibody to human BCMA protein. In some embodiments, among provided antibodies are antibodies in which binding to cynomolgus monkey BCMA protein is less than or at or about 10% of the binding of the antibody to human BCMA protein. In some embodiments, among provided antibodies are antibodies in which binding to cynomolgus monkey BCMA protein and/or a mouse BCMA protein is similar to or about the same as the binding of the antibody to human BCMA protein.

In some embodiments, the antibody specifically binds to and/or to bind with a particular affinity to a particular degree, to a BCMA protein, e.g., human BCMA, a mouse BCMA protein, or a non-human primate (e.g., cynomolgus monkey) BCMA protein.

In some embodiments, the provided antibodies are capable of binding BCMA protein, such as human BCMA protein, with at least a certain affinity, as measured by any of a number of known methods. In some embodiments, the affinity is represented by an equilibrium dissociation constant ($K_D$); in some embodiments, the affinity is represented by $EC_{50}$.

A variety of assays are known for assessing binding affinity and/or determining whether a binding molecule (e.g., an antibody or fragment thereof) specifically binds to a particular ligand (e.g., an antigen, such as a BCMA protein). It is within the level of a skilled artisan to determine the binding affinity of a binding molecule, e.g., an antibody, for an antigen, e.g., BCMA, such as human BCMA or cynomolgus BCMA or mouse BCMA, such as by using any of a number of binding assays that are well known in the art. For example, in some embodiments, a BIAcore® instrument can be used to determine the binding kinetics and constants of a complex between two proteins (e.g., an antibody or fragment thereof, and an antigen, such as a BCMA protein), using surface plasmon resonance (SPR) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed nucleic acids or binding of proteins.

In some embodiments, the binding molecule, e.g., antibody or fragment thereof, binds, such as specifically binds, to an antigen, e.g., a BCMA protein or an epitope therein, with an affinity or $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$. In some embodiments, the antibody or fragment thereof exhibits a binding affinity for the peptide epitope with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from $10^{-5}$ M to $10^{-13}$ M, such as $10^{-7}$ M to $10^{-11}$ M, $10^{-8}$ M to $10^{-10}$ M, or $10^{-9}$ M to $10^{-10}$ M. The on-rate (association rate constant; $k_{on}$ or $k_a$; units of 1/Ms) and the off-rate (dissociation rate constant; $k_{off}$ or $k_d$; units of 1/s) can be determined using any of the assay methods known in the art, for example, surface plasmon resonance (SPR).

In some embodiments, the binding affinity ($EC_{50}$) and/or the dissociation constant of the antibody (e.g. antigen-binding fragment) to about BCMA protein, such as human BCMA protein, is from or from about 0.01 nM to about 500 nM, from or from about 0.01 nM to about 400 nM, from or from about 0.01 nM to about 100 nM, from or from about 0.01 nM to about 50 nM, from or from about 0.01 nM to about 10 nM, from or from about 0.01 nM to about 1 nM, from or from about 0.01 nM to about 0.1 nM, is from or from about 0.1 nM to about 500 nM, from or from about 0.1 nM to about 400 nM, from or from about 0.1 nM to about 100 nM, from or from about 0.1 nM to about 50 nM, from or from about 0.1 nM to about 10 nM, from or from about 0.1 nM to about 1 nM, from or from about 0.5 nM to about 200 nM, from or from about 1 nM to about 500 nM, from or from about 1 nM to about 100 nM, from or from about 1 nM to about 50 nM, from or from about 1 nM to about 10 nM, from or from about 2 nM to about 50 nM, from or from about 10 nM to about 500 nM, from or from about 10 nM to about 100 nM, from or from about 10 nM to about 50 nM, from or from about 50 nM to about 500 nM, from or from about 50 nM to about 100 nM or from or from about 100 nM to about 500 nM. In certain embodiments, the binding affinity ($EC_{50}$) and/or the equilibrium dissociation constant, $K_D$, of the antibody to a BCMA protein, such as human BCMA protein, is at or less than or about 400 nM, 300 nM, 200 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies bind to a BCMA protein, such as human BCMA protein, with a sub-nanomolar binding affinity, for example, with a binding affinity less than about 1 nM, such as less than about 0.9 nM, about 0.8 nM, about 0.7 nM, about 0.6 nM, about 0.5 nM, about 0.4 nM, about 0.3 nM, about 0.2 nM or about 0.1 nM or less.

In some embodiments, the binding affinity may be classified as high affinity or as low affinity. In some cases, the binding molecule (e.g. antibody or fragment thereof) that exhibits low to moderate affinity binding exhibits a $K_A$ of up to $10^7$ $M^{-1}$, up to $10^6$ $M^{-1}$, up to $10^5$ M. In some cases, a binding molecule (e.g. antibody or fragment thereof) that exhibits high affinity binding to a particular epitope interacts with such epitope with a $K_A$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ M. In some embodiments, the binding affinity ($EC_{50}$) and/or the equilibrium dissociation constant, $K_D$, of the binding molecule, e.g., anti-BCMA antibody or fragment thereof, to a BCMA protein, is from or from about 0.01 nM to about 1 μM, 0.1 nM to 1 μM, 1 nM to 1 μM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity ($EC_{50}$) and/or the dissociation constant of the equilibrium dissociation constant, $K_D$, of the binding molecule, e.g., anti-BCMA antibody or fragment thereof, to a BCMA protein, is at or about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less.

In some embodiments, the binding affinity of a binding molecule, such as an anti-BCMA antibody, for different antigens, e.g., BCMA proteins from different species can be compared to determine the species cross-reactivity. For example, species cross-reactivity can be classified as high cross reactivity or low cross reactivity. In some embodiments, the equilibrium dissociation constant, $K_D$, for different antigens, e.g., BCMA proteins from different species such as human, cynomolgus monkey or mouse, can be compared to determine species cross-reactivity. In some embodiments, the species cross-reactivity of an anti-BCMA antibody can be high, e.g., the anti-BCMA antibody binds to human BCMA and a species variant BCMA to a similar degree, e.g., the ratio of $K_D$ for human BCMA and $K_D$ for the species variant BCMA is or is about 1. In some embodiments, the species cross-reactivity of an anti-BCMA antibody can be low, e.g., the anti-BCMA antibody has a high affinity for human BCMA but a low affinity for a species variant BCMA, or vice versa. For example, the ratio of $K_D$ for the species variant BCMA and $K_D$ for the human BCMA is more than 10, 15, 20, 25, 30, 40, 50, 60, 70, 80, 90, 100, 200, 500, 1000, 2000 or more, and the anti-BCMA antibody has low species cross-reactivity. The degree of species cross-reactivity can be compared with the species cross-reactivity of a known antibody.

In some embodiments, the provided antibodies or antigen binding fragments thereof bind to a similar degree to a human BCMA protein and a non-human BCMA protein or other non-BCMA proteins. For example, in some embodiments, the provided antibodies or antigen binding fragments thereof bind to a human BCMA protein, such as the human BCMA protein comprising the amino acid sequence of SEQ ID NO:367 (GenBank No. BAB60895.1), or SEQ ID NO:368 (NCBI No. NP_001183.2) or an allelic variant or splice variant thereof, with an equilibrium dissociation constant ($K_D$), and to a non-human BCMA, such as a cynomolgus monkey BCMA, such as the cynomolgus monkey BCMA protein set forth in SEQ ID NO:371 (GenBank No. EHH60172.1), with a $K_D$ that is similar, or about the same, or less than 2-fold different, or less than 5-fold different.

For example, in some embodiments, the provided antibodies or antigen binding fragments thereof bind to a human BCMA with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less, and binds to a cynomolgus monkey BCMA with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a mouse BCMA protein with a $K_D$ of about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a human BCMA, a cynomolgus monkey BCMA and a mouse BCMA with high affinity. In some embodiments, the provided antibodies or antigen binding fragments thereof bind to a human BCMA and cynomolgus monkey BCMA with a high affinity, and to a mouse BCMA with low affinity. In some embodiments, the provided antibodies or antigen binding fragments thereof bind to a human BCMA and BCMA from other species, or other variants of the BCMA protein, with high affinity.

In some embodiments, the total binding capacity ($R_{max}$), as measured using particular surface plasmon resonance (SPR) conditions, is used to determine the ability or capacity of binding of the provided antibody or antigen binding fragment thereof, to the antigen, e.g., a BCMA protein, such as a human BCMA protein. For SPR analysis, the "ligand" is the immobilized target molecule on the surface of the sensor, for example, a BCMA protein, and the "analyte" is the tested molecule, e.g., antibody, for binding to the "ligand". For example, the "analyte" can be any of the provided antibodies or antigen binding fragments thereof that binds to a BCMA protein. For a particular ligand and analyte pair in SPR, the $R_{max}$ can be determined assuming a 1:1 binding stoichiometry model, for a particular condition. In some embodiments, binding capacity ($R_{max}$) can be determined using the following formula: $R_{max}$ (RU)=(analyte molecular weight)/(ligand molecular weight)×immobilized ligand level (RU). In particular aspects of SPR conditions, the $R_{max}$ of binding between any of the provided antibody or antigen binding fragment thereof and a BCMA protein, such as a human BCMA or a cynomolgus BCMA, is at least or at least about 50 resonance units (RU), such as about 25 RU, 20 RU, 15 RU, 10 RU, 5 RU or 1 RU.

In some embodiments, the antibodies or antigen-binding fragment thereof, such as the human antibodies, specifically bind to a particular epitope or region of BCMA protein, such as generally an extracellular epitope or region. BCMA protein is a type III membrane 184 amino acid protein that contains an extracellular domain, a transmembrane domain, and a cytoplasmic domain. With reference to a human BCMA amino acid sequence set forth in SEQ ID NO:367, the extracellular domain corresponds to amino acids 1-54, amino acids 55-77 correspond to the transmembrane domain, and amino acids 78-184 correspond to the cytoplasmic domain.

In some embodiments, the antibodies or antigen-binding fragment thereof, binds, e.g., specifically binds, and/or recognizes, one or more epitopes in BCMA, e.g., human BCMA. In some embodiments, the epitopes are epitopes present on the extracellular domain of BCMA, e.g., human BCMA. In some embodiments, the epitopes include peptide epitopes. In some embodiments, the epitope includes linear epitopes and/or conformational epitopes or combination thereof. In some embodiments, the epitope(s) on BCMA, that the antibody or antigen-binding fragment thereof, e.g., anti-BCMA antibody or antigen-binding fragment thereof provided herein, include conformational epitopes, e.g., epitopes that include several peptide stretches from BCMA. In some embodiments, the anti-BCMA antibodies or antigen-binding fragment thereof provided herein bind to or recognize one or a combination of $_{21}CIPCQLR_{27}$ (set forth in SEQ ID NO:375), $_{30}SNTPPLTCQR_{39}$ (set forth in SEQ ID NO:379) and $_{44}SVTNSVK_{50}$ (set forth in SEQ ID NO:393). In some embodiments, the epitope of comprises $_{30}$SNTPPLTCQR$_{39}$ (SEQ ID NO:379) and/or $_{44}$SVTNSVK$_{50}$ (SEQ ID NO:393). In some embodiments, the anti-BCMA antibodies or antigen-binding fragment thereof provided herein bind to or recognize $_{30}$SNTPPLTCQR$_{39}$ (set forth in SEQ ID NO:379). In some embodiments, the anti-BCMA antibodies or antigen-binding fragment thereof provided herein bind to or recognize one or a combination of $_{8}$CSQNEYF$_{14}$ (set forth in SEQ ID NO:410) and $_{17}$LLHACIPCQLR$_{27}$ (set forth in SEQ ID NO:428). In some embodiments, the epitope comprises $_{17}$LLHACIPCQLR$_{27}$ (SEQ ID NO:428).

In some embodiments, the antibody or antigen-binding fragment binds to one or more epitope(s) of a human BCMA protein selected from among $_{21}$CIPCQLR$_{27}$ (SEQ ID NO:375), $_{30}$SNTPPLTCQR$_{39}$ (SEQ ID NO:379) and $_{44}$SVTNSVK$_{50}$ (SEQ ID NO:393), but does not include a $V_H$ region comprising a heavy chain complementarity determining region 1 (CDR-H1), CDR-H2, and/or CDR-H3, respectively, comprising the amino acid sequence of SEQ ID NOs:496, 507 and/or 513, respectively, and/or the antibody or antigen-binding fragment does not comprise a $V_L$ region comprising a light chain complementarity determining region 1 (CDR-L1), CDR-L2, and/or CDR-L3, respectively, comprising the amino acid sequence of SEQ ID NOs:517, 532 and/or 551; or does include an antibody or antigen-binding fragment thereof that comprises a $V_H$ region containing the amino acid sequence set forth in SEQ ID NO:577 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto, and/or a $V_L$ region containing the amino acid sequence set forth in SEQ ID NO:587 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto.

In some embodiments, the antibody or antigen-binding fragment binds to one or more epitope(s) of a human BCMA protein selected from among $_{8}$CSQNEYF$_{14}$ (SEQ ID NO:410) and $_{17}$LLHACIPCQLR$_{27}$ (SEQ ID NO:428), but does not comprise a $V_H$ region comprising a heavy chain complementarity determining region 1 (CDR-H1), CDR-H2, and/or CDR-H3, respectively, comprising the amino acid sequence of SEQ ID NOs:496, 507 and/or 513, respectively, and/or the antibody or antigen-binding fragment does not comprise a $V_L$ region comprising a light chain complementarity determining region 1 (CDR-L1), CDR-L2, and/or CDR-L3, respectively, comprising the amino acid sequence of SEQ ID NOs:517, 532 and/or 551; or does include an antibody or antigen-binding fragment thereof that comprises a $V_H$ region containing the amino acid sequence set forth in SEQ ID NO:577 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto, and/or a $V_L$ region containing the amino acid sequence set forth in SEQ ID NO:587 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto.

In some embodiments, the antibody or antigen-binding fragment does not comprise a $V_H$ region comprising a heavy chain complementarity determining region 1 (CDR-H1), CDR-H2, and/or CDR-H3, respectively, comprising the amino acid sequence of SEQ ID NOs:496, 507 and/or 513, respectively, and/or the antibody or antigen-binding fragment does not comprise a $V_L$ region comprising a light chain complementarity determining region 1 (CDR-L1), CDR-L2, and/or CDR-L3, respectively, comprising the amino acid sequence of SEQ ID NOs:517, 532 and/or 551; or does include an antibody or antigen-binding fragment thereof that comprises a $V_H$ region containing the amino acid sequence set forth in SEQ ID NO:577 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto, and/or a $V_L$ region containing the amino acid sequence set forth in SEQ ID NO:587 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto.

In some embodiments, the antibody or antigen-binding fragment does not comprise a $V_H$ region comprising a heavy chain complementarity determining region 1 (CDR-H1), CDR-H2, and/or CDR-H3, respectively, comprising the amino acid sequence of SEQ ID NOs:588, 589 and/or 590, respectively, and/or the antibody or antigen-binding fragment does not comprise a $V_L$ region comprising a light chain complementarity determining region 1 (CDR-L1), CDR-L2, and/or CDR-L3, respectively, comprising the amino acid sequence of SEQ ID NOs:591, 592 and/or 593; or does include an antibody or antigen-binding fragment thereof that comprises a $V_H$ region containing the amino acid sequence set forth in SEQ ID NO:594 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto, and/or a $V_L$ region containing the amino acid sequence set forth in SEQ ID NO:595 or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% homology thereto.

In some embodiments, the provided antibody or antigen-binding fragment thereof binds to the epitope of a human BCMA protein comprising $_{30}$SNTPPLTCQR$_{39}$ (SEQ ID NO:379) and/or $_{44}$SVTNSVK$_{50}$ (SEQ ID NO:393). For example, in some embodiments, the antibody or antigen-binding fragment thereof comprises a heavy chain complementarity determining region 3 (CDR-H3) comprising the amino acid sequence selected from any one of SEQ ID NOs: 7 and 157, or a CDR-H3 contained within the heavy chain variable ($V_H$) region amino acid sequence selected from any one of SEQ ID NOs:110, 256 and 519, and/or a light chain complementarity determining region 3 (CDR-L3) comprising the amino acid sequence selected from any one of SEQ ID NOs: 47, 51, 194 and 416, or a CDR-L3 contained within the light chain variable ($V_L$) region amino acid sequence selected from any one of SEQ ID NOs: 116, 120, 267 and 535. In some embodiments, the antibody or antigen-binding fragment thereof further comprises a heavy chain complementarity determining region 1 (CDR-H1) comprising the amino acid sequence selected from any one of SEQ ID NOs: 1 and 2, or a CDR-H1 contained within the heavy chain variable ($V_H$) region amino acid sequence selected from any one of SEQ ID NOs:110, 256 and 519, and/or a light chain complementarity determining region 1 (CDR-L1) comprising the amino acid sequence selected from any one of SEQ ID NOs: 26, 30, 178 and 380, or a CDR-L1 contained within the light chain variable ($V_L$) region amino acid sequence selected from any one of SEQ ID NOs: 116, 120, 267 and 535; a heavy chain complementarity determining region 2 (CDR-H2) comprising the amino acid sequence selected from any one of SEQ ID NOs: 4 or 5, or a CDR-H2 contained within the heavy chain variable ($V_H$) region amino acid sequence selected from any one of SEQ ID NOs:110, 256 and 519, and/or a light chain complementarity determining region 2 (CDR-L2) comprising the amino acid sequence selected from any one of SEQ ID NOs: 37, 39, 183 or 400, or a CDR-L2 contained within the light chain variable ($V_L$) region amino acid sequence selected from any one of SEQ ID NOs: 116, 120, 267 and 535. For example, in some embodiments, the antibody or antigen-binding fragment comprises a $V_H$ region comprising a CDR-H1, a CDR-H2, and a CDR-H3, respectively, comprising the amino acid sequence of a CDR-H1, a CDR-H2, and a CDR-H3 contained within the $V_H$ region amino acid sequence selected from any one of SEQ ID NOs: 110, 256 and 519; and/or a $V_L$ region comprising a CDR-L1, a CDR-L2, and a CDR-L3, respectively, comprising the amino acid sequence of a CDR-L1, a CDR-L2, and a CDR-L3 contained within the $V_L$ region amino acid sequence selected from any one of SEQ ID NOs: 116, 120, 267 and 535.

In some embodiments, the $V_H$ and $V_L$ regions of the antibody or antigen-binding fragment thereof comprise the amino acid sequences of SEQ ID NOs:110 and 116, respectively; the $V_H$ and $V_L$ regions of the antibody or antigen-binding fragment thereof comprise the amino acid sequences of SEQ ID NOs:110 and 120, respectively; the $V_H$ and $V_L$ regions of the antibody or antigen-binding fragment thereof comprise the amino acid sequences of SEQ ID NOs:256 and 267, respectively; or the $V_H$ and $V_L$ regions of the antibody or antigen-binding fragment thereof comprise the amino acid sequences of SEQ ID NOs:519 and 535, respectively, or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto, respectively.

In some embodiments, the antibody or antigen-binding fragment binds to the epitope of a human BCMA protein comprising $_{17}$LLHACIPCQLR$_{27}$ (SEQ ID NO:428). For example, in some embodiments, antibody or antigen-binding fragment comprises a heavy chain complementarity determining region 3 (CDR-H3) comprising the amino acid sequence of SEQ ID NO:10, or a CDR-H3 contained within the heavy chain variable ($V_H$) region amino acid sequence of SEQ ID NO:115, and/or a light chain complementarity determining region 3 (CDR-L3) comprising the amino acid sequence of SEQ ID NO:421, or a CDR-L3 contained within the light chain variable ($V_L$) region amino acid sequence of SEQ ID NO:536. In some embodiments, the antibody or antigen-binding fragment further comprises: a heavy chain complementarity determining region 1 (CDR-H1) comprising the amino acid sequence of SEQ ID NO:2, or a CDR-H1 contained within the heavy chain variable ($V_H$) region amino acid sequence of SEQ ID NO:115 and/or a light chain complementarity determining region 1 (CDR-L1) comprising the amino acid sequence selected from any one of SEQ ID NOs: 33, or a CDR-L1 contained within the light chain variable ($V_L$) region amino acid sequence selected from any one of SEQ ID NOs:536; and/or a heavy chain complementarity determining region 2 (CDR-H2) comprising the amino acid sequence of SEQ ID NO:5, or a CDR-H1 contained within the heavy chain variable ($V_H$) region amino acid sequence of SEQ ID NO:115 and/or a light chain complementarity determining region 2 (CDR-L2) comprising the amino acid sequence selected from any one of SEQ ID NOs:43, or a CDR-L1 contained within the light chain variable ($V_L$) region amino acid sequence selected from any one of SEQ ID NOs:536. In some embodiments, antibody or antigen-binding fragment comprises a $V_H$ region comprising a CDR-H1, a CDR-H2, and a CDR-H3, respectively, comprising the amino acid sequence of a CDR-H1, a CDR-H2, and a CDR-H3 contained within the $V_H$ region amino acid sequence of SEQ ID NO:115; and/or a $V_L$ region comprising a CDR-L1, a CDR-L2, and a CDR-L3, respectively, comprising the amino acid sequence of a CDR-L1, a CDR-L2, and a CDR-L3 contained within the $V_L$ region amino acid sequence of SEQ ID NO:536.

In some embodiments, the $V_H$ and $V_L$ regions of the antibody or antigen-binding fragment thereof comprise the amino acid sequences of SEQ ID NOs:115 and 536, respectively, or an amino acid sequence that has at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto, respectively.

In some embodiments, properties or features of the provided antibodies (e.g., antigen-binding fragments) are described in relation to properties observed for another antibody, e.g., a reference antibody. In some embodiments, the reference antibody is a non-human anti-BCMA antibody, such as a murine or chimeric or humanized anti-BCMA antibody. In some aspects, the reference antibody is the murine antibody designated C11D5.3 or A7D12.2 (see, e.g., International PCT Pub. No. WO2010/104949), and/or a fragment derived therefrom such as an scFv fragment thereof, and/or an antibody containing the $V_H$ and $V_L$ regions of such an antibody and/or the heavy and light chain CDRs of such an antibody. A chimeric antigen receptor (CAR) containing an antigen-binding scFv fragment of C11D5.3 has been demonstrated to effectively promote antitumor reactivity in a CAR therapy (Carpenter et al., *Clin Cancer Res.*, 2013, 19(8):2048-2060).

For example, in some embodiments, the reference antibody has a $V_H$ region containing the amino acid sequence set forth in SEQ ID NO:324, or comprises CDR-H1, CDR-H2, and/or CDR-H3 within such a sequence, and/or has a $V_L$ region containing the amino acid sequence set forth in SEQ ID NO:326, or comprises CDR-L1, CDR-L2, and/or CDR-L3 within such a sequence. For example, the reference antibody can be an antibody that contains a CDR-H1 sequence of DYSIN (SEQ ID NO:288), a CDR-H2 sequence of WINTETREPAYAYDFRG (SEQ ID NO:290), a CDR-H3 sequence of DYSYAMDY (SEQ ID NO:292), a CDR-L1 sequence of RASESVTILGSHLIH (SEQ ID NO:302), a CDR-L2 sequence of LASNVQT (SEQ ID NO:304) and/or a CDR-L3 sequence of LQSRTIPRT (SEQ ID NO:306). In some embodiments, the reference antibody is an scFv that comprises the sequence of amino acids set forth in SEQ ID NO:328 or 585. In some embodiments, the reference antibody has a $V_H$ region containing the amino acid sequence set forth in SEQ ID NO:325, or comprises CDR-H1, CDR-H2, and/or CDR-H3 within such a sequence, and/or has a $V_L$ region containing the amino acid sequence set forth in SEQ ID NO:327, or comprises CDR-L1, CDR-L2, and/or CDR-L3 within such a sequence. For example, the reference antibody can be an antibody that contains a CDR-H1 sequence of NFGMN (SEQ ID NO:289), a CDR-H2 sequence of WINTYTGESYFADDFKG (SEQ ID NO:291), a CDR-H3 sequence of GEIYYGYDGGFAY (SEQ ID NO:293), a CDR-L1 sequence of RASQDVNTAVS (SEQ ID NO:303), a CDR-L2 sequence of SASYRYT (SEQ ID NO:305) and/or a CDR-L3 sequence of QQHYSTPWT (SEQ ID NO:307). In some embodiments, the reference antibody is an scFv that comprises the sequence of amino acids set forth in SEQ ID NO:329 or 586.

In some embodiments, the provided antibody (e.g., antigen-binding fragment) contains heavy and light chain CDRs that are distinct from the CDRs present in the reference antibody or antibodies. In some embodiments, the provided antibody contains heavy and light chain CDRs that are distinct from the CDRs present in the $V_H$ region amino acid sequence set forth in SEQ ID NO:324 and/or the $V_L$ region amino acid sequence set forth in SEQ ID NO:326. In some embodiments, the provided antibody contains heavy and light chain CDRs that are distinct from the CDRs present in the $V_H$ region amino acid sequence set forth in SEQ ID NO:325 and/or the $V_L$ region amino acid sequence set forth in SEQ ID NO:327.

In some embodiments, the provided the antibodies or antigen-binding fragment thereof, binds, e.g., specifically binds, and/or recognizes, one or more epitopes in BCMA, e.g., human BCMA but do not comprise a $V_H$ region comprising a heavy chain complementarity determining region 1 (CDR-H1), CDR-H2, or CDR-H3, respectively, comprising the amino acid sequence of SEQ ID NOs:496, 507 or 513, respectively, and/or the antibody or antigen-binding fragment do not comprise a $V_L$ region comprising a light chain complementarity determining region 1 (CDR-L1), CDR-L2, or CDR-L3, respectively, comprising the amino acid sequence of SEQ ID NOs:517, 532 or 551. In some embodiments, the provided the antibodies or antigen-binding fragment thereof, binds, e.g., specifically binds, and/or recognizes, one or more epitopes in BCMA, e.g., human BCMA but do not comprise a $V_H$ region comprising a heavy chain complementarity determining region 1 (CDR-H1), CDR-H2, or CDR-H3, respectively, comprising the amino acid sequence of SEQ ID NOs:588, 589 or 590, respectively, and/or the antibody or antigen-binding fragment do not comprise a $V_L$ region comprising a light chain complementarity determining region 1 (CDR-L1), CDR-L2, or CDR-L3, respectively, comprising the amino acid sequence of SEQ ID NOs:588, 589 or 590. In some embodiments, the antibody or antigen-binding fragment thereof contains a distinct $V_H$ region and/or $V_L$ region from an antibody or antigen-binding fragment thereof comprising a $V_H$ region and a $V_L$ region amino acid sequence set forth in SEQ ID NOS: 577 and 587, respectively, or SEQ ID NOS: 594 and 595, respectively.

In some embodiments, the antibody or antigen-binding fragment does not comprise CDR-H1, CDR-H2, CDR-H3, CDR-L1, CDR-L2 and/or CDR-L3 sequences having at least 90%, 91%, 92%, 93%, 94%, 95%, 96%, 97%, 98% or 99% identity to the CDR-H1, CDR-H2, CDR-H3 and/or CDR-L1, CDR-L2, CDR-L3 sequences contained within an antibody comprising the amino acid sequence of SEQ ID NOs:328, 329, 585 and/or 586.

Among the provided antibodies (e.g., antigen-binding fragments) are those that compete for binding with and/or bind to the same or overlapping epitopes of BCMA protein as those bound by a reference antibody described herein but nonetheless contain distinct CDRs, e.g., distinct heavy and/or light chain CDR1, CDR2, and CDR3.

Among the provided antibodies (e.g., antigen-binding fragments) are those that do not compete for binding with and/or bind to a distinct epitope of BCMA protein as those bound by a reference antibody described herein.

In some embodiments, the reference antibody has a sequence present in an antibody or portion thereof as described herein, such as any of the provided exemplary antibodies. For example, in some embodiments, the reference antibody contains a CDR-H1 comprising the amino acid sequence selected from any one of SEQ ID NOs:1-3 and 140-144; a CDR-H2 comprising the amino acid sequence selected from any one of SEQ ID NOs:4-6, 145-148 and 372-374; a CDR-H3 comprising the amino acid sequence selected from any one of SEQ ID NOs:7-11, 149-157, 279-287 and 376-378; a CDR-L1 comprising the amino acid sequence selected from any one of SEQ ID NOs:26-36, 174-178, 380-392 and 394-398; CDR-L2 comprising the amino acid sequence selected from any one of SEQ ID NOs:37-46, 179-183, 399-409 and 411-414; and/or a CDR-L3 comprising the amino acid sequence selected from any one of SEQ ID NOs:47-58, 184-194, 415-427 and 429-433. For example, in some embodiments, the reference antibody has a $V_L$ region amino acid sequence selected from any one of SEQ ID NOs:116-127, 257-267, 534-550 and 552-557 and/or has a $V_H$ region amino acid sequence selected from any one of SEQ ID NOs:110-115, 247-256, 518-531 and 533. In some such embodiments, the antibody has heavy and/or light chain CDRs 1, 2, and/or 3 as present in such an antibody.

In some embodiments, the antibodies (e.g., antigen-binding fragment) display a binding preference for BCMA-expressing cells as compared to BCMA-negative cells, such as particular cells known and/or described herein to express BCMA and known not to express BCMA. In some embodiments, the binding preference is observed where a significantly greater degree of binding is measured to the BCMA-expressing, as compared to the non-expressing cells. In some embodiments, the fold change in degree of binding detected, for example, as measured by mean fluorescence intensity in a flow cytometry-based assay and/or dissociation constant or $EC_{50}$, to the BCMA-expressing cells as compared to the non-BCMA-expressing cells, is at least at or about 1.5, 2, 3, 4, 5, 6, or more, and/or is about as great, about the same, at least as great or at least about as great, or greater, than the fold change observed for the corresponding form of the reference antibody. In some cases, the total degree of observed binding to BCMA or to the BCMA-expressing cells is approximately the same, at least as great as, or greater than that observed for the corresponding form of the reference antibody.

In some embodiments, the antibody (e.g., antigen-binding fragment) specifically binds to an epitope that overlaps with the epitope of BCMA protein bound by a reference antibody. In some aspects, among such antibodies are antibodies that bind to the same or a similar epitope as the reference antibody. In some embodiments, two antibodies specifically bind to the same epitope and/or an overlapping epitope if all or essentially all amino acid mutations in the antigen that reduce or eliminate binding of one antibody reduce or eliminate binding of the other antibody.

In some embodiments, the antibody (e.g., antigen-binding fragment) specifically binds to an epitope that does not overlap with the epitope of BCMA protein bound by a reference antibody. In some aspects, among such antibodies are antibodies that bind to a different epitope as the reference antibody. In some embodiments, two antibodies specifically bind to the different epitope if all or essentially all amino acid mutations in the antigen that reduce or eliminate binding of one antibody do not reduce or eliminate binding of the other antibody.

An antibody "competes for binding" to BCMA protein with a reference antibody if it competitively inhibits binding of the reference antibody to BCMA protein, and/or if the reference antibody competitively inhibits binding of the antibody to BCMA protein. An antibody competitively inhibits binding of a reference antibody to an antigen if the presence of the antibody in excess detectably inhibits (blocks) binding of the other antibody to its antigen. A particular degree of inhibition may be specified.

Competitive inhibition assays are known and include ELISA-based, flow cytometry-based assays, and RIA-based assays. In some aspects, competitive inhibition assays are carried out by incorporating an excess of an unlabeled form of one of the antibodies and assessing its ability to block binding of the other antibody, which is labeled with a detectable marker, such that degree of binding and reduction thereof can be assessed by detection of the label or marker. In some examples, competitive binding can be measured using assays for molecular interaction and binding kinetics, such as surface plasmon resonance analysis.

Anti-BCMA antibodies (e.g., antigen-binding fragments) provided herein may be identified, screened for, or characterized for their physical/chemical properties and/or biological activities by various known assays. In one aspect, the antibody is tested for its antigen binding activity, e.g., by known methods such as ELISA, Western blotting, and/or flow cytometric assays, including cell-based binding assays, for example, assessing binding of the antibody (e.g., conjugated to a fluorescent marker or tagged) to a cell expressing the target antigen, e.g., BCMA, in some cases compared to results using cells that do not express the target antigen, e.g., BCMA. Binding affinity may be measured as $K_D$ or $EC_{50}$. In some examples, binding affinity, binding kinetics, and/or binding constants can be measured using assays to determine molecular interaction, such as surface plasmon resonance analysis.

Competition assays may be used to identify an antibody that competes with any of the antibodies (e.g., antigen-binding fragments) described herein. Assays for mapping epitopes bound by the antibodies and reference antibodies also may be used and are known.

c. Immunoconjugates

In some embodiments, the antibody (e.g., antigen-binding fragment) is or is part of an immunoconjugate, in which the antibody is conjugated to one or more heterologous molecule(s) or moiety, such as, but not limited to, a cytotoxic or an imaging agent. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments), or radioactive isotopes.

Among the immunoconjugates are antibody-drug conjugates (ADCs), in which an antibody is conjugated to one or more drugs, including but not limited to a maytansinoid (see U.S. Pat. Nos. 5,208,020, 5,416,064 and European Patent EP 0 425 235 B1); an auristatin such as monomethyl auristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

Also among the immunoconjugates are those in which the antibody (e.g., antigen-binding fragment) is conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes.

Also among the immunoconjugates are those in which the antibody (e.g., antigen-binding fragment) is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Conjugates of an antibody (e.g., antigen-binding fragment) and cytotoxic agent may be made using any of a number of known protein coupling agents, e.g., linkers, (see Vitetta et al., Science 238:1098 (1987), WO94/11026). In some embodiments, the linker is a peptide or a polypeptide or is a chemical linker. In some embodiments, the linker is a releasable linker or a cleavable linker. The linker may be a "cleavable linker" or a "releasable linker" facilitating release of a cytotoxic drug in the cell, such as acid-labile linkers, peptidase-sensitive linkers, photolabile linkers, dimethyl linkers, and disulfide-containing linkers (Chari et al., Cancer Res. 52:127-131 (1992); U.S. Pat. No. 5,208,020). In some embodiments, the releasable linker or the cleavable linker is released or cleaved in the presence of one or more conditions or factors present in the tumor microenvironment (TME), including includes matrix metalloproteinase (MMP), hypoxic conditions or acidic conditions.

d. Multispecific Antibodies

In certain embodiments, the BCMA-binding molecules, e.g., antibodies or polypeptides such as chimeric receptors containing the same, are multispecific. Among the multispecific binding molecules are multispecific antibodies, including, e.g. bispecific or trispecific antibodies. Multispecific binding partners, e.g., antibodies, have binding specificities for at least two different sites, which may be in the same or different antigens. In certain embodiments, one of the binding specificities is for BCMA and the other is for another antigen. In some embodiments, additional binding molecules bind to and/or recognize a third, or more antigens. In certain embodiments, bispecific antibodies may bind to two different epitopes of BCMA. Bispecific antibodies may also be used to localize cytotoxic agents to cells which express BCMA. Bispecific antibodies can be prepared as full length antibodies or antibody fragments. Among the multispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies (e.g., antigen-binding fragments). Also provided are multispecific cells containing the antibodies or polypeptides including the same, such as cells containing a cell surface protein including the anti-BCMA antibody and an additional cell surface protein, such as an additional chimeric receptor, which binds to a different antigen or a different epitope on BCMA.

Exemplary antigens include B cell specific antigens, other tumor-specific antigens, such as antigens expressed specifically on or associated with a leukemia (e.g., B cell leukemia), lymphoma (e.g., Hodgkin's lymphoma, non-Hodgkin's lymphoma, etc.), or a myeloma, e.g., a multiple myeloma (MM), a plasma cell malignancy (e.g., plasmacytoma). For example, antigens include those expressed specifically on or associated with B cell chronic lymphocytic leukemia (CLL), a diffuse large B-cell lymphoma (DLBCL), acute myeloid leukemia (AML), acute lymphocytic leukemia (ALL), Burkitt's lymphoma (e.g., endemic Burkitt's lymphoma or sporadic Burkitt's lymphoma), mantle cell lymphoma (MCL), non-small cell lung cancer (NSCLC), chronic myeloid (or myelogenous) leukemia (CML), hairy cell leukemia (HCL), small lymphocytic lymphoma (SLL), Marginal zone lymphoma, Hodgkin lymphoma (HL), non-Hodgkin lymphoma (NHL), Anaplastic large cell lymphoma (ALCL), refractory follicular lymphoma, Waldenstrom macroglobulinemia, follicular lymphoma, small non-cleaved cell lymphoma, mucosa-associated lymphatic tissue lymphoma (MALT), marginal zone lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), neuroblastoma, renal cell carcinoma, colon cancer, colorectal cancer, breast cancer, epithelial squamous cell cancer, melanoma, myeloma such as multiple myeloma (e.g., non-secretory multiple myeloma, smoldering multiple myeloma), stomach cancer, esophageal cancer, brain cancer, lung cancer (e.g., small-cell lung cancer), pancreatic cancer, cervical cancer, ovarian cancer, liver cancer (e.g., hepatic carcinoma, hepatoma, etc.), bladder cancer, prostate cancer, testicular cancer, thyroid cancer, uterine cancer, spleen cancer (e.g., splenic lymphoma), adrenal cancer and/or head and neck cancer, and antigens expressed on T cells.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the BCMA-binding molecules provided herein target an antigen on the same tumor type as the second or additional antigen. In some embodiments, the second or additional antigen may also be a universal tumor antigen or may be a tumor antigen specific to a tumor type.

Exemplary second or additional antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, ROR1, TRAIL-R1 (DR4), TRAIL-R2 (DR5), tEGFR, Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR vIII, FBP, FCRL5, FCRH5, fetal acetylcholine receptor, GD2, GD3, G protein-coupled receptor class C group 5 member D (GPRC5D), HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (D1), CS-1, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some aspects, the antigen, e.g., the second or additional antigen, such as the disease-specific antigen and/or related antigen, is expressed on multiple myeloma, such as G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (Ac-tRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

e. Variants

In certain embodiments, the antibodies (e.g., antigen-binding fragment) include one or more amino acid variations, e.g., substitutions, deletions, insertions, and/or mutations, compared to the sequence of an antibody described herein. Exemplary variants include those designed to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, the antibodies (e.g. antigen-binding fragment) include one or more amino acid substitutions, e.g., as compared to an antibody sequence described herein and/or compared to a sequence of a natural repertoire, e.g., human repertoire. Sites of interest for substitutional mutagenesis include the CDRs and FRs. Amino acid substitutions may be introduced into an antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC).

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human subject.

In some embodiments, alterations are made in CDR "hotspots," residues encoded by codons that undergo mutation at high frequency during the somatic maturation process (see, e.g., Chowdhury, Methods Mol. Biol. 207:179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ region and $V_L$ region sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

f. Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines. In some embodiments, an N-linked glycosylation, which is a glycosylation site that occurs at asparagines in the consensus sequence -Asn-Xaa-Ser/Thr is removed or inserted.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Ripka et al. Arch. Biochem. Biophys. 249:533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4):680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies (e.g., antigen-binding fragment) are modified to contain additional nonproteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinylpyrrolidone, poly-1, 3-dioxolane, poly-1, 3,6-trioxane, ethylene/maleic anhydride copolymer, polyamino acids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Recombinant Receptors

Also among the binding molecules are polypeptides containing any such antibodies or antigen-binding fragments provided herein, including single chain cell surface proteins, e.g., recombinant receptors, such as chimeric antigen receptors containing such antibodies or antigen-binding fragments. Among the provided binding molecules (e.g., BCMA-binding molecules) are single chain cell surface proteins, such as recombinant receptors (e.g., antigen receptors), that include one of the provided antibodies (e.g., antigen-binding fragment). The recombinant receptors include antigen receptors that specifically bind to BCMA, such as antigen receptors containing the provided anti-BCMA antibodies, e.g., antigen-binding fragments. Among the antigen receptors are functional non-TCR antigen receptors, such as chimeric antigen receptors (CARs). Also provided are cells expressing the recombinant receptors and uses thereof in adoptive cell therapy, such as treatment of diseases and disorders associated with BCMA expression.

Exemplary antigen receptors, including CARs, and methods for engineering and introducing such antigen receptors into cells, include those described, for example, in international patent application publication Nos. WO200014257, WO2013126726, WO2012/129514, WO2014031687, WO2013/166321, WO2013/071154, WO2013/123061 U.S. patent application publication Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application No. EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No. WO/2014055668 A1. Exemplary CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody or an antigen-binding fragment thereof, e.g., as provided herein.

Among the chimeric receptors are chimeric antigen receptors (CARs). The chimeric receptors, such as CARs, generally include an extracellular antigen binding domain that includes, is, or is comprised within, one of the provided anti-BCMA antibodies. Thus, the chimeric receptors, e.g., CARs, typically include in their extracellular portions one or more BCMA-binding molecules, such as one or more antigen-binding fragment, domain, or portion, or one or more antibody variable regions, and/or antibody molecules, such as those described herein. In some embodiments, the CAR includes a BCMA-binding portion or portions of the antibody molecule, such as a heavy chain variable ($V_H$) region and/or light chain variable ($V_L$) region of the antibody, e.g., an scFv antibody fragment.

BCMA-targeting CARs are described, for example, by Carpenter et al., Clin Cancer Res., 2013, 19(8):2048-2060.

In some embodiments, the recombinant receptor such as a CAR comprising an antibody (e.g., antigen-binding fragment) provided herein, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component (e.g., scFv) and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the spacer has the sequence set forth in SEQ ID NO:363, and is encoded by the sequence set forth in SEQ ID NO:364. In some embodiments, the spacer has the sequence set forth in SEQ ID NO:365. In some embodiments, the spacer has the sequence set forth in SEQ ID NO:366.

The antigen-recognition component generally is linked to one or more intracellular signaling components, such as signaling components that mimic activation through an antigen receptor complex, such as a TCR complex, in the case of a CAR, and/or signal via another cell surface receptor. Thus, in some embodiments, the BCMA-binding molecule (e.g., antibody or antigen binding fragment thereof) is linked to one or more transmembrane domains such as those described herein and intracellular signaling domains comprising one or more intracellular components such as those described herein. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane domains include those derived from (i.e. comprise at least the transmembrane domain(s) of) the alpha, beta or zeta chain of the T-cell receptor, CD3 epsilon, CD4, CD5, CD8, CD9, CD16, CD22, CD28, CD33, CD37, CD45, CD64, CD80, CD86, CD134, CD137, and/or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling domain of the CAR.

The receptor, e.g., the CAR, generally includes an intracellular signaling domain comprising at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the BCMA-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such classes of cytoplasmic signaling sequences.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, CD3 gamma, CD3 delta and CD3 epsilon. In some embodiments, the intracellular signaling domain in the CAR contain(s) a cytoplasmic signaling domain, portion thereof, or sequence derived from CD3 zeta.

In some embodiments, the CAR includes a signaling domain (e.g., an intracellular signaling domain) and/or transmembrane portion of a costimulatory molecule, such as a T cell costimulatory molecule. Exemplary costimulatory molecules include CD28, 4-1BB, OX40, DAP10, and ICOS. In some aspects, the same CAR includes both the activating or stimulatory components (e.g., cytoplasmic signaling sequence) and costimulatory components.

In some embodiments, the activating or stimulatory components are included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the BCMA-targeting CAR is the stimulatory or activating CAR; in other aspects, it is the costimulatory CAR. In some embodiments, the cells further include inhibitory CARs (iCARs, see Fedorov et al., Sci. Transl. Medicine, 5(215) (December, 2013), such as a CAR recognizing an antigen other than BCMA, whereby an activating or stimulatory signal delivered through the BCMA-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the nucleic acid sequences encoding a recombinant receptor, e.g., CAR, further includes a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A. Extrinsic marker genes may in some cases be utilized in connection with engineered cell to permit detection or selection of cells and, in some cases, also to promote cell suicide.

Exemplary surrogate markers can include truncated cell surface polypeptides, such as a truncated human epidermal growth factor receptor 2 (tHER2), a truncated epidermal growth factor receptor (EGFRt, exemplary EGFRt sequence set forth in SEQ ID NO:11 or 76) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 602 or 603 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 602 or 603.

In some embodiments, the marker is or comprises a fluorescent protein, such as green fluorescent protein (GFP), enhanced green fluorescent protein (EGFP), such as superfold GFP, red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain antibody comprising only the $V_H$ region and the intracellular signaling domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a co-stimulatory molecule (e.g., T cell costimulatory molecule), such as between the transmembrane domain and intracellular signaling domain. In some aspects, the T cell costimulatory molecule is CD28 or 4-1BB.

In some embodiments, the transmembrane domain of the receptor (e.g., CAR) is a transmembrane domain of human CD28 or variant thereof, e.g., a 27-amino acid transmembrane domain of a human CD28 (Accession No.: P10747.1). In some embodiments, the intracellular signaling domain comprises an intracellular costimulatory signaling domain of human CD28 or functional variant thereof, such as a 41 amino acid domain thereof and/or such a domain with an LL to GG substitution at positions 186-187 of a native CD28 protein. In some embodiments, the intracellular domain comprises an intracellular costimulatory signaling domain of 4-1BB or functional variant thereof, such as a 42-amino acid cytoplasmic domain of a human 4-1BB (Accession No. Q07011.1). In some embodiments, the intracellular signaling domain comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190.

In some aspects, the spacer contains only a hinge region of an IgG, such as only a hinge of IgG4 or IgG1, such as the hinge only spacer set forth in SEQ ID NO:363. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains, such as set forth in SEQ ID NO:366. In some embodiments, the spacer is an Ig hinge, e.g., an IgG4 hinge, linked to a CH3 domain only, such as set forth in SEQ ID NO:365. In some embodiments, the spacer is or comprises a glycine-serine rich sequence or other flexible linker such as known flexible linkers.

For example, in some embodiments, the CAR includes a BCMA antibody or fragment, such as any of the human BCMA antibodies, including sdAbs and scFvs, described herein, a spacer such as any of the Ig-hinge containing spacers, a CD28 transmembrane domain, a CD28 intracellular signaling domain, and a CD3 zeta signaling domain. In some embodiments, the CAR includes the BCMA antibody or fragment, such as any of the human BCMA antibodies, including sdAbs and scFvs described herein, a spacer such as any of the Ig-hinge containing spacers, a CD28 transmembrane domain, a 4-1BB intracellular signaling domain, and a CD3 zeta signaling domain. In some embodiments, such CAR constructs further includes a T2A ribosomal skip element and/or a tEGFR sequence, e.g., downstream of the CAR.

In certain embodiments, multispecific binding molecules, e.g., multispecific chimeric receptors, such as multispecific CARs, can contain any of the multispecific antibodies, including, e.g. bispecific antibodies, multispecific single-chain antibodies, e.g., diabodies, triabodies, and tetrabodies, tandem di-scFvs, and tandem tri-scFvs, such as any described above in Section I.A.

Also provided herein are single chain cell surface proteins comprising the scFv sequence selected from any of SEQ ID NOs:128-139, 268-278, 558-576 and 578-583. In some of any such embodiments, the scFv comprises the sequence selected from any of SEQ ID NOs:128, 132, 278 and 502. In some of any such embodiments, the scFv comprises the sequence of SEQ ID NO:560.

C. Engineered Cells

Also provided are cells such as engineered cells that contain a recombinant receptor (e.g., a chimeric antigen receptor) such as one that contains an extracellular domain including an anti-BCMA antibody or fragment as described herein. Also provided are populations of such cells, compositions containing such cells and/or enriched for such cells, such as in which cells expressing the BCMA-binding molecule make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types. In some embodiments, the cells (e.g., engineered cells) comprise a vector (e.g., a viral vector, expression vector, etc.) as described herein such as a vector comprising a nucleic acid encoding a recombinant receptor described herein.

a. Vectors and Methods for Genetic Engineering

Also provided are methods, nucleic acids, compositions, and kits, for expressing the binding molecules (e.g., anti-BCMA binding molecules), including recombinant receptors (e.g., CARs) comprising the binding molecules, and for producing the genetically engineered cells expressing such binding molecules. In some embodiments, one or more binding molecules, including recombinant receptors (e.g., CARs) can be genetically engineered into cells or plurality of cells. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), human immunodeficiency virus type 1 (HIV-1) or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, one or more binding molecules, including antibodies and/or recombinant receptors (e.g., CARs), can be genetically engineered to be expressed in cells or plurality of cells. In some embodiments, a first recombinant receptor and a second binding molecule, e.g., recombinant receptor, are encoded by the same or separate nucleic acid molecules. In some embodiments, additional binding molecules are engineered to be expressed in cells or a plurality of cells.

In some embodiments, the vector or construct can contain a single promoter that drives the expression of one or more nucleic acid molecules. In some embodiments, such nucleic acid molecules, e.g., transcripts, can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding a first and second chimeric receptor) by a message from a single promoter. Alternatively, in some cases, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. Genetic Vaccines and Ther. 2:13 (2004) and deFelipe et al. Traffic 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 601), equine rhinitis A virus (E2A, e.g., SEQ ID NO: 600), Thosea asigna virus (T2A, e.g., SEQ ID NO: 596 or 597), and porcine teschovirus-1 (P2A, e.g., SEQ ID NO: 598 or 599) as described in U.S. Patent Publication No. 20070116690. In some embodiments, the one or more different or separate promoters drive the expression of one or more nucleic acid molecules encoding the one or more binding molecules, e.g., recombinant receptors.

Any of the binding molecules, e.g., antibodies and/or recombinant receptors provided herein, e.g., BCMA-binding molecules and/or the additional recombinant receptors, can be encoded by polynucleotides containing one or more nucleic acid molecules encoding the receptors, in any combinations or arrangements. For example, one, two, three or more polynucleotides can encode one, two, three or more different receptors or domains. In some embodiments, one vector or construct contains nucleic acid molecules encoding one or more binding molecules, e.g., antibody and/or recombinant receptor, and a separate vector or construct contains nucleic acid molecules encoding an additional binding molecule, e.g., antibody and/or recombinant receptor. Each of the nucleic acid molecule can also encode one or more marker, such as a surface marker, e.g., truncated EGFR (tEGFR).

Also provided are compositions containing one or more of the nucleic acid molecules, vectors or constructs, such as any described above. In some embodiments, the nucleic acid molecules, vectors, constructs or compositions can be used to engineer cells, such as T cells, to express any of the binding molecules, e.g., antibody or recombinant receptor, and/or the additional binding molecules.

b. Preparation of Cells for Engineering

In some embodiments, preparation of the engineered cells includes one or more culture and/or preparation steps. The cells for introduction of the recombinant receptor (e.g., CAR) may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander, MACSiBeads, etc.).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084, are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

c. Engineered Cells, Vectors and Compositions for Multi-Targeting

Also provided are cells such as engineered cells that can bind to and/or target multiple antigens. In some embodiments, improved selectivity and specificity is achieved through strategies targeting multiple antigens. Such strategies generally involve multiple antigen-binding domains, which typically are present on distinct genetically engineered antigen receptors and specifically bind to distinct antigens. In some embodiments, the cells are engineered with the ability to bind more than one antigen. For example, in some embodiments, the cells are engineered to express multispecific binding molecules. In some embodiments, the cells express multiple binding molecules, e.g., recombinant receptors, each of which can target one antigen or multiple antigens, e.g., one receptor that targets BCMA, such as any described herein, and another receptor that targets another antigen, e.g., tumor antigen. In some aspects, a plurality of genetically engineered antigen receptors are introduced into the cell, which specifically bind to different antigens, each expressed in or on the disease or condition to be targeted with the cells or tissues or cells thereof. Such features can in some aspects address or reduce the likelihood of off-target effects or increase efficacy. For example, where a single antigen expressed in a disease or condition is also expressed on or in non-diseased or normal cells, such multi-targeting approaches can provide selectivity for desired cell types by requiring binding via multiple antigen receptors in order to activate the cell or induce a particular effector function. In some embodiments, a plurality of cells can be engineered to express one or more different binding molecules, e.g., recombinant receptors, each of which can target one antigen or multiple antigens.

Also provided are multispecific cells containing any of the binding molecules described herein, such as cells containing a cell surface protein including the anti-BCMA antibody and an additional cell surface protein, such as an additional chimeric receptor, which binds to a different antigen or a different epitope on BCMA. In some embodiments, provided are compositions of cells that express recombinant receptors, wherein one or more of the binding molecules, multispecific binding molecules and/or recombinant receptors bind and/or target BCMA. Also provided are compositions of cells containing a plurality of cells that express one or more different binding molecules, e.g., recombinant receptors that can target one or multiple antigens. In some embodiments, the multispecific binding molecules and/or recombinant receptors target one or more different epitopes on BCMA.

In some embodiments, provided are composition of cells, wherein each type of cell expresses one or more binding molecules, e.g., recombinant receptors. In some embodiments, the cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such cells are provided. In some embodiments, a composition containing one or more such cells is provided. In some embodiments, the one or more cells can express different antibodies, or the same antibody. In some embodiments, each of the cells expresses one or more antibodies, such as more than one antibody. In some embodiments, each of the cells expresses a multispecific binding molecule, e.g., a multispecific receptor, e.g., CAR.

In some embodiments, the cells include multi-targeting strategies that target BCMA and a second or additional antigen associated with a particular disease or condition. In some embodiments, the second or additional antigen is targeted by a multispecific binding molecule and/or multiple binding molecules and/or a plurality of cells, e.g., one or more cells, each engineered to express one or more recombinant receptors. In some embodiments, a recombinant receptor targeting a second or additional antigen is expressed on the same cell as a BCMA binding molecule, or on a different cell.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the BCMA-binding molecules provided herein target an antigen on the same tumor type as the second or additional antigen. In some embodiments, the second or additional antigen may also be a universal tumor antigen or may be a tumor antigen specific to a tumor type. In some embodiments, the cell further comprises an additional genetically engineered antigen receptor that recognizes a second or additional antigen expressed on a disease or condition to be treated and induces a stimulatory or activating signal.

Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, ROR1, TRAIL-R1 (DR4), TRAIL-R2 (DR5), B cell maturation antigen (BCMA), tEGFR, Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR vIII, FBP, FCRL5, FCRH5, fetal acetylcholine receptor, GD2, GD3, HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (D1), CS-1, BCMA, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some embodiments, the plurality of antigens, e.g., the first antigen, e.g., BCMA, and the second or additional antigens, are expressed on the cell, tissue, or disease or condition being targeted, such as on the cancer cell. In some aspects, the cell, tissue, disease or condition is multiple myeloma or a multiple myeloma cell. One or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is/are achieved.

In some aspects, the antigen, e.g., the second or additional antigen, such as the disease-specific antigen and/or related antigen, is expressed on multiple myeloma, such as CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011):924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the cells and methods include multi-targeting strategies, such as expression of two or more genetically engineered receptors on the cell, each recognizing a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, a plurality of cells, each engineered to express one or more recombinant receptors, are provided. For example, in some embodiments, one cell is engineered to express a binding molecule that binds and/or targets BCMA, and another cell is engineered to express a binding molecule that binds and/or targets an additional or second antigen. In some embodiments, the cells can each express a multispecific binding molecule, e.g., a multispecific recombinant receptor, where one or more of the target antigen is BCMA. In some of such embodiments, the plurality of cells can be administered together or separately. In some embodiments, some of the plurality of cells are administered simultaneously or concurrently with other cells, e.g., administered on the same day, and/or sequentially with or intermittently with, in any order, another engineered cell in the plurality. For example, in some embodiments, an engineered cell expressing a BCMA-binding molecule, e.g., CAR, is administered simultaneously with or sequentially with, in any order, another engineered cell expressing a binding molecule that binds a different target antigen or a different epitope on BCMA. In some embodiments, the plurality of cells can be in the same composition or in different compositions. Exemplary compositions of the cells include compositions described in Section II below.

II. Pharmaceutical Compositions

Also provided are compositions including the BCMA-binding molecules, immunoconjugates, recombinant receptors, and engineered cells, including pharmaceutical compositions and formulations.

Provided are pharmaceutical formulations comprising a BCMA-binding molecule (e.g., antibody), an immunoconjugate, a recombinant receptor (e.g., chimeric antigen receptor), engineered cells expressing said molecules (e.g., recombinant receptor), a plurality of engineered cells expressing said molecules (e.g., recombinant receptor) and/or additional agents for combination treatment or therapy. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies described herein can include lyophilized formulations and aqueous solutions.

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the binding molecules and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the binding molecules, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject.

The may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, intracranial, intrathoracic, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Also provided are pharmaceutical compositions for combination therapy. Any of the additional agents for combination therapy described herein, such as agents described in Section III.B, can be prepared and administered as one or more pharmaceutical compositions, with the BCMA-binding molecule (e.g., antibody), immunoconjugate, recombinant receptor (e.g., chimeric antigen receptor) and/or engineered cells expressing said molecules (e.g., recombinant receptor) described herein. The combination therapy can be administered in one or more pharmaceutical compositions, e.g., where the binding molecules, recombinant receptors and/or cells are in the same pharmaceutical composition as the additional agent, or in separate pharmaceutical compositions. For example, in some embodiments, the additional agent is an additional engineered cell, e.g., cell engineered to express a different recombinant receptor that targets a different antigen or a different epitope on BCMA, and is administered in the same composition or in a separate composition. In some embodiments, each of the pharmaceutical composition is formulated in a suitable formulation according to the particular binding molecule, recombinant receptor, cell, e.g., engineered cell, and/or additional agent, and the particular dosage regimen and/or method of delivery.

III. Methods and Uses

Also provided methods, such as methods of treatment, of using and uses of the BCMA-binding molecules, immunoconjugates, recombinant receptors, engineered cells, and pharmaceutical compositions and formulations thereof, such as in the treatment of diseases, conditions, and disorders in which BCMA is expressed, and/or detection, diagnostic, and prognostic methods. Also provided are methods of combination therapy and/or treatment.

A. Therapeutic and Prophylactic Methods and Uses

Also provided are methods of administering and uses, such as therapeutic and prophylactic uses, of the BCMA-binding molecules, including the anti-BCMA antibodies, e.g., antibody fragments and proteins containing the same such as the recombinant receptors (e.g., CARs), engineered cells expressing the recombinant receptors (e.g., CARs), plurality of engineered cells expressing the receptors, and/or compositions comprising the same. Such methods and uses include therapeutic methods and uses, for example, involving administration of the molecules (e.g., BCMA-binding molecules, recombinant receptors), cells (e.g., engineered cells), or compositions containing the same, to a subject having a disease, condition, or disorder associated with BCMA such as a disease, condition, or disorder associated with BCMA expression, and/or in which cells or tissues express, e.g., specifically express BCMA. In some embodiments, the molecule, cell, and/or composition is administered in an effective amount to effect treatment of the disease or disorder. Provided herein are uses of the binding molecules (e.g., anti-BCMA antibodies or antigen-binding fragments thereof), recombinant receptors (e.g., CARs), and cells (e.g., engineered cells) in such methods and treatments, and in the preparation of a medicament in order to carry out such therapeutic methods. In some embodiments, the methods are carried out by administering the binding molecules or cells, or compositions comprising the same, to the subject having, having had, or suspected of having the disease or condition. In some embodiments, the methods thereby treat the disease or condition or disorder in the subject. Also provided herein are of use of any of the compositions, such as pharmaceutical compositions provided herein, for the treatment of a disease or disorder associated with BCMA, for example, multiple myeloma.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or subject being treated. As is evident to one skilled in the art, a sufficient or significant delay can, in effect, encompass prevention, in that the subject does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided molecules and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, binding molecule, antibody, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, binding molecule, antibody, cells, or composition refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the molecules, antibodies, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" or an "individual" is a mammal. In some embodiments, a "mammal" includes humans, non-human primates, domestic and farm animals, and zoo, sports, or pet animals, such as dogs, horses, rabbits, cattle, pigs, hamsters, gerbils, mice, ferrets, rats, cats, monkeys, etc. In some embodiments, the subject is human.

Among the diseases to be treated is any disease or disorder associated with BCMA or any disease or disorder in which BCMA is specifically expressed and/or in which BCMA has been targeted for treatment (also referred to herein interchangeably as a "BCMA-associated disease or disorder"). Cancers associated with BCMA expression include hematologic malignancies such as multiple myeloma, Waldenstrom macroglobulinemia as well as both Hodgkin's and non-Hodgkin's lymphomas. See Coquery et al., *Crit Rev Immunol.*, 2012, 32(4):287-305 for a review of BCMA. Since BCMA has been implicated in mediating tumor cell survival, it is a potential target for cancer therapy. Anti-BCMA antibodies have been previously described such as the inhibitory anti-BCMA antibody SG1 which promoted antibody-dependent cell-mediated cytotoxicity of BCMA-expressing multiple myeloma cells. See Ryan et al., *Mol Cancer Ther.*, 2007, 6(11):3009-3018 and International PCT Pub. No. WO2010/104949. Chimeric antigen receptors containing mouse anti-human BCMA antibodies and cells expressing such chimeric receptors have also been previously described. See Carpenter et al., *Clin Cancer Res.*, 2013, 19(8):2048-2060.

In some embodiments, the disease or disorder associated with BCMA is a B cell-related disorder. In some embodiments, the disease or disorder associated with BCMA is one or more diseases or conditions from among glioblastoma, lymphomatoid granulomatosis, post-transplant lymphoproliferative disorder, an immunoregulatory disorder, heavy-chain disease, primary or immunocyte-associated amyloidosis, or monoclonal gammopathy of undetermined significance.

In some embodiments, the disease or disorder associated with BCMA is an autoimmune disease or disorder. Such autoimmune diseases or disorder include, but are not limited to, systemic lupus erythematosus (SLE), lupus nephritis, inflammatory bowel disease, rheumatoid arthritis (e.g., juvenile rheumatoid arthritis), ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In certain diseases and conditions, BCMA is expressed on malignant cells and cancers. In some embodiments, the cancer (e.g., a BCMA-expressing cancer) is a B cell malignancy. In some embodiments, the cancer (e.g., a BCMA-expressing cancer) is a leukemia (e.g., B cell leukemia), lymphoma (e.g., Hodgkin's lymphoma, non-Hodgkin's lymphoma, etc.), or a myeloma, e.g., a multiple myeloma (MM), a plasma cell malignancy (e.g., plasmacytoma). Lymphomas contemplated herein include, but are not limited to, Burkitt lymphoma (e.g., endemic Burkitt's lymphoma or sporadic Burkitt's lymphoma), non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). Leukemias contemplated here, include, but are not limited to, chronic lymphocytic leukemia (CLL), plasma cell leukemia or acute lymphocytic leukemia (ALL). Also contemplated herein are myelomas, e.g., multiple myeloma (MM, e.g., non-secretory multiple myeloma, smoldering multiple myeloma). Also contemplated herein are plasma cell malignancies including, but not limited to, plasmacytoma. Among the diseases, disorders or conditions associated with BCMA (e.g., a BCMA-expressing cancer) that can be treated include, but are not limited to, neuroblastoma, renal cell carcinoma, colon cancer, colorectal cancer, breast cancer, epithelial squamous cell cancer, melanoma, myeloma (e.g., multiple myeloma), stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

In some embodiments, the methods may identify a subject who has, is suspected to have, or is at risk for developing a BCMA-associated disease or disorder. Hence, provided are methods for identifying subjects with diseases or disorders associated with elevated BCMA expression and selecting them for treatment with a provided BCMA-binding molecule, including any of the anti-BCMA antibodies, e.g., antibody fragments and proteins containing the same such as the recombinant receptors (e.g., CARs), and/or engineered cells expressing the recombinant receptors.

For example, a subject may be screened for the presence of a disease or disorder associated with elevated BCMA expression, such as a BCMA-expressing cancer. In some embodiments, the methods include screening for or detecting the presence of a BCMA-associated disease, e.g. a tumor. Thus, in some aspects, a sample may be obtained from a patient suspected of having a disease or disorder associated with elevated BCMA expression and assayed for the expression level of BCMA. In some aspects, a subject who tests positive for a BCMA-associated disease or disorder may be selected for treatment by the present methods, and may be administered a therapeutically effective amount of a BCMA-binding molecule (e.g., anti-BCMA antibody or antigen-binding fragment thereof), recombinant receptor (e.g., CAR) comprising a BCMA-binding molecule, cells containing a recombinant receptor or a pharmaceutical composition thereof as described herein. In some embodiments, the methods can be used to monitor the size or density of a BCMA-expressing tissue, e.g. tumor, over time, e.g., before, during, or after treatment by the methods.

In some embodiments, the subject has persistent or relapsed disease, e.g., following treatment with another BCMA-specific antibody and/or cells expressing a BCMA-targeting chimeric receptor and/or other therapy, including chemotherapy, radiation, and/or hematopoietic stem cell transplantation (HSCT), e.g., allogenic HSCT. In some embodiments, the administration effectively treats the subject despite the subject having become resistant to another BCMA-targeted therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-BCMA antibodies, the degree of immunogenicity in some embodiments is reduced compared to CARs including a different antibody that binds to a similar, e.g., overlapping epitope and/or that competes for binding to BCMA with the provided antibody, such as a mouse or monkey or rabbit or humanized antibody.

In some embodiments, the methods include adoptive cell therapy, whereby genetically engineered cells expressing the provided recombinant receptors comprising a BCMA-binding molecule (e.g., CARs comprising anti-BCMA antibody or antigen-binding fragment thereof) are administered to subjects. Such administration can promote activation of the cells (e.g., T cell activation) in a BCMA-targeted manner, such that the cells of the disease or disorder are targeted for destruction.

Thus, the provided methods and uses include methods and uses for adoptive cell therapy. In some embodiments, the methods include administration of the cells, the plurality of cells a composition containing the cells or the plurality of cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a BCMA-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the subject, to whom the cells, cell populations, or compositions are administered is a non-human primate. In some embodiments, the non-human primate is a monkey (e.g., cynomolgus monkey) or an ape. The subject can be male or female and can be any suitable age, including infant, juvenile, adolescent, adult, and geriatric subjects. In some embodiments, the subject is a non-primate mammal, such as a rodent (e.g., mouse, rat, etc.). In some examples, the patient or subject is a validated animal model for disease, adoptive cell therapy, and/or for assessing toxic outcomes such as cytokine release syndrome (CRS).

The BCMA-binding molecules such as antibodies, recombinant receptors (e.g., CARs) containing the antibodies and cells expressing the same, can be administered by any suitable means, for example, by injection, e.g., intravenous or subcutaneous injections, intraocular injection, periocular injection, subretinal injection, intravitreal injection, transseptal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intracranial, intrathoracic, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the binding molecule, recombinant receptor or cell may depend on the type of disease to be treated, the type of binding molecule or recombinant receptor, the severity and course of the disease, whether the binding molecule or recombinant receptor is administered for preventive or therapeutic purposes, previous therapy, the patient's clinical history and response to the binding molecule, recombinant receptor or cell, and the discretion of the attending physician. The compositions and molecules and cells are in some embodiments suitably administered to the patient at one time or over a series of treatments.

Depending on the type and severity of the disease, dosages of binding molecules (e.g., anti-BCMA antibody or antigen-binding fragment thereof) or recombinant receptors may include about 1 µg/kg to about 15 mg/kg (e.g. 0.1 mg/kg-10 mg/kg), about 1 mg/kg to about 100 mg/kg, about 0.05 mg/kg to about 10 mg/kg, about 0.5 mg/kg, about 2.0 mg/kg, about 4.0 mg/kg or about 10 mg/kg. Multiple doses may be administered intermittently, e.g. every week or every three weeks. An initial higher loading dose, followed by one or more lower doses may be administered.

In certain embodiments, in the context of genetically engineered cells containing the binding molecules or recombinant receptors, a subject is administered the range of about one million to about 100 billion cells and/or that amount of cells per kilogram of body weight, such as, e.g., about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent dose is inversely correlated with disease burden. In some aspects, as in the context of a large disease burden, the subject is administered a low number of cells. In other embodiments, as in the context of a lower disease burden, the subject is administered a larger number of cells.

In some embodiments, the cells, binding molecules, or recombinant receptors are administered as part of a combination treatment, such as simultaneously with or sequentially with, in any order, another therapeutic intervention, such as another antibody or engineered cell or receptor or agent, such as a cytotoxic or therapeutic agent, such as any described in Section I.C or III.B.

The cells, binding molecules and/or recombinant receptors in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells, binding molecules and/or recombinant receptors are administered prior to the one or more additional therapeutic agents. In some embodiments, the cells, binding molecules and/or recombinant receptors are administered after to the one or more additional therapeutic agents.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy,* 32(7): 689-702

(2009), and Herman et al. *J. Immunological Methods*, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population in some embodiments are conjugated either directly or indirectly through a linker to a targeting moiety. The practice of conjugating compounds, e.g., the CAR or TCR, to targeting moieties is known in the art. See, for instance, Wadwa et al., *J. Drug Targeting*, 3(2):111 (1995), and U.S. Pat. No. 5,087,616.

B. Combination Therapy

Also provided are methods of combination therapy that includes administering and uses, such as therapeutic and prophylactic uses, of the BCMA-binding molecules, including the anti-BCMA antibodies, e.g., antibody fragments and proteins containing the same such as the recombinant receptors (e.g., CARs), engineered cells expressing the recombinant receptors (e.g., CARs), plurality of engineered cells expressing the receptors, and/or compositions comprising the same.

In some embodiments, the BCMA-binding molecule (e.g., antibody), immunoconjugate, recombinant receptor (e.g., chimeric antigen receptor) and/or engineered cells expressing said molecules (e.g., recombinant receptor) described herein are administered as part of a combination treatment or combination therapy, such as simultaneously with, sequentially with or intermittently with, in any order, one or more additional therapeutic intervention. In some embodiments, the one or more additional therapeutic intervention includes, for example, an antibody, an engineered cell, a receptor and/or an agent, such as a cell expressing a recombinant receptor, and/or cytotoxic or therapeutic agent, e.g., a chemotherapeutic agent. In some embodiments, the combination therapy includes administration of one or more additional agents, therapies and/or treatments, e.g., any of the additional agents, therapy and/or treatments described herein. In some embodiments, the combination therapy includes administration of one or more additional agents for treatment or therapy, such as an immunomodulatory agent, immune checkpoint inhibitor, adenosine pathway or adenosine receptor antagonist or agonist and kinase inhibitors. In some embodiments, the combination treatment or combination therapy includes an additional treatment, such as a surgical treatment, transplant, and/or radiation therapy. Also provided are methods of combination treatment or combination therapy that includes administering the binding molecules (e.g., BCMA-binding molecules), recombinant receptors, cells and/or compositions described herein and one or more additional therapeutic interventions.

In some embodiments, the additional agent for combination treatment or combination therapy enhances, boosts and/or promotes the efficacy and/or safety of the therapeutic effect of binding molecules, recombinant receptors, cells and/or compositions. In some embodiments, the additional agent enhances or improves the efficacy, survival or persistence of the administered cells, e.g., cells expressing the binding molecule or a recombinant receptor. In some embodiments, the additional agent is selected from among a protein phosphatase inhibitor, a kinase inhibitor, a cytokine, an immunomodulator, or an agent that decreases the level or activity of a regulatory T (Treg) cell. In some embodiments, the additional agent enhances safety, by virtue of reducing or ameliorating adverse effects of the administered binding molecules, recombinant receptors, cells and/or compositions. In some embodiments, the additional agent can treat the same disease, condition or a comorbidity. In some embodiments, the additional agent can ameliorate, reduce or eliminate one or more toxicities, adverse effects or side effects that are associated with administration of the binding molecules, recombinant receptors, cells and/or compositions, e.g., CAR-expressing cells.

In some embodiments, the additional therapy, treatment or agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the additional agent is a protein, a peptide, a nucleic acid, a small molecule agent, a cell, a toxin, a lipid, a carbohydrate or combinations thereof, or any other type of therapeutic agent, e.g. radiation. In some embodiments, the additional therapy, agent or treatment includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, antimetabolites, metabolic modulators, drugs that inhibit either the calcium dependent phosphatase calcineurin or the p70S6 kinase FK506) or inhibit the p70S6 kinase, alkylating agents, anthracyclines, vinca alkaloids, proteasome inhibitors, GITR agonists, protein tyrosine phosphatase inhibitors, protein kinase inhibitors, an oncolytic virus, and/or other types of immunotherapy. In some embodiments, the additional agent or treatment is bone marrow transplantation, T cell ablative therapy using chemotherapy agents such as, fludarabine, external-beam radiation therapy (XRT), cyclophosphamide, and/or antibody therapy.

In some embodiments, the cells, binding molecules (e.g., BCMA-binding molecules), recombinant receptors and/or compositions, e.g., CAR-expressing cells, are administered in combination with other engineered cells, e.g., other CAR-expressing cells. In some embodiments, the additional agent is a kinase inhibitor, e.g., an inhibitor of Bruton's tyrosine kinase (Btk), e.g., ibrutinib. In some embodiments, the additional agent is an adenosine pathway or adenosine receptor antagonist or agonist. In some embodiments, the additional agent is an immunomodulator such as thalidomide or a thalidomide derivative (e.g., lenalidomide). In some embodiments, the additional therapy, agent or treatment is a cytotoxic or chemotherapy agent, a biologic therapy (e.g., antibody, e.g., monoclonal antibody, or cellular therapy), or an inhibitor (e.g., kinase inhibitor).

In some embodiments, a chemotherapeutic agent (sometimes referred to as a cytotoxic agent) is administered to the subject to disrupt a lesion. In certain embodiments, the lesion is tumor. In particular embodiments, the lesion is cancerous. In particular embodiments, the chemotherapeutic agent is any agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. In particular embodiments, chemotherapeutic drugs include alkylating agents, anthracyclines, cytoskeletal disruptors (taxanes), epothilones, histone deacetylase inhibitors, topoisomerase inhibitors, topoisomerase II inhibitors, kinase inhibitors, nucleotide analogs and precursor analogs, peptide antibiotics, platinum-based agents, and vinca alkaloids and derivatives.

In certain embodiments, a lesion is disrupted by administering a chemotherapeutic agent to modulate genetically engineered cells in vivo. Chemotherapeutic agents may include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, exemplary chemotherapeutic agents include an anthracycline (e.g., doxorubicin, such as liposomal doxorubicin); a vinca alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzumab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the additional therapy or treatment is cell therapy, e.g., adoptive cell therapy. In some embodiments, the additional therapy includes administration of engineered cells, e.g., additional CAR-expressing cell. In some embodiments, the additional engineered cell is a CAR-expressing cell that expresses the same or different recombinant receptor as the engineered cells provided herein, e.g., anti-BCMA CAR-expressing cells. In some embodiments, the recombinant receptor, e.g., CAR, expressed on the additional engineered cell, recognizes a different antigen and/or epitope. In some embodiments, the recombinant receptor, e.g., CAR, expressed on the additional engineered cell, recognizes a different epitope of the same antigen as the recombinant receptors described herein, e.g., BCMA. In some embodiments, the recombinant receptor, e.g., CAR, expressed on the additional engineered cell, recognizes a different antigen, e.g., a different tumor antigen or combination of antigens. For example, in some embodiments, the recombinant receptor, e.g., CAR, expressed on the additional engineered cell, targets cancer cells that express early lineage markers, e.g., cancer stem cells, while other CAR-expressing cells target cancer cells that express later lineage markers. In such embodiments, the additional engineered cell is administered prior to, concurrently with, or after administration (e.g., infusion) of the CAR-expressing cells described herein. In some embodiments, the additional engineered cell expresses allogeneic CAR.

In some embodiments, the configurations of one or more of the CAR molecules comprise a primary intracellular signaling domain and two or more, e.g., 2, 3, 4, or 5 or more, costimulatory signaling domains. In some embodiments, the one or more of the CAR molecules may have the same or a different primary intracellular signaling domain, the same or different costimulatory signaling domains, or the same number or a different number of costimulatory signaling domains. In some embodiments, the one or more of the CAR molecules can be configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, the additional agent is any of the multispecific binding molecules and/or cells engineered to express one or more of the binding molecules described herein and/or cells engineered to express additional binding molecules, e.g., recombinant receptors, e.g., CAR, that target a different antigen. In some embodiments, the additional agent includes any of the cells or plurality of cells described herein, e.g., in Section I.C. In some embodiments, the additional agent is a cell engineered to express a recombinant receptor, e.g., CAR, targeting a different epitope and/or antigen, e.g., a different antigen associated with a disease or condition. In some embodiments, the additional agent is a cell engineered to express a recombinant receptor, e.g., CAR, targeting a second or additional antigen expressed in multiple myeloma, e.g., CD38, CD138, CS-1, BAFF-R, TACI and/or FcRH5.

In some embodiments, the additional agent is an immunomodulatory agent. In some embodiments, the combination therapy includes an immunomodulatory agent that can stimulate, amplify and/or otherwise enhance an anti-tumor immune response, e.g. anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the binding molecules, recombinant receptors, cells and/or compositions are administered in combination with an additional agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system.

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses. In some embodiments, the subject can be administered an additional agent that can enhance or boost the immune response, e.g., immune response effected by the binding molecules (e.g., BCMA-binding molecules), recombinant receptors, cells and/or compositions provided herein, against a disease or condition, e.g., a cancer, such as any described herein.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC), CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+(αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta). Immune checkpoint inhibitors include antibodies, or antigen binding fragments thereof, or other binding proteins that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (Avastin®)), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof. Other exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon .gamma., CAS 951209-71-5, available from IRX Therapeutics).

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L1. MDPL3280A and other human monoclonal antibodies to PD-L1 are described in U.S. Pat. No. 7,943,743 and U.S Publication No. 20120039906. Other anti-PD-L1 binding agents include YW243.55.570 (see WO2010/077634) and MDX-1105 (also referred to as BMS-936559, and, e.g., anti-PD-L1 binding agents described in WO2007/005874).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MHC class II molecules and activates antigen presenting cells (APC). Other antibodies are described, e.g., in WO2010/019570 and US 2015/0259420

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the additional agent is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146), or cross-reacts with CEACAM-1 and CEACAM-5 as described in, e.g., WO 2013/054331 and US 2014/0271618.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the additional agent includes a molecule that decreases the regulatory T cell (Treg) population. Methods that decrease the number of (e.g., deplete) Treg cells are known in the art and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse. In some embodiments, the additional agent includes a molecule targeting GITR and/or modulating GITR functions, such as a GITR agonist and/or a GITR antibody that depletes regulatory T cells (Tregs). In some embodiments, the additional agent includes cyclophosphamide. In some embodiments, the GITR binding molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the additional agent is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B 1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726. An exemplary anti-GITR antibody is TRX518.

In some embodiments, the additional agent enhances tumor infiltration or transmigration of the administered cells, e.g., CAR-expressing cells. For example, in some embodiments, the additional agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the additional agent that enhances tumor infiltration includes tyrosine kinase inhibitor sunitnib, heparanase, and/or chemokine receptors such as CCR2, CCR4, and CCR7.

In some embodiments, the additional agent is a structural or functional analog or derivative of thalidomide and/or an inhibitor of E3 ubiquitin ligase. In some embodiments, the immunomodulatory agent binds to cereblon (CRBN). In some embodiments, the immunomodulatory agent binds to the CRBN E3 ubiquitin-ligase complex. In some embodiments, the immunomodulatory agent binds to CRBN and the CRBN E3 ubiquitin-ligase complex. In some embodiments, the immunomodulatory agent up-regulates the protein or gene expression of CRBN. In some aspects, CRBN is the substrate adaptor for the $CRL4^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory agent induces the ubiquitination of KZF1 (Ikaros) and IKZF3 (Aiolos) and/or induces degradation of IKZF1 (Ikaros) and IKZF3 (Aiolos). In some embodiments, the immunomodulatory agent induces the ubiquitination of casein kinase 1A1 (CK1α) by the $CRL4^{CRBN}$ E3 ubiquitin ligase. In some embodiments, the ubiquitination of CK1α results in CK1α degradation.

In some embodiments, the additional agent is an inhibitor of the Ikaros (IKZF1) transcription factor. In some embodiments, the additional agent enhances ubiquitination of Ikaros. In some embodiments, the additional agent enhances the degradation of Ikaros. In some embodiments, the additional agent down-regulates the protein or gene expression of Ikaros. In some embodiments, administration of the additional agent causes a decrease in Ikaros protein levels.

In some embodiments, the additional agent is an inhibitor of the Aiolos (IKZF3) transcription factor. In some embodiments, the additional agent enhances ubiquitination of Aiolos. In some embodiments, the additional agent enhances the degradation of Aiolos. In some embodiments, the additional agent down-regulates the protein or gene expression of Aiolos. In some embodiments, administration of the additional agent causes a decrease in Aiolos protein levels.

In some embodiments, the additional agent is an inhibitor of both the Ikaros (IKZF1) and Aiolos (IKZF3) transcription factors. In some embodiments, the additional agent enhances ubiquitination of both Ikaros and Aiolos. In some embodiments, the additional agent enhances the degradation of both Ikaros and Aiolos. In some embodiments, the additional agent enhances ubiquitination and degradation of both Ikaros and Aiolos. In some embodiments, administration of the additional agent causes both Aiolos protein levels and Ikaros protein levels to decrease.

In some embodiments, the additional agent is a selective cytokine inhibitory drug (SelCID). In some embodiments, the additional agent inhibits the activity of phosphodiesterase-4 (PDE4). In some embodiments, the additional agent suppresses the enzymatic activity of the CDC25 phosphatases. In some embodiments, the additional agent alters the intracellular trafficking of CDC25 phosphatases.

In some embodiments, the additional agent is thalidomide (2-(2,6-dioxopiperidin-3-yl)-1H-isoindole-1,3(2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320,991; and 8,716,315; U.S. Appl. No. 2016/0313300; and PCT Pub. Nos. WO 2002/068414 and WO 2008/154252.

In some embodiments, the additional agent is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the additional agent is a compound of the following formula:

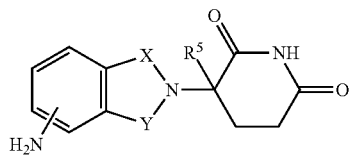

wherein one of X and Y is —C(O)— and the other of X and Y is —C(O)— or —CH$_2$—, and R$^5$ is hydrogen or lower alkyl, or a pharmaceutically acceptable salt thereof. In some embodiments, X is —C(O)— and Y is —CH$_2$—. In some embodiments, both X and Y are —C(O)—. In some embodiments, R$^5$ is hydrogen. In other embodiments, R$^5$ is methyl.

In some embodiments, the additional agent is a compound that belongs to a class of substituted 2-(2, 6-dioxopiperidin-3-yl)phthalate immunomodulatory compounds and substituted 2-(2,6-dioxopiperldin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference.

In some embodiments, the additional agent is a compound of the following formula:

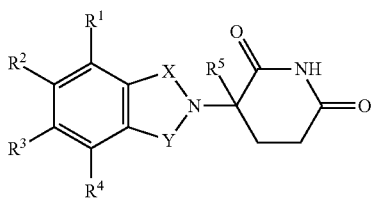

wherein
one of X and Y is —C(O)— and the other of X and Y is —C(O)— or —CH$_2$—;
(1) each of R$^1$, R$^2$, R$^3$, and R$^4$ are independently halo, alkyl of 1 to 4 carbon atoms, or alkoxy or 1 to 4 carbon atoms, or (2) one of R$^1$, R$^3$, R$^4$, and R$^5$ is —NHR$^a$ and the remaining of R$^1$, R$^2$, R$^3$, and R$^4$ is are hydrogen, wherein R$^a$ is hydrogen or alkyl of 1 to 8 carbon atoms;
R$^5$ is hydrogen or alkyl of 1 to 8 carbon atoms, benzyl, or halo;
provided that R$^5$ is other than hydrogen if X and Y are —C(O)— and (i) each of R$^1$, R$^2$, R$^3$, and R$^4$ is fluoro; or (ii) one of R$^1$, R$^2$, R$^3$, and R$^4$ is amino;
or a pharmaceutically acceptable salt thereof.

In some embodiments, the additional agent is a compound that belongs to a class of isoindole-immunomodulatory compounds disclosed in U.S. Pat. No. 7,091,353, U.S. Patent Publication No. 2003/0045552, and International Application No. PCT/USOI/50401 (International Publication No. WO02/059106), each of which are incorporated herein by reference. For example, in some embodiments, the additional agent is [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2, 6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2, 6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1, 3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; or N-{[2-(2,6-dioxo(3-piperidyl))-1,3-dioxoisoindolin-4-yl]methyl}(benzylamino)carboxamide.

In some embodiments, the additional agent is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the additional agent is a tetra substituted 2-(2,6-dioxopiperdin-3-yl)-1-oxoisoindolines described in U.S. Pat. No. 5,798, 368, which is incorporated herein by reference. In some embodiments, the additional agent is 1-oxo and 1,3-dioxo-2-(2,6-dioxopiperidin-3-yl) isoindolines disclosed in U.S. Pat. No. 6,403,613, which is incorporated herein by reference. In some embodiments the additional agent is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the additional agent is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)- amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the additional agent is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the additional agent is as described in Oshima, K. et al., *Nihon Rinsho.*, 72(6):1130-5 (2014); Millrine, D. et al., *Trends Mol Med.*, 23(4):348-364 (2017); and Collins, et al., *Biochem J.*, 474(7):1127-1147 (2017).

In some embodiments, the additional agent is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof. In some embodiments, the immunomodulatory compound is lenalidomide, or ((RS)-3-(4-Amino-1-oxo-1,3-dihydro-2H-isoindol-2-yl)piperidine-2,6-dione).

In certain embodiments, the lesion is disrupted by administering the thalidomide derivative lenalidomide, ((RS)-3-(4-Amino-1-oxo-1,3-dihydro-2H-isoindol-2-yl)piperidine-2,6-dione) to the subject. Lenalidomide is FDA approved for the treatment of multiple myeloma, myelodysplastic syndrome associated with deletion 5q, and most recently in relapsed/refractory mantle-cell lymphoma (MCL). Lenalidomide generally is a synthetic derivative of thalidomide, and is currently understood to have multiple immunomodulatory effects, including enforcement of immune synapse formation between T cell and antigen presenting cells (APCs). For example, in some cases, lenalidomide modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. In addition, lenalidomide is thought to decrease proliferation of pro-inflammatory cytokines including TNF-α, IL-1, IL-6, and IL-12 and enhance antibody-dependent cellular cytotoxicity (ADCC) via increased NK cell activation. Lenalidomide can also induce malignant B cells to express higher levels of immunostimulatory molecules such as CD80, CD86, HLA-DR, CD95, and CD40 (Fecteau et al., Blood (2014) 124(10):1637-1644). Cereblon, an E3 ubiquitin ligase, was identified as the primary target for thalidomide-induced teratogenesis (Ito et al., T., (2010) Science 327: 1345-1350). Lenalidomide also targets cereblon and it has been shown that this leads to the reduction of c-Myc and IRF4 expression while also increasing expression of p21 that leads to G1 cell-cycle arrest (Lopez-Girona et al., (2012) Leukemia 26: 2326-2335).

In some embodiments, the additional agent includes thalidomide drugs or analogs thereof and/or derivatives thereof, such as lenalidomide, pomalidomide or apremilast. See, e.g., Bertilaccio et al., Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). For example, in some cases, lenalidomide modulates T cell responses and results in increased interleukin (IL)-2 production in CD4+ and CD8+ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. Lenalidomide can also induce malignant B cells to express higher levels of immunostimulatory molecules such as CD80, CD86, HLA-DR, CD95, and CD40 (Fecteau et al., Blood (2014) 124(10): 1637-1644).

In some embodiments, the additional agent is a B-cell inhibitor. In some embodiments, the additional agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the additional agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the additional agent is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or R05072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the additional agent includes rituximab. In some embodiments, the CD20 inhibitor is a small molecule.

In some embodiments, the additional agent is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the immunomodulatory agent is a cytokine. In some embodiments, the immunomodulatory agent is a cytokine or is an agent that induces increased expression of a cytokine in the tumor microenvironment. Cytokines have important functions related to T cell expansion, differentiation, survival, and homeostasis. Cytokines that can be administered to the subject receiving the binding molecules (e.g., BCMA-binding molecules), recombinant receptors, cells and/or compositions provided herein include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the additional agent includes an interleukin-15 (IL-15) polypeptide, an interleukin-15 receptor alpha (IL-15Ra) polypeptide, or combination thereof, e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines. In some embodiments, the immunomodulatory agent is a Toll-like receptor (TLR) agonist, an adjuvant or a cytokine.

In some embodiments, the additional agent is an agent that ameliorates or neutralizes one or more toxicities or side effects associated with the cell therapy. In some embodiments, the additional agent is selected from among a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab, sarilumab, elsilimomab, CNTO 328, ALD518/BMS-945429, CNTO 136, CPSI-2364, CDP6038, VX30, ARGX-109, FE301, and FM101. In some embodiments, the anti-IL-6 antibody molecule is tocilizumab. In some embodiments, the additional agent is an IL-1R inhibitor, such as anakinra.

In some embodiments, the additional agent is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of proinflammatory cytokine production, and can lead to the synthesis of immunosuppressive molecules and development of Tregs (Sitkovsky et al., Cancer Immunol Res (2014) 2(7): 598-605). In some embodiments, the additional agent can reduce or reverse immunosuppressive effects of adenosine, adenosine analogs and/or adenosine signaling. In some embodiments, the additional agent can reduce or reverse hypoxia-driven A2-adenosinergic T cell immunosuppression. In some embodiments, the additional agent is selected from among antagonists of adenosine receptors, extracellular adenosine-degrading agents, inhibitors of adenosine generation by CD39/CD73 ectoenzymes, and inhibitors of hypoxia-HIF-1a signaling. In some embodiments, the additional agent is an adenosine receptor antagonist or agonist.

Inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the additional agent is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the additional agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

An antagonist is any substance that tends to nullify the action of another, as an agent that binds to a cell receptor without eliciting a biological response. In some embodiments, the antagonist is a chemical compound that is an antagonist for an adenosine receptor, such as the A2a, A2b, or A3 receptor. In some embodiments, the antagonist is a peptide, or a peptidomimetic, that binds the adenosine receptor but does not trigger a Gi protein dependent intracellular pathway. Exemplary antagonists are described in U.S. Pat. Nos. 5,565,566; 5,545,627, 5,981,524; 5,861,405; 6,066,642; 6,326,390; 5,670,501; 6,117,998; 6,232,297; 5,786,360; 5,424,297; 6,313,131, 5,504,090; and 6,322,771.

In some embodiments, the additional agent is an A2 receptor (A2R) antagonist, such as an A2a antagonist. Exemplary A2R antagonists include KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (B11014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the additional agent is an A2R antagonist described in, e.g., Ohta et al., Proc Natl Acad Sci USA (2006) 103:13132-13137; Jin et al., Cancer Res. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080, 554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In some embodiments, the antagonist is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the additional agent includes dominant negative mutant form of an adenosine receptor, such as A2a, A2b, or A3.

In some embodiments, the additional agent that inhibits extracellular adenosine includes agents that render extracellular adenosine non-functional (or decrease such function), such as a substance that modifies the structure of adenosine to inhibit the ability of adenosine to signal through adenosine receptors. In some embodiments, the additional agent is an extracellular adenosine-generating or adenosine-degrading enzyme, a modified form thereof or a modulator thereof. For example, in some embodiments, the additional agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the additional agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995) Hum Mutat. 5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the additional agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the additional agent can target ectoenzymes that generate or produce extracellular adenosine. In some embodiments, the additional agent targets CD39 and CD73 ectoenzymes, which function in tandem to generate extracellular adenosine. CD39 (also called ectonucleoside triphosphate diphosphohydrolase) converts extracellular ATP (or ADP) to 5'AMP. Subsequently, CD73 (also called 5' nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6): 1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the additional agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., Cancer Res. (2010) 70(16):6407-6411).

In some embodiments, the additional agent is an inhibitor of hypoxia inducible factor 1 alpha (HIF-1α) signaling. Exemplary inhibitors of HIF-1α include digoxin, acriflavine, sirtuin-7 and ganetespib.

In some embodiments, the additional agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the additional agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the kinase inhibitor is a BTK inhibitor, e.g., ibrutinib (PCI-32765). In some embodiments, 1, 2, 3, 4, 5, 6, 7, 8, 9, 10, 11, 12 or more cycles of ibrutinib are administered. In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival. Exemplary PI3K inhibitor includes idelalisib (PI3Kδ inhibitor). In some embodiments, the additional agent is idelalisib and rituximab.

In some embodiments, the additional agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the additional agent is an inhibitor of mitogen-activated protein kinase (MAPK), such as vemurafenib, dabrafenib, and trametinib.

In some embodiments, the additional agent is an agent that regulates pro- or anti-apoptotic proteins. In some embodiments, the additional agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the additional agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the additional agent includes an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. Plasmacytoid dendritic cells (pDCs), macrophages, and dendritic cells (DCs) can express IDO. In some aspects, a decrease in L-tryptophan (e.g., catalyzed by IDO) results in an immunosuppressive milieu by inducing T-cell anergy and apoptosis. Thus, in some aspects, an IDO inhibitor can enhance the efficacy of the binding molecules (e.g., BCMA-binding molecules), recombinant receptors, cells and/or compositions described herein, e.g., by decreasing the suppression or death of the administered CAR-expressing cell. Exemplary inhibitors of IDO include but are not limited to 1-methyl-tryptophan, indoximod, and INCB024360 (epacadostat).

In some embodiments, the additional agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the additional agent includes a hypomethylating agent, e.g., a DNA methyltransferase inhibitor, e.g., azacitidine or decitabine.

In another embodiment, the additional therapy is a transplantation, e.g., allogeneic stem cell transplant.

In some embodiments, the additional therapy is a lymphodepleting therapy. In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells.

In some embodiments, the additional agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the additional agent includes cytoprotective agents, such as neuroprotectants, free-radical scavengers, cardioprotectors, anthracycline extravasation neutralizers and nutrients.

In some embodiments, an antibody used as an additional agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or antiemetic), pain reliever, or cytoprotective agent described herein. In some embodiments, the additional agent is an antibody-drug conjugate.

In some embodiments, the additional agent can modulate, inhibit or stimulate particular factors at the DNA, RNA or protein levels, to enhance or boost the efficacy of the binding molecules (e.g., BCMA-binding molecules), recombinant receptors, cells and/or compositions provided herein. In some embodiments, the additional agent can modulate the factors at the nucleic acid level, e.g., DNA or RNA, within the administered cells, e.g., cells engineered to express recombinant receptors, e.g., CAR. In some embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the engineered cell, e.g., CAR-expressing cell. In some embodiments the inhibitor is an shRNA. In some embodiments, the inhibitory molecule is inhibited within the engineered cell, e.g., CAR-expressing cell. In some embodiments, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the inhibitory molecule is expressed within the engineered cell, e.g., CAR-expressing cell. See, e.g., Brummelkamp T R, et al. (2002) Science 296: 550-553; Miyagishi M, et al. (2002) Nat. Biotechnol. 19: 497-500.

In some embodiments, the additional agent is capable of disrupting the gene encoding an inhibitory molecule, such as any immune checkpoint inhibitors described herein. In some embodiments, disruption is by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the inhibitory molecule is not expressed or is not expressed in a form that is capable of being expressed on the cells surface and/or capable of mediating cell signaling. The disruption is generally carried out at the DNA level. The disruption generally is permanent, irreversible, or not transient.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, methods of producing or generating genetically engineered cells, e.g., CAR-expressing cells, include introducing into a population of cells nucleic acid molecules encoding a genetically engineered antigen receptor (e.g. CAR) and nucleic acid molecules encoding an agent targeting an inhibitory molecule that is a gene editing nuclease, such as a fusion of a DNA-targeting protein and a nuclease such as a ZFN or a TALEN, or an RNA-guided nuclease such as of the CRISPR-Cas9 system, specific for an inhibitory molecule.

Any of the additional agents described herein can be prepared and administered as combination therapy with the BCMA-binding molecule (e.g., antibody), immunoconjugate, recombinant receptor (e.g., chimeric antigen receptor) and/or engineered cells expressing said molecules (e.g., recombinant receptor) described herein, such as in pharmaceutical compositions comprising one or more agents of the combination therapy and a pharmaceutically acceptable carrier, such as any described herein. In some embodiments, the BCMA-binding molecule (e.g., antibody), immunoconjugate, recombinant receptor (e.g., chimeric antigen receptor), engineered cells expressing said molecules (e.g., recombinant receptor), plurality of engineered cells expressing said molecules (e.g., recombinant receptor) can be administered simultaneously, concurrently or sequentially, in any order with the additional agents, therapy or treatment, wherein such administration provides therapeutically effective levels each of the agents in the body of the subject. The agents can be co-administered with the binding molecules (e.g., BCMA-binding molecules), recombinant receptors, cells and/or compositions described herein, for example, as part of the same pharmaceutical composition or using the same method of delivery. In some embodiments, the additional agent is incubated with the engineered cell, e.g., CAR-expressing cells, prior to administration of the cells.

In some examples, the one or more additional agents are administered subsequent to or prior to the administration of the binding molecules (e.g., BCMA-binding molecules), recombinant receptors, cells and/or compositions described herein, separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one or more additional agents are administered multiple times and/or the binding molecules (e.g., BCMA-binding molecules), recombinant receptors, cells and/or compositions described herein, is administered multiple times. For example, in some embodiments, the additional agent is administered prior to the binding molecules (e.g., BCMA-binding molecules), recombinant receptors, cells and/or compositions described herein, e.g., two weeks, 12 days, 10 days, 8 days, one week, 6 days, 5 days, 4 days, 3 days, 2 days or 1 day before the administration. For example, in some embodiments, the additional agent is administered after the binding molecules (e.g., BCMA-binding molecules), recombinant receptors, cells and/or compositions described herein, e.g., two weeks, 12 days, 10 days, 8 days, one week, 6 days, 5 days, 4 days, 3 days, 2 days or 1 day after the administration.

The dose of the additional agent can be any therapeutically effective amount, e.g., any dose amount described herein, and the appropriate dosage of the additional agent may depend on the type of disease to be treated, the type, dose and/or frequency of the binding molecule, recombinant receptor, cell and/or composition administered, the severity and course of the disease, whether the binding molecule, recombinant receptor, cell and/or composition is administered for preventive or therapeutic purposes, previous therapy, the patient's clinical history and response to the binding molecule, recombinant receptor, cell and/or composition, and the discretion of the attending physician. The binding molecule, recombinant receptor, cell and/or composition and/or the additional agent and/or therapy can be administered to the patient at one time, repeated or administered over a series of treatments.

C. Diagnostic and Detection Methods

Also provided are methods involving use of the provided binding molecules, e.g., antibodies or antigen-binding fragments thereof, in detection of BCMA, for example, in diagnostic and/or prognostic methods in association with a BCMA-expressing disease or condition. The methods in some embodiments include incubating a biological sample with the antibody or antigen-binding fragment thereof and/or administering the antibody or antigen-binding fragment thereof to a subject. In certain embodiments, a biological sample includes a cell or tissue, such as tumor or cancer tissue. In certain embodiments, the contacting is under conditions permissive for binding of the anti-BCMA antibody to BCMA, and detecting whether a complex is formed between the anti-BCMA antibody and BCMA. Such a method may be an in vitro or in vivo method. In one embodiment, an anti-BCMA antibody (e.g., antigen-binding fragment) is used to select subjects eligible for therapy with an anti-BCMA antibody (e.g., antigen-binding fragment) or recombinant receptor, e.g. where BCMA is a biomarker for selection of patients.

In some embodiments, a sample, such as a cell, tissue sample, lysate, composition, or other sample derived therefrom is contacted with the anti-BCMA antibody (e.g., antigen-binding fragment) and binding or formation of a complex between the antibody and the sample (e.g., BCMA in the sample) is determined or detected. When binding in the test sample is demonstrated or detected as compared to a reference cell of the same tissue type, it may indicate the presence of an associated disease or condition. In some embodiments, the sample is from human tissues.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Exemplary labels include radionuclides (e.g. $^{125}$I, $^{131}$I, $^{35}$S, $^{3}$H, or $^{32}$P), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

For purposes of diagnosis, the antibodies (e.g., antigen-binding fragments) can be labeled with a detectable moiety including but not limited to radioisotopes, fluorescent labels, and various enzyme-substrate labels know in the art. Methods of conjugating labels to an antibody are known in the art.

In some embodiments, antibodies (e.g., antigen-binding fragments) need not be labeled, and the presence thereof can be detected using a labeled antibody which binds to the antibodies.

The provided antibodies (e.g., antigen-binding fragments) in some embodiments can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies (e.g., antigen-binding fragments) and polypeptides can also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized in vivo following administration to a subject.

The antibody (e.g., antigen-binding fragment) may also be used as staining reagent in pathology, e.g., using known techniques.

III. Articles of Manufacture or Kits

Also provided are articles of manufacture or kit containing the provided binding molecules (e.g., antibodies), recombinant receptors (e.g., CARs), genetically engineered cells, and/or compositions comprising the same. The articles of manufacture may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include an intravenous solution bags, vials, including those with stoppers pierceable by a needle for injection. The article of manufacture or kit may further include a package insert indicating that the compositions can be used to treat a particular condition such as a condition described herein (e.g., multiple myeloma). Alternatively, or additionally, the article of manufacture or kit may further include another or the same container comprising a pharmaceutically-acceptable buffer. It may further include other materials such as other buffers, diluents, filters, needles, and/or syringes.

The label or package insert may indicate that the composition is used for treating the BCMA-expressing or BCMA-associated disease, disorder or condition in an individual. The label or a package insert, which is on or associated with the container, may indicate directions for reconstitution and/or use of the formulation. The label or package insert may further indicate that the formulation is useful or intended for subcutaneous, intravenous, or other modes of administration for treating or preventing a BCMA-expressing or BCMA-associated disease, disorder or condition in an individual.

The container in some embodiments holds a composition which is by itself or combined with another composition effective for treating, preventing and/or diagnosing the condition. The article of manufacture or kit may include (a) a first container with a composition contained therein (i.e., first medicament), wherein the composition includes the antibody (e.g., anti-BCMA antibody) or antigen-binding fragment thereof or recombinant receptor (e.g., CAR); and (b) a second container with a composition contained therein (i.e., second medicament), wherein the composition includes a further agent, such as a cytotoxic or otherwise therapeutic agent, and which article or kit further comprises instructions on the label or package insert for treating the subject with the second medicament, in an effective amount.

IV. Definitions

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as an scFv of that antibody, has greater activity compared to the scFv form of the first antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-BCMA antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" and "sequence identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;

(5) residues that influence chain orientation: Gly, Pro;
(6) aromatic: Trp, Tyr, Phe.

Non-conservative amino acid substitutions will involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "composition" refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

IV. Exemplary Embodiments

Among the embodiments provided herein are:

1. An antibody or antigen-binding fragment thereof, wherein said antibody or antigen-binding fragment comprises a heavy chain variable ($V_H$) region comprising:

a heavy chain complementarity determining region 3 (CDR-H3) comprising the amino acid sequence selected from any one of SEQ ID NOs:7-11, 149-157, 279-287 and 376-378; or a CDR-H3 contained within the heavy chain variable ($V_H$) region amino acid sequence selected from any one of SEQ ID NOs:110-115, 247-256, 518-531 and 533.

2. An antibody or antigen-binding fragment thereof, wherein said antibody or antigen-binding fragment comprises a $V_H$ region having at least 90%, 91%, 92%, 93%, 94%, 95%, 96%, 97%, 98% or 99% sequence identity to the $V_H$ region amino acid sequence selected from any one of SEQ ID NOs:110-115, 247-256, 518-531 and 533.

3. The antibody or antigen-binding fragment of embodiment 2, wherein the $V_H$ region comprises a CDR-H3 comprising the amino acid sequence $X_1X_2X_3X_4X_5X_6X_7X_8X_9X_{10}X_{11}X_{12}X_{13}X_{14}$ (SEQ ID NO:355), wherein $X_1$ is A, D, E, G, L, V or W; $X_2$ is A, D, G, L, P, Q or S; $X_3$ is A, D, G, L or Y; $X_4$ is D, G, P, R, S, V, Y or null; $X_5$ is D, I, P, S, T, Y or null; $X_6$ is A, G, I, S, T, V, Y or null; $X_7$ is A, D, E, F, L, P, S, Y or null; $X_8$ is P, Q, T, Y or null; $X_9$ is D, G, R, Y or null; $X_{10}$ is A, F, Y or null; $X_{11}$ is D, F or null; $X_{12}$ is F or null; $X_{13}$ is D, T or Y; and $X_{14}$ is I, L, N, V or Y.

4. The antibody or antigen-binding fragment of embodiment 2 or embodiment 3, wherein the $V_H$ region comprises:

a CDR-H3 comprising the amino acid sequence selected from any one of SEQ ID NOs:7-11, 149-157, 279-287 and 376-378; or a CDR-H3 contained within the $V_H$ region amino acid sequence selected from any one of SEQ ID NOs:110-115, 247-256, 518-531 and 533.

5. The antibody or antigen-binding fragment of any one of embodiments 1-4, wherein the $V_H$ region comprises:

a heavy chain complementarity determining region 1 (CDR-H1) comprising the amino acid sequence $X_1X_2X_3MX_4$ (SEQ ID NO:353) $X_1$ is D or S; $X_2$ is Y or S; $X_3$ is A, G, W, or Y; and $X_4$ is H, Q, or S; and/or a heavy chain complementarity determining region 2 (CDR-H2) comprising the amino acid sequence $X_1IX_2X_3X_4X_5X_6X_7X_8X_9X_{10}X_{11}YX_{12}X_{13}X_{14}X_{15}X_{16}X_{17}$ (SEQ ID NO:354), wherein $X_1$ is F, G, H, V, W or Y; $X_2$ is N, R, S or V; $X_3$ is P, Q, S, V, W or Y; $X_4$ is K or null; $X_5$ is A or null; $X_6$ is D, G, N, S, or Y; $X_7$ is G or S; $X_8$ is G or S; $X_9$ is E, G, N, T or S; $X_{10}$ is I, K, or T; $X_{11}$ is E, G, N or Y; $X_{12}$ is A or V; $X_{13}$ is A, D or Q; $X_{14}$ is K or S; $X_{15}$ is F or V; $X_{16}$ is K or Q; and $X_{17}$ is E or G.

6. The antibody or antigen-binding fragment of any one of embodiments 1-5, wherein the $V_H$ region comprises:

a heavy chain complementarity determining region 1 (CDR-H1) comprising the amino acid sequence selected from any one of SEQ ID NOs:1-3 and 140-144; and/or a heavy chain complementarity determining region 2 (CDR-H2) comprising the amino acid sequence selected from any one of SEQ ID NOs:4-6, 145-148 and 372-374.

7. The antibody or antigen-binding fragment of any one of embodiments 1-6, wherein the $V_H$ region comprises:

a CDR-H1 contained within the $V_H$ region amino acid sequence selected from any one of SEQ ID NOs:110-115, 247-256, 518-531 and 533; and/or a CDR-H2 contained within the $V_H$ region amino acid sequence selected from any one of SEQ ID NOs:110-115, 247-256, 518-531 and 533.

8. The antibody or antigen-binding fragment thereof of embodiment 7, wherein:

the CDR-H1 comprises the amino acid sequence selected from any one of SEQ ID NOs: 1-3, 141, 143 and 144 or a CDR-H1 contained within the $V_H$ region amino acid sequence selected from any one of SEQ ID NOs:110-113, 115, 248, 252-256 and 518-522;

the CDR-H2 comprises the amino acid sequence selected from any one of SEQ ID NOs: 4-6, 145, 147, 148 and 372 or a CDR-H2 contained within the $V_H$ region amino acid sequence selected from any one of SEQ ID NOs:110-113, 115, 248, 252-256 and 518-522; and/or the CDR-H3 comprises the amino acid sequence selected from any one of SEQ ID NOs: 7-10, 149, 153-157 and 376 or a CDR-H3 contained within the $V_H$ region amino acid sequence selected from any one of SEQ ID NOs:110-113, 115, 248, 252-256 and 518-522.

9. The antibody or antigen-binding fragment thereof of embodiment 7 or embodiment 8, wherein:

the CDR-H1 comprises the amino acid sequence of SEQ ID NO:1 or a CDR-H1 contained within the $V_H$ region amino acid sequence selected from any one of SEQ ID NOs: 115 and 256;

the CDR-H2 comprises the amino acid sequence of SEQ ID NO:5 or a CDR-H2 contained within the $V_H$ region amino acid sequence selected from any one of SEQ ID NOs: 115 and 256; and/or the CDR-H3 comprises the amino acid sequence selected from any one of SEQ ID NOs: 10 and 157 or a CDR-H3 contained within the $V_H$ region amino acid sequence selected from any one of SEQ ID NOs: 115 and 256.

10. An antibody or antigen-binding fragment thereof, comprising a heavy chain variable ($V_H$) region comprising a heavy chain complementarity determining region 1 (CDR-H1), CDR-H2, and CDR-H3, wherein:

the CDR-H1 comprises the amino acid sequence selected from any one of SEQ ID NOs:1-3 and 140-144 or a CDR-H1 contained within the $V_H$ region amino acid sequence selected from any one of SEQ ID NOs:110-115, 247-256, 518-531 and 533;

the CDR-H2 comprises the amino acid sequence selected from any one of SEQ ID NOs:4-6, 145-148 and 372-374 or a CDR-H2 contained within the $V_H$ region amino acid sequence selected from any one of SEQ ID NOs:110-115, 247-256, 518-531 and 533; and/or the CDR-H3 comprises the amino acid sequence selected from any one of SEQ ID NOs:7-11, 149-157, 279-287 and 376-378 or a CDR-H3 contained within the $V_H$ region amino acid sequence selected from any one of SEQ ID NOs:110-115, 247-256, 518-531 and 533.

11. The antibody or antigen-binding fragment thereof of embodiment 10, wherein:

the CDR-H1 comprises the amino acid sequence selected from any one of SEQ ID NOs: 1-3, 141, 143 and 144 or a CDR-H1 contained within the $V_H$ region amino acid sequence selected from any one of SEQ ID NOs:110-113, 115, 248, 252-256 and 518-522;

the CDR-H2 comprises the amino acid sequence selected from any one of SEQ ID NOs: 4-6, 145, 147, 148 and 372 or a CDR-H2 contained within the $V_H$ region amino acid sequence selected from any one of SEQ ID NOs:110-113, 115, 248, 252-256 and 518-522; and/or the CDR-H3 comprises the amino acid sequence selected from any one of SEQ ID NOs: 7-10, 149, 153-157 and 376 or a CDR-H3 contained within the $V_H$ region amino acid sequence selected from any one of SEQ ID NOs:110-113, 115, 248, 252-256 and 518-522.

12. The antibody or antigen-binding fragment thereof of embodiment 10 or embodiment 11, wherein:

the CDR-H1 comprises the amino acid sequence of SEQ ID NO:1 or a CDR-H1 contained within the $V_H$ region amino acid sequence selected from any one of SEQ ID NOs: 115 and 256;

the CDR-H2 comprises the amino acid sequence of SEQ ID NO:5 or a CDR-H2 contained within the $V_H$ region amino acid sequence selected from any one of SEQ ID NOs: 115 and 256; and/or the CDR-H3 comprises the amino acid sequence selected from any one of SEQ ID NOs: 10 and 157 or a CDR-H3 contained within the $V_H$ region amino acid sequence selected from any one of SEQ ID NOs: 115 and 256.

13. The antibody or antigen-binding fragment of any one of embodiments 1-10, comprising a $V_H$ region comprising a CDR-H1, CDR-H2, and CDR-H3, selected from:

a CDR-H1, CDR-H2, and CDR-H3 comprising the amino acid sequence of SEQ ID NOs:1, 4, and 7, respectively;

a CDR-H1, CDR-H2, and CDR-H3 comprising the amino acid sequence of SEQ ID NOs:2, 5, and 8, respectively;

a CDR-H1, CDR-H2, and CDR-H3 comprising the amino acid sequence of SEQ ID NOs:2, 5, and 9, respectively;

a CDR-H1, CDR-H2, and CDR-H3 comprising the amino acid sequence of SEQ ID NOs:2, 5, and 10, respectively;

a CDR-H1, CDR-H2, and CDR-H3 comprising the amino acid sequence of SEQ ID NOs:3, 6, and 11, respectively;

a CDR-H1, CDR-H2, and CDR-H3 comprising the amino acid sequence of SEQ ID NOs:140, 145, and 149, respectively;

a CDR-H1, CDR-H2, and CDR-H3 comprising the amino acid sequence of SEQ ID NOs:141, 145, and 149, respectively;

a CDR-H1, CDR-H2, and CDR-H3 comprising the amino acid sequence of SEQ ID NOs:141, 145, and 150, respectively;
a CDR-H1, CDR-H2, and CDR-H3 comprising the amino acid sequence of SEQ ID NOs:142, 146, and 151, respectively;
a CDR-H1, CDR-H2, and CDR-H3 comprising the amino acid sequence of SEQ ID NOs:2, 5, and 152, respectively;
a CDR-H1, CDR-H2, and CDR-H3 comprising the amino acid sequence of SEQ ID NOs:143, 147, and 153, respectively;
a CDR-H1, CDR-H2, and CDR-H3 comprising the amino acid sequence of SEQ ID NOs:144, 148, and 154, respectively;
a CDR-H1, CDR-H2, and CDR-H3 comprising the amino acid sequence of SEQ ID NOs:3, 6, and 155, respectively;
a CDR-H1, CDR-H2, and CDR-H3 comprising the amino acid sequence of SEQ ID NOs:2, 5, and 156, respectively;
a CDR-H1, CDR-H2, and CDR-H3 comprising the amino acid sequence of SEQ ID NOs:2, 5, and 157, respectively;
a CDR-H1, CDR-H2, and CDR-H3 comprising the amino acid sequence of SEQ ID NOs:2, 6, and 376, respectively;
a CDR-H1, CDR-H2, and CDR-H3 comprising the amino acid sequence of SEQ ID NOs:3, 372, and 376, respectively;
a CDR-H1, CDR-H2, and CDR-H3 comprising the amino acid sequence of SEQ ID NOs:3, 6, and 376, respectively;
a CDR-H1, CDR-H2, and CDR-H3 comprising the amino acid sequence of SEQ ID NOs:3, 6, and 377, respectively;
a CDR-H1, CDR-H2, and CDR-H3 comprising the amino acid sequence of SEQ ID NOs:2, 373, and 152, respectively;
a CDR-H1, CDR-H2, and CDR-H3 comprising the amino acid sequence of SEQ ID NOs:2, 5, and 378, respectively;
or a CDR-H1, CDR-H2, and CDR-H3 comprising the amino acid sequence of SEQ ID NOs:2, 374, and 9, respectively.

14. The antibody or antigen-binding fragment of embodiment 13, wherein the CDR-H1, CDR-H2, and CDR-H3, are selected from:
a CDR-H1, CDR-H2, and CDR-H3 comprising the amino acid sequence of SEQ ID NOs:1, 4, and 7, respectively;
a CDR-H1, CDR-H2, and CDR-H3 comprising the amino acid sequence of SEQ ID NOs:2, 5, and 8, respectively;
a CDR-H1, CDR-H2, and CDR-H3 comprising the amino acid sequence of SEQ ID NOs:2, 5, and 9, respectively;
a CDR-H1, CDR-H2, and CDR-H3 comprising the amino acid sequence of SEQ ID NOs:2, 5, and 10, respectively;
a CDR-H1, CDR-H2, and CDR-H3 comprising the amino acid sequence of SEQ ID NOs:141, 145, and 149, respectively;
a CDR-H1, CDR-H2, and CDR-H3 comprising the amino acid sequence of SEQ ID NOs:143, 147, and 153, respectively;
a CDR-H1, CDR-H2, and CDR-H3 comprising the amino acid sequence of SEQ ID NOs:144, 148, and 154, respectively;
a CDR-H1, CDR-H2, and CDR-H3 comprising the amino acid sequence of SEQ ID NOs:3, 6, and 155, respectively;
a CDR-H1, CDR-H2, and CDR-H3 comprising the amino acid sequence of SEQ ID NOs:2, 5, and 156, respectively;
a CDR-H1, CDR-H2, and CDR-H3 comprising the amino acid sequence of SEQ ID NOs:2, 5, and 157, respectively;
a CDR-H1, CDR-H2, and CDR-H3 comprising the amino acid sequence of SEQ ID NOs:2, 6, and 376, respectively;
a CDR-H1, CDR-H2, and CDR-H3 comprising the amino acid sequence of SEQ ID NOs:3, 372, and 376, respectively;
or a CDR-H1, CDR-H2, and CDR-H3 comprising the amino acid sequence of and SEQ ID NOs:3, 6, and 376, respectively;

15. The antibody or antigen-binding fragment of embodiment 13, wherein the CDR-H1, CDR-H2, and CDR-H3, are selected from:
a CDR-H1, CDR-H2, and CDR-H3 comprising the amino acid sequence of SEQ ID NOs: 2, 5, and 10, respectively; or
a CDR-H1, CDR-H2, and CDR-H3 comprising the amino acid sequence of and SEQ ID NOs: 2, 5, and 157, respectively;

16. An antibody or antigen-binding fragment thereof, wherein said antibody or antigen-binding fragment comprises a $V_H$ region comprising a CDR-H1, a CDR-H2, and a CDR-H3, respectively, comprising the amino acid sequence of a CDR-H1, a CDR-H2, and a CDR-H3 contained within the $V_H$ region amino acid sequence selected from any one of SEQ ID NOs:110-115, 247-256, 518-531 and 533.

17. The antibody or antigen-binding fragment thereof of embodiment 16, wherein the CDR-H1, the CDR-H2, and the CDR-H3, respectively, comprise the amino acid sequence of a CDR-H1, a CDR-H2, and a CDR-H3 contained within the $V_H$ region amino acid sequence selected from any one of SEQ ID NOs: 110-113, 115, 248, 252-256 and 518-522.

18. The antibody or antigen-binding fragment thereof of embodiment 16 or embodiment 17, wherein the CDR-H1, the CDR-H2, and the CDR-H3, respectively, comprise the amino acid sequence of a CDR-H1, a CDR-H2, and a CDR-H3 contained within the $V_H$ region amino acid sequence selected from any one of SEQ ID NOs: 115 and 256.

19. The antibody or antigen-binding fragment of any one of embodiments 1-16, wherein the $V_H$ region comprises a framework region 1 (FR1), a FR2, a FR3, and/or a FR4 having at least 90%, 91%, 92%, 93%, 94%, 95%, 96%, 97%, 98%, or 99% sequence identity, respectively, to a FR1, FR2, FR3, and/or FR4 contained within the $V_H$ region amino acid sequence selected from any one of SEQ ID NOs:110-115, 247-256, 518-531 and 533.

20. The antibody or antigen-binding fragment of any one of embodiments 1-19, wherein the $V_H$ region comprises a FR1, a FR2, a FR3, and/or a FR4, selected from:
a FR1 comprising the amino acid sequence selected from any one of SEQ ID NOs:59-63, 195-203 and 434-439;
the FR2 comprising the amino acid sequence selected from any one of SEQ ID NOs:64-66 and 204-209;
a FR3 comprising the amino acid sequence selected from any one of SEQ ID NOs:67-69, 210-216, 441 and 443; and/or
a FR4 comprising the amino acid sequence selected from any one of SEQ ID NOs:70-71, 217-220, 444 and 445.

21. The antibody or antigen-binding fragment of any one of embodiments 1-16, wherein the $V_H$ region comprises the amino acid sequence selected from any one of SEQ ID NOs:110-115, 247-256, 518-531 and 533.

22. The antibody or antigen-binding fragment thereof of embodiment 21, wherein the $V_H$ region comprises the amino acid sequence selected from any one of SEQ ID NOs: 110-113, 115, 248, 252-256 and 518-522.

23. The antibody or antigen-binding fragment thereof of embodiment 21 or embodiment 22, wherein the $V_H$ region comprises the amino acid sequence selected from any one of SEQ ID NOs: 115 and 256.

24. The antibody or antigen-binding fragment of any one of embodiments 1-21, wherein the antibody or antigen-binding fragment does not comprise a light chain variable ($V_L$) region, does not comprise a light chain complementarity determining region (CDR-L1), CDR-L2, and/or CDR-L3, and/or is a single-domain antibody (sdAb) comprising only the $V_H$ region.

25. The antibody or antigen-binding fragment of any one of embodiments 1-24, wherein the antibody or antigen-binding fragment is an sdAb comprising only the $V_H$ region.

26. The antibody or antigen-binding fragment of any one of embodiments 1-21, wherein the antibody or antigen-binding fragment further comprises a $V_L$ region.

27. The antibody or antigen-binding fragment of embodiment 26, wherein the $V_L$ region has at least 90%, 91%, 92%, 93%, 94%, 95%, 96%, 97%, 98%, or 99% sequence identity to the $V_L$ region amino acid sequence selected from any one of SEQ ID NOs:116-127, 257-267, 534-550 and 552-557.

28. The antibody or antigen-binding fragment of embodiment 26 or embodiment 27, wherein the $V_L$ region comprises a light chain complementarity determining region 3 (CDR-L3) comprising the amino acid sequence $X_1X_2X_3X_4X_5X_6X_7X_8X_9X_{10}X_{11}X_{12}$, (SEQ ID NO:358), wherein $X_1$ is A, C, G, H, I, Q or S; $X_2$ is A, Q, S or V; $X_3$ is 5, W or Y; $X_4$ is D, F, G, H or Y; $X_5$ is D, G, M, R, S or T; $X_6$ is A, G, H, L, R, S, T or Y; $X_7$ is L, P, R, S or null; $X_8$ is D, G, N, R, S, T or null; $X_9$ is A, G, H, L, P or null; $X_{10}$ is F, S or null; $X_{11}$ is L, P, W or Y; and $X_{12}$ is S, T or V.

29. The antibody of antigen-binding fragment of any one of embodiments 26-28, wherein the $V_L$ region comprises a light chain complementarity determining region 3 (CDR-L3) comprising the amino acid sequence selected from any one of SEQ ID NOs:47-58, 184-194, 415-427 and 429-433, or a CDR-L3 contained within the $V_L$ region amino acid sequence selected from any one of SEQ ID NOs:116-127, 257-267, 534-550 and 552-557.

30. The antibody or antigen-binding fragment of any one of embodiments 26-29, wherein the $V_L$ region comprises:
a light chain complementarity determining region 1 (CDR-L1) comprising the amino acid sequence $X_1X_2X_3X_4X_5X_6X_7X_8X_9X_{10}X_{11}X_{12}X_{13}X_{14}X_{15}X_{16}X_{17}$ (SEQ ID NO:356), wherein $X_1$ is G, K, R, S or T; $X_2$ is A, G or S; $X_3$ is G, N, S or T; $X_4$ is G, K, N, Q, R or S; $X_5$ is S or null; $X_6$ is D, N, V or null; $X_7$ is L, V or null; $X_8$ is H, S, Y or null; $X_9$ is S, T or null; $X_{10}$ is S or null; $X_{11}$ is D, G, I, N, S or null; $X_{12}$ is D, E, G, K, I, N or null; $X_{13}$ is F, G, K, N, R, S, Y or null; $X_{14}$ is D, K, N, T or null; $X_{15}$ is A, D, G, L, N, S, T or Y; $X_{16}$ is L or V; $X_{17}$ is A, H, N, Q or S; and/or
a light chain complementarity determining region 2 (CDR-L2) comprising the amino acid sequence $X_1X_2X_3X_4X_5X_6X_7$ (SEQ ID NO:357), wherein $X_1$ is A, D, E, N, S, V or W; $X_2$ is A, D, N, S or V; $X_3$ is A, D, H, I, N or S; $X_4$ is D, K, N, Q, R or T; $X_5$ is L, R or V; $X_6$ is A, E, P or Q; and $X_7$ is A, D, S or T.

31. The antibody or antigen-binding fragment of any one of embodiments 26-30, wherein the $V_L$ region comprises:
a light chain complementarity determining region 1 (CDR-L1) comprising the amino acid sequence selected from any one of SEQ ID NOs:26-36, 174-178, 380-392 and 394-398; and/or
a light chain complementarity determining region 2 (CDR-L2) comprising the amino acid sequence selected from any one of SEQ ID NOs:37-46, 179-183, 399-409 and 411-414.

32. The antibody or antigen-binding fragment of any one of embodiments 26-31, wherein the $V_L$ region comprises:
a CDR-L1 contained within the $V_L$ region amino acid sequence selected from any one of SEQ ID NOs:116-127, 257-267, 534-550 and 552-557; and/or
a CDR-L2 contained within the $V_L$ region amino acid sequence selected from any one of SEQ ID NOs:116-127, 257-267, 534-550 and 552-557.

33. The antibody or antigen-binding fragment of any one of embodiments 26-32, wherein the $V_L$ region comprises:
a CDR-L1 comprising the amino acid sequence selected from any one of SEQ ID NOs:26-36, 174-178, 380-392 and 394-398;
a CDR-L2 comprising the amino acid sequence selected from any one of SEQ ID NOs:37-46, 179-183, 399-409 and 411-414; and/or
a CDR-L3 comprising the amino acid sequence selected from any one of SEQ ID NOs:47-58, 184-194, 415-427 and 429-433.

34. The antibody or antigen-binding fragment of embodiment 33, wherein the $V_L$ region comprises:
a CDR-L1 comprising the amino acid sequence selected from any one of SEQ ID NOs: 26-28, 30, 31, 33, 34, 174, 176-178 and 380-382;
a CDR-L2 comprising the amino acid sequence selected from any one of SEQ ID NOs: 37-39, 41, 43, 44, 179, 181-183 and 399-401; and/or
a CDR-L3 comprising the amino acid sequence selected from any one of SEQ ID NOs: 47-49, 51, 52, 55, 56, 185, 189-194, 415-418 and 421.

35. The antibody or antigen-binding fragment of embodiment 33 or embodiment 34, wherein the $V_L$ region comprises:
a CDR-L1 comprising the amino acid sequence selected from any one of SEQ ID NOs: 33 and 178;
a CDR-L2 comprising the amino acid sequence selected from any one of SEQ ID NOs: 43 and 183; and/or
a CDR-L3 comprising the amino acid sequence selected from any one of SEQ ID NOs: 194 and 421.

36. The antibody or antigen-binding fragment of any one of embodiments 26-33, wherein the $V_L$ region comprises a CDR-L1, CDR-L2, and CDR-L3 selected from:
a CDR-L1, CDR-L2, and CDR-L3 comprising the amino acid sequence of SEQ ID NOs:26, 37, and 47, respectively;
a CDR-L1, CDR-L2, and CDR-L3 comprising the amino acid sequence of SEQ ID NOs:27, 38, and 48, respectively;
a CDR-L1, CDR-L2, and CDR-L3 comprising the amino acid sequence of SEQ ID NOs:28, 39, and 49, respectively;
a CDR-L1, CDR-L2, and CDR-L3 comprising the amino acid sequence of SEQ ID NOs:29, 40, and 50, respectively;
a CDR-L1, CDR-L2, and CDR-L3 comprising the amino acid sequence of SEQ ID NOs:30, 39, and 51, respectively;
a CDR-L1, CDR-L2, and CDR-L3 comprising the amino acid sequence of SEQ ID NOs:31, 41, and 52, respectively;
a CDR-L1, CDR-L2, and CDR-L3 comprising the amino acid sequence of SEQ ID NOs:32, 42, and 53, respectively;
a CDR-L1, CDR-L2, and CDR-L3 comprising the amino acid sequence of SEQ ID NOs:30, 39, and 54, respectively;
a CDR-L1, CDR-L2, and CDR-L3 comprising the amino acid sequence of SEQ ID NOs:33, 43, and 55, respectively;
a CDR-L1, CDR-L2, and CDR-L3 comprising the amino acid sequence of SEQ ID NOs:34, 44, and 56, respectively;
a CDR-L1, CDR-L2, and CDR-L3 comprising the amino acid sequence of SEQ ID NOs:35, 45, and 57, respectively;
a CDR-L1, CDR-L2, and CDR-L3 comprising the amino acid sequence of SEQ ID NOs:36, 46, and 58, respectively;
a CDR-L1, CDR-L2, and CDR-L3 comprising the amino acid sequence of SEQ ID NOs:174, 179, and 184, respectively;
a CDR-L1, CDR-L2, and CDR-L3 comprising the amino acid sequence of SEQ ID NOs:174, 179, and 185, respectively;

a CDR-L1, CDR-L2, and CDR-L3 comprising the amino acid sequence of SEQ ID NOs:174, 179, and 186, respectively;
a CDR-L1, CDR-L2, and CDR-L3 comprising the amino acid sequence of SEQ ID NOs:174, 179, and 187, respectively;
a CDR-L1, CDR-L2, and CDR-L3 comprising the amino acid sequence of SEQ ID NOs:175, 180, and 188, respectively;
a CDR-L1, CDR-L2, and CDR-L3 comprising the amino acid sequence of SEQ ID NOs:174, 179, and 189, respectively;
a CDR-L1, CDR-L2, and CDR-L3 comprising the amino acid sequence of SEQ ID NOs:176, 181, and 190, respectively;
a CDR-L1, CDR-L2, and CDR-L3 comprising the amino acid sequence of SEQ ID NOs:177, 182, and 191, respectively;
a CDR-L1, CDR-L2, and CDR-L3 comprising the amino acid sequence of SEQ ID NOs:174, 179, and 192, respectively;
a CDR-L1, CDR-L2, and CDR-L3 comprising the amino acid sequence of SEQ ID NOs:178, 183, and 193, respectively;
a CDR-L1, CDR-L2, and CDR-L3 comprising the amino acid sequence of SEQ ID NOs:178, 183, and 194, respectively;
a CDR-L1, CDR-L2, and CDR-L3 comprising the amino acid sequence of SEQ ID NOs:30, 399, and 415, respectively;
a CDR-L1, CDR-L2, and CDR-L3 comprising the amino acid sequence of SEQ ID NOs:380, 400, and 416, respectively;
a CDR-L1, CDR-L2, and CDR-L3 comprising the amino acid sequence of SEQ ID NOs:33, 43, and 421, respectively;
a CDR-L1, CDR-L2, and CDR-L3 comprising the amino acid sequence of SEQ ID NOs:381, 401, and 417, respectively;
a CDR-L1, CDR-L2, and CDR-L3 comprising the amino acid sequence of SEQ ID NOs:382, 402, and 418, respectively;
a CDR-L1, CDR-L2, and CDR-L3 comprising the amino acid sequence of SEQ ID NOs:383, 403, and 419, respectively;
a CDR-L1, CDR-L2, and CDR-L3 comprising the amino acid sequence of SEQ ID NOs:384, 39, and 54, respectively;
a CDR-L1, CDR-L2, and CDR-L3 comprising the amino acid sequence of SEQ ID NOs:385, 180, and 58, respectively;
a CDR-L1, CDR-L2, and CDR-L3 comprising the amino acid sequence of SEQ ID NOs:175, 180, and 188, respectively;
a CDR-L1, CDR-L2, and CDR-L3 comprising the amino acid sequence of SEQ ID NOs:386, 404, and 420, respectively;
a CDR-L1, CDR-L2, and CDR-L3 comprising the amino acid sequence of SEQ ID NOs:387, 405, and 422, respectively;
a CDR-L1, CDR-L2, and CDR-L3 comprising the amino acid sequence of SEQ ID NOs:388, 406, and 423, respectively;
a CDR-L1, CDR-L2, and CDR-L3 comprising the amino acid sequence of SEQ ID NOs:388, 407, and 424, respectively;
a CDR-L1, CDR-L2, and CDR-L3 comprising the amino acid sequence of SEQ ID NOs:389, 408, and 425, respectively;
a CDR-L1, CDR-L2, and CDR-L3 comprising the amino acid sequence of SEQ ID NOs:390, 183, and 193, respectively;
a CDR-L1, CDR-L2, and CDR-L3 comprising the amino acid sequence of SEQ ID NOs:391, 409, and 426, respectively;
a CDR-L1, CDR-L2, and CDR-L3 comprising the amino acid sequence of SEQ ID NOs:392, 40, and 427, respectively;
a CDR-L1, CDR-L2, and CDR-L3 comprising the amino acid sequence of SEQ ID NOs:394, 39, and 429, respectively;
a CDR-L1, CDR-L2, and CDR-L3 comprising the amino acid sequence of SEQ ID NOs:395, 411, and 430, respectively;
a CDR-L1, CDR-L2, and CDR-L3 comprising the amino acid sequence of SEQ ID NOs:396, 412, and 431, respectively;
a CDR-L1, CDR-L2, and CDR-L3 comprising the amino acid sequence of SEQ ID NOs:396, 412, and 58, respectively;
a CDR-L1, CDR-L2, and CDR-L3 comprising the amino acid sequence of SEQ ID NOs:397, 413, and 432, respectively; or a CDR-L1, CDR-L2, and CDR-L3 comprising the amino acid sequence of SEQ ID NOs:398, 414, and 433, respectively.

37. The antibody or antigen-binding fragment of embodiment 36, wherein the CDR-L1, CDR-L2, and CDR-L3 are selected from:
a CDR-L1, CDR-L2, and CDR-L3 comprising the amino acid sequence of SEQ ID NOs:26, 37, and 47, respectively;
a CDR-L1, CDR-L2, and CDR-L3 comprising the amino acid sequence of SEQ ID NOs:27, 38, and 48, respectively;
a CDR-L1, CDR-L2, and CDR-L3 comprising the amino acid sequence of SEQ ID NOs:28, 39, and 49, respectively;
a CDR-L1, CDR-L2, and CDR-L3 comprising the amino acid sequence of SEQ ID NOs:29, 40, and 50, respectively;
a CDR-L1, CDR-L2, and CDR-L3 comprising the amino acid sequence of SEQ ID NOs:30, 39, and 51, respectively;
a CDR-L1, CDR-L2, and CDR-L3 comprising the amino acid sequence of SEQ ID NOs:31, 41, and 52, respectively;
a CDR-L1, CDR-L2, and CDR-L3 comprising the amino acid sequence of SEQ ID NOs:32, 42, and 53, respectively;
a CDR-L1, CDR-L2, and CDR-L3 comprising the amino acid sequence of SEQ ID NOs:30, 39, and 54, respectively;
a CDR-L1, CDR-L2, and CDR-L3 comprising the amino acid sequence of SEQ ID NOs:33, 43, and 55, respectively;
a CDR-L1, CDR-L2, and CDR-L3 comprising the amino acid sequence of SEQ ID NOs:34, 44, and 56, respectively;
a CDR-L1, CDR-L2, and CDR-L3 comprising the amino acid sequence of SEQ ID NOs:35, 45, and 57, respectively;
a CDR-L1, CDR-L2, and CDR-L3 comprising the amino acid sequence of SEQ ID NOs:36, 46, and 58, respectively;
a CDR-L1, CDR-L2, and CDR-L3 comprising the amino acid sequence of SEQ ID NOs:174, 179, and 184, respectively;
a CDR-L1, CDR-L2, and CDR-L3 comprising the amino acid sequence of SEQ ID NOs:174, 179, and 185, respectively;
a CDR-L1, CDR-L2, and CDR-L3 comprising the amino acid sequence of SEQ ID NOs:174, 179, and 186, respectively;
a CDR-L1, CDR-L2, and CDR-L3 comprising the amino acid sequence of SEQ ID NOs:174, 179, and 187, respectively;

a CDR-L1, CDR-L2, and CDR-L3 comprising the amino acid sequence of SEQ ID NOs:175, 180, and 188, respectively;
a CDR-L1, CDR-L2, and CDR-L3 comprising the amino acid sequence of SEQ ID NOs:174, 179, and 189, respectively;
a CDR-L1, CDR-L2, and CDR-L3 comprising the amino acid sequence of SEQ ID NOs:176, 181, and 190, respectively;
a CDR-L1, CDR-L2, and CDR-L3 comprising the amino acid sequence of SEQ ID NOs:177, 182, and 191, respectively;
a CDR-L1, CDR-L2, and CDR-L3 comprising the amino acid sequence of SEQ ID NOs:174, 179, and 192, respectively;
a CDR-L1, CDR-L2, and CDR-L3 comprising the amino acid sequence of SEQ ID NOs:178, 183, and 193, respectively;
a CDR-L1, CDR-L2, and CDR-L3 comprising the amino acid sequence of SEQ ID NOs:178, 183, and 194, respectively;
a CDR-L1, CDR-L2, and CDR-L3 comprising the amino acid sequence of SEQ ID NOs:30, 399, and 415, respectively;
a CDR-L1, CDR-L2, and CDR-L3 comprising the amino acid sequence of SEQ ID NOs:380, 400, and 416, respectively;
a CDR-L1, CDR-L2, and CDR-L3 comprising the amino acid sequence of SEQ ID NOs:33, 43, and 421, respectively;
a CDR-L1, CDR-L2, and CDR-L3 comprising the amino acid sequence of SEQ ID NOs:381, 401, and 417, respectively;
a CDR-L1, CDR-L2, and CDR-L3 comprising the amino acid sequence of SEQ ID NOs:382, 402, and 418, respectively;
a CDR-L1, CDR-L2, and CDR-L3 comprising the amino acid sequence of SEQ ID NOs:383, 403, and 419, respectively;
a CDR-L1, CDR-L2, and CDR-L3 comprising the amino acid sequence of SEQ ID NOs:384, 39, and 54, respectively;
a CDR-L1, CDR-L2, and CDR-L3 comprising the amino acid sequence of SEQ ID NOs:385, 180, and 58, respectively;
a CDR-L1, CDR-L2, and CDR-L3 comprising the amino acid sequence of SEQ ID NOs:175, 180, and 188, respectively;
a CDR-L1, CDR-L2, and CDR-L3 comprising the amino acid sequence of SEQ ID NOs:386, 404, and 420, respectively;
a CDR-L1, CDR-L2, and CDR-L3 comprising the amino acid sequence of SEQ ID NOs:387, 405, and 422, respectively;
a CDR-L1, CDR-L2, and CDR-L3 comprising the amino acid sequence of SEQ ID NOs:388, 406, and 423, respectively;
a CDR-L1, CDR-L2, and CDR-L3 comprising the amino acid sequence of SEQ ID NOs:388, 407, and 424, respectively;
a CDR-L1, CDR-L2, and CDR-L3 comprising the amino acid sequence of SEQ ID NOs:389, 408, and 425, respectively;
a CDR-L1, CDR-L2, and CDR-L3 comprising the amino acid sequence of SEQ ID NOs:390, 183, and 193, respectively;
a CDR-L1, CDR-L2, and CDR-L3 comprising the amino acid sequence of SEQ ID NOs:391, 409, and 426, respectively;
a CDR-L1, CDR-L2, and CDR-L3 comprising the amino acid sequence of SEQ ID NOs:392, 40, and 427, respectively;
a CDR-L1, CDR-L2, and CDR-L3 comprising the amino acid sequence of SEQ ID NOs:394, 39, and 429, respectively;
a CDR-L1, CDR-L2, and CDR-L3 comprising the amino acid sequence of SEQ ID NOs:395, 411, and 430, respectively;
a CDR-L1, CDR-L2, and CDR-L3 comprising the amino acid sequence of SEQ ID NOs:396, 412, and 431, respectively;
a CDR-L1, CDR-L2, and CDR-L3 comprising the amino acid sequence of SEQ ID NOs:396, 412, and 58, respectively;
a CDR-L1, CDR-L2, and CDR-L3 comprising the amino acid sequence of SEQ ID NOs:397, 413, and 432, respectively; or a CDR-L1, CDR-L2, and CDR-L3 comprising the amino acid sequence of SEQ ID NOs:398, 414, and 433, respectively.

38. The antibody or antigen-binding fragment of embodiment 36 or embodiment 37, wherein the CDR-L1, CDR-L2, and CDR-L3 are selected from:
a CDR-L1, CDR-L2, and CDR-L3 comprising the amino acid sequence of SEQ ID NOs: 178, 183, and 194, respectively; or a CDR-L1, CDR-L2, and CDR-L3 comprising the amino acid sequence of SEQ ID NOs: 33, 43, and 421, respectively.

39. The antibody or antigen-binding fragment of any one of embodiments 26-36, said antibody or antigen-binding fragment comprises a $V_L$ region comprising a CDR-L1, a CDR-L2, and a CDR-L3, respectively, comprising the amino acid sequence of a CDR-L1, a CDR-L2, and a CDR-L3 contained within the $V_L$ region amino acid sequence selected from any one of SEQ ID NOs:116-127, 257-267, 534-550 and 552-557.

40. The antibody or antigen-binding fragment thereof of embodiment 39, wherein the CDR-L1, the CDR-L2, and the CDR-L3, respectively, comprise the amino acid sequence of a CDR-L1, a CDR-L2, and a CDR-L3 contained within the $V_L$ region amino acid sequence selected from any one of SEQ ID NOs: 116-118, 120, 121, 124, 125, 258, 262-267 and 534-538.

41. The antibody or antigen-binding fragment thereof of embodiment 39 or embodiment 40, wherein the CDR-L1, the CDR-L2, and the CDR-L3, respectively, comprise the amino acid sequence of a CDR-L1, a CDR-L2, and a CDR-L3 contained within the $V_L$ region amino acid sequence selected from any one of SEQ ID NOs: 267 and 536.

42. The antibody or antigen-binding fragment of any one of embodiments 26-39, wherein the $V_L$ region comprises a framework region 1 (FR1), a FR2, a FR3, and/or a FR4 having at least 90%, 91%, 92%, 93%, 94%, 95%, 96%, 97%, 98%, or 99% sequence identity, respectively, to a FR1, FR2, FR3, and/or FR4 contained within the $V_L$ region amino acid sequence selected from any one of SEQ ID NOs:116-127, 257-267, 534-550 and 552-557.

43. The antibody or antigen-binding fragment of any one of embodiments 26-42, wherein the $V_H$ region comprises a FR1, a FR2, a FR3, and/or a FR4, selected from:
a FR1 comprising the amino acid sequence selected from any one of SEQ ID NOs:72-82, 221-227, 446-459 and 461-466;
a FR2 comprising the amino acid sequence selected from any one of SEQ ID NOs:83-92, 228-232, 467-477 and 479-482;

a FR3 comprising the amino acid sequence selected from any one of SEQ ID NOs:93-101, 233-242, 483-495 and 497-501; and/or a FR4 comprising the amino acid sequence selected from any one of SEQ ID NOs:102-109, 243-246, 502-506 and 508.

44. The antibody or antigen-binding fragment of any one of embodiments 26-43, wherein the $V_L$ region comprises the amino acid sequence selected from any one of SEQ ID NOs:116-127, 257-267, 534-550 and 552-557.

45. The antibody or antigen-binding fragment thereof of embodiment 44, wherein the $V_L$ region comprises the amino acid sequence selected from any one of SEQ ID NOs: 116-118, 120, 121, 124, 125, 258, 262-267 and 534-538.

46. The antibody or antigen-binding fragment thereof of embodiment 44 or embodiment 45, wherein the $V_L$ region comprises the amino acid sequence selected from any one of SEQ ID NOs:267 and 536.

47. An antibody or antigen-binding fragment thereof, comprising:

a heavy chain complementarity determining region 1 (CDR-H1), CDR-H2, and CDR-H3, respectively, comprising the amino acid sequences of CDR-H1, CDR-H2, and CDR-H3 contained within the $V_H$ region amino acid sequence selected from any one of SEQ ID NOs:110-115, 247-256, 518-531 and 533; and/or a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence selected from any one of SEQ ID NOs:116-127, 257-267, 534-550 and 552-557.

48. The antibody or antigen-binding fragment thereof of embodiment 47, wherein the CDR-H1, CDR-H2, and CDR-H3, respectively, comprise the amino acid sequences of CDR-H1, CDR-H2, and CDR-H3 contained within the $V_H$ region amino acid sequence selected from any one of SEQ ID NOs: 110-113, 115, 248, 252-256 and 518-522; and/or a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence selected from any one of SEQ ID NOs: 116-118, 120, 121, 124, 125, 258, 262-267 and 534-538.

49. The antibody or antigen-binding fragment thereof of embodiment 47 or embodiment 48, wherein the CDR-H1, CDR-H2, and CDR-H3, respectively, comprise the amino acid sequences of CDR-H1, CDR-H2, and CDR-H3 contained within the $V_H$ region amino acid sequence selected from any one of SEQ ID NOs: 115 and 256; and/or a light chain complementarity determining region 1 (CDR-L1), CDR-L2, and CDR-L3, respectively, comprising the amino acid sequences of CDR-L1, CDR-L2, and CDR-L3 contained within the $V_L$ region amino acid sequence selected from any one of SEQ ID NOs: 267 and 536.

50. An antibody or antigen-binding fragment thereof, comprising:

a $V_H$ region and a $V_L$ regions comprising the amino acid sequence having at least 90% identity to SEQ ID NOs:110 and 116, respectively;

a $V_H$ region and a $V_L$ regions comprising the amino acid sequence having at least 90% identity to SEQ ID NOs:111 and 117, respectively;

a $V_H$ region and a $V_L$ regions comprising the amino acid sequence having at least 90% identity to SEQ ID NOs:110 and 118, respectively;

a $V_H$ region and a $V_L$ regions comprising the amino acid sequence having at least 90% identity to SEQ ID NOs:110 and 119, respectively;

a $V_H$ region and a $V_L$ regions comprising the amino acid sequence having at least 90% identity to SEQ ID NOs:110 and 120, respectively;

a $V_H$ region and a $V_L$ regions comprising the amino acid sequence having at least 90% identity to SEQ ID NOs:110 and 121, respectively;

a $V_H$ region and a $V_L$ regions comprising the amino acid sequence having at least 90% identity to SEQ ID NOs:110 and 122, respectively;

a $V_H$ region and a $V_L$ regions comprising the amino acid sequence having at least 90% identity to SEQ ID NOs:110 and 123, respectively;

a $V_H$ region and a $V_L$ regions comprising the amino acid sequence having at least 90% identity to SEQ ID NOs:112 and 124, respectively;

a $V_H$ region and a $V_L$ regions comprising the amino acid sequence having at least 90% identity to SEQ ID NOs:113 and 125, respectively;

a $V_H$ region and a $V_L$ regions comprising the amino acid sequence having at least 90% identity to SEQ ID NOs:114 and 126, respectively;

a $V_H$ region and a $V_L$ regions comprising the amino acid sequence having at least 90% identity to SEQ ID NOs:115 and 127, respectively;

a $V_H$ region and a $V_L$ regions comprising the amino acid sequence having at least 90% identity to SEQ ID NOs:247 and 257, respectively;

a $V_H$ region and a $V_L$ regions comprising the amino acid sequence having at least 90% identity to SEQ ID NOs:248 and 258, respectively;

a $V_H$ region and a $V_L$ regions comprising the amino acid sequence having at least 90% identity to SEQ ID NOs:249 and 259, respectively;

a $V_H$ region and a $V_L$ regions comprising the amino acid sequence having at least 90% identity to SEQ ID NOs:250 and 260, respectively;

a $V_H$ region and a $V_L$ regions comprising the amino acid sequence having at least 90% identity to SEQ ID NOs:251 and 261, respectively;

a $V_H$ region and a $V_L$ regions comprising the amino acid sequence having at least 90% identity to SEQ ID NOs:252 and 262, respectively;

a $V_H$ region and a $V_L$ regions comprising the amino acid sequence having at least 90% identity to SEQ ID NOs:253 and 263, respectively;

a $V_H$ region and a $V_L$ regions comprising the amino acid sequence having at least 90% identity to SEQ ID NOs:254 and 264, respectively;

a $V_H$ region and a $V_L$ regions comprising the amino acid sequence having at least 90% identity to SEQ ID NOs:255 and 265, respectively;

a $V_H$ region and a $V_L$ regions comprising the amino acid sequence having at least 90% identity to SEQ ID NOs:256 and 266, respectively;

a $V_H$ region and a $V_L$ regions comprising the amino acid sequence having at least 90% identity to SEQ ID NOs:256 and 267, respectively;

a $V_H$ region and a $V_L$ regions comprising the amino acid sequence having at least 90% identity to SEQ ID NOs:518 and 534, respectively;

a $V_H$ region and a $V_L$ regions comprising the amino acid sequence having at least 90% identity to SEQ ID NOs:519 and 535, respectively;

a $V_H$ region and a $V_L$ regions comprising the amino acid sequence having at least 90% identity to SEQ ID NOs:115 and 536, respectively;

a $V_H$ region and a $V_L$ regions comprising the amino acid sequence having at least 90% identity to SEQ ID NOs:520 and 264, respectively;

a $V_H$ region and a $V_L$ regions comprising the amino acid sequence having at least 90% identity to SEQ ID NOs:521 and 537, respectively;

a $V_H$ region and a $V_L$ regions comprising the amino acid sequence having at least 90% identity to SEQ ID NOs:522 and 538, respectively;

a $V_H$ region and a $V_L$ regions comprising the amino acid sequence having at least 90% identity to SEQ ID NOs:523 and 539, respectively;

a $V_H$ region and a $V_L$ regions comprising the amino acid sequence having at least 90% identity to SEQ ID NOs:519 and 540, respectively;

a $V_H$ region and a $V_L$ regions comprising the amino acid sequence having at least 90% identity to SEQ ID NOs:524 and 541, respectively;

a $V_H$ region and a $V_L$ regions comprising the amino acid sequence having at least 90% identity to SEQ ID NOs:525 and 261, respectively;

a $V_H$ region and a $V_L$ regions comprising the amino acid sequence having at least 90% identity to SEQ ID NOs:526 and 542, respectively;

a $V_H$ region and a $V_L$ regions comprising the amino acid sequence having at least 90% identity to SEQ ID NOs:527 and 543, respectively;

a $V_H$ region and a $V_L$ regions comprising the amino acid sequence having at least 90% identity to SEQ ID NOs:528 and 544, respectively;

a $V_H$ region and a $V_L$ regions comprising the amino acid sequence having at least 90% identity to SEQ ID NOs:529 and 545, respectively;

a $V_H$ region and a $V_L$ regions comprising the amino acid sequence having at least 90% identity to SEQ ID NOs:528 and 546, respectively;

a $V_H$ region and a $V_L$ regions comprising the amino acid sequence having at least 90% identity to SEQ ID NOs:522 and 547, respectively;

a $V_H$ region and a $V_L$ regions comprising the amino acid sequence having at least 90% identity to SEQ ID NOs:256 and 548, respectively;

a $V_H$ region and a $V_L$ regions comprising the amino acid sequence having at least 90% identity to SEQ ID NOs:530 and 549, respectively;

a $V_H$ region and a $V_L$ regions comprising the amino acid sequence having at least 90% identity to SEQ ID NOs:531 and 550, respectively;

a $V_H$ region and a $V_L$ regions comprising the amino acid sequence having at least 90% identity to SEQ ID NOs:519 and 552, respectively;

a $V_H$ region and a $V_L$ regions comprising the amino acid sequence having at least 90% identity to SEQ ID NOs:110 and 553, respectively;

a $V_H$ region and a $V_L$ regions comprising the amino acid sequence having at least 90% identity to SEQ ID NOs:110 and 118, respectively;

a $V_H$ region and a $V_L$ regions comprising the amino acid sequence having at least 90% identity to SEQ ID NOs:533 and 554, respectively;

a $V_H$ region and a $V_L$ regions comprising the amino acid sequence having at least 90% identity to SEQ ID NOs:115 and 555, respectively;

a $V_H$ region and a $V_L$ regions comprising the amino acid sequence having at least 90% identity to SEQ ID NOs:524 and 556, respectively; or a $V_H$ region and a $V_L$ regions comprising the amino acid sequence having at least 90% identity to SEQ ID NOs:519 and 557, respectively.

51. The antibody or antigen-binding fragment thereof of embodiment 50, comprising: a $V_H$ region and a $V_L$ regions comprising the amino acid sequence having at least 90% identity to SEQ ID NOS:110 and 116, respectively;

a $V_H$ region and a $V_L$ regions comprising the amino acid sequence having at least 90% identity to SEQ ID NOs:111 and 117, respectively;

a $V_H$ region and a $V_L$ regions comprising the amino acid sequence having at least 90% identity to SEQ ID NOs:110 and 118, respectively;

a $V_H$ region and a $V_L$ regions comprising the amino acid sequence having at least 90% identity to SEQ ID NOs:110 and 120, respectively;

a $V_H$ region and a $V_L$ regions comprising the amino acid sequence having at least 90% identity to SEQ ID NOs:110 and 121, respectively;

a $V_H$ region and a $V_L$ regions comprising the amino acid sequence having at least 90% identity to SEQ ID NOs:112 and 124, respectively;

a $V_H$ region and a $V_L$ regions comprising the amino acid sequence having at least 90% identity to SEQ ID NOs:113 and 125, respectively;

a $V_H$ region and a $V_L$ regions comprising the amino acid sequence having at least 90% identity to SEQ ID NOs:248 and 258, respectively;

a $V_H$ region and a $V_L$ regions comprising the amino acid sequence having at least 90% identity to SEQ ID NOs:252 and 262, respectively;

a $V_H$ region and a $V_L$ regions comprising the amino acid sequence having at least 90% identity to SEQ ID NOs:253 and 263, respectively;

a $V_H$ region and a $V_L$ regions comprising the amino acid sequence having at least 90% identity to SEQ ID NOs:254 and 264, respectively;

a $V_H$ region and a $V_L$ regions comprising the amino acid sequence having at least 90% identity to SEQ ID NOs:255 and 265, respectively;

a $V_H$ region and a $V_L$ regions comprising the amino acid sequence having at least 90% identity to SEQ ID NOs:256 and 266, respectively;

a $V_H$ region and a $V_L$ regions comprising the amino acid sequence having at least 90% identity to SEQ ID NOs:256 and 267, respectively;

a $V_H$ region and a $V_L$ regions comprising the amino acid sequence having at least 90% identity to SEQ ID NOs:518 and 534, respectively;

a $V_H$ region and a $V_L$ regions comprising the amino acid sequence having at least 90% identity to SEQ ID NOs:519 and 535, respectively;

a $V_H$ region and a $V_L$ regions comprising the amino acid sequence having at least 90% identity to SEQ ID NOs:115 and 536, respectively;

a $V_H$ region and a $V_L$ regions comprising the amino acid sequence having at least 90% identity to SEQ ID NOs:520 and 264, respectively;

a $V_H$ region and a $V_L$ regions comprising the amino acid sequence having at least 90% identity to SEQ ID NOs:521 and 537, respectively; or a $V_H$ region and a $V_L$ regions comprising the amino acid sequence having at least 90% identity to and SEQ ID NOs:522 and 538, respectively.

52. The antibody or antigen-binding fragment thereof of embodiment 50 or embodiment 51, comprising:

a $V_H$ region and a $V_L$ regions comprising the amino acid sequence having at least 90% identity to SEQ ID NOS:256 and 267, respectively;

a $V_H$ region and a $V_L$ regions comprising the amino acid sequence having at least 90% identity to SEQ ID NOs:115 and 536, respectively;

53. The antibody or antigen-binding fragment of embodiment 50, comprising a $V_H$ region sequence that is at least at or about 91%, 92%, 93%, 94%, 95%, 96%, 97%, 98%, or 99% identical to such a SEQ ID NO and/or a $V_L$ region sequence that is at least at or about 91%, 92%, 93%, 94%, 95%, 96%, 97%, 98%, or 99% identical to such a SEQ ID NO.

54. The antibody or antigen-binding fragment of embodiment 50 or embodiment 53, wherein:

the $V_H$ and $V_L$ regions of the antibody or antigen-binding fragment thereof comprise the amino acid sequences of SEQ ID NOs:110 and 116, respectively;

the $V_H$ and $V_L$ regions of the antibody or antigen-binding fragment thereof comprise the amino acid sequences of SEQ ID NOs:111 and 117, respectively;

the $V_H$ and $V_L$ regions of the antibody or antigen-binding fragment thereof comprise the amino acid sequences of SEQ ID NOs:110 and 118, respectively;

the $V_H$ and $V_L$ regions of the antibody or antigen-binding fragment thereof comprise the amino acid sequences of SEQ ID NOs:110 and 119, respectively;

the $V_H$ and $V_L$ regions of the antibody or antigen-binding fragment thereof comprise the amino acid sequences of SEQ ID NOs:110 and 120, respectively;

the $V_H$ and $V_L$ regions of the antibody or antigen-binding fragment thereof comprise the amino acid sequences of SEQ ID NOs:110 and 121, respectively;

the $V_H$ and $V_L$ regions of the antibody or antigen-binding fragment thereof comprise the amino acid sequences of SEQ ID NOs:110 and 122, respectively;

the $V_H$ and $V_L$ regions of the antibody or antigen-binding fragment thereof comprise the amino acid sequences of SEQ ID NOs:110 and 123, respectively;

the $V_H$ and $V_L$ regions of the antibody or antigen-binding fragment thereof comprise the amino acid sequences of SEQ ID NOs:112 and 124, respectively;

the $V_H$ and $V_L$ regions of the antibody or antigen-binding fragment thereof comprise the amino acid sequences of SEQ ID NOs:113 and 125, respectively;

the $V_H$ and $V_L$ regions of the antibody or antigen-binding fragment thereof comprise the amino acid sequences of SEQ ID NOs:114 and 126, respectively;

the $V_H$ and $V_L$ regions of the antibody or antigen-binding fragment thereof comprise the amino acid sequences of SEQ ID NOs:115 and 127, respectively;

the $V_H$ and $V_L$ regions of the antibody or antigen-binding fragment thereof comprise the amino acid sequences of SEQ ID NOs:247 and 257, respectively;

the $V_H$ and $V_L$ regions of the antibody or antigen-binding fragment thereof comprise the amino acid sequences of SEQ ID NOs:248 and 258, respectively;

the $V_H$ and $V_L$ regions of the antibody or antigen-binding fragment thereof comprise the amino acid sequences of SEQ ID NOs:249 and 259, respectively;

the $V_H$ and $V_L$ regions of the antibody or antigen-binding fragment thereof comprise the amino acid sequences of SEQ ID NOs:250 and 260, respectively;

the $V_H$ and $V_L$ regions of the antibody or antigen-binding fragment thereof comprise the amino acid sequences of SEQ ID NOs:251 and 261, respectively;

the $V_H$ and $V_L$ regions of the antibody or antigen-binding fragment thereof comprise the amino acid sequences of SEQ ID NOs:252 and 262, respectively;

the $V_H$ and $V_L$ regions of the antibody or antigen-binding fragment thereof comprise the amino acid sequences of SEQ ID NOs:253 and 263, respectively;

the $V_H$ and $V_L$ regions of the antibody or antigen-binding fragment thereof comprise the amino acid sequences of SEQ ID NOs:254 and 264, respectively;

the $V_H$ and $V_L$ regions of the antibody or antigen-binding fragment thereof comprise the amino acid sequences of SEQ ID NOs:255 and 265, respectively;

the $V_H$ and $V_L$ regions of the antibody or antigen-binding fragment thereof comprise the amino acid sequences of SEQ ID NOs:256 and 266, respectively;

the $V_H$ and $V_L$ regions of the antibody or antigen-binding fragment thereof comprise the amino acid sequences of SEQ ID NOs:256 and 267, respectively;

the $V_H$ and $V_L$ regions of the antibody or antigen-binding fragment thereof comprise the amino acid sequences of SEQ ID NOs:518 and 534, respectively;

the $V_H$ and $V_L$ regions of the antibody or antigen-binding fragment thereof comprise the amino acid sequences of SEQ ID NOs:519 and 535, respectively;

the $V_H$ and $V_L$ regions of the antibody or antigen-binding fragment thereof comprise the amino acid sequences of SEQ ID NOs:115 and 536, respectively;

the $V_H$ and $V_L$ regions of the antibody or antigen-binding fragment thereof comprise the amino acid sequences of SEQ ID NOs:520 and 264, respectively;

the $V_H$ and $V_L$ regions of the antibody or antigen-binding fragment thereof comprise the amino acid sequences of SEQ ID NOs:521 and 537, respectively;

the $V_H$ and $V_L$ regions of the antibody or antigen-binding fragment thereof comprise the amino acid sequences of SEQ ID NOs:522 and 538, respectively;

the $V_H$ and $V_L$ regions of the antibody or antigen-binding fragment thereof comprise the amino acid sequences of SEQ ID NOs:523 and 539, respectively;

the $V_H$ and $V_L$ regions of the antibody or antigen-binding fragment thereof comprise the amino acid sequences of SEQ ID NOs:519 and 540, respectively;

the $V_H$ and $V_L$ regions of the antibody or antigen-binding fragment thereof comprise the amino acid sequences of SEQ ID NOs:524 and 541, respectively;

the $V_H$ and $V_L$ regions of the antibody or antigen-binding fragment thereof comprise the amino acid sequences of SEQ ID NOs:525 and 261, respectively;

the $V_H$ and $V_L$ regions of the antibody or antigen-binding fragment thereof comprise the amino acid sequences of SEQ ID NOs:526 and 542, respectively;

the $V_H$ and $V_L$ regions of the antibody or antigen-binding fragment thereof comprise the amino acid sequences of SEQ ID NOs:527 and 543, respectively;

the $V_H$ and $V_L$ regions of the antibody or antigen-binding fragment thereof comprise the amino acid sequences of SEQ ID NOs:528 and 544, respectively;

the $V_H$ and $V_L$ regions of the antibody or antigen-binding fragment thereof comprise the amino acid sequences of SEQ ID NOs:529 and 545, respectively;

the $V_H$ and $V_L$ regions of the antibody or antigen-binding fragment thereof comprise the amino acid sequences of SEQ ID NOs:528 and 546, respectively;

the $V_H$ and $V_L$ regions of the antibody or antigen-binding fragment thereof comprise the amino acid sequences of SEQ ID NOs:522 and 547, respectively;

the $V_H$ and $V_L$ regions of the antibody or antigen-binding fragment thereof comprise the amino acid sequences of SEQ ID NOs:256 and 548, respectively;

the $V_H$ and $V_L$ regions of the antibody or antigen-binding fragment thereof comprise the amino acid sequences of SEQ ID NOs:530 and 549, respectively;

the $V_H$ and $V_L$ regions of the antibody or antigen-binding fragment thereof comprise the amino acid sequences of SEQ ID NOs:531 and 550, respectively;

the $V_H$ and $V_L$ regions of the antibody or antigen-binding fragment thereof comprise the amino acid sequences of SEQ ID NOs:519 and 552, respectively;

the $V_H$ and $V_L$ regions of the antibody or antigen-binding fragment thereof comprise the amino acid sequences of SEQ ID NOs:110 and 553, respectively;

the $V_H$ and $V_L$ regions of the antibody or antigen-binding fragment thereof comprise the amino acid sequences of SEQ ID NOs:110 and 118, respectively;

the $V_H$ and $V_L$ regions of the antibody or antigen-binding fragment thereof comprise the amino acid sequences of SEQ ID NOs:533 and 554, respectively;

the $V_H$ and $V_L$ regions of the antibody or antigen-binding fragment thereof comprise the amino acid sequences of SEQ ID NOs:115 and 555, respectively;

the $V_H$ and $V_L$ regions of the antibody or antigen-binding fragment thereof comprise the amino acid sequences of SEQ ID NOs:524 and 556, respectively; or the $V_H$ and $V_L$ regions of the antibody or antigen-binding fragment thereof comprise the amino acid sequences of SEQ ID NOs:519 and 557, respectively.

55. The antibody or antigen-binding fragment thereof of embodiment 50, comprising: the $V_H$ and $V_L$ regions of the antibody or antigen-binding fragment thereof comprise the amino acid sequences of SEQ ID NOS:110 and 116, respectively;

the $V_H$ and $V_L$ regions of the antibody or antigen-binding fragment thereof comprise the amino acid sequences of SEQ ID NOs:111 and 117, respectively;

the $V_H$ and $V_L$ regions of the antibody or antigen-binding fragment thereof comprise the amino acid sequences of SEQ ID NOs:110 and 118, respectively;

the $V_H$ and $V_L$ regions of the antibody or antigen-binding fragment thereof comprise the amino acid sequences of SEQ ID NOs:110 and 120, respectively;

the $V_H$ and $V_L$ regions of the antibody or antigen-binding fragment thereof comprise the amino acid sequences of SEQ ID NOs:110 and 121, respectively;

the $V_H$ and $V_L$ regions of the antibody or antigen-binding fragment thereof comprise the amino acid sequences of SEQ ID NOs:112 and 124, respectively;

the $V_H$ and $V_L$ regions of the antibody or antigen-binding fragment thereof comprise the amino acid sequences of SEQ ID NOs:113 and 125, respectively;

the $V_H$ and $V_L$ regions of the antibody or antigen-binding fragment thereof comprise the amino acid sequences of SEQ ID NOs:248 and 258, respectively;

the $V_H$ and $V_L$ regions of the antibody or antigen-binding fragment thereof comprise the amino acid sequences of SEQ ID NOs:252 and 262, respectively;

the $V_H$ and $V_L$ regions of the antibody or antigen-binding fragment thereof comprise the amino acid sequences of SEQ ID NOs:253 and 263, respectively;

the $V_H$ and $V_L$ regions of the antibody or antigen-binding fragment thereof comprise the amino acid sequences of SEQ ID NOs:254 and 264, respectively;

the $V_H$ and $V_L$ regions of the antibody or antigen-binding fragment thereof comprise the amino acid sequences of SEQ ID NOs:255 and 265, respectively;

the $V_H$ and $V_L$ regions of the antibody or antigen-binding fragment thereof comprise the amino acid sequences of SEQ ID NOs:256 and 266, respectively;

the $V_H$ and $V_L$ regions of the antibody or antigen-binding fragment thereof comprise the amino acid sequences of SEQ ID NOs:256 and 267, respectively;

the $V_H$ and $V_L$ regions of the antibody or antigen-binding fragment thereof comprise the amino acid sequences of SEQ ID NOs:518 and 534, respectively;

the $V_H$ and $V_L$ regions of the antibody or antigen-binding fragment thereof comprise the amino acid sequences of SEQ ID NOs:519 and 535, respectively;

the $V_H$ and $V_L$ regions of the antibody or antigen-binding fragment thereof comprise the amino acid sequences of SEQ ID NOs:115 and 536, respectively;

the $V_H$ and $V_L$ regions of the antibody or antigen-binding fragment thereof comprise the amino acid sequences of SEQ ID NOs:520 and 264, respectively;

the $V_H$ and $V_L$ regions of the antibody or antigen-binding fragment thereof comprise the amino acid sequences of SEQ ID NOs:521 and 537, respectively; or the $V_H$ and $V_L$ regions of the antibody or antigen-binding fragment thereof comprise the amino acid sequences of and SEQ ID NOs:522 and 538, respectively.

56. The antibody or antigen-binding fragment thereof of embodiment 54 or embodiment 55, comprising:

the $V_H$ and $V_L$ regions of the antibody or antigen-binding fragment thereof comprise the amino acid sequences of SEQ ID NOS:256 and 267, respectively;

the $V_H$ and $V_L$ regions of the antibody or antigen-binding fragment thereof comprise the amino acid sequences of SEQ ID NOs:115 and 536, respectively;

57. The antibody or antigen-binding fragment of any one of embodiments 1-54, wherein said antibody or antigen-binding fragment specifically binds to a BCMA protein.

58. The antibody or antigen-binding fragment of embodiment 57, wherein the BCMA protein is a human BCMA protein, a mouse BCMA protein, or a non-human primate BCMA protein.

59. The antibody or antigen-binding fragment of embodiment 57, wherein the BCMA protein is a human BCMA protein.

60. The antibody or antigen-binding fragment of any of embodiments 1-59, wherein said antibody or antigen-binding fragment comprises a heavy chain complementarity determining region 3 (CDR-H3) comprising the amino acid sequence selected from any one of SEQ ID NOs: 7 and 157, or a CDR-H3 contained within the heavy chain variable ($V_H$) region amino acid sequence selected from any one of SEQ ID NOs:110, 256 and 519, and/or a light chain complementarity determining region 3 (CDR-L3) comprising the amino acid sequence selected from any one of SEQ ID NOs: 47, 51, 194 and 416, or a CDR-L3 contained within the light chain variable ($V_L$) region amino acid sequence selected from any one of SEQ ID NOs: 116, 120, 267 and 535.

61. The antibody or antigen-binding fragment of any of embodiments 1-60, wherein said antibody or antigen-binding fragment further comprises:

a heavy chain complementarity determining region 1 (CDR-H1) comprising the amino acid sequence selected from any one of SEQ ID NOs: 1 and 2, or a CDR-H1 contained within the heavy chain variable (V$_H$) region amino acid sequence selected from any one of SEQ ID NOs:110, 256 and 519, and/or a light chain complementarity determining region 1 (CDR-L1) comprising the amino acid sequence selected from any one of SEQ ID NOs: 26, 30, 178 and 380, or a CDR-L1 contained within the light chain variable (V$_L$) region amino acid sequence selected from any one of SEQ ID NOs: 116, 120, 267 and 535;

a heavy chain complementarity determining region 2 (CDR-H2) comprising the amino acid sequence selected from any one of SEQ ID NOs: 4 or 5, or a CDR-H2 contained within the heavy chain variable (V$_H$) region amino acid sequence selected from any one of SEQ ID NOs:110, 256 and 519, and/or a light chain complementarity determining region 2 (CDR-L2) comprising the amino acid sequence selected from any one of SEQ ID NOs: 37, 39, 183 or 400, or a CDR-L2 contained within the light chain variable (V$_L$) region amino acid sequence selected from any one of SEQ ID NOs: 116, 120, 267 and 535.

62. The antibody or antigen-binding fragment of any of embodiments 1-61, wherein said antibody or antigen-binding fragment comprises a V$_H$ region comprising a CDR-H1, a CDR-H2, and a CDR-H3, respectively, comprising the amino acid sequence of a CDR-H1, a CDR-H2, and a CDR-H3 contained within the V$_H$ region amino acid sequence selected from any one of SEQ ID NOs: 110, 256 and 519; and/or a V$_L$ region comprising a CDR-L1, a CDR-L2, and a CDR-L3, respectively, comprising the amino acid sequence of a CDR-L1, a CDR-L2, and a CDR-L3 contained within the V$_L$ region amino acid sequence selected from any one of SEQ ID NOs: 116, 120, 267 and 535.

63. The antibody or antigen-binding fragment of any of embodiments 1-62, wherein:

the V$_H$ and V$_L$ regions of the antibody or antigen-binding fragment thereof comprise the amino acid sequences of SEQ ID NOs:110 and 116, respectively;

the V$_H$ and V$_L$ regions of the antibody or antigen-binding fragment thereof comprise the amino acid sequences of SEQ ID NOs:110 and 120, respectively;

the V$_H$ and V$_L$ regions of the antibody or antigen-binding fragment thereof comprise the amino acid sequences of SEQ ID NOs:256 and 267, respectively; or the V$_H$ and V$_L$ regions of the antibody or antigen-binding fragment thereof comprise the amino acid sequences of SEQ ID NOs:519 and 535, respectively.

64. The antibody or antigen-binding fragment of any of embodiments 1-59, wherein said antibody or antigen-binding fragment comprises a heavy chain complementarity determining region 3 (CDR-H3) comprising the amino acid sequence of SEQ ID NO:10, or a CDR-H3 contained within the heavy chain variable (V$_H$) region amino acid sequence of SEQ ID NO:115, and/or a light chain complementarity determining region 3 (CDR-L3) comprising the amino acid sequence of SEQ ID NO:421, or a CDR-L3 contained within the light chain variable (V$_L$) region amino acid sequence of SEQ ID NO:536.

65. The antibody or antigen-binding fragment of any of embodiments 1-59 and 64, wherein said antibody or antigen-binding fragment further comprises:

a heavy chain complementarity determining region 1 (CDR-H1) comprising the amino acid sequence of SEQ ID NO:2, or a CDR-H1 contained within the heavy chain variable (V$_H$) region amino acid sequence of SEQ ID NO:115 and/or a light chain complementarity determining region 1 (CDR-L1) comprising the amino acid sequence selected from any one of SEQ ID NOs: 33, or a CDR-L1 contained within the light chain variable (V$_L$) region amino acid sequence selected from any one of SEQ ID NOs:536; and/or a heavy chain complementarity determining region 2 (CDR-H2) comprising the amino acid sequence of SEQ ID NO:5, or a CDR-H1 contained within the heavy chain variable (V$_H$) region amino acid sequence of SEQ ID NO:115 and/or a light chain complementarity determining region 2 (CDR-L2) comprising the amino acid sequence selected from any one of SEQ ID NOs:43, or a CDR-L1 contained within the light chain variable (V$_L$) region amino acid sequence selected from any one of SEQ ID NOs:536.

66. The antibody or antigen-binding fragment of any of embodiments 1-59 64 and 65, wherein said antibody or antigen-binding fragment comprises a V$_H$ region comprising a CDR-H1, a CDR-H2, and a CDR-H3, respectively, comprising the amino acid sequence of a CDR-H1, a CDR-H2, and a CDR-H3 contained within the V$_H$ region amino acid sequence of SEQ ID NO:115; and/or a V$_L$ region comprising a CDR-L1, a CDR-L2, and a CDR-L3, respectively, comprising the amino acid sequence of a CDR-L1, a CDR-L2, and a CDR-L3 contained within the V$_L$ region amino acid sequence of SEQ ID NO:536.

67. The antibody or antigen-binding fragment of any of embodiments 1-59 and 64, wherein the V$_H$ and V$_L$ regions of the antibody or antigen-binding fragment thereof comprise the amino acid sequences of SEQ ID NOs:115 and 536, respectively.

68. The antibody or antigen-binding fragment of any of embodiments 1-59, wherein the antibody or antigen-binding fragment further specifically binds to mouse BCMA or non-human primate BCMA.

69. The antibody or antigen-binding fragment of any one of embodiments 58-68, wherein said human BCMA protein comprises an amino acid sequence of SEQ ID NO:367 or 368.

70. The antibody or antigen-binding fragment of any one of embodiments 1-69, wherein the antibody or antigen-binding fragment is human.

71. The antibody or antigen-binding fragment thereof of any of embodiments 1-70, wherein the antibody is a human antibody.

72. The antibody or antigen-binding fragment of embodiment 70 or embodiment 71, wherein:

the antibody or antigen-binding fragment comprises a heavy chain variable (V$_H$) region, said V$_H$ region comprises a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or the antibody or antigen-binding fragment comprises a light chain variable (V$_L$) region, said V$_L$ region comprises a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

73. The antibody or antigen-binding fragment of any one of embodiments 70-72, wherein:
the CDR-H1 and/or CDR-H2 comprises a sequence 100% identical or with no more than one amino acid difference as compared to an amino acid sequence of a CDR-H1 and/or CDR-H2, respectively, within a sequence encoded by a germline nucleotide human heavy chain V segment; and/or
the CDR-L1 and/or CDR-L2 comprises a sequence 100% identical or with no more than one amino acid difference as compared to an amino acid sequence of a CDR-L1 and/or CDR-L2, respectively, within a sequence encoded by a germline nucleotide human kappa or lambda v segment.

74. The antibody or antigen-binding fragment of any one of embodiments 1-73, wherein the antibody or antigen-binding fragment is recombinant.

75. The antibody or antigen-binding fragment of any one of embodiments 1-74, wherein the antibody or antigen-binding fragment is monoclonal.

76. The antibody or antigen-binding fragment of any one of embodiments 1-75, that is an antigen-binding fragment.

77. The antibody or antigen-binding fragment of any one of embodiments 1-76, that is a single chain fragment.

78. The antibody or antigen-binding fragment of any one of embodiments 1-77, wherein the $V_H$ region is amino-terminal to the $V_L$ region.

79. The antibody or antigen-binding fragment of any of embodiments 1-78, wherein the $V_H$ region is carboxy-terminal to the $V_L$ region.

80. The antibody or antigen-binding fragment of any one of embodiments 1-79, that is a fragment comprising antibody $V_H$ and $V_L$ regions joined by a flexible linker.

81. The antibody or antigen-binding fragment of embodiment 77 or embodiment 80, wherein the fragment comprises an scFv.

82. The antibody or antigen-binding fragment of embodiment 81, wherein the scFv comprises a linker comprising the amino acid sequence GGGGSGGGGSGGGGS (SEQ ID NO:361).

83. The antibody or antigen-binding fragment of embodiment 81 or embodiment 82, wherein the scFv comprises the amino acid sequence selected from any one of SEQ ID NOs:128-139, 268-278, 558-576 and 578-583, or an amino acid sequence having at least 90%, 91%, 92%, 93%, 94%, 95%, 96%, 97%, 98%, or 99% sequence identity to the amino acid sequence selected from any one of SEQ ID NOs:128-139, 268-278, 558-576 and 578-583.

84. The antibody or antigen-binding fragment of any of embodiments 81-83, wherein the scFv comprises the amino acid sequence selected from any one of SEQ ID NOs: 128, 129, 130, 132, 133, 136, 137, 269, 273, 274, 275, 276, 277, 278, 558, 559, 560, 561, 562 and 563, or an amino acid sequence having at least 90%, 91%, 92%, 93%, 94%, 95%, 96%, 97%, 98%, or 99% sequence identity to the amino acid sequence selected from any one of SEQ ID NOs: 128, 129, 130, 132, 133, 136, 137, 269, 273, 274, 275, 276, 277, 278, 558, 559, 560, 561, 562 and 563.

85. The antibody or antigen-binding fragment of any of embodiments 81-84, wherein the scFv comprises the amino acid sequence selected from any one of SEQ ID NOs: 278 and 560, or an amino acid sequence having at least 90%, 91%, 92%, 93%, 94%, 95%, 96%, 97%, 98%, or 99% sequence identity to the amino acid sequence selected from any one of SEQ ID NOs: 278 and 560.

86. A single chain cell-surface protein, comprising the antibody or antigen-binding fragment of any one of embodiments 1-85.

87. A single chain cell surface protein comprising the scFv amino acid sequence selected from any one of SEQ ID NOs:128-139, 268-278, 558-576 and 578-583 or comprising the $V_H$ region amino acid sequence selected from any one of SEQ ID NOs:110-115, 247-256, 518-531 and 533.

88. The single chain cell surface protein of embodiment 87, wherein the scFv comprises the amino acid sequence selected from any one of SEQ ID NOs: 128, 129, 130, 132, 133, 136, 137, 269, 273, 274, 275, 276, 277, 278, 558, 559, 560, 561, 562 and 563.

89. The single chain cell surface protein of embodiment 87 or embodiment 88, wherein the scFv comprises the amino acid sequence selected from any one of SEQ ID NOs: 278 and 560.

90. The antibody or antigen-binding fragment of any one of embodiments 1-87, which further comprises at least a portion of an immunoglobulin constant region.

91. The antibody or antigen-binding fragment of embodiment 90, wherein the portion of an immunoglobulin constant region comprises at least a portion of the hinge region.

92. The antibody or antigen-binding fragment of embodiment 90, wherein the portion of an immunoglobulin constant region comprises an Fc region.

93. The antibody or antigen-binding fragment of embodiment 92, wherein the Fc region is an Fc region of a human IgG.

94. A conjugate, comprising the antibody or antigen-binding fragment of any one of embodiments 1-98 and a heterologous molecule or moiety.

95. A chimeric antigen receptor (CAR) comprising an extracellular portion comprising the antibody or antigen-binding fragment of any one of embodiments 1-93 and an intracellular signaling region.

96. The chimeric antigen receptor of embodiment 95, wherein the antibody or antigen-binding fragment comprises an sdAb comprising only the $V_H$ region or an scFv and the intracellular signaling region comprises an intracellular signaling domain.

97. The chimeric antigen receptor of embodiment 96, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

98. The chimeric antigen receptor of embodiment 97, wherein the intracellular signaling domain is or comprises an intracellular signaling domain of a CD3 chain, optionally a CD3-zeta (CD3ζ) chain, or a signaling portion thereof.

99. The chimeric antigen receptor of any of embodiments 95-98, wherein the recombinant receptor further comprises a transmembrane domain disposed between the extracellular domain and the intracellular signaling region.

100. The chimeric antigen receptor of embodiment 99, wherein the transmembrane domain comprises a transmembrane portion of CD28.

101. The chimeric antigen receptor of any of embodiments 95-100, wherein the intracellular signaling region further comprises a costimulatory signaling domain.

102. The chimeric antigen receptor of embodiment 101, wherein the costimulatory signaling domain comprises an intracellular signaling domain of a T cell costimulatory molecule or a signaling portion thereof.

103. The chimeric antigen receptor of embodiment 101 or embodiment 102, wherein the costimulatory signaling domain comprises an intracellular signaling domain of a CD28, a 4-1BB or an ICOS or a signaling portion thereof.

104. The chimeric antigen receptor of any of embodiments 101-103, wherein the costimulatory signaling domain is between the transmembrane domain and the intracellular signaling domain.

105. A polynucleotide encoding the antibody or antigen-binding fragment thereof of any one of embodiments 1-93, conjugate of embodiment 94 or the chimeric antigen receptor of any one of embodiments 95-104.

106. The polynucleotide of embodiment 105, further encoding a GM-CSF signal sequence, a CD8 signal sequence, an Ig kappa signal sequence or a CD33 signal sequence.

107. A vector, comprising the polynucleotide of embodiment 105 or embodiment 106.

108. The vector of embodiment 107, wherein the vector is an expression vector.

109. The vector of embodiment 107 or embodiment 108, wherein the vector is a viral vector.

110. The vector of embodiment 109, wherein the viral vector is a retroviral vector. 111. The vector of embodiment 109 or embodiment 110, wherein the viral vector is a lentiviral vector.

112. The vector of embodiment 111, wherein the lentiviral vector is derived from HIV-1.

113. An engineered cell comprising the vector of any one of embodiments 107-112.

114. An engineered cell expressing a receptor comprising the antibody or antigen-binding fragment of any one of embodiments 1-93, conjugate of embodiment 94 or the chimeric antigen receptor of any one of embodiments 95-102.

115. The engineered cell of embodiment 114 or embodiment 115, wherein the engineered cell is a T cell.

116. A composition comprising the antibody or antigen-binding fragment thereof of any one of embodiments 1-93, conjugate of embodiment 94, the chimeric antigen receptor of any one of embodiments 95-102, or the cell of any one of embodiments 113-115.

117. The composition of embodiment 116, further comprising a pharmaceutically acceptable excipient.

118. A method of treatment, comprising administering the composition of embodiment 116 or embodiment 117 to a subject having a disease or disorder associated with BCMA.

119. A method of treatment, comprising administering an antibody or antigen-binding fragment of any one of embodiments 1-93, conjugate of embodiment 94, the chimeric antigen receptor of any one of embodiments 95-102, or the cell of any one of embodiments 113-115 to a subject having a disease or disorder associated with BCMA.

120. The method of embodiment 118 or embodiment 119, wherein the disease or disorder associated with BCMA is associated with BCMA expression.

121. The method of any one of embodiments 118-120, wherein the disease or disorder associated with BCMA is a B cell-related disorder.

122. The method of any one of embodiments 118-121, wherein the disease or disorder associated with BCMA is an autoimmune disease or disorder.

123. The method of embodiment 122, wherein the autoimmune disease or disorder is systemic lupus erythematosus (SLE), lupus nephritis, inflammatory bowel disease, rheumatoid arthritis, ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis. 124. The method of any one of embodiments 118-121, wherein the disease or disorder associated with BCMA is a cancer.

125. The method of embodiment 124, wherein the cancer is a BCMA-expressing cancer.

126. The method of embodiment 124 or embodiment 125, wherein the cancer is a B cell malignancy.

127. The method of any one of embodiments 124-126, wherein the cancer is a lymphoma, a leukemia, or a plasma cell malignancy.

128. The method of embodiment 127, wherein the lymphoma is Burkitt's lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL).

129. The method of embodiment 127, wherein the leukemia is chronic lymphocytic leukemia (CLL), plasma cell leukemia or acute lymphocytic leukemia (ALL).

130. The method of embodiment 127, wherein the plasma cell malignancy is multiple myeloma (MM) or plasmacytoma.

131. A composition of embodiment 116 or embodiment 117 for use in treating a disease or disorder associated with BCMA.

132. Use of a composition of embodiment 116 or embodiment 117 for the manufacture of a medicament for treating a disease or disorder associated with BCMA.

133. The composition for use or use of embodiment 132, wherein the disease or disorder associated with BCMA is associated with BCMA expression.

134. The composition for use or use of any one of embodiments 131-133, wherein the disease or disorder associated with BCMA is a B cell-related disorder.

135. The composition for use or use of any one of embodiments 131-134, wherein the disease or disorder associated with BCMA is an autoimmune disease or disorder.

136. The composition for use or use of 135, wherein the autoimmune disease or disorder is systemic lupus erythematosus (SLE), lupus nephritis, inflammatory bowel disease, rheumatoid arthritis, ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or rapidly progressive glomerulonephritis.

137. The composition for use or use of any one of embodiments 131-134, wherein the disease or disorder associated with BCMA is a cancer.

138. The composition for use or use of embodiment 137, wherein the cancer is a BCMA-expressing cancer.

139. The composition for use or use of embodiment 137 or embodiment 138, wherein the cancer is a B cell malignancy.

140. The composition for use or use of embodiments 137-139, wherein the cancer is a lymphoma, a leukemia, or a plasma cell malignancy.

141. The composition for use or use of embodiment 140, wherein the lymphoma is Burkitt's lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL).

142. The composition for use or use of embodiment 140, wherein the leukemia is chronic lymphocytic leukemia (CLL), plasma cell leukemia or acute lymphocytic leukemia (ALL).

143. The composition for use or use of embodiment 140, wherein the plasma cell malignancy is multiple myeloma (MM) or plasmacytoma.

V. Examples

The following examples are included for illustrative purposes only and are not intended to limit the scope of the invention.

Example 1: Generation and Assessment of Anti-BCMA Antibodies ($V_H$ Chain Only)

Exemplary anti-BCMA antibodies containing a heavy chain variable ($V_H$) region that specifically bound to BCMA, even in the absence of a light chain variable ($V_L$) region, were generated and assessed.

1A. Library Selection and Antibody Generation

A number of BCMA-binding $V_H$ regions were generated through a series of selection steps carried out on members of a dsDNA-encoded His-tagged human normal donor antibody $V_H$ library displayed in a cell-free system. Members of the $V_H$ library were subjected to multiple rounds of screening to select $V_H$ regions that bound specifically to soluble human BCMA fused to an immunoglobulin Fc region (hBCMA-Fc). $V_H$ regions from selected hBCMA-Fc pools were screened, by flow cytometry using a fluorochrome-conjugated anti-HIS antibody, for binding to a recombinant HEK293 cell line expressing human BCMA (hBCMA/HEK293 cell line), as compared to the parental HEK293 cell line not expressing BCMA, as well as to for binding to a human myeloma cell line expressing endogenous BCMA (H929 cells). The results identified $V_H$ region clones that exhibited specific binding to hBCMA/HEK293 cells and, to a lesser degree, to H929 cells.

Exemplary $V_H$ clones exhibiting specific binding to cell lines expressing BCMA but not to BCMA-negative control cells were sequenced and purified for further characterization. Clones were purified and titrated, and their binding affinities ($EC_{50}$) to hBCMA/HEK293 cells were measured using a flow cytometry-based assay with the fluorochrome-conjugated anti-HIS-antibody. Table 3 lists heavy chain complementarity determining region 3 (CDR-H3) sequences of exemplary clones, containing human $V_H$3-derived framework regions and their respective binding affinities ($EC_{50}$) observed in this study.

TABLE 3

| CDR3 amino acid sequences for representative $V_H$ clones | | | |
|---|---|---|---|
| $V_H$ Clone Name | Heavy Chain CDR3 sequence (CDR-H3)[a] | CDR-H3 Sequence Identifier Number | $EC_{50}$ (nM)[b] |
| $V_H$-1 | VDGPPSFDI | SEQ ID NO: 10 | >100 |
| $V_H$-2 | WSAPTDY | SEQ ID NO: 7 | 25 |
| $V_H$-3 | VDGDDAFDI | SEQ ID NO: 279 | >100 |
| $V_H$-4 | DPLSWDSSGKGPR | SEQ ID NO: 280 | 100 |
| $V_H$-5 | ENYDFWSWRYYYDMDV | SEQ ID NO: 281 | >100 |
| $V_H$-6 | VDGPPSYDI | SEQ ID NO: 282 | >100 |
| $V_H$-7 | GDWDDAFDI | SEQ ID NO: 283 | >100 |
| $V_H$-8 | VDGDYVDDY | SEQ ID NO: 9 | ND |
| $V_H$-9 | VDGDYEDY | SEQ ID NO: 284 | >100 |
| $V_H$-10 | DVPSSGDDAFDI | SEQ ID NO: 285 | >100 |
| $V_H$-11 | VDGDDVFDI | SEQ ID NO: 286 | >100 |
| $V_H$-12 | VDGDAFDI | SEQ ID NO: 287 | 100 |

[a]Amino acid sequences shown according to Kabat numbering.
[b]ND indicates not detected

Example 2: Generation and Assessment of Anti-BCMA Antibodies (scFvs)

Exemplary anti-BCMA antibodies, formatted as single chain antibody fragments (scFvs), were identified and assessed for binding to BCMA.

2A. Library Selection and scFv Antibody Generation

Exemplary anti-BCMA scFv antibodies were generated through various selections, carried out on dsDNA-encoded human normal donor antibody libraries displayed in a cell-free system. In one approach, $V_H$ region library members enriched from a first round of screening in the approach described in Example 1 were paired by shuffling with members of a human normal donor $V_L$ library, to generate an scFv library, in $V_H$-$(G_4S)_3$-$V_L$ format. The resulting scFv libraries were enriched in subsequent rounds of selection for specific binding to BCMA-expressing HEK293 cells as compared to parental HEK293 cells.

In another approach, de novo selection was carried out by screening a normal donor-derived human scFv library for BCMA-specific binding to hBCMA-Fc in the presence or absence of competitive elution with a mouse anti-BCMA reference scFv antibody (either BCMA-C1, $V_L$-$V_H$ scFv antibody, SEQ ID NO:328; or BCMA-C2, $V_H$-$V_L$ scFv antibody, SEQ ID NO:329). After at least 2 rounds of selection, scFv binders were recovered.

Specific binding of resulting scFv clones to BCMA-expressing HEK293 cells, as compared to control cells not expressing BCMA, was assessed by flow cytometry either with in vitro translated crude cell lysate or with bacterially-produced supernatant. Certain scFv clones displaying binding preference for BCMA were further analyzed.

The selected scFv clones were sequenced using forward and reverse primers and purified for further characterization. Table 4 lists sequence identifiers (SEQ ID NO) corresponding to amino acid (aa) and nucleotide (nt) sequences of the scFv and amino acid sequences of the corresponding heavy chain ($V_H$) or light chain ($V_L$) variable regions, CDRs and framework regions (FRs). With respect to clone BCMA-22, the first residue of light chain CDR3 (a cysteine), which was observed to have been inherited from the germline framework region was replaced with a serine to generate an additional scFv, designated BCMA-23. Table 4 also sets forth the sequence of exemplary mouse anti-BCMA reference antibodies used as controls and in competition studies as described in subsequent Examples.

TABLE 4

Sequence identifier (SEQ ID NO) for Exemplary Clones and Reference Antibody

| | | Heavy Chain | | | Light Chain | | scFv | |
|---|---|---|---|---|---|---|---|---|
| Clone # | $V_H$ | CDR-H1, CDR-H2, CDR-H3 | $V_H$ FR (FR1, 2, 3, 4 Kabat) | $V_L$ | CDR-L1, CDR-L2, CDR-L3 | $V_L$ FR (FR1, 2, 3, 4, Kabat) | aa | nt |
| BCMA-1 | 110 | 1, 4, 7 (Kabat)<br>12, 16, 7 (Chothia)<br>19, 23, 7 (AbM) | 59, 64, 67, 70 | 116 | 26, 37, 47 (Kabat)<br>26, 37, 47 (Chothia)<br>26, 37, 47 (AbM) | 72, 83, 93, 102 | 128 | 330 |
| BCMA-2 | 111 | 2, 5, 8 (Kabat)<br>13, 17, 8 (Chothia)<br>20, 24, 8 (AbM) | 60, 65, 68, 71 | 117 | 27, 38, 48 (Kabat)<br>27, 38, 48 (Chothia)<br>27, 38, 48 (AbM) | 73, 84, 94, 103 | 129 | 331 |
| BCMA-3 | 110 | 1, 4, 7 (Kabat)<br>12, 16, 7 (Chothia)<br>19, 23, 7 (AbM) | 59, 64, 67, 70 | 118 | 28, 39, 49 (Kabat)<br>28, 39, 49 (Chothia)<br>28, 39, 49 (AbM) | 74, 85, 93, 104 | 130 | 332 |
| BCMA-4 | 110 | 1, 4, 7 (Kabat)<br>12, 16, 7 (Chothia)<br>19, 23, 7 (AbM) | 59, 64, 67, 70 | 119 | 29, 40, 50 (Kabat)<br>29, 40, 50 (Chothia)<br>29, 40, 50 (AbM) | 75, 86, 95, 104 | 131 | 333 |
| BCMA-5 | 110 | 1, 4, 7 (Kabat)<br>12, 16, 7 (Chothia)<br>19, 23, 7 (AbM) | 59, 64, 67, 70 | 120 | 30, 39, 51 (Kabat)<br>30, 39, 51 (Chothia)<br>30, 39, 51 (AbM) | 76, 85, 93, 105 | 132 | 334 |
| BCMA-6 | 110 | 1, 4, 7 (Kabat)<br>12, 16, 7 (Chothia)<br>19, 23, 7 (AbM) | 59, 64, 67, 70 | 121 | 31, 41, 52 (Kabat)<br>31, 41, 52 (Chothia)<br>31, 41, 52 (AbM) | 77, 87, 96, 104 | 133 | 335 |
| BCMA-7 | 110 | 1, 4, 7 (Kabat)<br>12, 16, 7 (Chothia)<br>19, 23, 7 (AbM) | 59, 64, 67, 70 | 122 | 32, 42, 53 (Kabat)<br>32, 42, 53 (Chothia)<br>32, 42, 53 (AbM) | 78, 88, 97, 106 | 134 | 336 |
| BCMA-8 | 110 | 1, 4, 7 (Kabat)<br>12, 16, 7 (Chothia)<br>19, 23, 7 (AbM) | 59, 64, 67, 70 | 123 | 30, 39, 54 (Kabat)<br>30, 39, 54 (Chothia)<br>30, 39, 54 (AbM) | 76, 85, 93, 107 | 135 | 337 |
| BCMA-9 | 112 | 2, 5, 9 (Kabat)<br>13, 17, 9 (Chothia)<br>20, 24, 9 (AbM) | 61, 65, 69, 70 | 124 | 33, 43, 55 (Kabat)<br>33, 43, 55 (Chothia)<br>33, 43, 55 (AbM) | 79, 89, 98, 108 | 136 | 338 |
| BCMA-10 | 113 | 2, 5, 10 (Kabat)<br>14, 17, 10 (Chothia)<br>21, 24, 10 (AbM) | 62, 65, 68, 71 | 125 | 34, 44, 56 (Kabat)<br>34, 44, 56 (Chothia)<br>34, 44, 56 (AbM) | 80, 90, 99, 108 | 137 | 339 |
| BCMA-11 | 114 | 3, 6, 11 (Kabat)<br>15, 18, 11 (Chothia)<br>22, 25, 11 (AbM) | 63, 66, 69, 71 | 126 | 35, 45, 57 (Kabat)<br>35, 45, 57 (Chothia)<br>35, 45, 57 (AbM) | 81, 91, 100, 108 | 138 | 340 |
| BCMA-12 | 115 | 2, 5, 10 (Kabat)<br>13, 17, 10 (Chothia)<br>20, 24, 10 (AbM) | 60, 65, 68, 71 | 127 | 36, 46, 58 (Kabat)<br>36, 46, 58 (Chothia)<br>36, 46, 58 (AbM) | 82, 92, 101, 109 | 139 | 341 |
| BCMA-13 | 247 | 140, 145, 149 (Kabat)<br>158, 161, 149 (Chothia)<br>165, 170, 149 (AbM) | 195, 204, 210, 217 | 257 | 174, 179, 184 (Kabat)<br>174, 179, 184 (Chothia)<br>174, 179, 184 (AbM) | 221, 228, 233, 243 | 268 | 342 |

TABLE 4-continued

Sequence identifier (SEQ ID NO) for Exemplary Clones and Reference Antibody

| | Heavy Chain | | | Light Chain | | | scFv | |
|---|---|---|---|---|---|---|---|---|
| Clone # | V_H | CDR-H1, CDR-H2, CDR-H3 | V_H FR (FR1, 2, 3, 4 Kabat) | V_L | CDR-L1, CDR-L2, CDR-L3 | V_L FR (FR1, 2, 3, 4, Kabat) | aa | nt |
| BCMA-14 | 248 | 141, 145, 149 (Kabat) 158, 161, 149 (Chothia) 166, 170, 149 (AbM) | 196, 204, 211, 218 | 258 | 174, 179, 185 (Kabat) 174, 179, 185 (Chothia) 174, 179, 185 (AbM) | 221, 228, 234, 109 | 269 | 343 |
| BCMA-15 | 249 | 141, 145, 150 (Kabat) 158, 161, 150 (Chothia) 166, 170, 150 (AbM) | 197, 204, 212, 70 | 259 | 174, 179, 186 (Kabat) 174, 179, 186 (Chothia) 174, 179, 186 (AbM) | 222, 228, 235, 109 | 270 | 344 |
| BCMA-16 | 250 | 142, 146, 151 (Kabat) 159, 162, 151 (Chothia) 167, 171, 151 (AbM) | 198, 205, 213, 70 | 260 | 174, 179, 187 (Kabat) 174, 179, 187 (Chothia) 174, 179, 187 (AbM) | 223, 228, 235, 109 | 271 | 345 |
| BCMA-17 | 251 | 2, 5, 152 (Kabat) 13, 17, 152 (Chothia) 20, 24, 152 (AbM) | 199, 206, 69, 219 | 261 | 175, 180, 188 (Kabat) 175, 180, 188 (Chothia) 175, 180, 188 (AbM) | 224, 229, 237, 109 | 272 | 346 |
| BCMA-18 | 252 | 143, 147, 153 (Kabat) 158, 163, 153 (Chothia) 168, 172, 153 (AbM) | 200, 207, 214, 70 | 262 | 174, 179, 189 (Kabat) 174, 179, 189 (Chothia) 174, 179, 189 (AbM) | 222, 228, 238, 109 | 273 | 347 |
| BCMA-19 | 253 | 144, 148, 154 (Kabat) 160, 164, 54 (Chothia) 169, 173, 154 (AbM) | 201, 208, 215, 220 | 263 | 176, 181, 190 (Kabat) 176, 181, 190 (Chothia) 176, 181, 190 (AbM) | 225, 230, 239, 244 | 274 | 348 |
| BCMA-20 | 254 | 3, 6, 155 (Kabat) 15, 18, 155 (Chothia) 22, 25, 155 (AbM) | 202, 209, 216, 70 | 264 | 177, 182, 191 (Kabat) 177, 182, 191 (Chothia) 177, 182, 191 (AbM) | 226, 231, 240, 245 | 275 | 349 |
| BCMA-21 | 255 | 2, 5, 156 (Kabat) 13, 17, 156 (Chothia) 20, 24, 156 (AbM) | 203, 65, 68, 70 | 265 | 174, 179, 192 (Kabat) 174, 179, 192 (Chothia) 174, 179, 192 (AbM) | 222, 228, 241, 246 | 276 | 350 |
| BCMA-22 | 256 | 2, 5, 157 (Kabat) 13, 17, 157 (Chothia) 20, 24, 157 (AbM) | 60, 65, 68, 70 | 266 | 178, 183, 193 (Kabat) 178, 183, 193 (Chothia) 178, 183, 193 (AbM) | 227, 232, 242, 246 | 277 | 351 |
| BCMA-23 | 256 | 2, 5, 157 (Kabat) 13, 17, 157 (Chothia) 20, 24, 157 (AbM) | 60, 65, 68, 70 | 267 | 178, 183, 194 (Kabat) 178, 183, 194 (Chothia) 178, 183, 194 (AbM) | 227, 232, 242, 246 | 278 | 352 |
| BCMA-24 | 518 | 2, 6, 376 (Kabat) 13, 18, 376 (Chothia) 20, 25, 376 (AbM) | 61, 65, 69, 71 | 534 | 30, 399, 415 (Kabat) 30, 399, 415 (Chothia) 30, 399, 415 (AbM) | 76, 85, 483, 508 | 558 | |
| BCMA-25 | 519 | 1, 4, 7 (Kabat) 12, 16, 7 (Chothia) 19, 23, 7 (AbM) | 436, 64, 67, 70 | 535 | 380, 400, 416 (Kabat) 380, 400, 416 (Chothia) 380, 400, 416 (AbM) | 446, 467, 484, 502 | 559 | |
| BCMA-26 | 115 | 2, 5, 10 (Kabat) 13, 17, 10 (Chothia) 20, 24, 10 (AbM) | 60, 65, 68, 71 | 536 | 33, 43, 421 (Kabat) 33, 43, 421 (Chothia) 33, 43, 421 (AbM) | 80, 89, 98, 108 | 560 | |
| BCMA-27 | 520 | 3, 6, 155 (Kabat) 15, 18, 155 (Chothia) 22, 25, 155 (AbM) | 434, 209, 216, 70 | 264 | 177, 182, 191 (Kabat) 177, 182, 191 (Chothia) 177, 182, 191 (AbM) | 226, 231, 240, 245 | 561 | |
| BCMA-28 | 521 | 3, 372, 376 (Kabat) 15, 514, 376 (Chothia) 22, 510, 376 (AbM) | 63, 209, 69, 444 | 537 | 381, 401, 417 (Kabat) 381, 401, 417 (Chothia) 381, 401, 417 (AbM) | 447, 468, 485, 508 | 562 | |
| BCMA-29 | 522 | 3, 6, 376 (Kabat) 15, 18, 376 (Chothia) 22, 25, 376 (AbM) | 63, 209, 69, 71 | 538 | 382, 402, 418 (Kabat) 382, 402, 418 (Chothia) 382, 402, 418 (AbM) | 448, 469, 486, 503 | 563 | |
| BCMA-30 | 523 | 3, 6, 377 (Kabat) 12, 18, 377 (Chothia) 509, 25, 377 (AbM) | 435, 209, 69, 71 | 539 | 383, 403, 419 (Kabat) 383, 403, 419 (Chothia) 383, 403, 419 (AbM) | 449, 470, 487, 104 | 564 | |
| BCMA-31 | 519 | 1, 4, 7 (Kabat) 12, 16, 7 (Chothia) 19, 23, 7 (AbM) | 436, 64, 67, 70 | 540 | 384, 39, 54 (Kabat) 384, 39, 54 (Chothia) 384, 39, 54 (AbM) | 450, 471, 93, 504 | 565 | |
| BCMA-32 | 524 | 2, 5, 10 (Kabat) 13, 17, 10 (Chothia) 20, 24, 10 (AbM) | 437, 65, 68, 71 | 541 | 385, 180, 58 (Kabat) 385, 180, 58 (Chothia) 385, 180, 58 (AbM) | 451, 472, 488, 109 | 566 | |
| BCMA-33 | 525 | 2, 373, 152 (Kabat) 13, 515, 152 (Chothia) 20, 511, 152 (AbM) | 199, 65, 69, 219 | 261 | 175, 180, 188 (Kabat) 175, 180, 188 (Chothia) 175, 180, 188 (AbM) | 224, 229, 237, 109 | 567 | |
| BCMA-34 | 526 | 3, 6, 11 (Kabat) 15, 18, 11 (Chothia) 22, 25, 11 (AbM) | 438, 209, 69, 71 | 542 | 386, 404, 420 (Kabat) 386, 404, 420 (Chothia) 386, 404, 420 (AbM) | 452, 84, 489, 504 | 568 | |
| BCMA-35 | 527 | 2, 5, 378 (Kabat) 13, 17, 378 (Chothia) 20, 24, 378 (AbM) | 61, 65, 69, 70 | 543 | 33, 43, 421 (Kabat) 33, 43, 421 (Chothia) 33, 43, 421 (AbM) | 453, 89, 98, 505 | 569 | |
| BCMA-36 | 528 | 2, 5, 9 (Kabat) 13, 17, 9 (Chothia) 20, 24, 9 (AbM) | 199, 65, 69, 70 | 544 | 387, 405, 422 (Kabat) 387, 405, 422 (Chothia) 387, 405, 422 (AbM) | 454, 473, 490, 109 | 570 | |

TABLE 4-continued

Sequence identifier (SEQ ID NO) for Exemplary Clones and Reference Antibody

| | Heavy Chain | | | Light Chain | | scFv | |
|---|---|---|---|---|---|---|---|
| | | | V$_H$ FR | | | V$_L$ FR | |
| | | CDR-H1, | (FR1, 2, | | CDR-L1, | (FR1, 2, | |
| | | CDR-H2, | 3, 4 | | CDR-L2, | 3, 4, | |
| Clone # | V$_H$ | CDR-H3 | Kabat) | V$_L$ | CDR-L3 | Kabat) | aa | nt |
| BCMA-37 | 529 | 2, 5, 9 (Kabat)<br>13, 17, 9 (Chothia)<br>20, 24, 9 (AbM) | 61, 65,<br>441, 70 | 545 | 388, 406, 423 (Kabat)<br>388, 406, 423 (Chothia)<br>388, 406, 423 (AbM) | 455, 474,<br>491, 109 | 571 | |
| BCMA-38 | 528 | 2, 5, 9 (Kabat)<br>13, 17, 9 (Chothia)<br>20, 24, 9 (AbM) | 199, 65,<br>69, 70 | 546 | 388, 407, 424 (Kabat)<br>388, 407, 424 (Chothia)<br>388, 407, 424 (AbM) | 456, 474,<br>492, 109 | 572 | |
| BCMA-39 | 522 | 3, 6, 376 (Kabat)<br>15, 18, 376 (Chothia)<br>22, 25, 376 (AbM) | 63, 209,<br>69, 71 | 547 | 389, 408, 425 (Kabat)<br>389, 408, 425 (Chothia)<br>389, 408, 425 (AbM) | 457, 475,<br>493, 103 | 573 | |
| BCMA-40 | 256 | 2, 5, 157 (Kabat)<br>13, 17, 157 (Chothia)<br>20, 24, 157 (AbM) | 60, 65,<br>68, 70 | 548 | 390, 183, 193 (Kabat)<br>390, 183, 193 (Chothia)<br>390, 183, 193 (AbM) | 227, 232,<br>242, 108 | 574 | |
| BCMA-41 | 530 | 2, 374, 9 (Kabat)<br>13, 516, 9 (Chothia)<br>20, 512, 9 (AbM) | 199, 65,<br>68, 70 | 549 | 391, 409, 426 (Kabat)<br>391, 409, 426 (Chothia)<br>391, 409, 426 (AbM) | 458, 476,<br>494, 109 | 575 | 584 |
| BCMA-42 | 531 | 1, 4, 7 (Kabat)<br>12, 16, 7 (Chothia)<br>19, 23, 7 (AbM) | 439, 64,<br>67, 70 | 550 | 392, 40, 427 (Kabat)<br>392, 40, 427 (Chothia)<br>392, 40, 427 (AbM) | 459, 477,<br>495, 506 | 576 | |
| BCMA-44 | 519 | 1, 4, 7 (Kabat)<br>12, 16, 7 (Chothia)<br>19, 23, 7 (AbM) | 436, 64,<br>67, 70 | 552 | 394, 39, 429 (Kabat)<br>394, 39, 429 (Chothia)<br>394, 39, 429 (AbM) | 461, 85,<br>93, 107 | 578 | |
| BCMA-45 | 110 | 1, 4, 7 (Kabat)<br>12, 16, 7 (Chothia)<br>19, 23, 7 (AbM) | 59, 64,<br>67, 70 | 553 | 395, 411, 430 (Kabat)<br>395, 411, 430 (Chothia)<br>395, 411, 430 (AbM) | 462, 479,<br>497, 105 | 579 | |
| BCMA-46 | 110 | 1, 4, 7 (Kabat)<br>12, 16, 7 (Chothia)<br>19, 23, 7 (AbM) | 59, 64,<br>67, 70 | 118 | 28, 39, 49 (Kabat)<br>28, 39, 49 (Chothia)<br>28, 39, 49 (AbM) | 74, 85,<br>93, 104 | 130 | |
| BCMA-47 | 533 | 2, 5, 10 (Kabat)<br>13, 17, 10 (Chothia)<br>20, 24, 10 (AbM) | 197, 65,<br>443, 445 | 554 | 396, 412, 431 (Kabat)<br>396, 412, 431 (Chothia)<br>396, 412, 431 (AbM) | 463, 480,<br>498, 108 | 580 | |
| BCMA-48 | 115 | 2, 5, 10 (Kabat)<br>13, 17, 10 (Chothia)<br>20, 24, 10 (AbM) | 60, 65,<br>68, 71 | 555 | 396, 412, 58 (Kabat)<br>396, 412, 58 (Chothia)<br>396, 412, 58 (AbM) | 464, 480,<br>499, 109 | 581 | |
| BCMA-49 | 524 | 2, 5, 10 (Kabat)<br>13, 17, 10 (Chothia)<br>20, 24, 10 (AbM) | 437, 65,<br>68, 71 | 556 | 397, 413, 432 (Kabat)<br>397, 413, 432 (Chothia)<br>397, 413, 432 (AbM) | 465, 481,<br>500, 109 | 582 | |
| BCMA-51 | 519 | 1, 4, 7 (Kabat)<br>12, 16, 7 (Chothia)<br>19, 23, 7 (AbM) | 436, 64,<br>67, 70 | 557 | 398, 414, 433 (Kabat)<br>398, 414, 433 (Chothia)<br>398, 414, 433 (AbM) | 466, 482,<br>501, 508 | 583 | |
| BCMA-C1, V$_H$-V$_L$ | 324 | 288, 290, 292 (Kabat)<br>294, 296, 292 (Chothia)<br>298, 300, 292 (AbM) | 308, 310,<br>312, 314 | 326 | 302, 304, 306 (Kabat)<br>302, 304, 306 (Chothia)<br>302, 304, 306 (AbM) | 316, 318,<br>320, 322 | 585 | |
| BCMA-C1, V$_L$-V$_H$ | 324 | 288, 290, 292 (Kabat)<br>294, 296, 292 (Chothia)<br>298, 300, 292 (AbM) | 308, 310,<br>312, 314 | 326 | 302, 304, 306 (Kabat)<br>302, 304, 306 (Chothia)<br>302, 304, 306 (AbM) | 316, 318,<br>320, 322 | 328 | |
| BCMA-C2, V$_H$-V$_L$ | 325 | 289, 291, 293 (Kabat)<br>295, 297, 293 (Chothia)<br>299, 301, 293 (AbM) | 309, 311,<br>313, 315 | 327 | 303, 305, 307 (Kabat)<br>303, 305, 307 (Chothia)<br>303, 305, 307 (AbM) | 317, 319,<br>321, 323 | 329 | |
| BCMA-C2, V$_L$-V$_H$ | 325 | 289, 291, 293 (Kabat)<br>295, 297, 293 (Chothia)<br>299, 301, 293 (AbM) | 309, 311,<br>313, 315 | 327 | 303, 305, 307 (Kabat)<br>303, 305, 307 (Chothia)<br>303, 305, 307 (AbM) | 317, 319,<br>321, 323 | 586 | |

2B. Binding Affinities

Clones were purified and titrated, and their binding affinities ($EC_{50}$) to hBMCA-expressing HEK293 cells was assessed using a flow cytometry-based assay using the fluorochrome-conjugated detection antibody as described in Example 1. $EC_{50}$ for mouse anti-BCMA antibodies, either BCMA-C1, V$_L$-V$_H$ scFv antibody (SEQ ID NO:328) or BCMA-C2, V$_H$-V$_L$ scFv antibody (SEQ ID NO:329), were also determined.

2C. Binding Selectivity

Binding of exemplary scFv clones to hBMCA-expressing HEK293 cells was assessed and binding was compared to parental HEK293 cells. The results showed that clones exhibited binding selectivity to hBMCA-expressing HEK293 cells over parental HEK293 cells. As an example, clones BCMA-18, -19, -20, -21 and -22 exhibited 2.2-fold, 4.2-fold, 10.8-fold, 3.4-fold and 7.5-fold selective binding, respectively.

Binding of exemplary scFv clones to hBMCA-overexpressing HEK293 cells as compared to OPM2 and RPMI-8226 cell lines that express moderate levels of endogenous BCMA was assessed. The results showed that many of the tested clones exhibited higher binding to hBMCA-expressing HEK293 cells, which express a high level of BCMA, compared to the OPM2 and RPMI-8226 cell lines that express moderate levels of BCMA. For example, clones BCMA-1, -2, -3, -4, -5, -7, -8, -9, -10, -12, -18, -19, -20, -21, -22, -30, -31 and -32 exhibited higher binding to hBCMAoverexpressing HEK293 cells. In this particular experiment, BCMA-13, -14 and -16 did not exhibit substantially higher binding to hBCMA-expressing HEK293 cells compared to negative control.

Example 3: Generation and Assessment of Anti-BCMA Antibodies (scFvs)

Epitopes recognized, e.g., specifically bound to, by exemplary anti-BCMA scFv clones (BCMA-1, BCMA-5, BCMA-9, BCMA-23, BCMA-25, BCMA-26, BCMA-52 and BCMA-55 anti-BCMA scFvs), were assessed using full discontinuous epitope mapping by Chemical Linkage of Peptides onto Scaffolds (CLIPS; Pepscan Presto BV, Lelystad, The Netherlands; see, e.g., Timmerman et al., (2007) J. Mol. Recognit. 20: 283-329). Mapping was carried out using anti-BCMA scFv clones, such as those fused with mouse Fc (scFv-mFc).

Linear and conformational peptide libraries of amino acid residues 1-54 of human BCMA (set forth as amino acid residues 1-54 of SEQ ID NO:367) were generated based on a combinatorial matrix design. Linear peptides and structural mimetics including single loop, α-helix, β-turn, combinatorial and linear disulfide bridge mimics, and discontinuous epitope mimics were used, along with positive and negative control peptides, on an amino-functionalized solid support.

Affinities for binding to the peptides in the epitope library were determined using ELISA. The peptide arrays were incubated with a solution containing the scFv overnight at 4° C. Affinity information was used in iterative screens to define the sequence and conformation of epitopes. Heat maps of affinity information for two or more loops were generated.

scFvs assessed were observed to recognized conformational epitopes that included several discontinuous peptide stretches of the BCMA peptide sequence. BCMA-1, BCMA-5, BCMA-23 and BCMA-25 scFv were observed to bind to a peptide of $_{30}$SNTPPLTCQR$_{39}$ (set forth in SEQ ID NO:608), which could be recognized in a linear form. In some aspects, such antibodies recognize a non-linear or linear epitope including residues of such peptide of SEQ ID NO: 608, and in some aspects to recognize a non-linear epitope further including residues of 21CIPCQLR$_{27}$ (set forth in SEQ ID NO:609), $_{30}$SNTPPLTCQR$_{39}$ (SEQ ID NO: 608) and/or 44SVTNSVK$_{50}$ (set forth in SEQ ID NO:610). The BCMA-26 scFv was observed to recognize an epitope comprising residues present in $_8$CSQNEYF$_{14}$ (set forth in SEQ ID NO:611) and $_{17}$LLHACIPCQLR$_{27}$ (set forth in SEQ ID NO:612). BCMA-52-scFv-mFc was observed to bind to an epitope containing residues of the following discontinuous peptides: $_{10}$QNEYF$_{14}$ (SEQ ID NO:613), $_{21}$CIPCQL$_{26}$ (SEQ ID NO:614), and $_7$CQRYC$_{41}$ (SEQ ID NO:615). BCMA-55-scFv-mFc was observed to specifically bind to an epitope containing residues present in peptides comprising discontinuous portions of the BCMA polypeptide sequence, individually comprising the following sequences: $_1$MLMAG$_6$ (SEQ ID NO:616), $_{13}$YFDSL$_{17}$ (SEQ ID NO:618), and $_{25}$QLRCSSNTPPL$_{35}$ (SEQ ID NO:619). In some embodiments, the provided antibody or receptor specifically binds to an epitope comprising residues present within one or more of, e.g., each of discontinuous peptides having the sequences of: MLMAG (SEQ ID NO:616), YFDSL (SEQ ID NO:618), and QLRCSSNTPPL (SEQ ID NO:619). In some aspects, the provided antibody or receptor specifically binds to an epitope comprising residues present within one or more of, e.g., each of, the following discontinuous peptides having the sequences of: MLMAG (SEQ ID NO:616), YFDSLL (SEQ ID NO:620), and QLRCSSNTPPL (SEQ ID NO:619); in some aspects, the provided antibody or receptor specifically binds to an epitope comprising residues present within one or more of, e.g., each of, the following discontinuous peptides having the sequences of: MLMAG (SEQ ID NO:617), QNEYFD-SLL (SEQ ID NO:617), and QLRCSSNTPPL (SEQ ID NO:619).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO | SEQUENCE | Description |
|---|---|---|
| 1 | DYAMS | BCMA-1, -3, -4, -5, -6, -7, -8, -25, -31, -42, -44, -45, -46, -51 CDR-H1 (aa) Kabat numbering |
| 2 | DYYMS | BCMA-2, -9, -10, -12, -17, -21, -22, -23, -24, -26, -32, -33, -35, -36, -37, -38, -40, -41, -47, -48, -49 CDR-H1 (aa) Kabat numbering |
| 3 | DYAMH | BCMA-11, -20, -27, -28, -29, -30, -34, -39 CDR-H1 (aa) Kabat numbering |

-continued

| SEQ ID NO | SEQUENCE | Description |
|---|---|---|
| 4 | FIRSKAYGGTTEYAASVKG | BCMA-1, -3, -4, -5, -6, -7, -8, -25, -31, -42, -44, -45, -46, -51 CDR-H2 (aa) Kabat numbering |
| 5 | YISSSGSTIYYADSVKG | BCMA-2, -9, -10, -12, -17, -21, -22, -23, -26, -32, -35, -36, -37, -38, -40, -47, -48, -49 CDR-H2 (aa) Kabat numbering |
| 6 | GISWNSGSIGYADSVKG | BCMA-11, -20, -24, -27, -29, -30, -34, -39 CDR-H2 (aa) Kabat numbering |
| 7 | WSAPTDY | BCMA-1, -3, -4, -5, -6, -7, -8, -25, -31, -42, -44, -45, -46, -51 and VH-2 CDR-H3 (aa) |
| 8 | VDGPPSSDI | BCMA-2 CDR-H3 (aa) |
| 9 | VDGDYVDDY | BCMA-9, -36, -37, -38, -41 and VH-8 CDR-H3 (aa) |
| 10 | VDGPPSFDI | BCMA-10, -12, -26, -32, -47, -48, -49 and VH-1 CDR-H3 (aa) |
| 11 | DLGPDYDPDAFDI | BCMA-11, -34 CDR-H3 (aa) |
| 12 | GFTFGDY | BCMA-1, -3, -4, -5, -6, -7, -8, -25, -30, -31, -42, -44, -45, -46, -51 CDR-H1 (aa) Chothia numbering |
| 13 | GFTFSDY | BCMA-2, -9, -12, -17, -21, -22, -23, -24, -26, -32, -33, -35, -36, -37, -38, -40, -47, -48, -49 CDR-H1 (aa) Chothia numbering |
| 14 | GFPFSDY | BCMA-10 CDR-H1 (aa) Chothia numbering |
| 15 | GFTFDDY | BCMA-11, -20, -27, -28, -29, -34, -39 CDR-H1 (aa) Chothia numbering |
| 16 | RSKAYGGT | BCMA-1, -3, -4, -5, -6, -7, -8, -25, -31, -42, -44, -45, -46, -51 CDR-H2 (aa) Chothia numbering |
| 17 | SSSGST | BCMA-2, -9, -10, -12, -17, -21, -22, -23, -26, -32, -35, -36, -38, -40, -47, -48 CDR-H2 (aa) Chothia numbering |
| 18 | SWNSGS | BCMA-11, -20, -24, -27, -29, -30, -34, -39 CDR-H2 (aa) Chothia numbering |

| SEQ ID NO | SEQUENCE | Description |
|---|---|---|
| 19 | GFTFGDYAMS | BCMA-1, -3, -4, -5, -6, -7, -8, -25, -31, -42, -44, -45, -46, -51 CDR-H1 (aa) AbM numbering |
| 20 | GFTFSDYYMS | BCMA-2, -9, -12, -17, -21, -22, -23, -24, -26, -32, -33, -35, -36, -37, -38, -40, -47, -48, -49 CDR-H1 (aa) AbM numbering |
| 21 | GFPFSDYYMS | BCMA-10 CDR-H1 (aa) AbM numbering |
| 22 | GFTFDDYAMH | BCMA-11, -20, -27, -28, -29, -34, -39 CDR-H1 (aa) AbM numbering |
| 23 | FIRSKAYGGTTE | BCMA-1, -3, -4, -5, -6, -7, -8, -25, -31, -42, -44, -45, -46, -51 CDR-H2 (aa) AbM numbering |
| 24 | YISSSGSTIY | BCMA-2, -9, -10, -12, -17, -21, -22, -23, -26, -32, -35, -36, -38, -40, -47, -48 CDR-H2 (aa) AbM numbering |
| 25 | GISWNSGSIG | BCMA-11, -20, -24, -27, -29, -30, -34, -39 CDR-H2 (aa) AbM numbering |
| 26 | KSSQSVLSTSNNKNYLA | BCMA-1 CDR-L1 (aa) |
| 27 | RASQSIKTNLA | BCMA-2 CDR-L1 (aa) |
| 28 | KSSQSVLHSSNNKNYLA | BCMA-3, -46 CDR-L1 (aa) |
| 29 | RASQDIRNSLA | BCMA-4 CDR-L1 (aa) |
| 30 | KSSQSVLYSSNNKNYLA | BCMA-5, -8, -24 CDR-L1 (aa) |
| 31 | RASQSISNSLA | BCMA-6 CDR-L1 (aa) |
| 32 | RASQDIGDYLA | BCMA-7 CDR-L1 (aa) |
| 33 | GANNIGSKSVH | BCMA-9, -26, -35 CDR-L1 (aa) |
| 34 | GGNNIERKNVH | BCMA-10 CDR-L1 (aa) |
| 35 | SGSSSNIGSNAVN | BCMA-11 CDR-L1 (aa) |
| 36 | SGSRSNIGNNYVS | BCMA-12 CDR-L1 (aa) |
| 37 | WASTREA | BCMA-1 CDR-L2 (aa) |
| 38 | AASTEAT | BCMA-2 CDR-L2 (aa) |
| 39 | WASTRES | BCMA-3, -5, -8, -31, -44, -46 CDR-L2 (aa) |
| 40 | AASRLES | BCMA-4, -42 CDR-L2 (aa) |

| SEQ ID NO | SEQUENCE | Description |
|---|---|---|
| 41 | AASNVED | BCMA-6 CDR-L2 (aa) |
| 42 | VASTLQS | BCMA-7 CDR-L2 (aa) |
| 43 | DDDDRPS | BCMA-9, -26, -35 CDR-L2 (aa) |
| 44 | DDSDRAS | BCMA-10 CDR-L2 (aa) |
| 45 | NSHQRPS | BCMA-11 CDR-L2 (aa) |
| 46 | DNAKRPS | BCMA-12 CDR-L2 (aa) |
| 47 | QQYFSSPYT | BCMA-1 CDR-L3 (aa) |
| 48 | QQYGSSPT | BCMA-2 CDR-L3 (aa) |
| 49 | QQYYTTPLT | BCMA-3, -46 CDR-L3 (aa) |
| 50 | QQYYSLPLS | BCMA-4 CDR-L3 (aa) |
| 51 | QQYYSTPWT | BCMA-5 CDR-L3 (aa) |
| 52 | QQSHMYPPT | BCMA-6 CDR-L3 (aa) |
| 53 | QQYHSHPWT | BCMA-7 CDR-L3 (aa) |
| 54 | QQYYSTPYT | BCMA-8, -31 CDR-L3 (aa) |
| 55 | HVWDRSRDHYV | BCMA-9 CDR-L3 (aa) |
| 56 | QAWDSSSTLYV | BCMA-10 CDR-L3 (aa) |
| 57 | AAWDDSLRGYV | BCMA-11 CDR-L3 (aa) |
| 58 | QVWDSSSDHWV | BCMA-12, -32, -48 CDR-L3 (aa) |
| 59 | QVQLVQSGGGLVQPGRSLRLSCTASGFTFG | BCMA-1, -3, -4, -5, -6, -7, -8, -45, -46 VH FR1 (aa) |
| 60 | EVQLVESGGGLVKPGGSLRLSCAASGFTFS | BCMA-2, -12, -22, -23, -26, -40, -48 VH FR1 (aa) |
| 61 | EVQLVQSGGGLVKPGGSLRLSCAASGFTFS | BCMA-9, -24, -35, -37 VH FR1 (aa) |
| 62 | EVQLVESGGGLVKPGGSLRLSCAASGFPFS | BCMA-10 VH FR1 (aa) |
| 63 | QVQLVQSGGGLVQPGRSLRLSCAASGFTFD | BCMA-11, -28, -29, -39 VH FR1 (aa) |
| 64 | WFRQAPGKGLEWVG | BCMA-1, -3, -4, -5, -6, -7, -8, -25, -31, -42, -44, -45, -46, -51 VH FR2 (aa) |
| 65 | WIRQAPGKGLEWVS | BCMA-2, -9, -10, -12, -21, -22, -23, -24, -26, -32, -33, -35, -36, -37, -38, -40, -41, -47, -48, 49 VH FR2 (aa) |
| 66 | WVRRAPGKGLEWVS | BCMA-11 VH FR2 (aa) |

-continued

| SEQ ID NO | SEQUENCE | Description |
|---|---|---|
| 67 | RFTISRDDSKSIAYLQMNSLKTEDTAVYYCAA | BCMA-1, -3, -4, -5, -6, -7, -8, -25, -31, -42, -44, -45, -46, -51 VH FR3 (aa) |
| 68 | RFTISRDNAKNSLYLQMNSLRAEDTAVYYCAK | BCMA-2, -10, -12, -21, -22, -23, -26, -32, -40, -41, -48, -49 VH FR3 (aa) |
| 69 | RFTISRDNAKNSLYLQMNSLRAEDTAVYYCAR | BCMA-9, -11, -17, -24, -28, -29, -30, -33, -34, -35, -36, -38, -39 VH FR3 (aa) |
| 70 | WGQGTLVTVSS | BCMA-1, -3, -4, -5, -6, -7, -8, -9, -15, -16, -18, -20, -21, -22, -23, -25, -27, -31, -35, -36, -37, -38, -40, -41, -42, -44, -45, -46, -51 VH FR4 (aa) |
| 71 | WGQGTMVTVSS | BCMA-2, -10, -11, -12, -24, -26, -29, -30, -32, -34, -39, -48, -49, -50 VH FR4 (aa) |
| 72 | DIVMTQSPDSLSVSPGERATISC | BCMA-1 VL FR1 (aa) |
| 73 | EIVMTQSPATLSVSPGETATLSC | BCMA-2 VL FR1 (aa) |
| 74 | DIVMTQSPDSLVVSLGERATINC | BCMA-3, -46 VL FR1 (aa) |
| 75 | AIRMTQSPSSLSASLGDRVTITC | BCMA-4 VL FR1 (aa) |
| 76 | DIVMTQSPDSLAVSLGERATINC | BCMA-5, -8, -24 VL FR1 (aa) |
| 77 | DIVMTQSPSSLSVSVGERVTITC | BCMA-6 VL FR1 (aa) |
| 78 | VIQLTQSPSSLSASVGDRVTITC | BCMA-7 VL FR1 (aa) |
| 79 | SYELTQPPSVSVAPGQTARVTC | BCMA-9 VL FR1 (aa) |
| 80 | SYVLTQPPSVSVAPGQTARITC | BCMA-10, -26 VL FR1 (aa) |
| 81 | QLVLTQPPSASGTPGQRVTISC | BCMA-11 VL FR1 (aa) |
| 82 | QSALTQPPSVSAAPGQKVTISC | BCMA-12 VL FR1 (aa) |
| 83 | WYQQKPGQPPRLLLY | BCMA-1 VL FR2 (aa) |
| 84 | WYQQKPGQAPRLLIY | BCMA-2, -34 VL FR2 (aa) |
| 85 | WYQQKPGQPPKLLIY | BCMA-3, -5, -8, -24, -44, -46 VL FR2 (aa) |
| 86 | WYQQRPGKAPKLLLS | BCMA-4 VL FR2 (aa) |
| 87 | WYKQRPGEAPKLLIH | BCMA-6 VL FR2 (aa) |
| 88 | WFQQRPGKAPKSLIY | BCMA-7 VL FR2 (aa) |
| 89 | WYQQKPGQAPMLVVY | BCMA-9, -26, -35 VL FR2 (aa) |
| 90 | WYQQKPGQAPVPVVY | BCMA-10 VL FR2 (aa) |

| SEQ ID NO | SEQUENCE | Description |
|---|---|---|
| 91 | WYQQLPGTAPEVLIY | BCMA-11 VL FR2 (aa) |
| 92 | WYQQLPGTAPKLLIY | BCMA-12 VL FR2 (aa) |
| 93 | GVPDRFSGSGSGTDFTLTISSLQAEDVAVYYC | BCMA-1, -3, -5, -8, -31, -44, -46 VL FR3 (aa) |
| 94 | GIPDRFSGSGSGTDFTLTITRLEPEDFAVYYC | BCMA-2 VL FR3 (aa) |
| 95 | GVPSRFSGTTSGAEYALSISSLQPEDVASYFC | BCMA-4 VL FR3 (aa) |
| 96 | GVPSRFSGRGSGTVFTLAISNVQPEDFATYYC | BCMA-6 VL FR3 (aa) |
| 97 | GVPSRFSGSGSGTHFTLTINSLQPEDFATYYC | BCMA-7 VL FR3 (aa) |
| 98 | GIPERFSGSNSGNTATLTISGVEAGDEADYFC | BCMA-9, -26, -35 VL FR3 (aa) |
| 99 | GIPERFSASNSGNTATLTISGAQATDEAEYYC | BCMA-10 VL FR3 (aa) |
| 100 | GVPDRFSGSKSGTSASLAINGLQSEDEADYYC | BCMA-11 VL FR3 (aa) |
| 101 | GIPDRFSGSKSGTSATLDIAGLQTGDEADYYC | BCMA-12 VL FR3 (aa) |
| 102 | FGHGTKLEIK | BCMA-1 VL FR4 (aa) |
| 103 | FGRGTKLEIK | BCMA-2, -39 VL FR4 (aa) |
| 104 | FGGGTKVEIK | BCMA-3, -4, -6, -30, -46 VL FR4 (aa) |
| 105 | FGQGTKVDIK | BCMA-5, -45 VL FR4 (aa) |
| 106 | FGPGTKVDIK | BCMA-7 VL FR4 (aa) |
| 107 | FGQGTKLEIK | BCMA-8, -44 VL FR4 (aa) |
| 108 | FGTGTKLTvL | BCMA-9, -10, -11, -26, -40, -47 VL FR4 (aa) |
| 109 | FGGGTKLTVL | BCMA-12, -14, -15, -16, -17, -18, -32, -33, -36, -37, -38, -41, -48, -49, -50 VL FR4 (aa) |
| 110 | QVQLVQSGGGLVQPGRSLRLSCTASGFTFGDYAMSWFRQAPGKGLEWVGFIRSKAYGGTTEYAASVKGRFTISRDDSKSIAYLQMNSLKTEDTAVYYCAAWSAPTDYWGQGTLVTVSS | BCMA-1, -3, -4, -5, -6, -7, -8, -45, -46 VH Chain (aa) |
| 111 | EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAKVDGPPSSDIWGQGTMVTVSS | BCMA-2 $V_H$ Chain (aa) |
| 112 | EVQLVQSGGGLVKPGGSLRLSCAASGFTFSDYYMSWIRQAPGKGLEWVSYISSSGSTIYYADSVKGRFTISRDNAKNSLYLQMNSLRAEDTAVYYCARVDGDYVDDYWGQGTLVTVSS | BCMA-9 $V_H$ Chain (aa) |
| 113 | EVQLVESGGGLVKPGGSLRLSCAASGFPFSDYYMSWIRQAPGKGLEWVSYISSSGSTIYYADSVKGRFTISRDNAKNSLYLQMNSLRAEDTAVYYCAKVDGPPSFDIWGQGTMVTVSS | BCMA-10 $V_H$ Chain (aa) |
| 114 | QVQLVQSGGGLVQPGRSLRLSCAASGFTFDDYAMHWVRRAPGKGLEWVSGISWNSGSIGYADSVKGRFTISRDNAKNSLYLQMNSLRAEDTAVYYCARDLGPDYDPDAFDIWGQGTMVTVSS | BCMA-11 $V_H$ Chain (aa) |
| 115 | EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAKVDGPPSFDIWGQGTMVTVSS | BCMA-12, -26, -48 $V_H$ Chain (aa) |
| 116 | DIVMTQSPDSLSVSPGERATISCKSSQSVLTSNNKNYLAWYQQKPGQPPRLLLYWASTREAGVPDRFSGSGSGTDFTLTISSLQAEDVAVYYCQQYFSSPYTFGHGTKLEIK | BCMA-1 $V_L$ Chain (aa) |
| 117 | EIVMTQSPATLSVSPGETATLSCRASQSIKTNLAWYQQKPGQAPRLLIYAASTRATGIPDRFSGSGSGTDFTLTITRLEPEDFAVYYCQQYGSSPTFGRGTKLEIK | BCMA-2 $V_L$ Chain (aa) |

| SEQ ID NO | SEQUENCE | Description |
|---|---|---|
| 118 | DIVMTQSPDSLVVSLGERATINCKSSQSVLHSSNNKNYLAWYQQKPGQPPKLLIYWASTR ESGVPDRFSGSGSGTDFTLTISSLQAEDVAVYYCQQYYTTPLTFGGGTKVEIK | BCMA-3, -46 VL Chain (aa) |
| 119 | AIRMTQSPSSLSASLGDRVTITCRASQDIRNSLAWYQQRPGKAPKLLLSAASRLESGVPS RFSGTTSGAEYALSISSLQPEDVASYFCQQYYSLPLSFGGGTKVEIK | BCMA-4 $V_L$ Chain (aa) |
| 120 | DIVMTQSPDSLAVSLGERATINCKSSQSVLYSSNNKNYLAWYQQKPGQPPKLLIYWASTR ESGVPDRFSGSGSGTDFTLTISSLQAEDVAVYYCQQYYSTPWTFGQGTKVDIK | BCMA-5 $V_L$ Chain (aa) |
| 121 | DIVMTQSPSSLSVSVGERVTITCRASQSISNSLAWYKQRPGEAPKLLIHAASNVEDGVPS RFSGRGSGTVFTLAISNVQPEDFATYYCQQSHMYPPTFGGGTKVEIK | BCMA-6 $V_L$ Chain (aa) |
| 122 | VIQLTQSPSSLSASVGDRVTITCRASQDIGDYLAWFQQRPGKAPKSLIYVASTLQSGVPS RFSGSGSGTHFTLTINSLQPEDFATYYCQQYHSHPWTFGPGTKVDIK | BCMA-7 $V_L$ Chain (aa) |
| 123 | DIVMTQSPDSLAVSLGERATINCKSSQSVLYSSNNKNYLAWYQQKPGQPPKLLIYWASTR ESGVPDRFSGSGSGTDFTLTISSLQAEDVAVYYCQQYYSTPYTFGQGTKLEIK | BCMA-8 $V_L$ Chain (aa) |
| 124 | SYELTQPPSVSVAPGQTARVTCGANNIGSKSVHWYQQKPGQAPMLVVYDDDDRPSGIPER FSGSNSGNTATLTISGVEAGDEADYFCHVWDRSRDHYVFGTGTKLTVL | BCMA-9 $V_L$ Chain (aa) |
| 125 | SYVLTQPPSVSVAPGQTARITCGGNNIERKNVHWYQQKPGQAPVPVVYDDSDRASGIPER FSASNSGNTATLTISGAQATDEAEYYCQAWDSSSTLYVFGTGTKLTVL | BCMA-10 $V_L$ Chain (aa) |
| 126 | QLVLTQPPSASGTPGQRVTISCSGSSSNIGSNAVNWYQQLPGTAPEVLIYNSHQRPSGVP DRFSGSKSGTSASLAINGLQSEDEADYYCAAWDDSLRGYVFGTGTKLTVL | BCMA-11 $V_L$ Chain (aa) |
| 127 | QSALTQPPSVSAAPGQKVTISCSGSRSNIGNNYVSWYQQLPGTAPKLLIYDNAKRPSGIP DRFSGSKSGTSATLDIAGLQTGDEADYYCQVWDSSSDHWVFGGGTKLTVL | BCMA-12 $V_L$ Chain (aa) |
| 128 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIVMTQSPDSLSVSPGERATISCKSSQSVLSTSNNKNYLAWYQQKPG QPPRLLLYWASTREAGVPDRFSGSGSGTDFTLTISSLQAEDVAVYYCQQYFSSPYTFGHG TKLEIK | BCMA-1 scFv (aa) |
| 129 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGPPSSDIWGQGTMVTVSSGG GGSGGGGSGGGGSEIVMTQSPATLSVSPGETATLSCRASQSIKTNLAWYQQKPGQAPRLL IYAASTRATGIPDRFSGSGSGTDFTLTITRLEPEDFAVYYCQQYGSSPTFGRGTKLEIK | BCMA-2 scFv (aa) |
| 130 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIVMTQSPDSLVVSLGERATINCKSSQSVLHSSNNKNYLAWYQQKPG QPPKLLIYWASTRESGVPDRFSGSGSGTDFTLTISSLQAEDVAVYYCQQYYTTPLTFGGG TKVEIK | BCMA-3, 46 scFv (aa) |
| 131 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSAIRMTQSPSSLSASLGDRVTITCRASQDIRNSLAWYQQRPGKAPKLL LSAASRLESGVPSRFSGTTSGAEYALSISSLQPEDVASYFCQQYYSLPLSFGGGTKVEIK | BCMA-4 scFv (aa) |
| 132 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIVMTQSPDSLAVSLGERATINCKSSQSVLYSSNNKNYLAWYQQKPG QPPKLLIYWASTRESGVPDRFSGSGSGTDFTLTISSLQAEDVAVYYCQQYYSTPWTFGQG TKVDIK | BCMA-5 scFv (aa) |
| 133 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIVMTQSPSSLSVSVGERVTITCRASQSISNSLAWYKQRPGEAPKLL IHAASNVEDGVPSRFSGRGSGTVFTLAISNVQPEDFATYYCQQSHMYPPTFGGGTKVEIK | BCMA-6 scFv (aa) |
| 134 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSVIQLTQSPSSLSASVGDRVTITCRASQDIGDYLAWFQQRPGKAPKSL IYVASTLQSGVPSRFSGSGSGTHFTLTINSLQPEDFATYYCQQYHSHPWTFGPGTKVDIK | BCMA-7 scFv (aa) |
| 135 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIVMTQSPDSLAVSLGERATINCKSSQSVLYSSNNKNYLAWYQQKPG | BCMA-8 scFv (aa) |

| SEQ ID NO | SEQUENCE | Description |
|---|---|---|
| | QPPKLLIYWASTRESGVPDRFSGSGSGTDFTLTISSLQAEDVAVYYCQQYYSTPYTFGQGTKLEIK | |
| 136 | EVQLVQSGGGLVKPGGSLRLSCAASGFTFSDYYMSWIRQAPGKGLEWVSYISSSGSTIYYADSVKGRFTISRDNAKNSLYLQMNSLRAEDTAVYYCARVDGDYVDDYWGQGTLVTVSSGGGGSGGGGSGGGGSSYELTQPPSVSVAPGQTARVTCGANNIGSKSVHWYQQKPGQAPMLVVYDDDDRPSGIPERFSGSNSGNTATLTISGVEAGDEADYFCHVWDRSRDHYVFGTGTKLTVL | BCMA-9 scFv (aa) |
| 137 | EVQLVESGGGLVKPGGSLRLSCAASGFPFSDYYMSWIRQAPGKGLEWVSYISSSGSTIYYADSVKGRFTISRDNAKNSLYLQMNSLRAEDTAVYYCAKVDGPPSFDIWGQGTMVTVSSGGGGSGGGGSGGGGSSYVLTQPPSVSVAPGQTARITCGGNNIERKNVHWYQQKPGQAPVPVVYDDSDRASGIPERFSASNSGNTATLTISGAQATDEAEYYCQAWDSSSTLYVFGTGTKLTVL | BCMA-10 scFv (aa) |
| 138 | QVQLVQSGGGLVQPGRSLRLSCAASGFTFDDYAMHWVRRAPGKGLEWVSGISWNSGSIGYADSVKGRFTISRDNAKNSLYLQMNSLRAEDTAVYYCARDLGPDYDPDAFDIWGQGTMVTVSSGGGGSGGGGSGGGGSQLVLTQPPSASGTPGQRVTISCSGSSSNIGSNAVNWYQQLPGTAPEVLIYNSHQRPSGVPDRFSGSKSGTSASLAINGLQSEDEADYYCAAWDDSLRGYVFGTGTKLTVL | BCMA-11 scFv (aa) |
| 139 | EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAKVDGPPSFDIWGQGTMVTVSSGGGGSGGGGSGGGGSQSALTQPPSVSAAPGQKVTISCSGSRSNIGNNYVSWYQQLPGTAPKLLIYDNAKRPSGIPDRFSGSKSGTSATLDIAGLQTGDEADYYCQVWDSSSDHWVFGGGTKLTVL | BCMA-12 scFv (aa) |
| 140 | SYAMH | BCMA-13 CDR-H1 (aa) Kabat numbering |
| 141 | SYGMH | BCMA-14, -15 CDR-H1 (aa) Kabat numbering |
| 142 | SSAMQ | BCMA-16 CDR-H1 (aa) Kabat numbering |
| 143 | SYWMS | BCMA-18 CDR-H1 (aa) Kabat numbering |
| 144 | SYYMH | BCMA-19 CDR-H1 (aa) Kabat numbering |
| 145 | VISYDGSNKYYADSVKG | BCMA-13, -14, -15 CDR-H2 (aa) Kabat numbering |
| 146 | WIVVGSGNTNYAQKFQE | BCMA-16 CDR-H2 (aa) Kabat numbering |
| 147 | HINQDGSEKYYVDSVKG | BCMA-18 CDR-H2 (aa) Kabat numbering |
| 148 | WINPNSGGTNYAQKFQG | BCMA-19 CDR-H2 (aa) Kabat numbering |
| 149 | LPGRDGYPGAFDY | BCMA-13, -14 CDR-H3 (aa) |
| 150 | DQYSSSAQRADFDY | BCMA-15 CDR-H3 (aa) |
| 151 | APYYDILTGYYL | BCMA-16 CDR-H3 (aa) |
| 152 | EADSSADY | BCMA-17, -33 CDR-H3 (aa) |
| 153 | WLAVTN | BCMA-18 CDR-H3 (aa) |
| 154 | DGGDV | BCMA-19 CDR-H3 (aa) |
| 155 | GGLGITPYYFDY | BCMA-20, -27 CDR-H3 (aa) |

-continued

| SEQ ID NO | SEQUENCE | Description |
|---|---|---|
| 156 | VDGGYTEDY | BCMA-21 CDR-H3 (aa) |
| 157 | VDGDYTEDY | BCMA-22, -23, -40 CDR-H3 (aa) |
| 158 | GFTFSSY | BCMA-13, -14, -15, -18 CDR-H1 (aa) Chothia numbering |
| 159 | GFTFTSS | BCMA-16 CDR-H1 (aa) Chothia numbering |
| 160 | GYTFTSY | BCMA-19 CDR-H1 (aa) Chothia numbering |
| 161 | SYDGSN | BCMA-13, -14, -15 CDR-H2 (aa) Chothia numbering |
| 162 | VVGSGN | BCMA-16 CDR-H2 (aa) Chothia numbering |
| 163 | NQDGSE | BCMA-18 CDR-H2 (aa) Chothia numbering |
| 164 | NPNSGG | BCMA-19 CDR-H2 (aa) Chothia numbering |
| 165 | GFTFSSYAMH | BCMA-13 CDR-H1 (aa) AbM numbering |
| 166 | GFTFSSYGMH | BCMA-14, -15 CDR-H1 (aa) AbM numbering |
| 167 | GFTFTSSAMQ | BCMA-16 CDR-H1 (aa) AbM numbering |
| 168 | GFTFSSYWMS | BCMA-18 CDR-H1 (aa) AbM numbering |
| 169 | GYTFTSYYMH | BCMA-19 CDR-H1 (aa) AbM numbering |
| 170 | VISYDGSNKY | BCMA-13, -14, -15 CDR-H2 (aa) AbM numbering |
| 171 | WIVVGSGNTN | BCMA-16 CDR-H2 (aa) AbM numbering |
| 172 | HINQDGSEKY | BCMA-18 CDR-H2 (aa) AbM numbering |
| 173 | WINPNSGGTN | BCMA-19 CDR-H2 (aa) AbM numbering |
| 174 | GSGSNIGSNDVS | BCMA-13, -14, -15, -16, -18, -21 CDR-L1 (aa) |
| 175 | GGNNIGFKGVQ | BCMA-17, -33 CDR-L1 (aa) |
| 176 | TGTSSDVGDYNYVA | BCMA-19 CDR-L1 (aa) |
| 177 | SGGKTVN | BCMA-20, -27 CDR-L1 (aa) |
| 178 | TGSSSDVGKYNLVS | BCMA-22, -23 CDR-L1 (aa) |

| SEQ ID NO | SEQUENCE | Description |
|---|---|---|
| 179 | WNDQRPS | BCMA-13, -14, -15, -16, -18, -21 CDR-L2 (aa) |
| 180 | DDSDRPS | BCMA-17, -32, -33 CDR-L2 (aa) |
| 181 | EVINRPS | BCMA-19 CDR-L2 (aa) |
| 182 | SNDQRPS | BCMA-20, -27 CDR-L2 (aa) |
| 183 | DVNKRPS | BCMA-22, -23, -40 CDR-L2 (aa) |
| 184 | AAWDDSLGGSWV | BCMA-13 CDR-L3 (aa) |
| 185 | AAWDDRLNGFWV | BCMA-14 CDR-L3 (aa) |
| 186 | AAWDDSLSGWV | BCMA-15 CDR-L3 (aa) |
| 187 | ASWDDSLSGWV | BCMA-16 CDR-L3 (aa) |
| 188 | QVWDSASDHWV | BCMA-17, -33 CDR-L3 (aa) |
| 189 | AAWDDSLNGWV | BCMA-18 CDR-L3 (aa) |
| 190 | ISYSRGSTPYV | BCMA-19 CDR-L3 (aa) |
| 191 | GSWDDSLNAWV | BCMA-20, -27 CDR-L3 (aa) |
| 192 | AAWDDSLNGYV | BCMA-21 CDR-L3 (aa) |
| 193 | CSYGGSRSYV | BCMA-22, -40 CDR-L3 (aa) |
| 194 | SSYGGSRSYV | BCMA-23 CDR-L3 (aa) |
| 195 | QMQLVQYGGGVVQPGRSLRLSCAASGFTFS | BCMA-13 VH FR1 (aa) |
| 196 | EVQLLESGGGVVQPGRSLRLSCAASGFTFS | BCMA-14 VH FR1 (aa) |
| 197 | QVQLLESGGGLVKPGGSLRLSCAASGFTFS | BCMA-15, -47 VH FR1 (aa) |
| 198 | EVQLVQSGPEVKKPGTSVKVSCKASGFTFT | BCMA-16 VH FR1 (aa) |
| 199 | QVQLVQSGGGLVKPGGSLRLSCAASGFTFS | BCMA-17, -33, -36, -38, -41 VH FR1 (aa) |
| 200 | EVQLLESGGGLVQPGGSLRLSCAASGFTFS | BCMA-18 VH FR1 (aa) |
| 201 | QVQLVQSGAEVKKPGASVKVSCKASGYTFT | BCMA-19 VH FR1 (aa) |
| 202 | EVQLLESGGGLVQPGRSLRLSCAASGFTFD | BCMA-20 VH FR1 (aa) |
| 203 | EVQLVESGGGLVKPGGSLKLSCAASGFTFS | BCMA-21 VH FR1 (aa) |
| 204 | WVRQAPGKGLEWVA | BCMA-13, -14, -15 VH FR2 (aa) |
| 205 | WVRQARGQRLEWIG | BCMA-16 VH FR2 (aa) |
| 206 | WIRLAPGKGLEWVS | BCMA-17 VH FR2 (aa) |
| 207 | WHRQAPGKGPEWVA | BCMA-18 VH FR2 (aa) |
| 208 | WVRQAPGQGLEWMG | BCMA-19 VH FR2 (aa) |

-continued

| SEQ ID NO | SEQUENCE | Description |
|---|---|---|
| 209 | WVRQAPGKGLEWVS | BCMA-20, -27, -28, -29, -30, -34, -39 VH FR2 (aa) |
| 210 | RFTISRDNSKNTLYLQMNSLKAEDTAVYYCAT | BCMA-13 VH FR3 (aa) |
| 211 | RFTISRDNSKNTLYLQMNSLRAEDTAVYYCAT | BCMA-14 VH FR3 (aa) |
| 212 | RFTISRDNSKNTLYLQMNSLRAEDTAVYYCAK | BCMA-15 VH FR3 (aa) |
| 213 | RVTITRDMSTSTAYMELSSLRSEDTAVYYCAA | BCMA-16 VH FR3 (aa) |
| 214 | RFTISRDNAESSLYLQMNSLRAEDTAVYYCAR | BCMA-18 VH FR3 (aa) |
| 215 | RVTMTRDTSISTAYMELSRLRSDDTAVYYCAR | BCMA-19 VH FR3 (aa) |
| 216 | RFTISRDNAKNSLYLQMNSLRAEDTALYYCAK | BCMA-20, -27 VH FR3 (aa) |
| 217 | RGQGTLVTVSS | BCMA-13 VH FR4 (aa) |
| 218 | RGPGTLVTVSS | BCMA-14 VH FR4 (aa) |
| 219 | WGQGTLVNVSS | BCMA-17, -33 VH FR4 (aa) |
| 220 | WGQGTTVTVSS | BCMA-19 VH FR4 (aa) |
| 221 | QAVLTQPPSASGTPGQRVTISC | BCMA-13, -14 VL FR1 (aa) |
| 222 | QSVLTQPPSASGTPGQRVTISC | BCMA-15, -18, -21 VL FR1 (aa) |
| 223 | QSALTQPPSASGTPGQRVTISC | BCMA-16 VL FR1 (aa) |
| 224 | QPVLTQPPSVSVAPGKTAMITC | BCMA-17, -33 VL FR1 (aa) |
| 225 | QAVLTQPASVSGSPGQSITISC | BCMA-19 VL FR1 (aa) |
| 226 | QPVLTQPPSASGTPGQRVTISC | BCMA-20, -27 VL FR1 (aa) |
| 227 | QSALTQPASVSGSPGQSITISC | BCMA-22, -23, -40 VL FR1 (aa) |
| 228 | WYQQIPGTAPKLLIY | BCMA-13, -14, -15, -16, -18, -21 VL FR2 (aa) |
| 229 | WYQQKTGQAPVLVVY | BCMA-17, -33 VL FR2 (aa) |
| 230 | WYQQHPGKDPKLMIF | BCMA-19 VL FR2 (aa) |
| 231 | WFRQVPGTAPQLLIY | BCMA-20, -27 VL FR2 (aa) |
| 232 | WYQQPPGKAPKLIIY | BCMA-22, -23, -40 VL FR2 (aa) |
| 233 | GVPDRFSASKSGTSASLAISGLRSEDEADYYC | BCMA-13 VL FR3 (aa) |
| 234 | GVPDRFSGSKSGASASLAISGLQSEDEADYYC | BCMA-14 VL FR3 (aa) |
| 235 | GVPDRFSGSKSGTSASLVISGLRSEDEADYYC | BCMA-15 VL FR3 (aa) |
| 236 | GVPDRFSGSKSGTSASLAISGLQSEDEADYYC | BCMA-16 VL FR3 (aa) |
| 237 | GIPERFSGSNSGNTATLTISRVEAGDEADYYC | BCMA-17, -33 VL FR3 (aa) |

-continued

| SEQ ID NO | SEQUENCE | Description |
|---|---|---|
| 238 | GVPDRFSGSKSGTSASLAISGLRSEDEADYYC | BCMA-18 VL FR3 (aa) |
| 239 | GVSDRFSGSKSGNTASLDISGLQPEDEADYYC | BCMA-19 VL FR3 (aa) |
| 240 | GVPDRFSGSKSGSSASLDISGLQSEDEAYYYC | BCMA-20, -27 VL FR3 (aa) |
| 241 | GVPDRFSGSKSGISASLAISGLRSEDEADYYC | BCMA-21 VL FR3 (aa) |
| 242 | GVSNRFSGSKSGNTATLTISGLQGDDEADYYC | BCMA-22, -23, -40 VL FR3 (aa) |
| 243 | FGGGTKVTVL | BCMA-13 VL FR4 (aa) |
| 244 | IGTGTKVTVL | BCMA-19 VL FR4 (aa) |
| 245 | FGGETKLTVL | BCMA-20, -27 VL FR4 (aa) |
| 246 | FGTGTKVTVL | BCMA-21, -22, -23 VL FR4 (aa) |
| 247 | QMQLVQYGGGVVQPGRSLRLSCAASGFTFSSYAMHWVRQAPGRGLEWVAVISYDGSNKYYADSVKGRFTISRDNSKNTLYLQMNSLKAEDTAVYYCATLPGRDGYPGAFDYRGQGTLVTVSS | BCMA-13 $V_H$ Chain (aa) |
| 248 | EVQLLESGGGVVQPGRSLRLSCAASGFTFSSYGMHWVRQAPGRGLEWVAVISYDGSNKYYADSVKGRFTISRDNSKNTLYLQMNSLRAEDTAVYYCATLPGRDGYPGAFDYRGPGTLVTVSS | BCMA-14 $V_H$ Chain (aa) |
| 249 | QVQLLESGGGLVKPGGSLRLSCAASGFTFSSYGMHWVRQAPGRGLEWVAVISYDGSNKYYADSVKGRFTISRDNSKNTLYLQMNSLRAEDTAVYYCAKDQYSSSAQRADFDYWGQGTLVTVSS | BCMA-15 $V_H$ Chain (aa) |
| 250 | EVQLVQSGPEVKKPGTSVKVSCKASGFTFTSSAMQWVRQARGQRLEWIGWIVVGSGNTNYAQKFQERVTITRDMSTSTAYMELSSLRSEDTAVYYCAAAPYYDILTGYYLWGQGTLVTVSS | BCMA-16 $V_H$ Chain (aa) |
| 251 | QVQLVQSGGGLVKPGGSLRLSCAASGFTFSDYYMSWIRLAPGRGLEWVSYISSSGSTIYYADSVKGRFTISRDNAKNSLYLQMNSLRAEDTAVYYCAREADSSADYWGQGTLVNVSS | BCMA-17 $V_H$ Chain (aa) |
| 252 | EVQLLESGGGLVQPGGSLRLSCAASGFTFSSYWMSWHRQAPGKGPEWVAHINQDGSEKYYVDSVKGRFTISRDNAESSLYLQMNSLRAEDTAVYYCARWLAVTNWGQGTLVTVSS | BCMA-18 $V_H$ Chain (aa) |
| 253 | QVQLVQSGAEVKKPGASVKVSCKASGYTFTSYYMHWVRQAPGQGLEWMGWINPNSGGTNYAQKFQGRVTMTRDTSISTAYMELSRLRSDDTAVYYCARDGGDVWGQGTTVTVSS | BCMA-19 $V_H$ Chain (aa) |
| 254 | EVQLLESGGGLVQPGRSLRLSCAASGFTFDDYAMHWVRQAPGRGLEWVSGISWNSGSIGYADSVKGRFTISRDNAKNSLYLQMNSLRAEDTALYYCAKGGLGITPYYFDYWGQGTLVTVSS | BCMA-20 $V_H$ Chain (aa) |
| 255 | EVQLVESGGGLVKPGGSLKLSCAASGFTFSDYYMSWIRQAPGRGLEWVSYISSSGSTIYYADSVKGRFTISRDNAKNSLYLQMNSLRAEDTAVYYCAKVDGGYTEDYWGQGTLVTVSS | BCMA-21 $V_H$ Chain (aa) |
| 256 | EVQLVESGGGLVKPGGSLRLSCAASGFTFSDYYMSWIRQAPGRGLEWVSYISSSGSTIYYADSVKGRFTISRDNAKNSLYLQMNSLRAEDTAVYYCAKVDGDYTEDYWGQGTLVTVSS | BCMA-22, -23, -40 $V_H$ Chain (aa) |
| 257 | QAVLTQPPSASGTPGQRVTISCSGSGSNIGSNDVSWYQQIPGTAPKLLIYWNDQRPSGVPDRFSASKSGTSASLAISGLRSEDEADYYCAAWDDSLGGSWVFGGGTKVTVL | BCMA-13 $V_L$ Chain (aa) |
| 258 | QAVLTQPPSASGTPGQRVTISCSGSGSNIGSNDVSWYQQIPGTAPKLLIYWNDQRPSGVPDRFSGSKSGASASLAISGLQSEDEADYYCAAWDDRLNGFWVFGGGTKLTVL | BCMA-14 $V_L$ Chain (aa) |
| 259 | QSVLTQPPSASGTPGQRVTISCSGSGSNIGSNDVSWYQQIPGTAPKLLIYWNDQRPSGVPDRFSGSKSGTSASLVISGLRSEDEADYYCAAWDDSLSGWVFGGGTKLTVL | BCMA-15 $V_L$ Chain (aa) |
| 260 | QSALTQPPSASGTPGQRVTISCSGSGSNIGSNDVSWYQQIPGTAPKLLIYWNDQRPSGVPDRFSGSKSGTSASLAISGLQSEDEADYYCASWDDSLSGWVFGGGTKLTVL | BCMA-16 $V_L$ Chain (aa) |
| 261 | QPVLTQPPSVSVAPGKTAMITCGGNNIGFKGVQWYQQKTGQAPVLVVYDDSDRPSGIPERFSGSNSGNTATLTISRVEAGDEADYYCQVWDSASDHWVFGGGTKLTVL | BCMA-17, -33 $V_L$ Chain (aa) |

| SEQ ID NO | SEQUENCE | Description |
|---|---|---|
| 262 | QSVLTQPPSASGTPGQRVTISCSGSGSNIGSNDVSWYQQIPGTAPKLLIYWNDQRPSGVP DRFSGSKSGTSASLAISGLRSEDEADYYCAAWDDSLNGWVFGGGTKLTVL | BCMA-18 V$_L$ Chain (aa) |
| 263 | QAVLTQPASVSGSPGQSITISCTGTSSDVGDYNYVAWYQQHPGKDPKLMIFEVINRPSGV SDRFSGSKSGNTASLDISGLQPEDEADYYCISYSRGSTPYVIGTGTKVTVL | BCMA-19 V$_L$ Chain (aa) |
| 264 | QPVLTQPPSASGTPGQRVTISCSGGKTVNWFRQVPGTAPQLLIYSNDQRPSGVPDRFSGS KSGSSASLDISGLQSEDEAYYYCGSWDDSLNAWVFGGETKLTVL | BCMA-20, -27 V$_L$ Chain (aa) |
| 265 | QSVLTQPPSASGTPGQRVTISCSGSGSNIGSNDVSWYQQIPGTAPKLLIYWNDQRPSGVP DRFSGSKSGISASLAISGLRSEDEADYYCAAWDDSLNGYVFGTGTKVTVL | BCMA-21 V$_L$ Chain (aa) |
| 266 | QSALTQPASVSGSPGQSITISCTGSSSDVGKYNLVSWYQQPPGKAPKLIIYDVNKRPSGV SNRFSGSKSGNTATLTISGLQGDDEADYYCCSYGGSRSYVFGTGTKVTVL | BCMA-22 V$_L$ Chain (aa) |
| 267 | QSALTQPASVSGSPGQSITISCTGSSSDVGKYNLVSWYQQPPGKAPKLIIYDVNKRPSGV SNRFSGSKSGNTATLTISGLQGDDEADYYCSSYGGSRSYVFGTGTKVTVL | BCMA-23 V$_L$ Chain (aa) |
| 268 | QMQLVQYGGGVVQPGRSLRLSCAASGFTFSSYAMHWVRQAPGRGLEWVAVISYDGSNKYY ADSVKGRFTISRDNSKNTLYLQMNSLKAEDTAVYYCATLPGRDGYPGAFDYRGQGTLVTV SSGGGGSGGGGSGGGGSQAVLTQFPSASGTPGQRVTISCSGSGSNIGSNDVSWYQQIPGT APKLLIYWNDQRPSGVPDRFSASKSGTSASLAISGLRSEDEADYYCAAWDDSLGGSWVFG GGTKVTVL | BCMA-13 scFv (aa) |
| 269 | EVQLLESGGGVVQPGRSLRLSCAASGFTFSSYGMHWVRQAPGRGLEWVAVISYDGSNKYY ADSVKGRFTISRDNSKNTLYLQMNSLRAEDTAVYYCATLPGRDGYPGAFDYRGPGTLVTV SSGGGGSGGGGSGGGGSQAVLTQFPSASGTPGQRVTISCSGSGSNIGSNDVSWYQQIPGT APKLLIYWNDQRPSGVPDRFSGSKSGASASLAISGLQSEDEADYYCAAWDDRLNGFWVFG GGTKLTVL | BCMA-14 scFv (aa) |
| 270 | QVQLLESGGGLVKPGGSLRLSCAASGFTFSSYGMHWVRQAPGRGLEWVAVISYDGSNKYY ADSVKGRFTISRDNSKNTLYLQMNSLRAEDTAVYYCAKDQYSSSAQRADFDYWGQGTLVT VSSGGGGSGGGGSGGGGSQSVLTQPPSASGTPGQRVTISCSGSGSNIGSNDVSWYQQIPG TAPKLLIYWNDQRPSGVPDRFSGSKSGTSASLVISGLRSEDEADYYCAAWDDSLSGWVFG GGTKLTVL | BCMA-15 scFv (aa) |
| 271 | EVQLVQSGPEVKKPGTSVKVSCKASGFTFTSSAMQWVRQARGQRLEWIGWIVVGSGNTNY AQKFQERVTITRDMSTSTAYMELSSLRSEDTAVYYCAAAPYYDILTGYYLWGQGTLVTVS SGGGGSGGGGSGGGGSQSALTQPPSASGTPGQRVTISCSGSGSNIGSNDVSWYQQIPGTA PKLLIYWNDQRPSGVPDRFSGSKSGTSASLAISGLQSEDEADYYCASWDDSLSGWVFGGG TKLTVL | BCMA-16 scFv (aa) |
| 272 | QVQLVQSGGGLVKPGGSLRLSCAASGFTFSDYYMSWIRLAPGKGLEWVSYISSSGSTIYY ADSVKGRFTISRDNAKNSLYLQMNSLRAEDTAVYYCAREADSSADYWGQGTLVNVSSGGG GSGGGGSGGGGSQPVLTQPPSVSAPGKTAMITCGGNNIGFKGVQWYQQKTGQAPVLVVY DDSDRPSGIPERFSGSNSGNTATLTISRVEAGDEADYYCQVWDSASDHWVFGGGTKLTVL | BCMA-17 scFv (aa) |
| 273 | EVQLLESGGGLVQPGGSLRLSCAASGFTFSSYWMSWHRQAPGKGPEWVAHINQDGSEKYY VDSVKGRFTISRDNAESSLYLQMNSLRAEDTAVYYCARWLAVTNWGQGTLVTVSSGGGGS GGGGSGGGGSQSVLTQPPSASGTPGQRVTISCSGSGSNIGSNDVSWYQQIPGTAPKLLIY WNDQRPSGVPDRFSGSKSGTSASLAISGLRSEDEADYYCAAWDDSLNGWVFGGGTKLTVL | BCMA-18 scFv (aa) |
| 274 | QVQLVQSGAEVKKPGASVKVSCKASGYTFTSYYMHWVRQGQGLEWMGWINPNSGGTNY AQKFQGRVTMTRDTSISTAYMELSRLRSDDTAVYYCARDGGDVWGQGTTVTVSSGGGGSG GGSGGGGSQAVLTQPASVSGSPGQSITISCTGTSSDVGDYNYVAWYQQHPGKDPKLMIF EVINRPSGVSDRFSGSKSGNTASLDISGLQPEDEADYYCISYSRGSTPYVIGTGTKVTVL | BCMA-19 scFv (aa) |
| 275 | EVQLLESGGGLVQPGRSLRLSCAASGFTFDDYAMHWVRQAPGKGLEWVSGISWNSGSIGY ADSVKGRFTISRDNAKNSLYLQMNSLRAEDTALYYCAKGGLGITPYYFDYWGQGTLVTVS SGGGGSGGGGSGGGGSQPVLTQPPSASGTPGQRVTISCSGGKTVNWFRQVPGTAPQLLIY SNDQRPSGVPDRFSGSKSGSSASLDISGLQSEDEAYYYCGSWDDSLNAWVFGGETKLTVL | BCMA-20 scFv (aa) |
| 276 | EVQLVESGGGLVKPGGSLKLSCAASGFTFSDYYMSWIRQAPGKGLEWVSYISSSGSTIYY ADSVKGRFTISRDNAKNSLYLQMNSLRAEDTAVYYCAKVDGGYTEDYWGQGTLVTVSSGG GGSGGGGSGGGGSQSVLTQPPSASGTPGQRVTISCSGSGSNIGSNDVSWYQQIPGTAPKL LIYWNDQRPSGVPDRFSGSKSGISASLAISGLRSEDEADYYCAAWDDSLNGYVFGTGTKV TVL | BCMA-21 scFv (aa) |
| 277 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGDYTEDYWGQGTLVTVSSGG GGSGGGGSGGGGSQSALTQPASVSGSPGQSITISCTGSSSDVGKYNLVSWYQQPPGKAPK LIIYDVNKRPSGVSNRFSGSKSGNTATLTISGLQGDDEADYYCCSYGGSRSYVFGTGTKV TVL | BCMA-22 scFv (aa) |

| SEQ ID NO | SEQUENCE | Description |
|---|---|---|
| 278 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGDYTEDYWGQGTLVTVSSGG GGSGGGGSGGGGSQSALTQPASVSGSPGQSITISCTGSSSDVGKYNLVSWYQQPPGKAPK LIIYDVNKRPSGVSNRFSGSKSGNTATLTISGLQGDDEADYYCSSYGGRSYVFGTGTKV TVL | BCMA-23 scFv (aa) |
| 279 | VDGDDAFDI | $V_H$-3 CDR-H3 (aa) |
| 280 | DPLSWDSSGKGPR | $V_H$-4 CDR-H3 (aa) |
| 281 | ENYDFWSWRYYYDMDV | $V_H$-5 CDR-H3 (aa) |
| 282 | VDGPPSYDI | $V_H$-6 CDR-H3 (aa) |
| 283 | GDWDDAFDI | $V_H$-7 CDR-H3 (aa) |
| 284 | VDGDYEDY | $V_H$-9 CDR-H3 (aa) |
| 285 | DVPSSGDDAFDI | $V_H$-10 CDR-H3 (aa) |
| 286 | VDGDDVFDI | $V_H$-11 CDR-H3 (aa) |
| 287 | VDGDAFDI | $V_H$-12 CDR-H3 (aa) |
| 288 | DYSIN | Reference Antibody 1 $V_H$ CDR-H1 (aa) |
| 289 | NFGMN | Reference Antibody 2 $V_H$ CDR-H1 (aa) |
| 290 | WINTETREPAYAYDFRG | Reference Antibody 1 $V_H$ CDR-H2 (aa) |
| 291 | WINTYTGESYFADDFKG | Reference Antibody 2 $V_H$ CDR-H2 (aa) |
| 292 | DYSYAMDY | Reference Antibody 1 $V_H$ CDR-H3 (aa) |
| 293 | GEIYYGYDGGFAY | Reference Antibody 2 $V_H$ CDR-H3 (aa) |
| 294 | GYTFTDY | Reference Antibody 1 $V_H$ CDR-H1 (aa) Chothia numbering |
| 295 | GYTFTNF | Reference Antibody 2 $V_H$ CDR-H1 (aa) Chothia numbering |
| 296 | NTETRE | Reference Antibody 1 $V_H$ CDR-H2 (aa) Chothia numbering |
| 297 | NTYTGE | Reference Antibody 2 $V_H$ CDR-H2 (aa) Chothia numbering |
| 298 | GYTFTDYSIN | Reference Antibody 1 $V_H$ CDR-H1 (aa) AbM numbering |
| 299 | GYTFTNFGMN | Reference Antibody 2 $V_H$ CDR-H1 (aa) AbM numbering |
| 300 | WINTETREPA | Reference Antibody 1 $V_H$ CDR-H2 (aa) AbM numbering |

| SEQ ID NO | SEQUENCE | Description |
|---|---|---|
| 301 | WINTYTGESY | Reference Antibody 2 $V_H$ CDR-H2 (aa) AbM numbering |
| 302 | RASESVTILGSHLIH | Reference Antibody 1 VL CDR-L1 (aa) |
| 303 | RASQDVNTAVS | Reference Antibody 2 VL CDR-L1 (aa) |
| 304 | LASNVQT | Reference Antibody 1 VL CDR-L2 (aa) |
| 305 | SASYRYT | Reference Antibody 2 VL CDR-L2 (aa) |
| 306 | LQSRTIPRT | Reference Antibody 1 VL CDR-L3 (aa) |
| 307 | QQHYSTPWT | Reference Antibody 2 VL CDR-L3 (aa) |
| 308 | QIQLVQSGPELKKPGETVKISCKASGYTFT | Reference Antibody 1 $V_H$ FR1 (aa) |
| 309 | QIQLVQSGPDLKKPGETVKLSCKASGYTFT | Reference Antibody 2 $V_H$ FR1 (aa) |
| 310 | WVKRAPGKGLKWMG | Reference Antibody 1 $V_H$ FR2 (aa) |
| 311 | WVKQAPGKGFKWMA | Reference Antibody 2 $V_H$ FR2 (aa) |
| 312 | RFAFSLETSASTAYLQINNLKYEDTATYFCAL | Reference Antibody 1 $V_H$ FR3 (aa) |
| 313 | RFAFSVETSATTAYLQINNLKTEDTATYFCAR | Reference Antibody 2 $V_H$ FR3 (aa) |
| 314 | WGQGTSVTVSS | Reference Antibody 1 $V_H$ FR4 (aa) |
| 315 | WGQGTLVTVSA | Reference Antibody 2 $V_H$ FR4 (aa) |
| 316 | DIVLTQSPPSLAMSLGKRATISC | Reference Antibody 1 $V_L$ FR1 (aa) |
| 317 | DVVMTQSHRFMSTSVGDRVSITC | Reference Antibody 2 $V_L$ FR1 (aa) |
| 318 | WYQQKPGQPPTLLIQ | Reference Antibody 1 $V_L$ FR2 (aa) |
| 319 | WYQQKPGQSPKLLIF | Reference Antibody 2 $V_L$ FR2 (aa) |
| 320 | GVPARFSGSGSRTDFTLTIDPVEEDDVAVYYC | Reference Antibody 1 $V_L$ FR3 (aa) |
| 321 | GVPDRFTGSGSGADFTLTISSVQAEDLAVYYC | Reference Antibody 2 $V_L$ FR3 (aa) |
| 322 | FGGGTKLEIK | Reference Antibody 1 $V_L$ FR4 (aa) |
| 323 | FGGGTKLDIK | Reference Antibody 2 $V_L$ FR4 (aa) |
| 324 | QIQLVQSGPELKKPGETVKISCKASGYTFTDYSINWVKRAPGKGLKWMGWINTETREPAYAYDFRGRFAFSLETSASTAYLQINNLKYEDTATYFCALDYSYAMDYWGQGTSVTVSS | Reference Antibody 1 $V_H$ Chain (aa) |

| SEQ ID NO | SEQUENCE | Description |
|---|---|---|
| 325 | QIQLVQSGPDLKKPGETVKLSCKASGYTFTNFGMNWVKQAPGKGFKWMAWINTYTGES ADDFKGRFAFSVETSATTAYLQINNLKTEDTATYFCARGEIYYGYDGGFAYWGQGTLVTV SA | YF Reference Antibody 2 $V_H$ Chain (aa) |
| 326 | DIVLTQSPPSLAMSLGKRATISCRASESVTILGSHLIHWYQQKPGQPPTLLIQLASNVQT GVPARFSGSGSRTDFTLTIDPVEEDDVAVYYCLQSRTIPRTFGGGTKLEIK | Reference Antibody 1 $V_L$ Chain (aa) |
| 327 | DVVMTQSHRFMSTSVGDRVSITCRASQDVNTAVSWYQQKPGQSPKLLIFSASYRYTGVPD RFTGSGSGADFTLTISSVQAEDLAVYYCQQHYSTPWTFGGGTKLDIK | Reference Antibody 2 $V_L$ Chain (aa) |
| 328 | DIVLTQSPPSLAMSLGKRATISCRASESVTILGSHLIHWYQQKPGQPPTLLIQLASNVQT GVPARFSGSGSRTDFTLTIDPVEEDDVAVYYCLQSRTIPRTFGGGTKLEIKGGGGSGGGG SGGGGSQIQLVQSGPELKKPGETVKISCKASGYTFTDYSINWVKRAPGKGLKWMGWINTE TREPAYAYDFRGRFAFSLETSASTAYLQINNLKYEDTATYFCALDYSYAMDYWGQGTSVT VSS | Reference 1 VL-VH scFv (aa) |
| 329 | QIQLVQSGPDLKKPGETVKLSCKASGYTFTNFGMNWVKQAPGKGFKWMAWINTYTGESYF ADDFKGRFAFSVETSATTAYLQINNLKTEDTATYFCARGEIYYGYDGGFAYWGQGTLVTV SAGGGSGGGGSGGGGSDVVMTQSHRFMSTSVGDRVSITCRASQDVNTAVSWYQQKPGQS PKLLIFSASYRYTGVPDRFTGSGSGADFTLTISSVQAEDLAVYYCQQHYSTPWTFGGGTK LDIK | Reference 2 VH-VL scFv (aa) |
| 330 | CAGGTGCAGCTGGTGCAGTCTGGGGGAGGCTTGGTACAGCCAGGGCGGTCCCTGAGACTC TCCTGTACAGCTTCTGGATTCACCTTTGGTGATTATGCTATGAGCTGGTTCCGCCAGGCT CCAGGGAAGGGGCTGGAGTGGGTAGGTTTCATTAGAAGCAAAGCTTATGGTGGGACAACA GAATACGCCGCGTCTGTGAAAGGCAGATTCACCATCTCAAGAGATGATTCCAAAAGCATC GCCTATCTGCAAATGAACAGCCTGAAAACCGAGGACACAGCCGTGTATTACTGTGCGGCC TGGAGTGCCCCGACTGACTACTGGGGCCAGGGAACCCTGGTCACCGTCTCCTCAGGTGGA GGCGGTTCAGGCGGAGGTGGCTCTGGCGGTGGCGGATCGGATATTGTGATGACCCAGTCT CCAGACTCCCTGTCTGTGTCTCCGGGCGAGAGGGCCACCATCAGCTGCAAGTCCAGCCAG AGTGTTTTATCCACCTCCAACAATAAGAACTATTTAGCTTGGTACCAGCAGAAACCAGGA CAGCCCCCTAGGCTGCTCCTTTACTGGGCATCTACCCGGGAGGCCGGGGTCCCTGACCGA TTCAGTGGCAGCGGGTCTGGGACAGATTTCACTCTCACCATCAGCAGCCTGCAGGCTGAA GATGTGGCGGTTTATTACTGTCAACAATATTTCAGTTCTCCGTACACTTTTGGCCACGGG ACCAAGCTGGAAATCAAA | BCMA-1 scFv (nt) |
| 331 | GAGGTGCAGCTGGTGGAGTCTGGGGGAGGCTTGGTCAAGCCTGGAGGGTCCCTGAGACTC TCCTGTGCAGCCTCTGGATTCACCTTCAGTGACTACTACATGAGCTGGATCCGCCAGGCT CCAGGGAAGGGGCTGGAGTGGGTTTCATACATTAGTAGTAGTGGTAGTACCATATACTAC GCAGACTCTGTGAAGGGCCGATTCACCATCTCCAGGGACAACGCCAAGAACTCACTGTAT CTGCAAATGAACAGCCTGAGAGCCGAGGACACGGCCGTGTATTACTGTGCGAAAGTGGAT GGCCCTCCTTCTTCTGATATCTGGGGCCAAGGGACAATGGTCACCGTCTCCTCAGGTGGA GGCGGTTCAGGCGGAGGTGGCTCTGGCGGTGGCGGATCGGAAATAGTGATGACGCAGTCT CCAGCCACCCTGTCTGTGTCTCCAGGGGAAAGAGCCACCCTCTCCTGCAGGGCCAGTCAG AGTATTAAGACCAACTTGGCCTGGTACCAGCAGAAACCTGGCCAGGCTCCCAGGCTCCTC ATCTATGCTGCATCCACCAGGGCACTGGCATCCCAGACAGATTCAGTGGCAGTGGGTCT GGGACAGACTTCACTCTCACCATCACCAGACTGGAGCCTGAAGATTTTGCAGTGTATTAC TGTCAGCAATATGGTAGCTCACCCACTTTTGGCCGGGGGACCAAGCTGGAAATCAAA | BCMA-2 scFv (nt) |
| 332 | CAGGTGCAGCTGGTGCAGTCTGGGGGAGGCTTGGTACAGCCAGGGCGGTCCCTGAGACTC TCCTGTACAGCTTCTGGATTCACCTTTGGTGATTATGCTATGAGCTGGTTCCGCCAGGCT CCAGGGAAGGGGCTGGAGTGGGTAGGTTTCATTAGAAGCAAAGCTTATGGTGGGACAACA GAATACGCCGCGTCTGTGAAAGGCAGATTCACCATCTCAAGAGATGATTCCAAAAGCATC GCCTATCTGCAAATGAACAGCCTGAAAACCGAGGACACAGCCGTGTATTACTGTGCGGCC TGGAGTGCCCCGACTGACTACTGGGGCCAGGGAACCCTGGTCACCGTCTCCTCAGGTGGA GGCGGTTCAGGCGGAGGTGGCTCTGGCGGTGGCGGATCGGATATTGTGATGACCCAGTCT CCAGACTCCCTGGTTGTGTCTCTGGGCGAGAGGGCCACCATCAACTGCAAGTCCAGCCAG AGTGTTTTACACAGCTCCAACAATAAGAATTACTTAGCTTGGTACCAGCAGAAACCAGGA CAGCCTCCTAAGCTGCTCATTTACTGGGCATCTACCCGGGAATCCGGGGTCCCTGACCGG TTCAGTGGCAGCGGGTCTGGGACAGATTTCACTCTCACCATCAGCAGCCTGCAGGCTGAA GATGTGGCAGTTTATTACTGTCAGCAGTATTATACTACTCCGCTCACTTTCGGCGGAGGG ACCAAGGTGGAAATCAAA | BCMA-3 scFv (nt) |
| 333 | CAGGTGCAGCTGGTGCAGTCTGGGGGAGGCTTGGTACAGCCAGGGCGGTCCCTGAGACTC TCCTGTACAGCTTCTGGATTCACCTTTGGTGATTATGCTATGAGCTGGTTCCGCCAGGCT CCAGGGAAGGGGCTGGAGTGGGTAGGTTTCATTAGAAGCAAAGCTTATGGTGGGACAACA GAATACGCCGCGTCTGTGAAAGGCAGATTCACCATCTCAAGAGATGATTCCAAAAGCATC GCCTATCTGCAAATGAACAGCCTGAAAACCGAGGACACAGCCGTGTATTACTGTGCGGCC TGGAGTGCCCCGACTGACTACTGGGGCCAGGGAACCCTGGTCACCGTCTCCTCAGGTGGA GGCGGTTCAGGCGGAGGTGGCTCTGGCGGTGGCGGATCGGCCATCCGGATGACCCAGTCT CCATCCTCCCTGTCCGCGTCTCTGGGGACAGAGTCACCATCACTTGCCGGGCGAGTCAG GACATTAGGAATTCTTTGGCCTGGTATCAGCAGAGGCCAGGGAAAGCCCCTAAACTCCTG | BCMA-4 scFv (nt) |

| SEQ ID NO | SEQUENCE | Description |
|---|---|---|
| | CTTTCTGCTGCATCCAGATTGGAAAGTGGGGTCCCTTCTAGGTTCAGTGGCACTACTTCT<br>GGGGCGGAGTATGCTCTCAGCATCAGCAGCCTGCAGCCTGAAGATGTCGCATCTTATTTC<br>TGTCAGCAGTATTATAGTCTCCCTCTCTCCTTCGGCGGAGGGACCAAGGTGGAAATCAAA | |
| 334 | CAGGTGCAGCTGGTGCAGTCTGGGGGAGGCTTGGTACAGCCAGGGCGGTCCCTGAGACTC<br>TCCTGTACAGCTTCTGGATTCACCTTTGGTGATTATGCTATGAGCTGGTTCCGCCAGGCT<br>CCAGGGAAGGGGCTGGAGTGGGTAGGTTTCATTAGAAGCAAAGCTTATGGTGGGACAACA<br>GAATACGCCGCGTCTGTGAAAGGCAGATTCACCATCTCAAGAGATGATTCCAAAAGCATC<br>GCCTATCTGCAAATGAACAGCCTGAAAACCGAGGACACAGCCGTGTATTACTGTGCGGCC<br>TGGAGTGCCCCGACTGACTACTGGGGCCAGGGAACCCTGGTCACCGTCTCCTCAGGTGGA<br>GGCGGTTCAGGCGGAGGTGGCTCTGGCGGTGGCGGATCGGACATCGTGATGACCCAGTCT<br>CCAGACTCCCTGGCTGTGTCTCTGGGCGAGAGGGCCACCATCAACTGCAAGTCCAGCCAG<br>AGTGTTTTATACAGCTCCAACAATAAGAACTACTTAGCTTGGTACCAGCAGAAACCAGGA<br>CAGCCTCCTAAGCTGCTCATTTACTGGGCATCTACCCGGGAATCCGGGGTCCCTGACCGA<br>TTCAGTGGCAGCGGGTCTGGGACAGATTTCACTCTCACCATCAGCAGCCTGCAGGCTGAA<br>GATGTGGCAGTTTATTACTGTCAGCAATATTATAGTACTCCGTGGACGTTCGGCCAAGGG<br>ACCAAGGTGGATATCAAA | BCMA-5 scFv (nt) |
| 335 | CAGGTGCAGCTGGTGCAGTCTGGGGGAGGCTTGGTACAGCCAGGGCGGTCCCTGAGACTC<br>TCCTGTACAGCTTCTGGATTCACCTTTGGTGATTATGCTATGAGCTGGTTCCGCCAGGCT<br>CCAGGGAAGGGGCTGGAGTGGGTAGGTTTCATTAGAAGCAAAGCTTATGGTGGGACAACA<br>GAATACGCCGCGTCTGTGAAAGGCAGATTCACCATCTCAAGAGATGATTCCAAAAGCATC<br>GCCTATCTGCAAATGAACAGCCTGAAAACCGAGGACACAGCCGTGTATTACTGTGCGGCC<br>TGGAGTGCCCCGACTGACTACTGGGGCCAGGGAACCCTGGTCACCGTCTCCTCAGGTGGA<br>GGCGGTTCAGGCGGAGGTGGCTCTGGCGGTGGCGGATCGGATATTGTGATGACCCAGTCT<br>CCATCGTCCCTGTCTGTGTCTGTAGGAGAGAGTCACCATCACTTGTCGGGCGAGTCAG<br>TCTATAAGTAATTCCTTAGCCTGGTATAAACAGAGACCGGGAGAAGCCCCTAAACTCCTG<br>ATACATGCTGCATCCAATGTGGAAGATGGGGTCCCTTCGAGGTTCAGCGGCAGGGGATCT<br>GGGACAGTTTTCACTCTCGCCATCAGCAATGTACAGCCTGAAGATTTCGCAACTTACTAC<br>TGTCAGCAGAGTCACATGTACCCTCCGACTTTCGGCGGGGGGACCAAGGTGGAAATCAAA | BCMA-6 scFv (nt) |
| 336 | CAGGTGCAGCTGGTGCAGTCTGGGGGAGGCTTGGTACAGCCAGGGCGGTCCCTGAGACTC<br>TCCTGTACAGCTTCTGGATTCACCTTTGGTGATTATGCTATGAGCTGGTTCCGCCAGGCT<br>CCAGGGAAGGGGCTGGAGTGGGTAGGTTTCATTAGAAGCAAAGCTTATGGTGGGACAACA<br>GAATACGCCGCGTCTGTGAAAGGCAGATTCACCATCTCAAGAGATGATTCCAAAAGCATC<br>GCCTATCTGCAAATGAACAGCCTGAAAACCGAGGACACAGCCGTGTATTACTGTGCGGCC<br>TGGAGTGCCCCGACTGACTACTGGGGCCAGGGAACCCTGGTCACCGTCTCCTCAGGTGGA<br>GGCGGTTCAGGCGGAGGTGGCTCTGGCGGTGGCGGATCGGTCATCCAGTTGACCCAGTCT<br>CCCTCCTCACTGTCTGCATCTGTAGGGGACAGAGTCACCATCACTTGTCGGGCGAGTCAG<br>GACATTGGCGATTATTTAGCCTGGTTTCAGCAGAGACCAGGGAAAGCCCCTAAGTCCCTG<br>ATCTATGTTGCGTCCACTTTGCAGAGTGGGGTCCCATCAAGGTTCAGCGGCAGTGGATCT<br>GGGACACACTTCACTCTCACCATCAACAGCCTGCAGCCTGAAGATTTTGCAACTTATTAC<br>TGCCAACAGTATCATAGTCACCCGTGGACGTTCGGCCCAGGGACCAAGGTGGATATCAAA | BCMA-7 scFv (nt) |
| 337 | CAGGTCCAGCTGGTGCAGTCTGGGGGAGGCTTGGTACAGCCAGGGCGGTCCCTGAGACTC<br>TCCTGTACAGCTTCTGGATTCACCTTTGGTGATTATGCTATGAGCTGGTTCCGCCAGGCT<br>CCAGGGAAGGGGCTGGAGTGGGTAGGTTTCATTAGAAGCAAAGCTTATGGTGGGACAACA<br>GAATACGCCGCGTCTGTGAAAGGCAGATTCACCATCTCAAGAGATGATTCCAAAAGCATC<br>GCCTATCTGCAAATGAACAGCCTGAAAACCGAGGACACAGCCGTGTATTACTGTGCGGCC<br>TGGAGTGCCCCGACTGACTACTGGGGCCAGGGAACCCTGGTCACCGTCTCCTCAGGTGGA<br>GGCGGTTCAGGCGGAGGTGGCTCTGGCGGTGGCGGATCGGATATTGTGATGACCCAGTCT<br>CCAGACTCCCTGGCTGTGTCTCTGGGCGAGAGGGCCACCATCAACTGCAAGTCCAGCCAG<br>AGTGTTTTATACAGCTCCAACAATAAGAACTACTTAGCTTGGTACCAGCAGAAACCAGGA<br>CAGCCTCCTAAGCTGCTCATTTACTGGGCATCTACCCGGGAATCCGGGGTCCCTGACCGA<br>TTCAGTGGCAGCGGGTCTGGGACAGATTTCACTCTCACCATCAGCAGCCTGCAGGCTGAA<br>GATGTGGCAGTTTATTACTGTCAGCAATATTATAGTACTCCGTACACTTTTGGCCAGGGG<br>ACCAAGCTGGAAATCAAA | BCMA-8 scFv (nt) |
| 338 | GAAGTGCAGCTGGTGCAGTCTGGGGGAGGCTTGGTCAAGCCTGGAGGGTCCCTGAGACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAGAGTGGAC<br>GGTGACTACGTCGATGACTACTGGGGCCAGGGAACCCTGGTCACCGTCTCCTCAGGTGGA<br>GGCGGTTCAGGCGGAGGTGGCTCTGGCGGTGGCGGATCGTCCTATGAGCTGACTCAGCCG<br>CCCTCGGTGTCTGTGGCCCCAGGACAGACGGCCAGGGTTACCTGTGGGCAAATAATATT<br>GGAAGCAAAAGTGTCCACTGGTACCAGCAGAAGCCAGGCCAGGCCCCCATGCTGGTCGTC<br>TATGATGATGACGACCGGCCCTCGGGATCCCTGAGCGATTCTCTGGCTCCAACTCTGGG<br>AACACGGCCACCCTGACCATCAGCGGGGTCGAGGCCGGGGATGAGGCCGACTACTTCTGT<br>CACGTGTGGGATAGAAGTCGTGATCATTATGTCTTCGGAACTGGGACCAAGCTGACCGTC<br>CTA | BCMA-9 scFv (nt) |

| SEQ ID NO | SEQUENCE | Description |
|---|---|---|
| 339 | GAAGTGCAGCTGGTGCAGTCTGGGGGAGGCTTGGTCAAGCCTGGAGGGTCCCTGAGACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAGAGTGGAC<br>GGTGACTACGTCGATGACTACTGGGGCCAGGGAACCCTGGTCACCGTCTCCTCAGGTGGA<br>GGCGGTTCAGGCGGAGGTGGCTCTGGCGGTGGCGGATCGTCCTATGAGCTGACTCAGCCG<br>CCCTCGGTGTCTGTGGCCCCAGGACAGACGGCCAGGGTTACCTGTGGGGCAAATAATATT<br>GGAAGCAAAAGTGTCCACTGGTACCAGCAGAAGCCAGGCCAGGCCCCCATGCTGGTCGTC<br>TATGATGATGACGACCGGCCCTCCGGGATCCCTGAGCGATTCTCTGGCTCCAACTCTGGG<br>AACACGGCCACCCTGACCATCAGCGGGGTCGAGGCCGGGGATGAGGCCGACTACTTCTGT<br>CACGTGTGGGATAGAAGTCGTGATCATTATGTCTTCGGAACTGGGACCAAGCTGACCGTC<br>CTA | BCMA-10 scFv (nt) |
| 340 | CAGGTGCAGCTGGTACAGTCTGGGGGAGGCTTGGTACAGCCTGGCAGGTCCCTGAGACTC<br>TCCTGTGCAGCCTCTGGATTCACCTTTGATGATTATGCCATGCACTGGGTCCGGCGAGCT<br>CCAGGGAAGGGCCTGGAGTGGGTCTCAGGTATTAGTTGGAATAGTGGTAGCATAGGCTAT<br>GCGGACTCTGTGAAGGGCCGATTCACCATCTCCAGAGACAACGCCAAGAACTCCCTGTAT<br>CTGCAAATGAACAGTCTGAGAGCTGAGGACACGGCCGTGTATTACTGTGCGAGAGATCTG<br>GGGCCCGACTACGATCCCGATGCTTTTGATATCTGGGGCCAAGGGACAATGGTCACCGTT<br>TCCTCAGGTGGAGGCGGTTCAGGCGGAGGTGGCTCTGGCGGTGGCGGATCGCAGCTTGTG<br>CTGACTCAGCCACCCTCAGCGTCTGGGACCCCCGGGCAGAGGGTCACCATCTCTTGTTCT<br>GGAAGCAGCTCCAACATCGGATAATGCTGTAAACTGGTACCAGCAGCTCCCAGGAACG<br>GCCCCCGAAGTCCTCATCTATAATAGTCATCAGCGGCCCTCAGGGGTCCCTGACCGATTC<br>TCTGGCTCCAAGTCTGGCACCTCAGCCTCCCTGGCCATCAATGGGCTCCAGTCTGAGGAC<br>GAGGCTGATTATTACTGTGCAGCATGGGATGACAGCCTGAGAGGTTACGTCTTCGGAACT<br>GGGACCAAGCTCACCGTCCTA | BCMA-11 scFv (nt) |
| 341 | GAGGTGCAGCTGGTGGAGTCTGGGGGAGGCTTGGTCAAGCCTGGAGGGTCCCTGAGACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAAAGTGGAT<br>GGCCCTCCTTCTTTTGATATCTGGGGCCAAGGGACAATGGTCACCGTCCTCAGGTGGA<br>GGCGGTTCAGGCGGAGGTGGCTCTGGCGGTGGCGGATCGCAGTCTGCCCTGACGCAGCCG<br>CCCTCAGTGTCTGGGCCCCAGGACAGAAGGTCACCATCTCCTGCTCTGGAAGCCGCTCC<br>AACATTGGGAATAATTATGTATCCTGGTACCAACAGCTCCCAGGAACAGCCCCCAAACTC<br>CTCATTTATGACAATGCTAAGCGACCCTCAGGAATTCCTGACCGATTCTCTGGCTCCAAG<br>TCTGGCACGTCAGCCACCCTGGACATCGCCGGACTCCAGACTGGGGATGAGGCCGACTAT<br>TACTGTCAGGTGTGGGATAGTAGTAGTGATCATTGGGTATTCGGCGGAGGGACCAAGCTC<br>ACCGTCCTA | BCMA-12 scFv (nt) |
| 342 | CAGATGCAGCTGGTGCAGTATGGGGGAGGCGTGGTCCAGCCTGGGAGGTCCCTGAGACTC<br>TCCTGTGCAGCCTCTGGATTCACCTTCAGTAGCTATGCTATGCACTGGGTCCGCCAGGCT<br>CCAGGCAAGGGGCTGGAGTGGGTGGCAGTTATATCATATGATGGAAGTAATAAATACTAC<br>GCAGACTCCGTGAAGGGCCGATTCACCATCTCCAGAGACAATTCCAAGAACACGCTGTAT<br>CTGCAAATGAACAGCCTGAAAGCTGAGGACACGGCTGTGTATTACTGTGCTACCCTACCC<br>GGTAGAGATGGCTACCCCGGAGCCTTTGACTACAGGGGCCAGGGAACCCTGGTCACCGTC<br>TCCTCAGGTGGAGGCGGTTCAGGCGGAGGTGGCTCTGGCGGTGGCGGATCGCAGGCTGTG<br>CTGACTCAGCCACCCTCAGCGTCTGGGACCCCCGGGCAGAGGGTCACCATCTCTTGTTCT<br>GGAAGCGGCTCCAACATCGGAAGTAATGATGTCCTGGTATCAGCAGATCCCAGGAACG<br>GCCCCCAAACTCCTCATCTACTGGAATGATCAGCGGCCCTCAGGGGTCCCTGACCGATTC<br>TCTGGCTCCAAGTCTGGCACCTCAGCCTCCCTGGCCATCAGTGGGCTCCGGTCCGAGGAT<br>GAGGCTGATTATTACTGTGCAGCATGGGATGACAGCCTGGGTGGTTCTTGGGTGTTCGGC<br>GGAGGGACCAAGGTCACCGTCCTA | BCMA-13 scFv (nt) |
| 343 | GAGGTGCAGCTGTTGGAGTCTGGGGGAGGCGTGGTCCAGCCTGGGAGGTCCCTGAGACTC<br>TCCTGTGCAGCGTCTGGATTCACCTTCAGTAGCTATGGCATGCACTGGGTCCGCCAGGCT<br>CCAGGCAAGGGGCTGGAGTGGGTGGCAGTTATATCATATGATGGAAGTAATAAATACTAC<br>GCAGACTCCGTGAAGGGCCGATTCACCATCTCCAGAGACAATTCCAAGAACACGCTGTAT<br>CTGCAAATGAACAGCCTGAGAGCTGAGGACACGGCTGTGTATTACTGTGCTACCCTACCC<br>GGTAGAGATGGCTACCCCGGAGCCTTTGACTACAGGGGCCCGGGAACCCTGGTCACCGTC<br>TCCTCAGGTGGAGGCGGTTCAGGCGGAGGTGGCTCTGGCGGTGGCGGATCGCAGGCTGTG<br>CTGACTCAGCCACCCTCAGCGTCTGGGACCCCCGGGCAGAGGGTCACCATCTCTTGTTCT<br>GGAAGCGGCTCCAACATCGGAAGTAATGATGTCCTGGTATCAGCAGATCCCAGGAACG<br>GCCCCCAAACTCCTCATCTACTGAATGATCAGCGGCCCTCAGGGGTCCCTGACCGTC<br>TCTGGCTCCAAGTCTGGCGCCTCAGCCTCTCTGGCCATCAGTGGGCTCCAGTCTGAGGAT<br>GAGGCTGATTATTATTGTGCAGCATGGGATGACAGGTTGAACGGTTTTGGGTGTTCGGC<br>GGAGGGACCAAGCTCACCGTCCTA | BCMA-14 scFv (nt) |
| 344 | CAGGTGCAGCTGTTGGAGTCTGGGGGAGGCCTGGTCAAGCCTGGGGGGTCCCTGAGACTC<br>TCCTGTGCAGCCTCTGGATTCACCTTCAGTAGCTATGGCATGCACTGGGTCCGCCAGGCT | BCMA-15 scFv (nt) |

| SEQ ID NO | SEQUENCE | Description |
|---|---|---|
| | CCAGGCAAGGGGCTGGAGTGGGTGGCAGTTATATCATATGATGGAAGTAATAAATACTAT<br>GCAGACTCCGTGAAGGGCCGATTCACCATCTCCAGAGACAATTCCAAGAACACGCTGTAT<br>CTGCAAATGAACAGCCTGAGAGCTGAGGACACGGCCGTGTATTACTGTGCGAAAGATCAG<br>TATAGCAGTAGCGCACAAAGGGCCGACTTTGACTACTGGGGCCAGGGAACCCTGGTCACC<br>GTCTCCTCAGGTGGAGGCGGTTCAGGCGGAGGTGGTTCTGGCGGTGGCGGATCGCAGTCT<br>GTGCTGACGCAGCCACCCTCAGCGTCTGGGACCCCCGGGCAGAGGGTCACCATCTCTTGT<br>TCTGGAAGCGGCTCCAACATCGGAAGTAATGATGTCTCCTGGTATCAGCAGATCCCAGGA<br>ACGGCCCCCAAACTCCTCATCTACTGGAATGATCAGCGGCCCTCAGGGGTCCCTGACCGG<br>TTCTCAGGCTCCAAGTCTGGCACCTCAGCCTCCCTGGTCATCAGTGGGCTCCGGTCCGAG<br>GATGAGGCTGATTATTACTGTGCAGCATGGGATGACAGCCTGAGTGGTTGGGTGTTCGGC<br>GGAGGGACCAAGCTGACCGTCCTA | |
| 345 | GAGGTCCAGCTGGTACAGTCTGGGCCTGAGGTGAAGAAGCCTGGGACCTCAGTGAAGGTC<br>TCCTGCAAGGCTTCTGGATTCACCTTTACTAGCTCTGCTATGCAGTGGGTGCGACAGGCT<br>CGTGGACAACGCCTTGAGTGGATAGGATGGATCGTCGTTGGCAGTGGTAACACAAACTAC<br>GCACAGAAGTTCCAGGAAAGAGTCACCATTACCAGGGACATGTCCACAAGCACAGCCTAC<br>ATGGAGCTGAGCAGCCTGAGATCCGAGGACACGGCCGTGTATTACTGTGCGGCAGCTCCG<br>TATTACGATATTTTGACTGGTTATTATTTATGGGGCCAGGGAACGCTGGTCACCGTCTCC<br>TCAGGTGGAGGCGGTTCTGGCGGAGGTGGCTCTGGCGGTGGCGGATCGCAGTCTGCCCTG<br>ACTCAGCCACCCTCAGCGTCTGGGACCCCCGGGCAGAGGGTCACCATCTCTTGTTCTGGA<br>AGCGGCTCCAACATCGGAAGTAATGATGTCTCCTGGTATCAGCAGATCCCAGGAACGGCC<br>CCCAAACTCCTCATCTACTGGAATGATCAGCGGCCCTCAGGGGTCCCTGACCGATTCTCT<br>GGCTCCAAGTCTGGCACCTCAGCCTCCCTGGCCATCAGTGGGCTCCAGTCTGAGGATGAG<br>GCTGATTATTACTGTGCATCATGGGATGACAGCCTGAGTGGTTGGGTGTTCGGCGGAGGG<br>ACCAAGCTGACCGTCCTA | BCMA-16 scFv (nt) |
| 346 | CAGGTTCAGCTGGTGCAGTCTGGGGGAGGCTTGGTCAAGCCTGGAGGGTCCCTGAGACTC<br>TCCTGTGCAGCCTCTGGATTCACCTTCAGTGACTACTACATGAGCTGGATCCGCCTGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAGAGAGGCC<br>GATAGTAGCGCTGACTACTGGGGCCAGGGAACCCTGGTCAACGTCTCCTCAGGTGGAGGC<br>GGTTCAGGCGGAGGTGGCTCTGGCGGTGGCGGATCGCAGCTGTGCTGACTCAGCCACCC<br>TCGGTGTCAGTGGCCCCAGGAAAGACGGCCATGATTACCTGTGGGGAAACAACATTGGA<br>TTTAAAGGTGTGCAGTGGTACCAGCAGAAGACAGGCCAGGCCCCTGTGCTGGTCGTCTAT<br>GATGATAGCGACCGGCCCTCAGGGATCCCTGAGCGATTCTCTGGCTCCAACTCTGGGAAC<br>ACGGCCACCCTGACCATCAGCAGGGTCGAAGCCGGGGATGAGGCCGGGATTATTACTGTCAG<br>GTGTGGGATAGTGCTAGTGATCATTGGGTGTTCGGCGGAGGGACCAAGCTGACCGTCCTA | BCMA-17 scFv (nt) |
| 347 | GAGGTGCAGCTGTTGGAGTCTGGGGGAGGCTTGGTCCAGCCTGGGGGGTCCCTGAGACTC<br>TCCTGTGCAGCCTCTGGATTCACGTTTAGTAGCTATTGGATGAGCTGGCACCGCCAGGCT<br>CCAGGGAAGGGGCCGGAGTGGGTGGCCCACATAAAACCAAGACGGAAGTGAGAAGTACTAT<br>GTGGACTCTGTGAAGGGCCGATTCACCATCTCCAGAGACAACGCCGAGAGTTCACTGTAT<br>CTGCAAATGAACAGCCTGAGAGCCGAGGACACGGCTGTGTATTACTGTGCGAGGTGGCTG<br>GCGGTTACTAACTGGGGCCAGGGAACCCTGGTCACCGTCTCCTCAGGTGGAGGCGGTTCA<br>GGCGGAGGTGGCTCTGGCGGTGGCGGATCGCAGTCTGTGTTGACTCAGCCACCCTCAGCG<br>TCTGGGACCCCCGGGCAGAGGGTCACCATCTCTTGTTCTGGAAGCGGCTCCAACATCGGA<br>AGTAATGATGTCTCCTGGTATCAGCAGATCCCAGGGACGGCCCCCAAACTCCTCATCTAC<br>TGGAATGATCAGCGGCCCTCAGGGGTCCCTGACCGATTCTCTGGCTCCAAGTCTGGCACC<br>TCAGCCTCCCTGGCCATCAGTGGGCTCCGGTCCGAGGATGAGGCTGATTATTACTGTGCA<br>GCATGGGATGACAGCCTGAATGGTTGGGTGTTCGGCGGAGGGACCAAGCTGACCGTCCTA | BCMA-18 scFv (nt) |
| 348 | CAGGTCCAGCTGGTACAGTCTGGGGCTGAGGTGAAGAAGCCTGGGGCCTCAGTGAAGGTC<br>TCCTGCAAGGCTTCTGGATACACCTTCACCAGCTACTATATGCACTGGGTGCGACAGGCC<br>CCTGGACAAGGGCTTGAGTGGATGGGATGGATCAACCCTAACAGTGGTGGCACAAACTAT<br>GCACAGAAGTTTCAGGGCAGGGTCACCATGACCAGGGACACGTCCATCAGCACAGCCTAC<br>ATGGAGCTGAGCAGGCTGAGATCTGACGACACGGCCGTGTATTACTGTGCGAGAGATGGT<br>GGGGACGTCTGGGGCCAAGGGACCACGGTCACCGTCTCCTCAGGTGGAGGCGGTTCAGGC<br>GGAGGTGGCTCTGGCGGTGGCGGATCGCAGGCTGTGCTGACTCAGCCTGCCTCCGTGTCT<br>GGGTCTCCTGGACAGTCGATCACCATCTCCTGCACTGGAACCAGCAGTGACGTTGGTGAT<br>TATAACTATGTCGCCTGGTATCAACAACACCCAGGCAAAGACCCCAAACTCATGATTTTT<br>GAGGTCATTAATCGGCCCTCAGGGGTTTCTGATCGCTTCTCTGGCTCCAAGTCTGGCAAC<br>ACGGCCTCCCTGGACATCTCTGGGCTCCAGCTCGAGGACGAGGCTGATTATTACTGCATC<br>TCATATTCACGAGGCAGCACTCCTTATGTCATCGGAACTGGGACCAAGGTGACCGTCCTA | BCMA-19 scFv (nt) |
| 349 | GAGGTGCAGCTGTTGGAGTCTGGGGGAGGCTTGGTACAGCCTGGCAGGTCCCTGAGACTC<br>TCCTGTGCAGCCTCTGGATTCACCTTTGATGATTATGCCATGCACTGGGTCCGGCAAGCT<br>CCAGGGAAGGGCCTGGAGTGGGTCTCAGGTATTAGTTGGAATAGTGGTAGCATAGGCTAT<br>GCGGACTCTGTGAAGGGCCGATTCACCATCTCCAGAGACAACGCCAAGAACTCCCTGTAT<br>CTGCAAATGAACAGTCTGAGAGCTGAGGACACGGCCTTGTATTACTGTGCAAAGGGGGCC<br>CTAGGAATAACCCCATACTACTTTGACTACTGGGGCCAGGGAACCCTGGTCACCGTCTCC<br>TCAGGTGGAGGCGGTTCAGGCGGAGGTGGCTCTGGCGGTGGCGGATCGCAGCCTGTGCTG<br>ACTCAGCCACCCTCAGCGTCTGGGACCCCCGGGCAGAGGGTCACCATCTCTTGTTCGGGA | BCMA-20 scFv (nt) |

| SEQ ID NO | SEQUENCE | Description |
|---|---|---|
| | GGCAAGACTGTAAACTGGTTCCGGCAGGTCCCAGGAACGGCCCCCCAACTCCTCATCTAT<br>AGTAATGATCAGCGGCCCTCAGGGGTCCCTGACCGATTCTCTGGCTCCAAGTCTGGCTCC<br>TCAGCCTCCCTGGACATCAGTGGGCTCCAGTCTGAGGATGAGGCTTATTATTACTGTGGA<br>TCATGGGATGACAGCCTCAATGCTTGGGTGTTCGGCGGAGAGACCAAGCTGACCGTCCTA | |
| 350 | GAAGTGCAGCTGGTGGAGTCTGGGGGAGGCTTGGTCAAGCCTGGAGGGTCCCTGAAACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAAAGTAGAC<br>GGAGGCTACACAGAGGACTACTGGGGCCAGGGAACCCTGGTCACCGTCTCCTCAGGTGGA<br>GGCGGTTCAGGCGGAGGTGGCTCTGGCGGTGGCGGATCGCAGTCTGTGCTGACTCAGCCA<br>CCCTCAGCGTCTGGGACCCCCGGGCAGAGGGTCACCATCTCTTGTTCTGGAAGCGGCTCC<br>AACATCGGAAGTAATGATGTCTCCTGGTATCAGCAGATCCCAGGAACGGCCCCCAAACTC<br>CTCATCTACTGGAATGATCAGCGGCCCTCAGGGGTCCCTGACCGGTTCTCAGGCTCCAAG<br>TCTGGCATCTCAGCCTCCCTGGCCATCAGCGGGCTCCGGTCCGAGGATGAGGCTGATTAT<br>TACTGTGCAGCATGGGATGACAGCCTGAATGGTTATGTCTTCGGAACTGGGACCAAGGTC<br>ACCGTCCTA | BCMA-21 scFv (nt) |
| 351 | GAAGTGCAGCTGGTGGAGTCTGGGGGAGGCTTGGTCAAGCCTGGAGGGTCCCTGAAACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAAAGTAGAC<br>GGAGACTACACAGAGGACTACTGGGGCCAGGGAACCCTGGTCACCGTCTCCTCAGGTGGA<br>GGCGGTTCAGGCGGAGGTGGCTCTGGCGGTGGCGGATCGCAGTCTGCCCTGACTCAGCCT<br>GCCTCCGTGTCTGGGTCTCCTGGACAGTCGATCACTATCTCCTGCACTGGAAGCAGCAGT<br>GATGTTGGCAAATATAATCTTGTCTCCTGGTACCAACAGCCCCAGGCAAAGCCCCCAAG<br>CTCATAATTTATGACGTCAATAAGCGGCCCTCAGGGGTTTCTAATCGCTTCTCTGGCTCC<br>AAGTCTGGCAACACGGCCACCCTGACAATCTCTGGGCTCCAGGGTGACGACGAGGCTGAT<br>TATTATTGTTGCTCATATGGAGGTAGTAGGTCTTATGTCTTCGGAACTGGGACCAAGGTG<br>ACCGTCCTA | BCMA-22 scFv (nt) |
| 352 | GAAGTGCAGCTGGTGGAGTCTGGGGGAGGCTTGGTCAAGCCTGGAGGGTCCCTGAAACTC<br>TCCTGTGCAGCCTCTGGATTCACCTTCAGTGACTACTACATGAGCTGGATCCGCCAGGCT<br>CCAGGGAAGGGGCTGGAGTGGGTTTCATACATTAGTAGTAGTGGTAGTACCATATACTAC<br>GCAGACTCTGTGAAGGGCCGATTCACCATCTCCAGGGACAACGCCAAGAACTCACTGTAT<br>CTGCAAATGAACAGCCTGAGAGCCGAGGACACGGCCGTGTATTACTGTGCGAAAGTAGAC<br>GGAGACTACACAGAGGACTACTGGGGCCAGGGAACCCTGGTCACCGTCTCCTCAGGTGGA<br>GGCGGTTCAGGCGGAGGTGGCTCTGGCGGTGGCGGATCGCAGTCTGCCCTGACTCAGCCT<br>GCCTCCGTGTCTGGGTCTCCTGGACAGTCGATCACTATCTCCTGCACTGGAAGCAGCAGT<br>GATGTTGGCAAATATAATCTTGTCTCCTGGTACCAACAGCCCCAGGCAAAGCCCCCAAG<br>CTCATAATTTATGACGTCAATAAGCGGCCCTCAGGGGTTTCTAATCGCTTCTCTGGCTCC<br>AAGTCTGGCAACACGGCCACCCTGACAATCTCTGGGCTCCAGGGTGACGACGAGGCTGAT<br>TATTATTGTAGCTCATATGGAGGTAGTAGGTCTTATGTCTTCGGAACTGGGACCAAGGTG<br>ACCGTCCTA | BCMA-23 scFv (nt) |
| 353 | $X_1X_2X_3MX_4$<br>$x_1$ = D or S;<br>$X_2$ = Y or S;<br>$X_3$ = A, G, W, or Y;<br>$X_4$ = H, Q, or S | Consensus CDR-H1 |
| 354 | $X_1IX_2X_3X_4X_5X_6X_7X_8X_9X_{10}X_{11}YX_{12}X_{13}X_{14}X_{15}X_{16}X_{17}$<br>$X_1$ = F, G, H, V, W or Y;<br>$X_2$ = N, R, S or V;<br>$X_3$ = P, Q, S, V, W or Y;<br>$X_4$ = K or null;<br>$X_5$ = A or null;<br>$X_6$ = D, G, N, S, or Y;<br>$X_7$ = G or S;<br>$x_8$ = G or S;<br>$X_9$ = E, G, N, T or S;<br>$X_{10}$ = I, K, or T;<br>$X_{11}$ = E, G, N or Y;<br>$X_{12}$ = A or V;<br>$X_{13}$ = A, D or Q;<br>$X_{14}$ = K or S;<br>$X_{15}$ = F or V;<br>$X_{16}$ = K or Q;<br>$X_{17}$ = E or G | Consensus CDR-H2 |

| SEQ ID NO | SEQUENCE | Description |
|---|---|---|
| 355 | $X_1X_2X_3X_4X_5X_6X_7X_8X_9X_{10}X_{11}X_{12}X_{13}X_{14}$<br>$X_1$ = A, D, E, G, L, V or W;<br>$X_2$ = A, D, G, L, P, Q or S;<br>$X_3$ = A, D, G, L or Y;<br>$X_4$ = D, G, P, R, S, V, Y or null;<br>$X_5$ = D, I, P, S, T, Y or null;<br>$X_6$ = A, G, I, S, T, V, Y or null;<br>$X_7$ = A, D, E, F, L, P, S, Y or null;<br>$X_8$ = P, Q, T, Y or null;<br>$X_9$ = D, G, R, Y or null;<br>$X_{10}$ = A, F, Y or null;<br>$X_{11}$ = D, F or null;<br>$X_{12}$ = F or null;<br>$X_{13}$ = D, T or Y;<br>$X_{14}$ = I, L, N, V or Y | Consensus CDR-H3 |
| 356 | $X_1X_2X_3X_4X_5X_6X_7X_8X_9X_{10}X_{11}X_{12}X_{13}X_{14}X_{15}X_{16}X_{17}$<br>$X_1$ = G, K, R, S or T;<br>$X_2$ = A, G or S;<br>$X_3$ = G, N, S or T;<br>$X_4$ = G, K, N, Q, R or S;<br>$X_5$ = S or null;<br>$X_6$ = D, N, V or null;<br>$X_7$ = L, V or null;<br>$X_8$ = H, S, Y or null;<br>$X_9$ = S, T or null;<br>$X_{10}$ = S or null;<br>$X_{11}$ = D, G, I, N, S or null;<br>$X_{12}$ = D, E, G, K, I, N or null;<br>$X_{13}$ = F, G, K, N, R, S, Y or null;<br>$X_{14}$ = D, K, N, T or null;<br>$X_{15}$ = A, D, G, L, N, S, T or Y;<br>$X_{16}$ = L or V;<br>$X_{17}$ = A, H, N, Q or S | Consensus CDR-L1 |
| 357 | $X_1X_2X_3X_4X_5X_6X_7$<br>$X_1$ = A, D, E, N, S, V or W;<br>$X_2$ = A, D, N, S or V;<br>$X_3$ = A, D, H, I, N or S;<br>$X_4$ = D, K, N, Q, R or T;<br>$X_5$ = L, R or V;<br>$X_6$ = A, E, P or Q;<br>$X_7$ = A, D, S or T | Consensus CDR-L2 |
| 358 | $X_1X_2X_3X_4X_5X_6X_7X_8X_9X_{10}X_{11}X_{12}$<br>$X_1$ = A, C, G, H, I, Q or S;<br>$X_2$ = A, Q, S or V;<br>$X_3$ = S, W or Y;<br>$X_4$ = D, F, G, H or Y;<br>$X_5$ = D, G, M, R, S or T;<br>$X_6$ = A, G, H, L, R, S, T or Y;<br>$X_7$ = L, P, R, S or null;<br>$X_8$ = D, G, N, R, S, T or null;<br>$X_9$ = A, G, H, L, P or null;<br>$X_{10}$ = F, S or null;<br>$X_{11}$ = L, P, W or Y;<br>$X_{12}$ = S, T or V | Consensus CDR-L3 |
| 359 | GGGGS | 4GS linker (aa) |
| 360 | GGGS | 3GS linker (aa) |
| 361 | GGGGSGGGGSGGGGS | (4GS)₃ linker (aa) |
| 362 | GSTSGSGKPGSGEGSTKG | Linker (aa) |
| 363 | ESKYGPPCPPCP | Spacer (IgG4hinge) (aa) |
| 364 | gaatctaagtacggaccgccctgccccccttgccct | Spacer (IgG4hinge) (nt) |
| 365 | ESKYGPPCPPCPGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | Hinge-CH3 spacer (aa) |

-continued

| SEQ ID NO | SEQUENCE | Description |
|---|---|---|
| 366 | ESKYGPPCPPCPAPEFLGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQKSLSLSLGK | Hinge-CH2-CH3 spacer (aa) |
| 367 | MLQMAGQCSQNEYFDSLLHACIPCQLRCSSNTPPLTCQRYCNASVTNSVKGTNAILWTCL GLSLIISLAVFVLMFLLRKISSEPLKDEFKNTGSGLLGMANIDLEKSRTGDEIILPRGLE YTVEECTCEDCIKSKPKVDSDHCFPLPAMEEGATILVTTKTNDYCKSLPAALSATEIEKS ISAR | Human BCMA; GenBank No. BAB60895.1 |
| 368 | MLQMAGQCSQNEYFDSLLHACIPCQLRCSSNTPPLTCQRYCNASVTNSVKGTNAILWTCL GLSLIISLAVFVLMFLLRKINSEPLKDEFKNTGSGLLGMANIDLEKSRTGDEIILPRGLE YTVEECTCEDCIKSKPKVDSDHCFPLPAMEEGATILVTTKTNDYCKSLPAALSATEIEKS ISAR | Human BCMA; NCBI No. NP_001183.2 |
| 369 | MLQMAGQCSQNEYFDSLLHACIPCQLRCSSNTPPLTCQRYCNARSGLLGMANIDLEKSRT GDEIILPRGLEYTVEECTCEDCIKSKPKVDSDHCFPLPAMEEGATILVTTKTNDYCKSLP AALSATEIEKSISAR | Human BCMA Variant; GenBank No. ABN42510.1 |
| 370 | MAQQCFHSEYFDSLLHACKPCHLRCSNPPATCQPYCDPSVTSSVKGTYTVLWIFLGLTLV LSLALFTISFLLRKMNPEALKDEPQSPGQLDGSAQLDKADTELTRIRAGDDRIFPRSLEY TVEECTCEDCVKSKPKGDSDHFFPLPAMEEGATILVTTKTGDYGKSSVPTALQSVMGMEK PTHTR | Mouse BCMA; NCBI No. NP_035738.1 |
| 371 | MLQMARQCSQNEYFDSLLHDCKPCQLRCSSTPPLTCQRYCNASMTNSVKGMNAILWTCLG LSLIISLAVFVLTFLLRKMSSEPLKDEFKNTGSGLLGMANIDLEKGRTGDEIVLPRGLEY TVEECTCEDCIKNKPKVDSDHCFPLPAMEEGATILVTTKTNDYCNSLSAALSVTEIEKSI SAR | Cynomolgus BCMA; GenBank No. EHH60172.1 |
| 372 | GISWNSGSIXYADSVKG | BCMA-28 CDR-H2 (aa) Kabat numbering |
| 373 | YISGSGSTIYYADSVKG | BCMA-33 CDR-H2 (aa) Kabat numbering |
| 374 | YISSSGNTIYYADSVKG | BCMA-41 CDR-H2 (aa) Kabat numbering |
| 375 | CIPCQLR | human BCMA epitope (residues 21-27) |
| 376 | DLGPPYGDDAFDI | BCMA-24, -28, -29, -39 CDR-H3 (aa) |
| 377 | DLDPDDAFDI | BCMA-30 CDR-H3 (aa) |
| 378 | VDGDYDDY | BCMA-35 CDR-H3 (aa) |
| 379 | SNTPPLTCQR | human BCMA epitope (residues 30-39) |
| 380 | RASQGISNYLA | BCMA-25 CDR-L1 (aa) |
| 381 | RSSQSLLHSNGYNYLD | BCMA-28 CDR-L1 (aa) |
| 382 | TGTSSDVGSYNLVS | BCMA-29 CDR-L1 (aa) |
| 383 | RASQPIRSNLA | BCMA-30 CDR-L1 (aa) |
| 384 | KSSQSVLNSSNNKNYVA | BCMA-31 CDR-L1 (aa) |
| 385 | GGNNIGSKGVH | BCMA-32 CDR-L1 (aa) |
| 386 | RASQSISNYLA | BCMA-34 CDR-L1 (aa) |
| 387 | GSSTGPVTSAHSPS | BCMA-36 CDR-L1 (aa) |
| 388 | GSSTGAVTNGHSPY | BCMA-37, -38 CDR-L1 (aa) |
| 389 | RASQGIRYELX | BCMA-39 CDR-L1 (aa) |

-continued

| SEQ ID NO | SEQUENCE | Description |
|---|---|---|
| 390 | TGSSSDVSKYNLVS | BCMA-40 CDR-L1 (aa) |
| 391 | SGSSSNIGGNSVD | BCMA-41 CDR-L1 (aa) |
| 392 | RASQGIGNGLA | BCMA-42 CDR-L1 (aa) |
| 393 | SVTNSVK | human BCMA epitope (residues 44-50) |
| 394 | KSSQNLLYSSNNKNYLA | BCMA-44 CDR-L1 (aa) |
| 395 | RASQGIGRSLA | BCMA-45 CDR-L1 (aa) |
| 396 | GGNNIGSKSVH | BCMA-47, -48 CDR-L1 (aa) |
| 397 | GGDQIGRKSVH | BCMA-49 CDR-L1 (aa) |
| 398 | RASQNIGDWLA | BCMA-51 CDR-L1 (aa) |
| 399 | WGSTRES | BCMA-24 CDR-L2 (aa) |
| 400 | SASTLQS | BCMA-25 CDR-L2 (aa) |
| 401 | LGSNRAS | BCMA-28 CDR-L2 (aa) |
| 402 | EVSKRPS | BCMA-29 CDR-L2 (aa) |
| 403 | SASTRAT | BCMA-30 CDR-L2 (aa) |
| 404 | DASNRAT | BCMA-34 CDR-L2 (aa) |
| 405 | ETTNRRS | BCMA-36 CDR-L2 (aa) |
| 406 | DTTNRHS | BCMA-37 CDR-L2 (aa) |
| 407 | DTNNRHS | BCMA-38 CDR-L2 (aa) |
| 408 | AASTLQS | BCMA-39 CDR-L2 (aa) |
| 409 | ANDRRPS | BCMA-41 CDR-L2 (aa) |
| 410 | CSQNEYF | human BCMA epitope (residues 8-14) |
| 411 | DASSLRS | BCMA-45 CDR-L2 (aa) |
| 412 | YDTDRPS | BCMA-47, -48 CDR-L2 (aa) |
| 413 | YDSDRPS | BCMA-49 CDR-L2 (aa) |
| 414 | GASILES | BCMA-51 CDR-L2 (aa) |
| 415 | QQYISLPWT | BCMA-24 CDR-L3 (aa) |
| 416 | QQSYTSRQT | BCMA-25 CDR-L3 (aa) |
| 417 | MQALQTPPWT | BCMA-28 CDR-L3 (aa) |
| 418 | CSYAGSSTSRDV | BCMA-29 CDR-L3 (aa) |
| 419 | RHYAPLT | BCMA-30 CDR-L3 (aa) |
| 420 | QQRSNWPPYT | BCMA-34 CDR-L3 (aa) |
| 421 | HLWDRSRDHYV | BCMA-26, -35 CDR-L3 (aa) |
| 422 | LLSSGDARMV | BCMA-36 CDR-L3 (aa) |
| 423 | SLSHAGDRVF | BCMA-37 CDR-L3 (aa) |

-continued

| SEQ ID NO | SEQUENCE | Description |
|---|---|---|
| 424 | LLSYSDARLA | BCMA-38 CDR-L3 (aa) |
| 425 | LQHNSYPLT | BCMA-39 CDR-L3 (aa) |
| 426 | ESWDDALNGHV | BCMA-41 CDR-L3 (aa) |
| 427 | QQYVEDALT | BCMA-42 CDR-L3 (aa) |
| 428 | LLHACIPCQLR | human BCMA epitope (residues 17-27) |
| 429 | QQYYSSPYT | BCMA-44 CDR-L3 (aa) |
| 430 | QQLNSYPWT | BCMA-45 CDR-L3 (aa) |
| 431 | QLWDSDSDDFA | BCMA-47 CDR-L3 (aa) |
| 432 | QVWDSSTGQYW | BCMA-49 CDR-L3 (aa) |
| 433 | QKYDGAPPWT | BCMA-51 CDR-L3 (aa) |
| 434 | EVQLLESGGGLVQPGRSLRLSCVASGFTFD | BCMA-27 VH FR1 (aa) |
| 435 | QVQLVQSGGGLVQPGRSLRLSCAASGFTFG | BCMA-30 VH FR1 (aa) |
| 436 | EVQLVQSGGGLVQPGRSLRLSCTASGFTFG | BCMA-25, -31, -44, -51 VH FR1 (aa) |
| 437 | QVQLVESGGGLVKPGGSLRLSCAASGFTFS | BCMA-32, -49 VH FR1 (aa) |
| 438 | TGQLVQSGGGLVQPGRSLRLSCAASGFTFD | BCMA-34 VH FR1 (aa) |
| 439 | EVQLLESGGGLVQPGRSLRLSCTASGFTFG | BCMA-42 VH FR1 (aa) |
| 440 | tcctatgagctgactcagccacccctcagcgtctgggaccccccgggcagagggtcaccatg tcttgttctggaaccagctccaacatcggaagtcactctgtaaactggtaccagcagctc ccaggaacggccccccaaactcctcatctatactaataatcagcggccctcaggggtccct gaccgattctctggctccaagtctggcacctcagctccctggccatcagtggcctccag tctgaggatgaggctgattattactgtgcagcatgggatggcagcctgaatggtctggta ttcggcggagggaccaagctgaccgtcctaggttctagaggtggtggtggtagcggcggc ggcggctctggtggtggtggatcccctcgagatggccgaggtgcagctggtgcagtctgga gcagaggtgaaaaagcccggggagtctctgaagatctcctgtaagggttctggatacagc tttaccagctactggatcggctgggtgcgccagatgcccgggaaaggcctggagtggatg gggatcatctatcctggtgactctgataccagatacagcccgtccttccaaggccacgtc accatctcagctgacaagtccatcagcactgcctacctgcagtggagcagcctgaaggcc tcggacaccgccatgtattactgtgcgcgctactctggttctttcgataactgggggtcaa ggtactctggtgaccgtctcctcagc | BCMA-52 scFv (nt) |
| 441 | RFTISRDNAKSSLYLQMNSLRAEDTAVYYCAR | BCMA-37 VH FR3 (aa) |
| 442 | SYELTQPPSASGTPGQRVTMSCSGTSSNIGSHSVNWYQQLPGTAPKLLIYTNNQRPSGVP DRFSGSKSGTSASLAISGLQSEDEADYYCAAWDGSLNGLVFGGGTKLTVLGSRGGGGSGG GGSGGGGSLEMAEVQLVQSGAEVKKPGESLKISCKGSGYSFTSYWIGWVRQMPGKGLEWM GIIYPGDSDTRYSPSFQGHVTISADKSISTAYLQWSSLKASDTAMYYCARYSGSFDNWGQ GTLVTVSS | BCMA-52 scFv (aa) |
| 443 | DSPSPGTTPKNSLYLQMNSLRAEDTAVYYCAK | BCMA-47 VH FR3 (aa) |
| 444 | GGQGTMVTVSS | BCMA-28 VH FR4 (aa) |
| 445 | WRQGTMVTVSS | BCMA-47 VH FR4 (aa) |
| 446 | DIQMTQSPAFLSASVGDRVTVTC | BCMA-25 VL FR1 (aa) |
| 447 | DIVMTQSPLSLSVTPGEPASISC | BCMA-28 VL FR1 (aa) |
| 448 | QPVLTQPASVGSPGQSITISC | BCMA-29 VL FR1 (aa) |
| 449 | EIVLTQSPATLSVSPGERATLSC | BCMA-30 VL FR1 (aa) |
| 450 | DVVMTQSPDSLAVSLGERATISC | BCMA-31 VL FR1 (aa) |

-continued

| SEQ ID NO | SEQUENCE | Description |
|---|---|---|
| 451 | QTVVTQPPSVSVAPGQTARITC | BCMA-32 VL FR1 (aa) |
| 452 | EIVMTQSPATLSLSPGDRATLSC | BCMA-34 VL FR1 (aa) |
| 453 | NFMLTQPPSVSVAPGQTARITC | BCMA-35 VL FR1 (aa) |
| 454 | QSVLTQEPSLTVSPGETVTLTC | BCMA-36 VL FR1 (aa) |
| 455 | QLVLTQEPSLTVSPGGTVTLTC | BCMA-37 VL FR1 (aa) |
| 456 | QAVLTQEPSLTVSPGGTVTLTC | BCMA-38 VL FR1 (aa) |
| 457 | DIQXTQSPSSLSASVGDRVTITC | BCMA-39 VL FR1 (aa) |
| 458 | QPVLTQPPSVSGTPGQRVTIPC | BCMA-41 VL FR1 (aa) |
| 459 | DIQMTQSPSLVSASVGDRVTITC | BCMA-42 VL FR1 (aa) |
| 460 | cagtctgccctgacacagcctgccagcgttagtgctagtcccggacagtctatcgccatc agctgtaccggcaccagctctgacgttggctggtatcagcagcaccctggcaaggcccct aagctgatgatctacgaggacagcaagaggcccagcggcgtgtccaatagattcagcggc agcaagagcggcaacaccgccagcctgacaattagcggactgcaggccgaggacgaggcc gattactactgcagcagcaacacccggtccagcacactggttttggcggaggcaccaag ctgacagtgctgggatctagaggtggcgaggatctggcggcggaggaagcggaggcggc ggatctcttgaaatggctgaagtgcagctggtgcagtctggcgccgagatgaagaaacct ggcgcctctctgaagctgagctgcaaggccagcggctacaccttcatcgactactacgtg tactggatgcggcaggcccctggacagggactcgaatctatgggctggatcaaccccaat agcggcggcaccaattacgcccagaaattccagggcagagtgaccatgaccagacacc agcatcagcaccgcctacatggaactgagccggctgagatccgacgacaccgccatgtac tactgcgcgagatctcagcgcgacggctacatggattattggggccagggaaccctggtc accgtgtccagc | BCMA-55 scFv (nt) |
| 461 | DVVMTQSPDSLAVSLGERATINC | BCMA-44 VL FR1 (aa) |
| 462 | AIRMTQSPSSLSASVGDRVTITC | BCMA-45 VL FR1 (aa) |
| 463 | QAVLTQPPSVSVAPGKTATITC | BCMA-47 VL FR1 (aa) |
| 464 | QPVLTQPPSVSVAPGKTATITC | BCMA-48 VL FR1 (aa) |
| 465 | LPVLTQPPSVSVAPGKTARITC | BCMA-49 VL FR1 (aa) |
| 466 | AIQLTQSPSTLSASVGDRVAITC | BCMA-51 VL FR1 (aa) |
| 467 | WYQQKPGNAPRLLIY | BCMA-25 VL FR2 (aa) |
| 468 | WYLQKPGQSPQLLIY | BCMA-28 VL FR2 (aa) |
| 469 | WYQQHPGKAPKLMIY | BCMA-29 VL FR2 (aa) |
| 470 | WYQQKPGQAPKLLIY | BCMA-30 VL FR2 (aa) |
| 471 | WYKQKPGQPPKLVIS | BCMA-31 VL FR2 (aa) |
| 472 | WYRQRPGQAPEVVIY | BCMA-32 VL FR2 (aa) |
| 473 | WFQKKPGQAPTTLIY | BCMA-36 VL FR2 (aa) |
| 474 | WFQQKPGQAPRTLIY | BCMA-37, -38 VL FR2 (aa) |
| 475 | WYQQKPGKAPKLLIY | BCMA-39 VL FR2 (aa) |
| 476 | WFQEVPGTAPKLLIY | BCMA-41 VL FR2 (aa) |
| 477 | WYQQKPGKAPKLLLF | BCMA-42 VL FR2 (aa) |
| 478 | QSALTQPASVSASPGQSIAISCTGTSSDVGWYQQHPGKAPKLMIYEDSKRPSGVSNRFSG SKSGNTASLTISGLQAEDEADYYCSSNTRSSTLVFGGGTKLTVLGSRGGGGSGGGGSGGG GSLEMAEVQLVQSGAEMKKPGASLKLSCKASGYTFIDYYVYWMRQAPGQGLESMGWINPN SGGTNYAQKFQGRVTMTRDTSISTAYMELSRLRSDDTAMYYCARSQRDGYMDYWGQGTLV TVSS | BCMA-55 scFv (aa) |

| SEQ ID NO | SEQUENCE | Description |
|---|---|---|
| 479 | WYKQKPGGVPQLLIH | BCMA-45 VL FR2 (aa) CMA-47, -48 VL FR2 |
| 480 | WYQRKPGQGPVVVIQ | BCMA-47, -48 VL-FR2 (aa) |
| 481 | WYQQKPGQAPVLVMS | BCMA-49 VL FR2 (aa) |
| 482 | WYQQKPGKAPKLLIF | BCMA-51 VL FR2 (aa) |
| 483 | GVPDRFSGSGSGTDFTLTISSLQAEDVAIYHC | BCMA-24 VL FR3 (aa) |
| 484 | GVPSRFRGTGYGTEFSLTIDSLQPEDFATYYC | BCMA-25 VL FR3 (aa) |
| 485 | GVPDRFSGSGSGTDFTLKISRVEAEDVGVYYC | BCMA-28 VL FR3 (aa) |
| 486 | GVSNRFSGSKSGNTASPTISGLQAEDEADYYC | BCMA-29 VL FR3 (aa) |
| 487 | GIPDRFSGSGSGTDFTLTISRLEHEDFAVYYR | BCMA-30 VL FR3 (aa) |
| 488 | GVPDRFSGSNSGNTATLTVRGVEAGDEADYYC | BCMA-32 VL FR3 (aa) |
| 489 | GIPARFSGSGSGTDFTLTISSLEPEDFAVYYC | BCMA-34 VL FR3 (aa) |
| 490 | WTPARFSGSLLGGKAALTLSGAQPEDEADYYC | BCMA-36 VL FR3 (aa) |
| 491 | WTPARFSGSLLGGKAALTLSGAQPEDEAEYYC | BCMA-37 VL FR3 (aa) |
| 492 | WTPARFSGSLLGGKAALTLSGAQPEDEADYFC | BCMA-38 VL FR3 (aa) |
| 493 | GVPSRFSGSGSGTDFALTIRSLQPEDFATYYC | BCMA-39 VL FR3 (aa) |
| 494 | GVPDRFSGTKSGTSASLAIRGLQSDDDAHYYC | BCMA-41 VL FR3 (aa) |
| 495 | GVPSRFSGSRSGTDYTLTISSLQPEDVATYYC | BCMA-42 VL FR3 (aa) |
| 496 | GYSFTSYW | BCMA-52 CDR-H1 (aa) |
| 497 | GVPSRFSGSGSGTEFTLTISGVQSEDSATYHC | BCMA-45 VL FR3 (aa) |
| 498 | GIPERFSGSKSGDTASLTISGVEAGDEADYYC | BCMA-47 VL FR3 (aa) |
| 499 | GIPERFSGSNSGNTATLTISRVEAGDEGDYYC | BCMA-48 VL FR3 (aa) |
| 500 | GIPERFSGSNSGNTATLTISRVEAGDEAAYYC | BCMA-49 VL FR3 (aa) |
| 501 | GVPSRFSGSGSGTDFTLTISSLQPEDVAVYYC | BCMA-51 VL FR3 (aa) |
| 502 | FGPGTRLDIK | BCMA-25 VL FR4 (aa) |
| 503 | FGXGTKLTVL | BCMA-29 VL FR4 (aa) |
| 504 | FGQGTKLDIK | BCMA-31, -34 VL FR4 (aa) |
| 505 | FGTGTKLDIK | BCMA-35 VL FR4 (aa) |
| 506 | FGGGTKVDIK | BCMA-42 VL FR4 (aa) |
| 507 | IYPGDSDT | BCMA-52 CDR-H2 (aa) |
| 508 | FGQGTKVEIK | BCMA-24, -28, -51 VL FR4 (aa) |
| 509 | GFTFGDYAMH | BCMA-30 CDR-H1 (aa) AbM numbering |
| 510 | GISWNSGSIX | BCMA-28 CDR-H2 (aa) AbM numbering |
| 511 | YISGSGSTIY | BCMA-33 CDR-H2 (aa) AbM numbering |

| SEQ ID NO | SEQUENCE | Description |
|---|---|---|
| 512 | YISSSGNTIY | BCMA-41 CDR-H2 AbM numbering |
| 513 | ARYSGSFDN | BCMA-52 CDR-H3 (aa) |
| 514 | SWNSG | BCMA-28 CDR-H2 (aa) Chothia numbering |
| 515 | SGSGST | BCMA-33 CDR-H2 (aa) Chothia numbering |
| 516 | SSSGNT | BCMA-41 CDR-H2 Chothia numbering |
| 517 | SSNIGSHS | BCMA-52 CDR-L1 (aa) |
| 518 | EVQLVQSGGGLVKPGGSLRLSCAASGFTFSDYYMSWIRQAPGKGLEWVSGISWNSGSIGYADSVKGRFTISRDNAKNSLYLQMNSLRAEDTAVYYCARDLGPPYGDDAFDIWGQGTMVTVSS | BCMA-24 VH chain (aa) |
| 519 | EVQLVQSGGGLVQPGRSLRLSCTASGFTFGDYAMSWFRQAPGKGLEWVGFIRSKAYGGTTEYAASVKGRFTISRDDSKSIAYLQMNSLKTEDTAVYYCAAWSAPTDYWGQGTLVTVSS | BCMA-25, -31, -44, -51 VH chain (aa) |
| 520 | EVQLLESGGGLVQPGRSLRLSCVASGFTFDDYAMHWVRQAPGKGLEWVSGISWNSGSIGYADSVKGRFTISRDNAKNSLYLQMNSLRAEDTALYYCAKGGLGITPYYFDYWGQGTLVTVSS | BCMA-27 VH chain (aa) |
| 521 | QVQLVQSGGGLVQPGRSLRLSCAASGFTFDDYAMHWVRQAPGKGLEWVSGISWNSGSIXYADSVKGRFTISRDNAKNSLYLQMNSLRAEDTAVYYCARDLGPPYGDDAFDIGGQGTMVTVSS | BCMA-28 VH chain (aa) |
| 522 | QVQLVQSGGGLVQPGRSLRLSCAASGFTFDDYAMHWVRQAPGKGLEWVSGISWNSGSIGYADSVKGRFTISRDNAKNSLYLQMNSLRAEDTAVYYCARDLGPPYGDDAFDIWGQGTMVTVSS | BCMA-29, -39 VH chain (aa) |
| 523 | QVQLVQSGGGLVQPGRSLRLSCAASGFTFGDYAMHWVRQAPGKGLEWVSGISWNSGSIGYADSVKGRFTISRDNAKNSLYLQMNSLRAEDTAVYYCARDLDPDDAFDIWGQGTMVTVSS | BCMA-30 VH chain (aa) |
| 524 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAKVDGPPSFDIWGQGTMVTVSS | BCMA-32, -49 VH chain (aa) |
| 525 | QVQLVQSGGGLVKPGGSLRLSCAASGFTFSDYYMSWIRQAPGKGLEWVSYISGSGSTIYYADSVKGRFTISRDNAKNSLYLQMNSLRAEDTAVYYCAREADSSADYWGQGTLVNVSS | BCMA-33 VH chain (aa) |
| 526 | TGQLVQSGGGLVQPGRSLRLSCAASGFTFDDYAMHWVRQAPGKGLEWVSGISWNSGSIGYADSVKGRFTISRDNAKNSLYLQMNSLRAEDTAVYYCARDLGPDYDPDAFDIWGQGTMVTVSS | BCMA-34 VH chain (aa) |
| 527 | EVQLVQSGGGLVKPGGSLRLSCAASGFTFSDYYMSWIRQAPGKGLEWVSYISSSGSTIYYADSVKGRFTISRDNAKNSLYLQMNSLRAEDTAVYYCARVDGDYDDYWGQGTLVTVSS | BCMA-35 VH chain (aa) |
| 528 | QVQLVQSGGGLVKPGGSLRLSCAASGFTFSDYYMSWIRQAPGKGLEWVSYISSSGSTIYYADSVKGRFTISRDNAKNSLYLQMNSLRAEDTAVYYCARVDGDYVDDYWGQGTLVTVSS | BCMA-36, 38 VH chain (aa) |
| 529 | EVQLVQSGGGLVKPGGSLRLSCAASGFTFSDYYMSWIRQAPGKGLEWVSYISSSGSTIYYADSVKGRFTISRDNAKSSLYLQMNSLRAEDTAVYYCARVDGDYVDDYWGQGTLVTVSS | BCMA-37 VH chain (aa) |
| 530 | QVQLVQSGGGLVKPGGSLRLSCAASGFTFSDYYMSWIRQAPGKGLEWVSYISSSGNTIYYADSVKGRFTISRDNAKNSLYLQMNSLRAEDTAVYYCAKVDGDYVDDYWGQGTLVTVSS | BCMA-41 VH chain (aa) |
| 531 | EVQLLESGGGLVQPGRSLRLSCTASGFTFGDYAMSWFRQAPGKGLEWVGFIRSKAYGGTTEYAASVKGRFTISRDDSKSIAYLQMNSLKTEDTAVYYCAAWSAPTDYWGQGTLVTVSS | BCMA-42 VH chain (aa) |
| 532 | TNN | BCMA-52 CDR-L2 (aa) |
| 533 | QVQLLESGGGLVKPGGSLRLSCAASGFTFSDYYMSWIRQAPGKGLEWVSYISSSGSTIYYADSVKGDSPSPGTTPKNSLYLQMNSLRAEDTAVYYCAKVDGPPSFDIWRQGTMVTVSS | BCMA-47 VH chain (aa) |
| 534 | DIVMTQSPDSLAVSLGERATINCKSSQSVLYSSNNKNYLAWYQQKPGQPPKLLIYWGSTRESGVPDRFSGSGSGTDFTLTISSLQAEDVAIYHCQQYISLPWTFGQGTKVEIK | BCMA-24 VL chain (aa) |
| 535 | DIQMTQSPAFLSASVGDRVTVTCRASQGISNYLAWYQQKPGNAPRLLIYSASTLQSGVPSRFRGTGYGTEFSLTIDSLQPEDFATYYCQQSYTSRQTFGPGTRLDIK | BCMA-25 VL chain (aa) |

| SEQ ID NO | SEQUENCE | Description |
|---|---|---|
| 536 | SYVLTQPPSVSVAPGQTARITCGANNIGSKSVHWYQQKPGQAPMLVVYDDDDRPSGIPER FSGSNSGNTATLTISGVEAGDEADYFCHLWDRSRDHYVFGTGTKLTVL | BCMA-26 VL chain (aa) |
| 537 | DIVMTQSPLSLSVTPGEPASISCRSSQSLLHSNGYNYLDWYLQKPGQSPQLLIYLGSNRA SGVPDRFSGSGSGTDFTLKISRVEAEDVGVYYCMQALQTPPWTFGQGTKVEIK | BCMA-28 VL chain (aa) |
| 538 | QPVLTQPASVSGSPGQSITISCTGTSSDVGSYNLVSWYQQHPGKAPKLMIYEVSKRPSGV SNRFSGSKSGNTASPTISGLQAEDEADYYCCSYAGSSTSRDVFGXGTKLTVL | BCMA-29 VL chain (aa) |
| 539 | EIVLTQSPATLSVSPGERATLSCRASQPIRSNLAWYQQKPGQAPKLLIYSASTRATGIPD RFSGSGSGTDFTLTISRLEHEDFAVYYRRHYAPLTFGGGTKVEIK | BCMA-30 VL chain (aa) |
| 540 | DVVMTQSPDSLAVSLGERATISCKSSQSVLNSSNNKNYVAWYKQKPGQPPKLVISWASTR ESGVPDRFSGSGSGTDFTLTISSLQAEDVAVYYCQQYYSTPYTFGQGTKLDIK | BCMA-31 VL chain (aa) |
| 541 | QTVVTQPPSVSVAPGQTARITCGGNNIGSKGVHWYRQRPGQAPEVVIYDDSDRPSGVPDR FSGSNSGNTATLTVRGVEAGDEADYYCQVWDSSSDHWVFGGGTKLTVL | BCMA-32 VL chain (aa) |
| 542 | EIVMTQSPATLSLSPGDRATLSCRASQSISNYLAWYQQKPGQAPRLLIYDASNRATGIPA RFSGSGSGTDFTLTISSLEPEDFAVYYCQQRSNWPPYTFGQGTKLDIK | BCMA-34 VL chain (aa) |
| 543 | NFMLTQPPSVSVAPGQTARITCGANNIGSKSVHWYQQKPGQAPMLVVYDDDDRPSGIPER FSGSNSGNTATLTISGVEAGDEADYFCHLWDRSRDHYVFGTGTKLDIK | BCMA-35 VL chain (aa) |
| 544 | QSVLTQEPSLTVSPGETVTLTCGSSTGPVTSAHSPSWFQKKPGQAPTTLIYETTNRHSWT PARFSGSLLGGKAALTLSGAQPEDEADYYCLLSSGDARMVFGGGTKLTVL | BCMA-36 VL chain (aa) |
| 545 | QLVLTQEPSLTVSPGGTVTLTCGSSTGAVTNGHSPYWFQQKPGQAPRTLIYDTTNRHSWT PARFSGSLLGGKAALTLSGAQPEDEAEYYCSLSHAGDRVFFGGGTKLTVL | BCMA-37 VL chain (aa) |
| 546 | QAVLTQEPSLTVSPGGTVTLTCGSSTGAVTNGHSPYWFQQKPGQAPRTLIYDTNNRHSWT PARFSGSLLGGKAALTLSGAQPEDEADYFCLLSYSDARLAFGGGTKLTVL | BCMA-38 VL chain (aa) |
| 547 | DIQXTQSPSSLSASVGDRVTITCRASQGIRYELXWYQQKPGKAPKLLIYAASTLQSGVPS RFSGSGSGTDFALTIRSLQPEDFATYYCLQHNSYPLTFGRGTKLEIK | BCMA-39 VL chain (aa) |
| 548 | QSALTQPASVSGSPGQSITISCTGSSSDVSKYNLVSWYQQPPGKAPKLIIYDVNKRPSGV SNRFSGSKSGNTATLTISGLQGDDEADYYCCSYGGSRSYVFGTGTKLTVL | BCMA-40 VL chain (aa) |
| 549 | QPVLTQPPSVSGTPGQRVTIPCSGSSSNIGGNSVDWFQEVPGTAPKLLIYANDRRPSGVP DRFSGTKSGTSASLAIRGLQSDDDAHYYCESWDDALNGHVFGGGTKLTVL | BCMA-41 VL chain (aa) |
| 550 | DIQMTQSPSLVSASVGDRVTITCRASQGIGNGLAWYQQKPGKAPKLLLFAASRLESGVPS RFSGSRSGTDYTLTISSLQPEDVATYYCQQYVEDALTFGGGTKVDIK | BCMA-42 VL chain (aa) |
| 551 | AAWDGSLNGLV | BCMA-52 CDR-L3 (aa) |
| 552 | DVVMTQSPDSLAVSLGERATINCKSSQNLLYSSNNKNYLAWYQQKPGQPPKLLIYWASTR ESGVPDRFSGSGSGTDFTLTISSLQAEDVAVYYCQQYYSSPYTFGQGTKLEIK | BCMA-44 VL chain (aa) |
| 553 | AIRMTQSPSSLSASVGDRVTITCRASQGIGRSLAWYKQKPGGVPQLLIHDASSLRSGVPS RFSGSGSGTEFTLTISGVQSEDSATYHCQQLNGYPWTFGQGTKVDIK | BCMA-45 VL chain (aa) |
| 554 | QAVLTQPPSVSVAPGKTATITCGGNNIGSKSVHWYQRKPGQGPVVVIQYDTDRPSGIPER FSGSKSGDTASLTISGVEAGDEADYYCQLWDSDSDDFAFGTGTKLTVL | BCMA-47 VL chain (aa) |
| 555 | QPVLTQPPSVSVAPGKTATITCGNNIGSKSVHWYQRKPGQGPVVVIQYDTDRPSGIPER FSGSNSGNTATLTISRVEAGDEGDYYCQVWDSSSDHWVFGGGTKLTVL | BCMA-48 VL chain (aa) |
| 556 | LPVLTQPPSVSVAPGKTARITCGGDQIGRKSVHWYQQKPGQAPVLVMSYDSDRPSGIPER FSGSNSGNTATLTISRVEAGDEAAYYCQVWDSSTGQYVVFGGGTKLTVL | BCMA-49 VL chain (aa) |
| 557 | AIQLTQSPSTLSASVGDRVAITCRASQNIGDWLAWYQQKPGKAPKLLIFGASILESGVPS RFSGSGSGTDFTLTISSLQPEDVAVYYCQKYDGAPPWTFGQGTKVEIK | BCMA-51 VL chain (aa) |
| 558 | EVQLVQSGGGLVKPGGSLRLSCAASGFTFSDYYMSWIRQAPGKGLEWVSGISWNSGSIGY ADSVKGRFTISRDNAKNSLYLQMNSLRAEDTAVYYCARDLGPPYGDDAFDIWGQGTMVTV SSGGGGSGGGGSGGGGSDIVMTQSPDSLAVSLGERATINCKSSQSVLYSSNNKNYLAWYQ QKPGQPPKLLIYWGSTRESGVPDXFSGSGSGTDFTLTISSLQAEDVAIYHCQQYISLPWT FGQGTKVEIK | BCMA-24 scFv sequence (aa) |

-continued

| SEQ ID NO | SEQUENCE | Description |
|---|---|---|
| 559 | EVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIQMTQSPAFLSASVGDRVTVTCRASQGISNYLAWYQQKPGNAPRLL IYSASTLQSGVPSRFRGTGYGTEFSLTIDSLQPEDFATYYCQQSYTSRQTFGPGTRLDIK | BCMA-25 scFv sequence (aa) |
| 560 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGPPSFDIWGQGTMVTVSSGG GGSGGGGSGGGGSSYVLTQPPSVSVAPGQTARITCGANNIGSKSVHWYQQKPGQAPMLVV YDDDDRPSGIPERFSGSNSGNTATLTISGVEAGDEADYFCHLWDRSRDHYVFGTGTKLTV L | BCMA-26 scFv sequence (aa) |
| 561 | EVQLLESGGGLVQPGRSLRLSCVASGFTFDDYAMHWVRQAPGKGLEWVSGISWNSGSIGY ADSVKGRFTISRDNAKNSLYLQMNSLRAEDTALYYCAKGGLGITPYYFDYWGQGTLVTVS SGGGGSGGGGSGGGGSQPVLTQPPSASGTPGQRVTISCSGGKTVNWFRQVPGTAPQLLIY SNDQRPSGVPDRFSGSKSGSSASLDISGLQSEDEAYYYCGSWDDSLNAWVFGGETKLTVL | BCMA-27 scFv sequence (aa) |
| 562 | QVQLVQSGGGLVQPGRSLRLSCAASGFTFDDYAMHWVRQAPGKGLEWVSGISWNSGSIXY ADSVKGRFTISRDNAKNSLYLQMNSLRAEDTAVYYCARDLGPPYGDDAFDIGGQGTMVTV SSGGGGSGGGGSGGGGSDIVMTQSPLSLSVTPGEPASISCRSSQSLLHSNGYNYLDWYLQ KPGQSPQLLIYLGSNRASGVPDRFSGSGSGTDFTLKISRVEAEDVGVYYCMQALQTPPWT FGQGTKVEIK | BCMA-28 scFv sequence (aa) |
| 563 | QVQLVQSGGGLVQPGRSLRLSCAASGFTFDDYAMHWVRQAPGKGLEWVSGISWNSGSIGY ADSVKGRFTISRDNAKNSLYLQMNSLRAEDTAVYYCARDLGPPYGDDAFDIWGQGTMVTV SSGGGGSGGGGSGGGGSQPVLTQPASVSGSPGQSITISCTGTSSDVGSYNLVSWYQQHPG KAPKLMIYEVSKRPSGVSNRFSGSKSGNTASPTISGLQAEDEADYYCCSYAGSSTSRDVF GXGTKLTVL | BCMA-29 scFv sequence (aa) |
| 564 | QVQLVQSGGGLVQPGRSLRLSCAASGFTFGDYAMHWVRQAPGKGLEWVSGISWNSGSIGY ADSVKGRFTISRDNAKNSLYLQMNSLRAEDTAVYYCARDLDPDDAFDIWGQGTMVTVSSG GGGSGGGGSGGGGSEIVLTQSPATLSVSPGERATLSCRASQPIRSNLAWYQQKPGQAPKL LIYSASTRATGIPDRFSGSGSGTDFTLTISRLEHEDFAVYYRRHYAPLTFGGGTKVEIK | BCMA-30 scFv sequence (aa) |
| 565 | EVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDVVMTQSPDSLAVSLGERATISCKSSQSVLNSSNNKNYVAWYKQKPG QPPKLVISWASTRESGVPDRFSGSGSGTDFTLTISSLQAEDVAVYYCQQYYSTPYTFGQG TKLDIK | BCMA-31 scFv sequence (aa) |
| 566 | QVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGPPSFDIWGQGTMVTVSSGG GGSGGGGSGGGGSQTVVTQPPSVSVAPGQTARITCGGNNIGSKGVHWYQRPGQAPEVVI YDDSDRPSGVPDRFSGSNSGNTATLTVRGVEAGDEADYYCQVWDSSSDHWVFGGGTKLTV L | BCMA-32 scFv sequence (aa) |
| 567 | QVQLVQSGGGLVKPGGSLRLSCAASGFTFSDYYMSWIRQAPGKGLEWVSYISGSGSTIYY ADSVKGRFTISRDNAKNSLYLQMNSLRAEDTAVYYCAREADSSADYWGQGTLVNVSSGGG GSGGGGSGGGGSQPVLTQPPSVSVAPGKTAMITCGGNNIGFKGVQWYQQKTGQAPVLVVY DDSDRPSGIPERFSGSNSGNTATLTISRVEAGDEADYYCQVWDSASDHWVFGGGTKLTVL | BCMA-33 scFv sequence (aa) |
| 568 | TGQLVQSGGGLVQPGRSLRLSCAASGFTFDDYAMHWVRQAPGKGLEWVSGISWNSGSIGY ADSVKGRFTISRDNAKNSLYLQMNSLRAEDTAVYYCARDLGPDYDPDAFDIWGQGTMVTV SSGGGGSGGGGSGGGGSEIVMTQSPATLSLSPGDRATLSCRASQSISNYLAWYQQKPGQA PRLLIYDASNRATGIPARFSGSGSGTDFTLTISSLEPEDFAVYYCQQRSNWPPYTFGQGT KLDIK | BCMA-34 scFv sequence (aa) |
| 569 | EVQLVQSGGGLVKPGGSLRLSCAASGFTFSDYYMSWIRQAPGKGLEWVSYISSSGSTIYY ADSVKGRFTISRDNAKNSLYLQMNSLRAEDTAVYYCARVDGDYDDYWGQGTLVTVSSGGG GSGGGGSGGGGSNFMLTQPPSVSVAPGQTARITCGANNIGSKSVHWYQQKPGQAPMLVVY DDDDRPSGIPERFSGSNSGNTATLTISGVEAGDEADYFCHLWDRSRDHYVFGTGTKLDIK | BCMA-35 scFv sequence (aa) |
| 570 | QVQLVQSGGGLVKPGGSLRLSCAASGFTFSDYYMSWIRQAPGKGLEWVSYISSSGSTIYY ADSVKGRFTISRDNAKNSLYLQMNSLRAEDTAVYYCARVDGDYVDDWGQGTLVTVSSGGG GGSGGGGSGGGGSQSVLTQEPSLTVSPGETVTLTCGSSTGPVTSAHSPSWFQKKPGQAPT TLIYETTNRHSWTPARFSGSLLGGKAALTLSGAQPEDEADYYCLLSSGDARMVFGGGTKL TVL | BCMA-36 scFv sequence (aa) |
| 571 | EVQLVQSGGGLVKPGGSLRLSCAASGFTFSDYYMSWIRQAPGKGLEWVSYISSSGSTIYY ADSVKGRFTISRDNAKSSLYLQMNSLRAEDTAVYYCARVDGDYDDYWGQGTLVTVSSGGG GGSGGGGSGGGGSQLVLTQEPSLTVSPGGTVTLTCGSSTGAVTNGHSPYWFQQKPGQAPR TLIYDTTNRHSWTPARFSGSLLGGKAALTLSGAQPEDEAEYYCSLSHAGDRVFFGGGTKL TVL | BCMA-37 scFv sequence (aa) |

-continued

| SEQ ID NO | SEQUENCE | Description |
|---|---|---|
| 572 | QVQLVQSGGGLVKPGGSLRLSCAASGFTFSDYYMSWIRQAPGKGLEWVSYISSSGSTIYY ADSVKGRFTISRDNAKNSLYLQMNSLRAEDTAVYYCARVDGDYVDDYWGQGTLVTVSSGG GGSGGGGSGGGGSQAVLTQEPSLTVSPGGTVTLTCGSSTGAVTNGHSPYWFQQKPGQAPR TLIYDTNNRHSWTPARFSGSLLGGKAALTLSGAQPEDEADYFCLLSYSDARLAFGGGTKL TVL | BCMA-38 scFv sequence (aa) |
| 573 | QVQLVQSGGGLVQPGRSLRLSCAASGFTFDDYAMHWVRQAPGKGLEWVSGISWNSGSIGY ADSVKGRFTISRDNAKNSLYLQMNSLRAEDTAVYYCARDLGPPYGDDAFDIWGQGTMVTV SSGGGGSGGGGSGGGGSDIQXTQSPSSLSASVGDRVTITCRASQGIRYELXWYQQKPGKA PKLLIYAASTLQSGVPSRFSGSGSTDFALTIRSLQPEDFATYYCLQHNSYPLTFGRGTK LEIK | BCMA-39 scFv sequence (aa) |
| 574 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGDYTEDYWGQGTLVTVSSGG GGSGGGGSGGGGSQSALTQPASVSGSPGQSITISCTGSSSDVSKYNLVSWYQQPPGKAPK LIIYDVNKRPSGVSNRFSGSKSGNTATLTISGLQGDDEADYYCCSYGGSRSYVFGTGTKL TVL | BCMA-40 scFv sequence (aa) |
| 575 | QVQLVQSGGGLVKPGGSLRLSCAASGFTFSDYYMSWIRQAPGKGLEWVSYISSSGNTIYY ADSVKGRFTISRDNAKNSLYLQMNSLRAEDTAVYYCAKVDGDYVDDYWGQGTLVTVSSGG GGSGGGGSGGGGSQPVLTQPPSVSGTPGQRVTIPCSGSSSNIGGNSVDWFQEVPGTAPKL LIYANDRRPSGVPDRFSGTKSGTSASLAIRGLQSDDDAHYYCESWDDALNGHVFGGGTKL TVL | BCMA-41 scFv sequence (aa) |
| 576 | EVQLLESGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDIQMTQSPSLVSASVGDRVTITCRASQGIGNGLAWYQQKPGKAPKLL LFAASRLESGVPSRFSGSRSGTDYTLTISSLQPEDVATYYCQQYVEDALTFGGGTKVDIK | BCMA-42 scFv sequence (aa) |
| 577 | EVQLVQSGAEVKKPGESLKISCKGSGYSFTSYWIGWVRQMPGKGLEWMGIIYPGDSDTRY SPSFQGHVTISADKSISTAYLQWSSLKASDTAMYYCARYSGSFDNWGQGTLVTVSS | BCMA-52 VH (aa) |
| 578 | EVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSDVVMTQSPDSLAVSLGERATINCKSSQNLLYSSNNKNYLAWYQQKPG QPPKLLIYWASTRESGVPDRFSGSGSGTDFTLTISSLQAEDVAVYYCQQYYSSPYTFGQG TKLEIK | BCMA-44 scFv sequence (aa) |
| 579 | QVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSAIRMTQSPSSLSASVGDRVTITCRASQGIGRSLAWYKQKPGGVPQLL IHDASSLRSGVPSRFSGSGSGTEFTLTISGVQSEDSATYHCQQLNGYPWTFGQGTKVDIK | BCMA-45 scFv sequence (aa) |
| 580 | QVQLLESGGGLVKPGGSLRLSCAASGFTFSDYYMSWIRQAPGKGLEWVSYISSSGSTIYY ADSVKGDSPSPGTTPKNSLYLQMNSLRAEDTAVYYCAKVDGPPSFDIWRQGTMVTVSSGG GGSGGGGSGGGGSQAVLTQPPSVSVAPGKTATITCGGNNIGSKSVHWYQRKPGQGPVVVI QYDTDRPSGIPERFSGSKSGDTASLTISGVEAGDEADYYCQLWDSDSDDFAFGTGTKLTV L | BCMA-47 scFv sequence (aa) |
| 581 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGPPSFDIWGQGTMVTVSSGG GGSGGGGSGGGGSQPVLTQPPSVSVAPGKTATITCGGNNIGSKSVHWYQRKPGQGPVVVI QYDTDRPSGIPERFSGSNSGNTATLTISRVEAGDEGDYYCQVWDSSSDHWVFGGGTKLTV L | BCMA-48 scFv sequence (aa) |
| 582 | EVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCAKVDGPPSFDIWGQGTMVTVSSGG GGSGGGGSGGGGSLPVLTQPPSVSVAPGKTARITCGGDQIGRKSVHWYQQKPGQAPVLVM SYDSDRPSGIPERFSGSNSGNTATLTISRVEAGDEAAYYCQVWDSSTGQYVVFGGGTKLT VL | BCMA-49 scFv sequence (aa) |
| 583 | EVQLVQSGGGLVQPGRSLRLSCTASGFTFGDYAMSWFRQAPGKGLEWVGFIRSKAYGGTT EYAASVKGRFTISRDDSKSIAYLQMNSLKTEDTAVYYCAAWSAPTDYWGQGTLVTVSSGG GGSGGGGSGGGGSAIQLTQSPSTLSASVGDRVAITCRASQNIGDWLAWYQQKPGKAPKLL IFGASILESGVPSRFSGSGSGTDFTLTISSLQPEDVAVYYCQKYDGAPPWTFGQGTKVEI K | BCMA-51 scFv sequence (aa) |
| 584 | CAGGTGCAGCTGGTGCAATCTGGGGGAGGCTTGGTCAAGCCTGGAGGGTCCCTGAGACTC TCCTGTGCAGCCTCTGGATTCACCTTCAGTGACTACTACATGAGCTGGATCCGCCAGGCT CCAGGGAAGGGGCTGGAGTGGGTTTCATACATTAGTAGTAGTGGTAATACCATATACTAC GCAGACTCTGTAAAGGGCCGATTCACCATCTCCAGGGACAACGCCAAAAACTCACTGTAT CTGCAAATGAACAGCCTGAGAGCCGAGGACACGGCCGTGTATTACTGTGCGAAAGTGGAC | BCMA-41 scFv sequence (nt) |

-continued

| SEQ ID NO | SEQUENCE | Description |
|---|---|---|
|  | GGTGACTACGTCGATGACTACTGGGGCCAGGGAACCCTGGTCACCGTCTCCTCAGGTGGA<br>GGCGGTTCAGGCGGAGGTGGCTCTGGCGGTGGCGGATCGCAGCCTGTGCTGACTCAGCCA<br>CCCTCAGTGTCTGGGACCCCCGGGCAGAGGGTCACCATCCCTTGTTCTGGAAGCAGCTCC<br>AACATCGGAGGTAACTCTGTAGACTGGTTCCAGGAGGTCCCAGGGACGGCCCCCAAACTC<br>CTCATCTACGCTAATGATCGGCGGCCCTCGGGTGTCCCTGACCGCTTCTCTGGCACCAAG<br>TCGGGCACCTCAGCCTCCCTGGCCATCAGGGGGCTCCAGTCTGACGATGACGCTCATTAT<br>TACTGTGAATCCTGGGACGATGCCCTGAACGGTCACGTGTTCGGCGGAGGGACCAAGCTG<br>ACCGTCCTA |  |
| 585 | QIQLVQSGPELKKPGETVKISCKASGYTFTDYSINWVKRAPGKGLKWMGWINTETREPAY<br>AYDFRGRFAFSLETSASTAYLQINNLKYEDTATYFCALDYSYAMDYWGQGTSVTVSSGGG<br>GSGGGGSGGGGSDIVLTQSPPSLAMSLGKRATISCRASESVTILGSHLIHWYQQKPGQPP<br>TLLIQLASNVQTGVPARFSGSGSRTDFTLTIDPVEEDDVAVYYCLQSRTIPRTFGGGTKL<br>EIK | Reference 1 VH-VL scFv (aa) |
| 586 | DVVMTQSHRFMSTSVGDRVSITCRASQDVNTAVSWYQQKPGQSPKLLIFSASYRYTGVPD<br>RFTGSGSGADFTLTISSVQAEDLAVYYCQQHYSTPWTFGGGTKLDIKGGGGSGGGGSGGG<br>GSQIQLVQSGPDLKKPGETVKLSCKASGYTFTNFGMNWVKQAPGKGFKWMAWINTYTGES<br>YFADDFKGRFAFSVETSATTAYLQINNLKTEDTATYFCARGEIYYGYDGGFAYWGQGTLV<br>TVSA | Reference 2 VL-VH scFv (aa) |
| 587 | SYELTQPPSASGTPGQRVTMSCSGTSSNIGSHSVNWYQQLPGTAPKLLIYTNNQRPSGVP<br>DRFSGSKSGTSASLAISGLQSEDEADYYCAAWDGSLNGLVFGGGTKLTVLG | BCMA-52 VL (aa) |
| 588 | GYTFIDYY | BCMA-55 CDR-H1 (aa) |
| 589 | INPNSGGT | BCMA-55 CDR-H2 (aa) |
| 590 | ARSQRDGYMDY | BCMA-55 CDR-H3 (aa) |
| 591 | ISCTGTSSD | BCMA-55 CDR-L1 (aa) |
| 592 | EDS | BCMA-55 CDR-L2 (aa) |
| 593 | SSNTRSSTLV | BCMA-55 CDR-L3 (aa) |
| 594 | EVQLVQSGAEMKKPGASLKLSCKASGYTFIDYYVYWMRQAPGQGLESMGWINPNSGGTNY<br>AQKFQGRVTMTRDTSISTAYMELSRLRSDDTAMYYCARSQRDGYMDYWGQGTLVTVSS | BCMA-55 VH (aa) |
| 595 | QSALTQPASVSASPGQSIAISCTGTSSDVGWYQQHPGKAPKLMIYEDSKRPSGVSNRFSG<br>SKSGNTASLTISGLQAEDEADYYCSSNTRSSTLVFGGGTKLTVLG | BCMA-55 VL (aa) |
| 596 | LEGGGEGRGSLLTCGDVEENPGPR | T2A |
| 597 | EGRGSLLTCGDVEENPGP | T2A |
| 598 | GSGATNFSLLKQAGDVEENPGP | P2A |
| 599 | ATNFSLLKQAGDVEENPGP | P2A |
| 600 | QCTNYALLKLAGDVESNPGP | E2A |
| 601 | VKQTLNFDLLKLAGDVESNPGP | F2A |
| 602 | MLLLVTSLLLCELPHPAFLLIPRKVCNGIGIGEFKDSLSINATNIKHFKNCTSISGDLHI<br>LPVAFRGDSFTHTPPLDPQELDILKTVKEITGFLLIQAWPENRTDLHAFENLEIIRGRTK<br>QHGQFSLAVVSLNITSLGLRSLKEISDGDVIISGNKNLCYANTINWKKLFGTSGQKTKII<br>SNRGENSCKATGQVCHALCSPEGCWGPEPRDCVSCRNVSRGRECVDKCNLLEGEPREFVE<br>NSECIQCHPECLPQAMNITCTGRGPDNCIQCAHYIDGPHCVKTCPAGVMGENNTLVWKYA<br>DAGHVCHLCHPNCTYGCTPGLEGCPTNGPKIPSIATGMVGALLLLLVVALGIGLFM | EGFRt |
| 603 | RKVCNGIGIGEFKDSLSINATNIKHFKNCTSISGDLHILPVAFRGDSFTHTPPLDPQELD<br>ILKTVKEITGFLLIQAWPENRTDLHAFENLEIIRGRTKQHGQFSLAVVSLNITSLGLRSL<br>KEISDGDVIISGNKNLCYANTINWKKLFGTSGQKTKIISNRGENSCKATGQVCHALCSPE<br>GCWGPEPRDCVSCRNVSRGRECVDKCNLLEGEPREFVENSECIQCHPECLPQAMNITCTG<br>RGPDNCIQCAHYIDGPHCVKTCPAGVMGENNTLVWKYADAGHVCHLCHPNCTYGCTPGL<br>EGCPTNGPKIPSIATGMVGALLLLLVVALGIGLFM | EGFRt |
| 604 | GAGGTGCAGCTGGTGCAGAGCGGAGGAGGCCTGGTGCAGCCTGGCAGGTCCCTGCGCCTG<br>TCTTGCACCGCCAGCGGCTTCACATTTGGCGACTATGCCATGTCCTGGTTCAGGCAGGCA<br>CCAGGCAAGGGCCTGGAGTGGGTGGCTTTATCCGCTCAAGGCCTACGGCGGCACCACA<br>GAGTATGCCGCCAGCGTGAAGGGCCGGTTCACCATCAGCCGGGACGACTCTAAGAGCATC<br>GCCTACCTGCAGATGAACTCTCTGAAGACCGAGGACACAGCCGTGTACTATTGCGCAGCA | BCMA-25 scFv sequence (nt) |

| SEQ ID NO | SEQUENCE | Description |
|---|---|---|
|  | TGGAGCGCCCCAACCGATTATTGGGGCCAGGGCACCCTGGTGACAGTGAGCTCCGGCGGC<br>GGCGGCTCTGGAGGAGGAGGAAGCGGAGGAGGAGGATCCGACATCCAGATGACACAGTCC<br>CCTGCCTTTCTGTCCGCCTCTGTGGGCGATAGGGTGACCGTGAACATGTCGCGCCTCCCAG<br>GGCATCTCTAACTACCTGGCCTGGTATCAGCAGAAGCCCGGCAATGCCCCTCGGCTGCTG<br>ATCTACAGCGCCTCCACCCTGCAGAGCGGAGTGCCCTCCCGGTTCAGAGGAACCGGCTAT<br>GGCACAGAGTTTTCTCTGACCATCGACGCCTGCAGCCAGAGGATTTCGCCACATACTAT<br>TGTCAGCAGTCTTACACCAGCCGGCAGACATTTGGCCCCGGCACAAGACTGGATATCAAG |  |
| 605 | GAGGTGCAGCTGGTGGAGTCCGGAGGAGGCCTGGTGAAGCCAGGAGGCTCTCTGAGGCTG<br>AGCTGCGCAGCCTCCGGCTTCACCTTTTCTGACTACTATATGAGCTGGATCAGGCAGGCA<br>CCAGGCAAGGGCCTGGAGTGGGTGTCTTACATCAGCTCCTCTGGCAGCACAATCTACTAT<br>GCCGACTCCGTGAAGGGCAGGTTCACCATCTCTCGCGATAACGCCAAGAATAGCCTGTAT<br>CTGCAGATGAACTCCCTGCGGGCCGAGGATACAGCCGTGTACTATTGCGCCAAGGTGGAC<br>GGCCCCCCTTCCTTTGATATCTGGGGCCAGGGCACAATGGTGACCGTGAGCTCCGGAGGA<br>GGAGGATCCGGCGGAGGAGGCTCTGGCGGCGGCGGCTCTAGCTATGTGCTGACCCAGCCA<br>CCATCCGTGTCTGTGGCACCTGGACAGACAGCAAGGATCACCTGTGGAGCAAACAATATC<br>GGCAGCAAGTCCGTGCACTGGTACCAGCAGAAGCCTGGCCAGGCCCCAATGCTGGTGGTG<br>TATGACGATGACGATCGGCCCAGCGGCATCCCTGAGAGATTTTCTGGCAGCAACTCCGGC<br>AATACCGCCACACTGACCATCTCTGGAGTGGAGGCAGGCGACGAGGCAGATTACTTCTGT<br>CACCTGTGGGACCGGAGCAGAGATCACTACGTGTTCGGCACAGGCACCAAGCTGACCGTG<br>CTG | BCMA-26 scFv sequence (nt) |
| 606 | tcctatgagctgactcagccaccctcagcgtctgggaccccgggcagagggtcaccatg<br>tcttgttctggaaccagctccaacatcggaagtcactctctgtaaactggtaccagcagctc<br>ccaggaacggcccccaaactcctcatctatactaataatcagcggccctcaggggtccct<br>gaccgattctctggctccaagtctggcacctcagccctcctggccatcagtggcctccag<br>tctgaggatgaggctgattattactgtgcagcatggatggcagcctgaatggtctggta<br>ttcggcggagggaccaagctgaccgtcctaggttctagaggtggtggtggtagcggcggc<br>ggcggctctggtggtggtggatccctgagatggccgaggtgcagctggtgcagtctgga<br>gcagaggtgaaaaagcccggggagtctctgaagatctcctgtaagggttctggatacagc<br>tttaccagctactggatcggctgggtgcgccagatgcccgggaaaggcctggagtggatg<br>gggatcatctatcctggtgactctgataccagatacagcccgtcctccaaggccacgtc<br>accatctcagctgacaagtccatcagcactgcctacctgcagtggagcagcctgaaggcc<br>tcggacaccgccatgtattactgtgcgcgctactctggttcttctcgataactgggggtcaa<br>ggtactctggtgaccgtctcctca | BCMA-52 scFv sequence (nt) |
| 607 | caatctgccctgactcagcctgcctccgtgtctgcgtctcctggacagtcgatc<br>gccatctcctgcactggaaccagcagtgacgttggttggtatcaacagcaccca<br>ggcaaagcccccaaactcatgatttatgaggacagtaagcggccctcagggggtt<br>tctaatcgcttctctggctccaagtctggcaacacggcctcctgaccatctct<br>gggctccaggctgaggacgaggctgattattactgcagctcaaatacaagaagc<br>agcactttggtgttcggcggagggaccaagctgaccgtcctaggttctagaggt<br>ggtggtggtagcggcggcggcggctctggtggtggtggatccctcgagatggcc<br>gaagtgcagctggtgcagtctggggctgagatgaagaagcctggggcctcactg<br>aagctctcctgcaaggcttctggatacaccttcatcgactactatgtatactgg<br>atgcgacaggcccctggacaaggcttgagtccatgggatggatcaaccctaac<br>agtggtggcacaaactatgcacagaagtttcagggcagggtcaccatgaccagg<br>gacacgtccatcagcacagcctacatggagctgagcaggctgagatctgacgac<br>accgccatgtattactgtgcgcgctcccagcgtgacggttacatggattactgg<br>ggtcaaggtactctggtgaccgtctcctca | BCMA-55 scFv sequence (nt) |
| 608 | SNTPPLTCQR | BCMA epitope |
| 609 | CIPCQLR | BCMA epitope |
| 610 | SVTNSVK | BCMA epitope |
| 611 | CSQNEYF | BCMA epitope |
| 612 | LLHACIPCQLR | BCMA epitope |
| 613 | QNEYF | BCMA epitope |
| 614 | CIPCQL | BCMA epitope |
| 615 | CQRYC | BCMA epitope |
| 616 | MLMAG | BCMA epitope |
| 617 | QNEYFDSLL | BCMA epitope |
| 618 | YFDSL | BCMA epitope |

| SEQ ID NO | SEQUENCE | Description |
|---|---|---|
| 619 | QLRCSSNTPPL | BCMA epitope |
| 620 | YFDSLL | BCMA epitope |

The invention claimed is:

1. An anti-B cell maturation antigen (BCMA) antibody or an antigen-binding fragment thereof, comprising a heavy chain variable ($V_H$) region and a light chain variable ($V_L$) region, wherein:

the $V_H$ region comprises a CDR-H1, CDR-H2, and CDR-H3 comprising the amino acid sequence of SEQ ID NOS:2, 5, and 8, respectively, and the $V_L$ region comprises a CDR-L1, CDR-L2, and CDR-L3 comprising the amino acid sequence of SEQ ID NOS:27, 38, and 48, respectively;

the $V_H$ region comprises a CDR-H1, CDR-H2, and CDR-H3 comprising the amino acid sequence of SEQ ID NOS:2, 5, and 9, respectively, and the $V_L$ region comprises a CDR-L1, CDR-L2, and CDR-L3 comprising the amino acid sequence of SEQ ID NOS:33, 43, and 55, respectively;

the $V_H$ region comprises a CDR-H1, CDR-H2, and CDR-H3 comprising the amino acid sequence of SEQ ID NOS:3, 6, and 11, respectively, and the $V_L$ region comprises a CDR-L1, CDR-L2, and CDR-L3 comprising the amino acid sequence of SEQ ID NOS:35, 45, and 57, respectively;

the $V_H$ region comprises a CDR-H1, CDR-H2, and CDR-H3 comprising the amino acid sequence of SEQ ID NOS:140, 145, and 149, respectively, and the $V_L$ region comprises a CDR-L1, CDR-L2, and CDR-L3 comprising the amino acid sequence of SEQ ID NOS:174, 179, and 184, respectively;

the $V_H$ region comprises a CDR-H1, CDR-H2, and CDR-H3 comprising the amino acid sequence of SEQ ID NOS:141, 145, and 149, respectively, and the $V_L$ region comprises a CDR-L1, CDR-L2, and CDR-L3 comprising the amino acid sequence of SEQ ID NOS:174, 179, and 185, respectively;

the $V_H$ region comprises a CDR-H1, CDR-H2, and CDR-H3 comprising the amino acid sequence of SEQ ID NOS:141, 145, and 150, respectively, and the $V_L$ region comprises a CDR-L1, CDR-L2, and CDR-L3 comprising the amino acid sequence of SEQ ID NOS:174, 179, and 186, respectively;

the $V_H$ region comprises a CDR-H1, CDR-H2, and CDR-H3 comprising the amino acid sequence of SEQ ID NOS:142, 146, and 151, respectively, and the $V_L$ region comprises a CDR-L1, CDR-L2, and CDR-L3 comprising the amino acid sequence of SEQ ID NOS:174, 179, and 187, respectively;

the $V_H$ region comprises a CDR-H1, CDR-H2, and CDR-H3 comprising the amino acid sequence of SEQ ID NOS:2, 5, and 152, respectively, and the $V_L$ region comprises a CDR-L1, CDR-L2, and CDR-L3 comprising the amino acid sequence of SEQ ID NOS:175, 180, and 188, respectively;

the $V_H$ region comprises a CDR-H1, CDR-H2, and CDR-H3 comprising the amino acid sequence of SEQ ID NOS:143, 147, and 153, respectively, and the $V_L$ region comprises a CDR-L1, CDR-L2, and CDR-L3 comprising the amino acid sequence of SEQ ID NOS:174, 179, and 189, respectively;

the $V_H$ region comprises a CDR-H1, CDR-H2, and CDR-H3 comprising the amino acid sequence of SEQ ID NOS:144, 148, and 154, respectively, and the $V_L$ region comprises a CDR-L1, CDR-L2, and CDR-L3 comprising the amino acid sequence of SEQ ID NOS:176, 181, and 190, respectively;

the $V_H$ region comprises a CDR-H1, CDR-H2, and CDR-H3 comprising the amino acid sequence of SEQ ID NOS:3, 6, and 155, respectively, and the $V_L$ region comprises a CDR-L1, CDR-L2, and CDR-L3 comprising the amino acid sequence of SEQ ID NOS:177, 182, and 191, respectively;

the $V_H$ region comprises a CDR-H1, CDR-H2, and CDR-H3 comprising the amino acid sequence of SEQ ID NOS:2, 5, and 156, respectively, and the $V_L$ region comprises a CDR-L1, CDR-L2, and CDR-L3 comprising the amino acid sequence of SEQ ID NOS:174, 179, and 192, respectively;

the $V_H$ region comprises a CDR-H1, CDR-H2, and CDR-H3 comprising the amino acid sequence of SEQ ID NOS:2, 6, and 376, respectively, and the $V_L$ region comprises a CDR-L1, CDR-L2, and CDR-L3 comprising the amino acid sequence of SEQ ID NOS:30, 399, and 415, respectively;

the $V_H$ region comprises a CDR-H1, CDR-H2, and CDR-H3 comprising the amino acid sequence of SEQ ID NOS:3, 6, and 155, respectively, and the $V_L$ region comprises a CDR-L1, CDR-L2, and CDR-L3 comprising the amino acid sequence of SEQ ID NOS:177, 182, and 191, respectively;

the $V_H$ region comprises a CDR-H1, CDR-H2, and CDR-H3 comprising the amino acid sequence of SEQ ID NOS:3, 372, and 376, respectively, and the $V_L$ region comprises a CDR-L1, CDR-L2, and CDR-L3 comprising the amino acid sequence of SEQ ID NOS:381, 401, and 417, respectively;

the $V_H$ region comprises a CDR-H1, CDR-H2, and CDR-H3 comprising the amino acid sequence of SEQ ID NOS:3, 6, and 376, respectively, and the $V_L$ region comprises a CDR-L1, CDR-L2, and CDR-L3 comprising the amino acid sequence of SEQ ID NOS:382, 402, and 418, respectively;

the $V_H$ region comprises a CDR-H1, CDR-H2, and CDR-H3 comprising the amino acid sequence of SEQ ID NOS:3, 6, and 377, respectively, and the $V_L$ region comprises a CDR-L1, CDR-L2, and CDR-L3 comprising the amino acid sequence of SEQ ID NOS:383, 403, and 419, respectively;

the $V_H$ region comprises a CDR-H1, CDR-H2, and CDR-H3 comprising the amino acid sequence of SEQ ID NOS:2, 373, and 152, respectively, and the $V_L$ region comprises a CDR-L1, CDR-L2, and CDR-L3 comprising the amino acid sequence of SEQ ID NOS:175, 180, and 188, respectively;

the $V_H$ region comprises a CDR-H1, CDR-H2, and CDR-H3 comprising the amino acid sequence of SEQ ID NOS:3, 6, and 11, respectively, and the $V_L$ region comprises a CDR-L1, CDR-L2, and CDR-L3 comprising the amino acid sequence of SEQ ID NOS:386, 404, and 420, respectively;

the $V_H$ region comprises a CDR-H1, CDR-H2, and CDR-H3 comprising the amino acid sequence of SEQ ID NOS:2, 5, and 9, respectively, and the $V_L$ region comprises a CDR-L1, CDR-L2, and CDR-L3 comprising the amino acid sequence of SEQ ID NOS:387, 405, and 422, respectively;

the $V_H$ region comprises a CDR-H1, CDR-H2, and CDR-H3 comprising the amino acid sequence of SEQ ID NOS:2, 5, and 9, respectively, and the $V_L$ region comprises a CDR-L1, CDR-L2, and CDR-L3 comprising the amino acid sequence of SEQ ID NOS:388, 406, and 423, respectively;

the $V_H$ region comprises a CDR-H1, CDR-H2, and CDR-H3 comprising the amino acid sequence of SEQ ID NOS:2, 5, and 9, respectively, and the $V_L$ region comprises a CDR-L1, CDR-L2, and CDR-L3 comprising the amino acid sequence of SEQ ID NOS:388, 407, and 424, respectively;

the $V_H$ region comprises a CDR-H1, CDR-H2, and CDR-H3 comprising the amino acid sequence of SEQ ID NOS:3, 6, and 376, respectively, and the $V_L$ region comprises a CDR-L1, CDR-L2, and CDR-L3 comprising the amino acid sequence of SEQ ID NOS:389, 408, and 425, respectively;

the $V_H$ region comprises a CDR-H1, CDR-H2, and CDR-H3 comprising the amino acid sequence of SEQ ID NOS:2, 374, and 9, respectively, and the $V_L$ region comprises a CDR-L1, CDR-L2, and CDR-L3 comprising the amino acid sequence of SEQ ID NOS:391, 409, and 426, respectively.

2. An anti-B cell maturation antigen (BCMA) antibody or an antigen-binding fragment thereof, comprising a heavy chain variable ($V_H$) region and a light chain variable ($V_L$) region, wherein:

the $V_H$ region comprises a CDR-H1, CDR-H2 and CDR-H3 contained within the $V_H$ region amino acid sequence of SEQ ID NO:111, and the $V_L$ region comprises a CDR-L1, CDR-L2 and CDR-L3 contained within the $V_L$ region amino acid sequence of SEQ ID NO:117;

the $V_H$ region comprises a CDR-H1, CDR-H2 and CDR-H3 contained within the $V_H$ region amino acid sequence of SEQ ID NO:112, and the $V_L$ region comprises a CDR-L1, CDR-L2 and CDR-L3 contained within the $V_L$ region amino acid sequence of SEQ ID NO:124;

the $V_H$ region comprises a CDR-H1, CDR-H2 and CDR-H3 contained within the $V_H$ region amino acid sequence of SEQ ID NO:114, and the $V_L$ region comprises a CDR-L1, CDR-L2 and CDR-L3 contained within the $V_L$ region amino acid sequence of SEQ ID NO:126;

the $V_H$ region comprises a CDR-H1, CDR-H2 and CDR-H3 contained within the $V_H$ region amino acid sequence of SEQ ID NO:247, and the $V_L$ region comprises a CDR-L1, CDR-L2 and CDR-L3 contained within the $V_L$ region amino acid sequence of SEQ ID NO:257;

the $V_H$ region comprises a CDR-H1, CDR-H2 and CDR-H3 contained within the $V_H$ region amino acid sequence of SEQ ID NO:248, and the $V_L$ region comprises a CDR-L1, CDR-L2 and CDR-L3 contained within the $V_L$ region amino acid sequence of SEQ ID NO:258;

the $V_H$ region comprises a CDR-H1, CDR-H2 and CDR-H3 contained within the $V_H$ region amino acid sequence of SEQ ID NO:249, and the $V_L$ region comprises a CDR-L1, CDR-L2 and CDR-L3 contained within the $V_L$ region amino acid sequence of SEQ ID NO:259;

the $V_H$ region comprises a CDR-H1, CDR-H2 and CDR-H3 contained within the $V_H$ region amino acid sequence of SEQ ID NO:250, and the $V_L$ region comprises a CDR-L1, CDR-L2 and CDR-L3 contained within the $V_L$ region amino acid sequence of SEQ ID NO:260;

the $V_H$ region comprises a CDR-H1, CDR-H2 and CDR-H3 contained within the $V_H$ region amino acid sequence of SEQ ID NO:251, and the $V_L$ region comprises a CDR-L1, CDR-L2 and CDR-L3 contained within the $V_L$ region amino acid sequence of SEQ ID NO:261;

the $V_H$ region comprises a CDR-H1, CDR-H2 and CDR-H3 contained within the $V_H$ region amino acid sequence of SEQ ID NO:252, and the $V_L$ region comprises a CDR-L1, CDR-L2 and CDR-L3 contained within the $V_L$ region amino acid sequence of SEQ ID NO:262;

the $V_H$ region comprises a CDR-H1, CDR-H2 and CDR-H3 contained within the $V_H$ region amino acid sequence of SEQ ID NO:253, and the $V_L$ region comprises a CDR-L1, CDR-L2 and CDR-L3 contained within the $V_L$ region amino acid sequence of SEQ ID NO:263;

the $V_H$ region comprises a CDR-H1, CDR-H2 and CDR-H3 contained within the $V_H$ region amino acid sequence of SEQ ID NO:254, and the $V_L$ region comprises a CDR-L1, CDR-L2 and CDR-L3 contained within the $V_L$ region amino acid sequence of SEQ ID NO:264;

the $V_H$ region comprises a CDR-H1, CDR-H2 and CDR-H3 contained within the $V_H$ region amino acid sequence of SEQ ID NO:255, and the $V_L$ region comprises a CDR-L1, CDR-L2 and CDR-L3 contained within the $V_L$ region amino acid sequence of SEQ ID NO:265;

the $V_H$ region comprises a CDR-H1, CDR-H2 and CDR-H3 contained within the $V_H$ region amino acid sequence of SEQ ID NO:518, and the $V_L$ region comprises a CDR-L1, CDR-L2 and CDR-L3 contained within the $V_L$ region amino acid sequence of SEQ ID NO:534;

the $V_H$ region comprises a CDR-H1, CDR-H2 and CDR-H3 contained within the $V_H$ region amino acid sequence of SEQ ID NO:520, and the $V_L$ region comprises a CDR-L1, CDR-L2 and CDR-L3 contained within the $V_L$ region amino acid sequence of SEQ ID NO:264;

the $V_H$ region comprises a CDR-H1, CDR-H2 and CDR-H3 contained within the $V_H$ region amino acid sequence of SEQ ID NO:521, and the $V_L$ region comprises a CDR-L1, CDR-L2 and CDR-L3 contained within the $V_L$ region amino acid sequence of SEQ ID NO:537;

the $V_H$ region comprises a CDR-H1, CDR-H2 and CDR-H3 contained within the $V_H$ region amino acid sequence of SEQ ID NO:522, and the $V_L$ region comprises a CDR-L1, CDR-L2 and CDR-L3 contained within the V$_L$ region amino acid sequence of SEQ ID NO:538;

the V$_H$ region comprises a CDR-H1, CDR-H2 and CDR-H3 contained within the V$_H$ region amino acid sequence of SEQ ID NO:523, and the V$_L$ region comprises a CDR-L1, CDR-L2 and CDR-L3 contained within the V$_L$ region amino acid sequence of SEQ ID NO:539;

the V$_H$ region comprises a CDR-H1, CDR-H2 and CDR-H3 contained within the V$_H$ region amino acid sequence of SEQ ID NO:525, and the V$_L$ region comprises a CDR-L1, CDR-L2 and CDR-L3 contained within the V$_L$ region amino acid sequence of SEQ ID NO:261;

the V$_H$ region comprises a CDR-H1, CDR-H2 and CDR-H3 contained within the V$_H$ region amino acid sequence of SEQ ID NO:526, and the V$_L$ region comprises a CDR-L1, CDR-L2 and CDR-L3 contained within the V$_L$ region amino acid sequence of SEQ ID NO:542;

the V$_H$ region comprises a CDR-H1, CDR-H2 and CDR-H3 contained within the V$_H$ region amino acid sequence of SEQ ID NO:528, and the V$_L$ region comprises a CDR-L1, CDR-L2 and CDR-L3 contained within the V$_L$ region amino acid sequence of SEQ ID NO:544;

the V$_H$ region comprises a CDR-H1, CDR-H2 and CDR-H3 contained within the V$_H$ region amino acid sequence of SEQ ID NO:529, and the V$_L$ region comprises a CDR-L1, CDR-L2 and CDR-L3 contained within the V$_L$ region amino acid sequence of SEQ ID NO:545;

the V$_H$ region comprises a CDR-H1, CDR-H2 and CDR-H3 contained within the V$_H$ region amino acid sequence of SEQ ID NO:528, and the V$_L$ region comprises a CDR-L1, CDR-L2 and CDR-L3 contained within the V$_L$ region amino acid sequence of SEQ ID NO:546;

the V$_H$ region comprises a CDR-H1, CDR-H2 and CDR-H3 contained within the V$_H$ region amino acid sequence of SEQ ID NO:522, and the V$_L$ region comprises a CDR-L1, CDR-L2 and CDR-L3 contained within the V$_L$ region amino acid sequence of SEQ ID NO:547;

the V$_H$ region comprises a CDR-H1, CDR-H2 and CDR-H3 contained within the V$_H$ region amino acid sequence of SEQ ID NO:530, and the V$_L$ region comprises a CDR-L1, CDR-L2 and CDR-L3 contained within the V$_L$ region amino acid sequence of SEQ ID NO:549.

3. The anti-BCMA antibody or antigen-binding fragment thereof of claim 1, wherein:

the V$_H$ region and the V$_L$ region comprise amino acid sequences having at least 90% sequence identity to SEQ ID NOS:111 and 117, respectively;

the V$_H$ region and the V$_L$ region comprise amino acid sequences having at least 90% sequence identity to SEQ ID NOS:112 and 124, respectively;

the V$_H$ region and the V$_L$ region comprise amino acid sequences having at least 90% sequence identity to SEQ ID NOS:114 and 126, respectively;

the V$_H$ region and the V$_L$ region comprise amino acid sequences having at least 90% sequence identity to SEQ ID NOS:247 and 257, respectively;

the V$_H$ region and the V$_L$ region comprise amino acid sequences having at least 90% sequence identity to SEQ ID NOS:248 and 258, respectively;

the V$_H$ region and the V$_L$ region comprise amino acid sequences having at least 90% sequence identity to SEQ ID NOS:249 and 259, respectively;

the V$_H$ region and the V$_L$ region comprise amino acid sequences having at least 90% sequence identity to SEQ ID NOS:250 and 260, respectively;

the V$_H$ region and the V$_L$ region comprise amino acid sequences having at least 90% sequence identity to SEQ ID NOS:251 and 261, respectively;

the V$_H$ region and the V$_L$ region comprise amino acid sequences having at least 90% sequence identity to SEQ ID NOS:252 and 262, respectively;

the V$_H$ region and the V$_L$ region comprise amino acid sequences having at least 90% sequence identity to SEQ ID NOS:253 and 263, respectively;

the V$_H$ region and the V$_L$ region comprise amino acid sequences having at least 90% sequence identity to SEQ ID NOS:254 and 264, respectively;

the V$_H$ region and the V$_L$ region comprise amino acid sequences having at least 90% sequence identity to SEQ ID NOS:255 and 265, respectively;

the V$_H$ region and the V$_L$ region comprise amino acid sequences having at least 90% sequence identity to SEQ ID NOS:518 and 534, respectively;

the V$_H$ region and the V$_L$ region comprise amino acid sequences having at least 90% sequence identity to SEQ ID NOS:520 and 264, respectively;

the V$_H$ region and the V$_L$ region comprise amino acid sequences having at least 90% sequence identity to SEQ ID NOS:521 and 537, respectively;

the V$_H$ region and the V$_L$ region comprise amino acid sequences having at least 90% sequence identity to SEQ ID NOS:522 and 538, respectively;

the V$_H$ region and the V$_L$ region comprise amino acid sequences having at least 90% sequence identity to SEQ ID NOS:523 and 539, respectively;

the V$_H$ region and the V$_L$ region comprise amino acid sequences having at least 90% sequence identity to SEQ ID NOS:525 and 261, respectively;

the V$_H$ region and the V$_L$ region comprise amino acid sequences having at least 90% sequence identity to SEQ ID NOS:526 and 542, respectively;

the V$_H$ region and the V$_L$ region comprise amino acid sequences having at least 90% sequence identity to SEQ ID NOS:528 and 544, respectively;

the V$_H$ region and the V$_L$ region comprise amino acid sequences having at least 90% sequence identity to SEQ ID NOS:529 and 545, respectively;

the V$_H$ region and the V$_L$ region comprise amino acid sequences having at least 90% sequence identity to SEQ ID NOS:528 and 546, respectively;

the V$_H$ region and the V$_L$ region comprise amino acid sequences having at least 90% sequence identity to SEQ ID NOS:522 and 547, respectively;

the V$_H$ region and the V$_L$ region comprise amino acid sequences having at least 90% sequence identity to SEQ ID NOS:530 and 549, respectively.

4. The anti-BCMA antibody or antigen-binding fragment thereof of claim 1, wherein:

the V$_H$ and V$_L$ regions comprise the amino acid sequences set forth in SEQ ID NOS:111 and 117, respectively;

the V$_H$ and V$_L$ regions comprise the amino acid sequences set forth in SEQ ID NOS:112 and 124, respectively;

the $V_H$ and $V_L$ regions comprise the amino acid sequences set forth in SEQ ID NOS:114 and 126, respectively;
the $V_H$ and $V_L$ regions comprise the amino acid sequences set forth in SEQ ID NOS:115 and 127, respectively;
the $V_H$ and $V_L$ regions comprise the amino acid sequences set forth in SEQ ID NOS:247 and 257, respectively;
the $V_H$ and $V_L$ regions comprise the amino acid sequences set forth in SEQ ID NOS:248 and 258, respectively;
the $V_H$ and $V_L$ regions comprise the amino acid sequences set forth in SEQ ID NOS:249 and 259, respectively;
the $V_H$ and $V_L$ regions comprise the amino acid sequences set forth in SEQ ID NOS:250 and 260, respectively;
the $V_H$ and $V_L$ regions comprise the amino acid sequences set forth in SEQ ID NOS:251 and 261, respectively;
the $V_H$ and $V_L$ regions comprise the amino acid sequences set forth in SEQ ID NOS:252 and 262, respectively;
the $V_H$ and $V_L$ regions comprise the amino acid sequences set forth in SEQ ID NOS:253 and 263, respectively;
the $V_H$ and $V_L$ regions comprise the amino acid sequences set forth in SEQ ID NOS:254 and 264, respectively;
the $V_H$ and $V_L$ regions comprise the amino acid sequences set forth in SEQ ID NOS:255 and 265, respectively;
the $V_H$ and $V_L$ regions comprise the amino acid sequences set forth in SEQ ID NOS:518 and 534, respectively;
the $V_H$ and $V_L$ regions comprise the amino acid sequences set forth in SEQ ID NOS:520 and 264, respectively;
the $V_H$ and $V_L$ regions comprise the amino acid sequences set forth in SEQ ID NOS:521 and 537, respectively;
the $V_H$ and $V_L$ regions comprise the amino acid sequences set forth in SEQ ID NOS:522 and 538, respectively;
the $V_H$ and $V_L$ regions comprise the amino acid sequences set forth in SEQ ID NOS:523 and 539, respectively;
the $V_H$ and $V_L$ regions comprise the amino acid sequences set forth in SEQ ID NOS:525 and 261, respectively;
the $V_H$ and $V_L$ regions comprise the amino acid sequences set forth in SEQ ID NOS:526 and 542, respectively;
the $V_H$ and $V_L$ regions comprise the amino acid sequences set forth in SEQ ID NOS:528 and 544, respectively;
the $V_H$ and $V_L$ regions comprise the amino acid sequences set forth in SEQ ID NOS:529 and 545, respectively;
the $V_H$ and $V_L$ regions comprise the amino acid sequences set forth in SEQ ID NOS:528 and 546, respectively;
the $V_H$ and $V_L$ regions comprise the amino acid sequences set forth in SEQ ID NOS:522 and 547, respectively;
the $V_H$ and $V_L$ regions comprise the amino acid sequences set forth in SEQ ID NOS:530 and 549, respectively.

5. The anti-BCMA antibody or antigen-binding fragment thereof of claim 1, wherein the antibody or antigen-binding fragment is recombinant.

6. The anti-BCMA antibody or antigen-binding fragment thereof of claim 1, that is an antigen-binding fragment.

7. The anti-BCMA antibody or antigen-binding fragment thereof of claim 6, wherein the fragment comprises an scFv.

8. The anti-BCMA antibody or antigen-binding fragment thereof of claim 7, wherein the scFv comprises an amino acid sequence selected from any one of SEQ ID NOS:129, 136, 138, 268-276, 558, 561-564, 567-568, 570-573 and 575, or an amino acid sequence having at least 90% sequence identity to an amino acid sequence selected from any one of SEQ ID NOS:129, 136, 138, 268-276, 558, 561-564, 567-568, 570-573 and 575.

9. The scFv of claim 7, wherein the $V_H$ region is amino-terminal to the $V_L$ region or the $V_H$ region is carboxy-terminal to the $V_L$ region.

10. The anti-BCMA antibody or antigen-binding fragment thereof of claim 1, wherein the antibody or antigen-binding fragment thereof specifically binds to a B cell maturation antigen (BCMA) protein.

11. The anti-BCMA antibody or antigen-binding fragment thereof of claim 1, wherein the antibody or antigen-binding fragment thereof is human.

12. A single chain cell surface protein comprising the anti-BCMA antibody or antigen-binding fragment thereof of claim 1.

13. A conjugate comprising the anti-BCMA antibody or antigen-binding fragment thereof of claim 1 and a heterologous molecule or moiety.

14. A chimeric antigen receptor (CAR) comprising an extracellular domain comprising the anti-BCMA antibody or antigen-binding fragment thereof of claim 1 and an intracellular signaling region.

15. The CAR of claim 14, wherein the antibody or antigen-binding fragment thereof comprises an scFv, and the intracellular signaling region comprises an intracellular signaling domain.

16. The CAR of claim 15, wherein the intracellular signaling domain comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

17. The CAR of claim 15, wherein the intracellular signaling domain comprises an intracellular signaling domain of a CD3-zeta (CD3ζ) chain.

18. The CAR of claim 15, further comprising a transmembrane domain between the extracellular domain and the intracellular signaling region.

19. The CAR of claim 18, wherein the transmembrane domain comprises a transmembrane portion of CD28.

20. The CAR of claim 19, wherein the intracellular signaling region further comprises a costimulatory signaling domain.

21. The CAR of claim 20, wherein the costimulatory signaling domain comprises an intracellular signaling domain of a CD28, a 4-1BB or an ICOS.

22. The CAR of claim 20, wherein the costimulatory signaling domain comprises an intracellular signaling domain of a 4-1BB.

23. A polynucleotide encoding the anti-BCMA antibody or antigen-binding fragment thereof of claim 1.

24. A polynucleotide encoding the CAR of claim 14.

25. A polynucleotide encoding the single chain cell surface protein of claim 12.

26. A polynucleotide encoding the conjugate of claim 13.

27. A vector comprising the polynucleotide of 23.

28. A vector comprising the polynucleotide of 24.

29. An engineered cell comprising the CAR of claim 14.

30. An engineered cell comprising the polynucleotide of claim 24.

31. The engineered cell of claim 29, wherein the engineered cell is a T cell.

32. The engineered cell of claim 30, wherein the engineered cell is a T cell.

33. A composition comprising the engineered cell of claim 29.

34. A composition comprising the engineered cell of claim 31.

35. A composition comprising the engineered cell of claim 32.

* * * * *

SEQUENCE LISTING

<160> NUMBER OF SEQ ID NOS: 620

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 CDR-H1 (aa) Kabat numbering

<400> SEQUENCE: 1

Asp Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -10, -12, -17, -21, -22, -23, -24,
      -26, -32, -33, -35, -36, -37, -38, -40, -41, -47,
      -48, -49 CDR-H1 (aa) Kabat numbering

<400> SEQUENCE: 2

Asp Tyr Tyr Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -27, -28, -29, -30, -34, -39
      CDR-H1 (aa) Kabat numbering

<400> SEQUENCE: 3

Asp Tyr Ala Met His
1               5

<210> SEQ ID NO 4
<211> LENGTH: 19
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 CDR-H2 (aa) Kabat numbering

```
-continued

<400> SEQUENCE: 4

Phe Ile Arg Ser Lys Ala Tyr Gly Gly Thr Thr Glu Tyr Ala Ala Ser
1               5                   10                  15

Val Lys Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -10, -12, -17, -21, -22, -23, -26,
      -32, -35, -36, -37, -38, -40, -47, -48, -49 CDR-H2
      (aa) Kabat numbering

<400> SEQUENCE: 5

Tyr Ile Ser Ser Ser Gly Ser Thr Ile Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -24, -27, -29, -30, -34, -39
      CDR-H2 (aa) Kabat numbering

<400> SEQUENCE: 6

Gly Ile Ser Trp Asn Ser Gly Ser Ile Gly Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 and VH-2 CDR-H3 (aa)

<400> SEQUENCE: 7

Trp Ser Ala Pro Thr Asp Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 CDR-H3 (aa)

<400> SEQUENCE: 8

Val Asp Gly Pro Pro Ser Ser Asp Ile
1               5

<210> SEQ ID NO 9
<211> LENGTH: 9
```

```
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -36, -37, -38, -41 and VH-8 CDR-H3 (aa)

<400> SEQUENCE: 9

Val Asp Gly Asp Tyr Val Asp Asp Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10, -12, -26, -32, -47, -48, -49 and VH-1
      CDR-H3 (aa)

<400> SEQUENCE: 10

Val Asp Gly Pro Pro Ser Phe Asp Ile
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -34 CDR-H3 (aa)

<400> SEQUENCE: 11

Asp Leu Gly Pro Asp Tyr Asp Pro Asp Ala Phe Asp Ile
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -30, -31,
      -42, -44, -45, -46, -51 CDR-H1 (aa) Chothia
      numbering

<400> SEQUENCE: 12

Gly Phe Thr Phe Gly Asp Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -12, -17, -21, -22, -23, -24, -26,
      -32, -33, -35, -36, -37, -38, -40, -41, -47, -48,
      -49 CDR-H1 (aa) Chothia numbering

<400> SEQUENCE: 13

Gly Phe Thr Phe Ser Asp Tyr
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 CDR-H1 (aa) Chothia numbering

<400> SEQUENCE: 14

Gly Phe Pro Phe Ser Asp Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -27, -28, -29, -34, -39 CDR-H1
      (aa) Chothia numbering

<400> SEQUENCE: 15

Gly Phe Thr Phe Asp Asp Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 CDR-H2 (aa) Chothia numbering

<400> SEQUENCE: 16

Arg Ser Lys Ala Tyr Gly Gly Thr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -10, -12, -17, -21, -22, -23, -26,
      -32, -35, -36, -37, -38, -40, -47, -48 CDR-H2 (aa)
      Chothia numbering

<400> SEQUENCE: 17

Ser Ser Ser Gly Ser Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -24, -27, -29, -30, -34, -39
      CDR-H2 (aa) Chothia numbering

<400> SEQUENCE: 18

Ser Trp Asn Ser Gly Ser
1               5
```

-continued

```
<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 CDR-H1 (aa) AbM numbering

<400> SEQUENCE: 19

Gly Phe Thr Phe Gly Asp Tyr Ala Met Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -12, -17, -21, -22, -23, -24, -26,
      -32, -33, -35, -36, -37, -38, -40, -41, -47, -48,
      -49 CDR-H1 (aa) AbM numbering

<400> SEQUENCE: 20

Gly Phe Thr Phe Ser Asp Tyr Tyr Met Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 CDR-H1 (aa) AbM numbering

<400> SEQUENCE: 21

Gly Phe Pro Phe Ser Asp Tyr Tyr Met Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -27, -28, -29, -34, -39 CDR-H1
      (aa) AbM numbering

<400> SEQUENCE: 22

Gly Phe Thr Phe Asp Asp Tyr Ala Met His
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 CDR-H2 (aa) AbM numbering

<400> SEQUENCE: 23

Phe Ile Arg Ser Lys Ala Tyr Gly Gly Thr Thr Glu
1               5                   10
```

```
<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -10, -12, -17, -21, -22, -23, -26,
      -32, -35, -36, -37, -38, -40, -47, -48, -49 CDR-H2
      (aa) AbM numbering

<400> SEQUENCE: 24

Tyr Ile Ser Ser Ser Gly Ser Thr Ile Tyr
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -20, -24, -27, -29, -30, -34, -39
      CDR-H2 (aa) AbM numbering

<400> SEQUENCE: 25

Gly Ile Ser Trp Asn Ser Gly Ser Ile Gly
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 CDR-L1 (aa)

<400> SEQUENCE: 26

Lys Ser Ser Gln Ser Val Leu Ser Thr Ser Asn Asn Lys Asn Tyr Leu
1               5                   10                  15

Ala

<210> SEQ ID NO 27
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 CDR-L1 (aa)

<400> SEQUENCE: 27

Arg Ala Ser Gln Ser Ile Lys Thr Asn Leu Ala
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, -46 CDR-L1 (aa)
```

<400> SEQUENCE: 28

Lys Ser Ser Gln Ser Val Leu His Ser Ser Asn Asn Lys Asn Tyr Leu
1               5                   10                  15

Ala

<210> SEQ ID NO 29
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 CDR-L1 (aa)

<400> SEQUENCE: 29

Arg Ala Ser Gln Asp Ile Arg Asn Ser Leu Ala
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-5, -8, -24 CDR-L1 (aa)

<400> SEQUENCE: 30

Lys Ser Ser Gln Ser Val Leu Tyr Ser Ser Asn Asn Lys Asn Tyr Leu
1               5                   10                  15

Ala

<210> SEQ ID NO 31
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 CDR-L1 (aa)

<400> SEQUENCE: 31

Arg Ala Ser Gln Ser Ile Ser Asn Ser Leu Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 CDR-L1 (aa)

<400> SEQUENCE: 32

Arg Ala Ser Gln Asp Ile Gly Asp Tyr Leu Ala
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -26, -35 CDR-L1 (aa)

```
<400> SEQUENCE: 33

Gly Ala Asn Asn Ile Gly Ser Lys Ser Val His
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 CDR-L1 (aa)

<400> SEQUENCE: 34

Gly Gly Asn Asn Ile Glu Arg Lys Asn Val His
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 CDR-L1 (aa)

<400> SEQUENCE: 35

Ser Gly Ser Ser Ser Asn Ile Gly Ser Asn Ala Val Asn
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 CDR-L1 (aa)

<400> SEQUENCE: 36

Ser Gly Ser Arg Ser Asn Ile Gly Asn Asn Tyr Val Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 CDR-L2 (aa)

<400> SEQUENCE: 37

Trp Ala Ser Thr Arg Glu Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 CDR-L2 (aa)
```

```
<400> SEQUENCE: 38

Ala Ala Ser Thr Arg Ala Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, -5, -8, -31, -44, -46 CDR-L2 (aa)

<400> SEQUENCE: 39

Trp Ala Ser Thr Arg Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4, -42 CDR-L2 (aa)

<400> SEQUENCE: 40

Ala Ala Ser Arg Leu Glu Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 CDR-L2 (aa)

<400> SEQUENCE: 41

Ala Ala Ser Asn Val Glu Asp
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 CDR-L2 (aa)

<400> SEQUENCE: 42

Val Ala Ser Thr Leu Gln Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -26, -35 CDR-L2 (aa)
```

```
<400> SEQUENCE: 43

Asp Asp Asp Asp Arg Pro Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 CDR-L2 (aa)

<400> SEQUENCE: 44

Asp Asp Ser Asp Arg Ala Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 CDR-L2 (aa)

<400> SEQUENCE: 45

Asn Ser His Gln Arg Pro Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 CDR-L2 (aa)

<400> SEQUENCE: 46

Asp Asn Ala Lys Arg Pro Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 CDR-L3 (aa)

<400> SEQUENCE: 47

Gln Gln Tyr Phe Ser Ser Pro Tyr Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 CDR-L3 (aa)
```

```
<400> SEQUENCE: 48

Gln Gln Tyr Gly Ser Ser Pro Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, -46 CDR-L3 (aa)

<400> SEQUENCE: 49

Gln Gln Tyr Tyr Thr Thr Pro Leu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 CDR-L3 (aa)

<400> SEQUENCE: 50

Gln Gln Tyr Tyr Ser Leu Pro Leu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-5 CDR-L3 (aa)

<400> SEQUENCE: 51

Gln Gln Tyr Tyr Ser Thr Pro Trp Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 CDR-L3 (aa)

<400> SEQUENCE: 52

Gln Gln Ser His Met Tyr Pro Pro Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 CDR-L3 (aa)
```

```
<400> SEQUENCE: 53

Gln Gln Tyr His Ser His Pro Trp Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-8, -31 CDR-L3 (aa)

<400> SEQUENCE: 54

Gln Gln Tyr Tyr Ser Thr Pro Tyr Thr
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9 CDR-L3 (aa)

<400> SEQUENCE: 55

His Val Trp Asp Arg Ser Arg Asp His Tyr Val
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 CDR-L3 (aa)

<400> SEQUENCE: 56

Gln Ala Trp Asp Ser Ser Ser Thr Leu Tyr Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 CDR-L3 (aa)

<400> SEQUENCE: 57

Ala Ala Trp Asp Asp Ser Leu Arg Gly Tyr Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12, -32, -48 CDR-L3 (aa)
```

```
<400> SEQUENCE: 58

Gln Val Trp Asp Ser Ser Asp His Trp Val
1               5                   10

<210> SEQ ID NO 59
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -45, -46 VH FR1
      (aa)

<400> SEQUENCE: 59

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -12, -22, -23, -26, -40, -48 VH FR1
      (aa)

<400> SEQUENCE: 60

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -24, -35, -37 VH FR1 (aa)

<400> SEQUENCE: 61

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 VH FR1 (aa)

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser
            20                  25                  30
```

<210> SEQ ID NO 63
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11, -28, -29, -39 VH FR1 (aa)

<400> SEQUENCE: 63

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 64
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 VH FR2 (aa)

<400> SEQUENCE: 64

Trp Phe Arg Gln Ala Pro Gly Lys Gly Leu Glu Trp Val Gly
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -9, -10, -12, -21, -22, -23, -24, -26,
      -32, -33, -35, -36, -37, -38, -40, -41, -47, -48,
      -49 VH FR2 (aa)

<400> SEQUENCE: 65

Trp Ile Arg Gln Ala Pro Gly Lys Gly Leu Glu Trp Val Ser
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VH FR2 (aa)

<400> SEQUENCE: 66

Trp Val Arg Arg Ala Pro Gly Lys Gly Leu Glu Trp Val Ser
1               5                   10

<210> SEQ ID NO 67
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -25, -31, -42,
      -44, -45, -46, -51 VH FR3 (aa)

<400> SEQUENCE: 67

Arg Phe Thr Ile Ser Arg Asp Asp Ser Lys Ser Ile Ala Tyr Leu Gln
1               5                   10                  15

Met Asn Ser Leu Lys Thr Glu Asp Thr Ala Val Tyr Tyr Cys Ala Ala
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -10, -12, -21, -22, -23, -26, -32, -40,
      -41, -48, -49 VH FR3 (aa)

<400> SEQUENCE: 68

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -11, -17, -24, -28, -29, -30, -33, -34,
      -35, -36, -38, -39 VH FR3 (aa)

<400> SEQUENCE: 69

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 70
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -9, -15, -16,
      -18, -20, -21, -22, -23, -25, -27, -31, -35, -36, -37,
      -38, -40, -41, -42, -44, -45, -46, -51 VH FR4 (aa)

<400> SEQUENCE: 70

Trp Gly Gln Gly Thr Leu Val Thr Val Ser Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -10, -11, -12, -24, -26, -29, -30, -32,
      -34, -39, -48, -49, -50 VH FR4 (aa)

<400> SEQUENCE: 71

Trp Gly Gln Gly Thr Met Val Thr Val Ser Ser
1               5                   10

```
<210> SEQ ID NO 72
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 VL FR1 (aa)

<400> SEQUENCE: 72

Asp Ile Val Met Thr Gln Ser Pro Asp Ser Leu Ser Val Ser Pro Gly
1               5                   10                  15

Glu Arg Ala Thr Ile Ser Cys
            20

<210> SEQ ID NO 73
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 VL FR1 (aa)

<400> SEQUENCE: 73

Glu Ile Val Met Thr Gln Ser Pro Ala Thr Leu Ser Val Ser Pro Gly
1               5                   10                  15

Glu Thr Ala Thr Leu Ser Cys
            20

<210> SEQ ID NO 74
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, -46 VL FR1 (aa)

<400> SEQUENCE: 74

Asp Ile Val Met Thr Gln Ser Pro Asp Ser Leu Val Val Ser Leu Gly
1               5                   10                  15

Glu Arg Ala Thr Ile Asn Cys
            20

<210> SEQ ID NO 75
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 VL FR1 (aa)

<400> SEQUENCE: 75

Ala Ile Arg Met Thr Gln Ser Pro Ser Ser Leu Ser Ala Ser Leu Gly
1               5                   10                  15

Asp Arg Val Thr Ile Thr Cys
            20

<210> SEQ ID NO 76
<211> LENGTH: 23
<212> TYPE: PRT
<213> ORGANISM: Artificial Sequence
<220> FEATURE:
```

```
<223> OTHER INFORMATION: Synthetic
<220> FEATURE:
<223> OTHER INFORMATION: BCMA-5, -8, -24 VL FR1 (aa)

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 VL FR1 (aa)

<400> SEQUENCE: 77

Asp Ile Val Met Thr Gln Ser Pro Ser Ser Leu Ser Val Ser Val Gly
1               5                   10                  15

Glu Arg Val Thr Ile Thr Cys
            20

<210> SEQ ID NO 78
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 VL FR1 (aa)

<400> SEQUENCE: 78

Val Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 79
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9 VL FR1 (aa)

<400> SEQUENCE: 79

Ser Tyr Glu Leu Thr Gln Pro Pro Ser Val Ser Val Ala Pro Gly Gln
1               5                   10                  15

Thr Ala Arg Val Thr Cys
            20

<210> SEQ ID NO 80
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10, -26 VL FR1 (aa)
```

<400> SEQUENCE: 80

Ser Tyr Val Leu Thr Gln Pro Pro Ser Val Ser Val Ala Pro Gly Gln
1               5                   10                  15

Thr Ala Arg Ile Thr Cys
            20

<210> SEQ ID NO 81
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VL FR1 (aa)

<400> SEQUENCE: 81

Gln Leu Val Leu Thr Gln Pro Pro Ser Ala Ser Gly Thr Pro Gly Gln
1               5                   10                  15

Arg Val Thr Ile Ser Cys
            20

<210> SEQ ID NO 82
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 VL FR1 (aa)

<400> SEQUENCE: 82

Gln Ser Ala Leu Thr Gln Pro Pro Ser Val Ser Ala Ala Pro Gly Gln
1               5                   10                  15

Lys Val Thr Ile Ser Cys
            20

<210> SEQ ID NO 83
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 VL FR2 (aa)

<400> SEQUENCE: 83

Trp Tyr Gln Gln Lys Pro Gly Gln Pro Pro Arg Leu Leu Leu Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -34 VL FR2 (aa)

<400> SEQUENCE: 84

Trp Tyr Gln Gln Lys Pro Gly Gln Ala Pro Arg Leu Leu Ile Tyr
1               5                   10                  15

<210> SEQ ID NO 85
<211> LENGTH: 15
<212> TYPE: PRT

```
<213> ORGANISM: Artificial Sequence
<220> FEATURE:
<223> OTHER INFORMATION: Synthetic
<220> FEATURE:
<223> OTHER INFORMATION: BCMA-3, -5, -8, -24, -44, -46 VL FR2 (aa)

<400> SEQUENCE: 85

Trp Tyr Gln Gln Lys Pro Gly Gln Pro Pro Lys Leu Leu Ile Tyr
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 VL FR2 (aa)

<400> SEQUENCE: 86

Trp Tyr Gln Gln Arg Pro Gly Lys Ala Pro Lys Leu Leu Leu Ser
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 VL FR2 (aa)

<400> SEQUENCE: 87

Trp Tyr Lys Gln Arg Pro Gly Glu Ala Pro Lys Leu Leu Ile His
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 VL FR2 (aa)

<400> SEQUENCE: 88

Trp Phe Gln Gln Arg Pro Gly Lys Ala Pro Lys Ser Leu Ile Tyr
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -26, -35 VL FR2 (aa)

<400> SEQUENCE: 89

Trp Tyr Gln Gln Lys Pro Gly Gln Ala Pro Met Leu Val Val Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic
<220> FEATURE:
```

```
<223> OTHER INFORMATION: BCMA-10 VL FR2 (aa)

<400> SEQUENCE: 90

Trp Tyr Gln Gln Lys Pro Gly Gln Ala Pro Val Pro Val Val Tyr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VL FR2 (aa)

<400> SEQUENCE: 91

Trp Tyr Gln Gln Leu Pro Gly Thr Ala Pro Glu Val Leu Ile Tyr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 VL FR2 (aa)

<400> SEQUENCE: 92

Trp Tyr Gln Gln Leu Pro Gly Thr Ala Pro Lys Leu Leu Ile Tyr
1               5                   10                  15

<210> SEQ ID NO 93
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -5, -8, -31, -44, -46 VL FR3 (aa)

<400> SEQUENCE: 93

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 VL FR3 (aa)

<400> SEQUENCE: 94

Gly Ile Pro Asp Arg Phe Ser Gly Ser Gly Ser Gly Thr Asp Phe Thr
1               5                   10                  15

Leu Thr Ile Thr Arg Leu Glu Pro Glu Asp Phe Ala Val Tyr Tyr Cys
            20                  25                  30

<210> SEQ ID NO 95
<211> LENGTH: 32
<212> TYPE: PRT
<213> ORGANISM: Artificial Sequence
<220> FEATURE:
```

<223> OTHER INFORMATION: Synthetic
<220> FEATURE:
<223> OTHER INFORMATION: BCMA-4 VL FR3 (aa)

<400> SEQUENCE: 95

Gly Val Pro Ser Arg Phe Ser Gly Thr Thr Ser Gly Ala Glu Tyr Ala
1               5                   10                  15

Leu Ser Ile Ser Ser Leu Gln Pro Glu Asp Val Ala Ser Tyr Phe Cys
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 VL FR3 (aa)

<400> SEQUENCE: 96

Gly Val Pro Ser Arg Phe Ser Gly Arg Gly Ser Gly Thr Val Phe Thr
1               5                   10                  15

Leu Ala Ile Ser Asn Val Gln Pro Glu Asp Phe Ala Thr Tyr Tyr Cys
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 VL FR3 (aa)

<400> SEQUENCE: 97

Gly Val Pro Ser Arg Phe Ser Gly Ser Gly Ser Gly Thr His Phe Thr
1               5                   10                  15

Leu Thr Ile Asn Ser Leu Gln Pro Glu Asp Phe Ala Thr Tyr Tyr Cys
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -26, -35 VL FR3 (aa)

<400> SEQUENCE: 98

Gly Ile Pro Glu Arg Phe Ser Gly Ser Asn Ser Gly Asn Thr Ala Thr
1               5                   10                  15

Leu Thr Ile Ser Gly Val Glu Ala Gly Asp Glu Ala Asp Tyr Phe Cys
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 VL FR3 (aa)

```
<400> SEQUENCE: 99

Gly Ile Pro Glu Arg Phe Ser Ala Ser Asn Ser Gly Asn Thr Ala Thr
1               5                   10                  15

Leu Thr Ile Ser Gly Ala Gln Ala Thr Asp Glu Ala Glu Tyr Tyr Cys
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VL FR3 (aa)

<400> SEQUENCE: 100

Gly Val Pro Asp Arg Phe Ser Gly Ser Lys Ser Gly Thr Ser Ala Ser
1               5                   10                  15

Leu Ala Ile Asn Gly Leu Gln Ser Glu Asp Glu Ala Asp Tyr Tyr Cys
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 VL FR3 (aa)

<400> SEQUENCE: 101

Gly Ile Pro Asp Arg Phe Ser Gly Ser Lys Ser Gly Thr Ser Ala Thr
1               5                   10                  15

Leu Asp Ile Ala Gly Leu Gln Thr Gly Asp Glu Ala Asp Tyr Tyr Cys
            20                  25                  30

<210> SEQ ID NO 102
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 VL FR4 (aa)

<400> SEQUENCE: 102

Phe Gly His Gly Thr Lys Leu Glu Ile Lys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2, -39 VL FR4 (aa)

<400> SEQUENCE: 103

Phe Gly Arg Gly Thr Lys Leu Glu Ile Lys
1               5                   10

<210> SEQ ID NO 104
<211> LENGTH: 10
<212> TYPE: PRT
```

```
<213> ORGANISM: Artificial Sequence
<220> FEATURE:
<223> OTHER INFORMATION: Synthetic
<220> FEATURE:
<223> OTHER INFORMATION: BCMA-3, -4, -6, -30, -46 VL FR4 (aa)

<400> SEQUENCE: 104

Phe Gly Gly Gly Thr Lys Val Glu Ile Lys
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-5, -45 VL FR4 (aa)

<400> SEQUENCE: 105

Phe Gly Gln Gly Thr Lys Val Asp Ile Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 VL FR4 (aa)

<400> SEQUENCE: 106

Phe Gly Pro Gly Thr Lys Val Asp Ile Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-8, -44 VL FR4 (aa)

<400> SEQUENCE: 107

Phe Gly Gln Gly Thr Lys Leu Glu Ile Lys
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9, -10, -11, -26, -40, -47 VL FR4 (aa)

<400> SEQUENCE: 108

Phe Gly Thr Gly Thr Lys Leu Thr Val Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic
<220> FEATURE:
```

<223> OTHER INFORMATION: BCMA-12, -14, -15, -16, -17, -18, -32, -33,
      -36, -37, -38, -41, -48, -49, -50 VL FR4 (aa)

<400> SEQUENCE: 109

Phe Gly Gly Gly Thr Lys Leu Thr Val Leu
1               5                   10

<210> SEQ ID NO 110
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1, -3, -4, -5, -6, -7, -8, -45, -46 VH
      Chain (aa)

<400> SEQUENCE: 110

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 VH Chain (aa)

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Lys Val Asp Gly Pro Pro Ser Ser Asp Ile Trp Gly Gln Gly Thr
                100                 105                 110

Met Val Thr Val Ser Ser
        115

<210> SEQ ID NO 112
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9 VH Chain (aa)

<400> SEQUENCE: 112

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Tyr Trp Gly Gln Gly Thr
                100                 105                 110

Leu Val Thr Val Ser Ser
        115

<210> SEQ ID NO 113
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 VH Chain (aa)

<400> SEQUENCE: 113

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
                100                 105                 110

Met Val Thr Val Ser Ser
        115
```

<210> SEQ ID NO 114
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VH Chain (aa)

<400> SEQUENCE: 114

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Asp Tyr Asp Pro Asp Ala Phe Asp Ile Trp
            100                 105                 110

Gly Gln Gly Thr Met Val Thr Val Ser Ser
        115                 120

<210> SEQ ID NO 115
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12, -26, -48 VH Chain (aa)

<400> SEQUENCE: 115

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser
        115

<210> SEQ ID NO 116
<211> LENGTH: 113
<212> TYPE: PRT
<213> ORGANISM: Artificial Sequence
<220> FEATURE:
<223> OTHER INFORMATION: Synthetic

```
<220> FEATURE:
<223> OTHER INFORMATION: BCMA-1 VL Chain (aa)

<400> SEQUENCE: 116

Asp Ile Val Met Thr Gln Ser Pro Asp Ser Leu Ser Val Ser Pro Gly
1               5                   10                  15

Glu Arg Ala Thr Ile Ser Cys Lys Ser Ser Gln Ser Val Leu Ser Thr
            20                  25                  30

Ser Asn Asn Lys Asn Tyr Leu Ala Trp Tyr Gln Gln Lys Pro Gly Gln
        35                  40                  45

Pro Pro Arg Leu Leu Leu Tyr Trp Ala Ser Thr Arg Glu Ala Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Ser Pro Tyr Thr Phe Gly His Gly Thr Lys Leu Glu Ile
            100                 105                 110

Lys

<210> SEQ ID NO 117
<211> LENGTH: 106
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 VL Chain (aa)

<400> SEQUENCE: 117

Glu Ile Val Met Thr Gln Ser Pro Ala Thr Leu Ser Val Ser Pro Gly
1               5                   10                  15

Glu Thr Ala Thr Leu Ser Cys Arg Ala Ser Gln Ser Ile Lys Thr Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Asp Arg Phe Ser Gly
50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Thr
                85                  90                  95

Phe Gly Arg Gly Thr Lys Leu Glu Ile Lys
            100                 105

<210> SEQ ID NO 118
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, -46 VL Chain (aa)

<400> SEQUENCE: 118

Asp Ile Val Met Thr Gln Ser Pro Asp Ser Leu Val Val Ser Leu Gly
1               5                   10                  15

Glu Arg Ala Thr Ile Asn Cys Lys Ser Ser Gln Ser Val Leu His Ser
            20                  25                  30
```

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                   70                  75                  80

Ile Ser Ser Leu Gln Ala Glu Asp Val Ala Val Tyr Tyr Cys Gln Gln
                 85                  90                  95

Tyr Tyr Thr Thr Pro Leu Thr Phe Gly Gly Gly Thr Lys Val Glu Ile
             100                 105                 110

Lys

<210> SEQ ID NO 119
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 VL Chain (aa)

<400> SEQUENCE: 119

Ala Ile Arg Met Thr Gln Ser Pro Ser Ser Leu Ser Ala Ser Leu Gly
1               5                   10                  15

Asp Arg Val Thr Ile Thr Cys Arg Ala Ser Gln Asp Ile Arg Asn Ser
                20                  25                  30

Leu Ala Trp Tyr Gln Gln Arg Pro Gly Lys Ala Pro Lys Leu Leu Leu
            35                  40                  45

Ser Ala Ala Ser Arg Leu Glu Ser Gly Val Pro Ser Arg Phe Ser Gly
        50                  55                  60

Thr Thr Ser Gly Ala Glu Tyr Ala Leu Ser Ile Ser Ser Leu Gln Pro
65                  70                  75                  80

Glu Asp Val Ala Ser Tyr Phe Cys Gln Gln Tyr Tyr Ser Leu Pro Leu
                85                  90                  95

Ser Phe Gly Gly Gly Thr Lys Val Glu Ile Lys
            100                 105

<210> SEQ ID NO 120
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-5 VL Chain (aa)

<400> SEQUENCE: 120

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Asp Ile
            100                 105                 110

Lys

<210> SEQ ID NO 121
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 VL Chain (aa)

<400> SEQUENCE: 121

Asp Ile Val Met Thr Gln Ser Pro Ser Ser Leu Ser Val Ser Val Gly
1               5                   10                  15

Glu Arg Val Thr Ile Thr Cys Arg Ala Ser Gln Ser Ile Ser Asn Ser
            20                  25                  30

Leu Ala Trp Tyr Lys Gln Arg Pro Gly Glu Ala Pro Lys Leu Leu Ile
        35                  40                  45

His Ala Ala Ser Asn Val Glu Asp Gly Val Pro Ser Arg Phe Ser Gly
50                  55                  60

Arg Gly Ser Gly Thr Val Phe Thr Leu Ala Ile Ser Asn Val Gln Pro
65                  70                  75                  80

Glu Asp Phe Ala Thr Tyr Tyr Cys Gln Gln Ser His Met Tyr Pro Pro
                85                  90                  95

Thr Phe Gly Gly Gly Thr Lys Val Glu Ile Lys
            100                 105

<210> SEQ ID NO 122
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 VL Chain (aa)

<400> SEQUENCE: 122

Val Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Asp Tyr
            20                  25                  30

Leu Ala Trp Phe Gln Gln Arg Pro Gly Lys Ala Pro Lys Ser Leu Ile
        35                  40                  45

Tyr Val Ala Ser Thr Leu Gln Ser Gly Val Pro Ser Arg Phe Ser Gly
    50                  55                  60

Ser Gly Ser Gly Thr His Phe Thr Leu Thr Ile Asn Ser Leu Gln Pro
65                  70                  75                  80

Glu Asp Phe Ala Thr Tyr Tyr Cys Gln Gln Tyr His Ser His Pro Trp
                85                  90                  95

Thr Phe Gly Pro Gly Thr Lys Val Asp Ile Lys
            100                 105

<210> SEQ ID NO 123
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-8 VL Chain (aa)

<400> SEQUENCE: 123

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 124
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9 VL Chain (aa)

<400> SEQUENCE: 124

Ser Tyr Glu Leu Thr Gln Pro Pro Ser Val Ser Val Ala Pro Gly Gln
1               5                   10                  15

Thr Ala Arg Val Thr Cys Gly Ala Asn Asn Ile Gly Ser Lys Ser Val
            20                  25                  30

His Trp Tyr Gln Gln Lys Pro Gly Gln Ala Pro Met Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Val Trp Asp Arg Ser Arg Asp His
                85                  90                  95

Tyr Val Phe Gly Thr Gly Thr Lys Leu Thr Val Leu
            100                 105

<210> SEQ ID NO 125
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 VL Chain (aa)

<400> SEQUENCE: 125

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Glu Arg Lys Asn Val
            20                  25                  30

His Trp Tyr Gln Gln Lys Pro Gly Gln Ala Pro Val Val Tyr
            35                  40                  45

Asp Asp Ser Asp Arg Ala Ser Gly Ile Pro Glu Arg Phe Ser Ala Ser
 50                  55                  60

Asn Ser Gly Asn Thr Ala Thr Leu Thr Ile Ser Gly Ala Gln Ala Thr
65                  70                  75                  80

Asp Glu Ala Glu Tyr Tyr Cys Gln Ala Trp Asp Ser Ser Thr Leu
                85                  90                  95

Tyr Val Phe Gly Thr Gly Thr Lys Leu Thr Val Leu
            100                 105

<210> SEQ ID NO 126
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 VL Chain (aa)

<400> SEQUENCE: 126

Gln Leu Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Glu Val Leu
            35                  40                  45

Ile Tyr Asn Ser His Gln Arg Pro Ser Gly Val Pro Asp Arg Phe Ser
 50                  55                  60

Gly Ser Lys Ser Gly Thr Ser Ala Ser Leu Ala Ile Asn Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu
            100                 105                 110

<210> SEQ ID NO 127
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 VL Chain (aa)

<400> SEQUENCE: 127

Gln Ser Ala Leu Thr Gln Pro Pro Ser Val Ser Ala Ala Pro Gly Gln
1               5                   10                  15

Lys Val Thr Ile Ser Cys Ser Gly Ser Arg Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Ala Lys Arg Pro Ser Gly Ile Pro Asp Arg Phe Ser
 50                  55                  60

Gly Ser Lys Ser Gly Thr Ser Ala Thr Leu Asp Ile Ala Gly Leu Gln
65                  70                  75                  80

Thr Gly Asp Glu Ala Asp Tyr Tyr Cys Gln Val Trp Asp Ser Ser Ser
                85                  90                  95

Asp His Trp Val Phe Gly Gly Gly Thr Lys Leu Thr Val Leu
            100                 105                 110

<210> SEQ ID NO 128
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-1 scFv (aa)

<400> SEQUENCE: 128

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ser Val Ser Pro Gly Glu Arg Ala Thr Ile Ser Cys Lys Ser Ser Gln
145                 150                 155                 160

Ser Val Leu Ser Thr Ser Asn Asn Lys Asn Tyr Leu Ala Trp Tyr Gln
                165                 170                 175

Gln Lys Pro Gly Gln Pro Pro Arg Leu Leu Leu Tyr Trp Ala Ser Thr
            180                 185                 190

Arg Glu Ala Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Tyr Phe Ser Ser Pro Tyr Thr Phe Gly His Gly
225                 230                 235                 240

Thr Lys Leu Glu Ile Lys
                245

<210> SEQ ID NO 129
<211> LENGTH: 239
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-2 scFv (aa)

<400> SEQUENCE: 129

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Pro Pro Ser Ser Asp Ile Trp Gly Gln Gly Thr
            100                 105                 110

Met Val Thr Val Ser Ser Gly Gly Gly Ser Gly Gly Gly Gly Ser
            115                 120                 125

Gly Gly Gly Gly Ser Glu Ile Val Met Thr Gln Ser Pro Ala Thr Leu
        130                 135                 140

Ser Val Ser Pro Gly Glu Thr Ala Thr Leu Ser Cys Arg Ala Ser Gln
145                 150                 155                 160

Ser Ile Lys Thr Asn Leu Ala Trp Tyr Gln Gln Lys Pro Gly Gln Ala
                165                 170                 175

Pro Arg Leu Leu Ile Tyr Ala Ala Ser Thr Arg Ala Thr Gly Ile Pro
            180                 185                 190

Asp Arg Phe Ser Gly Ser Gly Ser Gly Thr Asp Phe Thr Leu Thr Ile
            195                 200                 205

Thr Arg Leu Glu Pro Glu Asp Phe Ala Val Tyr Tyr Cys Gln Gln Tyr
    210                 215                 220

Gly Ser Ser Pro Thr Phe Gly Arg Gly Thr Lys Leu Glu Ile Lys
225                 230                 235

<210> SEQ ID NO 130
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-3, 46 scFv (aa)

<400> SEQUENCE: 130

Gln Val Gln Leu Val Glu Ser Gly Gly Gly Leu Val Gln Pro Gly Arg
  1               5                  10                  15

Ser Leu Arg Leu Ser Cys Thr Ala Ser Gly Phe Thr Phe Gly Asp Tyr
             20                  25                  30

Ala Met Ser Trp Phe Arg Gln Ala Pro Gly Lys Gly Leu Glu Trp Val
         35                  40                  45

Gly Phe Ile Arg Ser Lys Ala Tyr Gly Gly Thr Thr Glu Tyr Ala Ala
     50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
            115                 120                 125
```

```
Gly Gly Gly Gly Ser Asp Ile Val Met Thr Gln Ser Pro Asp Ser Leu
            130                 135                 140

Val Val Ser Leu Gly Glu Arg Ala Thr Ile Asn Cys Lys Ser Ser Gln
145                 150                 155                 160

Ser Val Leu His Ser Ser Asn Asn Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
            210                 215                 220

Tyr Tyr Cys Gln Gln Tyr Tyr Thr Thr Pro Leu Thr Phe Gly Gly Gly
225                 230                 235                 240

Thr Lys Val Glu Ile Lys
                245

<210> SEQ ID NO 131
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-4 scFv (aa)

<400> SEQUENCE: 131

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Ala Ile Arg Met Thr Gln Ser Pro Ser Ser Leu
130                 135                 140

Ser Ala Ser Leu Gly Asp Arg Val Thr Ile Thr Cys Arg Ala Ser Gln
145                 150                 155                 160

Asp Ile Arg Asn Ser Leu Ala Trp Tyr Gln Gln Arg Pro Gly Lys Ala
                165                 170                 175

Pro Lys Leu Leu Leu Ser Ala Ala Ser Arg Leu Glu Ser Gly Val Pro
            180                 185                 190

Ser Arg Phe Ser Gly Thr Thr Ser Gly Ala Glu Tyr Ala Leu Ser Ile
            195                 200                 205

Ser Ser Leu Gln Pro Glu Asp Val Ala Ser Tyr Phe Cys Gln Gln Tyr
            210                 215                 220
```

```
Tyr Ser Leu Pro Leu Ser Phe Gly Gly Gly Thr Lys Val Glu Ile Lys
225                 230                 235                 240
```

<210> SEQ ID NO 132
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-5 scFv (aa)

<400> SEQUENCE: 132

```
Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Val Leu Tyr Ser Ser Asn Asn Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Tyr Tyr Ser Thr Pro Trp Thr Phe Gly Gln Gly
225                 230                 235                 240

Thr Lys Val Asp Ile Lys
                245
```

<210> SEQ ID NO 133
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-6 scFv (aa)

<400> SEQUENCE: 133

```
Gln Val Gln Leu Val Gln Ser Gly Gly Gly Leu Val Gln Pro Gly Arg
1               5                   10                  15
```

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Ser Ser Leu
        130                 135                 140

Ser Val Ser Val Gly Glu Arg Val Thr Ile Thr Cys Arg Ala Ser Gln
145                 150                 155                 160

Ser Ile Ser Asn Ser Leu Ala Trp Tyr Lys Gln Arg Pro Gly Glu Ala
                165                 170                 175

Pro Lys Leu Leu Ile His Ala Ala Ser Asn Val Glu Asp Gly Val Pro
            180                 185                 190

Ser Arg Phe Ser Gly Arg Gly Ser Gly Thr Val Phe Thr Leu Ala Ile
        195                 200                 205

Ser Asn Val Gln Pro Glu Asp Phe Ala Thr Tyr Tyr Cys Gln Gln Ser
    210                 215                 220

His Met Tyr Pro Pro Thr Phe Gly Gly Gly Thr Lys Val Glu Ile Lys
225                 230                 235                 240

<210> SEQ ID NO 134
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-7 scFv (aa)

<400> SEQUENCE: 134

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
                100                 105                 110

Leu Val Thr Val Ser Ser Gly Gly Gly Gly Ser Gly Gly Gly Gly Ser
            115                 120                 125

```
Gly Gly Gly Gly Ser Val Ile Gln Leu Thr Gln Ser Pro Ser Ser Leu
            130                 135                 140

Ser Ala Ser Val Gly Asp Arg Val Thr Ile Thr Cys Arg Ala Ser Gln
145                 150                 155                 160

Asp Ile Gly Asp Tyr Leu Ala Trp Phe Gln Gln Arg Pro Gly Lys Ala
                165                 170                 175

Pro Lys Ser Leu Ile Tyr Val Ala Ser Thr Leu Gln Ser Gly Val Pro
            180                 185                 190

Ser Arg Phe Ser Gly Ser Gly Ser Gly Thr His Phe Thr Leu Thr Ile
        195                 200                 205

Asn Ser Leu Gln Pro Glu Asp Phe Ala Thr Tyr Tyr Cys Gln Gln Tyr
210                 215                 220

His Ser His Pro Trp Thr Phe Gly Pro Gly Thr Lys Val Asp Ile Lys
225                 230                 235                 240
```

<210> SEQ ID NO 135
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-8 scFv (aa)

<400> SEQUENCE: 135

```
Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Val Leu Tyr Ser Ser Asn Asn Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220
```

Tyr Tyr Cys Gln Gln Tyr Tyr Ser Thr Pro Tyr Thr Phe Gly Gln Gly
225                 230                 235                 240

Thr Lys Leu Glu Ile Lys
                245

<210> SEQ ID NO 136
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-9 scFv (aa)

<400> SEQUENCE: 136

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Ser Tyr Glu Leu Thr Gln Pro Pro Ser Val Ser
    130                 135                 140

Val Ala Pro Gly Gln Thr Ala Arg Val Thr Cys Gly Ala Asn Asn Ile
145                 150                 155                 160

Gly Ser Lys Ser Val His Trp Tyr Gln Gln Lys Pro Gly Gln Ala Pro
                165                 170                 175

Met Leu Val Val Tyr Asp Asp Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Val Trp Asp
    210                 215                 220

Arg Ser Arg Asp His Tyr Val Phe Gly Thr Gly Thr Lys Leu Thr Val
225                 230                 235                 240

Leu

<210> SEQ ID NO 137
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-10 scFv (aa)

<400> SEQUENCE: 137

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Ser Tyr Val Leu Thr Gln Pro Pro Ser Val Ser
130                 135                 140

Val Ala Pro Gly Gln Thr Ala Arg Ile Thr Cys Gly Gly Asn Asn Ile
145                 150                 155                 160

Glu Arg Lys Asn Val His Trp Tyr Gln Gln Lys Pro Gly Gln Ala Pro
                165                 170                 175

Val Pro Val Tyr Asp Asp Ser Asp Arg Ala Ser Gly Ile Pro Glu
            180                 185                 190

Arg Phe Ser Ala Ser Asn Ser Gly Asn Thr Ala Thr Leu Thr Ile Ser
            195                 200                 205

Gly Ala Gln Ala Thr Asp Glu Ala Glu Tyr Tyr Cys Gln Ala Trp Asp
    210                 215                 220

Ser Ser Ser Thr Leu Tyr Val Phe Gly Thr Gly Thr Lys Leu Thr Val
225                 230                 235                 240

Leu

<210> SEQ ID NO 138
<211> LENGTH: 247
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-11 scFv (aa)

<400> SEQUENCE: 138

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Asp Tyr Asp Pro Asp Ala Phe Asp Ile Trp
            100                 105                 110

Gly Gln Gly Thr Met Val Thr Val Ser Ser Gly Gly Gly Ser Gly
        115                 120                 125

Gly Gly Gly Ser Gly Gly Gly Ser Gln Leu Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Ser Asn Ile Gly Ser Asn Ala Val Asn Trp Tyr Gln Gln
                165                 170                 175

Leu Pro Gly Thr Ala Pro Glu Val Leu Ile Tyr Asn Ser His Gln Arg
            180                 185                 190

Pro Ser Gly Val Pro Asp Arg Phe Ser Gly Ser Lys Ser Gly Thr Ser
        195                 200                 205

Ala Ser Leu Ala Ile Asn Gly Leu Gln Ser Glu Asp Glu Ala Asp Tyr
    210                 215                 220

Tyr Cys Ala Ala Trp Asp Asp Ser Leu Arg Gly Tyr Val Phe Gly Thr
225                 230                 235                 240

Gly Thr Lys Leu Thr Val Leu
            245

<210> SEQ ID NO 139
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-12 scFv (aa)

<400> SEQUENCE: 139

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ser Val Ser
    130                 135                 140

Ala Ala Pro Gly Gln Lys Val Thr Ile Ser Cys Ser Gly Ser Arg Ser
145                 150                 155                 160

Asn Ile Gly Asn Asn Tyr Val Ser Trp Tyr Gln Gln Leu Pro Gly Thr
                165                 170                 175

Ala Pro Lys Leu Leu Ile Tyr Asp Asn Ala Lys Arg Pro Ser Gly Ile
            180                 185                 190

-continued

```
Pro Asp Arg Phe Ser Gly Ser Lys Ser Gly Thr Ser Ala Thr Leu Asp
            195                 200                 205

Ile Ala Gly Leu Gln Thr Gly Asp Glu Ala Asp Tyr Tyr Cys Gln Val
        210                 215                 220

Trp Asp Ser Ser Asp His Trp Val Phe Gly Gly Gly Thr Lys Leu
225                 230                 235                 240

Thr Val Leu

<210> SEQ ID NO 140
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 CDR-H1 (aa) Kabat numbering

<400> SEQUENCE: 140

Ser Tyr Ala Met His
1               5

<210> SEQ ID NO 141
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14, -15 CDR-H1 (aa) Kabat numbering

<400> SEQUENCE: 141

Ser Tyr Gly Met His
1               5

<210> SEQ ID NO 142
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H1 (aa) Kabat numbering

<400> SEQUENCE: 142

Ser Ser Ala Met Gln
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H1 (aa) Kabat numbering

<400> SEQUENCE: 143

Ser Tyr Trp Met Ser
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic
<220> FEATURE:
```

<223> OTHER INFORMATION: BCMA-19 CDR-H1 (aa) Kabat numbering

<400> SEQUENCE: 144

Ser Tyr Tyr Met His
1               5

<210> SEQ ID NO 145
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15 CDR-H2 (aa) Kabat numbering

<400> SEQUENCE: 145

Val Ile Ser Tyr Asp Gly Ser Asn Lys Tyr Tyr Ala Asp Ser Val Lys
1               5                   10                  15

Gly

<210> SEQ ID NO 146
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H2 (aa) Kabat numbering

<400> SEQUENCE: 146

Trp Ile Val Val Gly Ser Gly Asn Thr Asn Tyr Ala Gln Lys Phe Gln
1               5                   10                  15

Glu

<210> SEQ ID NO 147
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H2 (aa) Kabat numbering

<400> SEQUENCE: 147

His Ile Asn Gln Asp Gly Ser Glu Lys Tyr Tyr Val Asp Ser Val Lys
1               5                   10                  15

Gly

<210> SEQ ID NO 148
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-H2 (aa) Kabat numbering

<400> SEQUENCE: 148

Trp Ile Asn Pro Asn Ser Gly Gly Thr Asn Tyr Ala Gln Lys Phe Gln
1               5                   10                  15

Gly

<210> SEQ ID NO 149
<211> LENGTH: 13
<212> TYPE: PRT

<213> ORGANISM: Artificial Sequence
<220> FEATURE:
<223> OTHER INFORMATION: Synthetic
<220> FEATURE:
<223> OTHER INFORMATION: BCMA-13, -14 CDR-H3 (aa)

<400> SEQUENCE: 149

Leu Pro Gly Arg Asp Gly Tyr Pro Gly Ala Phe Asp Tyr
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 CDR-H3 (aa)

<400> SEQUENCE: 150

Asp Gln Tyr Ser Ser Ser Ala Gln Arg Ala Asp Phe Asp Tyr
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H3 (aa)

<400> SEQUENCE: 151

Ala Pro Tyr Tyr Asp Ile Leu Thr Gly Tyr Tyr Leu
1               5                   10

<210> SEQ ID NO 152
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 CDR-H3 (aa)

<400> SEQUENCE: 152

Glu Ala Asp Ser Ser Ala Asp Tyr
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H3 (aa)

<400> SEQUENCE: 153

Trp Leu Ala Val Thr Asn
1               5

<210> SEQ ID NO 154
<211> LENGTH: 5
<212> TYPE: PRT
<213> ORGANISM: Artificial Sequence
<220> FEATURE:
<223> OTHER INFORMATION: Synthetic
<220> FEATURE:

<223> OTHER INFORMATION: BCMA-19 CDR-H3 (aa)

<400> SEQUENCE: 154

Asp Gly Gly Asp Val
1               5

<210> SEQ ID NO 155
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 CDR-H3 (aa)

<400> SEQUENCE: 155

Gly Gly Leu Gly Ile Thr Pro Tyr Tyr Phe Asp Tyr
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 CDR-H3 (aa)

<400> SEQUENCE: 156

Val Asp Gly Gly Tyr Thr Glu Asp Tyr
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 CDR-H3 (aa)

<400> SEQUENCE: 157

Val Asp Gly Asp Tyr Thr Glu Asp Tyr
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15, -18 CDR-H1 (aa) Chothia
      numbering

<400> SEQUENCE: 158

Gly Phe Thr Phe Ser Ser Tyr
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H1 (aa) Chothia numbering

```
<400> SEQUENCE: 159

Gly Phe Thr Phe Thr Ser Ser
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-H1 (aa) Chothia numbering

<400> SEQUENCE: 160

Gly Tyr Thr Phe Thr Ser Tyr
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15 CDR-H2 (aa) Chothia numbering

<400> SEQUENCE: 161

Ser Tyr Asp Gly Ser Asn
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H2 (aa) Chothia numbering

<400> SEQUENCE: 162

Val Val Gly Ser Gly Asn
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H2 (aa) Chothia numbering

<400> SEQUENCE: 163

Asn Gln Asp Gly Ser Glu
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-H2 (aa) Chothia numbering
```

<400> SEQUENCE: 164

Asn Pro Asn Ser Gly Gly
1               5

<210> SEQ ID NO 165
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 CDR-H1 (aa) AbM numbering

<400> SEQUENCE: 165

Gly Phe Thr Phe Ser Ser Tyr Ala Met His
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14, -15 CDR-H1 (aa) AbM numbering

<400> SEQUENCE: 166

Gly Phe Thr Phe Ser Ser Tyr Gly Met His
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H1 (aa) AbM numbering

<400> SEQUENCE: 167

Gly Phe Thr Phe Thr Ser Ser Ala Met Gln
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H1 (aa) AbM numbering

<400> SEQUENCE: 168

Gly Phe Thr Phe Ser Ser Tyr Trp Met Ser
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-H1 (aa) AbM numbering

<400> SEQUENCE: 169

Gly Tyr Thr Phe Thr Ser Tyr Tyr Met His
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15 CDR-H2 (aa) AbM numbering

<400> SEQUENCE: 170

Val Ile Ser Tyr Asp Gly Ser Asn Lys Tyr
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-H2 (aa) AbM numbering

<400> SEQUENCE: 171

Trp Ile Val Val Gly Ser Gly Asn Thr Asn
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-H2 (aa) AbM numbering

<400> SEQUENCE: 172

His Ile Asn Gln Asp Gly Ser Glu Lys Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-H2 (aa) AbM numbering

<400> SEQUENCE: 173

Trp Ile Asn Pro Asn Ser Gly Gly Thr Asn
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15, -16, -18, -21 CDR-L1 (aa)

```
<400> SEQUENCE: 174

Gly Ser Gly Ser Asn Ile Gly Ser Asn Asp Val Ser
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 CDR-L1 (aa)

<400> SEQUENCE: 175

Gly Gly Asn Asn Ile Gly Phe Lys Gly Val Gln
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-L1 (aa)

<400> SEQUENCE: 176

Thr Gly Thr Ser Ser Asp Val Gly Asp Tyr Asn Tyr Val Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 CDR-L1 (aa)

<400> SEQUENCE: 177

Ser Gly Gly Lys Thr Val Asn
1               5

<210> SEQ ID NO 178
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23 CDR-L1 (aa)

<400> SEQUENCE: 178

Thr Gly Ser Ser Ser Asp Val Gly Lys Tyr Asn Leu Val Ser
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15, -16, -18, -21 CDR-L2 (aa)
```

```
<400> SEQUENCE: 179

Trp Asn Asp Gln Arg Pro Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -32, -33 CDR-L2 (aa)

<400> SEQUENCE: 180

Asp Asp Ser Asp Arg Pro Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-L2 (aa)

<400> SEQUENCE: 181

Glu Val Ile Asn Arg Pro Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 CDR-L2 (aa)

<400> SEQUENCE: 182

Ser Asn Asp Gln Arg Pro Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 CDR-L2 (aa)

<400> SEQUENCE: 183

Asp Val Asn Lys Arg Pro Ser
1               5

<210> SEQ ID NO 184
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 CDR-L3 (aa)
```

```
<400> SEQUENCE: 184

Ala Ala Trp Asp Asp Ser Leu Gly Gly Ser Trp Val
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 CDR-L3 (aa)

<400> SEQUENCE: 185

Ala Ala Trp Asp Asp Arg Leu Asn Gly Phe Trp Val
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 CDR-L3 (aa)

<400> SEQUENCE: 186

Ala Ala Trp Asp Asp Ser Leu Ser Gly Trp Val
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 CDR-L3 (aa)

<400> SEQUENCE: 187

Ala Ser Trp Asp Asp Ser Leu Ser Gly Trp Val
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 CDR-L3 (aa)

<400> SEQUENCE: 188

Gln Val Trp Asp Ser Ala Ser Asp His Trp Val
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 CDR-L3 (aa)
```

<400> SEQUENCE: 189

Ala Ala Trp Asp Asp Ser Leu Asn Gly Trp Val
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 CDR-L3 (aa)

<400> SEQUENCE: 190

Ile Ser Tyr Ser Arg Gly Ser Thr Pro Tyr Val
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 CDR-L3 (aa)

<400> SEQUENCE: 191

Gly Ser Trp Asp Asp Ser Leu Asn Ala Trp Val
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 CDR-L3 (aa)

<400> SEQUENCE: 192

Ala Ala Trp Asp Asp Ser Leu Asn Gly Tyr Val
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -40 CDR-L3 (aa)

<400> SEQUENCE: 193

Cys Ser Tyr Gly Gly Ser Arg Ser Tyr Val
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-23 CDR-L3 (aa)

```
<400> SEQUENCE: 194

Ser Ser Tyr Gly Gly Ser Arg Ser Tyr Val
1               5                   10

<210> SEQ ID NO 195
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VH FR1 (aa)

<400> SEQUENCE: 195

Gln Met Gln Leu Val Gln Tyr Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VH FR1 (aa)

<400> SEQUENCE: 196

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15, -47 VH FR1 (aa)

<400> SEQUENCE: 197

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VH FR1 (aa)

<400> SEQUENCE: 198

Glu Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr
            20                  25                  30
```

-continued

```
<210> SEQ ID NO 199
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33, -36, -38, -41 VH FR1 (aa)

<400> SEQUENCE: 199

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 200
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VH FR1 (aa)

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 201
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VH FR1 (aa)

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 202
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20 VH FR1 (aa)

<400> SEQUENCE: 202

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: Synthetic
<220> FEATURE:
```

<223> OTHER INFORMATION: BCMA-21 VH FR1 (aa)

<400> SEQUENCE: 203

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 204
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15 VH FR2 (aa)

<400> SEQUENCE: 204

Trp Val Arg Gln Ala Pro Gly Lys Gly Leu Glu Trp Val Ala
1               5                   10

<210> SEQ ID NO 205
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VH FR2 (aa)

<400> SEQUENCE: 205

Trp Val Arg Gln Ala Arg Gly Gln Arg Leu Glu Trp Ile Gly
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17 VH FR2 (aa)

<400> SEQUENCE: 206

Trp Ile Arg Leu Ala Pro Gly Lys Gly Leu Glu Trp Val Ser
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VH FR2 (aa)

<400> SEQUENCE: 207

Trp His Arg Gln Ala Pro Gly Lys Gly Pro Glu Trp Val Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VH FR2 (aa)

-continued

<400> SEQUENCE: 208

Trp Val Arg Gln Ala Pro Gly Gln Gly Leu Glu Trp Met Gly
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27, -28, -29, -30, -34, -39 VH FR2
      (aa)

<400> SEQUENCE: 209

Trp Val Arg Gln Ala Pro Gly Lys Gly Leu Glu Trp Val Ser
1               5                   10

<210> SEQ ID NO 210
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VH FR3 (aa)

<400> SEQUENCE: 210

Arg Phe Thr Ile Ser Arg Asp Asn Ser Lys Asn Thr Leu Tyr Leu Gln
1               5                   10                  15

Met Asn Ser Leu Lys Ala Glu Asp Thr Ala Val Tyr Tyr Cys Ala Thr
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VH FR3 (aa)

<400> SEQUENCE: 211

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Thr
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 VH FR3 (aa)

<400> SEQUENCE: 212

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 213
<211> LENGTH: 32

```
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VH FR3 (aa)

<400> SEQUENCE: 213

Arg Val Thr Ile Thr Arg Asp Met Ser Thr Ser Thr Ala Tyr Met Glu
1               5                   10                  15

Leu Ser Ser Leu Arg Ser Glu Asp Thr Ala Val Tyr Tyr Cys Ala Ala
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VH FR3 (aa)

<400> SEQUENCE: 214

Arg Phe Thr Ile Ser Arg Asp Asn Ala Glu Ser Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VH FR3 (aa)

<400> SEQUENCE: 215

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VH FR3 (aa)

<400> SEQUENCE: 216

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

<210> SEQ ID NO 217
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VH FR4 (aa)
```

```
<400> SEQUENCE: 217

Arg Gly Gln Gly Thr Leu Val Thr Val Ser Ser
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VH FR4 (aa)

<400> SEQUENCE: 218

Arg Gly Pro Gly Thr Leu Val Thr Val Ser Ser
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 VH FR4 (aa)

<400> SEQUENCE: 219

Trp Gly Gln Gly Thr Leu Val Asn Val Ser Ser
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VH FR4 (aa)

<400> SEQUENCE: 220

Trp Gly Gln Gly Thr Thr Val Thr Val Ser Ser
1               5                   10

<210> SEQ ID NO 221
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14 VL FR1 (aa)

<400> SEQUENCE: 221

Gln Ala Val Leu Thr Gln Pro Pro Ser Ala Ser Gly Thr Pro Gly Gln
1               5                   10                  15

Arg Val Thr Ile Ser Cys
            20

<210> SEQ ID NO 222
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15, -18, -21 VL FR1 (aa)
```

```
<400> SEQUENCE: 222

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 223
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VL FR1 (aa)

<400> SEQUENCE: 223

Gln Ser Ala Leu Thr Gln Pro Pro Ser Ala Ser Gly Thr Pro Gly Gln
1               5                   10                  15

Arg Val Thr Ile Ser Cys
            20

<210> SEQ ID NO 224
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 VL FR1 (aa)

<400> SEQUENCE: 224

Gln Pro Val Leu Thr Gln Pro Pro Ser Val Ser Val Ala Pro Gly Lys
1               5                   10                  15

Thr Ala Met Ile Thr Cys
            20

<210> SEQ ID NO 225
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VL FR1 (aa)

<400> SEQUENCE: 225

Gln Ala Val Leu Thr Gln Pro Ala Ser Val Ser Gly Ser Pro Gly Gln
1               5                   10                  15

Ser Ile Thr Ile Ser Cys
            20

<210> SEQ ID NO 226
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VL FR1 (aa)

<400> SEQUENCE: 226

Gln Pro Val Leu Thr Gln Pro Pro Ser Ala Ser Gly Thr Pro Gly Gln
1               5                   10                  15

Arg Val Thr Ile Ser Cys
            20
```

<210> SEQ ID NO 227
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 VL FR1 (aa)

<400> SEQUENCE: 227

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 228
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13, -14, -15, -16, -18, -21 VL FR2 (aa)

<400> SEQUENCE: 228

Trp Tyr Gln Gln Ile Pro Gly Thr Ala Pro Lys Leu Leu Ile Tyr
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 VL FR2 (aa)

<400> SEQUENCE: 229

Trp Tyr Gln Gln Lys Thr Gly Gln Ala Pro Val Leu Val Val Tyr
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VL FR2 (aa)

<400> SEQUENCE: 230

Trp Tyr Gln Gln His Pro Gly Lys Asp Pro Lys Leu Met Ile Phe
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VL FR2 (aa)

<400> SEQUENCE: 231

Trp Phe Arg Gln Val Pro Gly Thr Ala Pro Gln Leu Leu Ile Tyr
1               5                   10                  15

```
<210> SEQ ID NO 232
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 VL FR2 (aa)

<400> SEQUENCE: 232

Trp Tyr Gln Gln Pro Pro Gly Lys Ala Pro Lys Leu Ile Ile Tyr
1               5                   10                  15

<210> SEQ ID NO 233
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VL FR3 (aa)

<400> SEQUENCE: 233

Gly Val Pro Asp Arg Phe Ser Ala Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VL FR3 (aa)

<400> SEQUENCE: 234

Gly Val Pro Asp Arg Phe Ser Gly Ser Lys Ser Gly Ala Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 VL FR3 (aa)

<400> SEQUENCE: 235

Gly Val Pro Asp Arg Phe Ser Gly Ser Lys Ser Gly Thr Ser Ala Ser
1               5                   10                  15

Leu Val Ile Ser Gly Leu Arg Ser Glu Asp Glu Ala Asp Tyr Tyr Cys
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VL FR3 (aa)
```

<400> SEQUENCE: 236

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 VL FR3 (aa)

<400> SEQUENCE: 237

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VL FR3 (aa)

<400> SEQUENCE: 238

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VL FR3 (aa)

<400> SEQUENCE: 239

Gly Val Ser Asp Arg Phe Ser Gly Ser Lys Ser Gly Asn Thr Ala Ser
1               5                   10                  15

Leu Asp Ile Ser Gly Leu Gln Pro Glu Asp Glu Ala Asp Tyr Tyr Cys
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VL FR3 (aa)

<400> SEQUENCE: 240

Gly Val Pro Asp Arg Phe Ser Gly Ser Lys Ser Gly Ser Ser Ala Ser
1               5                   10                  15

```
Leu Asp Ile Ser Gly Leu Gln Ser Glu Asp Glu Ala Tyr Tyr Tyr Cys
        20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 VL FR3 (aa)

<400> SEQUENCE: 241

Gly Val Pro Asp Arg Phe Ser Gly Ser Lys Ser Gly Ile Ser Ala Ser
1               5                   10                  15

Leu Ala Ile Ser Gly Leu Arg Ser Glu Asp Glu Ala Asp Tyr Tyr Cys
        20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 VL FR3 (aa)

<400> SEQUENCE: 242

Gly Val Ser Asn Arg Phe Ser Gly Ser Lys Ser Gly Asn Thr Ala Thr
1               5                   10                  15

Leu Thr Ile Ser Gly Leu Gln Gly Asp Asp Glu Ala Asp Tyr Tyr Cys
        20                  25                  30

<210> SEQ ID NO 243
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VL FR4 (aa)

<400> SEQUENCE: 243

Phe Gly Gly Gly Thr Lys Val Thr Val Leu
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VL FR4 (aa)

<400> SEQUENCE: 244

Ile Gly Thr Gly Thr Lys Val Thr Val Leu
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VL FR4 (aa)
```

-continued

<400> SEQUENCE: 245

Phe Gly Gly Glu Thr Lys Leu Thr Val Leu
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21, -22, -23 VL FR4 (aa)

<400> SEQUENCE: 246

Phe Gly Thr Gly Thr Lys Val Thr Val Leu
1               5                   10

<210> SEQ ID NO 247
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 VH Chain (aa)

<400> SEQUENCE: 247

Gln Met Gln Leu Val Gln Tyr Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Thr Leu Pro Gly Arg Asp Gly Tyr Pro Gly Ala Phe Asp Tyr Arg
            100                 105                 110

Gly Gln Gly Thr Leu Val Thr Val Ser Ser
        115                 120

<210> SEQ ID NO 248
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VH Chain (aa)

<400> SEQUENCE: 248

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Leu Pro Gly Arg Asp Gly Tyr Pro Gly Ala Phe Asp Tyr Arg
                100                 105                 110

Gly Pro Gly Thr Leu Val Thr Val Ser Ser
            115                 120
```

<210> SEQ ID NO 249
<211> LENGTH: 123
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 VH Chain (aa)

<400> SEQUENCE: 249

```
Gln Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gln Tyr Ser Ser Ser Ala Gln Arg Ala Asp Phe Asp Tyr
                100                 105                 110

Trp Gly Gln Gly Thr Leu Val Thr Val Ser Ser
            115                 120
```

<210> SEQ ID NO 250
<211> LENGTH: 121
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VH Chain (aa)

<400> SEQUENCE: 250

```
Glu Val Gln Leu Val Gln Ser Gly Pro Glu Val Lys Lys Pro Gly Thr
 1               5                  10                  15

Ser Val Lys Val Ser Cys Lys Ala Ser Gly Phe Thr Phe Thr Ser Ser
                20                  25                  30

Ala Met Gln Trp Val Arg Gln Ala Arg Gly Gln Arg Leu Glu Trp Ile
            35                  40                  45

Gly Trp Ile Val Val Gly Ser Gly Asn Thr Asn Tyr Ala Gln Lys Phe
        50                  55                  60

Gln Glu Arg Val Thr Ile Thr Arg Asp Met Ser Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Ala Ala Pro Tyr Tyr Asp Ile Leu Thr Gly Tyr Tyr Leu Trp Gly
            100                 105                 110

Gln Gly Thr Leu Val Thr Val Ser Ser
        115                 120

<210> SEQ ID NO 251
<211> LENGTH: 117
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17 VH Chain (aa)

<400> SEQUENCE: 251

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Leu Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asp Ser Ser Ala Asp Tyr Trp Gly Gln Gly Thr Leu
            100                 105                 110

Val Asn Val Ser Ser
        115

<210> SEQ ID NO 252
<211> LENGTH: 115
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VH Chain (aa)

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp His Arg Gln Ala Pro Gly Lys Gly Pro Glu Trp Val
        35                  40                  45

Ala His Ile Asn Gln Asp Gly Ser Glu Lys Tyr Tyr Val Asp Ser Val
    50                  55                  60

Lys Gly Arg Phe Thr Ile Ser Arg Asp Asn Ala Glu Ser Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Trp Leu Ala Val Thr Asn Trp Gly Gln Gly Thr Leu Val Thr
            100                 105                 110

Val Ser Ser
        115

<210> SEQ ID NO 253
<211> LENGTH: 114
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VH Chain (aa)

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Asp Val Trp Gly Gln Gly Thr Thr Val Thr Val
            100                 105                 110

Ser Ser

<210> SEQ ID NO 254
<211> LENGTH: 121
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20 VH Chain (aa)

<400> SEQUENCE: 254

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gly Leu Gly Ile Thr Pro Tyr Tyr Phe Asp Tyr Trp Gly
            100                 105                 110

Gln Gly Thr Leu Val Thr Val Ser Ser
        115                 120
```

<210> SEQ ID NO 255
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 VH Chain (aa)

<400> SEQUENCE: 255

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Gly Tyr Thr Glu Asp Tyr Trp Gly Gln Gly Thr
            100                 105                 110

Leu Val Thr Val Ser Ser
        115

<210> SEQ ID NO 256
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22, -23, -40 VH Chain (aa)

<400> SEQUENCE: 256

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser
        115

<210> SEQ ID NO 257
<211> LENGTH: 111
<212> TYPE: PRT
<213> ORGANISM: Artificial Sequence
<220> FEATURE:
<223> OTHER INFORMATION: Synthetic
<220> FEATURE:

<223> OTHER INFORMATION: BCMA-13 VL Chain (aa)

<400> SEQUENCE: 257

Gln Ala Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30

Asp Val Ser Trp Tyr Gln Gln Ile Pro Gly Thr Ala Pro Lys Leu Leu
        35                  40                  45

Ile Tyr Trp Asn Asp Gln Arg Pro Ser Gly Val Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Gly Gly Ser Trp Val Phe Gly Gly Gly Thr Lys Val Thr Val Leu
            100                 105                 110

<210> SEQ ID NO 258
<211> LENGTH: 111
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 VL Chain (aa)

<400> SEQUENCE: 258

Gln Ala Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30

Asp Val Ser Trp Tyr Gln Gln Ile Pro Gly Thr Ala Pro Lys Leu Leu
        35                  40                  45

Ile Tyr Trp Asn Asp Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Arg Leu
                85                  90                  95

Asn Gly Phe Trp Val Phe Gly Gly Gly Thr Lys Leu Thr Val Leu
            100                 105                 110

<210> SEQ ID NO 259
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 VL Chain (aa)

<400> SEQUENCE: 259

Gln Ser Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30

Asp Val Ser Trp Tyr Gln Gln Ile Pro Gly Thr Ala Pro Lys Leu Leu
        35                  40                  45

```
Ile Tyr Trp Asn Asp Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
                100                 105                 110
```

<210> SEQ ID NO 260
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 VL Chain (aa)

<400> SEQUENCE: 260

```
Gln Ser Ala Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
                20                  25                  30

Asp Val Ser Trp Tyr Gln Gln Ile Pro Gly Thr Ala Pro Lys Leu Leu
            35                  40                  45

Ile Tyr Trp Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Ser Gly Trp Val Phe Gly Gly Gly Thr Lys Leu Thr Val Leu
                100                 105                 110
```

<210> SEQ ID NO 261
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17, -33 VL Chain (aa)

<400> SEQUENCE: 261

```
Gln Pro Val Leu Thr Gln Pro Pro Ser Val Ser Val Ala Pro Gly Lys
1               5                   10                  15

Thr Ala Met Ile Thr Cys Gly Gly Asn Asn Ile Gly Phe Lys Gly Val
                20                  25                  30

Gln Trp Tyr Gln Gln Lys Thr Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ala Ser Asp His
                85                  90                  95

Trp Val Phe Gly Gly Gly Thr Lys Leu Thr Val Leu
                100                 105
```

```
<210> SEQ ID NO 262
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 VL Chain (aa)

<400> SEQUENCE: 262

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Ile Pro Gly Thr Ala Pro Lys Leu Leu
        35                  40                  45

Ile Tyr Trp Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 263
<211> LENGTH: 111
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 VL Chain (aa)

<400> SEQUENCE: 263

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Tyr Val Ala Trp Tyr Gln Gln His Pro Gly Lys Asp Pro Lys Leu
        35                  40                  45

Met Ile Phe Glu Val Ile Asn Arg Pro Ser Gly Val Ser Asp Arg Phe
    50                  55                  60

Ser Gly Ser Lys Ser Gly Asn Thr Ala Ser Leu Asp Ile Ser Gly Leu
65                  70                  75                  80

Gln Pro Glu Asp Glu Ala Asp Tyr Tyr Cys Ile Ser Tyr Ser Arg Gly
                85                  90                  95

Ser Thr Pro Tyr Val Ile Gly Thr Gly Thr Lys Val Thr Val Leu
            100                 105                 110

<210> SEQ ID NO 264
<211> LENGTH: 104
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20, -27 VL Chain (aa)

<400> SEQUENCE: 264

Gln Pro Val Leu Thr Gln Pro Pro Ser Ala Ser Gly Thr Pro Gly Gln
1               5                   10                  15
```

```
Arg Val Thr Ile Ser Cys Ser Gly Gly Lys Thr Val Asn Trp Phe Arg
            20                  25                  30

Gln Val Pro Gly Thr Ala Pro Gln Leu Leu Ile Tyr Ser Asn Asp Gln
        35                  40                  45

Arg Pro Ser Gly Val Pro Asp Arg Phe Ser Gly Ser Lys Ser Gly Ser
    50                  55                  60

Ser Ala Ser Leu Asp Ile Ser Gly Leu Gln Ser Glu Asp Glu Ala Tyr
65              70                  75                  80

Tyr Tyr Cys Gly Ser Trp Asp Ser Leu Asn Ala Trp Val Phe Gly
            85                  90                  95

Gly Glu Thr Lys Leu Thr Val Leu
                100
```

```
<210> SEQ ID NO 265
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 VL Chain (aa)

<400> SEQUENCE: 265

Gln Ser Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30

Asp Val Ser Trp Tyr Gln Gln Ile Pro Gly Thr Ala Pro Lys Leu Leu
        35                  40                  45

Ile Tyr Trp Asn Asp Gln Arg Pro Ser Gly Val Pro Asp Arg Phe Ser
    50                  55                  60

Gly Ser Lys Ser Gly Ile Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
                100                 105                 110
```

```
<210> SEQ ID NO 266
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22 VL Chain (aa)

<400> SEQUENCE: 266

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Gly Lys Tyr
            20                  25                  30

Asn Leu Val Ser Trp Tyr Gln Gln Pro Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Thr Leu Thr Ile Ser Gly Leu
65              70                  75                  80
```

Gln Gly Asp Asp Glu Ala Asp Tyr Tyr Cys Ser Tyr Gly Gly Ser
                85                  90                  95

Arg Ser Tyr Val Phe Gly Thr Gly Thr Lys Val Thr Val Leu
            100                 105                 110

<210> SEQ ID NO 267
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-23 VL Chain (aa)

<400> SEQUENCE: 267

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Lys Tyr
            20                  25                  30

Asn Leu Val Ser Trp Tyr Gln Gln Pro Gly Lys Ala Pro Lys Leu
            35                  40                  45

Ile Ile Tyr Asp Val Asn Lys Arg Pro Ser Gly Val Ser Asn Arg Phe
50                  55                  60

Ser Gly Ser Lys Ser Gly Asn Thr Ala Thr Leu Thr Ile Ser Gly Leu
65                  70                  75                  80

Gln Gly Asp Asp Glu Ala Asp Tyr Tyr Cys Ser Ser Tyr Gly Gly Ser
                85                  90                  95

Arg Ser Tyr Val Phe Gly Thr Gly Thr Lys Val Thr Val Leu
            100                 105                 110

<210> SEQ ID NO 268
<211> LENGTH: 248
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-13 scFv (aa)

<400> SEQUENCE: 268

Gln Met Gln Leu Val Gln Tyr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Thr Leu Pro Gly Arg Asp Gly Tyr Pro Gly Ala Phe Asp Tyr Arg
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Gln Ala Val Leu Thr Gln Pro
            130                 135                 140

```
Pro Ser Ala Ser Gly Thr Pro Gly Gln Arg Val Thr Ile Ser Cys Ser
145                 150                 155                 160

Gly Ser Gly Ser Asn Ile Gly Ser Asn Asp Val Ser Trp Tyr Gln Gln
                165                 170                 175

Ile Pro Gly Thr Ala Pro Lys Leu Leu Ile Tyr Trp Asn Asp Gln Arg
            180                 185                 190

Pro Ser Gly Val Pro Asp Arg Phe Ser Ala Ser Lys Ser Gly Thr Ser
            195                 200                 205

Ala Ser Leu Ala Ile Ser Gly Leu Arg Ser Glu Asp Glu Ala Asp Tyr
        210                 215                 220

Tyr Cys Ala Ala Trp Asp Asp Ser Leu Gly Gly Ser Trp Val Phe Gly
225                 230                 235                 240

Gly Gly Thr Lys Val Thr Val Leu
                245

<210> SEQ ID NO 269
<211> LENGTH: 248
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-14 scFv (aa)

<400> SEQUENCE: 269

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Pro Gly Arg Asp Gly Tyr Pro Gly Ala Phe Asp Tyr Arg
            100                 105                 110

Gly Pro Gly Thr Leu Val Thr Val Ser Ser Gly Gly Gly Gly Ser Gly
        115                 120                 125

Gly Gly Gly Ser Gly Gly Gly Gly Ser Gln Ala Val Leu Thr Gln Pro
130                 135                 140

Pro Ser Ala Ser Gly Thr Pro Gly Gln Arg Val Thr Ile Ser Cys Ser
145                 150                 155                 160

Gly Ser Gly Ser Asn Ile Gly Ser Asn Asp Val Ser Trp Tyr Gln Gln
                165                 170                 175

Ile Pro Gly Thr Ala Pro Lys Leu Leu Ile Tyr Trp Asn Asp Gln Arg
            180                 185                 190

Pro Ser Gly Val Pro Asp Arg Phe Ser Gly Ser Lys Ser Gly Ala Ser
            195                 200                 205

Ala Ser Leu Ala Ile Ser Gly Leu Gln Ser Glu Asp Glu Ala Asp Tyr
        210                 215                 220

Tyr Cys Ala Ala Trp Asp Asp Arg Leu Asn Gly Phe Trp Val Phe Gly
225                 230                 235                 240
```

Gly Gly Thr Lys Leu Thr Val Leu
            245

<210> SEQ ID NO 270
<211> LENGTH: 248
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-15 scFv (aa)

<400> SEQUENCE: 270

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Tyr Ser Ser Ala Gln Arg Ala Asp Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gln Ser Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Gly Ser Asn Ile Gly Ser Asn Asp Val Ser Trp Tyr Gln
                165                 170                 175

Gln Ile Pro Gly Thr Ala Pro Lys Leu Leu Ile Tyr Trp Asn Asp Gln
            180                 185                 190

Arg Pro Ser Gly Val Pro Asp Arg Phe Ser Gly Ser Lys Ser Gly Thr
        195                 200                 205

Ser Ala Ser Leu Val Ile Ser Gly Leu Arg Ser Glu Asp Glu Ala Asp
    210                 215                 220

Tyr Tyr Cys Ala Ala Trp Asp Asp Ser Leu Ser Gly Trp Val Phe Gly
225                 230                 235                 240

Gly Gly Thr Lys Leu Thr Val Leu
            245

<210> SEQ ID NO 271
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-16 scFv (aa)

<400> SEQUENCE: 271

Glu Val Gln Leu Val Gln Ser Gly Pro Glu Val Lys Lys Pro Gly Thr
1               5                   10                  15

```
Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ala Pro Tyr Tyr Asp Ile Leu Thr Gly Tyr Tyr Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Thr Pro Gly Gln Arg Val Thr Ile Ser Cys Ser Gly
145                 150                 155                 160

Ser Gly Ser Asn Ile Gly Ser Asn Asp Val Ser Trp Tyr Gln Gln Ile
                165                 170                 175

Pro Gly Thr Ala Pro Lys Leu Leu Ile Tyr Trp Asn Asp Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Gln Ser Glu Asp Glu Ala Asp Tyr Tyr
    210                 215                 220

Cys Ala Ser Trp Asp Asp Ser Leu Ser Gly Trp Val Phe Gly Gly Gly
225                 230                 235                 240

Thr Lys Leu Thr Val Leu
            245

<210> SEQ ID NO 272
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-17 scFv (aa)

<400> SEQUENCE: 272

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Leu Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asp Ser Ser Ala Asp Tyr Trp Gly Gln Gly Thr Leu
            100                 105                 110
```

Val Asn Val Ser Ser Gly Gly Gly Ser Gly Gly Gly Ser Gly
            115                 120                 125

Gly Gly Gly Ser Gln Pro Val Leu Thr Gln Pro Pro Ser Val Ser Val
130                 135                 140

Ala Pro Gly Lys Thr Ala Met Ile Thr Cys Gly Gly Asn Asn Ile Gly
145                 150                 155                 160

Phe Lys Gly Val Gln Trp Tyr Gln Gln Lys Thr Gly Gln Ala Pro Val
                165                 170                 175

Leu Val Val Tyr Asp Asp Ser Asp Arg Pro Ser Gly Ile Pro Glu Arg
            180                 185                 190

Phe Ser Gly Ser Asn Ser Gly Asn Thr Ala Thr Leu Thr Ile Ser Arg
        195                 200                 205

Val Glu Ala Gly Asp Glu Ala Asp Tyr Tyr Cys Gln Val Trp Asp Ser
    210                 215                 220

Ala Ser Asp His Trp Val Phe Gly Gly Gly Thr Lys Leu Thr Val Leu
225                 230                 235                 240

<210> SEQ ID NO 273
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-18 scFv (aa)

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp His Arg Gln Ala Pro Gly Lys Gly Pro Glu Trp Val
        35                  40                  45

Ala His Ile Asn Gln Asp Gly Ser Glu Lys Tyr Tyr Val Asp Ser Val
    50                  55                  60

Lys Gly Arg Phe Thr Ile Ser Arg Asp Asn Ala Glu Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Leu Ala Val Thr Asn Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gln Ser Val Leu Thr Gln Pro Pro Ser Ala Ser Gly Thr Pro
130                 135                 140

Gly Gln Arg Val Thr Ile Ser Cys Ser Gly Ser Gly Ser Asn Ile Gly
145                 150                 155                 160

Ser Asn Asp Val Ser Trp Tyr Gln Gln Ile Pro Gly Thr Ala Pro Lys
                165                 170                 175

Leu Leu Ile Tyr Trp Asn Asp Gln Arg Pro Ser Gly Val Pro Asp Arg
            180                 185                 190

Phe Ser Gly Ser Lys Ser Gly Thr Ser Ala Leu Ala Ile Ser Gly
        195                 200                 205

Leu Arg Ser Glu Asp Glu Ala Asp Tyr Tyr Cys Ala Ala Trp Asp Asp
    210                 215                 220

Ser Leu Asn Gly Trp Val Phe Gly Gly Gly Thr Lys Leu Thr Val Leu
225                 230                 235                 240

<210> SEQ ID NO 274
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-19 scFv (aa)

<400> SEQUENCE: 274

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Asp Val Trp Gly Gln Gly Thr Thr Val Thr Val
            100                 105                 110

Ser Ser Gly Gly Gly Gly Ser Gly Gly Gly Gly Ser Gly Gly Gly Gly
            115                 120                 125

Ser Gln Ala Val Leu Thr Gln Pro Ala Ser Val Ser Gly Ser Pro Gly
        130                 135                 140

Gln Ser Ile Thr Ile Ser Cys Thr Gly Thr Ser Ser Asp Val Gly Asp
145                 150                 155                 160

Tyr Asn Tyr Val Ala Trp Tyr Gln Gln His Pro Gly Lys Asp Pro Lys
                165                 170                 175

Leu Met Ile Phe Glu Val Ile Asn Arg Pro Ser Gly Val Ser Asp Arg
            180                 185                 190

Phe Ser Gly Ser Lys Ser Gly Asn Thr Ala Ser Leu Asp Ile Ser Gly
        195                 200                 205

Leu Gln Pro Glu Asp Glu Ala Asp Tyr Tyr Cys Ile Ser Tyr Ser Arg
    210                 215                 220

Gly Ser Thr Pro Tyr Val Ile Gly Thr Gly Thr Lys Val Thr Val Leu
225                 230                 235                 240

<210> SEQ ID NO 275
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-20 scFv (aa)

<400> SEQUENCE: 275

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

```
Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
             85                  90                  95

Ala Lys Gly Gly Leu Gly Ile Thr Pro Tyr Tyr Phe Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gln Pro Val Leu Thr Gln Pro Pro
            130                 135                 140

Ser Ala Ser Gly Thr Pro Gly Gln Arg Val Thr Ile Ser Cys Ser Gly
145                 150                 155                 160

Gly Lys Thr Val Asn Trp Phe Arg Gln Val Pro Gly Thr Ala Pro Gln
                165                 170                 175

Leu Leu Ile Tyr Ser Asn Asp Gln Arg Pro Ser Gly Val Pro Asp Arg
            180                 185                 190

Phe Ser Gly Ser Lys Ser Gly Ser Ala Ser Leu Asp Ile Ser Gly
            195                 200                 205

Leu Gln Ser Glu Asp Glu Ala Tyr Tyr Tyr Cys Gly Ser Trp Asp Asp
            210                 215                 220

Ser Leu Asn Ala Trp Val Phe Gly Gly Glu Thr Lys Leu Thr Val Leu
225                 230                 235                 240

<210> SEQ ID NO 276
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-21 scFv (aa)

<400> SEQUENCE: 276

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Lys Val Asp Gly Gly Tyr Thr Glu Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Gln Ser Val Leu Thr Gln Pro Pro Ser Ala Ser
            130                 135                 140
```

```
Gly Thr Pro Gly Gln Arg Val Thr Ile Ser Cys Ser Gly Ser Gly Ser
145                 150                 155                 160

Asn Ile Gly Ser Asn Asp Val Ser Trp Tyr Gln Gln Ile Pro Gly Thr
                165                 170                 175

Ala Pro Lys Leu Leu Ile Tyr Trp Asn Asp Gln Arg Pro Ser Gly Val
            180                 185                 190

Pro Asp Arg Phe Ser Gly Ser Lys Ser Gly Ile Ser Ala Ser Leu Ala
        195                 200                 205

Ile Ser Gly Leu Arg Ser Glu Asp Glu Ala Asp Tyr Tyr Cys Ala Ala
    210                 215                 220

Trp Asp Asp Ser Leu Asn Gly Tyr Val Phe Gly Thr Gly Thr Lys Val
225                 230                 235                 240

Thr Val Leu

<210> SEQ ID NO 277
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-22 scFv (aa)

<400> SEQUENCE: 277

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Ser Ser Ser
145                 150                 155                 160

Asp Val Gly Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
            180                 185                 190

Val Ser Asn Arg Phe Ser Gly Ser Lys Ser Gly Asn Thr Ala Thr Leu
        195                 200                 205

Thr Ile Ser Gly Leu Gln Gly Asp Asp Glu Ala Asp Tyr Tyr Cys Cys
    210                 215                 220

Ser Tyr Gly Gly Ser Arg Ser Tyr Val Phe Gly Thr Gly Thr Lys Val
225                 230                 235                 240

Thr Val Leu
```

<210> SEQ ID NO 278
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-23 scFv (aa)

<400> SEQUENCE: 278

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Ser Ser Ser
145                 150                 155                 160

Asp Val Gly Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
            180                 185                 190

Val Ser Asn Arg Phe Ser Gly Ser Lys Ser Gly Asn Thr Ala Thr Leu
        195                 200                 205

Thr Ile Ser Gly Leu Gln Gly Asp Asp Glu Ala Asp Tyr Tyr Cys Ser
    210                 215                 220

Ser Tyr Gly Gly Ser Arg Ser Tyr Val Phe Gly Thr Gly Thr Lys Val
225                 230                 235                 240

Thr Val Leu

<210> SEQ ID NO 279
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: VH-3 CDR-H3 (aa)

<400> SEQUENCE: 279

Val Asp Gly Asp Asp Ala Phe Asp Ile
1               5

<210> SEQ ID NO 280
<211> LENGTH: 13
<212> TYPE: PRT

```
<213> ORGANISM: Artificial Sequence
<220> FEATURE:
<223> OTHER INFORMATION: Synthetic
<220> FEATURE:
<223> OTHER INFORMATION: VH-4 CDR-H3 (aa)

<400> SEQUENCE: 280

Asp Pro Leu Ser Trp Asp Ser Ser Gly Lys Gly Pro Arg
1               5                   10

<210> SEQ ID NO 281
<211> LENGTH: 16
<212> TYPE: PRT
<213> ORGANISM: Artificial Sequence
<220> FEATURE:
<223> OTHER INFORMATION: Synthetic
<220> FEATURE:
<223> OTHER INFORMATION: VH-5 CDR-H3 (aa)

<400> SEQUENCE: 281

Glu Asn Tyr Asp Phe Trp Ser Trp Arg Tyr Tyr Tyr Asp Met Asp Val
1               5                   10                  15

<210> SEQ ID NO 282
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: VH-6 CDR-H3 (aa)

<400> SEQUENCE: 282

Val Asp Gly Pro Pro Ser Tyr Asp Ile
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: VH-7 CDR-H3 (aa)

<400> SEQUENCE: 283

Gly Asp Trp Asp Asp Ala Phe Asp Ile
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: VH-9 CDR-H3 (aa)

<400> SEQUENCE: 284

Val Asp Gly Asp Tyr Glu Asp Tyr
1               5

<210> SEQ ID NO 285
<211> LENGTH: 12
<212> TYPE: PRT
<213> ORGANISM: Artificial Sequence
<220> FEATURE:
<223> OTHER INFORMATION: Synthetic
<220> FEATURE:
```

<223> OTHER INFORMATION: VH-10 CDR-H3 (aa)

<400> SEQUENCE: 285

Asp Val Pro Ser Ser Gly Asp Asp Ala Phe Asp Ile
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: VH-11 CDR-H3 (aa)

<400> SEQUENCE: 286

Val Asp Gly Asp Asp Val Phe Asp Ile
1               5

<210> SEQ ID NO 287
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: VH-12 CDR-H3 (aa)

<400> SEQUENCE: 287

Val Asp Gly Asp Ala Phe Asp Ile
1               5

<210> SEQ ID NO 288
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H1 (aa)

<400> SEQUENCE: 288

Asp Tyr Ser Ile Asn
1               5

<210> SEQ ID NO 289
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H1 (aa)

<400> SEQUENCE: 289

Asn Phe Gly Met Asn
1               5

<210> SEQ ID NO 290
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H2 (aa)

<400> SEQUENCE: 290

Trp Ile Asn Thr Glu Thr Arg Glu Pro Ala Tyr Ala Tyr Asp Phe Arg
1               5                   10                  15

Gly

<210> SEQ ID NO 291
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H2 (aa)

<400> SEQUENCE: 291

Trp Ile Asn Thr Tyr Thr Gly Glu Ser Tyr Phe Ala Asp Asp Phe Lys
1               5                   10                  15

Gly

<210> SEQ ID NO 292
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H3 (aa)

<400> SEQUENCE: 292

Asp Tyr Ser Tyr Ala Met Asp Tyr
1               5

<210> SEQ ID NO 293
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H3 (aa)

<400> SEQUENCE: 293

Gly Glu Ile Tyr Tyr Gly Tyr Asp Gly Gly Phe Ala Tyr
1               5                   10

<210> SEQ ID NO 294
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H1 (aa) Chothia numbering

<400> SEQUENCE: 294

Gly Tyr Thr Phe Thr Asp Tyr
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H1 (aa) Chothia numbering

```
<400> SEQUENCE: 295

Gly Tyr Thr Phe Thr Asn Phe
1               5

<210> SEQ ID NO 296
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H2 (aa) Chothia numbering

<400> SEQUENCE: 296

Asn Thr Glu Thr Arg Glu
1               5

<210> SEQ ID NO 297
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H2 (aa) Chothia numbering

<400> SEQUENCE: 297

Asn Thr Tyr Thr Gly Glu
1               5

<210> SEQ ID NO 298
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H1 (aa) AbM numbering

<400> SEQUENCE: 298

Gly Tyr Thr Phe Thr Asp Tyr Ser Ile Asn
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H1 (aa) AbM numbering

<400> SEQUENCE: 299

Gly Tyr Thr Phe Thr Asn Phe Gly Met Asn
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH CDR-H2 (aa) AbM numbering
```

```
<400> SEQUENCE: 300

Trp Ile Asn Thr Glu Thr Arg Glu Pro Ala
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH CDR-H2 (aa) AbM numbering

<400> SEQUENCE: 301

Trp Ile Asn Thr Tyr Thr Gly Glu Ser Tyr
1               5                   10

<210> SEQ ID NO 302
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL CDR-L1 (aa)

<400> SEQUENCE: 302

Arg Ala Ser Glu Ser Val Thr Ile Leu Gly Ser His Leu Ile His
1               5                   10                  15

<210> SEQ ID NO 303
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL CDR-L1 (aa)

<400> SEQUENCE: 303

Arg Ala Ser Gln Asp Val Asn Thr Ala Val Ser
1               5                   10

<210> SEQ ID NO 304
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL CDR-L2 (aa)

<400> SEQUENCE: 304

Leu Ala Ser Asn Val Gln Thr
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL CDR-L2 (aa)
```

<400> SEQUENCE: 305

Ser Ala Ser Tyr Arg Tyr Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL CDR-L3 (aa)

<400> SEQUENCE: 306

Leu Gln Ser Arg Thr Ile Pro Arg Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL CDR-L3 (aa)

<400> SEQUENCE: 307

Gln Gln His Tyr Ser Thr Pro Trp Thr
1               5

<210> SEQ ID NO 308
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH FR1 (aa)

<400> SEQUENCE: 308

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 309
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH FR1 (aa)

<400> SEQUENCE: 309

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr
            20                  25                  30

<210> SEQ ID NO 310
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH FR2 (aa)

<400> SEQUENCE: 310

Trp Val Lys Arg Ala Pro Gly Lys Gly Leu Lys Trp Met Gly
1               5                   10

<210> SEQ ID NO 311
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH FR2 (aa)

<400> SEQUENCE: 311

Trp Val Lys Gln Ala Pro Gly Lys Gly Phe Lys Trp Met Ala
1               5                   10

<210> SEQ ID NO 312
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH FR3 (aa)

<400> SEQUENCE: 312

Arg Phe Ala Phe Ser Leu Glu Thr Ser Ala Ser Thr Ala Tyr Leu Gln
1               5                   10                  15

Ile Asn Asn Leu Lys Tyr Glu Asp Thr Ala Thr Tyr Phe Cys Ala Leu
            20                  25                  30

<210> SEQ ID NO 313
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH FR3 (aa)

<400> SEQUENCE: 313

Arg Phe Ala Phe Ser Val Glu Thr Ser Ala Thr Thr Ala Tyr Leu Gln
1               5                   10                  15

Ile Asn Asn Leu Lys Thr Glu Asp Thr Ala Thr Tyr Phe Cys Ala Arg
            20                  25                  30

<210> SEQ ID NO 314
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH FR4 (aa)

<400> SEQUENCE: 314

Trp Gly Gln Gly Thr Ser Val Thr Val Ser Ser
1               5                   10

<210> SEQ ID NO 315
<211> LENGTH: 11
<212> TYPE: PRT
<213> ORGANISM: Artificial Sequence

```
<220> FEATURE:
<223> OTHER INFORMATION: Synthetic
<220> FEATURE:
<223> OTHER INFORMATION: BCMA-C2 VH FR4 (aa)

<400> SEQUENCE: 315

Trp Gly Gln Gly Thr Leu Val Thr Val Ser Ala
1               5                   10

<210> SEQ ID NO 316
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL FR1 (aa)

<400> SEQUENCE: 316

Asp Ile Val Leu Thr Gln Ser Pro Pro Ser Leu Ala Met Ser Leu Gly
1               5                   10                  15

Lys Arg Ala Thr Ile Ser Cys
            20

<210> SEQ ID NO 317
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL FR1 (aa)

<400> SEQUENCE: 317

Asp Val Val Met Thr Gln Ser His Arg Phe Met Ser Thr Ser Val Gly
1               5                   10                  15

Asp Arg Val Ser Ile Thr Cys
            20

<210> SEQ ID NO 318
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL FR2 (aa)

<400> SEQUENCE: 318

Trp Tyr Gln Gln Lys Pro Gly Gln Pro Pro Thr Leu Leu Ile Gln
1               5                   10                  15

<210> SEQ ID NO 319
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL FR2 (aa)

<400> SEQUENCE: 319

Trp Tyr Gln Gln Lys Pro Gly Gln Ser Pro Lys Leu Leu Ile Phe
1               5                   10                  15

<210> SEQ ID NO 320
<211> LENGTH: 32
```

```
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL FR3 (aa)

<400> SEQUENCE: 320

Gly Val Pro Ala Arg Phe Ser Gly Ser Gly Ser Arg Thr Asp Phe Thr
1               5                   10                  15

Leu Thr Ile Asp Pro Val Glu Glu Asp Val Ala Val Tyr Tyr Cys
            20                  25                  30

<210> SEQ ID NO 321
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL FR3 (aa)

<400> SEQUENCE: 321

Gly Val Pro Asp Arg Phe Thr Gly Ser Gly Ser Gly Ala Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 322
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL FR4 (aa)

<400> SEQUENCE: 322

Phe Gly Gly Gly Thr Lys Leu Glu Ile Lys
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL FR4 (aa)

<400> SEQUENCE: 323

Phe Gly Gly Gly Thr Lys Leu Asp Ile Lys
1               5                   10

<210> SEQ ID NO 324
<211> LENGTH: 117
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH Chain (aa)

<400> SEQUENCE: 324

Gln Ile Gln Leu Val Gln Ser Gly Pro Glu Leu Lys Lys Pro Gly Glu
1               5                   10                  15
```

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 325
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VH Chain (aa)

<400> SEQUENCE: 325

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
        115                 120

<210> SEQ ID NO 326
<211> LENGTH: 111
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL Chain (aa)

<400> SEQUENCE: 326

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

```
Thr Leu Leu Ile Gln Leu Ala Ser Asn Val Gln Thr Gly Val Pro Ala
        50                  55                  60

Arg Phe Ser Gly Ser Gly Ser Arg Thr Asp Phe Thr Leu Thr Ile Asp
 65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
                100                 105                 110

<210> SEQ ID NO 327
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2 VL Chain (aa)

<400> SEQUENCE: 327

Asp Val Val Met Thr Gln Ser His Arg Phe Met Ser Thr Ser Val Gly
 1               5                  10                  15

Asp Arg Val Ser Ile Thr Cys Arg Ala Ser Gln Asp Val Asn Thr Ala
                20                  25                  30

Val Ser Trp Tyr Gln Gln Lys Pro Gly Gln Ser Pro Lys Leu Leu Ile
            35                  40                  45

Phe Ser Ala Ser Tyr Arg Tyr Thr Gly Val Pro Asp Arg Phe Thr Gly
 50                  55                  60

Ser Gly Ser Gly Ala Asp Phe Thr Leu Thr Ile Ser Ser Val Gln Ala
 65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys
                100                 105

<210> SEQ ID NO 328
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VL-VH scFv (aa)

<400> SEQUENCE: 328

Asp Ile Val Leu Thr Gln Ser Pro Pro Ser Leu Ala Met Ser Leu Gly
 1               5                  10                  15

Lys Arg Ala Thr Ile Ser Cys Arg Ala Ser Glu Ser Val Thr Ile Leu
                20                  25                  30

Gly Ser His Leu Ile His Trp Tyr Gln Gln Lys Pro Gly Gln Pro Pro
            35                  40                  45

Thr Leu Leu Ile Gln Leu Ala Ser Asn Val Gln Thr Gly Val Pro Ala
        50                  55                  60

Arg Phe Ser Gly Ser Gly Ser Arg Thr Asp Phe Thr Leu Thr Ile Asp
 65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
                100                 105                 110
```

```
Gly Gly Gly Ser Gly Gly Gly Ser Gly Gly Gly Ser Gln Ile
        115                 120                 125

Gln Leu Val Gln Ser Gly Pro Glu Leu Lys Lys Pro Gly Glu Thr Val
130                 135                 140

Lys Ile Ser Cys Lys Ala Ser Gly Tyr Thr Phe Thr Asp Tyr Ser Ile
145                 150                 155                 160

Asn Trp Val Lys Arg Ala Pro Gly Lys Gly Leu Lys Trp Met Gly Trp
                165                 170                 175

Ile Asn Thr Glu Thr Arg Glu Pro Ala Tyr Ala Tyr Asp Phe Arg Gly
            180                 185                 190

Arg Phe Ala Phe Ser Leu Glu Thr Ser Ala Ser Thr Ala Tyr Leu Gln
        195                 200                 205

Ile Asn Asn Leu Lys Tyr Glu Asp Thr Ala Thr Tyr Phe Cys Ala Leu
    210                 215                 220

Asp Tyr Ser Tyr Ala Met Asp Tyr Trp Gly Gln Gly Thr Ser Val Thr
225                 230                 235                 240

Val Ser Ser

<210> SEQ ID NO 329
<211> LENGTH: 244
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2  VH-VL scFv (aa)

<400> SEQUENCE: 329

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
            85                  90                  95

Ala Arg Gly Glu Ile Tyr Tyr Gly Tyr Asp Gly Gly Phe Ala Tyr Trp
        100                 105                 110

Gly Gln Gly Thr Leu Val Thr Val Ser Ala Gly Gly Gly Ser Gly
        115                 120                 125

Gly Gly Gly Ser Gly Gly Gly Gly Ser Asp Val Val Met Thr Gln Ser
    130                 135                 140

His Arg Phe Met Ser Thr Ser Val Gly Asp Arg Val Ser Ile Thr Cys
145                 150                 155                 160

Arg Ala Ser Gln Asp Val Asn Thr Ala Val Ser Trp Tyr Gln Gln Lys
                165                 170                 175

Pro Gly Gln Ser Pro Lys Leu Leu Ile Phe Ser Ala Ser Tyr Arg Tyr
            180                 185                 190

Thr Gly Val Pro Asp Arg Phe Thr Gly Ser Gly Ser Gly Ala Asp Phe
        195                 200                 205
```

```
Thr Leu Thr Ile Ser Ser Val Gln Ala Glu Asp Leu Ala Val Tyr Tyr
    210                 215                 220

Cys Gln Gln His Tyr Ser Thr Pro Trp Thr Phe Gly Gly Gly Thr Lys
225                 230                 235                 240

Leu Asp Ile Lys

<210> SEQ ID NO 330
<211> LENGTH: 738
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-1 scFv (nt)

<400> SEQUENCE: 330
caggtgcagc tggtgcagtc tgggggaggc ttggtacagc cagggcggtc cctgagactc      60
tcctgtacag cttctggatt cacctttggt gattatgcta tgagctggtt ccgccaggct     120
ccagggaagg gctggagtg gtaggtttc attagaagca aagcttatgg tggacaaca       180 gaatacgccg cgtctgtgaa aggcagattc accatctcaa gagatgattc aaaaagcatc     240
gcctatctgc aaatgaacag cctgaaaacc gaggacacag ccgtgtatta ctgtgcggcc     300
tggagtgccc cgactgacta ctggggccag ggaaccctgg tcaccgtctc ctcaggtgga     360
ggcggttcag gcggaggtgg ctctggcggt ggcggatcgg atattgtgat gacccagtct     420
ccagactccc tgtctgtgtc tccgggcgag agggccacca tcagctgcaa gtccagccag     480
agtgttttat ccacctccaa caataagaac tatttagctt ggtatcagca gaaaccagga     540
cagcccccta ggctgctcct ttactgggca tctacccggg aggccggggt ccctgaccga     600
ttcagtggca gcgggtctgg gacagatttc actctcacca tcagcagcct gcaggctgaa     660
gatgtggcgg tttattactg tcaacaatat ttcagttctc cgtacacttt tggccacggg     720
accaagctgg aaatcaaa                                                   738

<210> SEQ ID NO 331
<211> LENGTH: 717
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-2 scFv (nt)

<400> SEQUENCE: 331
gaggtgcagc tggtggagtc tgggggaggc ttggtcaagc ctggagggtc cctgagactc      60
tcctgtgcag cctctggatt cacctttcagt gactactaca tgagctggat ccgccaggct    120
ccagggaagg gctggagtg gtttcatac attagtagta gtggtagtac catatactac       180
gcagactctg tgaagggccg attcaccatc tccagggaca cgccaagaa ctcactgtat      240 ctgcaaatga acagcctgag agccgaggac acggccgtgt attactgtgc gaaagtggat     300 ggcccctcctt cttctgatat ctggggccaa gggacaatgg tcaccgtctc ctcaggtgga    360
ggcggttcag gcggaggtgg ctctggcggt ggcggatcgg aaatagtgat gacgcagtct     420
ccagccaccc tgtctgtgtc tccggggaa acagccaccc tctcctgcag ggccagtcag     480
agtattaaga ccaacttggc ctggtaccag cagaaacctg gccaggctcc caggctcctc    540
atctatgctg catccaccag ggccactggc atcccagaca gattcagtgg cagtgggtct     600
```

| gggacagact tcactctcac catcaccaga ctggagcctg aagatttttgc agtgtattac | 660 |
| tgtcagcaat atggtagctc acccactttt ggccggggga ccaagctgga aatcaaa | 717 |

<210> SEQ ID NO 332
<211> LENGTH: 738
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-3 scFv (nt)

<400> SEQUENCE: 332

| caggtgcagc tggtgcagtc tgggggaggc ttggtacagc cagggcggtc cctgagactc | 60 |
| tcctgtacag cttctggatt cacctttggt gattatgcta tgagctggtt ccgccaggct | 120 |
| ccagggaagg ggctggagtg ggtaggtttc attagaagca aagcttatgg tgggacaaca | 180 |
| gaatacgccg cgtctgtgaa aggcagattc accatctcaa gagatgattc caaaagcatc | 240 |
| gcctatctgc aaatgaacag cctgaaaacc gaggacacag ccgtgtatta ctgtgcggcc | 300 |
| tggagtgccc cgactgacta ctggggccag ggaaccctgg tcaccgtctc ctcaggtgga | 360 |
| ggcggttcag gcggaggtgg ctctggcggt ggcggatcgg atattgtgat gacccagtct | 420 |
| ccagactccc tggttgtgtc tctgggcgag agggccacca tcaactgcaa gtccagccag | 480 |
| agtgttttac acagctccaa caataagaat tacttagctt ggtaccagca gaaaccagga | 540 |
| cagcctccta agctgctcat ttactgggca tctacccggg aatccggggt ccctgaccgg | 600 |
| ttcagtggca gcgggtctgg gacagatttc actctcacca tcagcagcct gcaggctgaa | 660 |
| gatgtggcag tttattactg tcagcagtat tatactactc cgctcacttt cggcggaggg | 720 |
| accaaggtgg aaatcaaa | 738 |

<210> SEQ ID NO 333
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-4 scFv (nt)

<400> SEQUENCE: 333

| caggtgcagc tggtgcagtc tgggggaggc ttggtacagc cagggcggtc cctgagactc | 60 |
| tcctgtacag cttctggatt cacctttggt gattatgcta tgagctggtt ccgccaggct | 120 |
| ccagggaagg ggctggagtg ggtaggtttc attagaagca aagcttatgg tgggacaaca | 180 |
| gaatacgccg cgtctgtgaa aggcagattc accatctcaa gagatgattc caaaagcatc | 240 |
| gcctatctgc aaatgaacag cctgaaaacc gaggacacag ccgtgtatta ctgtgcggcc | 300 |
| tggagtgccc cgactgacta ctggggccag ggaaccctgg tcaccgtctc ctcaggtgga | 360 |
| ggcggttcag gcggaggtgg ctctggcggt ggcggatcgg ccatccggat gacccagtct | 420 |
| ccatcctccc tgtccgcgtc tctggggac agagtcacca tcacttgccg ggcgagtcag | 480 |
| gacattagga attctttggc ctggtatcag cagaggccag gaaagccccc taaactcctg | 540 |
| ctttctgctg catccagatt ggaaagtggg gtcccttcta ggttcagtgg cactacttct | 600 |
| ggggcggagt atgctctcag catcagcagc ctgcagcctg aagatgtcgc atcttatttc | 660 |
| tgtcagcagt attatagtct ccctctctcc ttcggcggag ggaccaaggt ggaaatcaaa | 720 |

<210> SEQ ID NO 334
<211> LENGTH: 738
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-5 scFv (nt)

<400> SEQUENCE: 334

```
caggtgcagc tggtgcagtc tggggggaggc ttggtacagc cagggcggtc cctgagactc      60
tcctgtacag cttctggatt cacctttggt gattatgcta tgagctggtt ccgccaggct     120
ccagggaagg ggctggagtg ggtaggtttc attagaagca aagcttatgg tgggacaaca     180
gaatacgccg cgtctgtgaa aggcagattc accatctcaa gagatgattc caaaagcatc     240
gcctatctgc aaatgaacag cctgaaaacc gaggacacag ccgtgtatta ctgtgcggcc     300
tggagtgccc cgactgacta ctggggccag ggaaccctgg tcaccgtctc ctcaggtgga     360
ggcggttcag gcggaggtgg ctctggcggt ggcggatcgg acatcgtgat gacccagtct     420
ccagactccc tggctgtgtc tctgggcgag agggccacca tcaactgcaa gtccagccag     480
agtgttttat acagctccaa caataagaac tacttagctt ggtaccagca gaaaccagga     540
cagcctccta agctgctcat ttactgggca tctacccggg aatccggggt ccctgaccga     600
ttcagtggca gcgggtctgg gacagatttc actctcacca tcagcagcct gcaggctgaa     660
gatgtggcag tttattactg tcagcaatat tatagtactc cgtggacgtt cggccaaggg     720
accaaggtgg atatcaaa                                                   738
```

<210> SEQ ID NO 335
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-6 scFv (nt)

<400> SEQUENCE: 335

```
caggtgcagc tggtgcagtc tggggggaggc ttggtacagc cagggcggtc cctgagactc      60
tcctgtacag cttctggatt cacctttggt gattatgcta tgagctggtt ccgccaggct     120
ccagggaagg ggctggagtg ggtaggtttc attagaagca aagcttatgg tgggacaaca     180
gaatacgccg cgtctgtgaa aggcagattc accatctcaa gagatgattc caaaagcatc     240
gcctatctgc aaatgaacag cctgaaaacc gaggacacag ccgtgtatta ctgtgcggcc     300
tggagtgccc cgactgacta ctggggccag ggaaccctgg tcaccgtctc ctcaggtgga     360
ggcggttcag gcggaggtgg ctctggcggt ggcggatcgg atattgtgat gacccagtct     420
ccatcgtccc tgtctgtgtc tgtaggagag agagtcacca tcacttgtcg ggcgagtcag     480
tctataagta attccttagc ctggtataaa cagagaccgg agaagcccc taaactcctg      540 atacatgctg catccaatgt ggaagatggg gtcccttcga ggttcagcgg cagggatct      600 gggacagttt tcactctcgc catcagcaat gtacagcctg aagatttcgc aacttactac     660
tgtcagcaga gtcacatgta ccctccgact ttcggcgggg gaccaaggt ggaaatcaaa     720
```

<210> SEQ ID NO 336
<211> LENGTH: 720
<212> TYPE: DNA
<213> ORGANISM: Artificial Sequence
<220> FEATURE:

```
<223> OTHER INFORMATION: Synthetic
<220> FEATURE:
<223> OTHER INFORMATION: BCMA-7 scFv (nt)

<400> SEQUENCE: 336
caggtgcagc tggtgcagtc tgggggaggc ttggtacagc cagggcggtc cctgagactc      60
tcctgtacag cttctggatt cacctttggt gattatgcta tgagctggtt ccgccaggct     120
ccagggaagg gctggagtg gtaggtttc attagaagca aagcttatgg tggacaaca       180 gaatacgccg cgtctgtgaa aggcagattc accatctcaa gagatgattc caaaagcatc    240
gcctatctgc aaatgaacag cctgaaaacc gaggacacag ccgtgtatta ctgtgcggcc    300
tggagtgccc cgactgacta ctggggccag ggaaccctgg tcaccgtctc ctcaggtgga    360
ggcggttcag gcggaggtgg ctctggcggt ggcggatcgg tcatccagtt gacccagtct    420
ccctcctcac tgtctgcatc tgtagggac agagtcacca tcacttgtcg ggcgagtcag     480
gacattggcg attatttagc ctggtttcag cagagaccag ggaaagcccc taagtccctg    540
atctatgttg cgtccacttt gcagagtggg gtcccatcaa ggttcagcgg cagtggatct    600
gggacacact tcactctcac catcaacagc ctgcagcctg aagattttgc aacttattac    660
tgccaacagt atcatagtca cccgtggacg ttcggcccag ggaccaaggt ggatatcaaa    720

<210> SEQ ID NO 337
<211> LENGTH: 738
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-8 scFv (nt)

<400> SEQUENCE: 337
caggtccagc tggtgcagtc tgggggaggc ttggtacagc cagggcggtc cctgagactc     60
tcctgtacag cttctggatt cacctttggt gattatgcta tgagctggtt ccgccaggct    120
ccagggaagg gctggagtg gtaggtttc attagaagca aagcttatgg tggacaaca      180 gaatacgccg cgtctgtgaa aggcagattc accatctcaa gagatgattc caaaagcatc   240
gcctatctgc aaatgaacag cctgaaaacc gaggacacag ccgtgtatta ctgtgcggcc   300
tggagtgccc cgactgacta ctggggccag ggaaccctgg tcaccgtctc ctcaggtgga   360
ggcggttcag gcggaggtgg ctctggcggt ggcggatcgg atattgtgat gacccagtct   420
ccagactccc tggctgtgtc tctgggcgag agggccacca tcaactgcaa gtccagccag   480
agtgttttat acagctccaa caataagaac tacttagctt ggtaccagca gaaaccagga   540
cagcctccta agctgctcat ttactgggca tctacccggg aatccggggt ccctgaccga   600
ttcagtggca gcgggtctgg gacagatttc actctcacca tcagcagcct gcaggctgaa   660
gatgtggcag tttattactg tcagcaatat tatagtactc cgtacacttt tggccagggg   720
accaagctgg aaatcaaa                                                 738

<210> SEQ ID NO 338
<211> LENGTH: 723
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-9 scFv (nt)
```

<400> SEQUENCE: 338

```
gaagtgcagc tggtgcagtc tggggaggc ttggtcaagc ctggagggtc cctgagactc      60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat     240
ctgcaaatga acagcctgag agccgaggac acggccgtgt attactgtgc gagagtggac    300
ggtgactacg tcgatgacta ctggggccag ggaaccctgg tcaccgtctc ctcaggtgga    360
ggcggttcag gcggaggtgg ctctggcggt ggcggatcgt cctatgagct gactcagccg    420
ccctcggtgt ctgtggcccc aggacagacg gccagggtta cctgtggggc aaataatatt    480
ggaagcaaaa gtgtccactg gtaccagcag aagccaggcc aggcccccat gctggtcgtc    540
tatgatgatg acgaccggcc ctccgggatc cctgagcgat tctctggctc caactctggg    600
aacacggcca ccctgaccat cagcggggtc gaggccgggg atgaggccga ctacttctgt    660
cacgtgtggg atagaagtcg tgatcattat gtcttcggaa ctgggaccaa gctgaccgtc    720
cta                                                                   723
```

<210> SEQ ID NO 339
<211> LENGTH: 723
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-10 scFv (nt)

<400> SEQUENCE: 339

```
gaagtgcagc tggtgcagtc tggggaggc ttggtcaagc ctggagggtc cctgagactc      60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat     240
ctgcaaatga acagcctgag agccgaggac acggccgtgt attactgtgc gagagtggac    300
ggtgactacg tcgatgacta ctggggccag ggaaccctgg tcaccgtctc ctcaggtgga    360
ggcggttcag gcggaggtgg ctctggcggt ggcggatcgt cctatgagct gactcagccg    420
ccctcggtgt ctgtggcccc aggacagacg gccagggtta cctgtggggc aaataatatt    480
ggaagcaaaa gtgtccactg gtaccagcag aagccaggcc aggcccccat gctggtcgtc    540
tatgatgatg acgaccggcc ctccgggatc cctgagcgat tctctggctc caactctggg    600
aacacggcca ccctgaccat cagcggggtc gaggccgggg atgaggccga ctacttctgt    660
cacgtgtggg atagaagtcg tgatcattat gtcttcggaa ctgggaccaa gctgaccgtc    720
cta                                                                   723
```

<210> SEQ ID NO 340
<211> LENGTH: 741
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-11 scFv (nt)

<400> SEQUENCE: 340

```
caggtgcagc tggtacagtc tgggggaggc ttggtacagc ctggcaggtc cctgagactc    60
tcctgtgcag cctctggatt cacctttgat gattatgcca tgcactgggt ccggcgagct   120
ccagggaagg gcctggagtg ggtctcaggt attagttgga atagtggtag cataggctat   180
gcggactctg tgaagggccg attcaccatc tccagagaca acgccaagaa ctccctgtat   240
ctgcaaatga acagtctgag agctgaggac acggccgtgt attactgtgc gagagatctg   300
gggcccgact acgatcccga tgcttttgat atctggggcc aagggacaat ggtcaccgtt   360
tcctcaggtg gaggcggttc aggcggaggt ggctctggcg gtggcggatc gcagcttgtg   420
ctgactcagc accctcagc gtctgggacc ccgggcaga gggtcaccat ctcttgttct   480
ggaagcagct ccaacatcgg aagtaatgct gtaaactggt accagcagct cccaggaacg   540
gccccccaag tcctcatcta taatagtcat cagcggccct caggggtccc tgaccgattc   600
tctggctcca agtctggcac ctcagcctcc ctggccatca tgggctcca gtctgaggac   660
gaggctgatt attactgtgc agcatgggat gacagcctga ggttacgt cttcggaact   720
gggaccaagc tcaccgtcct a                                              741
```

<210> SEQ ID NO 341
<211> LENGTH: 729
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-12 scFv (nt)

<400> SEQUENCE: 341

```
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggccgtgt attactgtgc gaaagtggat   300
ggccctcctt cttttgatat ctggggccaa gggacaatgg tcaccgtctc ctcaggtgga   360
ggcggttcag gcggaggtgg ctctggcggt ggcggatcgc agtctgccct gacgcagccg   420
ccctcagtgt ctgcggcccc aggacagaag gtcaccatct cctgctctgg aagccgctcc   480
aacattggga taattatgt atcctggtac aacagctcc aggaacagc ccccaaactc   540
ctcatttatg acaatgctaa gcgaccctca ggaattcctg accgattctc tggctccaag   600
tctggcacgt cagccaccct ggacatcgcc ggactccaga ctggggatga ggccgactat   660
tactgtcagg tgtgggatag tagtagtgat cattgggtat tcggcggagg gaccaagctc   720
accgtcctaa                                                          729
```

<210> SEQ ID NO 342
<211> LENGTH: 744
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-13 scFv (nt)

<400> SEQUENCE: 342

```
cagatgcagc tggtgcagta tgggggaggc gtggtccagc ctggagggtc cctgagactc    60
tcctgtgcag cctctggatt caccttcagt agctatgcta tgcactgggt ccgccaggct   120
ccaggcaagg ggctggagtg ggtggcagtt atatcatatg atggaagtaa taaatactac   180
gcagactccg tgaagggccg attcaccatc tccagagaca attccaagaa cacgctgtat   240
ctgcaaatga acagcctgaa agctgaggac acggctgtgt attactgtgc tacccctaccc   300
ggtagagatg ctaccccgg agcctttgac tacaggggcc agggaaccct ggtcaccgtc   360
tcctcaggtg gaggcggttc aggcggaggt ggctctggcg gtggcggatc gcaggctgtg   420
ctgactcagc caccctcagc gtctgggacc cccgggcaga gggtcaccat ctcttgttct   480
ggaagcggct ccaacatcgg aagtaatgat gtctcctggt atcagcagat cccaggaacg   540
gccccccaaac tcctcatcta ctggaatgat cagcggccct caggggtccc tgaccgattc   600
tctgcctcca gtctggcac tcagcctcc ctggccatca gtgggctccg gtccgaggat   660
gaggctgatt attactgtgc agcatgggat gacagcctgg tggttcttg ggtgttcggc   720
ggagggacca aggtcaccgt ccta                                          744
```

<210> SEQ ID NO 343
<211> LENGTH: 744
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-14 scFv (nt)

<400> SEQUENCE: 343

```
gaggtgcagc tgttggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatcatatg atggaagtaa taaatactac   180
gcagactccg tgaagggccg attcaccatc tccagagaca attccaagaa cacgctgtat   240
ctgcaaatga acagcctgag agctgaggac acggctgtgt attactgtgc tacccctaccc   300
ggtagagatg ctaccccgg agcctttgac tacaggggcc cgggaaccct ggtcaccgtc   360
tcctcaggtg gaggcggttc aggcggaggt ggctctggcg gtggcggatc gcaggctgtg   420
ctgactcagc caccctcagc gtctgggacc cccgggcaga gggtcaccat ctcttgttct   480
ggaagcggct ccaacatcgg aagtaatgat gtctcctggt atcagcagat cccaggaacg   540
gccccccaaac tcctcatcta ctggaatgat cagcggccct caggggtccc tgaccgattc   600
tctggctcca gtctggcgc tcagcctct ctggccatca gtgggctcca gtctgaggat   660
gaggctgatt attattgtgc agcatgggat gacaggttga acggttttg ggtgttcggc   720
ggagggacca agctcaccgt ccta                                          744
```

<210> SEQ ID NO 344
<211> LENGTH: 744
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-15 scFv (nt)

<400> SEQUENCE: 344

```
caggtgcagc tgttggagtc tgggggaggc ctggtcaagc ctggggggtc cctgagactc      60
tcctgtgcag cctctggatt caccttcagt agctatggca tgcactgggt ccgccaggct     120
ccaggcaagg gctggagtg gtggcagtt atatcatatg atggaagtaa taaatactat      180
gcagactccg tgaagggccg attcaccatc tccagagaca attccaagaa cacgctgtat    240
ctgcaaatga acagcctgag agctgaggac acggctgtgt attactgtgc gaaagatcag    300
tatagcagta gcgcacaaag gccgactttt gactactggg gccagggaac cctggtcacc    360
gtctcctcag gtgaggcgg ttcaggcgga gtggttctg gcgtggcgg atcgcagtct       420
gtgctgacgc agccaccctc agcgtctggg accccgggc agagggtcac catctcttgt     480
tctggaagcg gctccaacat cggaagtaat gatgtctcct ggtatcagca gatcccagga    540
acggccccca aactcctcat ctactggaat gatcagcggc cctcagggt ccctgaccgg     600
ttctcaggct ccaagtctgg cacctcagcc tccctggtca tcagtgggct ccggtccgag    660
gatgaggctg attattactg tgcagcatgg gatgacagcc tgagtggttg ggtgttcggc    720
ggagggacca agctgaccgt ccta                                           744
```

<210> SEQ ID NO 345
<211> LENGTH: 738
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-16 scFv (nt)

<400> SEQUENCE: 345

```
gaggtccagc tggtacagtc tgggcctgag gtgaagaagc ctgggacctc agtgaaggtc      60
tcctgcaagg cttctggatt caccttact agctctgcta tgcagtgggt gcgacaggct     120
cgtggacaac gccttgagtg gataggatgg atcgtcgttg cagtggtaa cacaaactac     180
gcacagaagt tccaggaaag agtcaccatt accaggaca tgtccacaag cacagcctac     240
atggagctga gcagcctgag atccgaggac acggccgtgt attactgtgc ggcagctccg    300
tattacgata tttttgactgg ttattatttta tggggccagg gaacgctggt caccgtctcc   360
tcaggtggag gcggttctgg cggaggtggc tctggcggtg gcggatcgca gtctgccctg    420
actcagccac cctcagcgtc tgggaccccc gggcagaggg tcaccatctc ttgttctgga    480
agcggctcca acatcggaag taatgatgtc tcctggtatc agcagatccc aggaacggcc    540
cccaaactcc tcatctactg gaatgatcag cggccctcag gggtccctga ccgattctct    600
ggctccaagt ctggcacctc agcctccctg gccatcagtg gctccagtc tgaggatgag    660
gctgattatt actgtgcatc atgggatgac agcctgagtg gttgggtgtt cggcggaggg    720
accaagctga ccgtccta                                                  738
```

<210> SEQ ID NO 346
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-17 scFv (nt)

<400> SEQUENCE: 346

```
caggttcagc tggtgcagtc tgggggaggc ttggtcaagc ctggagggtc cctgagactc    60
tcctgtgcag cctctggatt caccttcagt gactactaca tgagctggat ccgcctggct   120
ccagggaagg gctggagtg gtttcatac attagtagta gtggtagtac catatactac   180
gcagactctg tgaagggccg attcaccatc tccaggaca acgccaagaa ctcactgtat   240
ctgcaaatga acagcctgag agccgaggac acggccgtgt attactgtgc gagagaggcc   300
gatagtagcg ctgactactg gggccaggga accctggtca acgtctcctc aggtggaggc   360
ggttcaggcg gaggtggctc tggcggtggc ggatcgcagc tgtgctgac tcagccaccc   420
tcggtgtcag tggccccagg aaagacggcc atgattacct gtgggggaaa caacattgga   480
tttaaaggtg tgcagtggta ccagcagaag acaggccagg ccctgtgct ggtcgtctat   540
gatgatagcg accggccctc agggatccct gagcgattct ctggctccaa ctctgggaac   600
acggccaccc tgaccatcag cagggtcgaa gccggggatg aggccgatta ttactgtcag   660
gtgtgggata tgctagtga tcattgggtg ttcggcggag ggaccaagct gaccgtccta   720
```

<210> SEQ ID NO 347
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-18 scFv (nt)

<400> SEQUENCE: 347

```
gaggtgcagc tgttggagtc tgggggaggc ttggtccagc ctggggggtc cctgagactc    60
tcctgtgcag cctctggatt cacgtttagt agctattgga tgagctggca ccgccaggct   120
ccagggaagg ggccggagtg ggtggcccac ataaaccaag acggaagtga aagtactat   180
gtggactctg tgaagggccg attcaccatc tccagagaca acgccgagag ttcactgtat   240
ctgcaaatga acagcctgag agccgaggac acggctgtgt attactgtgc gaggtggctg   300
gcggttacta actggggcca gggaaccctg gtcaccgtct cctcaggtgg aggcggttca   360
ggcggaggtg gctctggcgg tggcggatcg cagtctgtgt tgactcagcc accctcagcg   420
tctgggaccc ccgggcagag ggtcaccatc tcttgttctg gaagcggctc caacatcgga   480
agtaatgatg tctcctggta tcagcagatc cagggacgg cccccaaact cctcatctac   540
tggaatgatc agcggccctc agggggtccct gaccgattct ctggctccaa gtctggcacc   600
tcagcctccc tggccatcag tgggctccgg tccgaggatg aggctgatta ttactgtgca   660
gcatgggatg acagcctgaa tggttgggtg ttcggcggag ggaccaagct gaccgtccta   720
```

<210> SEQ ID NO 348
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-19 scFv (nt)

<400> SEQUENCE: 348

| | | | | |
|---|---|---|---|---|
| caggtccagc tggtacagtc tgggctgag gtgaagaagc tggggcctc agtgaaggtc | | | | 60 |
| tcctgcaagg cttctggata caccttcacc agctactata tgcactgggt gcgacaggcc | | | | 120 |
| cctggacaag gcttgagtg gatgggatgg atcaaccct a cagtggtgg cacaaactat | | | | 180 |
| gcacagaagt tcagggcag gtcaccatg accaggaca cgtccatcag cacagcctac | | | | 240 |
| atggagctga gcaggctgag atctgacgac acggccgtgt attactgtgc gagagatggt | | | | 300 |
| ggggacgtct ggggccaagg gaccacggtc accgtctcct caggtggagg cggttcaggc | | | | 360 |
| ggaggtggct ctggcggtgg cggatcgcag gctgtgctga ctcagcctgc tccgtgtct | | | | 420 |
| gggtctcctg gacagtcgat caccatctcc tgcactggaa ccagcagtga cgttggtgat | | | | 480 |
| tataactatg tcgcctggta tcaacaacac ccaggcaaag cccccaaact catgattttt | | | | 540 |
| gaggtcatta atcggccctc aggggtttct gatcgcttct ctggctccaa gtctggcaac | | | | 600 |
| acggcctccc tgacatctc tgggctccag cctgaggacg aggctgatta ttactgcatc | | | | 660 |
| tcatattcac gaggcagcac tccttatgtc atcggaactg ggaccaaggt gaccgtccta | | | | 720 |

<210> SEQ ID NO 349
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-20 scFv (nt)

<400> SEQUENCE: 349

| | | | | |
|---|---|---|---|---|
| gaggtgcagc tgttggagtc tgggggaggc ttggtacagc ctggcaggtc cctgagactc | | | | 60 |
| tcctgtgcag cctctggatt caccttgat gattatgcca tgcactgggt ccggcaagct | | | | 120 |
| ccagggaagg gcctggagtg gtctcaggt attagttgga atagtggtag cataggctat | | | | 180 |
| gcggactctg tgaagggccg attcaccatc tccagagaca acgccaagaa ctccctgtat | | | | 240 |
| ctgcaaatga acagtctgag agctgaggac acggccttgt attactgtgc aaaggggggc | | | | 300 |
| ctaggaataa ccccatacta ctttgactac tggggccagg gaaccctggt caccgtctcc | | | | 360 |
| tcaggtggag gcggttcagg cggaggtggc tctggcggtg gcggatcgca gcctgtgctg | | | | 420 |
| actcagccac cctcagcgtc tgggaccccc gggcagaggg tcaccatctc ttgttcggga | | | | 480 |
| ggcaagactg taaactggtt ccggcaggtc ccaggaacgg cccccaact cctcatctat | | | | 540 |
| agtaatgatc agcggccctc aggggtccct gaccgattct ctggctccaa gtctggctcc | | | | 600 |
| tcagcctccc tggacatcag tgggctccag tctgaggatg aggcttatta ttactgtgga | | | | 660 |
| tcatgggatg acagcctcaa tgcttgggtg ttcggcggag agaccaagct gaccgtccta | | | | 720 |

<210> SEQ ID NO 350
<211> LENGTH: 729
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-21 scFv (nt)

<400> SEQUENCE: 350

```
gaagtgcagc tggtggagtc tgggggaggc ttggtcaagc ctggagggtc cctgaaactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca cgccaagaa ctcactgtat    240
ctgcaaatga acagcctgag agccgaggac acggccgtgt attactgtgc gaaagtagac   300
ggaggctaca cagaggacta ctggggccag ggaaccctgg tcaccgtctc ctcaggtgga   360
ggcggttcag gcggaggtgg ctctggcggt ggcggatcgc agtctgtgct gactcagcca   420
ccctcagcgt ctgggacccc cgggcagagg gtcaccatct cttgttctgg aagcggctcc   480
aacatcggaa gtaatgatgt ctcctggtat cagcagatcc caggaacggc ccccaaactc   540
ctcatctact ggaatgatca gcggccctca ggggtccctg accggttctc aggctccaag   600
tctggcatct cagcctccct ggccatcagc gggctccggt ccgaggatga ggctgattat   660
tactgtgcag catgggatga cagcctgaat ggttatgtct tcggaactgg gaccaaggtc   720
accgtccta                                                            729
```

<210> SEQ ID NO 351
<211> LENGTH: 729
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-22 scFv (nt)

<400> SEQUENCE: 351

```
gaagtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca cgccaagaa ctcactgtat    240
ctgcaaatga acagcctgag agccgaggac acggccgtgt attactgtgc gaaagtagac   300
ggagactaca cagaggacta ctggggccag ggaaccctgg tcaccgtctc ctcaggtgga   360
ggcggttcag gcggaggtgg ctctggcggt ggcggatcgc agtctgccct gactcagcct   420
gcctccgtgt ctgggtctcc tggacagtcg atcactatct cctgcactgg aagcagcagt   480
gatgttggca aatataatct tgtctcctgg taccaacagc cccaggcaa agccccccaag   540
ctcataattt atgacgtcaa taagcggccc tcagggtttt ctaatcgctt ctctggctcc   600
aagtctggca acacggccac cctgacaatc tctgggctcc agggtgacga cgaggctgat   660
tattattgtt gctcatatgg aagtagtagg tcttatgtct tcggaactgg gaccaaggtg   720
accgtccta                                                            729
```

<210> SEQ ID NO 352
<211> LENGTH: 729
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-23 scFv (nt)

<400> SEQUENCE: 352

```
gaagtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gaaagtagac     300
ggagactaca cagaggacta ctggggccag ggaaccctgg tcaccgtctc ctcaggtgga     360
ggcggttcag gcgaggtgg ctctggcggt ggcggatcgc agtctgccct gactcagcct     420
gcctccgtgt ctgggtctcc tggacagtcg atcactatct cctgcactgg aagcagcagt     480
gatgttggca aatataatct tgtctcctgg taccaacagc ccccaggcaa agcccccaag     540
ctcataattt atgacgtcaa taagcggccc tcaggggttt ctaatcgctt ctctggctcc     600
aagtctggca acacggccac cctgacaatc tctgggctcc aggtgacga cgaggctgat     660
tattattgta gctcatatgg aagtagtagg tcttatgtct tcggaactgg gaccaaggtg     720
accgtccta                                                             729
```

```
<210> SEQ ID NO 353
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-H1
<220> FEATURE:
<221> NAME/KEY: VARIANT
<222> LOCATION: 1
<223> OTHER INFORMATION: Xaa = D or S
<220> FEATURE:
<221> NAME/KEY: VARIANT
<222> LOCATION: 2
<223> OTHER INFORMATION: Xaa = Y or S
<220> FEATURE:
<221> NAME/KEY: VARIANT
<222> LOCATION: 3
<223> OTHER INFORMATION: Xaa = A, G, W or Y
<220> FEATURE:
<221> NAME/KEY: VARIANT
<222> LOCATION: 5
<223> OTHER INFORMATION: Xaa = H, Q or S

<400> SEQUENCE: 353

Xaa Xaa Xaa Met Xaa
1               5

<210> SEQ ID NO 354
<211> LENGTH: 19
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-H2
<220> FEATURE:
<221> NAME/KEY: VARIANT
<222> LOCATION: 1
<223> OTHER INFORMATION: Xaa = F, G, H, V, W or Y
<220> FEATURE:
<221> NAME/KEY: VARIANT
<222> LOCATION: 3
<223> OTHER INFORMATION: Xaa = N, R, S or V
<220> FEATURE:
<221> NAME/KEY: VARIANT
```

```
<222> LOCATION: 4
<223> OTHER INFORMATION: Xaa = P, Q, S, V, W or Y
<220> FEATURE:
<221> NAME/KEY: VARIANT
<222> LOCATION: 5
<223> OTHER INFORMATION: Xaa = K or null
<220> FEATURE:
<221> NAME/KEY: VARIANT
<222> LOCATION: 6
<223> OTHER INFORMATION: Xaa = A or null
<220> FEATURE:
<221> NAME/KEY: VARIANT
<222> LOCATION: 7
<223> OTHER INFORMATION: Xaa = D, G, N, S, or Y
<220> FEATURE:
<221> NAME/KEY: VARIANT
<222> LOCATION: 8
<223> OTHER INFORMATION: Xaa = G or S
<220> FEATURE:
<221> NAME/KEY: VARIANT
<222> LOCATION: 9
<223> OTHER INFORMATION: Xaa = G or S
<220> FEATURE:
<221> NAME/KEY: VARIANT
<222> LOCATION: 10
<223> OTHER INFORMATION: Xaa = E, G, N, T or S
<220> FEATURE:
<221> NAME/KEY: VARIANT
<222> LOCATION: 11
<223> OTHER INFORMATION: Xaa = I, K, or T
<220> FEATURE:
<221> NAME/KEY: VARIANT
<222> LOCATION: 12
<223> OTHER INFORMATION: Xaa = E, G, N or Y
<220> FEATURE:
<221> NAME/KEY: VARIANT
<222> LOCATION: 14
<223> OTHER INFORMATION: Xaa = A or V
<220> FEATURE:
<221> NAME/KEY: VARIANT
<222> LOCATION: 15
<223> OTHER INFORMATION: Xaa = A, D or Q
<220> FEATURE:
<221> NAME/KEY: VARIANT
<222> LOCATION: 16
<223> OTHER INFORMATION: Xaa = K or S
<220> FEATURE:
<221> NAME/KEY: VARIANT
<222> LOCATION: 17
<223> OTHER INFORMATION: Xaa = F or V
<220> FEATURE:
<221> NAME/KEY: VARIANT
<222> LOCATION: 18
<223> OTHER INFORMATION: Xaa = K or Q
<220> FEATURE:
<221> NAME/KEY: VARIANT
<222> LOCATION: 19
<223> OTHER INFORMATION: Xaa = E or G

<400> SEQUENCE: 354

Xaa Ile Xaa Xaa Xaa Xaa Xaa Xaa Xaa Xaa Xaa Xaa Tyr Xaa Xaa Xaa
1               5                   10                  15

Xaa Xaa Xaa

<210> SEQ ID NO 355
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-H3
<220> FEATURE:
<221> NAME/KEY: VARIANT
<222> LOCATION: 1
<223> OTHER INFORMATION: Xaa = A, D, E, G, L, V or W
```

```
<220> FEATURE:
<221> NAME/KEY: VARIANT
<222> LOCATION: 2
<223> OTHER INFORMATION: Xaa = A, D, G, L, P, Q or S
<220> FEATURE:
<221> NAME/KEY: VARIANT
<222> LOCATION: 3
<223> OTHER INFORMATION: Xaa = A, D, G, L or Y
<220> FEATURE:
<221> NAME/KEY: VARIANT
<222> LOCATION: 4
<223> OTHER INFORMATION: Xaa = D, G, P, R, S, V, Y or null
<220> FEATURE:
<221> NAME/KEY: VARIANT
<222> LOCATION: 5
<223> OTHER INFORMATION: Xaa = D, I, P, S, T, Y or null
<220> FEATURE:
<221> NAME/KEY: VARIANT
<222> LOCATION: 6
<223> OTHER INFORMATION: Xaa = A, G, I, S, T, V, Y or null
<220> FEATURE:
<221> NAME/KEY: VARIANT
<222> LOCATION: 7
<223> OTHER INFORMATION: Xaa = A, D, E, F, L, P, S, Y or null
<220> FEATURE:
<221> NAME/KEY: VARIANT
<222> LOCATION: 8
<223> OTHER INFORMATION: Xaa = P, Q, T, Y or null
<220> FEATURE:
<221> NAME/KEY: VARIANT
<222> LOCATION: 9
<223> OTHER INFORMATION: Xaa = D, G, R, Y or null
<220> FEATURE:
<221> NAME/KEY: VARIANT
<222> LOCATION: 10
<223> OTHER INFORMATION: Xaa = A, F, Y or null
<220> FEATURE:
<221> NAME/KEY: VARIANT
<222> LOCATION: 11
<223> OTHER INFORMATION: Xaa = D, F or null
<220> FEATURE:
<221> NAME/KEY: VARIANT
<222> LOCATION: 12
<223> OTHER INFORMATION: Xaa = F or null
<220> FEATURE:
<221> NAME/KEY: VARIANT
<222> LOCATION: 13
<223> OTHER INFORMATION: Xaa = D, T or Y
<220> FEATURE:
<221> NAME/KEY: VARIANT
<222> LOCATION: 14
<223> OTHER INFORMATION: Xaa = I, L, N, V or Y

<400> SEQUENCE: 355

Xaa Xaa Xaa Xaa Xaa Xaa Xaa Xaa Xaa Xaa Xaa Xaa Xaa Xaa
 1               5                   10

<210> SEQ ID NO 356
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-L1
<220> FEATURE:
<221> NAME/KEY: VARIANT
<222> LOCATION: 1
<223> OTHER INFORMATION: Xaa = G, K, R, S or T
<220> FEATURE:
<221> NAME/KEY: VARIANT
<222> LOCATION: 2
<223> OTHER INFORMATION: Xaa = A, G or S
<220> FEATURE:
<221> NAME/KEY: VARIANT
<222> LOCATION: 3
<223> OTHER INFORMATION: Xaa = G, N, S or T
```

```
<220> FEATURE:
<221> NAME/KEY: VARIANT
<222> LOCATION: 4
<223> OTHER INFORMATION: Xaa = G, K, N, Q, R or S
<220> FEATURE:
<221> NAME/KEY: VARIANT
<222> LOCATION: 5
<223> OTHER INFORMATION: Xaa = S or null
<220> FEATURE:
<221> NAME/KEY: VARIANT
<222> LOCATION: 6
<223> OTHER INFORMATION: Xaa = D, N, V or null
<220> FEATURE:
<221> NAME/KEY: VARIANT
<222> LOCATION: 7
<223> OTHER INFORMATION: Xaa = L, V or null
<220> FEATURE:
<221> NAME/KEY: VARIANT
<222> LOCATION: 8
<223> OTHER INFORMATION: Xaa = H, S, Y or null
<220> FEATURE:
<221> NAME/KEY: VARIANT
<222> LOCATION: 9
<223> OTHER INFORMATION: Xaa = S, T or null
<220> FEATURE:
<221> NAME/KEY: VARIANT
<222> LOCATION: 10
<223> OTHER INFORMATION: Xaa = S or null
<220> FEATURE:
<221> NAME/KEY: VARIANT
<222> LOCATION: 11
<223> OTHER INFORMATION: Xaa = D, G, I, N, S or null
<220> FEATURE:
<221> NAME/KEY: VARIANT
<222> LOCATION: 12
<223> OTHER INFORMATION: Xaa = D, E, G, K, I, N or null
<220> FEATURE:
<221> NAME/KEY: VARIANT
<222> LOCATION: 13
<223> OTHER INFORMATION: Xaa = F, G, K, N, R, S, Y or null
<220> FEATURE:
<221> NAME/KEY: VARIANT
<222> LOCATION: 14
<223> OTHER INFORMATION: Xaa = D, K, N, T or null
<220> FEATURE:
<221> NAME/KEY: VARIANT
<222> LOCATION: 15
<223> OTHER INFORMATION: Xaa = A, D, G, L, N, S, T or Y
<220> FEATURE:
<221> NAME/KEY: VARIANT
<222> LOCATION: 16
<223> OTHER INFORMATION: Xaa = L or V
<220> FEATURE:
<221> NAME/KEY: VARIANT
<222> LOCATION: 17
<223> OTHER INFORMATION: Xaa = A, H, N, Q or S

<400> SEQUENCE: 356

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 357
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-L2
<220> FEATURE:
<221> NAME/KEY: VARIANT
<222> LOCATION: 1
<223> OTHER INFORMATION: Xaa = A, D, E, N, S, V or W
<220> FEATURE:
<221> NAME/KEY: VARIANT
```

```
<222> LOCATION: 2
<223> OTHER INFORMATION: Xaa = A, D, N, S or V
<220> FEATURE:
<221> NAME/KEY: VARIANT
<222> LOCATION: 3
<223> OTHER INFORMATION: Xaa = A, D, H, I, N or S
<220> FEATURE:
<221> NAME/KEY: VARIANT
<222> LOCATION: 4
<223> OTHER INFORMATION: Xaa = D, K, N, Q, R or T
<220> FEATURE:
<221> NAME/KEY: VARIANT
<222> LOCATION: 5
<223> OTHER INFORMATION: Xaa = L, R or V
<220> FEATURE:
<221> NAME/KEY: VARIANT
<222> LOCATION: 6
<223> OTHER INFORMATION: Xaa = A, E, P or Q
<220> FEATURE:
<221> NAME/KEY: VARIANT
<222> LOCATION: 7
<223> OTHER INFORMATION: Xaa = A, D, S or T

<400> SEQUENCE: 357

Xaa Xaa Xaa Xaa Xaa Xaa Xaa
1               5

<210> SEQ ID NO 358
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: Consensus CDR-L3
<220> FEATURE:
<221> NAME/KEY: VARIANT
<222> LOCATION: 1
<223> OTHER INFORMATION: Xaa = A, C, G, H, I, Q or S
<220> FEATURE:
<221> NAME/KEY: VARIANT
<222> LOCATION: 2
<223> OTHER INFORMATION: Xaa = A, Q, S or V
<220> FEATURE:
<221> NAME/KEY: VARIANT
<222> LOCATION: 3
<223> OTHER INFORMATION: Xaa = S, W or Y
<220> FEATURE:
<221> NAME/KEY: VARIANT
<222> LOCATION: 4
<223> OTHER INFORMATION: Xaa = D, F, G, H or Y
<220> FEATURE:
<221> NAME/KEY: VARIANT
<222> LOCATION: 5
<223> OTHER INFORMATION: Xaa = D, G, M, R, S or T
<220> FEATURE:
<221> NAME/KEY: VARIANT
<222> LOCATION: 6
<223> OTHER INFORMATION: Xaa = A, G, H, L, R, S, T or Y
<220> FEATURE:
<221> NAME/KEY: VARIANT
<222> LOCATION: 7
<223> OTHER INFORMATION: Xaa = L, P, R, S or null
<220> FEATURE:
<221> NAME/KEY: VARIANT
<222> LOCATION: 8
<223> OTHER INFORMATION: Xaa = D, G, N, R, S, T or null
<220> FEATURE:
<221> NAME/KEY: VARIANT
<222> LOCATION: 9
<223> OTHER INFORMATION: Xaa = A, G, H, L, P or null
<220> FEATURE:
<221> NAME/KEY: VARIANT
<222> LOCATION: 10
<223> OTHER INFORMATION: Xaa = F, S or null
<220> FEATURE:
<221> NAME/KEY: VARIANT
```

```
<222> LOCATION: 11
<223> OTHER INFORMATION: Xaa = L, P, W or Y
<220> FEATURE:
<221> NAME/KEY: VARIANT
<222> LOCATION: 12
<223> OTHER INFORMATION: Xaa = S, T or V

<400> SEQUENCE: 358

Xaa Xaa Xaa Xaa Xaa Xaa Xaa Xaa Xaa Xaa Xaa Xaa
1               5                   10

<210> SEQ ID NO 359
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: 4GS linker (aa)

<400> SEQUENCE: 359

Gly Gly Gly Gly Ser
1               5

<210> SEQ ID NO 360
<211> LENGTH: 4
<212> TYPE: PRT
<213> ORGANISM: Artificial Sequence
<220> FEATURE:
<223> OTHER INFORMATION: Synthetic
<220> FEATURE:
<223> OTHER INFORMATION: 3GS linker (aa)

<400> SEQUENCE: 360

Gly Gly Gly Ser
1

<210> SEQ ID NO 361
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: (4GS)3 linker (aa)

<400> SEQUENCE: 361

Gly Gly Gly Gly Ser Gly Gly Gly Gly Ser Gly Gly Gly Gly Ser
1               5                   10                  15

<210> SEQ ID NO 362
<211> LENGTH: 18
<212> TYPE: PRT
<213> ORGANISM: Artificial Sequence
<220> FEATURE:
<223> OTHER INFORMATION: Synthetic
<220> FEATURE:
<223> OTHER INFORMATION: Linker (aa)

<400> SEQUENCE: 362

Gly Ser Thr Ser Gly Ser Gly Lys Pro Gly Ser Gly Glu Gly Ser Thr
1               5                   10                  15

Lys Gly

<210> SEQ ID NO 363
<211> LENGTH: 12
<212> TYPE: PRT
<213> ORGANISM: Artificial Sequence
```

```
<220> FEATURE:
<223> OTHER INFORMATION: Synthetic
<220> FEATURE:
<223> OTHER INFORMATION: Spacer (IgG4hinge) (aa)

<400> SEQUENCE: 363

Glu Ser Lys Tyr Gly Pro Pro Cys Pro Pro Cys Pro
1               5                   10

<210> SEQ ID NO 364
<211> LENGTH: 36
<212> TYPE: DNA
<213> ORGANISM: Artificial Sequence
<220> FEATURE:
<223> OTHER INFORMATION: Synthetic
<220> FEATURE:
<223> OTHER INFORMATION: Spacer (IgG4hinge) (nt)

<400> SEQUENCE: 364
gaatctaagt acggaccgcc ctgcccccct tgccct                            36

<210> SEQ ID NO 365
<211> LENGTH: 119
<212> TYPE: PRT
<213> ORGANISM: Artificial Sequence
<220> FEATURE:
<223> OTHER INFORMATION: Synthetic
<220> FEATURE:
<223> OTHER INFORMATION: Hinge-CH3 spacer (aa)

<400> SEQUENCE: 365

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 366
<211> LENGTH: 229
<212> TYPE: PRT
<213> ORGANISM: Artificial Sequence
<220> FEATURE:
<223> OTHER INFORMATION: Synthetic
<220> FEATURE:
<223> OTHER INFORMATION: Hinge-CH2-CH3 spacer (aa)

<400> SEQUENCE: 366

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30
```

-continued

Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 367
<211> LENGTH: 184
<212> TYPE: PRT
<213> ORGANISM: Homo sapiens
<220> FEATURE:
<223> OTHER INFORMATION: Synthetic
<220> FEATURE:
<223> OTHER INFORMATION: Human BCMA; GenBank No. BAB60895.1

<400> SEQUENCE: 367

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 368
<211> LENGTH: 184
<212> TYPE: PRT
<213> ORGANISM: Homo sapiens
<220> FEATURE:
<223> OTHER INFORMATION: Human BCMA; NCBI No. NP_001183.2

<400> SEQUENCE: 368

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 369
<211> LENGTH: 135
<212> TYPE: PRT
<213> ORGANISM: Homo sapiens
<220> FEATURE:
<223> OTHER INFORMATION: Human BCMA Variant; GenBank No. ABN42510.1

<400> SEQUENCE: 369

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Arg Ser Gly Leu Leu
            35                  40                  45

Gly Met Ala Asn Ile Asp Leu Glu Lys Ser Arg Thr Gly Asp Glu Ile
50                  55                  60

Ile Leu Pro Arg Gly Leu Glu Tyr Thr Val Glu Cys Thr Cys Glu
65                  70                  75                  80
```

```
Asp Cys Ile Lys Ser Lys Pro Lys Val Asp Ser Asp His Cys Phe Pro
                85                  90                  95

Leu Pro Ala Met Glu Glu Gly Ala Thr Ile Leu Val Thr Thr Lys Thr
            100                 105                 110

Asn Asp Tyr Cys Lys Ser Leu Pro Ala Ala Leu Ser Ala Thr Glu Ile
        115                 120                 125

Glu Lys Ser Ile Ser Ala Arg
    130             135

<210> SEQ ID NO 370
<211> LENGTH: 185
<212> TYPE: PRT
<213> ORGANISM: Mus musculus
<220> FEATURE:
<223> OTHER INFORMATION: Mouse BCMA; NCBI No. NP_035738.1

<400> SEQUENCE: 370

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185

<210> SEQ ID NO 371
<211> LENGTH: 183
<212> TYPE: PRT
<213> ORGANISM: Macaca fascicular
<220> FEATURE:
<223> OTHER INFORMATION: Cynomolgus BCMA; GenBank No. EHH60172.1

<400> SEQUENCE: 371

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45
```

Lys Gly Met Asn Ala Ile Leu Trp Thr Cys Leu Gly Leu Ser Leu Ile
            50                  55                  60

Ile Ser Leu Ala Val Phe Val Leu Thr Phe Leu Leu Arg Lys Met Ser
 65                  70                  75                  80

Ser Glu Pro Leu Lys Asp Glu Phe Lys Asn Thr Gly Ser Gly Leu Leu
                    85                  90                  95

Gly Met Ala Asn Ile Asp Leu Glu Lys Gly Arg Thr Gly Asp Glu Ile
                100                 105                 110

Val Leu Pro Arg Gly Leu Glu Tyr Thr Val Glu Glu Cys Thr Cys Glu
            115                 120                 125

Asp Cys Ile Lys Asn Lys Pro Lys Val Asp Ser Asp His Cys Phe Pro
    130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
            180

<210> SEQ ID NO 372
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-H2 (aa) Kabat numbering
<220> FEATURE:
<221> NAME/KEY: VARIANT
<222> LOCATION: 10
<223> OTHER INFORMATION: Xaa = any amino acid

<400> SEQUENCE: 372

Gly Ile Ser Trp Asn Ser Gly Ser Ile Xaa Tyr Ala Asp Ser Val Lys
 1               5                  10                  15

Gly

<210> SEQ ID NO 373
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-33 CDR-H2 (aa) Kabat numbering

<400> SEQUENCE: 373

Tyr Ile Ser Gly Ser Gly Ser Thr Ile Tyr Tyr Ala Asp Ser Val Lys
 1               5                  10                  15

Gly

<210> SEQ ID NO 374
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-H2 Kabat numbering

<400> SEQUENCE: 374

Tyr Ile Ser Ser Ser Gly Asn Thr Ile Tyr Tyr Ala Asp Ser Val Lys
1               5                   10                  15
Gly

<210> SEQ ID NO 375
<211> LENGTH: 7
<212> TYPE: PRT
<213> ORGANISM: Homo sapiens
<220> FEATURE:
<223> OTHER INFORMATION: human BCMA epitope (residues 21-27)

<400> SEQUENCE: 375

Cys Ile Pro Cys Gln Leu Arg
1               5

<210> SEQ ID NO 376
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24, -28, -29, -39 CDR-H3 (aa)

<400> SEQUENCE: 376

Asp Leu Gly Pro Pro Tyr Gly Asp Asp Ala Phe Asp Ile
1               5                   10

<210> SEQ ID NO 377
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 CDR-H3 (aa)

<400> SEQUENCE: 377

Asp Leu Asp Pro Asp Asp Ala Phe Asp Ile
1               5                   10

<210> SEQ ID NO 378
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 CDR-H3 (aa)

<400> SEQUENCE: 378

Val Asp Gly Asp Tyr Asp Asp Tyr
1               5

<210> SEQ ID NO 379
<211> LENGTH: 10
<212> TYPE: PRT
<213> ORGANISM: Homo sapiens
<220> FEATURE:
<223> OTHER INFORMATION: human BCMA epitope (residues 30-39)

<400> SEQUENCE: 379

Ser Asn Thr Pro Pro Leu Thr Cys Gln Arg
1               5                   10

```
<210> SEQ ID NO 380
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 CDR-L1 (aa)

<400> SEQUENCE: 380

Arg Ala Ser Gln Gly Ile Ser Asn Tyr Leu Ala
1               5                   10

<210> SEQ ID NO 381
<211> LENGTH: 16
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-L1 (aa)

<400> SEQUENCE: 381

Arg Ser Ser Gln Ser Leu Leu His Ser Asn Gly Tyr Asn Tyr Leu Asp
1               5                   10                  15

<210> SEQ ID NO 382
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 CDR-L1 (aa)

<400> SEQUENCE: 382

Thr Gly Thr Ser Ser Asp Val Gly Ser Tyr Asn Leu Val Ser
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 CDR-L1 (aa)

<400> SEQUENCE: 383

Arg Ala Ser Gln Pro Ile Arg Ser Asn Leu Ala
1               5                   10

<210> SEQ ID NO 384
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-31 CDR-L1 (aa)

<400> SEQUENCE: 384

Lys Ser Ser Gln Ser Val Leu Asn Ser Ser Asn Asn Lys Asn Tyr Val
1               5                   10                  15
Ala

<210> SEQ ID NO 385
```

```
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 CDR-L1 (aa)

<400> SEQUENCE: 385

Gly Gly Asn Asn Ile Gly Ser Lys Gly Val His
1               5                   10

<210> SEQ ID NO 386
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 CDR-L1 (aa)

<400> SEQUENCE: 386

Arg Ala Ser Gln Ser Ile Ser Asn Tyr Leu Ala
1               5                   10

<210> SEQ ID NO 387
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 CDR-L1 (aa)

<400> SEQUENCE: 387

Gly Ser Ser Thr Gly Pro Val Thr Ser Ala His Ser Pro Ser
1               5                   10

<210> SEQ ID NO 388
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37, -38 CDR-L1 (aa)

<400> SEQUENCE: 388

Gly Ser Ser Thr Gly Ala Val Thr Asn Gly His Ser Pro Tyr
1               5                   10

<210> SEQ ID NO 389
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 CDR-L1 (aa)
<220> FEATURE:
<221> NAME/KEY: VARIANT
<222> LOCATION: 11
<223> OTHER INFORMATION: Xaa = any amino acid

<400> SEQUENCE: 389

Arg Ala Ser Gln Gly Ile Arg Tyr Glu Leu Xaa
1               5                   10

<210> SEQ ID NO 390
```

```
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-40 CDR-L1 (aa)

<400> SEQUENCE: 390

Thr Gly Ser Ser Ser Asp Val Ser Lys Tyr Asn Leu Val Ser
1               5                   10

<210> SEQ ID NO 391
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-L1 (aa)

<400> SEQUENCE: 391

Ser Gly Ser Ser Ser Asn Ile Gly Gly Asn Ser Val Asp
1               5                   10

<210> SEQ ID NO 392
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 CDR-L1 (aa)

<400> SEQUENCE: 392

Arg Ala Ser Gln Gly Ile Gly Asn Gly Leu Ala
1               5                   10

<210> SEQ ID NO 393
<211> LENGTH: 7
<212> TYPE: PRT
<213> ORGANISM: Homo sapiens
<220> FEATURE:
<223> OTHER INFORMATION: human BCMA epitope (residues 44-50)

<400> SEQUENCE: 393

Ser Val Thr Asn Ser Val Lys
1               5

<210> SEQ ID NO 394
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-44 CDR-L1 (aa)

<400> SEQUENCE: 394

Lys Ser Ser Gln Asn Leu Leu Tyr Ser Ser Asn Asn Lys Asn Tyr Leu
1               5                   10                  15

Ala

<210> SEQ ID NO 395
<211> LENGTH: 11
<212> TYPE: PRT
<213> ORGANISM: Artificial Sequence
<220> FEATURE:
```

<223> OTHER INFORMATION: Synthetic
<220> FEATURE:
<223> OTHER INFORMATION: BCMA-45 CDR-L1 (aa)

<400> SEQUENCE: 395

Arg Ala Ser Gln Gly Ile Gly Arg Ser Leu Ala
1               5                   10

<210> SEQ ID NO 396
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47, -48 CDR-L1 (aa)

<400> SEQUENCE: 396

Gly Gly Asn Asn Ile Gly Ser Lys Ser Val His
1               5                   10

<210> SEQ ID NO 397
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 CDR-L1 (aa)

<400> SEQUENCE: 397

Gly Gly Asp Gln Ile Gly Arg Lys Ser Val His
1               5                   10

<210> SEQ ID NO 398
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 CDR-L1 (aa)

<400> SEQUENCE: 398

Arg Ala Ser Gln Asn Ile Gly Asp Trp Leu Ala
1               5                   10

<210> SEQ ID NO 399
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 CDR-L2 (aa)

<400> SEQUENCE: 399

Trp Gly Ser Thr Arg Glu Ser
1               5

<210> SEQ ID NO 400
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 CDR-L2 (aa)

```
<400> SEQUENCE: 400

Ser Ala Ser Thr Leu Gln Ser
1               5

<210> SEQ ID NO 401
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-L2 (aa)

<400> SEQUENCE: 401

Leu Gly Ser Asn Arg Ala Ser
1               5

<210> SEQ ID NO 402
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 CDR-L2 (aa)

<400> SEQUENCE: 402

Glu Val Ser Lys Arg Pro Ser
1               5

<210> SEQ ID NO 403
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 CDR-L2 (aa)

<400> SEQUENCE: 403

Ser Ala Ser Thr Arg Ala Thr
1               5

<210> SEQ ID NO 404
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 CDR-L2 (aa)

<400> SEQUENCE: 404

Asp Ala Ser Asn Arg Ala Thr
1               5

<210> SEQ ID NO 405
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 CDR-L2 (aa)

<400> SEQUENCE: 405

Glu Thr Thr Asn Arg His Ser
1               5
```

```
<210> SEQ ID NO 406
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 CDR-L2 (aa)

<400> SEQUENCE: 406

Asp Thr Thr Asn Arg His Ser
1               5

<210> SEQ ID NO 407
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 CDR-L2 (aa)

<400> SEQUENCE: 407

Asp Thr Asn Asn Arg His Ser
1               5

<210> SEQ ID NO 408
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 CDR-L2 (aa)

<400> SEQUENCE: 408

Ala Ala Ser Thr Leu Gln Ser
1               5

<210> SEQ ID NO 409
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-L2 (aa)

<400> SEQUENCE: 409

Ala Asn Asp Arg Arg Pro Ser
1               5

<210> SEQ ID NO 410
<211> LENGTH: 7
<212> TYPE: PRT
<213> ORGANISM: Homo sapiens
<220> FEATURE:
<223> OTHER INFORMATION: human BCMA epitope (residues 8-15)

<400> SEQUENCE: 410

Cys Ser Gln Asn Glu Tyr Phe
1               5

<210> SEQ ID NO 411
<211> LENGTH: 7
<212> TYPE: PRT
<213> ORGANISM: Artificial Sequence
```

```
<220> FEATURE:
<223> OTHER INFORMATION: Synthetic
<220> FEATURE:
<223> OTHER INFORMATION: BCMA-45 CDR-L2 (aa)

<400> SEQUENCE: 411

Asp Ala Ser Ser Leu Arg Ser
1               5

<210> SEQ ID NO 412
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47, -48 CDR-L2 (aa)

<400> SEQUENCE: 412

Tyr Asp Thr Asp Arg Pro Ser
1               5

<210> SEQ ID NO 413
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 CDR-L2 (aa)

<400> SEQUENCE: 413

Tyr Asp Ser Asp Arg Pro Ser
1               5

<210> SEQ ID NO 414
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 CDR-L2 (aa)

<400> SEQUENCE: 414

Gly Ala Ser Ile Leu Glu Ser
1               5

<210> SEQ ID NO 415
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 CDR-L3 (aa)

<400> SEQUENCE: 415

Gln Gln Tyr Ile Ser Leu Pro Trp Thr
1               5

<210> SEQ ID NO 416
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 CDR-L3 (aa)
```

```
<400> SEQUENCE: 416

Gln Gln Ser Tyr Thr Ser Arg Gln Thr
1               5

<210> SEQ ID NO 417
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-L3 (aa)

<400> SEQUENCE: 417

Met Gln Ala Leu Gln Thr Pro Pro Trp Thr
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 CDR-L3 (aa)

<400> SEQUENCE: 418

Cys Ser Tyr Ala Gly Ser Ser Thr Ser Arg Asp Val
1               5                   10

<210> SEQ ID NO 419
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 CDR-L3 (aa)

<400> SEQUENCE: 419

Arg His Tyr Ala Pro Leu Thr
1               5

<210> SEQ ID NO 420
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 CDR-L3 (aa)

<400> SEQUENCE: 420

Gln Gln Arg Ser Asn Trp Pro Pro Tyr Thr
1               5                   10

<210> SEQ ID NO 421
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-26, -35 CDR-L3 (aa)
```

<400> SEQUENCE: 421

His Leu Trp Asp Arg Ser Arg Asp His Tyr Val
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 CDR-L3 (aa)

<400> SEQUENCE: 422

Leu Leu Ser Ser Gly Asp Ala Arg Met Val
1               5                   10

<210> SEQ ID NO 423
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 CDR-L3 (aa)

<400> SEQUENCE: 423

Ser Leu Ser His Ala Gly Asp Arg Val Phe
1               5                   10

<210> SEQ ID NO 424
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 CDR-L3 (aa)

<400> SEQUENCE: 424

Leu Leu Ser Tyr Ser Asp Ala Arg Leu Ala
1               5                   10

<210> SEQ ID NO 425
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 CDR-L3 (aa)

<400> SEQUENCE: 425

Leu Gln His Asn Ser Tyr Pro Leu Thr
1               5

<210> SEQ ID NO 426
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-L3 (aa)

```
<400> SEQUENCE: 426

Glu Ser Trp Asp Asp Ala Leu Asn Gly His Val
1               5                   10

<210> SEQ ID NO 427
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 CDR-L3 (aa)

<400> SEQUENCE: 427

Gln Gln Tyr Val Glu Asp Ala Leu Thr
1               5

<210> SEQ ID NO 428
<211> LENGTH: 11
<212> TYPE: PRT
<213> ORGANISM: Homo sapiens
<220> FEATURE:
<223> OTHER INFORMATION: human BCMA epitope (residues 17-27)

<400> SEQUENCE: 428

Leu Leu His Ala Cys Ile Pro Cys Gln Leu Arg
1               5                   10

<210> SEQ ID NO 429
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-44 CDR-L3 (aa)

<400> SEQUENCE: 429

Gln Gln Tyr Tyr Ser Ser Pro Tyr Thr
1               5

<210> SEQ ID NO 430
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-45 CDR-L3 (aa)

<400> SEQUENCE: 430

Gln Gln Leu Asn Gly Tyr Pro Trp Thr
1               5

<210> SEQ ID NO 431
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 CDR-L3 (aa)

<400> SEQUENCE: 431

Gln Leu Trp Asp Ser Asp Ser Asp Asp Phe Ala
1               5                   10
```

```
<210> SEQ ID NO 432
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 CDR-L3 (aa)

<400> SEQUENCE: 432

Gln Val Trp Asp Ser Ser Thr Gly Gln Tyr Val Val
1               5                   10

<210> SEQ ID NO 433
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 CDR-L3 (aa)

<400> SEQUENCE: 433

Gln Lys Tyr Asp Gly Ala Pro Pro Trp Thr
1               5                   10

<210> SEQ ID NO 434
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-27 VH FR1 (aa)

<400> SEQUENCE: 434

Glu Val Gln Leu Leu Glu Ser Gly Gly Gly Leu Val Gln Pro Gly Arg
1               5                   10                  15

Ser Leu Arg Leu Ser Cys Val Ala Ser Gly Phe Thr Phe Asp
            20                  25                  30

<210> SEQ ID NO 435
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VH FR1 (aa)

<400> SEQUENCE: 435

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Gly
            20                  25                  30

<210> SEQ ID NO 436
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25, -31, -44, -51 VH FR1 (aa)
```

-continued

<400> SEQUENCE: 436

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly
            20                  25                  30

<210> SEQ ID NO 437
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32, -49 VH FR1 (aa)

<400> SEQUENCE: 437

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 438
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 VH FR1 (aa)

<400> SEQUENCE: 438

Thr Gly Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 439
<211> LENGTH: 30
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VH FR1 (aa)

<400> SEQUENCE: 439

Glu Val Gln Leu Leu Glu Ser Gly Gly Gly Leu Val Gln Pro Gly Arg
1               5                   10                  15

Ser Leu Arg Leu Ser Cys Thr Ala Ser Gly Phe Thr Phe Gly
            20                  25                  30

<210> SEQ ID NO 440
<211> LENGTH: 746
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-52 scFv (nt)

<400> SEQUENCE: 440
tcctatgagc tgactcagcc accctcagcg tctgggaccc ccggggcagag ggtcaccatg      60 tcttgttctg gaaccagctc caacatcgga agtcactctg taaactggta ccagcagctc     120

-continued

```
ccaggaacgg ccccccaaact cctcatctat actaataatc agcggccctc aggggtccct      180
gaccgattct ctggctccaa gtctggcacc tcagcctccc tggccatcag tggcctccag      240
tctgaggatg aggctgatta ttactgtgca gcatgggatg gcagcctgaa tggtctggta      300
ttcggcggag ggaccaagct gaccgtccta ggttctagag gtggtggtgg tagcggcggc      360
ggcggctctg gtggtggtgg atccctcgag atggccgagg tgcagctggt gcagtctgga      420
gcagaggtga aaaagcccgg ggagtctctg aagatctcct gtaagggttc tggatacagc      480
tttaccagct actggatcgg ctgggtgcgc cagatgcccg ggaaaggcct ggagtggatg      540
gggatcatct atcctggtga ctctgatacc agatacagcc cgtccttcca aggccacgtc      600
accatctcag ctgacaagtc catcagcact gcctacctgc agtggagcag cctgaaggcc      660
tcggacaccg ccatgtatta ctgtgcgcgc tactctggtt ctttcgataa ctggggtcaa      720
ggtactctgg tgaccgtctc ctcagc                                           746
```

<210> SEQ ID NO 441
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 VH FR3 (aa)

<400> SEQUENCE: 441

```
Arg Phe Thr Ile Ser Arg Asp Asn Ala Lys Ser Ser Leu Tyr Leu Gln
1               5                   10                  15
Met Asn Ser Leu Arg Ala Glu Asp Thr Ala Val Tyr Tyr Cys Ala Arg
            20                  25                  30
```

<210> SEQ ID NO 442
<211> LENGTH: 248
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 scFv (aa)

<400> SEQUENCE: 442

```
Ser Tyr Glu Leu Thr Gln Pro Pro Ser Ala Ser Gly Thr Pro Gly Gln
1               5                   10                  15
Arg Val Thr Met Ser Cys Ser Gly Thr Ser Ser Asn Ile Gly Ser His
            20                  25                  30
Ser Val Asn Trp Tyr Gln Gln Leu Pro Gly Thr Ala Pro Lys Leu Leu
        35                  40                  45
Ile Tyr Thr Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Gly Ser Leu
                85                  90                  95
Asn Gly Leu Val Phe Gly Gly Gly Thr Lys Leu Thr Val Leu Gly Ser
            100                 105                 110
Arg Gly Gly Gly Gly Ser Gly Gly Gly Gly Ser Gly Gly Gly Gly Ser
        115                 120                 125
Leu Glu Met Ala Glu Val Gln Leu Val Gln Ser Gly Ala Glu Val Lys
    130                 135                 140
```

```
Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser
                245
```

<210> SEQ ID NO 443
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VH FR3 (aa)

<400> SEQUENCE: 443

```
Asp Ser Pro Ser Pro Gly Thr Thr Pro Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 444
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VH FR4 (aa)

<400> SEQUENCE: 444

```
Gly Gly Gln Gly Thr Met Val Thr Val Ser Ser
1               5                   10
```

<210> SEQ ID NO 445
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VH FR4 (aa)

<400> SEQUENCE: 445

```
Trp Arg Gln Gly Thr Met Val Thr Val Ser Ser
1               5                   10
```

<210> SEQ ID NO 446
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 VL FR1 (aa)

-continued

```
<400> SEQUENCE: 446

Asp Ile Gln Met Thr Gln Ser Pro Ala Phe Leu Ser Ala Ser Val Gly
1               5                   10                  15

Asp Arg Val Thr Val Thr Cys
            20

<210> SEQ ID NO 447
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VL FR1 (aa)

<400> SEQUENCE: 447

Asp Ile Val Met Thr Gln Ser Pro Leu Ser Leu Ser Val Thr Pro Gly
1               5                   10                  15

Glu Pro Ala Ser Ile Ser Cys
            20

<210> SEQ ID NO 448
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 VL FR1 (aa)

<400> SEQUENCE: 448

Gln Pro Val Leu Thr Gln Pro Ala Ser Val Ser Gly Ser Pro Gly Gln
1               5                   10                  15

Ser Ile Thr Ile Ser Cys
            20

<210> SEQ ID NO 449
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VL FR1 (aa)

<400> SEQUENCE: 449

Glu Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 450
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-31 VL FR1 (aa)

<400> SEQUENCE: 450

Asp Val Val Met Thr Gln Ser Pro Asp Ser Leu Ala Val Ser Leu Gly
1               5                   10                  15

Glu Arg Ala Thr Ile Ser Cys
            20
```

<210> SEQ ID NO 451
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 VL FR1 (aa)

<400> SEQUENCE: 451

Gln Thr Val Val Thr Gln Pro Pro Ser Val Ser Val Ala Pro Gly Gln
1               5                   10                  15

Thr Ala Arg Ile Thr Cys
            20

<210> SEQ ID NO 452
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 VL FR1 (aa)

<400> SEQUENCE: 452

Glu Ile Val Met Thr Gln Ser Pro Ala Thr Leu Ser Leu Ser Pro Gly
1               5                   10                  15

Asp Arg Ala Thr Leu Ser Cys
            20

<210> SEQ ID NO 453
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 VL FR1 (aa)

<400> SEQUENCE: 453

Asn Phe Met Leu Thr Gln Pro Pro Ser Val Ser Val Ala Pro Gly Gln
1               5                   10                  15

Thr Ala Arg Ile Thr Cys
            20

<210> SEQ ID NO 454
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 VL FR1 (aa)

<400> SEQUENCE: 454

Gln Ser Val Leu Thr Gln Glu Pro Ser Leu Thr Val Ser Pro Gly Glu
1               5                   10                  15

Thr Val Thr Leu Thr Cys
            20

<210> SEQ ID NO 455
<211> LENGTH: 22
<212> TYPE: PRT
<213> ORGANISM: Artificial Sequence
<220> FEATURE:

<223> OTHER INFORMATION: Synthetic
<220> FEATURE:
<223> OTHER INFORMATION: BCMA-37 VL FR1 (aa)

<400> SEQUENCE: 455

Gln Leu Val Leu Thr Gln Glu Pro Ser Leu Thr Val Ser Pro Gly Gly
1               5                   10                  15

Thr Val Thr Leu Thr Cys
            20

<210> SEQ ID NO 456
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 VL FR1 (aa)

<400> SEQUENCE: 456

Gln Ala Val Leu Thr Gln Glu Pro Ser Leu Thr Val Ser Pro Gly Gly
1               5                   10                  15

Thr Val Thr Leu Thr Cys
            20

<210> SEQ ID NO 457
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 VL FR1 (aa)
<220> FEATURE:
<221> NAME/KEY: VARIANT
<222> LOCATION: 4
<223> OTHER INFORMATION: Xaa = any amino acid

<400> SEQUENCE: 457

Asp Ile Gln Xaa Thr Gln Ser Pro Ser Ser Leu Ser Ala Ser Val Gly
1               5                   10                  15

Asp Arg Val Thr Ile Thr Cys
            20

<210> SEQ ID NO 458
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 VL FR1 (aa)

<400> SEQUENCE: 458

Gln Pro Val Leu Thr Gln Pro Pro Ser Val Ser Gly Thr Pro Gly Gln
1               5                   10                  15

Arg Val Thr Ile Pro Cys
            20

<210> SEQ ID NO 459
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VL FR1 (aa)

-continued

```
<400> SEQUENCE: 459

Asp Ile Gln Met Thr Gln Ser Pro Ser Leu Val Ser Ala Ser Val Gly
 1               5                   10                  15

Asp Arg Val Thr Ile Thr Cys
            20

<210> SEQ ID NO 460
<211> LENGTH: 732
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-55 scFv (nt)
      (O/SSE)

<400> SEQUENCE: 460
cagtctgccc tgacacagcc tgccagcgtt agtgctagtc ccggacagtc tatcgccatc     60
agctgtaccg gcaccagctc tgacgttggc tggtatcagc agcaccctgg caaggcccct    120
aagctgatga tctacgagga cagcaagagg cccagcggcg tgtccaatag attcagcggc    180
agcaagagcg gcaacaccgc cagcctgaca attagcggac tgcaggccga ggacgaggcc    240
gattactact gcagcagcaa cacccggtcc agcacactgg ttttggcgg aggcaccaag    300 ctgacagtgc tgggatctag aggtggcgga ggatctggcg gcggaggaag cggaggcggc    360
ggatctcttg aaatggctga agtgcagctg gtgcagtctg gcgccgagat gaagaaacct    420
ggcgcctctc tgaagctgag ctgcaaggcc agcggctaca ccttcatcga ctactacgtg    480
tactggatgc ggcaggcccc tggacaggga ctcgaatcta tgggctggat caaccccaat    540
agcggcggca ccaattacgc ccagaaattc agggcagag tgaccatgac cagagacacc    600
agcatcagca ccgcctacat ggaactgagc cggctgagat ccgacgacac cgccatgtac    660
tactgcgcca gatctcagcg cgacggctac atggattatt ggggccaggg aaccctggtc    720
accgtgtcca gc                                                         732

<210> SEQ ID NO 461
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-44 VL FR1 (aa)

<400> SEQUENCE: 461

Asp Val Val Met Thr Gln Ser Pro Asp Ser Leu Ala Val Ser Leu Gly
 1               5                   10                  15

Glu Arg Ala Thr Ile Asn Cys
            20

<210> SEQ ID NO 462
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-45 VL FR1 (aa)
```

```
<400> SEQUENCE: 462

Ala Ile Arg Met Thr Gln Ser Pro Ser Ser Leu Ser Ala Ser Val Gly
1               5                   10                  15

Asp Arg Val Thr Ile Thr Cys
            20

<210> SEQ ID NO 463
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VL FR1 (aa)

<400> SEQUENCE: 463

Gln Ala Val Leu Thr Gln Pro Pro Ser Val Ser Val Ala Pro Gly Lys
1               5                   10                  15

Thr Ala Thr Ile Thr Cys
            20

<210> SEQ ID NO 464
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-48 VL FR1 (aa)

<400> SEQUENCE: 464

Gln Pro Val Leu Thr Gln Pro Pro Ser Val Ser Val Ala Pro Gly Lys
1               5                   10                  15

Thr Ala Thr Ile Thr Cys
            20

<210> SEQ ID NO 465
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 VL FR1 (aa)

<400> SEQUENCE: 465

Leu Pro Val Leu Thr Gln Pro Pro Ser Val Ser Val Ala Pro Gly Lys
1               5                   10                  15

Thr Ala Arg Ile Thr Cys
            20

<210> SEQ ID NO 466
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 VL FR1 (aa)
```

<400> SEQUENCE: 466

Ala Ile Gln Leu Thr Gln Ser Pro Ser Thr Leu Ser Ala Ser Val Gly
1               5                   10                  15

Asp Arg Val Ala Ile Thr Cys
            20

<210> SEQ ID NO 467
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 VL FR2 (aa)

<400> SEQUENCE: 467

Trp Tyr Gln Gln Lys Pro Gly Asn Ala Pro Arg Leu Leu Ile Tyr
1               5                   10                  15

<210> SEQ ID NO 468
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VL FR2 (aa)

<400> SEQUENCE: 468

Trp Tyr Leu Gln Lys Pro Gly Gln Ser Pro Gln Leu Leu Ile Tyr
1               5                   10                  15

<210> SEQ ID NO 469
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 VL FR2 (aa)

<400> SEQUENCE: 469

Trp Tyr Gln Gln His Pro Gly Lys Ala Pro Lys Leu Met Ile Tyr
1               5                   10                  15

<210> SEQ ID NO 470
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VL FR2 (aa)

<400> SEQUENCE: 470

Trp Tyr Gln Gln Lys Pro Gly Gln Ala Pro Lys Leu Leu Ile Tyr
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-31 VL FR2 (aa)

```
<400> SEQUENCE: 471

Trp Tyr Lys Gln Lys Pro Gly Gln Pro Pro Lys Leu Val Ile Ser
1               5                   10                  15

<210> SEQ ID NO 472
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 VL FR2 (aa)

<400> SEQUENCE: 472

Trp Tyr Arg Gln Arg Pro Gly Gln Ala Pro Glu Val Val Ile Tyr
1               5                   10                  15

<210> SEQ ID NO 473
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 VL FR2 (aa)

<400> SEQUENCE: 473

Trp Phe Gln Lys Lys Pro Gly Gln Ala Pro Thr Thr Leu Ile Tyr
1               5                   10                  15

<210> SEQ ID NO 474
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37, -38 VL FR2 (aa)

<400> SEQUENCE: 474

Trp Phe Gln Gln Lys Pro Gly Gln Ala Pro Arg Thr Leu Ile Tyr
1               5                   10                  15

<210> SEQ ID NO 475
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 VL FR2 (aa)

<400> SEQUENCE: 475

Trp Tyr Gln Gln Lys Pro Gly Lys Ala Pro Lys Leu Leu Ile Tyr
1               5                   10                  15

<210> SEQ ID NO 476
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 VL FR2 (aa)

<400> SEQUENCE: 476

Trp Phe Gln Glu Val Pro Gly Thr Ala Pro Lys Leu Leu Ile Tyr
1               5                   10                  15
```

<210> SEQ ID NO 477
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VL FR2 (aa)

<400> SEQUENCE: 477

Trp Tyr Gln Gln Lys Pro Gly Lys Ala Pro Lys Leu Leu Leu Phe
1               5                   10                  15

<210> SEQ ID NO 478
<211> LENGTH: 244
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 scFv (aa)

<400> SEQUENCE: 478

Gln Ser Ala Leu Thr Gln Pro Ala Ser Val Ser Ala Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser

<210> SEQ ID NO 479
<211> LENGTH: 15
<212> TYPE: PRT

```
<213> ORGANISM: Artificial Sequence
<220> FEATURE:
<223> OTHER INFORMATION: Synthetic
<220> FEATURE:
<223> OTHER INFORMATION: BCMA-45 VL FR2 (aa)

<400> SEQUENCE: 479

Trp Tyr Lys Gln Lys Pro Gly Gly Val Pro Gln Leu Leu Ile His
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47, -48 VL FR2 (aa)

<400> SEQUENCE: 480

Trp Tyr Gln Arg Lys Pro Gly Gln Gly Pro Val Val Val Ile Gln
1               5                   10                  15

<210> SEQ ID NO 481
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 VL FR2 (aa)

<400> SEQUENCE: 481

Trp Tyr Gln Gln Lys Pro Gly Gln Ala Pro Val Leu Val Met Ser
1               5                   10                  15

<210> SEQ ID NO 482
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 VL FR2 (aa)

<400> SEQUENCE: 482

Trp Tyr Gln Gln Lys Pro Gly Lys Ala Pro Lys Leu Leu Ile Phe
1               5                   10                  15

<210> SEQ ID NO 483
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 VL FR3 (aa)

<400> SEQUENCE: 483

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Ile Tyr His Cys
                20                  25                  30

<210> SEQ ID NO 484
<211> LENGTH: 32
<212> TYPE: PRT
<213> ORGANISM: Artificial Sequence
```

```
<220> FEATURE:
<223> OTHER INFORMATION: Synthetic
<220> FEATURE:
<223> OTHER INFORMATION: BCMA-25 VL FR3 (aa)

<400> SEQUENCE: 484

Gly Val Pro Ser Arg Phe Arg Gly Thr Gly Tyr Gly Thr Glu Phe Ser
1               5                   10                  15

Leu Thr Ile Asp Ser Leu Gln Pro Glu Asp Phe Ala Thr Tyr Tyr Cys
            20                  25                  30

<210> SEQ ID NO 485
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VL FR3 (aa)

<400> SEQUENCE: 485

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 486
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 VL FR3 (aa)

<400> SEQUENCE: 486

Gly Val Ser Asn Arg Phe Ser Gly Ser Lys Ser Gly Asn Thr Ala Ser
1               5                   10                  15

Pro Thr Ile Ser Gly Leu Gln Ala Glu Asp Glu Ala Asp Tyr Tyr Cys
            20                  25                  30

<210> SEQ ID NO 487
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VL FR3 (aa)

<400> SEQUENCE: 487

Gly Ile Pro Asp Arg Phe Ser Gly Ser Gly Ser Gly Thr Asp Phe Thr
1               5                   10                  15

Leu Thr Ile Ser Arg Leu Glu His Glu Asp Phe Ala Val Tyr Tyr Arg
            20                  25                  30

<210> SEQ ID NO 488
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 VL FR3 (aa)
```

-continued

```
<400> SEQUENCE: 488

Gly Val Pro Asp Arg Phe Ser Gly Ser Asn Ser Gly Asn Thr Ala Thr
1               5                   10                  15

Leu Thr Val Arg Gly Val Glu Ala Gly Asp Glu Ala Asp Tyr Tyr Cys
            20                  25                  30

<210> SEQ ID NO 489
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 VL FR3 (aa)

<400> SEQUENCE: 489

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 490
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 VL FR3 (aa)

<400> SEQUENCE: 490

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Asp Tyr Tyr Cys
            20                  25                  30

<210> SEQ ID NO 491
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 VL FR3 (aa)

<400> SEQUENCE: 491

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
            20                  25                  30

<210> SEQ ID NO 492
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 VL FR3 (aa)

<400> SEQUENCE: 492

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Asp Tyr Phe Cys
            20                  25                  30
```

```
<210> SEQ ID NO 493
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-39 VL FR3 (aa)

<400> SEQUENCE: 493

Gly Val Pro Ser Arg Phe Ser Gly Ser Gly Ser Gly Thr Asp Phe Ala
1               5                   10                  15

Leu Thr Ile Arg Ser Leu Gln Pro Glu Asp Phe Ala Thr Tyr Tyr Cys
            20                  25                  30

<210> SEQ ID NO 494
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 VL FR3 (aa)

<400> SEQUENCE: 494

Gly Val Pro Asp Arg Phe Ser Gly Thr Lys Ser Gly Thr Ser Ala Ser
1               5                   10                  15

Leu Ala Ile Arg Gly Leu Gln Ser Asp Asp Asp Ala His Tyr Tyr Cys
            20                  25                  30

<210> SEQ ID NO 495
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VL FR3 (aa)

<400> SEQUENCE: 495

Gly Val Pro Ser Arg Phe Ser Gly Ser Arg Ser Gly Thr Asp Tyr Thr
1               5                   10                  15

Leu Thr Ile Ser Ser Leu Gln Pro Glu Asp Val Ala Thr Tyr Tyr Cys
            20                  25                  30

<210> SEQ ID NO 496
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 CDR-H1 (aa)

<400> SEQUENCE: 496

Gly Tyr Ser Phe Thr Ser Tyr Trp
1               5

<210> SEQ ID NO 497
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-45 VL FR3 (aa)
```

```
<400> SEQUENCE: 497

Gly Val Pro Ser Arg Phe Ser Gly Ser Gly Ser Gly Thr Glu Phe Thr
1               5                   10                  15

Leu Thr Ile Ser Gly Val Gln Ser Glu Asp Ser Ala Thr Tyr His Cys
            20                  25                  30

<210> SEQ ID NO 498
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VL FR3 (aa)

<400> SEQUENCE: 498

Gly Ile Pro Glu Arg Phe Ser Gly Ser Lys Ser Gly Asp Thr Ala Ser
1               5                   10                  15

Leu Thr Ile Ser Gly Val Glu Ala Gly Asp Glu Ala Asp Tyr Tyr Cys
            20                  25                  30

<210> SEQ ID NO 499
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-48 VL FR3 (aa)

<400> SEQUENCE: 499

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Gly Asp Tyr Tyr Cys
            20                  25                  30

<210> SEQ ID NO 500
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 VL FR3 (aa)

<400> SEQUENCE: 500

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Ala Tyr Tyr Cys
            20                  25                  30

<210> SEQ ID NO 501
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 VL FR3 (aa)

<400> SEQUENCE: 501

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Val Tyr Tyr Cys
            20                  25                  30
```

```
<210> SEQ ID NO 502
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 VL FR4 (aa)

<400> SEQUENCE: 502

Phe Gly Pro Gly Thr Arg Leu Asp Ile Lys
1               5                   10

<210> SEQ ID NO 503
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 VL FR4 (aa)
<220> FEATURE:
<221> NAME/KEY: VARIANT
<222> LOCATION: 3
<223> OTHER INFORMATION: Xaa = any amino acid

<400> SEQUENCE: 503

Phe Gly Xaa Gly Thr Lys Leu Thr Val Leu
1               5                   10

<210> SEQ ID NO 504
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-31, -34 VL FR4 (aa)

<400> SEQUENCE: 504

Phe Gly Gln Gly Thr Lys Leu Asp Ile Lys
1               5                   10

<210> SEQ ID NO 505
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 VL FR4 (aa)

<400> SEQUENCE: 505

Phe Gly Thr Gly Thr Lys Leu Asp Ile Lys
1               5                   10

<210> SEQ ID NO 506
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VL FR4 (aa)

<400> SEQUENCE: 506

Phe Gly Gly Gly Thr Lys Val Asp Ile Lys
1               5                   10
```

<210> SEQ ID NO 507
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 CDR-H2 (aa)

<400> SEQUENCE: 507

Ile Tyr Pro Gly Asp Ser Asp Thr
1               5

<210> SEQ ID NO 508
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24, -28, -51 VL FR4 (aa)

<400> SEQUENCE: 508

Phe Gly Gln Gly Thr Lys Val Glu Ile Lys
1               5                   10

<210> SEQ ID NO 509
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 CDR-H1 (aa) AbM numbering

<400> SEQUENCE: 509

Gly Phe Thr Phe Gly Asp Tyr Ala Met His
1               5                   10

<210> SEQ ID NO 510
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-H2 (aa) AbM numbering
<220> FEATURE:
<221> NAME/KEY: VARIANT
<222> LOCATION: 10
<223> OTHER INFORMATION: Xaa = any amino acid

<400> SEQUENCE: 510

Gly Ile Ser Trp Asn Ser Gly Ser Ile Xaa
1               5                   10

<210> SEQ ID NO 511
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-33 CDR-H2 (aa) AbM numbering

<400> SEQUENCE: 511

Tyr Ile Ser Gly Ser Gly Ser Thr Ile Tyr
1               5                   10

```
<210> SEQ ID NO 512
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-H2 AbM numbering

<400> SEQUENCE: 512

Tyr Ile Ser Ser Ser Gly Asn Thr Ile Tyr
1               5                   10

<210> SEQ ID NO 513
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 CDR-H3 (aa)

<400> SEQUENCE: 513

Ala Arg Tyr Ser Gly Ser Phe Asp Asn
1               5

<210> SEQ ID NO 514
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 CDR-H2 (aa) Chothia numbering

<400> SEQUENCE: 514

Ser Trp Asn Ser Gly
1               5

<210> SEQ ID NO 515
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-33 CDR-H2 (aa) Chothia numbering

<400> SEQUENCE: 515

Ser Gly Ser Gly Ser Thr
1               5

<210> SEQ ID NO 516
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 CDR-H2 Chothia numbering

<400> SEQUENCE: 516

Ser Ser Ser Gly Asn Thr
1               5

<210> SEQ ID NO 517
<211> LENGTH: 8
<212> TYPE: PRT
```

```
<213> ORGANISM: Artificial Sequence
<220> FEATURE:
<223> OTHER INFORMATION: Synthetic
<220> FEATURE:
<223> OTHER INFORMATION: BCMA-52 CDR-L1 (aa)

<400> SEQUENCE: 517

Ser Ser Asn Ile Gly Ser His Ser
1               5

<210> SEQ ID NO 518
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 VH chain (aa)

<400> SEQUENCE: 518

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Trp
            100                 105                 110

Gly Gln Gly Thr Met Val Thr Val Ser Ser
        115                 120

<210> SEQ ID NO 519
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25, -31, -44, -51 VH chain (aa)

<400> SEQUENCE: 519

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110
```

```
Leu Val Thr Val Ser Ser
        115

<210> SEQ ID NO 520
<211> LENGTH: 121
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-27 VH chain (aa)

<400> SEQUENCE: 520

Glu Val Gln Leu Leu Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gly Leu Gly Ile Thr Pro Tyr Tyr Phe Asp Tyr Trp Gly
            100                 105                 110

Gln Gly Thr Leu Val Thr Val Ser Ser
        115                 120

<210> SEQ ID NO 521
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VH chain (aa)
<220> FEATURE:
<221> NAME/KEY: VARIANT
<222> LOCATION: 59
<223> OTHER INFORMATION: Xaa = any amino acid

<400> SEQUENCE: 521

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Xaa Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Gly
            100                 105                 110

Gly Gln Gly Thr Met Val Thr Val Ser Ser
        115                 120
```

```
<210> SEQ ID NO 522
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29, -39 VH chain (aa)

<400> SEQUENCE: 522

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Trp
            100                 105                 110

Gly Gln Gly Thr Met Val Thr Val Ser Ser
        115                 120

<210> SEQ ID NO 523
<211> LENGTH: 119
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VH chain (aa)

<400> SEQUENCE: 523

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asp Pro Asp Asp Ala Phe Asp Ile Trp Gly Gln Gly
            100                 105                 110

Thr Met Val Thr Val Ser Ser
        115

<210> SEQ ID NO 524
<211> LENGTH: 118
<212> TYPE: PRT
<213> ORGANISM: Artificial Sequence
<220> FEATURE:
```

<223> OTHER INFORMATION: Synthetic
<220> FEATURE:
<223> OTHER INFORMATION: BCMA-32, -49 VH chain (aa)

<400> SEQUENCE: 524

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser
        115

<210> SEQ ID NO 525
<211> LENGTH: 117
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-33 VH chain (aa)

<400> SEQUENCE: 525

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asp Ser Ser Ala Asp Tyr Trp Gly Gln Gly Thr Leu
            100                 105                 110

Val Asn Val Ser Ser
        115

<210> SEQ ID NO 526
<211> LENGTH: 122
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 VH chain (aa)

<400> SEQUENCE: 526

Thr Gly Gln Leu Val Gln Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Asp Tyr Asp Pro Asp Ala Phe Asp Ile Trp
            100                 105                 110

Gly Gln Gly Thr Met Val Thr Val Ser Ser
        115                 120

<210> SEQ ID NO 527
<211> LENGTH: 117
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 VH chain (aa)

<400> SEQUENCE: 527

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Asp Asp Tyr Trp Gly Gln Gly Thr Leu
            100                 105                 110

Val Thr Val Ser Ser
        115

<210> SEQ ID NO 528
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36, 38 VH chain (aa)

<400> SEQUENCE: 528

Gln Val Gln Leu Val Gln Ser Gly Gly Gly Leu Val Lys Pro Gly Gly
1               5                   10                  15

-continued

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Asp Tyr Trp Gly Gln Gly Thr
            100                 105                 110

Leu Val Thr Val Ser Ser
        115
```

<210> SEQ ID NO 529
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 VH chain (aa)

<400> SEQUENCE: 529

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Asp Tyr Trp Gly Gln Gly Thr
            100                 105                 110

Leu Val Thr Val Ser Ser
        115
```

<210> SEQ ID NO 530
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 VH chain (aa)

<400> SEQUENCE: 530

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45
```

```
Ser Tyr Ile Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Asp Tyr Val Asp Asp Tyr Trp Gly Gln Gly Thr
            100                 105                 110

Leu Val Thr Val Ser Ser
        115

<210> SEQ ID NO 531
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VH chain (aa)

<400> SEQUENCE: 531

Glu Val Gln Leu Leu Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
                 20                  25                  30

Ala Met Ser Trp Phe Arg Gln Ala Pro Gly Lys Gly Leu Glu Trp Val
             35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Ala Ala Trp Ser Ala Pro Thr Asp Tyr Trp Gly Gln Gly Thr
            100                 105                 110

Leu Val Thr Val Ser Ser
        115

<210> SEQ ID NO 532
<211> LENGTH: 3
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 CDR-L2 (aa)

<400> SEQUENCE: 532

Thr Asn Asn
 1

<210> SEQ ID NO 533
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VH chain (aa)
```

<400> SEQUENCE: 533

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Asp Ser Pro Ser Pro Gly Thr Thr Pro Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Arg Gln Gly Thr
            100                 105                 110

Met Val Thr Val Ser Ser
            115

<210> SEQ ID NO 534
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 VL chain (aa)

<400> SEQUENCE: 534

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Gly Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr His Cys Gln Gln
                85                  90                  95

Tyr Ile Ser Leu Pro Trp Thr Phe Gly Gln Gly Thr Lys Val Glu Ile
            100                 105                 110

Lys

<210> SEQ ID NO 535
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 VL chain (aa)

<400> SEQUENCE: 535

Asp Ile Gln Met Thr Gln Ser Pro Ala Phe Leu Ser Ala Ser Val Gly
1               5                   10                  15

Asp Arg Val Thr Val Thr Cys Arg Ala Ser Gln Gly Ile Ser Asn Tyr
            20                  25                  30

```
Leu Ala Trp Tyr Gln Gln Lys Pro Gly Asn Ala Pro Arg Leu Leu Ile
        35                  40                  45

Tyr Ser Ala Ser Thr Leu Gln Ser Gly Val Pro Ser Arg Phe Arg Gly
    50                  55                  60

Thr Gly Tyr Gly Thr Glu Phe Ser Leu Thr Ile Asp Ser Leu Gln Pro
65                  70                  75                  80

Glu Asp Phe Ala Thr Tyr Tyr Cys Gln Gln Ser Tyr Thr Ser Arg Gln
                85                  90                  95

Thr Phe Gly Pro Gly Thr Arg Leu Asp Ile Lys
                100                 105

<210> SEQ ID NO 536
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-26 VL chain (aa)

<400> SEQUENCE: 536

Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
                20                  25                  30

His Trp Tyr Gln Gln Lys Pro Gly Gln Ala Pro Met Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Leu Trp Asp Arg Ser Arg Asp His
                85                  90                  95

Tyr Val Phe Gly Thr Gly Thr Lys Leu Thr Val Leu
                100                 105

<210> SEQ ID NO 537
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 VL chain (aa)

<400> SEQUENCE: 537

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Leu Gln Thr Pro Pro Trp Thr Phe Gly Gln Gly Thr Lys Val Glu Ile
            100                 105                 110

Lys

<210> SEQ ID NO 538
<211> LENGTH: 112
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 VL chain (aa)
<220> FEATURE:
<221> NAME/KEY: VARIANT
<222> LOCATION: 105
<223> OTHER INFORMATION: Xaa = any amino acid

<400> SEQUENCE: 538

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Pro Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Ser Arg Asp Val Phe Gly Xaa Gly Thr Lys Leu Thr Val Leu
            100                 105                 110

<210> SEQ ID NO 539
<211> LENGTH: 105
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 VL chain (aa)

<400> SEQUENCE: 539

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Pro Ile Arg Ser Asn
            20                  25                  30

Leu Ala Trp Tyr Gln Gln Lys Pro Gly Gln Ala Pro Lys Leu Leu Ile
        35                  40                  45

Tyr Ser Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu His
65                  70                  75                  80

Glu Asp Phe Ala Val Tyr Tyr Arg Arg His Tyr Ala Pro Leu Thr Phe
                85                  90                  95

Gly Gly Gly Thr Lys Val Glu Ile Lys
            100                 105

<210> SEQ ID NO 540
<211> LENGTH: 113
<212> TYPE: PRT

<213> ORGANISM: Artificial Sequence
<220> FEATURE:
<223> OTHER INFORMATION: Synthetic
<220> FEATURE:
<223> OTHER INFORMATION: BCMA-31 VL chain (aa)

<400> SEQUENCE: 540

Asp Val Val Met Thr Gln Ser Pro Asp Ser Leu Ala Val Ser Leu Gly
1               5                   10                  15

Glu Arg Ala Thr Ile Ser Cys Lys Ser Gln Ser Val Leu Asn Ser
            20                  25                  30

Ser Asn Asn Lys Asn Tyr Val Ala Trp Tyr Lys Gln Lys Pro Gly Gln
        35                  40                  45

Pro Pro Lys Leu Val Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Asp Ile
            100                 105                 110

Lys

<210> SEQ ID NO 541
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 VL chain (aa)

<400> SEQUENCE: 541

Gln Thr Val Val Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Arg Gln Arg Pro Gly Gln Ala Pro Glu Val Val Ile Tyr
        35                  40                  45

Asp Asp Ser Asp Arg Pro Ser Gly Val Pro Asp Arg Phe Ser Gly Ser
    50                  55                  60

Asn Ser Gly Asn Thr Ala Thr Leu Thr Val Arg Gly Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 542
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 VL chain (aa)

<400> SEQUENCE: 542

Glu Ile Val Met Thr Gln Ser Pro Ala Thr Leu Ser Leu Ser Pro Gly
1               5                   10                  15

-continued

Asp Arg Ala Thr Leu Ser Cys Arg Ala Ser Gln Ser Ile Ser Asn Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                 85                  90                  95

Tyr Thr Phe Gly Gln Gly Thr Lys Leu Asp Ile Lys
            100                 105

<210> SEQ ID NO 543
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 VL chain (aa)

<400> SEQUENCE: 543

Asn Phe Met Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
                20                  25                  30

His Trp Tyr Gln Gln Lys Pro Gly Gln Ala Pro Met Leu Val Val Tyr
             35                  40                  45

Asp Asp Asp Asp Arg Pro Ser Gly Ile Pro Glu Arg Phe Ser Gly Ser
         50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Leu Trp Asp Arg Ser Arg Asp His
                 85                  90                  95

Tyr Val Phe Gly Thr Gly Thr Lys Leu Asp Ile Lys
            100                 105

<210> SEQ ID NO 544
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 VL chain (aa)

<400> SEQUENCE: 544

Gln Ser Val Leu Thr Gln Glu Pro Ser Leu Thr Val Ser Pro Gly Glu
1               5                   10                  15

Thr Val Thr Leu Thr Cys Gly Ser Ser Thr Gly Pro Val Thr Ser Ala
                20                  25                  30

His Ser Pro Ser Trp Phe Gln Lys Lys Pro Gly Gln Ala Pro Thr Thr
             35                  40                  45

Leu Ile Tyr Glu Thr Thr Asn Arg His Ser Trp Thr Pro Ala Arg Phe
         50                  55                  60

Ser Gly Ser Leu Leu Gly Gly Lys Ala Ala Leu Thr Leu Ser Gly Ala
65                  70                  75                  80

Gln Pro Glu Asp Glu Ala Asp Tyr Tyr Cys Leu Leu Ser Ser Gly Asp
            85                  90                  95

Ala Arg Met Val Phe Gly Gly Gly Thr Lys Leu Thr Val Leu
            100                 105                 110

<210> SEQ ID NO 545
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 VL chain (aa)

<400> SEQUENCE: 545

Gln Leu Val Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Asn Gly
            20                  25                  30

His Ser Pro Tyr Trp Phe Gln Gln Lys Pro Gly Gln Ala Pro Arg Thr
            35                  40                  45

Leu Ile Tyr Asp Thr Thr Asn Arg His Ser Trp Thr Pro Ala Arg Phe
    50                  55                  60

Ser Gly Ser Leu Leu Gly Gly Lys Ala Ala Leu Thr Leu Ser Gly Ala
65              70                  75                  80

Gln Pro Glu Asp Glu Ala Glu Tyr Tyr Cys Ser Leu Ser His Ala Gly
            85                  90                  95

Asp Arg Val Phe Phe Gly Gly Gly Thr Lys Leu Thr Val Leu
            100                 105                 110

<210> SEQ ID NO 546
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 VL chain (aa)

<400> SEQUENCE: 546

Gln Ala Val Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Asn Gly
            20                  25                  30

His Ser Pro Tyr Trp Phe Gln Gln Lys Pro Gly Gln Ala Pro Arg Thr
            35                  40                  45

Leu Ile Tyr Asp Thr Asn Asn Arg His Ser Trp Thr Pro Ala Arg Phe
    50                  55                  60

Ser Gly Ser Leu Leu Gly Gly Lys Ala Ala Leu Thr Leu Ser Gly Ala
65              70                  75                  80

Gln Pro Glu Asp Glu Ala Asp Tyr Phe Cys Leu Leu Ser Tyr Ser Asp
            85                  90                  95

Ala Arg Leu Ala Phe Gly Gly Gly Thr Lys Leu Thr Val Leu
            100                 105                 110

<210> SEQ ID NO 547
<211> LENGTH: 107
<212> TYPE: PRT
<213> ORGANISM: Artificial Sequence
<220> FEATURE:

```
<223> OTHER INFORMATION: Synthetic
<220> FEATURE:
<223> OTHER INFORMATION: BCMA-39 VL chain (aa)
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 34
<223> OTHER INFORMATION: Xaa = any amino acid

<400> SEQUENCE: 547
```

Asp Ile Gln Xaa Thr Gln Ser Pro Ser Leu Ser Ala Ser Val Gly
1               5                   10                  15

Asp Arg Val Thr Ile Thr Cys Arg Ala Ser Gln Gly Ile Arg Tyr Glu
            20                  25                  30

Leu Xaa Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ala Leu Thr Ile Arg Ser Leu Gln Pro
65              70                  75                  80

Glu Asp Phe Ala Thr Tyr Tyr Cys Leu Gln His Asn Ser Tyr Pro Leu
                85                  90                  95

Thr Phe Gly Arg Gly Thr Lys Leu Glu Ile Lys
            100                 105

```
<210> SEQ ID NO 548
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-40 VL chain (aa)

<400> SEQUENCE: 548
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ser Lys Tyr
            20                  25                  30

Asn Leu Val Ser Trp Tyr Gln Gln Pro Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Thr Leu Thr Ile Ser Gly Leu
65              70                  75                  80

Gln Gly Asp Asp Glu Ala Asp Tyr Tyr Cys Cys Ser Tyr Gly Gly Ser
                85                  90                  95

Arg Ser Tyr Val Phe Gly Thr Gly Thr Lys Leu Thr Val Leu
            100                 105                 110

```
<210> SEQ ID NO 549
<211> LENGTH: 110
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 VL chain (aa)
```

-continued

<400> SEQUENCE: 549

Gln Pro Val Leu Thr Gln Pro Pro Ser Val Ser Gly Thr Pro Gly Gln
1               5                   10                  15

Arg Val Thr Ile Pro Cys Ser Gly Ser Ser Asn Ile Gly Gly Asn
                20                  25                  30

Ser Val Asp Trp Phe Gln Glu Val Pro Gly Thr Ala Pro Lys Leu Leu
            35                  40                  45

Ile Tyr Ala Asn Asp Arg Arg Pro Ser Gly Val Pro Asp Arg Phe Ser
50                  55                  60

Gly Thr Lys Ser Gly Thr Ser Ala Ser Leu Ala Ile Arg Gly Leu Gln
65                  70                  75                  80

Ser Asp Asp Asp Ala His Tyr Tyr Cys Glu Ser Trp Asp Asp Ala Leu
                85                  90                  95

Asn Gly His Val Phe Gly Gly Gly Thr Lys Leu Thr Val Leu
                100                 105                 110

<210> SEQ ID NO 550
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 VL chain (aa)

<400> SEQUENCE: 550

Asp Ile Gln Met Thr Gln Ser Pro Ser Leu Val Ser Ala Ser Val Gly
1               5                   10                  15

Asp Arg Val Thr Ile Thr Cys Arg Ala Ser Gln Gly Ile Gly Asn Gly
                20                  25                  30

Leu Ala Trp Tyr Gln Gln Lys Pro Gly Lys Ala Pro Lys Leu Leu Leu
            35                  40                  45

Phe Ala Ala Ser Arg Leu Glu Ser Gly Val Pro Ser Arg Phe Ser Gly
50                  55                  60

Ser Arg Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Val Glu Asp Ala Leu
                85                  90                  95

Thr Phe Gly Gly Gly Thr Lys Val Asp Ile Lys
                100                 105

<210> SEQ ID NO 551
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 CDR-L3 (aa)

<400> SEQUENCE: 551

Ala Ala Trp Asp Gly Ser Leu Asn Gly Leu Val
1               5                   10

<210> SEQ ID NO 552
<211> LENGTH: 113
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-44 VL chain (aa)

<400> SEQUENCE: 552

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Asn Leu Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Thr Phe Gly Gln Gly Thr Lys Leu Glu Ile
            100                 105                 110

Lys

<210> SEQ ID NO 553
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-45 VL chain (aa)

<400> SEQUENCE: 553

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Arg Ser
            20                  25                  30

Leu Ala Trp Tyr Lys Gln Lys Pro Gly Gly Val Pro Gln Leu Leu Ile
        35                  40                  45

His Asp Ala Ser Ser Leu Arg Ser Gly Val Pro Ser Arg Phe Ser Gly
50                  55                  60

Ser Gly Ser Gly Thr Glu Phe Thr Leu Thr Ile Ser Gly Val Gln Ser
65                  70                  75                  80

Glu Asp Ser Ala Thr Tyr His Cys Gln Gln Leu Asn Gly Tyr Pro Trp
                85                  90                  95

Thr Phe Gly Gln Gly Thr Lys Val Asp Ile Lys
            100                 105

<210> SEQ ID NO 554
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-47 VL chain (aa)

<400> SEQUENCE: 554

Gln Ala Val Leu Thr Gln Pro Pro Ser Val Ser Val Ala Pro Gly Lys
1               5                   10                  15

Thr Ala Thr Ile Thr Cys Gly Gly Asn Asn Ile Gly Ser Lys Ser Val
            20                  25                  30

```
His Trp Tyr Gln Arg Lys Pro Gly Gln Gly Pro Val Val Ile Gln
            35                  40                  45

Tyr Asp Thr Asp Arg Pro Ser Gly Ile Pro Glu Arg Phe Ser Gly Ser
 50                  55                  60

Lys Ser Gly Asp Thr Ala Ser Leu Thr Ile Ser Gly Val Glu Ala Gly
 65                  70                  75                  80

Asp Glu Ala Asp Tyr Tyr Cys Gln Leu Trp Asp Ser Asp Ser Asp Asp
                 85                  90                  95

Phe Ala Phe Gly Thr Gly Thr Lys Leu Thr Val Leu
            100                 105

<210> SEQ ID NO 555
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-48 VL chain (aa)

<400> SEQUENCE: 555

Gln Pro Val Leu Thr Gln Pro Pro Ser Val Ser Val Ala Pro Gly Lys
 1               5                  10                  15

Thr Ala Thr Ile Thr Cys Gly Gly Asn Asn Ile Gly Ser Lys Ser Val
            20                  25                  30

His Trp Tyr Gln Arg Lys Pro Gly Gln Gly Pro Val Val Ile Gln
            35                  40                  45

Tyr Asp Thr Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Gly Asp Tyr Tyr Cys Gln Val Trp Asp Ser Ser Ser Asp His
                 85                  90                  95

Trp Val Phe Gly Gly Gly Thr Lys Leu Thr Val Leu
            100                 105

<210> SEQ ID NO 556
<211> LENGTH: 109
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 VL chain (aa)

<400> SEQUENCE: 556

Leu Pro Val Leu Thr Gln Pro Pro Ser Val Ser Val Ala Pro Gly Lys
 1               5                  10                  15

Thr Ala Arg Ile Thr Cys Gly Gly Asp Gln Ile Gly Arg Lys Ser Val
            20                  25                  30

His Trp Tyr Gln Gln Lys Pro Gly Gln Ala Pro Val Leu Val Met Ser
            35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Ala Tyr Tyr Cys Gln Val Trp Asp Ser Ser Thr Gly Gln
                 85                  90                  95
```

```
Tyr Val Val Phe Gly Gly Gly Thr Lys Leu Thr Val Leu
                100                 105
```

```
<210> SEQ ID NO 557
<211> LENGTH: 108
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 VL chain (aa)

<400> SEQUENCE: 557

Ala Ile Gln Leu Thr Gln Ser Pro Ser Thr Leu Ser Ala Ser Val Gly
1               5                   10                  15

Asp Arg Val Ala Ile Thr Cys Arg Ala Ser Gln Asn Ile Gly Asp Trp
            20                  25                  30

Leu Ala Trp Tyr Gln Gln Lys Pro Gly Lys Ala Pro Lys Leu Leu Ile
        35                  40                  45

Phe Gly Ala Ser Ile Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Val Tyr Tyr Cys Gln Lys Tyr Asp Gly Ala Pro Pro
                85                  90                  95

Trp Thr Phe Gly Gln Gly Thr Lys Val Glu Ile Lys
            100                 105
```

```
<210> SEQ ID NO 558
<211> LENGTH: 250
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-24 scFv sequence (aa)
<220> FEATURE:
<221> NAME/KEY: VARIANT
<222> LOCATION: 204
<223> OTHER INFORMATION: Xaa = any amino acid

<400> SEQUENCE: 558

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Trp
                100                 105                 110

Gly Gln Gly Thr Met Val Thr Val Ser Ser Gly Gly Gly Gly Ser Gly
            115                 120                 125

Gly Gly Gly Ser Gly Gly Gly Gly Ser Asp Ile Val Met Thr Gln Ser
        130                 135                 140
```

```
Pro Asp Ser Leu Ala Val Ser Leu Gly Glu Arg Ala Thr Ile Asn Cys
145                 150                 155                 160

Lys Ser Ser Gln Ser Val Leu Tyr Ser Ser Asn Asn Lys Asn Tyr Leu
            165                 170                 175

Ala Trp Tyr Gln Gln Lys Pro Gly Gln Pro Pro Lys Leu Leu Ile Tyr
            180                 185                 190

Trp Gly Ser Thr Arg Glu Ser Gly Val Pro Asp Xaa Phe Ser Gly Ser
            195                 200                 205

Gly Ser Gly Thr Asp Phe Thr Leu Thr Ile Ser Ser Leu Gln Ala Glu
            210                 215                 220

Asp Val Ala Ile Tyr His Cys Gln Gln Tyr Ile Ser Leu Pro Trp Thr
225                 230                 235                 240

Phe Gly Gln Gly Thr Lys Val Glu Ile Lys
            245                 250

<210> SEQ ID NO 559
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-25 scFv sequence (aa)

<400> SEQUENCE: 559

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Asp Ile Gln Met Thr Gln Ser Pro Ala Phe Leu
        130                 135                 140

Ser Ala Ser Val Gly Asp Arg Val Thr Val Thr Cys Arg Ala Ser Gln
145                 150                 155                 160

Gly Ile Ser Asn Tyr Leu Ala Trp Tyr Gln Gln Lys Pro Gly Asn Ala
            165                 170                 175

Pro Arg Leu Leu Ile Tyr Ser Ala Ser Thr Leu Gln Ser Gly Val Pro
            180                 185                 190

Ser Arg Phe Arg Gly Thr Gly Tyr Gly Thr Glu Phe Ser Leu Thr Ile
            195                 200                 205

Asp Ser Leu Gln Pro Glu Asp Phe Ala Thr Tyr Tyr Cys Gln Gln Ser
            210                 215                 220

Tyr Thr Ser Arg Gln Thr Phe Gly Pro Gly Thr Arg Leu Asp Ile Lys
225                 230                 235                 240
```

<210> SEQ ID NO 560
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-26 scFv sequence (aa)

<400> SEQUENCE: 560

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ser Tyr Val Leu Thr Gln Pro Pro Ser Val Ser
    130                 135                 140

Val Ala Pro Gly Gln Thr Ala Arg Ile Thr Cys Gly Ala Asn Asn Ile
145                 150                 155                 160

Gly Ser Lys Ser Val His Trp Tyr Gln Gln Lys Pro Gly Gln Ala Pro
                165                 170                 175

Met Leu Val Val Tyr Asp Asp Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Leu Trp Asp
    210                 215                 220

Arg Ser Arg Asp His Tyr Val Phe Gly Thr Gly Thr Lys Leu Thr Val
225                 230                 235                 240

Leu

<210> SEQ ID NO 561
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-27 scFv sequence (aa)

<400> SEQUENCE: 561

Glu Val Gln Leu Leu Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

```
Ser Gly Ile Ser Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Gly Leu Gly Ile Thr Pro Tyr Tyr Phe Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Gln Pro Val Leu Thr Gln Pro Pro
        130                 135                 140

Ser Ala Ser Gly Thr Pro Gly Gln Arg Val Thr Ile Ser Cys Ser Gly
145                 150                 155                 160

Gly Lys Thr Val Asn Trp Phe Arg Gln Val Pro Gly Thr Ala Pro Gln
                165                 170                 175

Leu Leu Ile Tyr Ser Asn Asp Gln Arg Pro Ser Gly Val Pro Asp Arg
                180                 185                 190

Phe Ser Gly Ser Lys Ser Gly Ser Ala Ser Leu Asp Ile Ser Gly
            195                 200                 205

Leu Gln Ser Glu Asp Glu Ala Tyr Tyr Tyr Cys Gly Ser Trp Asp Asp
            210                 215                 220

Ser Leu Asn Ala Trp Val Phe Gly Gly Glu Thr Lys Leu Thr Val Leu
225                 230                 235                 240
```

<210> SEQ ID NO 562
<211> LENGTH: 250
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-28 scFv sequence (aa)
<220> FEATURE:
<221> NAME/KEY: VARIANT
<222> LOCATION: 59
<223> OTHER INFORMATION: Xaa = any amino acid

<400> SEQUENCE: 562

```
Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Xaa Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Gly Pro Pro Tyr Gly Asp Asp Ala Phe Asp Ile Gly
            100                 105                 110

Gly Gln Gly Thr Met Val Thr Val Ser Ser Gly Gly Gly Gly Ser Gly
            115                 120                 125

Gly Gly Gly Ser Gly Gly Gly Gly Ser Asp Ile Val Met Thr Gln Ser
        130                 135                 140
```

```
Pro Leu Ser Leu Ser Val Thr Pro Gly Glu Pro Ala Ser Ile Ser Cys
145                 150                 155                 160

Arg Ser Ser Gln Ser Leu Leu His Ser Asn Gly Tyr Asn Tyr Leu Asp
            165                 170                 175

Trp Tyr Leu Gln Lys Pro Gly Gln Ser Pro Gln Leu Leu Ile Tyr Leu
            180                 185                 190

Gly Ser Asn Arg Ala Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
            210                 215                 220

Val Gly Val Tyr Tyr Cys Met Gln Ala Leu Gln Thr Pro Pro Trp Thr
225                 230                 235                 240

Phe Gly Gln Gly Thr Lys Val Glu Ile Lys
                245                 250

<210> SEQ ID NO 563
<211> LENGTH: 249
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-29 scFv sequence (aa)
<220> FEATURE:
<221> NAME/KEY: VARIANT
<222> LOCATION: 242
<223> OTHER INFORMATION: Xaa = any amino acid

<400> SEQUENCE: 563

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Trp
            100                 105                 110

Gly Gln Gly Thr Met Val Thr Val Ser Ser Gly Gly Gly Gly Ser Gly
            115                 120                 125

Gly Gly Gly Ser Gly Gly Gly Gly Ser Gln Pro Val Leu Thr Gln Pro
        130                 135                 140

Ala Ser Val Ser Gly Ser Pro Gly Gln Ser Ile Thr Ile Ser Cys Thr
145                 150                 155                 160

Gly Thr Ser Ser Asp Val Gly Ser Tyr Asn Leu Val Ser Trp Tyr Gln
                165                 170                 175

Gln His Pro Gly Lys Ala Pro Lys Leu Met Ile Tyr Glu Val Ser Lys
            180                 185                 190

Arg Pro Ser Gly Val Ser Asn Arg Phe Ser Gly Ser Lys Ser Gly Asn
            195                 200                 205

Thr Ala Ser Pro Thr Ile Ser Gly Leu Gln Ala Glu Asp Glu Ala Asp
        210                 215                 220
```

-continued

```
Tyr Tyr Cys Cys Ser Tyr Ala Gly Ser Ser Thr Ser Arg Asp Val Phe
225                 230                 235                 240

Gly Xaa Gly Thr Lys Leu Thr Val Leu
            245
```

<210> SEQ ID NO 564
<211> LENGTH: 239
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-30 scFv sequence (aa)

<400> SEQUENCE: 564

```
Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asp Pro Asp Asp Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ala Thr
    130                 135                 140

Leu Ser Val Ser Pro Gly Glu Arg Ala Thr Leu Ser Cys Arg Ala Ser
145                 150                 155                 160

Gln Pro Ile Arg Ser Asn Leu Ala Trp Tyr Gln Gln Lys Pro Gly Gln
                165                 170                 175

Ala Pro Lys Leu Leu Ile Tyr Ser Ala Ser Thr Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu His Glu Asp Phe Ala Val Tyr Tyr Arg Arg His
    210                 215                 220

Tyr Ala Pro Leu Thr Phe Gly Gly Gly Thr Lys Val Glu Ile Lys
225                 230                 235
```

<210> SEQ ID NO 565
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-31 scFv sequence (aa)

<400> SEQUENCE: 565

```
Glu Val Gln Leu Val Gln Ser Gly Gly Gly Leu Val Gln Pro Gly Arg
1               5                   10                  15
```

```
Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Val Val Met Thr Gln Ser Pro Asp Ser Leu
    130                 135                 140

Ala Val Ser Leu Gly Glu Arg Ala Thr Ile Ser Cys Lys Ser Ser Gln
145                 150                 155                 160

Ser Val Leu Asn Ser Ser Asn Asn Lys Asn Tyr Val Ala Trp Tyr Lys
                165                 170                 175

Gln Lys Pro Gly Gln Pro Pro Lys Leu Val Ile Ser Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Tyr Tyr Ser Thr Pro Tyr Thr Phe Gly Gln Gly
225                 230                 235                 240

Thr Lys Leu Asp Ile Lys
                245

<210> SEQ ID NO 566
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-32 scFv sequence (aa)

<400> SEQUENCE: 566

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110
```

Met Val Thr Val Ser Ser Gly Gly Gly Ser Gly Gly Gly Ser
            115                 120                 125

Gly Gly Gly Gly Ser Gln Thr Val Thr Gln Pro Pro Ser Val Ser
130                 135                 140

Val Ala Pro Gly Gln Thr Ala Arg Ile Thr Cys Gly Gly Asn Asn Ile
145                 150                 155                 160

Gly Ser Lys Gly Val His Trp Tyr Arg Gln Arg Pro Gly Gln Ala Pro
                165                 170                 175

Glu Val Val Ile Tyr Asp Asp Ser Asp Arg Pro Ser Gly Val Pro Asp
                180                 185                 190

Arg Phe Ser Gly Ser Asn Ser Gly Asn Thr Ala Thr Leu Thr Val Arg
            195                 200                 205

Gly Val Glu Ala Gly Asp Glu Ala Asp Tyr Tyr Cys Gln Val Trp Asp
210                 215                 220

Ser Ser Ser Asp His Trp Val Phe Gly Gly Gly Thr Lys Leu Thr Val
225                 230                 235                 240

Leu

<210> SEQ ID NO 567
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-33 scFv sequence (aa)

<400> SEQUENCE: 567

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asp Ser Ser Ala Asp Tyr Trp Gly Gln Gly Thr Leu
            100                 105                 110

Val Asn Val Ser Ser Gly Gly Gly Gly Ser Gly Gly Gly Gly Ser Gly
        115                 120                 125

Gly Gly Gly Ser Gln Pro Val Leu Thr Gln Pro Pro Ser Val Ser Val
    130                 135                 140

Ala Pro Gly Lys Thr Ala Met Ile Thr Cys Gly Gly Asn Asn Ile Gly
145                 150                 155                 160

Phe Lys Gly Val Gln Trp Tyr Gln Gln Lys Thr Gly Gln Ala Pro Val
                165                 170                 175

Leu Val Val Tyr Asp Asp Ser Asp Arg Pro Ser Gly Ile Pro Glu Arg
                180                 185                 190

Phe Ser Gly Ser Asn Ser Gly Asn Thr Ala Thr Leu Thr Ile Ser Arg
            195                 200                 205

Val Glu Ala Gly Asp Glu Ala Asp Tyr Tyr Cys Gln Val Trp Asp Ser
    210                 215                 220

Ala Ser Asp His Trp Val Phe Gly Gly Gly Thr Lys Leu Thr Val Leu
225                 230                 235                 240

<210> SEQ ID NO 568
<211> LENGTH: 245
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-34 scFv sequence (aa)

<400> SEQUENCE: 568

Thr Gly Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Asp Tyr Asp Pro Ala Phe Asp Ile Trp
            100                 105                 110

Gly Gln Gly Thr Met Val Thr Val Ser Ser Gly Gly Gly Gly Ser Gly
            115                 120                 125

Gly Gly Gly Ser Gly Gly Gly Gly Ser Glu Ile Val Met Thr Gln Ser
        130                 135                 140

Pro Ala Thr Leu Ser Leu Ser Pro Gly Asp Arg Ala Thr Leu Ser Cys
145                 150                 155                 160

Arg Ala Ser Gln Ser Ile Ser Asn Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Arg Ser Asn Trp Pro Pro Tyr Thr Phe Gly Gln Gly Thr
225                 230                 235                 240

Lys Leu Asp Ile Lys
            245

<210> SEQ ID NO 569
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-35 scFv sequence (aa)

<400> SEQUENCE: 569

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Asp Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Asn Phe Met Leu Thr Gln Pro Pro Ser Val Ser Val
130                 135                 140

Ala Pro Gly Gln Thr Ala Arg Ile Thr Cys Gly Ala Asn Asn Ile Gly
145                 150                 155                 160

Ser Lys Ser Val His Trp Tyr Gln Gln Lys Pro Gly Gln Ala Pro Met
                165                 170                 175

Leu Val Val Tyr Asp Asp Asp Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Val Glu Ala Gly Asp Glu Ala Asp Tyr Phe Cys His Leu Trp Asp Arg
210                 215                 220

Ser Arg Asp His Tyr Val Phe Gly Thr Gly Thr Lys Leu Asp Ile Lys
225                 230                 235                 240
```

<210> SEQ ID NO 570
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-36 scFv sequence (aa)

<400> SEQUENCE: 570

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Val Asp Gly Asp Tyr Val Asp Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Gln Ser Val Leu Thr Gln Glu Pro Ser Leu Thr
            130                 135                 140

Val Ser Pro Gly Glu Thr Val Thr Leu Thr Cys Gly Ser Ser Thr Gly
145                 150                 155                 160

Pro Val Thr Ser Ala His Ser Pro Ser Trp Phe Gln Lys Lys Pro Gly
                165                 170                 175

Gln Ala Pro Thr Thr Leu Ile Tyr Glu Thr Thr Asn Arg His Ser Trp
            180                 185                 190

Thr Pro Ala Arg Phe Ser Gly Ser Leu Leu Gly Gly Lys Ala Ala Leu
            195                 200                 205

Thr Leu Ser Gly Ala Gln Pro Glu Asp Glu Ala Asp Tyr Tyr Cys Leu
            210                 215                 220

Leu Ser Ser Gly Asp Ala Arg Met Val Phe Gly Gly Gly Thr Lys Leu
225                 230                 235                 240

Thr Val Leu

<210> SEQ ID NO 571
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-37 scFv sequence (aa)

<400> SEQUENCE: 571

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Gln Leu Val Leu Thr Gln Glu Pro Ser Leu Thr
            130                 135                 140

Val Ser Pro Gly Gly Thr Val Thr Leu Thr Cys Gly Ser Ser Thr Gly
145                 150                 155                 160

Ala Val Thr Asn Gly His Ser Pro Tyr Trp Phe Gln Gln Lys Pro Gly
                165                 170                 175

Gln Ala Pro Arg Thr Leu Ile Tyr Asp Thr Thr Asn Arg His Ser Trp
            180                 185                 190
```

Thr Pro Ala Arg Phe Ser Gly Ser Leu Leu Gly Gly Lys Ala Ala Leu
        195                 200                 205

Thr Leu Ser Gly Ala Gln Pro Glu Asp Glu Ala Glu Tyr Tyr Cys Ser
        210                 215                 220

Leu Ser His Ala Gly Asp Arg Val Phe Phe Gly Gly Gly Thr Lys Leu
225                 230                 235                 240

Thr Val Leu

<210> SEQ ID NO 572
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-38 scFv sequence (aa)

<400> SEQUENCE: 572

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asp Gly Asp Tyr Val Asp Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Val Leu Thr Gln Glu Pro Ser Leu Thr
130                 135                 140

Val Ser Pro Gly Gly Thr Val Thr Leu Thr Cys Gly Ser Ser Thr Gly
145                 150                 155                 160

Ala Val Thr Asn Gly His Ser Pro Tyr Trp Phe Gln Gln Lys Pro Gly
                165                 170                 175

Gln Ala Pro Arg Thr Leu Ile Tyr Asp Thr Asn Asn Arg His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Glu Asp Glu Ala Asp Tyr Phe Cys Leu
        210                 215                 220

Leu Ser Tyr Ser Asp Ala Arg Leu Ala Phe Gly Gly Gly Thr Lys Leu
225                 230                 235                 240

Thr Val Leu

<210> SEQ ID NO 573
<211> LENGTH: 244
<212> TYPE: PRT
<213> ORGANISM: Artificial Sequence
<220> FEATURE:
<223> OTHER INFORMATION: Synthetic
<220> FEATURE:

<223> OTHER INFORMATION: BCMA-39 scFv sequence (aa)
<220> FEATURE:
<221> NAME/KEY: VARIANT
<222> LOCATION: 141
<223> OTHER INFORMATION: Xaa = any amino acid
<220> FEATURE:
<221> NAME/KEY: VARIANT
<222> LOCATION: 171
<223> OTHER INFORMATION: Xaa = any amino acid

<400> SEQUENCE: 573

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Pro Pro Tyr Gly Asp Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Asp Ile Gln Xaa Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Arg Tyr Glu Leu Xaa Trp Tyr Gln Gln Lys
                165                 170                 175

Pro Gly Lys Ala Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Ala Leu Thr Ile Arg Ser Leu Gln Pro Glu Asp Phe Ala Thr Tyr Tyr
    210                 215                 220

Cys Leu Gln His Asn Ser Tyr Pro Leu Thr Phe Gly Arg Gly Thr Lys
225                 230                 235                 240

Leu Glu Ile Lys

<210> SEQ ID NO 574
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-40 scFv sequence (aa)

<400> SEQUENCE: 574

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Asp Tyr Thr Glu Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gln Ser Ala Leu Thr Gln Pro Ala Ser Val Ser
        130                 135                 140

Gly Ser Pro Gly Gln Ser Ile Thr Ile Ser Cys Thr Gly Ser Ser Ser
145                 150                 155                 160

Asp Val Ser Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
                180                 185                 190

Val Ser Asn Arg Phe Ser Gly Ser Lys Ser Gly Asn Thr Ala Thr Leu
            195                 200                 205

Thr Ile Ser Gly Leu Gln Gly Asp Asp Glu Ala Asp Tyr Tyr Cys Cys
        210                 215                 220

Ser Tyr Gly Gly Ser Arg Ser Tyr Val Phe Gly Thr Gly Thr Lys Leu
225                 230                 235                 240

Thr Val Leu

<210> SEQ ID NO 575
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-41 scFv sequence (aa)

<400> SEQUENCE: 575

Gln Val Gln Leu Val Gln Ser Gly Gly Gly Leu Val Lys Pro Gly Gly
 1                   5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Asp Tyr Val Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gln Pro Val Leu Thr Gln Pro Pro Ser Val Ser
        130                 135                 140

```
Gly Thr Pro Gly Gln Arg Val Thr Ile Pro Cys Ser Gly Ser Ser
145                 150                 155                 160

Asn Ile Gly Gly Asn Ser Val Asp Trp Phe Gln Glu Val Pro Gly Thr
                165                 170                 175

Ala Pro Lys Leu Leu Ile Tyr Ala Asn Asp Arg Arg Pro Ser Gly Val
            180                 185                 190

Pro Asp Arg Phe Ser Gly Thr Lys Ser Gly Thr Ser Ala Ser Leu Ala
        195                 200                 205

Ile Arg Gly Leu Gln Ser Asp Asp Ala His Tyr Tyr Cys Glu Ser
    210                 215                 220

Trp Asp Asp Ala Leu Asn Gly His Val Phe Gly Gly Gly Thr Lys Leu
225                 230                 235                 240

Thr Val Leu

<210> SEQ ID NO 576
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-42 scFv sequence (aa)

<400> SEQUENCE: 576

Glu Val Gln Leu Leu Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Ile Gln Met Thr Gln Ser Pro Ser Leu Val
    130                 135                 140

Ser Ala Ser Val Gly Asp Arg Val Thr Ile Thr Cys Arg Ala Ser Gln
145                 150                 155                 160

Gly Ile Gly Asn Gly Leu Ala Trp Tyr Gln Gln Lys Pro Gly Lys Ala
                165                 170                 175

Pro Lys Leu Leu Leu Phe Ala Ala Ser Arg Leu Glu Ser Gly Val Pro
            180                 185                 190

Ser Arg Phe Ser Gly Ser Arg Ser Gly Thr Asp Tyr Thr Leu Thr Ile
        195                 200                 205

Ser Ser Leu Gln Pro Glu Asp Val Ala Thr Tyr Tyr Cys Gln Gln Tyr
    210                 215                 220

Val Glu Asp Ala Leu Thr Phe Gly Gly Gly Thr Lys Val Asp Ile Lys
225                 230                 235                 240
```

<210> SEQ ID NO 577
<211> LENGTH: 116
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-52 VH (aa)

<400> SEQUENCE: 577

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115

<210> SEQ ID NO 578
<211> LENGTH: 246
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-44 scFv sequence (aa)

<400> SEQUENCE: 578

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Val Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Asn Leu Leu Tyr Ser Ser Asn Asn Lys Asn Tyr Leu Ala Trp Tyr Gln
                165                 170                 175

-continued

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
210                 215                 220

Tyr Tyr Cys Gln Gln Tyr Tyr Ser Ser Pro Tyr Thr Phe Gly Gln Gly
225                 230                 235                 240

Thr Lys Leu Glu Ile Lys
                245

<210> SEQ ID NO 579
<211> LENGTH: 240
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-45 scFv sequence (aa)

<400> SEQUENCE: 579

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Ser Gly Gly Gly Ser
        115                 120                 125

Gly Gly Gly Gly Ser Ala Ile Arg Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Gly Ile Gly Arg Ser Leu Ala Trp Tyr Lys Gln Lys Pro Gly Gly Val
                165                 170                 175

Pro Gln Leu Leu Ile His Asp Ala Ser Ser Leu Arg Ser Gly Val Pro
            180                 185                 190

Ser Arg Phe Ser Gly Ser Gly Ser Gly Thr Glu Phe Thr Leu Thr Ile
        195                 200                 205

Ser Gly Val Gln Ser Glu Asp Ser Ala Thr Tyr His Cys Gln Gln Leu
    210                 215                 220

Asn Gly Tyr Pro Trp Thr Phe Gly Gln Gly Thr Lys Val Asp Ile Lys
225                 230                 235                 240

<210> SEQ ID NO 580
<211> LENGTH: 241
<212> TYPE: PRT
<213> ORGANISM: Artificial Sequence
<220> FEATURE:

<223> OTHER INFORMATION: Synthetic
<220> FEATURE:
<223> OTHER INFORMATION: BCMA-47 scFv sequence (aa)

<400> SEQUENCE: 580

```
Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Asp Ser Pro Ser Pro Gly Thr Thr Pro Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Arg Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gln Ala Val Leu Thr Gln Pro Pro Ser Val Ser
    130                 135                 140

Val Ala Pro Gly Lys Thr Ala Thr Ile Thr Cys Gly Gly Asn Asn Ile
145                 150                 155                 160

Gly Ser Lys Ser Val His Trp Tyr Gln Arg Lys Pro Gly Gln Gly Pro
                165                 170                 175

Val Val Val Ile Gln Tyr Asp Thr Asp Arg Pro Ser Gly Ile Pro Glu
            180                 185                 190

Arg Phe Ser Gly Ser Lys Ser Gly Asp Thr Ala Ser Leu Thr Ile Ser
        195                 200                 205

Gly Val Glu Ala Gly Asp Glu Ala Asp Tyr Tyr Cys Gln Leu Trp Asp
    210                 215                 220

Ser Asp Ser Asp Asp Phe Ala Phe Gly Thr Gly Thr Lys Leu Thr Val
225                 230                 235                 240

Leu
```

<210> SEQ ID NO 581
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-48 scFv sequence (aa)

<400> SEQUENCE: 581

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Gln Pro Val Leu Thr Gln Pro Pro Ser Val Ser
        130                 135                 140

Val Ala Pro Gly Lys Thr Ala Thr Ile Thr Cys Gly Gly Asn Asn Ile
145                 150                 155                 160

Gly Ser Lys Ser Val His Trp Tyr Gln Arg Lys Pro Gly Gln Gly Pro
                165                 170                 175

Val Val Val Ile Gln Tyr Asp Thr Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Arg Val Glu Ala Gly Asp Glu Gly Asp Tyr Tyr Cys Gln Val Trp Asp
    210                 215                 220

Ser Ser Ser Asp His Trp Val Phe Gly Gly Gly Thr Lys Leu Thr Val
225                 230                 235                 240

Leu

<210> SEQ ID NO 582
<211> LENGTH: 242
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-49 scFv sequence (aa)

<400> SEQUENCE: 582

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Leu Pro Val Leu Thr Gln Pro Pro Ser Val Ser
        130                 135                 140

Val Ala Pro Gly Lys Thr Ala Arg Ile Thr Cys Gly Gly Asp Gln Ile
145                 150                 155                 160

Gly Arg Lys Ser Val His Trp Tyr Gln Gln Lys Pro Gly Gln Ala Pro
                165                 170                 175
```

-continued

Val Leu Val Met Ser Tyr Asp Ser Asp Arg Pro Ser Gly Ile Pro Glu
              180                 185                 190

Arg Phe Ser Gly Ser Asn Ser Gly Asn Thr Ala Thr Leu Thr Ile Ser
          195                 200                 205

Arg Val Glu Ala Gly Asp Glu Ala Ala Tyr Tyr Cys Gln Val Trp Asp
    210                 215                 220

Ser Ser Thr Gly Gln Tyr Val Val Phe Gly Gly Thr Lys Leu Thr
225             230                 235                 240

Val Leu

<210> SEQ ID NO 583
<211> LENGTH: 241
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-51 scFv sequence (aa)

<400> SEQUENCE: 583

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Ile Gln Leu Thr Gln Ser Pro Ser Thr Leu
    130                 135                 140

Ser Ala Ser Val Gly Asp Arg Val Ala Ile Thr Cys Arg Ala Ser Gln
145                 150                 155                 160

Asn Ile Gly Asp Trp Leu Ala Trp Tyr Gln Gln Lys Pro Gly Lys Ala
                165                 170                 175

Pro Lys Leu Leu Ile Phe Gly Ala Ser Ile Leu Glu Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Val Ala Val Tyr Tyr Cys Gln Lys Tyr
    210                 215                 220

Asp Gly Ala Pro Pro Trp Thr Phe Gly Gln Gly Thr Lys Val Glu Ile
225                 230                 235                 240

Lys

<210> SEQ ID NO 584
<211> LENGTH: 729
<212> TYPE: DNA
<213> ORGANISM: Artificial Sequence

```
<220> FEATURE:
<223> OTHER INFORMATION: Synthetic
<220> FEATURE:
<223> OTHER INFORMATION: BCMA-41 scFv sequence (nt)

<400> SEQUENCE: 584
caggtgcagc tggtgcaatc tgggggaggc ttggtcaagc ctggagggtc cctgagactc        60
tcctgtgcag cctctggatt caccttcagt gactactaca tgagctggat ccgccaggct       120
ccagggaagg ggctggagtg ggtttcatac attagtagta gtggtaatac catatactac       180
gcagactctg taaagggccg attcaccatc tccagggaca acgccaaaaa ctcactgtat       240
ctgcaaatga acagcctgag agccgaggac acggccgtgt attactgtgc gaaagtggac       300
ggtgactacg tcgatgacta ctggggccag ggaaccctgg tcaccgtctc ctcaggtgga       360
ggcggttcag gcggaggtgg ctctggcggt ggcggatcgc agcctgtgct gactcagcca       420
ccctcagtgt ctgggacccc cgggcagagg gtcaccatcc cttgttctgg aagcagctcc       480
aacatcggag gtaactctgt agactggttc caggaggtcc agggacggc ccccaaactc        540 ctcatctacg ctaatgatcg gcggccctcg ggtgtccctg accgcttctc tggcaccaag       600
tcgggcacct cagcctccct ggccatcagg gggctccagt ctgacgatga cgctcattat       660
tactgtgaat cctgggacga tgccctgaac ggtcacgtgt tcggcggagg gaccaagctg       720
accgtccta                                                                  729
```

```
<210> SEQ ID NO 585
<211> LENGTH: 243
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C1 VH-VL scFv (aa)

<400> SEQUENCE: 585

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile His Trp Tyr Gln Gln Lys Pro
                165                 170                 175
```

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
            195                 200                 205

Leu Thr Ile Asp Pro Val Glu Glu Asp Val Ala Val Tyr Tyr Cys
210                 215                 220

Leu Gln Ser Arg Thr Ile Pro Arg Thr Phe Gly Gly Gly Thr Lys Leu
225                 230                 235                 240

Glu Ile Lys

<210> SEQ ID NO 586
<211> LENGTH: 244
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-C2  VL-VH scFv (aa)

<400> SEQUENCE: 586

Asp Val Val Met Thr Gln Ser His Arg Phe Met Ser Thr Ser Val Gly
1               5                   10                  15

Asp Arg Val Ser Ile Thr Cys Arg Ala Ser Gln Asp Val Asn Thr Ala
            20                  25                  30

Val Ser Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
            85                  90                  95

Thr Phe Gly Gly Gly Thr Lys Leu Asp Ile Lys Gly Gly Gly Gly Ser
            100                 105                 110

Gly Gly Gly Gly Ser Gly Gly Gly Ser Gln Ile Gln Leu Val Gln
            115                 120                 125

Ser Gly Pro Asp Leu Lys Lys Pro Gly Glu Thr Val Lys Leu Ser Cys
130                 135                 140

Lys Ala Ser Gly Tyr Thr Phe Thr Asn Phe Gly Met Asn Trp Val Lys
145                 150                 155                 160

Gln Ala Pro Gly Lys Gly Phe Lys Trp Met Ala Trp Ile Asn Thr Tyr
            165                 170                 175

Thr Gly Glu Ser Tyr Phe Ala Asp Asp Phe Lys Gly Arg Phe Ala Phe
            180                 185                 190

Ser Val Glu Thr Ser Ala Thr Thr Ala Tyr Leu Gln Ile Asn Asn Leu
        195                 200                 205

Lys Thr Glu Asp Thr Ala Thr Tyr Phe Cys Ala Arg Gly Glu Ile Tyr
210                 215                 220

Tyr Gly Tyr Asp Gly Gly Phe Ala Tyr Trp Gly Gln Gly Thr Leu Val
225                 230                 235                 240

Thr Val Ser Ala

<210> SEQ ID NO 587
<211> LENGTH: 111
<212> TYPE: PRT
<213> ORGANISM: Artificial Sequence

```
<220> FEATURE:
<223> OTHER INFORMATION: Synthetic
<220> FEATURE:
<223> OTHER INFORMATION: BCMA-52 VL (aa)

<400> SEQUENCE: 587

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110

<210> SEQ ID NO 588
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 CDR-H1 (aa)

<400> SEQUENCE: 588

Gly Tyr Thr Phe Ile Asp Tyr Tyr
1               5

<210> SEQ ID NO 589
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 CDR-H2 (aa)

<400> SEQUENCE: 589

Ile Asn Pro Asn Ser Gly Gly Thr
1               5

<210> SEQ ID NO 590
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 CDR-H3 (aa)

<400> SEQUENCE: 590

Ala Arg Ser Gln Arg Asp Gly Tyr Met Asp Tyr
1               5                   10

<210> SEQ ID NO 591
<211> LENGTH: 9
<212> TYPE: PRT
<213> ORGANISM: Artificial Sequence
<220> FEATURE:
```

<223> OTHER INFORMATION: Synthetic
<220> FEATURE:
<223> OTHER INFORMATION: BCMA-55 CDR-L1 (aa)

<400> SEQUENCE: 591

Ile Ser Cys Thr Gly Thr Ser Ser Asp
1               5

<210> SEQ ID NO 592
<211> LENGTH: 3
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 CDR-L2 (aa)

<400> SEQUENCE: 592

Glu Asp Ser
1

<210> SEQ ID NO 593
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 CDR-L3 (aa)

<400> SEQUENCE: 593

Ser Ser Asn Thr Arg Ser Ser Thr Leu Val
1               5                   10

<210> SEQ ID NO 594
<211> LENGTH: 118
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA-55 VH (aa)

<400> SEQUENCE: 594

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115

<210> SEQ ID NO 595
<211> LENGTH: 105
<212> TYPE: PRT

```
<213> ORGANISM: Artificial Sequence
<220> FEATURE:
<223> OTHER INFORMATION: Synthetic
<220> FEATURE:
<223> OTHER INFORMATION: BCMA-55 VL (aa)

<400> SEQUENCE: 595

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105

<210> SEQ ID NO 596
<211> LENGTH: 24
<212> TYPE: PRT
<213> ORGANISM: Artificial Sequence
<220> FEATURE:
<223> OTHER INFORMATION: Synthetic
<220> FEATURE:
<223> OTHER INFORMATION: T2A

<400> SEQUENCE: 596

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 597
<211> LENGTH: 18
<212> TYPE: PRT
<213> ORGANISM: Artificial Sequence
<220> FEATURE:
<223> OTHER INFORMATION: Synthetic
<220> FEATURE:
<223> OTHER INFORMATION: T2A

<400> SEQUENCE: 597

Glu Gly Arg Gly Ser Leu Leu Thr Cys Gly Asp Val Glu Glu Asn Pro
1               5                   10                  15

Gly Pro

<210> SEQ ID NO 598
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: P2A

<400> SEQUENCE: 598

Gly Ser Gly Ala Thr Asn Phe Ser Leu Leu Lys Gln Ala Gly Asp Val
1               5                   10                  15
```

Glu Glu Asn Pro Gly Pro
            20

<210> SEQ ID NO 599
<211> LENGTH: 19
<212> TYPE: PRT
<213> ORGANISM: Artificial Sequence
<220> FEATURE:
<223> OTHER INFORMATION: Synthetic
<220> FEATURE:
<223> OTHER INFORMATION: P2A

<400> SEQUENCE: 599

Ala Thr Asn Phe Ser Leu Leu Lys Gln Ala Gly Asp Val Glu Asn
1               5                   10                  15

Pro Gly Pro

<210> SEQ ID NO 600
<211> LENGTH: 20
<212> TYPE: PRT
<213> ORGANISM: Artificial Sequence
<220> FEATURE:
<223> OTHER INFORMATION: Synthetic
<220> FEATURE:
<223> OTHER INFORMATION: E2A

<400> SEQUENCE: 600

Gln Cys Thr Asn Tyr Ala Leu Leu Lys Leu Ala Gly Asp Val Glu Ser
1               5                   10                  15

Asn Pro Gly Pro
            20

<210> SEQ ID NO 601
<211> LENGTH: 22
<212> TYPE: PRT
<213> ORGANISM: Artificial Sequence
<220> FEATURE:
<223> OTHER INFORMATION: Synthetic
<220> FEATURE:
<223> OTHER INFORMATION: F2A

<400> SEQUENCE: 601

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 602
<211> LENGTH: 357
<212> TYPE: PRT
<213> ORGANISM: Artificial Sequence
<220> FEATURE:
<223> OTHER INFORMATION: Synthetic
<220> FEATURE:
<223> OTHER INFORMATION: EGFRt

<400> SEQUENCE: 602

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
        50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
            85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
            165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
            245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
            325                 330                 335

Thr Gly Met Val Gly Ala Leu Leu Leu Leu Leu Val Val Ala Leu Gly
            340                 345                 350

Ile Gly Leu Phe Met
        355

<210> SEQ ID NO 603
<211> LENGTH: 335
<212> TYPE: PRT
<213> ORGANISM: Artificial Sequence
<220> FEATURE:
<223> OTHER INFORMATION: Synthetic
<220> FEATURE:
<223> OTHER INFORMATION: EGFRt

<400> SEQUENCE: 603

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
             100                 105                 110

Thr Ser Leu Gly Leu Arg Ser Leu Lys Glu Ile Ser Asp Gly Asp Val
         115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 604
<211> LENGTH: 720
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-25 scFv sequence (nt)

<400> SEQUENCE: 604
gaggtgcagc tggtgcagag cggaggaggc ctggtgcagc ctggcaggtc cctgcgcctg     60
tcttgcaccg ccagcggctt cacatttggc gactatgcca tgtcctggtt caggcaggca    120
ccaggcaagg gcctggagtg gtgggctttt atccgctcta aggcctacgg cggcaccaca    180
gagtatgccg ccagcgtgaa gggccggttc accatcagcc gggacgactc taagagcatc    240
gcctacctgc agatgaactc tctgaagacc gaggacacag ccgtgtacta ttgcgcagca    300
tggagcgccc caaccgatta ttggggccag ggcaccctgg tgacagtgag ctccggcggc    360
ggcggctctg gaggaggagg aagcggagga ggaggatccg acatccagat gacacagtcc    420

```
cctgcctttc tgtccgcctc tgtgggcgat agggtgaccg tgacatgtcg cgcctcccag      480
ggcatctcta actacctggc ctggtatcag cagaagccg gcaatgcccc tcggctgctg      540
atctacagcg cctccaccct gcagagcgga gtgccctccc ggttcagagg aaccggctat      600
ggcacagagt tttctctgac catcgacagc ctgcagccag aggatttcgc cacatactat      660
tgtcagcagt cttacaccag ccggcagaca tttggccccg gcacaagact ggatatcaag      720
```

<210> SEQ ID NO 605
<211> LENGTH: 723
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-26 scFv sequence (nt)

<400> SEQUENCE: 605

```
gaggtgcagc tggtggagtc cggaggaggc ctggtgaagc caggaggctc tctgaggctg       60
agctgcgcag cctccggctt caccttttct gactactata tgagctggat caggcaggca      120
ccaggcaagg gcctggagtg ggtgtcttac atcagctcct ctggcagcac aatctactat      180
gccgactccg tgaagggcag gttcaccatc tctcgcgata cgccaagaa tagcctgtat      240 ctgcagatga actccctgcg ggccgaggat acagccgtgt actattgcgc caaggtggac      300
ggcccccctt cctttgatat ctggggccag ggcacaatgg tgaccgtgag ctccggagga      360
ggaggatccg gcggaggagg ctctggcggc ggcggctcta gctatgtgct gacccagcca      420
ccatccgtgt ctgtggcacc tggacagaca gcaaggatca cctgtggagc aaacaatatc      480
ggcagcaagt ccgtgcactg gtaccagcag aagcctggcc aggcccccaat gctggtggtg      540 tatgacgatg acgatcggcc cagcggcatc cctgagagat tttctggcag caactccggc      600
aataccgcca cactgaccat ctctggagtg gaggcaggcg acgaggcaga ttacttctgt      660
cacctgtggg accggagcag agatcactac gtgttcggca caggcaccaa gctgaccgtg      720
ctg                                                                   723
```

<210> SEQ ID NO 606
<211> LENGTH: 744
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-52 scFv sequence (nt)

<400> SEQUENCE: 606

```
tcctatgagc tgactcagcc accctcagcg tctgggaccc ccgggcagag ggtcaccatg       60
tcttgttctg gaaccagctc caacatcgga agtcactctg taaactggta ccagcagctc      120
ccaggaacgg cccccaaact cctcatctat actaataatc agcggccctc aggggtccct      180
gaccgattct ctggctccaa gtctggcacc tcagcctccc tggccatcag tggcctccag      240
tctgaggatg aggctgatta ttactgtgca gcatgggatg gcagcctgaa tggtctggta      300
ttcggcggag ggaccaagct gaccgtccta ggttctagag gtggtggtgg tagcggcggc      360
ggcggctctg gtggtggtgg atccctcgag atggccgagg tgcagctggt gcagtctgga      420
gcagaggtga aaaagcccgg ggagtctctg aagatctcct gtaagggttc tggatacagc      480
tttaccagct actggatcgg ctgggtgcgc cagatgcccg ggaaaggcct ggagtggatg      540
```

```
gggatcatct atcctggtga ctctgatacc agatacagcc cgtccttcca aggccacgtc    600
accatctcag ctgacaagtc catcagcact gcctacctgc agtggagcag cctgaaggcc    660
tcggacaccg ccatgtatta ctgtgcgcgc tactctggtt ctttcgataa ctggggtcaa    720
ggtactctgg tgaccgtctc ctca                                           744
```

<210> SEQ ID NO 607
<211> LENGTH: 732
<212> TYPE: DNA
<213> ORGANISM: Artificial Sequence
<220> FEATURE:
<223> OTHER INFORMATION: Synthetic
<220> FEATURE:
<223> OTHER INFORMATION: BCMA-55 scFv sequence (nt)

<400> SEQUENCE: 607

```
caatctgccc tgactcagcc tgcctccgtg tctgcgtctc ctggacagtc gatcgccatc     60
tcctgcactg gaaccagcag tgacgttggt tggtatcaac agcacccagg caaagccccc    120
aaactcatga tttatgagga cagtaagcgg ccctcagggg tttctaatcg cttctctggc    180
tccaagtctg gcaacacggc ctccctgacc atctctgggc tccaggctga ggacgaggct    240
gattattact gcagctcaaa tacaagaagc agcactttgg tgttcggcgg agggaccaag    300
ctgaccgtcc taggttctag aggtggtggt ggtagcggcg cggcggctc tggtggtggt    360 ggatccctcg agatggccga agtgcagctg gtgcagtctg gggctgagat gaagaagcct    420
ggggcctcac tgaagctctc ctgcaaggct tctggataca ccttcatcga ctactatgta    480
tactggatgc gacaggcccc tggacaaggg cttgagtcca tgggatggat caaccctaac    540
agtggtggca caactatgc acagaagttt cagggcaggg tcaccatgac cagggacacg    600
tccatcagca gcctacat ggagctgagc aggctgagat ctgacgacac cgccatgtat    660
tactgtgcgc gctcccagcg tgacggttac atggattact ggggtcaagg tactctggtg    720
accgtctcct ca                                                         732
```

<210> SEQ ID NO 608
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 608

Ser Asn Thr Pro Pro Leu Thr Cys Gln Arg
1               5                   10

<210> SEQ ID NO 609
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 609

Cys Ile Pro Cys Gln Leu Arg
1               5

<210> SEQ ID NO 610
<211> LENGTH: 7

```
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 610

Ser Val Thr Asn Ser Val Lys
1               5

<210> SEQ ID NO 611
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 611

Cys Ser Gln Asn Glu Tyr Phe
1               5

<210> SEQ ID NO 612
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 612

Leu Leu His Ala Cys Ile Pro Cys Gln Leu Arg
1               5                   10

<210> SEQ ID NO 613
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 613

Gln Asn Glu Tyr Phe
1               5

<210> SEQ ID NO 614
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 614

Cys Ile Pro Cys Gln Leu
1               5

<210> SEQ ID NO 615
<211> LENGTH: 5
<212> TYPE: PRT
<213> ORGANISM: Artificial Sequence
<220> FEATURE:
<223> OTHER INFORMATION: Synthetic
```

<220> FEATURE:
<223> OTHER INFORMATION: BCMA epitope

<400> SEQUENCE: 615

Cys Gln Arg Tyr Cys
1               5

<210> SEQ ID NO 616
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 616

Met Leu Met Ala Gly
1               5

<210> SEQ ID NO 617
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 617

Gln Asn Glu Tyr Phe Asp Ser Leu Leu
1               5

<210> SEQ ID NO 618
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 618

Tyr Phe Asp Ser Leu
1               5

<210> SEQ ID NO 619
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

<400> SEQUENCE: 619

Gln Leu Arg Cys Ser Ser Asn Thr Pro Pro Leu
1               5                   10

<210> SEQ ID NO 620
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: BCMA epitope

```
<400> SEQUENCE: 620

Tyr Phe Asp Ser Leu Leu
1               5
```